(12) United States Patent
Berthel et al.

(10) Patent No.: US 8,258,134 B2
(45) Date of Patent: Sep. 4, 2012

(54) PYRIDAZINONE GLUCOKINASE ACTIVATORS

(75) Inventors: Steven Joseph Berthel, Mendham Township, NJ (US); Nancy-Ellen Haynes, Cranford, NJ (US); Robert Francis Kester, West Orange, NJ (US); Lee Apostle McDermott, East Windsor, NJ (US); Yimin Qian, Wayne, NJ (US); Ramakanth Sarabu, Towaco, NJ (US); Nathan Robert Scott, Livingston, NJ (US); Jefferson Wright Tilley, North Caldwell, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 544 days.

(21) Appl. No.: 12/400,319

(22) Filed: Mar. 9, 2009

(65) Prior Publication Data

US 2009/0264434 A1    Oct. 22, 2009

Related U.S. Application Data

(60) Provisional application No. 61/114,654, filed on Nov. 14, 2008, provisional application No. 61/045,318, filed on Apr. 16, 2008.

(51) Int. Cl.
| | |
|---|---|
| C07D 401/06 | (2006.01) |
| C07D 401/14 | (2006.01) |
| C07D 237/32 | (2006.01) |
| C07D 237/10 | (2006.01) |
| A61K 31/501 | (2006.01) |
| A61K 31/502 | (2006.01) |
| A61P 5/50 | (2006.01) |

(52) U.S. Cl. ............. 514/247; 514/252.05; 514/252.04; 514/252.03; 514/252.02; 514/248; 544/238; 544/237; 544/224

(58) Field of Classification Search .................. 544/239, 544/240, 238, 237, 224; 514/247, 252.01, 514/252.05, 252.04, 252.03, 252.02, 248
See application file for complete search history.

(56) References Cited

U.S. PATENT DOCUMENTS

| | | |
|---|---|---|
| 2006/0167053 A1 | 7/2006 | IIno et al. |
| 2006/0258701 A1 | 11/2006 | Mitsuya et al. |
| 2010/0216642 A1* | 8/2010 | Fusaka .......................... 504/238 |
| 2010/0222325 A1* | 9/2010 | Berthel et al. ........... 514/210.21 |
| 2010/0286390 A1* | 11/2010 | Shigeta et al. ................ 544/114 |
| 2011/0098269 A1* | 4/2011 | Becknell et al. ........... 514/210.2 |

FOREIGN PATENT DOCUMENTS

| | | |
|---|---|---|
| EP | 1 600 442 A1 | 11/2005 |
| WO | WO 00/58293 | 10/2000 |
| WO | WO 01/83465 A2 | 11/2001 |
| WO | WO 01/85706 A1 | 11/2001 |
| WO | WO 01/85707 A1 | 11/2001 |
| WO | WO 02/46173 | 6/2002 |
| WO | WO 03/015774 A1 | 2/2003 |
| WO | WO 03/095438 A1 | 11/2003 |
| WO | WO 2004/052869 A1 | 6/2004 |
| WO | WO 2004/072031 A2 | 8/2004 |
| WO | WO 2004/072066 A1 | 8/2004 |
| WO | WO 2004/076420 A1 | 9/2004 |
| WO | WO 2004/081001 A1 | 9/2004 |
| WO | WO 2005/080359 A1 | 9/2005 |
| WO | WO 2005/080360 | 9/2005 |
| WO | WO 2005/090332 A1 | 9/2005 |
| WO | WO 2005/095418 A1 | 10/2005 |
| WO | WO 2005/103021 A1 | 11/2005 |
| WO | WO 2005/121110 A1 | 12/2005 |
| WO | WO 2006/016194 A1 | 2/2006 |
| WO | WO 2006/040529 A1 | 4/2006 |
| WO | WO 2006/125972 A1 | 11/2006 |
| WO | WO 2007/007040 A1 | 1/2007 |
| WO | WO 2007/007041 A1 | 1/2007 |
| WO | WO 2007/007042 A1 | 1/2007 |
| WO | WO 2007/007886 A1 | 1/2007 |
| WO | WO 2007/017649 A1 | 2/2007 |
| WO | WO 2007/026761 A1 | 3/2007 |
| WO | WO 2007/041365 A2 | 4/2007 |
| WO | WO 2007/041366 A1 | 4/2007 |
| WO | WO 2007/051845 A1 | 5/2007 |
| WO | WO 2007/051846 A1 | 5/2007 |
| WO | WO 2007/051847 A1 | 5/2007 |
| WO | WO 2004/050645 A1 | 6/2007 |
| WO | WO 2007/104034 A2 | 9/2007 |
| WO | WO 2007/122482 A1 | 11/2007 |
| WO | WO 2006/058923 A1 | 6/2008 |

* cited by examiner

*Primary Examiner* — James O Wilson
*Assistant Examiner* — Cecilia M Jaisle
(74) *Attorney, Agent, or Firm* — George W. Johnston; Dennis P. Tramaloni; Samuel H. Megerditchian

(57) ABSTRACT

Provided herein are compounds of the formula (I):

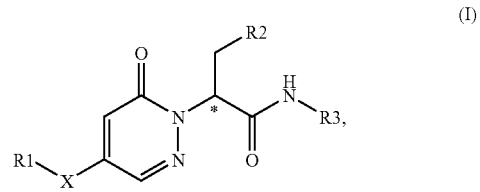

as well as pharmaceutically acceptable salts thereof, wherein the substituents are as those disclosed in the specification. These compounds, and the pharmaceutical compositions containing them, are useful for the treatment of metabolic diseases and disorders such as, for example, type II diabetes mellitus.

2 Claims, No Drawings

PYRIDAZINONE GLUCOKINASE ACTIVATORS

PRIORITY TO RELATED APPLICATION(S)

This application claims the benefit of U.S. Provisional Application No. 61/114,654, filed Nov. 14, 2008, and U.S. Provisional Application No. 61/045,318, filed Apr. 16, 2008. The entire contents of the above-identified applications are hereby incorporated by reference.

FIELD OF THE INVENTION

The invention is directed to compounds of the formula (I):

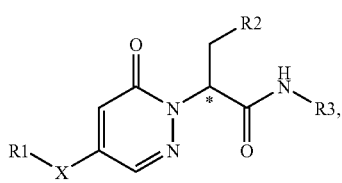

and salts thereof, and to pharmaceutical compositions comprising said compounds.

All documents cited or relied upon below are expressly incorporated herein by reference.

BACKGROUND OF THE INVENTION

Glucokinase (GK) is one of four hexokinases that are found in mammals (Colowick, S. P., in *The Enzymes*, Vol. 9 (P. Boyer, ed.) Academic Press, New York, N.Y., pages 1-48, 1973). The hexokinases catalyze the first step in the metabolism of glucose, i.e., the conversion of glucose to glucose-6-phosphate. Glucokinase has a limited cellular distribution, being found principally in pancreatic β-cells and liver parenchymal cells. In addition, GK is a rate-controlling enzyme for glucose metabolism in these two cell types that are known to play critical roles in whole-body glucose homeostasis (Chipkin, S. R., Kelly, K. L., and Ruderman, N. B. in *Joslin's Diabetes* (C. R. Khan and G. C. Wier, eds.), Lea and Febiger, Philadelphia, Pa., pages 97-115, 1994). The concentration of glucose at which GK demonstrates half-maximal activity is approximately 8 mM. The other three hexokinases are saturated with glucose at much lower concentrations (<1 mM). Therefore, the flux of glucose through the GK pathway rises as the concentration of glucose in the blood increases from fasting (5 mM) to postprandial (≈10-15 mM) levels following a carbohydrate-containing meal (Printz, R. G., Magnuson, M. A., and Granner, D. K. in *Ann. Rev. Nutrition* Vol. 13 (R. E. Olson, D. M. Bier, and D. B. McCormick, eds.), Annual Review, Inc., Palo Alto, Calif., pages 463-496, 1993). These findings contributed over a decade ago to the hypothesis that GK functions as a glucose sensor in β-cells and hepatocytes (Meglasson, M. D. and Matschinsky, F. M. *Amer. J. Physiol.* 246, E1-E13, 1984). In recent years, studies in transgenic animals have confirmed that GK does indeed play a critical role in whole-body glucose homeostasis. Animals that do not express GK die within days of birth with severe diabetes while animals overexpressing GK have improved glucose tolerance (Grupe, A., Hultgren, B., Ryan, A. et al., *Cell* 83, 69-78, 1995; Ferrie, T., Riu, E., Bosch, F. et al., *FASEB J.*, 10, 1213-1218, 1996). An increase in glucose exposure is coupled through GK in β-cells to increased insulin secretion and in hepatocytes to increased glycogen deposition and perhaps decreased glucose production.

The finding that type II maturity-onset diabetes of the young (MODY-2) is caused by loss of function mutations in the GK gene suggests that GK also functions as a glucose sensor in humans (Liang, Y., Kesavan, P., Wang, L. et al., *Biochem. J.* 309, 167-173, 1995). Additional evidence supporting an important role for GK in the regulation of glucose metabolism in humans was provided by the identification of patients that express a mutant form of GK with increased enzymatic activity. These patients exhibit a fasting hypoglycemia associated with an inappropriately elevated level of plasma insulin (Glaser, B., Kesavan, P., Heyman, M. et al., *New England J. Med.* 338, 226-230, 1998). While mutations of the GK gene are not found in the majority of patients with type II diabetes, compounds that activate GK and, thereby, increase the sensitivity of the GK sensor system will still be useful in the treatment of the hyperglycemia characteristic of all type II diabetes. Glucokinase activators will increase the flux of glucose metabolism in β-cells and hepatocytes, which will be coupled to increased insulin secretion. Such agents would be useful for treating type II diabetes.

SUMMARY OF THE INVENTION

The present invention is directed to compounds of the formula I:

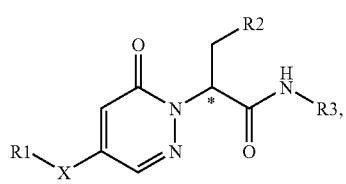

as well as pharmaceutically acceptable salts thereof, pharmaceutical compositions containing them and to methods of treating diseases and disorders. The compounds and compositions disclosed herein are glucokinase activators useful for the treatment of metabolic diseases and disorders, preferably diabetes mellitus, more preferably type II diabetes mellitus.

DETAILED DESCRIPTION OF THE INVENTION

In an embodiment of the present invention, provided is a compound of the formula (I)

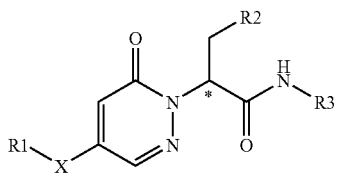

wherein:
X is oxygen, nitrogen, sulfur, carbon or absent;
$R_1$ is
  hydrogen,
  lower alkyl,
  cycloalkyl,
  $CH_2$-cycloalkyl,
  heterocycloalkyl, aryl, unsubstituted or mono-, bi- or tri-substituted independently with halogen, alkyl, alkoxy, —S(O$_2$)-lower alkyl, —CH$_2$-aryl, heteroaryl, cyano, alkoyl, —O-aryl, cycloalkyl, heterocycloalkyl or —C(O)-heterocycloalkyl, heteroaryl, unsubstituted or substituted with halogen or lower alkyl, 2,3-dihydro-benzo[1,4]dioxin-5-yl,
2,3-dihydro-benzo[1,4]dioxin-2-ylmethyl
5,6,7,8-tetrahydro-naphthalen-1-yl,
1H-indol-4-yl,
2,2-dimethyl-2,3-dihydro-benzofuran-7-yl,
7-methyl-indan-4-yl,
2,3-dihydro-benzo[1,4]dioxin-5-yl,
naphthalen-1-yl or
isoquinolin;

R$_2$ is
lower alkyl,
cycloalkyl,
heterocycloalkyl,
aryl, unsubstituted or mono- or bi-substituted independently with halogen, or
heteroaryl having at least one ring heteroatom being either O or S; and R$_3$ is
lower alkyl-carbamoyl or
an unsubstituted or substituted heteroaryl connected by a ring carbon atom to the amine group shown, with one heteroatom being nitrogen which is adjacent to the connecting ring carbon atom, said substituted heteroaryl being substituted at a position other than adjacent to said connecting carbon atom independently with halogen, lower alkyl, ester, acid, cycloalkyl, aryl, —CH$_2$-aryl, heterocycloalkyl or —CH$_2$-heterocycloalkyl, or pharmaceutically acceptable salts thereof.

In another embodiment of the present invention, provided is a compound of formula I(c):

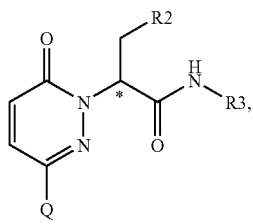

I(c)

wherein:
Q is —O-aryl;
R$_2$ is
lower alkyl,
cycloalkyl,
heterocycloalkyl,
aryl, unsubstituted or mono- or bi-substituted independently with halogen, or
heteroaryl having at least one ring heteroatom being either O or S; and R$_3$ is
lower alkyl-carbamoyl or
an unsubstituted or substituted heteroaryl connected by a ring carbon atom to the amine group shown, with one heteroatom being nitrogen which is adjacent to the connecting ring carbon atom, said substituted heteroaryl being substituted at a position other than adjacent to said connecting carbon atom independently with halogen, lower alkyl, ester, acid, cycloalkyl, aryl, —CH$_2$-aryl, heterocycloalkyl or —CH$_2$-heterocycloalkyl, or pharmaceutically acceptable salts thereof.

In a further embodiment of the present invention, provided is a compound of formula I(d):

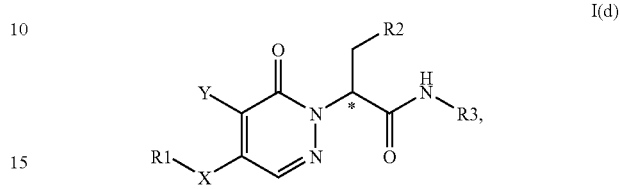

I(d)

wherein:
X is oxygen;
Y is halogen, lower alkyl or aryl;
R$_1$ is
hydrogen,
lower alkyl,
cycloalkyl,
CH$_2$-cycloalkyl,
heterocycloalkyl,
aryl, unsubstituted or mono-, bi- or tri-substituted independently with halogen, alkyl, alkoxy, —CF$_3$, —S(O$_2$)CH$_3$, —CH$_2$-aryl, heteroaryl, cyano, alkoyl, —O-aryl, cycloalkyl, heterocycloalkyl or —C(O)-heterocycloalkyl, heteroaryl, unsubstituted or substituted with halogen or lower alkyl, 2,3-dihydro-benzo[1,4]dioxin-5-yl,
2,3-dihydro-benzo[1,4]dioxin-2-ylmethyl
5,6,7,8-tetrahydro-naphthalen-1-yloxy,
1H-indol-4-yl,
2,2-dimethyl-2,3-dihydro-benzofuran-7-yl,
7-methyl-indan-4-yl,
2,3-dihydro-benzo[1,4]dioxin-5-yl,
naphthalen-1-yloxy or
isoquinolin;

R$_2$ is
lower alkyl,
cycloalkyl,
heterocycloalkyl,
aryl, unsubstituted or mono- or bi-substituted independently with halogen, or
heteroaryl having at least one ring heteroatom being either O or S; and R$_3$ is
lower alkyl-carbamoyl or
an unsubstituted or substituted heteroaryl connected by a ring carbon atom to the amine group shown, with one heteroatom being nitrogen which is adjacent to the connecting ring carbon atom, said substituted heteroaryl being substituted at a position other than adjacent to said connecting carbon atom independently with halogen, lower alkyl, ester, acid, cycloalkyl, aryl, —CH$_2$-aryl, heterocycloalkyl or —CH$_2$-heterocycloalkyl, or pharmaceutically acceptable salts thereof.

In a yet another embodiment of the present invention, provided is a compound of formula I(e):

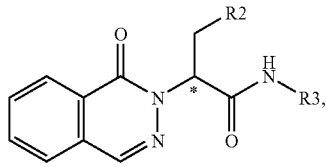

wherein:
R$_2$ is
  lower alkyl,
  cycloalkyl,
  heterocycloalkyl,
  aryl, unsubstituted or mono- or bi-substituted independently with halogen, or
  heteroaryl having at least one ring heteroatom being either O or S; and
R$_3$ is
  lower alkyl-carbamoyl or
  an unsubstituted or substituted heteroaryl connected by a ring carbon atom to the amine group shown, with one heteroatom being nitrogen which is adjacent to the connecting ring carbon atom, said substituted heteroaryl being substituted at a position other than adjacent to said connecting carbon atom independently with halogen, lower alkyl, ester, acid, cycloalkyl, aryl, —CH$_2$-aryl, heterocycloalkyl or —CH$_2$-heterocycloalkyl,
wherein the phenyl moiety in the 2H-phthalazin-1-one shown in formula I(e) may be unsubstituted or mono-, bi- or tri-substituted with halogen, lower alkyl or alkoxy, or pharmaceutically acceptable salts thereof.

In a still yet another preferred embodiment of the present invention, provided is a pharmaceutical composition, comprising a therapeutically effective amount of a compound according to formula (I) or a pharmaceutically acceptable salt thereof and a pharmaceutically acceptable carrier.

It is to be understood that the terminology employed herein is for the purpose of describing particular embodiments, and is not intended to be limiting. Further, although any methods, devices and materials similar or equivalent to those described herein can be used in the practice or testing of the invention, the preferred methods, devices and materials are now described.

As used herein, the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "cycloalkyl" refers to a monovalent mono- or polycarbocyclic radical of three to ten, preferably three to six carbon atoms. This term is further exemplified by radicals such as cyclopropyl, cyclobutyl, cyclopentyl, cyclohexyl, cycloheptyl, bornyl, adamantyl, indenyl and the like. In a preferred embodiment, the "cycloalkyl" moieties can optionally be substituted with one, two, three or four substituents with the understanding that said substituents are not, in turn, substituted further unless indicated otherwise in the Examples or claims below. Each substituent can independently be, for example, alkyl, alkoxy, halogen, amino, hydroxyl or oxygen (O═) unless otherwise specifically indicated. Examples of cycloalkyl moieties include, but are not limited to, optionally substituted cyclopropyl, optionally substituted cyclobutyl, optionally substituted cyclopentyl, optionally substituted cyclopentenyl, optionally substituted cyclohexyl, optionally substituted cyclohexylene, optionally substituted cycloheptyl.

The term "heterocycloalkyl" denotes a mono- or polycyclic alkyl ring, wherein one, two or three of the carbon ring atoms is replaced by a heteroatom such as N, O or S. Examples of heterocycloalkyl groups include, but are not limited to, morpholinyl, thiomorpholinyl, piperazinyl, piperidinyl, pyrrolidinyl, tetrahydropyranyl, tetrahydrofuranyl, 1,3-dioxanyl and the like. The heterocycloalkyl groups may be unsubstituted or substituted and attachment may be through their carbon frame or through their heteroatom(s) where appropriate, with the understanding that said substituents are not, in turn, substituted further unless indicated otherwise in the Examples or claims below.

The term "lower alkyl", alone or in combination with other groups, refers to a branched or straight-chain alkyl radical of one to nine carbon atoms, preferably one to six carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like.

The term "aryl" refers to an aromatic mono- or polycarbocyclic radical of 6 to 12 carbon atoms having at least one aromatic ring. Examples of such groups include, but are not limited to, phenyl, napthyl. 1,2,3,4-tetrahydronaphtalene, 1,2-dihydronaphtalene, indanyl, 1H-indenyl and the like.

The alkyl, lower alkyl and aryl groups may be substituted or unsubstituted. When substituted, there will generally be, for example, 1 to 4 substituents present, with the understanding that said substituents are not, in turn, substituted further unless indicated otherwise in the Examples or claims below. These substituents may optionally form a ring with the alkyl, loweralkyl or aryl group they are connected with. Substituents may include, for example: carbon-containing groups such as alkyl, aryl, arylalkyl; halogen atoms and halogen-containing groups such as haloalkyl (e.g. trifluoromethyl); oxygen-containing groups such as alcohols (e.g. hydroxyl, hydroxyalkyl, aryl(hydroxyl)alkyl), ethers (e.g. alkoxy, aryloxy, alkoxyalkyl, aryloxyalkyl, more preferably, for example, methoxy and ethoxy), aldehydes (e.g. carboxaldehyde), ketones (e.g. alkylcarbonyl, alkylcarbonylalkyl, arylcarbonyl, arylalkylcarbonyl, arylcarbonylalkyl), acids (e.g. carboxy, carboxyalkyl), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono- or di-alkylaminocarbonylalkyl, arylaminocarbonyl), carbamates (e.g. alkoxycarbonylamino, aryloxycarbonylamino, aminocarbonyloxy, mono- or di-alkylaminocarbonyloxy, arylminocarbonloxy) and ureas (e.g. mono- or di-alkylaminocarbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arylsulfinyl, arylsulfonyl, arylthioalkyl, arylsulfinylalkyl, arylsulfonylalkyl); and heterocyclic groups containing one or more heteroatoms, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazol idinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

The term "heteroaryl," refers to an aromatic mono- or polycyclic radical of 5 to 12 atoms having at least one aromatic ring containing one, two, or three ring heteroatoms selected from N, O, and S, with the remaining ring atoms being C. One or two ring carbon atoms of the heteroaryl group may be replaced with a carbonyl group.

The heteroaryl group described above may be substituted independently with one, two, or three substituents, with the understanding that said substituents are not, in turn, substituted further unless indicated otherwise in the Examples or claims below. These substituents may optionally form a ring with the heteroaryl group to which they are connected. Substituents may include, for example: carbon-containing groups such as alkyl, aryl, arylalkyl; halogen atoms and halogen-containing groups such as haloalkyl (e.g. trifluoromethyl); oxygen-containing groups such as alcohols (e.g. hydroxyl, hydroxyalkyl, aryl(hydroxyl)alkyl), ethers (e.g. alkoxy, aryloxy, alkoxyalkyl, aryloxyalkyl), aldehydes (e.g. carboxaldehyde), ketones (e.g. alkylcarbonyl, alkylcarbonylalkyl, arylcarbonyl, arylalkylcarbonyl, arylcarbonylalkyl), acids (e.g. carboxy, carboxyalkyl), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono- or di-alkylaminocarbonylalkyl, arylaminocarbonyl), carbamates (e.g. alkoxycarbonylamino, aryloxycarbonylamino, aminocarbonyloxy, mono- or di-alkylaminocarbonyloxy, arylminocarbonloxy) and ureas (e.g. mono- or di-alkylaminocarbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arylsulfinyl, arylsulfonyl, arylthioalkyl, arylsulfinylalkyl, arylsulfonylalkyl); and heterocyclic groups containing one or more heteroatoms, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazol idinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

As used herein, the term "alkoxy" means alkyl-O—; and "alkoyl" means alkyl-CO—. Alkoxy substituent groups or alkoxy-containing substituent groups may be substituted by, for example, one or more alkyl groups with the understanding that said substituents are not, in turn, substituted further unless indicated otherwise in the Examples or claims below.

As used herein, the term "halogen" means a fluorine, chlorine, bromine or iodine radical, preferably a fluorine, chlorine or bromine radical, and more preferably a fluorine or chlorine radical.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with chiral adsorbents or eluant). The invention embraces all of these forms.

As used herein, the term "pharmaceutically acceptable salt" means any pharmaceutically acceptable salt of the compound of formula (I). Salts may be prepared from pharmaceutically acceptable non-toxic acids and bases including inorganic and organic acids and bases. Such acids include, for example, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. Particularly preferred are fumaric, hydrochloric, hydrobromic, phosphoric, succinic, sulfuric and methanesulfonic acids. Acceptable base salts include alkali metal (e.g. sodium, potassium), alkaline earth metal (e.g. calcium, magnesium) and aluminium salts.

In the practice of the method of the present invention, an effective amount of any one of the compounds of this invention or a combination of any of the compounds of this invention or a pharmaceutically acceptable salt thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form or solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The dose of a compound of the present invention depends on a number of factors, such as, for example, the manner of administration, the age and the body weight of the subject, and the condition of the subject to be treated, and ultimately will be decided by the attending physician or veterinarian. Such an amount of the active compound as determined by the attending physician or veterinarian is referred to herein, and in the claims, as a "therapeutically effective amount". For example, the dose of a compound of the present invention is typically in the range of about 1 to about 1000 mg per day. Preferably, the therapeutically effective amount is in an amount of from about 1 mg to about 500 mg per day.

It will be appreciated, that the compounds of general formula I in this invention may be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

Compounds of the present invention can be prepared beginning with commercially available starting materials and utilizing general synthetic techniques and procedures known to those skilled in the art. Outlined below are reaction schemes suitable for preparing such compounds. Chemicals may be purchased from companies such as for example Aldrich, Argonaut Technologies, VWR and Lancaster. Chromatography supplies and equipment may be purchased from such companies as for example AnaLogix, Inc, Burlington, Wis.; Biotage AB, Charlottesville, Va.; Analytical Sales and Services, Inc., Pompton Plains, N.J.; Teledyne Isco, Lincoln, Nebr.; VWR International, Bridgeport, N.J.; Varian Inc., Palo Alto, Calif., and Multigram II Mettler Toledo Instrument Newark, Del. Biotage, ISCO and Analogix columns are prepacked silica gel columns used in standard chromatography.

Preferably, the compounds of formula I, for example Ia, Ib, Id and Ie can be prepared by the following General Reaction Scheme I. Preferably, the compounds of formula Ic can be prepared by the following General Reaction Scheme II:

General Reaction Schemes

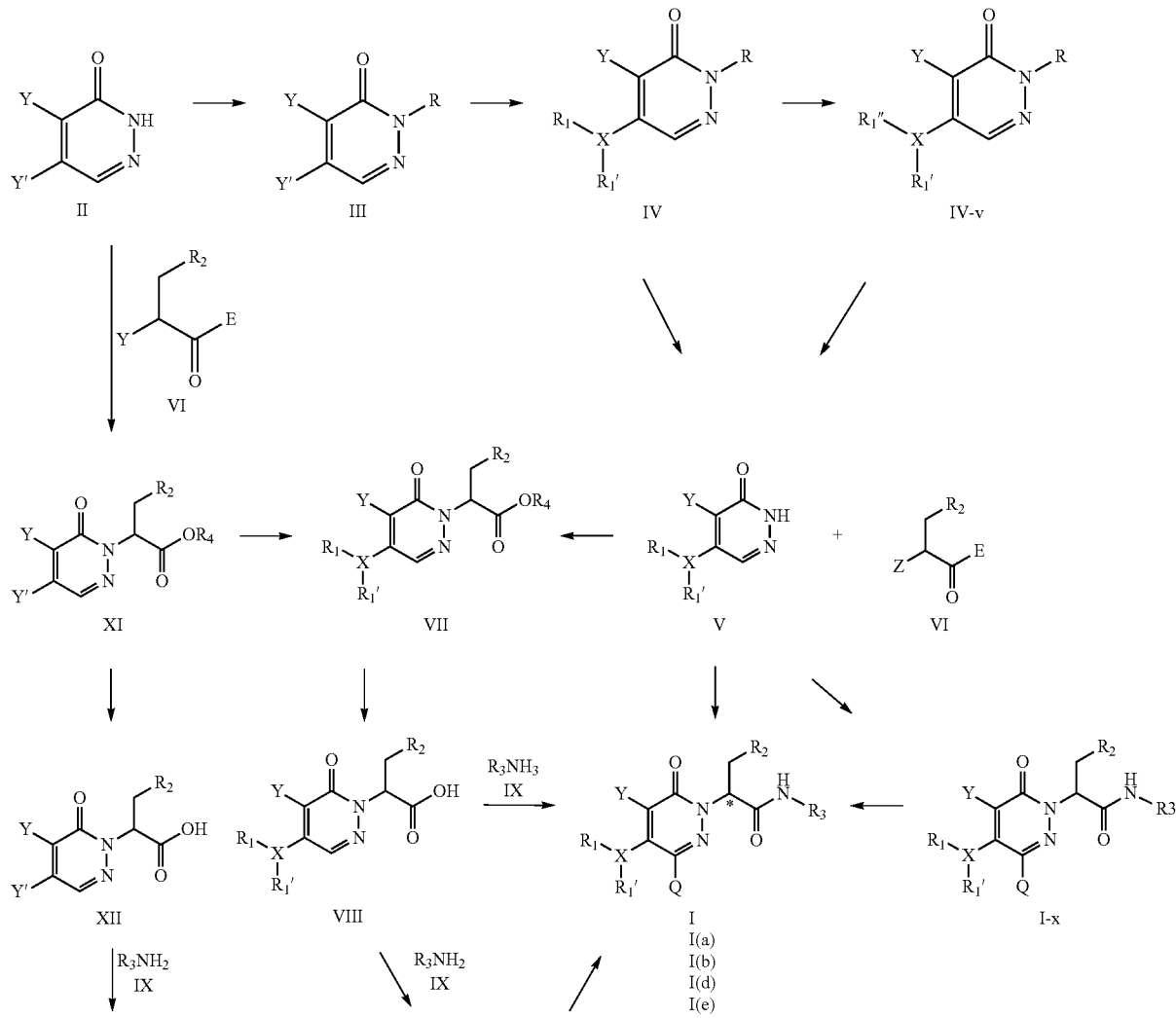

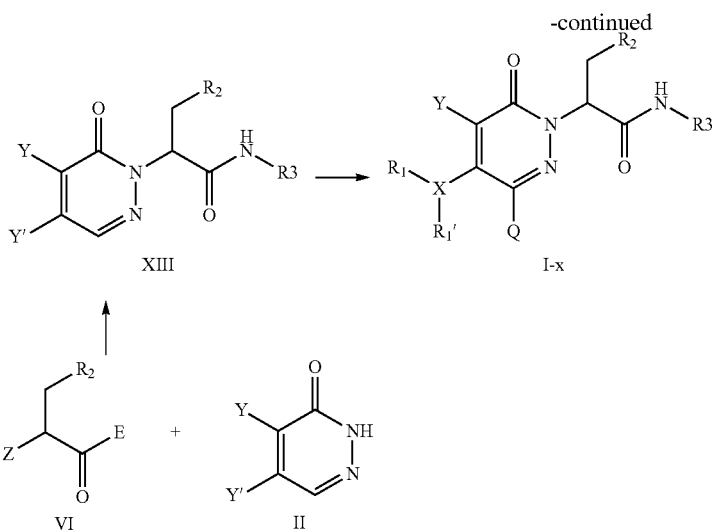

I(a) where Q = H; Y = H; X = O
I(b) where Q = H; Y = H; X = O
I(d) where Q = H; Y = halogen, alkyl or aryl; X = O, S, CH₂ or N
I(e) where Q = H; X, Y, R1 from a 6 membered benzofused ring.

General Reaction Scheme II

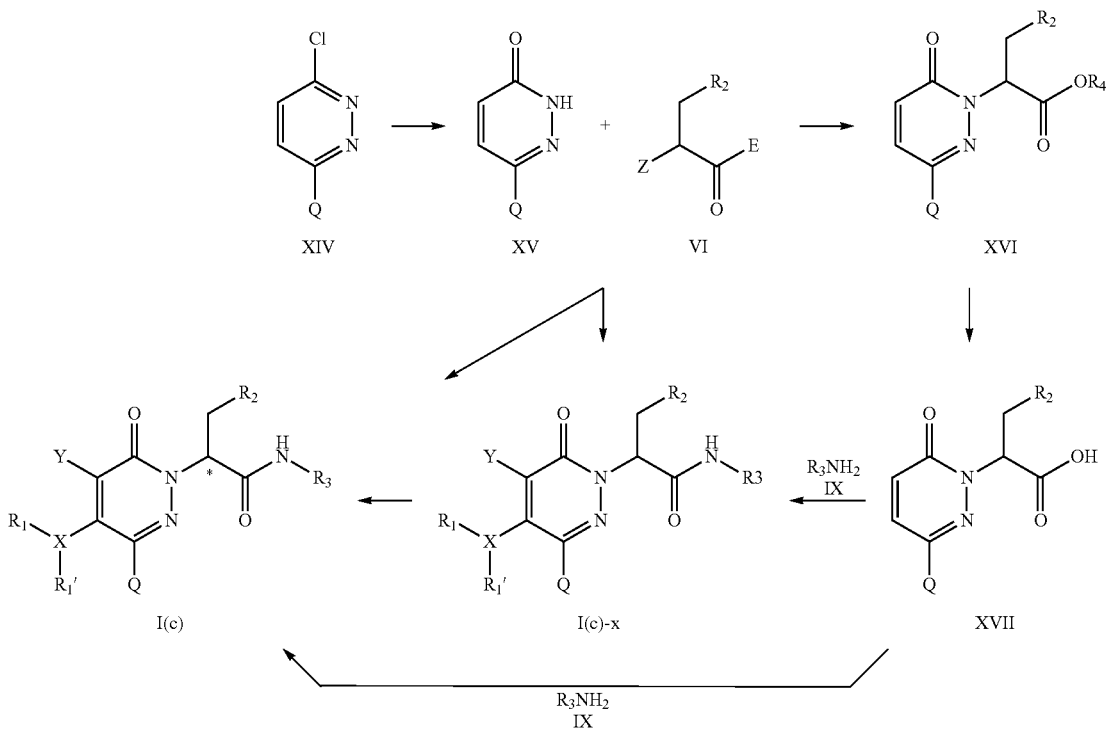

The compound of formula II where Y and Y' are chloro is readily available from commercial sources or can be prepared from 3,4-dichloro-5-hydroxy-5H-furan-2-one (see for example, Yanagita, M. *J. Pharm. Soc. of Japan,* 1952, 72, 1383-1384). The compound of formula II where Y and Y' are chloro can also be produced using hydrazine, a hydrazine equivalent or a substituted hydrazine and then reacted with 3,4-dichloro-5-hydroxy-5H-furan-2-one which can be prepared using the following reference; Yanagita, M. *J. Pharm. Soc. of Japan,* 1952, 72, 1383-1384 (see for example, Kaminski, J., Moo-Puc, R., Cedillo-Rivera, R., Kazimierczuk, Z. *Synth. Comm.,* 2006, 36, 2719-2726). The compound of formula II where Y is hydrogen and Y' is a halogen preferably iodo can be produced from commercially available starting materials. Any conventional method can be utilized to effect this conversion (see for example, Krajsovszky, G.; et al, *J. Molecular Structure,* 2005, 713, 235-243).

The compound of formula II where Y' is chloro and Y is alkyl or aryl can be prepared from the compound of formula III where R=tert-butyl and Y, Y' are chloro by treating with an appropriate Grignard reagent as described in PCT Int. Appl. WO 9507264.

The compound of formula II where Y is H and Y' is alkyl can be prepared from the compound of formula II where Y is H and Y' is iodo by treating with a boronic acid under Suzuki conditions as described in Haider, N.; Wobus, A. *Heterocycles,* 2006, 68 2549-2561.

In the compounds of formula III, it is preferred that the amino group be protected. The amino group can be protected with any conventional protecting group (see for example, Greene, T. W. *Protective Groups in Organic Synthesis*; John Wiley & Sons, Inc.: New York, 1991) preferably tetrahydropyranyl (THP) (see for example, Greene, T. W. *Protective Groups in Organic Synthesis*; John Wiley & Sons, Inc.: New York, 1991, p. 394; Bryant, R. D., Kunng, F.-A., South, M. S. *J Heterocyclic Chem.,* 1995, 32, 1473-1476). The protecting group may be removed from the amino group after preparing the corresponding amine protected compounds of formula IV to obtain the corresponding amines. The amino protecting group, preferably THP, can be removed using any conventional method to remove protecting groups (see for example, Greene, T. W. *Protective Groups in Organic Synthesis*; John Wiley & Sons, Inc.: New York, 1991; Bryant, R. D., Kunng, F.-A., South, M. S. *J. Heterocyclic Chem.,* 1995, 32, 1473-1476) preferably acid hydrolysis.

The compounds of formula IV can be made when X is oxygen, carbon, nitrogen and sulfur. When X is carbon or nitrogen, R1' may be H or lower alkyl. When X is sulfur, R1' may be one connected oxygen (i.e. sulfoxide) or two connected oxygens (i.e. sulfone). When X is oxygen, carbon, nitrogen or sulfur, Y may be hydrogen, chloro, other halogen or lower alkyl, $R_1$ may be aryl, substituted aryl, heteroaryl, substituted heteroaryl, heteroalkyl, substituted heteroalkyl, lower alkyl, cycloalkyl, $(CH_2)_n$cycloalkyl, $(CH_2)_n$aryl, substituted $(CH_2)_n$aryl, substituted cycloalkyl, or substituted $(CH_2)_n$cycloalkyl and R maybe any nitrogen protecting group preferably tetrahydropyranyl (see for example, Greene, T. W. *Protective Groups in Organic Synthesis*; John Wiley & Sons, Inc.: New York, 1991, p. 394; Bryant, R. D., Kunng, F.-A., South, M. S. *J Heterocyclic Chem.,* 1995, 32, 1473-1476).

The compounds of formula III can be converted to compounds of formula IV where X is oxygen, $R_1$ is aryl, substituted aryl, heteroaryl or substituted heteroaryl and R is any nitrogen protecting group, preferably tetrahydropyranyl, by treatment with the appropriate phenol. The appropriate phenol can be obtained through commercial sources or through chemical synthesis. Any conventional method of producing a phenol can also be utilized (see for example, Gonzalez, Concepcion; Castedo, Luis. Departamento de Quimica Organica, Facultad de Ciencias, Universidad de Santiago, Lugo, Spain. Editor(s): Rappoport, Zvi. Chemistry of Phenols (2003), 1 395-489. Publisher: John Wiley & Sons Ltd., Chichester, UK and references cited therein; George, T.; Mabon, R.; Sweeney, G.; Sweeney, J. B.; Tavassoli, A. *J. Chem. Soc. Perkin* 1 2000, 16, 2529-2574 and references cited therein). Any conventional method used to convert Y' of formula III to the appropriate aryl, substituted aryl, heteroaryl or substituted heteroaryl compound of formula IV where X is oxygen can be utilized to effect this conversion (see for example, *J Heterocyclic Chem.* 1995, 32, 1473).

The compound of formula III can be converted to compounds of formula IV where X is oxygen and $R_1$ is aryl, substituted aryl, heteroaryl or substituted heteroaryl and R is any nitrogen protecting group, preferably tetrahydropyranyl, by treatment with the appropriate reagent (see for example, Kweon, D.-H., Kang, Y.-J., Chung, H.-A., Yoo, Y.-J., *J. Heterocyclic Chem.* 1998, 35, 819-826). More preferably the following reagents, which are all commercially available, can be used: phenol, 2-methoxy-phenol, 3-methoxy-phenol, 4-methoxy-phenol, 2-trifluoromethyl-phenol, 3-trifluoromethyl-phenol, 4-trifluoromethyl-phenol, (2-hydroxy-phenyl)-pyrrolidin-1-yl-methanone, 2-cyclohexylphenol, 2-cyclopentylphenol, 2-phenylphenol, 1-naphthol, 5,6,7,8-tetrahydro-1-naphthol, 2'-hydroxyacetophenone, 2-hydroxybenzonitrile, o-cresol, 3-fluorophenol, 2-fluorophenol, 2,3-difluorophenol, 2,4-difluorophenol, 2,5-difluorophenol, 2,6-difluorophenol, 2-(methylsulfonyl)-phenol, 3-phenoxyphenol, 3-hydroxy-2-methylpyridine, 2-(1-pyrrolidino)-phenol, 2-(1-piperidino)-phenol, 2-(4-morpholino)-phenol, 3-hydroxypyridine, 8-hydroxyquinoline, 5-hydroxyisoquinoline, 5-hydroxyquinoline, 2,3,6-trimethyl-phenol, 2,2-dimethyl-2,3-dihydro-benzofuran-7-ol, 2-tert-butyl-phenol, 2,3-dichloro-phenol, 7-methyl-indan-4-ol, 3-fluoro-pyridin-2-ol, 1H-indol-4-ol, 3-hydroxy-2-methyl-pyran-4-one, 2-trifluoromethoxy-phenol, 6-methyl-pyridin-2-ol, 2-fluoro-5-methyl-phenol, 2-(2-hydroxy-ethyl)-phenol, 4,6-dimethyl-pyrimidin-2-ol, 2-methyl-5-trifluoromethyl-2,4-dihydro-pyrazol-3-one, 3-chloro-2-fluoro-phenol, 2,6-difluoro-3-methyl-phenol, 2-fluoro-4-methoxy-phenol, 2,4-dimethyl-phenol, 2-chloro-4-methoxy-phenol, 2-chloro-4-trifluoromethoxy-phenol, 3-ethoxy-2,6-difluoro-phenol, 2-chloro-3-methoxy-phenol, 2-chloro-phenol, 2,3-dihydro-benzo[1,4]dioxin-5-ol, 2-(2-chloro-phenyl)-ethanol and 2-chloro-3-trifluoromethyl-phenol.

For the compounds of formula IV where X is oxygen, $R_1$ is aryl, substituted aryl, heteroaryl or substituted heteroaryl and R is a protecting group, preferably THP, R can be converted to the compound of formula IV where R is hydrogen by any conventional method of removing a protecting group from an amine (see for example, Bryant, R. D., Kunng, F.-A., South, M. S. *J. Heterocyclic Chem.,* 1995, 32, 1473-1476).

For the compounds of formula IV where X is oxygen, $R_1$ is aryl, substituted aryl, heteroaryl or substituted heteroaryl and R is hydrogen, Y can be converted from a halogen, preferably chloro, to compounds of formula V where Y is hydrogen. This can be achieved through any conventional means of reduction to remove a halogen (see for example, Tavares, F. X., Boucheron, J. A., Dickerson, S. H., Griffin, R. J., Preugschat, F., Thomson, S. A., Wang, T. Y., Zhou, H.-Q. *J. Med. Chem.,* 2004, 47, 4716-4730). For the compounds of formula V where it is desired that Y is maintained as a halogen, the reduction step may be omitted. When a group that may be affected by the reduction conditions is present in $R_1$, it may be desirable to start from the compound of formula II where Y is already hydrogen and Y' is a halogen, preferably iodo, as previously described (see for example, Krajsovszky, G.; et al, *J. Molecular Structure,* 2005, 713, 235-243).

For the compounds of formula IV where X is oxygen, R is hydrogen and $R_1$ is aryl, substituted aryl, heteroaryl or substituted heteroaryl which contains a functionality that may be affected by the conversion of Y from a halogen to a hydrogen, $R_1$ may need to be chemically converted to a protected or a modified form, $R_1"$, of the original functionality. This chemical modification can be performed using any standard method to convert a functional group to a protected or a stable, yet chemically reversible, form of itself. These protected or modified compounds of formula IV-x may then treated under any conventional method to convert Y from a halogen to a hydrogen (see for example, Tavares, F. X., Boucheron, J. A., Dickerson, S. H., Griffin, R. J., Preugschat, F., Thomson, S. A., Wang, T. Y., Zhou, H.-Q. *J. Med. Chem.,* 2004, 47, 4716-

4730). Upon completion of this step, the compound of formula IV-x can then be converted back to the original $R_1$ functionality under any conventional methods necessary to provide compounds of formula V.

The compounds of formula III can be converted to compounds of formula IV where X is oxygen, $R_1$ is alkyl, cycloalkyl, substituted cycloalkyl, heteroalkyl, substituted heteroalkyl, heterocycloalkyl or substituted heterocycloalkyl and R is a protecting group, preferably THP, by treatment with the appropriate hydroxyl derivative. More preferably the sodium salt of the appropriate hydroxyl derivative (see for example, Tavares, F. X., Boucheron, J. A., Dickerson, S. H., Griffin, R. J., Preugschat, F., Thomson, S. A., Wang, T. Y., Zhou, H.-Q. *J. Med. Chem.*, 2004, 47, 4716-4730). More preferably the following alcohols, which are all commercially available, cyclopentanol, cyclopentyl-methanol, cyclobutanol and 2,6-dimethyl-cyclohexanol.

For the compounds of formula IV where X is oxygen, $R_1$ is alkyl, cycloalkyl, substituted cycloalkyl, heteroalkyl, substituted heteroalkyl, heterocycloalkyl or substituted heterocycloalkyl and R is a protecting group, preferably THP, R can be converted to the compound of formula IV where R is hydrogen by any conventional method of removing a protecting group from an amine (see for example, Bryant, R. D., Kunng, F.-A., South, M. S. *J. Heterocyclic Chem.*, 1995, 32, 1473-1476). Compounds of this formula may also be commercially available.

For the compounds of formula IV where X is oxygen, $R_1$ is alkyl, cycloalkyl, substituted cycloalkyl, heteroalkyl, substituted heteroalkyl, heterocycloalkyl or substituted heterocycloalkyl and R is hydrogen, Y can be converted from a halogen, preferably chloro, to compounds of formula V where Y is hydrogen. This can be achieved through any conventional means of reduction to remove a halogen (see for example, Tavares, F. X., Boucheron, J. A., Dickerson, S. H., Griffin, R. J., Preugschat, F., Thomson, S. A., Wang, T. Y., Zhou, H.-Q. *J. Med. Chem.*, 2004, 47, 4716-4730). For the compounds of formula V where it is desired that Y is maintained as a halogen, the reduction step may be omitted. When a group that may be affected by the reduction conditions is present in $R_1$, it may be desirable to start from the compound of formula II where Y is already hydrogen and Y' is a halogen, preferably iodo, as previously described (see for example, Krajsovszky, G.; et al, *J. Molecular Structure*, 2005, 713, 235-243).

For the compounds of formula IV where X is oxygen, R is hydrogen and $R_1$ is alkyl, cycloalkyl, substituted cycloalkyl, heteroalkyl, substituted heteroalkyl, heterocycloalkyl or substituted heterocycloalkyl which contains a functionality that may be affected by the conversion of Y from a halogen to a hydrogen, $R_1$ may need to be chemically converted to a protected or a modified form, $R_1''$, of the original functionality. This chemical modification can be performed using any standard method to convert a functional group to a protected or a stable, yet chemically reversible, form of itself. These protected or modified compounds of formula IV-x may then treated under any conventional method to convert Y from a halogen to a hydrogen (see for example, Tavares, F. X., Boucheron, J. A., Dickerson, S. H., Griffin, R. J., Preugschat, F., Thomson, S. A., Wang, T. Y., Zhou, H.-Q. *J. Med. Chem.*, 2004, 47, 4716-4730). Upon completion of this step, the compound of formula IV-x can then be converted back to the original $R_1$ functionality under any conventional methods necessary to provide compounds of formula V.

The compounds of formula III can be converted to the compounds of formula IV where X is carbon, $R_1'$ is hydrogen, $R_1$ is aryl, substituted aryl, heteroaryl or substituted heteroaryl and R is a protecting group, preferably THP, by treatment with an appropriate reagent such as a nitrile. This reagent can be obtained through commercial sources or through chemical synthesis. Any conventional method of producing an appropriate nitrile compound can also be utilized (see for example PCT Inter. Appl. WO 2000/17204). Any conventional method used to convert Y' of formula III, where Y' is a halogen preferably chloro, to the appropriate aryl, substituted aryl, heteroaryl or substituted heteroaryl compound of formula IV where X is carbon can be utilized to effect this conversion (see for example PCT Inter. Appl. WO 2000/17204; Carroll, R. D., et. al., *J. Med. Chem.*, 1983, 26, 96-100; PCT Inter. Appl. WO 2007/009913). If an appropriate nitrile reagent is utilized, the nitrile can be removed using appropriate conditions (PCT Inter. Appl. WO 2007/009913).

The compounds of formula III can be converted to the compounds of formula IV where X is carbon, $R_1'$ is hydrogen or lower alkyl, $R_1$ is aryl, substituted aryl, heteroaryl or substituted heteroaryl and R is a protecting group, preferably THP, by treatment with an appropriate bromide reagent as well (see for example, Menta, E., Oliva, A. *J. Heterocyclic Chem.*, 1997, 34, 27-32-; Krapcho, A. P., Ellis, M. *J. Fluorine Chem.*, 1998, 90, 139-147)

The compounds of formula IV where X is carbon, $R_1'$ is hydrogen or lower alkyl, $R_1$ is aryl, substituted aryl, heteroaryl or substituted heteroaryl and where R is an amine protecting group, preferably THP, can be converted to the compound of formula IV where R is hydrogen by any conventional method of removing a protecting group from an amine (see for example, Bryant, R. D., Kunng, F.-A., South, M. S. *J. Heterocyclic Chem.*, 1995, 32, 1473-1476)

For the compounds of formula IV where X is carbon, $R_1'$ is hydrogen or lower alkyl, $R_1$ is aryl, substituted aryl, heteroaryl or substituted heteroaryl and R is hydrogen, Y can be converted from a halogen, preferably chloro, to compounds of formula V where Y is hydrogen. This can be achieved through any conventional means of reduction to remove a halogen (see for example, Tavares, F. X., Boucheron, J. A., Dickerson, S. H., Griffin, R. J., Preugschat, F., Thomson, S. A., Wang, T. Y., Zhou, H.-Q. *J. Med. Chem.*, 2004, 47, 4716-4730). For the compounds of formula V where it is desired that Y is maintained as a halogen, the reduction step may be omitted. When a group that may be affected by the reduction conditions is present in $R_1$, it may be desirable to start from the compound of formula II where Y is already hydrogen and Y' is a halogen, preferably iodo, as previously described (see for example, Krajsovszky, G.; et al, *J. Molecular Structure*, 2005, 713, 235-243).

For the compounds of formula IV where X is carbon, R is hydrogen, $R_1'$ is hydrogen or lower alkyl, and $R_1$ is aryl, substituted aryl, heteroaryl or substituted heteroaryl groups which contain functionality that may be affected by the conversion of Y from a halogen to a hydrogen, $R_1$ may need to be chemically converted to a protected or a modified form, $R_1''$, of the original functionality. This chemical modification can be performed using any standard method to convert a functional group to a protected or a stable, yet chemically reversible, form of itself. These protected or modified compounds of formula IV-x may then treated under any conventional method to convert Y from a halogen to a hydrogen (see for example, Tavares, F. X., Boucheron, J. A., Dickerson, S. H., Griffin, R. J., Preugschat, F., Thomson, S. A., Wang, T. Y., Zhou, H.-Q. *J. Med. Chem.*, 2004, 47, 4716-4730). Upon completion of this step, the compound of formula IV-x can then be converted back to the original $R_1$ functionality under any conventional methods necessary to provide compounds of formula V.

The compounds of formula III can be converted to compounds of formula IV where X is nitrogen, $R_1'$ is hydrogen or lower alkyl, $R_1$ is aryl, substituted aryl, heteroaryl or substituted heteroaryl and R is an amine protecting group, preferably THP, by treatment with the appropriate reagent which will ultimately afford a compound of formula IV where X is nitrogen. The appropriate reagent may be an aromatic amine which can be obtained through commercial sources or through chemical synthesis. Any conventional method of producing an appropriate aromatic amine can be utilized. Any conventional method used to convert Y' of formula III, where Y' is a halogen, preferably chloro, to the appropriate aryl, substituted aryl, heteroaryl or substituted heteroaryl compound of formula IV where X is nitrogen can be utilized to effect this conversion (see for example, Halasz, B. D.-H., Monsieurs, K., Elias, O., Karolyhazy, L., Tapolcsanyi, P., Maes, B. U. W., Riedl, Z., Hajos, G., Dommisse, R. A., Lemiere, G. L. F., Kosmrlj, J., Matyus, P., *Tetrahedron*, 2004, 60, 2283-2291).

The compounds of formula IV where X is nitrogen, $R_1'$ is hydrogen or lower alkyl, $R_1$ is aryl, substituted aryl, heteroaryl or substituted heteroaryl and R is an amine protecting group, preferably THP, can be converted to the compound of formula IV where R is hydrogen by any conventional method of removing a protecting group from an amine (see for example, Bryant, R. D., Kunng, F.-A., South, M. S. *J. Heterocyclic Chem.*, 1995, 32, 1473-1476).

For the compounds of formula IV where X is nitrogen, $R_1'$ is hydrogen or lower alkyl, $R_1$ is aryl, substituted aryl, heteroaryl or substituted heteroaryl and R is hydrogen, Y can be converted from a halogen, preferably chloro, to compounds of formula V where Y is hydrogen. This can be achieved through any conventional means of reduction to remove a halogen (see for example, Tavares, F. X., Boucheron, J. A., Dickerson, S. H., Griffin, R. J., Preugschat, F., Thomson, S. A., Wang, T. Y., Zhou, H.-Q. *J. Med. Chem.*, 2004, 47, 4716-4730). For the compounds of formula V where it is desired that Y is maintained as a halogen, the reduction step may be omitted. When a group that may be affected by the reduction conditions is present in $R_1$, it may be desirable to start from the compound of formula II where Y is already hydrogen and Y' is a halogen, preferably iodo, as previously described (see for example, Krajsovszky, G.; et al, *J. Molecular Structure*, 2005, 713, 235-243).

For the compounds of formula IV where X is nitrogen, R is hydrogen, $R_1'$ is hydrogen or lower alkyl and $R_1$ is aryl, substituted aryl, heteroaryl or substituted heteroaryl which contains a functionality that may be affected by the conversion of Y from a halogen to a hydrogen, $R_1$ may need to be chemically converted to a protected or a modified form, $R_1''$, of the original functionality. This chemical modification can be performed using any standard method to convert a functional group to a protected or a stable, yet chemically reversible, form of itself. These protected or modified compounds of formula IV-x may then treated under any conventional method to convert Y from a halogen to a hydrogen (see for example, Tavares, F. X., Boucheron, J. A., Dickerson, S. H., Griffin, R. J., Preugschat, F., Thomson, S. A., Wang, T. Y., Zhou, H.-Q. *J. Med. Chem.*, 2004, 47, 4716-4730). Upon completion of this step, the compound of formula IV-x can then be converted back to the original $R_1$ functionality under any conventional methods necessary to provide compounds of formula V.

The compounds of formula III can be converted to compounds of formula IV where X is sulfur, Y is hydrogen, halogen or lower alkyl, $R_1$ is aryl, substituted aryl, heteroaryl, substituted heteroaryl, alkyl, cycloalkyl, substituted cycloalkyl, heteroalkyl, substituted heteroalkyl, heterocycloalkyl, or substituted heterocycloalkyl and R is an amine protecting group, preferably THP, by treatment with the appropriate thiol (see for example, Chung, H.-A., Kang, Y.-J., Kweon, D.-H., Yoon, Y.-J., *J. Heterocyclic Chem.*, 1999, 36, 413-421).

The compounds of formula IV where X is sulfur, Y is hydrogen, halogen or lower alkyl, $R_1$ is aryl, substituted aryl, heteroaryl, substituted heteroaryl, alkyl, cycloalkyl, substituted cycloalkyl, heteroalkyl, substituted heteroalkyl, heterocycloalkyl, or substituted heterocycloalkyl and R is an amine protecting group, preferably THP, R can be converted to the compound of formula IV where R is hydrogen by any conventional method of removing a protecting group from an amine (see for example, Bryant, R. D., Kunng, F.-A., South, M. S. *J. Heterocyclic Chem.*, 1995, 32, 1473-1476).

If it is desired to produce the compounds of formula V where Y is hydrogen and where X is sulfur, $R_1$ is aryl, substituted aryl, heteroaryl, substituted heteroaryl, alkyl, cycloalkyl, substituted cycloalkyl, heteroalkyl, substituted heteroalkyl, heterocycloalkyl, or substituted heterocycloalkyl and R is H, it may be desirable to start from the compound of formula II where Y is already hydrogen and Y' is a halogen, preferably iodo, as previously described (see for example, Krajsovszky, G.; et al, *J Molecular Structure*, 2005, 713, 235-243). If it is desired to produce the compounds of formula V where Y is a halogen, it is appropriate to start from the compound of formula II where Y is a halogen.

The compounds of formula V where Y is either hydrogen, halogen or lower alkyl, X is sulfur, $R_1$ is aryl, substituted aryl, heteroaryl, substituted heteroaryl, alkyl, cycloalkyl, substituted cycloalkyl, heteroalkyl, substituted heteroalkyl, heterocycloalkyl, or substituted heterocycloalkyl and can be converted to the compounds of formula V where $R_1'$ is one connected oxygen (i.e. sulfoxide) or two connected oxygens (i.e. sulfone) through any conventional method of selectively oxidizing sulfur (see for example, Sotelo, E., Fraiz, N., Yanez, M., Terrades, V., Laguna, R., Cano, E., Ravina, E. *Bioorg. Med. Chem.*, 2002, 10, 2873-2882).

The compound of formula V where the variables Y, X, $R_1$, $R_1'$ together form a substituted or unsubstituted fused aryl, heteroaryl, cycloalkyl or heterocycloalkyl system may be commercially available or synthetically accessible. Examples of such commercially available or synthetically accessible systems include 2H-phthalazin-1-one and 5,6,7,8-tetrahydro-2H-phthalazin-1-one.

A number of amino acids are also available from commercial sources. Where not commercially available, amino acids can be prepared using literature methods.

The compounds of formula VI may be prepared from amino acids and protected amino acids. The compounds of formula VI may be prepared where $R_2$ is aryl, substituted aryl, heteroaryl, substituted heteroaryl, alkyl, cycloalkyl, substituted cycloalkyl, heteroalkyl, substituted heteroalkyl, heterocycloalkyl, or substituted heterocycloalkyl and E is hydroxyl or a functionalized hydroxyl and Z is amino or a functionalized or protected amino. When these compounds are available from commercially available sources, the appropriate protected or unprotected amino acid may be converted to the desired halo ester, where bromide is the preferred halogen, through conventional methods. An example of a method to convert an amino group to a halogen, preferably bromide utilizes the formation of a diazonium species which can then be converted in situ to a halogen, preferably bromide (see for example, Archer, C. H., Thomas, N. R., Gani, D. *Tet. Asymm.*, 1993, 4(6), 1141-1152; Dener, J. M., Zhang, L.-H., Rapoport, H. *J. Org. Chem.*, 1993, 58, 1159-1166; Souers, A. J., Schurer, S., Kwack, H., Virgilio, A. A., Ellman, J. A, *Synthesis,* 1999, 4, 583-585). The resulting halo-acid may either be maintained as the acid or may then be converted to an appropriately functionalized ester or amide by any conventional method of converting an acid to an ester or an amide (see for example, Archer, C. H., Thomas, N. R., Gani, D. *Tet. Asymm.,* 1993, 4(6), 1141-1152; PCT Int Appl. WO 03/055482 A1).

The compounds of formula VI where $R_2$ is aryl, substituted aryl, heteroaryl, substituted heteroaryl, alkyl, cycloalkyl, substituted cycloalkyl, heteroalkyl, substituted heteroalkyl, heterocycloalkyl, or substituted heterocycloalkyl and E is hydroxyl or a functionalized hydroxyl and Z is halogen, preferably bromide, or any functional group that may be displaced or coupled through a carbon may be produced from commercially available material (see for example, U.S. Pat. No. 4,977,144). For example, the appropriate $R_2$ derivative may be reacted with a malonate derivative under standard conditions to produce a substituted malonate (see for example, Kortylewicz, Z. P., Galardy, R. E., *J. Med. Chem.,* 1990, 33, 263-273). The resulting substituted malonate may then be treated under hydrolysis conditions to form the resulting diacid (see for example, Kortylewicz, Z. P., Galardy, R. E., *J. Med. Chem.,* 1990, 33, 263-273). The diacid may then be heated under such conditions that will promote a decarboxylation to form the appropriately substituted acid (see for example, Kortylewicz, Z. P., Galardy, R. E., *J. Med. Chem.,* 1990, 33, 263-273). In some instances, the desired mono-acid is available from commercial sources. The resulting substituted acid can then be treated under conditions that may form an acid chloride (see for example, Epstein, J. W., Brabander, H. J., Fanshawe, W. J., Hofmann, C. M., McKenzie, T. C., Safir, S. R., Osterberg, A. C., Cosulich, D. B., Lovell, F. M., *J. Med. Chem.,* 1981, 24, 481-490). In some instances, the desired acid chloride is available from commercial sources. The resulting acid chloride can then be treated under standard conditions to form the corresponding compound of formula VI where Z is a halogen, preferably bromide (see for example, Epstein, J. W., Brabander, H. J., Fanshawe, W. J., Hofmann, C. M., McKenzie, T. C., Safir, S. R., Osterberg, A. C., Cosulich, D. B., Lovell, F. M., *J. Med. Chem.,* 1981, 24, 481-490). The remaining acid chloride can then be treated with a hydroxyl containing reagent, such as methanol, to form the corresponding compound of formula VI where E is functionalized through an oxygen linker or the acid chloride may be treated with an amine or functionalized amine to form the corresponding compound of formula VI where E is functionalized through a nitrogen linker.

For the compounds of formula VI in cases where $R_2$ is aryl, substituted aryl, heteroaryl, substituted heteroaryl, alkyl, cycloalkyl, substituted cycloalkyl, heteroalkyl, substituted heteroalkyl, heterocycloalkyl, or substituted heterocycloalkyl and the amino acid or functionalized version thereof is not available from commercial sources, the amino acid may be produced if desired through conventional methods. Synthesis of compounds for formula I where X is oxygen, nitrogen, carbon or sulfur would require amino acid derivatives of formula VI where E is hydroxyl or a functionalized hydroxyl and Z is amino or a functionalized or protected amino. Several natural and unnatural amino acids are commercially available or readily available via several methods reported in the literature (see reviews, for e.g. D. J. Ager, in Handbook of chiral chemicals, $2^{nd}$ Edition, p 11-30, CRC Press). Among these methods are asymmetric hydrogenation of the enamides (see for example Ager, D. J., Laneman, S. A., *The Synthesis of Unnatural Amino Acids, in Asymmetric Catalysis on Industrial Scale,* Blaser, H.-U., Schmidt, E., Wiley-VCH: Weinheim, 2004, p 23), chiral auxiliary derived asymmetric induction methods (see for example Schollkopf, U. *Pure and App. Chem.* 1983, 55, 1799-1806; Oppolzer, W.; Moretti, R. *Tetrahedron,* 1988, 44, 5541; Evans, D. A.; Britton, T. C.; Ellman, J. A.; Dorow, R. L. *J. Amer. Chem. Soc.,* 1990, 112, p 4011) and asymmetric methods using chiral phase transfer catalyzed alkylations (see for example O'Donnell, M. J., *Acc. Chem. Research* 2004, 37, 506). Using these methods compounds of formula VI, where $R_2$ is alkyl, cycloalkyl, haloalkyl, heterocycloalkyl, aryl or heteroaryl groups can be prepared.

The alkyl and cycloalkyl amino acids such as, cyclopentyl alanine, cyclohexyl alanine, and cyclobutyl alanine are either commercially available or are readily available from corresponding halides or tosylates or mesylates via the general methods described above. Similarly, aryl and heteroaryl containing amino acids are either commercially available or can be prepared from readily accessible aryl or heteroaryl methyl halides, using the standard methods, described before. Amino acids such as, 2,6-fluorophenyl alanine, 2-thienyl alanine, 2-amino-3-isoxazol-5-yl-propionic acid can be prepared. Several fluoro- and chloro-substituted leucines, for example, 2-amino-4-fluoro-4-methyl-pentanoic acid, 2-amino-4-chloro-4-methyl-pentanoic acid, 2-amino-5,5,5-trifluoro-4-methyl-pentanoic acid, 2-amino-4,4-difluoro-butyric acid, 2-amino-4,4,4-trifluoro-butyric acid, and 2-amino-4,4-dichloro-butyric acid are readily accessible from known methods described in literature (Gauthier, J. Y. et al, *Bioorg. & Med. Chem. Lett.,* 2008, 923-928). Hydroxy substituted leucine, 2-amino-4-hydroxy-4-methyl-pentanoic acid, can be prepared from appropriately substituted leucine, via its N-bromosuccinimide reaction, as reported (Easton, C. J. et al, *Tetrahedron Lett.,* 1990, 131, 7059) Similarly, fluoro-substituted cycloalkyl amino acids can be obtained via known methods (see for example, Qiu, X.-L.; Meng, W.-D.; Qing, F.-L., *Tetrahedron,* 2004, 60, 6711). If a gem-difluoro cycloalkyl is required, it can be obtained via the corresponding keto-derivative, using diethylaminosulfurtrifluoride (DAST) reagent (Middleton, W. J.; Bingham, E. M., *Organic Syn.,* 1977, 57, 50; Haas, A.; Lieb, M., *Chimia,* 1985, 35, 134). Cycloalkanone containing amino acids, for example, cyclopentan-3-one, can be prepared using the appropriately protected cyclopentane-3-one methyl tosylate or mesylate (PCT Int. Appl. WO 2003095438; PCT Int. Appl. WO 2007115968) resulting in the preparation of protected amino acid, 2-amino-3-(8,8-dimethyl-6,10-dioxa-spiro[4.5]dec-2-yl)-propionic acid via the general methods of amino acid synthesis described above. Amino acid derivatives, with pyrrolidinone ring, 2-amino-3-(2-oxo-pyrrolidin-3-yl)-propionic acid methyl ester can be prepared using literature reports (Ramsamy, K.; Olsen, R. K.; Emery, T., *Synthesis,* 1982, 1, 42-43, Eustache, J.; Grob, A.; Lam, C.; Sellier, O.; Schulz, G. *Bioorg. Med. Chem. Lett.,* 1998 8, 2961-2966). Heterocycloalkyl containing amino acid, is commercially available, 2-amino-3-(tetrahydro-pyran-4-yl)-propionic acid, while the corresponding analog, 2-amino-3-(tetrahydro-pyran-2-yl)-propionic acid can be prepared using reported procedures (PCT Int. Appl. WO2001005783; PCT Int. Appl. WO2007070201). The amino acids with 2-tetrahydrofuran ring, 2-amino-3-(tetrahydro-furan-2-yl)-propionic acid can be prepared from the 2-furyl derivative via the hydrogenation of 2-furyl ring and subsequent diastereomer separation using standard methods (see for example, PCT Int. Appl. WO 2004033462; PCT Int. Appl. WO9214706). Amino acids with bicyclic systems like norbornyl rings are readily accessible. For example commercially available 2-norborananemethanol, which can be converted to the amino acid derivative using standard methods described above.

For amino acid derivatives of Formula VI where $R_2$ is cycloalkyl substituted with a flourine on the methine ring attachment carbon atom, such as 2-amino-3-(1-fluoro-cyclobutyl)-propionic acid, 2-amino-3-(1-fluoro-cyclopentyl)-propionic acid, or 2-amino-3-(1-fluoro-cyclohexyl)-propionic acid. These compounds can be prepared by alkylating (benzhydrylidene-amino)-acetic acid alkyl esters with triflate, tosylate or mesylate derivatives of the corresponding (1-fluoro-cycloalkyl)-methanol analogs or the corresponding bromides. The resulting benzhydrylidene derivatives can be converted to the amino acids using standard procedures (see for example Venkatraman, S.; Bogen, S. L.; Arasappan, A.; Bennett, F.; Chen, K.; Jao, E.; Liu, Y.-T.; Lovey, R.; Hendrata, S.; Huang, Y.; Pan, W.; et al.; *J. Med. Chem.;* 2006 49, 6074-6086) The triflate, tosylate or mesylate derivatives can be prepared from the alcohols using any conditions known for converting an alcohol to a triflate, tosylate or mesylate. The bromide derivatives can be prepared from the alcohols using any conditions known for converting an alcohol to a bromide. The (1-fluoro-cycloalkyl)-methanol analogs are known in the literature (see for example; Mongelli, N.; Animati, F.; D'Alessio, R.; Zuliani, L.; Gandolfi, C. *Synthesis* 1988, 4, 310-13.; PCT Int. Appl. WO 2006064286) or can be prepared from the corresponding epoxide (Demjanow; D. *Chem. Ber.* 1922, 55, 2725) by treatment with an appropriate fluorinating reagent, for example pyridine-hydroflouride (see for example Haufe, G.; Wessel, U.; Schulze, K; Alvernhe, G.; *J. Fluorine Chem.;* 1995; 74; 283-292.)

For amino acid derivatives of Formula VI where $R_2$ is alkyl or cycloalkyl substituted with a hydroxyl group on the methine ring attachment carbon atom, such as 2-amino-4-hydroxy-4-methyl-pentanoic acid, 2-amino-3-(1-hydroxycyclobutyl)-propionic acid, 2-amino-3-(1-hydroxy-cyclopentyl)-propionic acid, or 2-amino-3-(1-hydroxycyclohexyl)-propionic acid. These compounds can be prepared by alkylating (benzhydrylidene-amino)-acetic acid alkyl esters with triflate, tosylate or mesylate derivatives of the corresponding (1-hydroxy-cycloalkyl)-methanol analogs (1-hydroxymethyl-cyclohexanol is commercially available; for 2-methyl-propane-1,2-diol see Richardson, W. H. *J. Org. Chem.* 1989, 54, 4677-4684.; Richardson, W. H.; Lovett, M. B.; Olson, L. *J. Org. Chem.* 1989, 54, 3523-3525., for 1-hydroxymethyl-cyclopentanol see Tamao, K.; Ishida, N. *Tetrahedron Lett.* 1984, 25, 4245-4248, for 1-hydroxymethyl-cyclobutanol see Roberts, J. D.; Sauer, C. W. *J. Am. Chem. Soc.* 1949, 71, 3925-3929; Wade, P. A.; Kondracki, P. A. *J. Org. Chem.* 1993, 58, 3140-3147), corresponding bromides (for 1-halo-2-methyl-propan-2-ol see Mueller, D. C.; Seyferth, D. *Organometal. Chem. Syn.* 1971, 1, 127-144, for 1-halomethyl-cyclopentanol see Traynham, J. G.; Pascual, O, S. *Tetrahedron* 1959, 7, 165-172; Okabe, M.; Tada, M. *Bull. Chem. Soc. Jpn* 1982, 55, 1498-1503; Baumstark, A. L.; Niroomand, F.; Vasquez, P. C. *J. Org. Chem.* 1984, 49, 4497-4500; Tabuchi, T.; Inanaga, J.; Yamaguchi, M. *Tetrahedron Lett.* 1986, 27, 3891-3894; Canorme, P.; Belley, M.; Fytas, G.; Plamondon, J. *Can. J. Chem.* 1988, 66, 168-173.; Jereb, M.; Zupan, M.; Stavber, S. *Green Chem.* 2005, 7, 100-104, for 1-halomethyl-cyclobutanol see Traynham, J. G.; Pascual, O, S. *Tetrahedron* 1959, 7, 165-172; Erickson, K. L.; Kim, K. *J. Org. Chem.* 1971, 36, 2915-2916; Erickson, K. L. *J. Org. Chem.* 1973, 38, 1463-1469, for 1-halomethyl-cyclohexanol see Detty, M. R. *J. Org. Chem.* 1980, 45, 924-926.; Detty, M. R.; Seidler, M. D. *J. Org. Chem.* 1981, 46, 1283-1292; Baumstark, A. L.; Niroomand, F.; Vasquez, P. C. *J. Org. Chem.* 1984, 49, 4497-4500), or corresponding tertiary alcohol protected analogs (for 1-hydroxy-2-methyl-propan-2-ol see Denmark, S. E.; Stavenger, R. A. *J. Am. Chem. Soc.* 2000, 122, 8837-8847, for 1-hydroxymethyl-cyclopentanol see PCT Inter. Appl. WO19960117, for 1-hydroxymethyl-cyclohexanol see Tamino, K.; Shimizu, T.; Kuwahara, M.; Kuwajima, I. *J. Org. Chem.* 1998, 63, 2422-2423). The resulting benzhydrylidene derivatives can be converted to the amino acids using standard procedures (see for example Venkatraman, S.; Bogen, S. L.; Arasappan, A.; Bennett, F.; Chen, K.; Jao, E.; Liu, Y.-T.; Lovey, R.; Hendrata, S.; Huang, Y.; Pan, W.; et al.; *J. Med. Chem.;* 2006 49, 6074-6086) The triflate, tosylate or mesylate derivatives can be prepared from the alcohols using any conditions known for converting an alcohol to a triflate, tosylate or mesylate. The bromide derivatives can be prepared from the alcohols using any conditions known for converting an alcohol to a bromide. Alternatively these compounds can be prepared by condensing the corresponding aldehydes with glycine, protected glycine or protected glycine phosphonate derivatives followed by hydrogenation (see for example Ojima, I.; Kato, K.; Nakahashi, K.; Fuchikami, T.; Fujita, M. *J. Org. Chem.* 1989, 54, 4511-4522 Alexander, P. A.; Marsden, S. P.; Munoz Subtil, D. M.; Reader, J. C. *Org. Lett.* 2005, 7, 5433-5436; Davies, J. R.; Kane, P. D.; Moody, C. J.; Slawin, A. M. Z. *J. Org. Chem.* 2005, 70, 5840-5851). The corresponding alcohol protected aldehydes are known in the literature (for protected 2-hydroxy-2-methyl-propionaldehyde see Denmark, S. E.; Stavenger, R. A. *J. Am. Chem. Soc.* 2000, 122, 8837-8847; Frezza, M.; Soulere, L.; Queneau, Y.; Doutheau, A. *Tetrahedron Lett.* 2005, 46, 6495-6498; Trost, B. M.; Shin, S.; Sclafani, J. A. *J. Am. Chem. Soc.* 2005, 127, 8602-8603, for protected 1-hydroxy-cyclopentanecarbaldehyde see Parkes, K. E. B.; Pattenden, G. J. *Chem. Soc., Perkin Trans.* 1 1988, 1119-1134, for protected 1-hydroxy-cyclohexanecarbaldehyde see Ito, Y.; Matsuura, T.; Murakami, M. *J. Am. Chem. Soc.* 1987, 109, 7888-7890; Matsuda, T.; Tanino, K.; Kuwajima, I. *Tetrahedron Lett.* 1989, 30, 4267-4270; Hayashi, M.; Yoshiga, T.; Oguni, N. *Synlett* 1991, 479-480; Hayashi, M.; Yoshiga, T.; Nakatani, K.; Ono, K.; Oguni, N. *Tetrahedron* 1994, 50, 2821-2830; Tamino, K.; Shimizu, T.; Kuwahara, M.; Kuwajima, I. *J. Org. Chem.* 1998, 63, 2422-2423) or can be prepared form the alcohols using any method suitable for oxidizing a primary alcohol to an aldehyde. Unmasking of the alcohol functionality can be accomplished using any conditions known for converting a protected alcohol such as a silyl protected alcohol or an ester protected alcohol to an alcohol.

For amino acid derivatives of Formula VI where $R_2$ is a geminal dihaloalkyl group such as 2-amino-4,4-difluoro-butyric acid, 2-amino-4,4-dichloro-butyric acid or 2-amino-4,4-difluoro-pentanoic acid, these compounds, or their suitably protected derivatives, can be prepared as described in the literature (PCT Int. Appl. WO 2005040142, *Synthesis* 1996, 12, 1419-1421).

The compounds of formula VII may be produced from the compounds of formula V and VI. For the compounds of formula V, X may be oxygen, carbon, nitrogen or sulfur. For the compounds of formula V, when X is carbon or nitrogen, $R_1'$ may be H or lower alkyl. For the compounds of formula V, when X is sulfur, $R_1'$ may have one connected oxygen (i.e. sulfoxide) or two connected oxygens (i.e. sulfone). For the compounds of formula V, when X is oxygen, carbon, nitrogen or sulfur, Y may be hydrogen, halogen or lower alkyl, and $R_1$ may be aryl, substituted aryl, heteroaryl, substituted heteroaryl, heteroalkyl, substituted heteroalkyl, lower alkyl, cycloalkyl, $(CH_2)_n$cycloalkyl, $(CH_2)_n$aryl, substituted $(CH_2)_n$aryl, substituted cycloalkyl, or substituted $(CH_2)_n$cycloalkyl. Additionally, the compounds of formula VII may be produced from the compounds of formula V and VI where the variables Y, X, $R_1$, $R_1'$ represent a substituted or unsubstituted fused aryl, heteroaryl, cycloalkyl or heterocycloalkyl system. Compounds of formula V, where Y, X, $R_1$, $R_1'$ represent a substituted or unsubstituted fused aryl, heteroaryl, cycloalkyl or heterocycloalkyl system, such as substituted 1-(2H)-phthalazinones are commercially available or are known in the literature. For the compounds of formula VI, $R_2$ may be aryl, substituted aryl, heteroaryl, substituted heteroaryl, alkyl, cycloalkyl, substituted cycloalkyl, heteroalkyl, substituted heteroalkyl, heterocycloalkyl, or substituted heterocycloalkyl, E may be an oxygen linked substituent and Z may be halogen, preferably bromide, or any functional group that may be displaced or coupled through a nitrogen. For example, the appropriate compound of formula V and the appropriate compound of formula VI may be treated under conditions that will provide for the displacement of Z or the coupling through Z to form the compound of formula VII (see for example, New, J. S., Christopher, W. L., Jass, P. A., *J. Org. Chem.*, 1989, 54, 990-992)

The compounds of formula XI may be produced from the compounds of formula II where Y is hydrogen and Y' is a halogen, preferably iodo, and VI. For the compounds of formula VI, $R_2$ may be aryl, substituted aryl, heteroaryl, substituted heteroaryl, alkyl, cycloalkyl, substituted cycloalkyl, heteroalkyl, substituted heteroalkyl, heterocycloalkyl, or substituted heterocycloalkyl, E may be an oxygen linked substitutent and Z may be halogen, preferably bromide, or any functional group that may be displaced or coupled through a nitrogen. For example, the appropriate compound of formula II and the appropriate compound of formula VI may be treated under conditions that will provide for the displacement of Z or the coupling through Z to form the compound of formula XI (see for example, New, J. S., Christopher, W. L., Jass, P. A., *J. Org. Chem.*, 1989, 54, 990-992).

The compounds of formula XI where Y is hydrogen and Y' is a halogen, preferably iodo, can be converted to compounds of formula VII where X is oxygen, $R_1$ is aryl, substituted aryl, heteroaryl or substituted heteroaryl by treatment with the appropriate phenol. The appropriate phenol can be obtained through commercial sources or through chemical synthesis. Any conventional method of producing a phenol can also be utilized (see for example, Gonzalez, Concepcion; Castedo, Luis. Departamento de Quimica Organica, Facultad de Ciencias, Universidad de Santiago, Lugo, Spain. Editor(s): Rappoport, Zvi. Chemistry of Phenols (2003), 1 395-489. Publisher: John Wiley & Sons Ltd., Chichester, UK and references cited therein; George, T.; Mabon, R.; Sweeney, G.; Sweeney, J. B.; Tavassoli, A. J. Chem. Soc. Perkin 1 2000, 16, 2529-2574 and references cited therein). Any conventional method used to convert Y' of formula XI to the appropriate aryl, substituted aryl, heteroaryl or substituted heteroaryl compound of formula XI where X is oxygen can be utilized to effect this conversion (see for example, *J. Heterocyclic Chem.* 1995, 32, 1473).

The compounds of formula XI where Y is hydrogen and Y' is a halogen, preferably iodo, can be converted to compounds of formula VII where X is oxygen and $R_1$ is aryl, substituted aryl, heteroaryl or substituted heteroaryl by treatment with the appropriate reagent (see for example, Kweon, D.-H., Kang, Y.-J., Chung, H.-A., Yoo, Y.-J., *J. Heterocyclic Chem.* 1998, 35, 819-826). More preferably the following reagents, which are all commercially available, can be used: phenol, 2-methoxy-phenol, 3-methoxy-phenol, 4-methoxy-phenol, 2-trifluoromethyl-phenol, 3-trifluoromethyl-phenol, 4-trifluoromethyl-phenol, (2-hydroxy-phenyl)-pyrrolidin-1-yl-methanone, 2-cyclohexylphenol, 2-cyclopentylphenol, 2-phenylphenol, 1-naphthol, 5,6,7,8-tetrahydro-1-naphthol, 2'-hydroxyacetophenone, 2-hydroxybenzonitrile, o-cresol, 3-fluorophenol, 2-fluorophenol, 2,3-difluorophenol, 2,4-difluorophenol, 2,5-difluorophenol, 2,6-difluorophenol, 2-(methylsulfonyl)-phenol, 3-phenoxyphenol, 3-hydroxy-2-methylpyridine, 2-(1-pyrrolidino)-phenol, 2-(1-piperidino)-phenol, 2-(4-morpholino)-phenol, 3-hydroxypyridine, 8-hydroxyquinoline, 5-hydroxyisoquinoline, 5-hydroxyquinoline, 2,3,6-trimethyl-phenol, 2,2-dimethyl-2,3-dihydro-benzofuran-7-ol, 2-tert-butyl-phenol, 2,3-dichloro-phenol, 7-methyl-indan-4-ol, 3-fluoro-pyridin-2-ol, 1H-indol-4-ol, 3-hydroxy-2-methyl-pyran-4-one, 2-trifluoromethoxyphenol, 6-methyl-pyridin-2-ol, 2-fluoro-5-methyl-phenol, 2-(2-hydroxy-ethyl)-phenol, 4,6-dimethyl-pyrimidin-2-ol, 2-methyl-5-trifluoromethyl-2,4-dihydro-pyrazol-3-one, 3-chloro-2-fluoro-phenol, 2,6-difluoro-3-methyl-phenol, 2-fluoro-4-methoxy-phenol, 2,4-dimethyl-phenol, 2-chloro-4-methoxy-phenol, 2-chloro-4-trifluoromethoxy-phenol, 3-ethoxy-2,6-difluoro-phenol, 2-chloro-3-methoxy-phenol, 2-chloro-phenol, 2,3-dihydro-benzo[1,4]dioxin-5-ol, 2-(2-chloro-phenyl)-ethanol and 2-chloro-3-trifluoromethyl-phenol.

The compounds of formula XI where Y is hydrogen and Y' is a halogen, preferably iodo, can be converted to compounds of formula VII where X is oxygen, $R_1$ is alkyl, cycloalkyl, substituted cycloalkyl, heteroalkyl, substituted heteroalkyl, heterocycloalkyl or substituted heterocycloalkyl by treatment with the appropriate hydroxyl derivative. More preferably the sodium salt of the appropriate hydroxyl derivative (see for example, Tavares, F. X., Boucheron, J. A., Dickerson, S. H., Griffin, R. J., Preugschat, F., Thomson, S. A., Wang, T. Y., Zhou, H.-Q. *J. Med. Chem.*, 2004, 47, 4716-4730). More preferably the following alcohols, which are all commercially available, cyclopentanol, cyclopentyl-methanol, cyclobutanol and 2,6-dimethyl-cyclohexanol.

The compounds of formula XI where Y is hydrogen and Y' is a halogen, preferably iodo, can be converted to the compounds of formula VII where X is carbon, $R_1'$ is hydrogen, $R_1$ is aryl, substituted aryl, heteroaryl or substituted heteroaryl by treatment with an appropriate reagent such as a nitrile. This reagent can be obtained through commercial sources or through chemical synthesis. Any conventional method of producing an appropriate nitrile compound can also be utilized (see for example PCT Inter. Appl. WO 2000/17204). Any conventional method used to convert Y' of formula XI, where Y' is a halogen preferably iodo, to the appropriate aryl, substituted aryl, heteroaryl or substituted heteroaryl compound of formula VII where X is carbon can be utilized to effect this conversion (see for example, PCT Inter. Appl. WO 2000/17204; Carroll, R. D., et. al., *J. Med. Chem.*, 1983, 26, 96-100; PCT Inter. Appl WO 2007/009913). If an appropriate nitrile reagent is utilized, the nitrile can be removed using appropriate conditions (see for example, PCT Inter. Appl. WO 2007/009913).

The compounds of formula XI where Y is hydrogen and Y' is a halogen, preferably iodo, can be converted to the compounds of formula VII where X is carbon, $R_1'$ is hydrogen or lower alkyl, $R_1$ is aryl, substituted aryl, heteroaryl or substituted heteroaryl by treatment with an appropriate bromide reagent as well (see for example, Menta, E., Oliva, A. *J. Heterocyclic Chem.*, 1997, 34, 27-32-; Krapcho, A. P., Ellis, M. *J. Fluorine Chem.*, 1998, 90, 139-147).

The compounds of formula XI where Y is hydrogen and Y' is a halogen, preferably iodo, can be converted to compounds of formula VII where X is nitrogen, $R_1'$ is hydrogen or lower alkyl, $R_1$ is aryl, substituted aryl, heteroaryl or substituted heteroaryl by treatment with the appropriate reagent which will ultimately afford a compound of formula VII where X is nitrogen. The appropriate reagent may be an aromatic amine which can be obtained through commercial sources or through chemical synthesis. Any conventional method of producing an appropriate aromatic amine can be utilized. Any conventional method used to convert Y' of formula XI, where Y' is a halogen, preferably iodo, to the appropriate aryl, substituted aryl, heteroaryl or substituted heteroaryl compound of formula VII where X is nitrogen can be utilized to effect this conversion (see for example, Halasz, B. D.-H., Monsieurs, K., Elias, O., Karolyhazy, L., Tapolcsanyi, P., Maes, B. U. W., Riedl, Z., Hajos, G., Dommisse, R. A., Lemiere, G. L. F., Kosmrlj, J., Matyus, P., *Tetrahedron,* 2004, 60, 2283-2291).

The compounds of formula XI where Y is hydrogen and Y' is a halogen, preferably iodo, can be converted to compounds of formula VII where X is sulfur, Y is hydrogen, and $R_1$ is aryl, substituted aryl, heteroaryl, substituted heteroaryl, alkyl, cycloalkyl, substituted cycloalkyl, heteroalkyl, substituted heteroalkyl, heterocycloalkyl, or substituted heterocycloalkyl by treatment with the appropriate thiol (see for example, Chung, H.-A., Kang, Y.-J., Kweon, D.-H., Yoon, Y.-J., *J. Heterocyclic Chem.,* 1999, 36, 413-421).

The compounds of formula VII where Y is hydrogen, and X is sulfur, $R_1$ is aryl, substituted aryl, heteroaryl, substituted heteroaryl, alkyl, cycloalkyl, substituted cycloalkyl, heteroalkyl, substituted heteroalkyl, heterocycloalkyl, or substituted heterocycloalkyl and can be converted to the compounds of formula VII where $R_1$' is one connected oxygen (i.e. sulfoxide) or two connected oxygens (i.e. sulfone) through any conventional method of selectively oxidizing sulfur (see for example, Sotelo, E., Fraiz, N., Yanez, M., Terrades, V., Laguna, R., Cano, E., Ravina, E. *Bioorg. Med. Chem.,* 2002, 10, 2873-2882).

The compounds of formula XI may be produced from the compounds of formula II where Y is halogen, preferably chloro, and Y' is a halogen, preferably chloro, and VI. For the compounds of formula VI, $R_2$ may be aryl, substituted aryl, heteroaryl, substituted heteroaryl, alkyl, cycloalkyl, substituted cycloalkyl, heteroalkyl, substituted heteroalkyl, heterocycloalkyl, or substituted heterocycloalkyl, E may be an oxygen linked substitutent and Z may be halogen, preferably bromide, or any functional group that may be displaced or coupled through a nitrogen. For example, the appropriate compound of formula II and the appropriate compound of formula VI may be treated under conditions that will provide for the displacement of Z or the coupling through Z to form the compound of formula XI (see for example, New, J. S., Christopher, W. L., Jass, P. A., *J. Org. Chem.,* 1989, 54, 990-992).

The compounds of formula XI where Y is halogen, preferably chloro, and Y' is a halogen, preferably chloro, can be converted to compounds of formula VII where X is oxygen, Y is halogen, preferably chloro, and $R_1$ is aryl, substituted aryl, heteroaryl or substituted heteroaryl by treatment with the appropriate phenol. The appropriate phenol can be obtained through commercial sources or through chemical synthesis. Any conventional method of producing a phenol can also be utilized (see for example, Gonzalez, Concepcion; Castedo, Luis. Departamento de Quimica Organica, Facultad de Ciencias, Universidad de Santiago, Lugo, Spain. Editor(s): Rappoport, Zvi. Chemistry of Phenols (2003), 1 395-489. Publisher: John Wiley & Sons Ltd., Chichester, UK and references cited therein; George, T.; Mabon, R.; Sweeney, G.; Sweeney, J. B.; Tavassoli, A. *J. Chem. Soc. Perkin* 1 2000, 16, 2529-2574 and references cited therein). Any conventional method used to convert Y' of formula XI to the appropriate aryl, substituted aryl, heteroaryl or substituted heteroaryl compound of formula VII where X is oxygen can be utilized to effect this conversion (see for example, *J. Heterocyclic Chem.* 1995, 32, 1473). Compounds of formula VII where Y is halogen, preferably chloro, may then treated under any conventional method to convert Y from a halogen to a hydrogen (see for example, Tavares, F. X., Boucheron, J. A., Dickerson, S. H., Griffin, R. J., Preugschat, F., Thomson, S. A., Wang, T. Y., Zhou, H.-Q. *J. Med. Chem.,* 2004, 47, 4716-4730).

The compounds of formula XI where Y is halogen, preferably chloro, and Y' is a halogen, preferably chloro, can be converted to compounds of formula VII where X is oxygen, Y is halogen, preferably chloro, and $R_1$ is aryl, substituted aryl, heteroaryl or substituted heteroaryl by treatment with the appropriate reagent (see for example, Kweon, D.-H., Kang, Y.-J., Chung, H.-A., Yoo, Y.-J., *J. Heterocyclic Chem.* 1998, 35, 819-826). More preferably the following reagents, which are all commercially available, can be used: phenol, 2-methoxy-phenol, 3-methoxy-phenol, 4-methoxy-phenol, 2-trifluoromethyl-phenol, 3-trifluoromethyl-phenol, 4-trifluoromethyl-phenol, (2-hydroxy-phenyl)-pyrrolidin-1-yl-methanone, 2-cyclohexylphenol, 2-cyclopentylphenol, 2-phenylphenol, 1-naphthol, 5,6,7,8-tetrahydro-1-naphthol, 2'-hydroxyacetophenone, 2-hydroxybenzonitrile, o-cresol, 3-fluorophenol, 2-fluorophenol, 2,3-difluorophenol, 2,4-difluorophenol, 2,5-difluorophenol, 2,6-difluorophenol, 2-(methylsulfonyl)-phenol, 3-phenoxyphenol, 3-hydroxy-2-methylpyridine, 2-(1-pyrrolidino)-phenol, 2-(1-piperidino)-phenol, 2-(4-morpholino)-phenol, 3-hydroxypyridine, 8-hydroxyquinoline, 5-hydroxyisoquinoline, 5-hydroxyquinoline, 2,3,6-trimethyl-phenol, 2,2-dimethyl-2,3-dihydro-benzofuran-7-ol, 2-tert-butyl-phenol, 2,3-dichloro-phenol, 7-methyl-indan-4-ol, 3-fluoro-pyridin-2-ol, 1H-indol-4-ol, 3-hydroxy-2-methyl-pyran-4-one, 2-trifluoromethoxy-phenol, 6-methyl-pyridin-2-ol, 2-fluoro-5-methyl-phenol, 2-(2-hydroxy-ethyl)-phenol, 4,6-dimethyl-pyrimidin-2-ol, 2-methyl-5-trifluoromethyl-2,4-dihydro-pyrazol-3-one, 3-chloro-2-fluoro-phenol, 2,6-difluoro-3-methyl-phenol, 2-fluoro-4-methoxy-phenol, 2,4-dimethyl-phenol, 2-chloro-4-methoxy-phenol, 2-chloro-4-trifluoromethoxy-phenol, 3-ethoxy-2,6-difluoro-phenol, 2-chloro-3-methoxy-phenol, 2-chloro-phenol, 2,3-dihydro-benzo[1,4]dioxin-5-ol, 2-(2-chloro-phenyl)-ethanol and 2-chloro-3-trifluoromethyl-phenol. Compounds of formula VII where Y is halogen, preferably chloro, may then treated under any conventional method to convert Y from a halogen to a hydrogen (see for example, Tavares, F. X., Boucheron, J. A., Dickerson, S. H., Griffin, R. J., Preugschat, F., Thomson, S. A., Wang, T. Y., Zhou, H.-Q. *J. Med. Chem.,* 2004, 47, 4716-4730).

The compounds of formula XI where Y is halogen, preferably chloro, and Y' is a halogen, preferably chloro, can be converted to compounds of formula VII where X is oxygen, Y is halogen, preferably chloro, $R_1$ is alkyl, cycloalkyl, substituted cycloalkyl, heteroalkyl, substituted heteroalkyl, heterocycloalkyl or substituted heterocycloalkyl by treatment with the appropriate hydroxyl derivative. More preferably the sodium salt of the appropriate hydroxyl derivative (see for example, Tavares, F. X., Boucheron, J. A., Dickerson, S. H., Griffin, R. J., Preugschat, F., Thomson, S. A., Wang, T. Y., Zhou, H.-Q. *J. Med. Chem.,* 2004, 47, 4716-4730). More preferably the following alcohols, which are all commercially available, cyclopentanol, cyclopentyl-methanol, cyclobutanol and 2,6-dimethyl-cyclohexanol. Compounds of formula VII where Y is halogen, preferably chloro, may then treated under any conventional method to convert Y from a halogen to a hydrogen (see for example, Tavares, F. X., Boucheron, J. A., Dickerson, S. H., Griffin, R. J., Preugschat, F., Thomson, S. A., Wang, T. Y., Zhou, H.-Q. *J. Med. Chem.*, 2004, 47, 4716-4730).

The compounds of formula XI where Y is halogen, preferably chloro, and Y' is a halogen, preferably chloro, can be converted to compounds of formula VII where X is carbon, Y is halogen, preferably chloro, $R_1$' is hydrogen, $R_1$ is aryl, substituted aryl, heteroaryl or substituted heteroaryl by treatment with an appropriate reagent such as a nitrile. This reagent can be obtained through commercial sources or through chemical synthesis. Any conventional method of producing an appropriate nitrile compound can also be utilized (see for example, PCT Inter. Appl. WO 2000/17204). Any conventional method used to convert Y' of formula XI, where Y' is a halogen preferably chloro, to the appropriate aryl, substituted aryl, heteroaryl or substituted heteroaryl compound of formula VII where X is carbon can be utilized to effect this conversion (see for example, Salturo, F., et. al., PCT WO 2000/17204; Carroll, R. D., et. al., *J. Med. Chem.*, 1983, 26, 96-100; PCT Inter. Appl. WO 2007/009913). If an appropriate nitrile reagent is utilized, the nitrile can be removed using conventional methods (see for example PCT Inter. Appl., WO 2007/009913). Compounds of formula VII where Y is halogen, preferably chloro, may then treated under any conventional method to convert Y from a halogen to a hydrogen (see for example, Tavares, F. X., Boucheron, J. A., Dickerson, S. H., Griffin, R. J., Preugschat, F., Thomson, S. A., Wang, T. Y., Zhou, H.-Q. *J. Med. Chem.*, 2004, 47, 4716-4730).

The compounds of formula XI where Y is halogen, preferably chloro, and Y' is a halogen, preferably chloro, can be converted to compounds of formula VII where X is carbon, Y is halogen, preferably chloro, $R_1$' is hydrogen or lower alkyl, $R_1$ is aryl, substituted aryl, heteroaryl or substituted heteroaryl by treatment with an appropriate bromide reagent as well (see for example, Menta, E., Oliva, A. *J. Heterocyclic Chem.*, 1997, 34, 27-32-; Krapcho, A. P., Ellis, M. *J. Fluorine Chem.*, 1998, 90, 139-147). Compounds of formula VII where Y is halogen, preferably chloro, may then treated under any conventional method to convert Y from a halogen to a hydrogen (see for example, Tavares, F. X., Boucheron, J. A., Dickerson, S. H., Griffin, R. J., Preugschat, F., Thomson, S. A., Wang, T. Y., Zhou, H.-Q. *J. Med. Chem.*, 2004, 47, 4716-4730).

The compounds of formula XI where Y is halogen, preferably chloro, and Y' is a halogen, preferably chloro, can be converted to compounds of formula VII where X is nitrogen, Y is halogen, preferably chloro, $R_1$' is hydrogen or lower alkyl, $R_1$ is aryl, substituted aryl, heteroaryl or substituted heteroaryl by treatment with the appropriate reagent which will ultimately afford a compound of formula VII where X is nitrogen. The appropriate reagent may be an aromatic amine which can be obtained through commercial sources or through chemical synthesis. Any conventional method of producing an appropriate aromatic amine can be utilized. Any conventional method used to convert Y' of formula XI, where Y' is a halogen, preferably chloro, to the appropriate aryl, substituted aryl, heteroaryl or substituted heteroaryl compound of formula VII where X is nitrogen can be utilized to effect this conversion (see for example, Halasz, B. D.-H., Monsieurs, K., Elias, O., Karolyhazy, L., Tapolcsanyi, P., Maes, B. U. W., Riedl, Z., Hajos, G., Dommisse, R. A., Lemiere, G. L. F., Kosmrlj, J., Matyus, P., *Tetrahedron*, 2004, 60, 2283-2291). Compounds of formula VII where Y is halogen, preferably chloro, may then treated under any conventional method to convert Y from a halogen to a hydrogen (see for example, Tavares, F. X., Boucheron, J. A., Dickerson, S. H., Griffin, R. J., Preugschat, F., Thomson, S. A., Wang, T. Y., Zhou, H.-Q. *J. Med. Chem.*, 2004, 47, 4716-4730).

The compounds of formula XI where Y is halogen, preferably chloro, and Y' is a halogen, preferably chloro, can be converted to compounds of formula VII where X is sulfur, Y is halogen, preferably chloro, and $R_1$ is aryl, substituted aryl, heteroaryl, substituted heteroaryl, alkyl, cycloalkyl, substituted cycloalkyl, heteroalkyl, substituted heteroalkyl, heterocycloalkyl, or substituted heterocycloalkyl by treatment with the appropriate thiol (see for example, Chung, H.-A., Kang, Y.-J., Kweon, D.-H., Yoon, Y.-J., *J. Heterocyclic Chem.*, 1999, 36, 413-421).

The compounds of formula VII where Y is halogen, preferably chloro, and X is sulfur, $R_1$ is aryl, substituted aryl, heteroaryl, substituted heteroaryl, alkyl, cycloalkyl, substituted cycloalkyl, heteroalkyl, substituted heteroalkyl, heterocycloalkyl, or substituted heterocycloalkyl and can be converted to the compounds of formula VII where $R_1$' is one connected oxygen (i.e. sulfoxide) or two connected oxygens (i.e. sulfone) through any conventional method of selectively oxidizing sulfur (see for example, Sotelo, E., Fraiz, N., Yanez, M., Terrades, V., Laguna, R., Cano, E., Ravina, E. *Bioorg. Med. Chem.*, 2002, 10, 2873-2882).

The compounds of formula I or I-x may be produced from the compounds of formula V and VI. For the compounds of formula V, X may be oxygen, carbon, nitrogen or sulfur. For the compounds of formula V, when X is carbon or nitrogen, $R_1$' may be H or lower alkyl. For the compounds of formula V, when X is sulfur, $R_1$' may have one connected oxygen (i.e. sulfoxide) or two connected oxygens (i.e. sulfone). For the compounds of formula V, when X is oxygen, carbon, nitrogen or sulfur, Y may be hydrogen, halogen or lower alkyl, and $R_1$ may be aryl, substituted aryl, heteroaryl, substituted heteroaryl, heteroalkyl, substituted heteroalkyl, lower alkyl, cycloalkyl, $(CH_2)_n$cycloalkyl, $(CH_2)_n$aryl, substituted $(CH_2)_n$aryl, substituted cycloalkyl, or substituted $(CH_2)_n$cycloalkyl. Additionally, the compounds of formula I may be produced from the compounds of formula V and VI where the variables Y, X, $R_1$, $R_1$' represent a substituted or unsubstituted fused aryl, heteroaryl, cycloalkyl or heterocycloalkyl system. Compounds of formula V, where Y, X, $R_1$, $R_1$' represent a substituted or unsubstituted fused aryl, heteroaryl, cycloalkyl or heterocycloalkyl system, such as substituted 1-(2H)-phthalazinones are commercially available or are known in the literature. For the compounds of formula VI, $R_2$ may be aryl, substituted aryl, heteroaryl, substituted heteroaryl, alkyl, cycloalkyl, substituted cycloalkyl, heteroalkyl, substituted heteroalkyl, heterocycloalkyl, or substituted heterocycloalkyl, E may be a nitrogen linked substitutent and Z may be halogen, preferably bromide, or any functional group that may be displaced or coupled through a nitrogen. For example, the appropriate compound of formula V and the appropriate compound of formula VI may be treated under conditions that will provide for the displacement of Z or the coupling through Z to form the compound of formula I or I-x (see for example, New, J. S., Christopher, W. L., Jass, P. A., *J. Org. Chem.*, 1989, 54, 990-992).

The compounds of formula VIII may be produced from compounds of formula VIII. For the compounds of formula VII, X may be oxygen, carbon, nitrogen or sulfur. For the compounds of formula VII, when X is carbon or nitrogen, $R_1$' may be H or lower alkyl. For the compounds of formula VII, when X is sulfur, $R_1$' may have one connected oxygen (i.e. sulfoxide) or two connected oxygens (i.e. sulfone). For the compounds of formula VII, when X is oxygen, carbon, nitrogen or sulfur, Y may be hydrogen, halogen, or alkyl, and $R_1$ may be aryl, substituted aryl, heteroaryl, substituted heteroaryl, heteroalkyl, substituted heteroalkyl, lower alkyl, cycloalkyl, $(CH_2)_n$cycloalkyl, $(CH_2)_n$aryl, substituted $(CH_2)_n$aryl, substituted cycloalkyl, or substituted $(CH_2)_n$cycloalkyl. Additionally, the compounds of formula VII may be produced from the compounds of formula V and VI where the variables Y, X, $R_1$, $R_1'$ represent a substituted or unsubstituted fused aryl, heteroaryl, cycloalkyl or heterocycloalkyl system. Compounds of formula V, where Y, X, $R_1$, $R_1'$ represent a substituted or unsubstituted fused aryl, heteroaryl, cycloalkyl or heterocycloalkyl system, such as substituted 1-(2H)-phthalazinones are commercially available or are known in the literature. For the compounds of formula VII, $R_2$ may be aryl, substituted aryl, heteroaryl, substituted heteroaryl, alkyl, cycloalkyl, substituted cycloalkyl, heteroalkyl, substituted heteroalkyl, heterocycloalkyl, or substituted heterocycloalkyl, For the compounds of formula VII, $R_4$ may be an alkyl or any substituent that may be removed through conventional methods to convert an ester to a carboxylic acid, preferably via hydrolysis (see for example, New, J. S., Christopher, W. L., Jass, P. A., *J. Org. Chem.*, 1989, 54, 990-992).

The compounds of formula XII may be produced from compounds of formula XI. For the compounds of formula XI, Y is hydrogen and Y' is a halogen, preferably iodo. For the compounds of formula XI, $R_2$ may be aryl, substituted aryl, heteroaryl, substituted heteroaryl, alkyl, cycloalkyl, substituted cycloalkyl, heteroalkyl, substituted heteroalkyl, heterocycloalkyl, or substituted heterocycloalkyl, For the compounds of formula XI, $R_4$ may be an alkyl or any substituent that may be removed through conventional methods to convert an ester to a carboxylic acid, preferably via hydrolysis (see for example, New, J. S., Christopher, W. L., Jass, P. A., *J. Org. Chem.*, 1989, 54, 990-992).

The compounds of formula I-x may be produced from compounds of formula VIII and the compounds of formula IX. For the compounds of formula VIII, X may be oxygen, carbon, nitrogen or sulfur. For the compounds of formula VIII, when X is carbon or nitrogen, $R_1'$ may be H or lower alkyl. For the compounds of formula VIII, when X is sulfur, $R_1'$ may have one connected oxygen (i.e. sulfoxide) or two connected oxygens (i.e. sulfone). For the compounds of formula VIII, when X is oxygen, carbon, nitrogen or sulfur, Y may be hydrogen, halogen or lower alkyl, and $R_1$ may be aryl, substituted aryl, heteroaryl, substituted heteroaryl, heteroalkyl, substituted heteroalkyl, lower alkyl, cycloalkyl, $(CH_2)_n$cycloalkyl, $(CH_2)_n$aryl, substituted $(CH_2)_n$aryl, substituted cycloalkyl, or substituted $(CH_2)_n$cycloalkyl. Additionally, the compounds of formula VIII may be produced from the compounds of formula VII where the variables Y, X, $R_1$, $R_1'$ represent a substituted or unsubstituted fused aryl, heteroaryl, cycloalkyl or heterocycloalkyl system. For the compounds of formula VIII, $R_2$ may be aryl, substituted aryl, heteroaryl, substituted heteroaryl, alkyl, cycloalkyl, substituted cycloalkyl, heteroalkyl, substituted heteroalkyl, heterocycloalkyl, or substituted heterocycloalkyl.

The compounds of formula XIII may be produced from compounds of formula XII and the compounds of formula IX. For the compounds of formula XII, Y is hydrogen and Y' is a halogen. For the compounds of formula XII, $R_2$ may be aryl, substituted aryl, heteroaryl, substituted heteroaryl, alkyl, cycloalkyl, substituted cycloalkyl, heteroalkyl, substituted heteroalkyl, heterocycloalkyl, or substituted heterocycloalkyl.

Compounds of formula IX may be unsubstituted or substituted heteroaryl or heterocycloalkyl groups which are commercially available or known in the literature. More preferred heteroaryl groups include 2H-[1,2,3]triazol-4-yl, 1H-indol-7-yl, 5H-carbazol-1-yl, 2,3-dihydro-1H-indol-7-yl, 1H-pyrrolo[2,3-c]pyridin-7-yl, 4,5,6,6a-tetrahydro-3αH-cyclopenta[b]thiophen-2-yl, 2H-[1,2,4]triazol-3-yl, pyrimidin-4-yl, furazan-3-yl, pyridazin-3-yl, (Z)-4,6,8,10-tetrathia-5,7,9,11-tetraaza-cyclopentacyclodecen-5-yl, thiazol-4-yl, dihydro-1H-[1,2,4]triazol-3-yl, isoxazol-5-yl, 1H-imidazol-2-yl, 1H-benzoimidazol-2-yl, [1,2,5]thiadiazol-3-yl, oxazol-2-yl, benzooxazol-2-yl, 4,5-dihydro-oxazol-2-yl, pyrimidin-2-yl, [1,2,4]oxadiazol-5-yl, isoxazol-3-yl, [1,2,4]triazin-3-yl, [1,2,4]triazolo[1,5-a]pyridin-2-yl, 1H-indazol-3-yl, isoquinolin-3-yl, and quinolin-2-yl. Most preferred heteroaryl groups include 1H-pyrazol-3-yl, pyrazin-2-yl, pyridin-2-yl, thiazol-2-yl, [1,3,4]thiadiazol-2-yl, and [1,2,4]thiadiazol-5-yl.

If it is desired to produce the compound of formula IX, where $R_3$ is a substituted 1H-pyrazol-3-yl group, most preferably: 1-acetyl-1H-pyrazol-3-yl, 1-tert-butoxycarbonyl-5-methyl-1H-pyrazol-3-yl, 1,5-dimethyl-1H-pyrazol-3-yl, or 5-methyl-1H-pyrazol-3-yl, these compounds are commercially available.

If it is desired to produce the compound of formula IX, where $R_3$ is a substituted 1H-pyrazol-3-yl group, most preferably: 1-(2-tert-butoxycarbonylamino-ethyl)-1H-pyrazol-3-yl, 1-(2-isopropoxy-ethyl)-1H-pyrazol-3-yl, 1-(2-methoxy-2-methyl-propyl)-1H-pyrazol-3-yl, 1-(2-hydroxy-2-methyl-propyl)-1H-pyrazol-3-yl, 1-(2-hydroxy-propyl)-1H-pyrazol-3-yl, 1-(2-methyl-2-triethylsilanyloxy-propyl)-1H-pyrazol-3-yl, 1-(1-hydroxy-cyclopropyl methyl)-1H-pyrazol-3-yl, 1-(4-methoxycarbonyl-cyclohexyl methyl)-1H-pyrazol-3-yl, 1-2-(tert-butyl-dimethyl-silanyloxy)-ethyl-1H-pyrazol-3-yl, 1-(3-carboxy-benzyl)-1H-pyrazol-3-yl, 1-1-(4-methoxycarbonyl-phenyl)-butyl-1H-pyrazol-3-yl, 1-(3-tert-butoxycarbonylamino-benzyl)-1H-pyrazol-3-yl, 1-(3-methoxycarbonyl-benzyl)-1H-pyrazol-3-yl, 1-(4-tert-butoxycarbonylamino-but-2-ynyl)-1H-pyrazol-3-yl, 1-(4-hydroxy-but-2-ynyl)-1H-pyrazol-3-yl, 1-(3-methyl-but-2-enyl)-1H-pyrazol-3-yl, 1-(3-hydroxy-3-methyl-butyl)-1H-pyrazol-3-yl, 1-(4-methoxycarbonyl-benzyl)-1H-pyrazol-3-yl, 1-(3-methyl-butyl)-1H-pyrazol-3-yl, 1-isobutyl-1H-pyrazol-3-yl, 1-octyl-1H-pyrazol-3-yl, 1-hexyl-1H-pyrazol-3-yl, 1-(3-hydroxy-3-methyl-butyryl)-1H-pyrazol-3-yl, 1-((R)-2,3-dihydroxy-propyl)-1H-pyrazol-3-yl, 1-((S)-2,3-dihydroxy-propyl)-1H-pyrazol-3-yl, 1-ethanesulfonyl-1H-pyrazol-3-yl, 1-(4-methoxy-benzyl)-1H-pyrazol-3-yl, 1-(4-cyano-benzyl)-1H-pyrazol-3-yl, 1-(3-hydroxy-propyl)-1H-pyrazol-3-yl, 1-methanesulfonyl methyl-1H-pyrazol-3-yl, 1-(4-methanesulfonyl-benzyl)-1H-pyrazol-3-yl, 1-carbamoyl methyl-1H-pyrazol-3-yl, 1-(2-tert-butoxycarbonyl-ethyl)-1H-pyrazol-3-yl, 1-tert-butoxycarbonyl methyl-1H-pyrazol-3-yl, 1-propyl-1H-pyrazol-3-yl, 1-(4-chloro-benzyl)-1H-pyrazol-3-yl, 1-(2-methoxy-ethyl)-1H-pyrazol-3-yl, 1-cyclopropylmethyl-1H-pyrazol-3-yl, 1-(3,4-dichloro-benzyl)-1H-pyrazol-3-yl, 1-phenethyl-1H-pyrazol-3-yl, 1-tert-butoxycarbonyl-1H-pyrazol-3-yl, 1-isopropyl-1H-pyrazol-3-yl, 1-(4-methyl-benzyl)-1H-pyrazol-3-yl, 1-(4-hydroxy-butyl)-1H-pyrazol-3-yl, 1-butyl-1H-pyrazol-3-yl, 1-ethyl-1H-pyrazol-3-yl, 1-benzyl-1H-pyrazol-3-yl, 1-methyl-1H-pyrazol-3-yl, or 1H-pyrazol-3-yl, these compounds are commercially available or can be prepared as described in U.S. Pat. Appl. US 2008021032.

If it is desired to produce the compound of formula IX, where $R_3$ is a substituted 1H-pyrazol-3-yl group, most preferably: 1-(dimethyl-phosphinoylmethyl)-1H-pyrazol-3-yl, 1-(diethoxy-phosphorylmethyl)-5-methyl-1H-pyrazol-3-yl, or 1-(diethoxy-phosphorylmethyl)-1H-pyrazol-3-yl, these compounds can be prepared as described in PCT Int. Appl. WO 2008005964.

If it is desired to produce the compound of formula IX, where $R_3$ is 1-difluoromethyl-1H-pyrazol-3-yl, this compound can be prepared as described in PCT Int. Appl. WO 2005090332.

If it is desired to produce the compound of formula IX, where $R_3$ is a substituted pyrazin-2-yl group, most preferably: 5-cyano-pyrazin-2-yl, 5-methylsulfanyl-pyrazin-2-yl, 5-chloro-pyrazin-2-yl, pyrazin-2-yl, 5-methoxy-pyrazin-2-yl, 5-methyl-pyrazin-2-yl or 5-bromo-pyrazin-2-yl these compounds are commercially available.

If it is desired to produce the compound of formula IX, where $R_3$ is a substituted pyrazin-2-yl group, most preferably: 5-(diethoxy-phosphorylmethyl)-pyrazin-2-yl, 5-(diisopropoxy-phosphorylmethyl)-pyrazin-2-yl, or 5-(ethoxy-methyl-phosphinoylmethyl)-pyrazin-2-yl these compounds can be prepared as described in PCT Int. Appl. WO 2008005964.

If it is desired to produce the compound of formula IX, where $R_3$ is a substituted pyrazin-2-yl group, most preferably: 5-methoxycarbonyl-pyrazin-2-yl, 5-dimethylamino-pyrazin-2-yl, 5-thiophen-2-yl-pyrazin-2-yl, 5-(3-methoxy-phenyl)-pyrazin-2-yl, 5-(2-hydroxy-phenyl)-pyrazin-2-yl, 5-(2-methoxy-phenyl)-pyrazin-2-yl, 5-vinyl-pyrazin-2-yl, 5-{[1-(9H-fluoren-9-ylmethoxycarbonylamino)-meth-(E)-ylidene]-amino}-pyrazin-2-yl, 5-methanesulfonylamino-pyrazin-2-yl, 5-dimethoxymethyl-pyrazin-2-yl, 5-{1-[(E)-tert-butoxyimino]-ethyl}-pyrazin-2-yl, 5-tert-butoxycarbonyl-pyrazin-2-yl, 5-methylsulfanylmethyl-pyrazin-2-yl, 5-cyanomethyl-pyrazin-2-yl, 5-(1,1-dimethoxy-ethyl)-pyrazin-2-yl, 5-(bis-ethoxycarbonyl-methyl)-pyrazin-2-yl, 5-[1,3]dioxolan-2-yl-pyrazin-2-yl, 5-[1,3]dioxolan-2-ylmethyl-pyrazin-2-yl, 5-(2-methoxy-ethoxy)-pyrazin-2-yl, 5-allyloxy-pyrazin-2-yl, 5-(2,2-dimethoxy-ethyl)-pyrazin-2-yl, 5-(2,2-dimethyl-[1,3]dioxolan-4-yl)-pyrazin-2-yl, 5-(2-benzyloxy-1-benzyloxymethyl-ethoxycarbonyl)-pyrazin-2-yl, 5-[2-(tetrahydro-pyran-2-yloxy)-ethoxy]-pyrazin-2-yl, 5-(2-methyl-propenyl)-pyrazin-2-yl, 5-(4-methyl-2,5-dioxo-imidazolidin-4-yl)-pyrazin-2-yl, 5-(tetrahydro-furan-2-yl)-pyrazin-2-yl, 5-(2-methoxy-ethylamino)-pyrazin-2-yl, 5-(2-triethylsilanyloxy-ethylamino)-pyrazin-2-yl, 5-(1H-indol-5-yl)-pyrazin-2-yl, 5-(5,6-dihydro-4H-pyran-2-yl)-pyrazin-2-yl, 5-thiophen-3-yl-pyrazin-2-yl, 5-furan-3-yl-pyrazin-2-yl, 5-(5-cyano-thiophen-2-yl)-pyrazin-2-yl, 5-(4,5-dihydro-1H-imidazol-2-yl)-pyrazin-2-yl, 5-allyl-pyrazin-2-yl these compounds can be prepared as described in PCT Int. Appl. WO 2004052869.

If it is desired to produce the compound of formula IX, where $R_3$ is a substituted pyrazin-2-yl group, most preferably: 5-cyclopropyl-pyrazin-2-yl, 5-tert-butoxycarbonylamino-pyrazin-2-yl, 5-(tert-butoxycarbonyl-methyl-amino)-pyrazin-2-yl, 5-(2-oxo-pyrrolidin-1-yl)-pyrazin-2-yl, 5-[2-(tert-butyl-dimethyl-silanyloxy)-ethoxy]-pyrazin-2-yl, 5-isopropoxy-pyrazin-2-yl, or 5-(4-acetyl-3-methyl-piperazin-1-ylmethyl)-pyrazin-2-yl these compounds can be prepared as described in PCT Int. Appl. WO 2007007886.

If it is desired to produce the compound of formula IX, where $R_3$ is a substituted thiazol-2-yl group, most preferably: 4-(4-isopropyl-phenyl)-thiazol-2-yl, 4,5,6,7-tetrahydro-benzothiazol-2-yl, 4,5-dimethyl-thiazol-2-yl, 4,5-dimethyl-thiazol-2-yl, 4-acetyl-thiazol-2-yl, 4-carbamoyl-thiazol-2-yl, 4-carboxymethyl-thiazol-2-yl, 4-chloromethyl-thiazol-2-yl, 4-cyano-thiazol-2-yl, 4-ethoxycarbonyl-4,5,6,7-tetrahydro-benzothiazol-2-yl, 4-ethoxycarbonylmethyl-5-ethyl-thiazol-2-yl, 4-ethoxycarbonylmethyl-5-methyl-thiazol-2-yl, 4-ethoxycarbonyl methyl-thiazol-2-yl, 4-ethoxycarbonyl-thiazol-2-yl, 4-ethoxyoxalyl-thiazol-2-yl, 4-formyl-thiazol-2-yl, 4-hydroxymethyl-thiazol-2-yl, 4-isopropyl-thiazol-2-yl, 4-methoxycarbonylmethyl-thiazol-2-yl, 4-methoxycarbonyl-thiazol-2-yl, 4-methyl-thiazol-2-yl, 4-tert-butyl-thiazol-2-yl, 4-trifluoromethyl-thiazol-2-yl, 5-(2-hydroxy-ethylcarbamoyl)-4-methyl-thiazol-2-yl, 5-acetyl-4-methyl-thiazol-2-yl, 5-bromo-thiazol-2-yl, 5-bromo-thiazol-2-yl, 5-bromo-thiazol-2-yl, 5-chloro-thiazol-2-yl, 5-chloro-thiazol-2-yl, 5-chloro-thiazolo[5,4-b]pyridin-2-yl, 5-ethoxycarbonyl-4-methyl-thiazol-2-yl, 5-ethoxycarbonylmethylsulfanyl-thiazol-2-yl, 5-ethoxycarbonyl-thiazol-2-yl, 5-fluoro-thiazol-2-yl, 5-fluoro-thiazol-2-yl, 5-formyl-thiazol-2-yl, 5-hydroxymethyl-thiazol-2-yl, 5-isopropyl-4-methoxycarbonyl-thiazol-2-yl, 5-methanesulfonyl-thiazol-2-yl, 5-methoxycarbonylmethyl-thiazol-2-yl, 5-methoxycarbonyl-thiazol-2-yl, 5-methoxy-thiazol-2-yl, 5-methoxy-thiazolo[5,4-b]pyridin-2-yl, 5-methyl-4,5,6,7-tetrahydro-thiazolo[5,4-c]pyridin-2-yl, 5-methyl-thiazol-2-yl, 5-nitro-thiazol-2-yl, 5-thiocyanato-thiazol-2-yl, 6,7-dihydro-4H-pyrano[4,3-d]thiazol-2-yl, 6-bromo-thiazolo[4,5-b]pyrazin-2-yl, 6-carboxymethyl-benzothiazol-2-yl, 6-fluoro-benzothiazol-2-yl, 6-methanesulfonyl-benzothiazol-2-yl, 6-nitro-benzothiazol-2-yl, benzothiazol-2-yl, thiazol-2-yl, thiazolo[5,4-b]pyridin-2-yl, 4-chloromethyl-thiazol-2-yl, or 4,5,6,7-tetrahydro-benzothiazol-2-yl these compounds are commercially available.

If it is desired to produce the compound of formula IX, where $R_3$ is a substituted thiazol-2-yl group, most preferably: 5-(3-cyano-phenoxy)-thiazol-2-yl, 5-(3-methoxycarbonyl-phenoxy)-thiazol-2-yl, 5-(4-methoxycarbonyl-phenoxy)-thiazol-2-yl, 5-(5-methoxycarbonyl-pyridin-3-yloxy)-thiazol-2-yl, 5-(6-fluoro-pyridin-3-yloxy)-thiazol-2-yl, or 5-(3,4-bis-methoxycarbonyl-phenoxy)-thiazol-2-yl these compounds can be prepared as described in PCT Int. Appl. WO 2008005914.

If it is desired to produce the compound of formula IX, where $R_3$ is a substituted thiazol-2-yl group, most preferably: 4-(diethoxy-phosphorylmethyl)-5-isopropyl-thiazol-2-yl, 4-(diisopropoxy-phosphorylmethyl)-thiazol-2-yl, 4-(dimethyl-phosphinoyloxymethyl)-thiazol-2-yl, 4-(ethoxy-methyl-phosphinoylmethyl)-thiazol-2-yl, 4-(ethoxy-methyl-phosphinoyloxymethyl)-thiazol-2-yl, 4-[2-(diethoxy-phosphoryl)-1-hydroxy-ethyl]-thiazol-2-yl, 4-[2-(diethoxy-phosphoryl)-ethyl]-thiazol-2-yl, 5-(diethoxy-phosphoryl)-thiazol-2-yl, 5-(diethoxy-phosphorylmethyl)-thiazol-2-yl, 4-(2-oxido-[1,3,2]dioxaphosphinan-2-ylmethyl)-thiazol-2-yl, 4-((S)-ethoxy-methyl-phosphinoylmethyl)-thiazol-2-yl, 4-(diethoxy-phosphorylmethyl)-thiazol-2-yl, 4-(diethoxy-phosphoryl)-thiazol-2-yl or 4-bromo-thiazol-2-yl these compounds can be prepared as described in PCT Int. Appl. WO 2008005964.

If it is desired to produce the compound of formula IX, where $R_3$ is a substituted thiazol-2-yl group, most preferably: 4-(2-ethoxycarbonyl-ethylsulfanylmethyl)-thiazol-2-yl, 4-carboxymethylsulfanylmethyl-thiazol-2-yl, or 5-(2-ethoxycarbonyl-ethylsulfanyl)-thiazol-2-yl these compounds can be prepared as described in PCT Int. Appl. WO 2007125103.

If it is desired to produce the compound of formula IX, where $R_3$ is a substituted thiazol-2-yl group, most preferably: 4-methoxy-6-methoxycarbonyl-benzothiazol-2-yl this compound can be prepared as described in PCT Int. Appl. WO 2007122482.

If it is desired to produce the compound of formula IX, where $R_3$ is a substituted thiazol-2-yl group, most preferably: 4-(1-acetyl-piperidin-4-yl)-thiazol-2-yl this compound can be prepared as described in PCT Int. Appl. WO 2007089512.

If it is desired to produce the compound of formula IX, where $R_3$ is a substituted thiazol-2-yl group, most preferably:

5-bromo-thiazolo[5,4-b]pyridin-2-yl this compound can be prepared as described in PCT Int. Appl. WO 2007041365.

If it is desired to produce the compound of formula IX, where $R_3$ is a substituted thiazol-2-yl group, most preferably: 4-(1,2-bis-benzoyloxy-ethyl)-thiazol-2-yl, 4-(1,3-diacetoxypropyl)-thiazol-2-yl, 4-(2,2,4-trimethyl-[1,3]dioxolan-4-yl)-thiazol-2-yl, 4-(2,2,5,5-tetramethyl-[1,3]dioxolan-4-yl)-thiazol-2-yl, 4-(2,2-dimethyl-[1,3]dioxolan-4-yl)-thiazol-2-yl, 4-(2-acetoxy-1-acetoxymethyl-1-methyl-ethyl)-thiazol-2-yl, 4-(2-acetoxy-1-acetoxymethyl-ethyl)-thiazol-2-yl, 4-(3-acetoxy-2-acetoxymethyl-propyl)-thiazol-2-yl, 4-(4-ethyl-2,2-dimethyl-[1,3]dioxolan-4-yl)-thiazol-2-yl, 4-(ethoxycarbonyl-hydroxy-methyl)-5-ethyl-thiazol-2-yl, 5-bromo-4-ethoxyoxalyl-thiazol-2-yl, 5-chloro-4-ethoxyoxalyl-thiazol-2-yl, 4-(1,1-bis-ethoxycarbonyl-ethyl)-thiazol-2-yl, 5-(ethoxycarbonyl-hydroxy-methyl)-thiazol-2-yl or 4-((S)-1,2-bis-benzoyloxy-ethyl)-thiazol-2-yl these compounds can be prepared as described in PCT Int. Appl. WO 2007026761.

If it is desired to produce the compound of formula IX, where $R_3$ is a substituted thiazol-2-yl group, most preferably: 5-(1-ethoxycarbonyl-1-methyl-ethylsulfanyl)-thiazol-2-yl, 5-(1-ethoxycarbonyl-cyclopropylsulfamoyl)-thiazol-2-yl, 5-(1-methoxycarbonyl-cyclobutylsulfamoyl)-thiazol-2-yl, 5-(2,6-dimethyl-piperidine-1-sulfonyl)-thiazol-2-yl, 5-(2-ethoxycarbonyl-ethylsulfamoyl)-thiazol-2-yl, 5-(2-methoxycarbonyl-ethylsulfanyl)-thiazol-2-yl, 5-(2-methoxycarbonyl-pyrrolidine-1-sulfonyl)-thiazol-2-yl, 5-(ethoxycarbonylmethyl-sulfamoyl)-4-methyl-thiazol-2-yl, 5-(ethoxycarbonylmethyl-sulfamoyl)-thiazol-2-yl, 5-(methoxycarbonyl methyl-methyl-sulfamoyl)-4-methyl-thiazol-2-yl, 5-(methoxycarbonylmethyl-sulfamoyl)-thiazol-2-yl, 5-(piperidine-1-sulfonyl)-thiazol-2-yl, 5-imidazol-1-yl-thiazol-2-yl, 5-isopropylsulfamoyl-thiazol-2-yl, 5-tert-butylsulfamoyl-thiazol-2-yl, or 5-((S)-2-methoxycarbonyl-pyrrolidine-1-sulfonyl)-thiazol-2-yl these compounds can be prepared as described in PCT Int. Appl. WO 2007006760.

If it is desired to produce the compound of formula IX, where $R_3$ is a substituted thiazol-2-yl group, most preferably: 5-(2-carboxy-ethylsulfanyl)-thiazol-2-yl this compound can be prepared as described in PCT Int. Appl. WO 2007006814.

If it is desired to produce the compound of formula IX, where $R_3$ is a substituted thiazol-2-yl group, most preferably: 4-methyl-5-(4-methyl-piperazine-1-sulfonyl)-thiazol-2-yl, 5-(4-methyl-piperazin-1-yl)-thiazol-2-yl, 5-chloro-4-ethoxycarbonylmethyl-thiazol-2-yl, or 5-chloro-4-ethoxycarbonylmethyl-thiazol-2-yl these compounds can be prepared as described in PCT Int. Appl. WO 2006058923.

If it is desired to produce the compound of formula IX, where $R_3$ is a substituted thiazol-2-yl group, most preferably: 5-fluoro-thiazolo[5,4-b]pyridin-2-yl or thiazolo[4,5-b]pyrazin-2-yl these compounds can be prepared as described in PCT Int. Appl. WO 2005090332.

If it is desired to produce the compound of formula IX, where $R_3$ is a substituted thiazol-2-yl group, most preferably: 4-ethoxycarbonylmethyl-5-imidazol-1-yl-thiazol-2-yl, 4-methyl-5-(1-methyl-piperidin-4-ylsulfamoyl)-thiazol-2-yl, 5-(2-ethoxycarbonyl-ethylsulfanyl)-4-methyl-thiazol-2-yl, 5-(4-methyl-piperazine-1-sulfonyl)-thiazol-2-yl, 5-(ethoxycarbonylmethyl-methyl-amino)-thiazol-2-yl, or 4-carboxymethylsulfanyl-thiazol-2-yl these compounds can be prepared as described in PCT Int. Appl. WO 2005066145.

If it is desired to produce the compound of formula IX, where $R_3$ is a substituted thiazol-2-yl group, most preferably: 4-methoxymethyl-thiazol-2-yl, 5-(1-amino-1-methyl-ethyl)-thiazol-2-yl, 5-trifluoromethyl-thiazol-2-yl, 4-acetoxymethyl-thiazol-2-yl or thiazolo[4,5-b]pyridin-2-yl these compounds can be prepared as described in PCT Int. Appl. WO 2004081001.

If it is desired to produce the compound of formula IX, where $R_3$ is a substituted thiazol-2-yl group, most preferably: 4-(1-hydroxy-1-methyl-ethyl)-thiazol-2-yl, 4-(tert-butyl-dimethyl-silanyloxymethyl)-thiazol-2-yl, 4-[1-(tert-butyl-dimethyl-silanyloxy)-ethyl]-thiazol-2-yl, 4-[(R)-1-(tert-butyl-dimethyl-silanyloxy)-ethyl]-thiazol-2-yl, thieno[3,2-d]thiazol-2-yl or 4-[1-(tert-butyl-dimethyl-silanyloxy)-ethyl]-thiazol-2-yl these compounds can be prepared as described in PCT Int. Appl. WO 2004076420.

If it is desired to produce the compound of formula IX, where $R_3$ is a substituted thiazol-2-yl group, most preferably: 5-fluoro-thiazol-2-yl this compound can be prepared as described in PCT Int. Appl. WO 2004072031.

If it is desired to produce the compound of formula IX, where $R_3$ is a substituted thiazol-2-yl group, most preferably: 4-(2-methoxycarbonyl-ethylsulfanylmethyl)-thiazol-2-yl, 4-[2-(tert-butyl-dimethyl-silanyloxy)-ethyl]-thiazol-2-yl, 4-azidomethyl-thiazol-2-yl, 4-methylcarbamoylmethyl-thiazol-2-yl, or 2'-[3-(2-cyclopentanecarbonyl-4-methyl-phenyl)-ureido]-[4,4']bithiazolyl-2-yl these compounds can be prepared as described in PCT Int. Appl. WO 2004002481.

If it is desired to produce the compound of formula IX, where $R_3$ is a substituted thiazol-2-yl group, most preferably: 5-ethoxyoxalyl-thiazol-2-yl this compound can be prepared as described in U.S. Pat. No. 6,610,846.

If it is desired to produce the compound of formula IX, where $R_3$ is a substituted thiazol-2-yl group, most preferably: 4-hydroxymethyl-thiazol-2-yl this compound can be prepared as described in PCT Int. Appl. WO 2001085706.

If it is desired to produce the compound of formula IX, where $R_3$ is a substituted thiazol-2-yl group, most preferably: 5-formyl-thiazol-2-yl, 5-methoxymethyl-thiazol-2-yl, 5-(2-dimethylamino-ethoxy)-thiazolo[5,4-b]pyridin-2-yl, 5-ethoxycarbonylmethoxy-thiazolo[5,4-b]pyridin-2-yl, 5-tert-butoxycarbonylmethoxy-thiazolo[5,4-b]pyridin-2-yl, 5-(2-hydroxy-ethoxy)-thiazolo[5,4-b]pyridin-2-yl, 5-carbamoylmethoxy-thiazolo[5,4-b]pyridin-2-yl, 5-methylcarbamoyl methoxy-thiazolo[5,4-b]pyridin-2-yl, 5-(2-tert-butoxycarbonylamino-ethoxy)-thiazolo[5,4-b]pyridin-2-yl, 5-(2-amino-ethoxy)-thiazolo[5,4-b]pyridin-2-yl, 5-[2-(tert-butoxycarbonyl-methyl-amino)-ethoxy]-thiazolo[5,4-b]pyridin-2-yl, 5-dimethylsulfamoyl-thiazol-2-yl, 4-(2-dimethylcarbamoyl-ethyl)-thiazol-2-yl, 5-(3-dimethylamino-propyl)-thiazol-2-yl, 5-(3-dimethylamino-propyl)-thiazol-2-yl, 5-[2-(tert-butyl-dimethyl-silanyloxy)-ethoxy]-thiazolo[5,4-b]pyridin-2-yl, 5-(2-dimethylamino-ethylsulfanyl)-thiazol-2-yl, 5-(4-methyl-4H-[1,2,4]triazol-3-ylsulfanyl)-thiazol-2-yl, 5-(2-hydroxy-ethylsulfanyl)-thiazol-2-yl, 5-(3-hydroxy-propylsulfanyl)-thiazol-2-yl, 5-(2-tert-butoxycarbonylamino-ethylsulfanyl)-thiazol-2-yl, 6-methoxy-thiazolo[4,5-b]pyrazin-2-yl, thiazolo[5,4-d]pyrimidin-2-yl, 5-methoxy-thiazolo[5,4-d]pyrimidin-2-yl, 5-dimethylamino-thiazolo[5,4-b]pyridin-2-yl, 5-hydroxymethyl-thiazolo[5,4-b]pyridin-2-yl, 5-(tert-butyl-dimethyl-silanyloxymethyl)-thiazolo[5,4-b]pyridin-2-yl, 5-[(2-dimethylamino-ethyl)-methyl-amino]-thiazolo[5,4-b]pyridin-2-yl, 6-{[2-(tert-butoxycarbonyl-methyl-amino)-ethyl]-methyl-amino}-thiazolo[5,4-b]pyridin-2-yl, 5-(2-dimethylamino-ethylamino)-thiazolo[5,4-b]pyridin-2-yl, 5-{[2-(tert-butyl-dimethyl-silanyloxy)-ethyl]-methyl-amino}-thiazolo[5,4-b]pyridin-2-yl, 5-[2-(tert-butyl-dimethyl-silanyloxy)-ethylamino]-thiazolo[5,4-b]pyridin-2-yl, 5-methylamino-thiazolo[5,4-b]pyridin-2-yl, 5-(1-tert-butoxycarbonyl-piperidin-4-yloxy)-thiazolo[5,4-b]pyridin-2-yl, 5-((S)-1-tert-butoxycarbonyl-pyrrolidin-3- yloxy)-thiazolo[5,4-b]pyridin-2-yl, 5-(1-tert-butoxycarbonyl-pyrrolidin-3-yloxy)-thiazolo[5,4-b]pyridin-2-yl, 5-(1-tert-butoxycarbonyl-azetidin-3-yloxy)-thiazolo[5,4-b]pyridin-2-yl, 5-(2-tert-butoxycarbonylamino-2-methyl-propoxy)-thiazolo[5,4-b]pyridin-2-yl, 5-[3-(tert-butoxycarbonyl-methyl-amino)-propoxy]-thiazolo[5,4-b]pyridin-2-yl, 4-(4-methyl-piperazin-1-ylmethyl)-thiazol-2-yl, 4-(4-methyl-[1,4]diazepan-1-ylmethyl)-thiazol-2-yl, 5-(4-acetyl-3-methyl-piperazin-1-ylmethyl)-thiazol-2-yl, 5-(4-methyl-piperazin-1-ylmethyl)-thiazol-2-yl, 5-(1-tert-butoxycarbonyl-piperidin-4-ylsulfanyl)-thiazol-2-yl, 6-[2-(tert-butyl-dimethyl-silanyloxy)-ethoxy]-benzothiazol-2-yl, 6-[2-(tert-butoxycarbonyl-methyl-amino)-ethoxy]-benzothiazol-2-yl, 6-(2-dimethylamino-ethoxy)-benzothiazol-2-yl, 5-amino-thiazolo[5,4-b]pyridin-2-yl, or 5-oxo-4,5-dihydro-thiazolo[5,4-b]pyridin-2-yl, these compounds can be prepared as described in PCT Int. Appl. WO 2007007886.

If it is desired to produce the compound of formula IX, where $R_3$ is a substituted pyridin-2-yl group, most preferably: 5-hydroxymethyl-pyridin-2-yl, 5-trifluoromethyl-pyridin-2-yl, 5-sulfamoyl-pyridin-2-yl, 5-bromo-6-methyl-pyridin-2-yl, 5-carboxymethyl-pyridin-2-yl, 5-methoxycarbonyl-pyridin-2-yl, 5-phenyl-pyridin-2-yl, 4-ethyl-pyridin-2-yl, isoquinolin-3-yl, 5-fluoro-pyridin-2-yl, 5-acetyl-pyridin-2-yl, 6-bromo-pyridin-2-yl, 1-oxy-pyridin-2-yl, 4-ethoxycarbonyl-pyridin-2-yl, 4-methoxy-pyridin-2-yl, 5-nitro-pyridin-2-yl, 5-cyano-pyridin-2-yl, 5-carboxy-pyridin-2-yl, 6-methyl-pyridin-2-yl, 5-methyl-pyridin-2-yl, 5-chloro-pyridin-2-yl, 5-bromo-pyridin-2-yl, 4-methyl-pyridin-2-yl, quinolin-2-yl, pyridin-2-yl, or 5-carbamoyl-pyridin-2-yl these compounds are commercially available.

If it is desired to produce the compound of formula IX, where $R_3$ is a substituted pyridin-2-yl, most preferably: 4-bromo-pyridin-2-yl or 5-(diethoxy-phosphorylmethyl)-pyridin-2-yl these compounds can be prepared as described in: Ryono, D. E.; Cheng, P. T. W.; Bolton, S. A.; Chen, S. S.; Shi, Y.; Meng, W.; Tino, J. A.; Zhang, H.; Sulsky, R. B. in PCT Int. Appl. (Bristol-Myers Squibb Company, USA) WO 2008005964 A2 20080110, 2008.

If it is desired to produce the compound of formula IX, where $R_3$ is a substituted pyridin-2-yl group, most preferably: 5-(tert-butyl-dimethyl-silanyloxymethyl)-pyridin-2-yl this compound can be prepared as described in: Bai, H.; Bailey, S.; Bhumralkar, D. R.; Bi, F.; Guo, F.; He, M.; Humphries, P. S.; Ling, A. L.; Lou, J.; Nukui, S.; Zhou, R. in PCT Int. Appl. (Pfizer Products Inc., USA) WO 2007122482 A1 20071101, 2007.

If it is desired to produce the compound of formula IX, where $R_3$ is a substituted pyridin-2-yl group, most preferably: 5-benzyloxy-pyridin-2-yl this compound can be prepared as described in: Aicher, T. D.; Boyd, S. A.; Chicarelli, M. J.; Condroski, K. R.; Hinklin, R. J.; Singh, A. in PCT Int. Appl. (Array Biopharma Inc., USA) WO 2007117381 A2 20071018, 2007.

If it is desired to produce the compound of formula IX, where $R_3$ is a substituted pyridin-2-yl group, most preferably: 4-(2,6-difluoro-phenoxy)-pyridin-2-yl, 4-(quinolin-5-yloxy)-pyridin-2-yl, 5-bromo-4-(2,6-difluoro-phenoxy)-pyridin-2-yl, 5-bromo-4-(5-ethoxycarbonyl-2,4-dimethyl-pyridin-3-yloxy)-pyridin-2-yl, 5-bromo-4-(5-ethoxycarbonyl-2,4-dimethyl-pyridin-3-yloxy)-pyridin-2-yl, 5-bromo-4-ethoxycarbonyl methyl-pyridin-2-yl, 4-ethoxycarbonyl methyl-pyridin-2-yl, 4-benzyloxy-5-bromo-pyridin-2-yl, 5-bromo-4-(4-methoxy-benzylsulfanyl)-pyridin-2-yl, 4-(4-methoxy-benzylsulfanyl)-pyridin-2-yl, 5-bromo-4-(2-chloro-5-ethoxycarbonyl-phenoxy)-pyridin-2-yl, 4-(2-chloro-5-ethoxycarbonyl-phenoxy)-pyridin-2-yl, or 4-benzyloxy-pyridin-2-yl these compounds can be prepared as described in: Aicher, T. D.; Boyd, S. A.; Chicarelli, M. J.; Condroski, K. R.; Hinklin, R. J.; Singh, A.; Turner, T. M.; Rustam, F. G. in PCT Int. Appl. (Array Biopharma Inc., USA) WO 2007089512 A1 20070809, 2007.

If it is desired to produce the compound of formula IX, where $R_3$ is a substituted pyridin-2-yl group, most preferably: 5-[5-(2-methoxy-phenyl)-1H-pyrazol-3-yl]-pyridin-2-yl this compound can be prepared as described in: Cao, S. X.; Feng, J.; Gwaltney, S. L.; Hosfield, D. J.; Imaeda, Y.; Takakura, N.; Tang, M. in PCT Int. Appl. (Takeda San Diego, Inc., USA) WO 2007061923 A2 20070531, 2007.

If it is desired to produce the compound of formula IX, where $R_3$ is a substituted pyridin-2-yl group, most preferably: 5-benzyloxycarbonyl-pyridin-2-yl, 5-methoxymethoxymethyl-pyridin-2-yl, 3-trimethylsilyloxycarbonyl-pyridin-2-yl, 5-((E)-2-ethoxycarbonyl-vinyl)-pyridin-2-yl, or 5-methanesulfonyl-pyridin-2-yl these compounds can be prepared as described in: Dudash, J.; Rybczynski, P.; Urbanski, M.; Xiang, A.; Zeck, R.; Zhang, X.; Zhang, Y. in U.S. Pat Appl. (USA). US 2007099930 A1 20070503, 2007).

If it is desired to produce the compound of formula IX, where $R_3$ is a substituted pyridin-2-yl group, most preferably: 5-(4-acetyl-3-methyl-piperazin-1-ylmethyl)-pyridin-2-yl, 5-methoxycarbonylmethylsulfanyl-pyridin-2-yl, or 2-aminothiazolo[5,4-b]pyridin-5-yl these compounds can be prepared as described in: Sugawara, K.; Matsudaira, T.; Sugama, H.; Nawano, M.; Ohashi, R. in PCT Int. Appl. (Tanabe Seiyaku Co., Ltd., Japan) WO 2007007886 A1 20070118, 2007.

If it is desired to produce the compound of formula IX, where $R_3$ is a substituted pyridin-2-yl group, most preferably these compounds can be prepared as described in: Murray, A.; Lau, J.; Jeppesen, L.; Vedso, P.; Ankersen, M.; Lundbeck, J. M.; Kristiansen, M.; Valcarce-Lopez, M. C.; Polisetti, D. R.; Subramanian, G.; Andrews, R. C.; Christen, D. P.; Cooper, J. T.; Santhosh, K. C. in PCT Int. Appl. (Novo Nordisk A/S, Den.) WO 2005066145 A1 20050721, 2005.

If it is desired to produce the compound of formula IX, where $R_3$ is a substituted pyridin-2-yl group, most preferably: 5-(tetrahydro-furan-2-yl)-pyridin-2-yl, 5-methanesulfonylamino-pyridin-2-yl or 5-dimethylamino-pyridin-2-yl these compounds can be prepared as described in: Chen, S.; Corbett, W. L.; Guertin, K. R.; Haynes, N.-E.; Kester, R. F.; Mennona, F. A.; Mischke, S. G.; Qian, Y.; Sarabu, R.; Scott, N. R.; Thakkar, K. C. in PCT Int. Appl. (F. Hoffmann-La Roche Ag, Switz.) WO 2004052869 A1 20040624, 2004.

If it is desired to produce the compound of formula IX, where $R_3$ is a substituted pyridin-2-yl group, most preferably: 5-[tert-butoxycarbonyl-(2-methoxy-ethyl)-amino]-pyridin-2-yl this compound can be prepared as described in: Boyd, S.; Caulkett, P. W. R.; Hargreaves, R. B.; Bowker, S. S.; James, R.; Johnstone, C.; Jones, C. D.; McKerrecher, D.; Block, M. H. in PCT Int. Appl. (Astrazeneca AB, Swed.; Astrazeneca UK Limited) WO 2003015774 A1 20030227, 2003.

If it is desired to produce the compound of formula IX, where $R_3$ is a substituted [1,3,4]thiadiazol-2-yl, group, most preferably: 5-hydroxymethyl-[1,3,4]thiadiazol-2-yl this compound can be prepared as described in Shaban, M. A. E.; Mostafa, M. A.; Nasr, A. Z.; *Pharmazie* 2003, 58, 367-371.

If it is desired to produce the compound of formula IX, where $R_3$ is a substituted [1,2,4]thiadiazol-5-yl, group, most preferably: 3-(2-hydroxy-ethyl)-[1,2,4]thiadiazol-5-yl, this compound can be prepared as described in Jpn. Kokai Tokkyo Koho JP 08151386.

If it is desired to produce the compound of formula IX, where $R_3$ is a substituted [1,3,4]thiadiazol-2-yl group, most preferably: 5-(thiazol-2-ylcarbamoylmethylsulfanyl)-[1,3,4]

thiadiazol-2-yl, 5-(1-tert-butoxycarbonyl-1-methyl-ethylsulfanyl)-[1,3,4]thiadiazol-2-yl, 5-ethoxycarbonylmethyl-[1,3,4]thiadiazol-2-yl, 5-ethoxycarbonyl-[1,3,4]thiadiazol-2-yl, 5-cyclopropyl-[1,3,4]thiadiazol-2-yl, 5-ethoxycarbonylmethylsulfanyl-[1,3,4]thiadiazol-2-yl, 5-ethylsulfanyl-[1,3,4]thiadiazol-2-yl, 5-trifluoromethyl-[1,3,4]thiadiazol-2-yl, 5-methylsulfanyl-[1,3,4]thiadiazol-2-yl, 5-furan-2-yl-[1,3,4]thiadiazol-2-yl, [1,3,4]thiadiazol-2-yl, 5-thioxo-4,5-dihydro-[1,3,4]thiadiazol-2-yl, 5-phenyl-[1,3,4]thiadiazol-2-yl, or 5-methyl-[1,3,4]thiadiazol-2-yl these compounds are commercially available.

If it is desired to produce the compound of formula IX, where $R_3$ is a substituted [1,3,4]thiadiazol-2-yl group, most preferably: 5-phenylsulfamoyl-[1,3,4]thiadiazol-2-yl, 5-isopropylsulfamoyl-[1,3,4]thiadiazol-2-yl, 5-(2-methoxy-ethylsulfamoyl)-[1,3,4]thiadiazol-2-yl, 5-(piperidine-1-sulfonyl)-[1,3,4]thiadiazol-2-yl, 5-(ethoxycarbonylmethyl-methyl-sulfamoyl)-[1,3,4]thiadiazol-2-yl, or 5-(ethoxycarbonylmethyl-sulfamoyl)-[1,3,4]thiadiazol-2-yl, these compounds can be prepared as described in PCT Int. Appl. WO2007006760.

If it is desired to produce the compound of formula IX, where $R_3$ is a substituted [1,3,4]thiadiazol-2-yl group, most preferably: 5-(3-ethoxycarbonyl-propylsulfanyl)-[1,3,4]thiadiazol-2-yl this compound can be prepared as described in PCT Int. Appl. WO 2005080360.

If it is desired to produce the compound of formula IX, where $R_3$ is a substituted [1,3,4]thiadiazol-2-yl group, most preferably: 5-(2-ethoxycarbonyl-ethylsulfanyl)-[1,3,4]thiadiazol-2-yl or 5-(2-methoxycarbonyl-ethyl)-[1,3,4]thiadiazol-2-yl these compounds can be prepared as described in PCT Int. Appl. WO 2007006814.

If it is desired to produce the compound of formula IX, where $R_3$ is a substituted [1,2,4]thiadiazol-5-yl group, most preferably: 3-methoxy-[1,2,4]thiadiazol-5-yl, 3-methyl-[1,2,4]thiadiazol-5-yl, [1,2,4]thiadiazol-5-yl, or 3-methylsulfanyl-[1,2,4]thiadiazol-5-yl these compounds are commercially available.

If it is desired to produce the compound of formula IX, where $R_3$ is a substituted [1,2,4]thiadiazol-5-yl group, most preferably: 3-hydroxymethyl-[1,2,4]thiadiazol-5-yl or 3-cyclopropyl-[1,2,4]thiadiazol-5-yl these compounds can be prepared as described in PCT Int. Appl. WO 2004081001.

If it is desired to produce the compound of formula IX, where $R_3$ is a substituted [1,2,4]thiadiazol-5-yl group, most preferably: 3-(tert-butyl-dimethyl-silanyloxymethyl)-[1,2,4]thiadiazol-5-yl this compound can be prepared as described in PCT Int. Appl. WO 2004076420.

If it is desired to produce the compound of formula IX, where $R_3$ is a substituted [1,2,4]thiadiazol-5-yl group, most preferably: 3-(tert-butyl-dimethyl-silanyloxymethyl)-[1,2,4]thiadiazol-5-yl this compound can be prepared as described in PCT Int. Appl. WO 2004076420.

If it is desired to produce the compound of formula IX, where $R_3$ is a substituted 2H-[1,2,3]triazol-4-yl group, preferably: 2-methyl-2H-[1,2,3]triazol-4-yl this compound can be prepared as described in PCT Int. Appl. WO 2007122482.

If it is desired to produce the compound of formula IX, where $R_3$ is a substituted 2H-[1,2,3]triazol-4-yl group, preferably: 3H-[1,2,3]triazol-4-yl this compound can be prepared as described in PCT Int. Appl. WO 2004076420.

If it is desired to produce the compound of formula IX, where $R_3$ is a substituted 1H-pyrazol-3-yl-benzooxazol-4-yl group, preferably: 5-methyl-1H-pyrazol-3-yl-benzooxazol-4-yl this compound can be prepared as described in PCT Int. Appl. WO 2007061923.

If it is desired to produce the compound of formula IX, where $R_3$ is a substituted 1H-indol-7-yl group, preferably: 4,5-dihydro-thiazol-2-yl-1H-indol-7-yl, 4,5-dimethyl-thiazol-2-yl-1H-indol-7-yl, 2-thiazol-2-yl-1H-indol-7-yl, 2-[1,2,4]thiadiazol-5-yl-1H-indol-7-yl, 2-pyridin-2-yl-1H-indol-7-yl, 3-methyl-2-propionyl-1H-indol-7-yl these compounds can be prepared as described in PCT Int. Appl. WO 2006112549.

If it is desired to produce the compound of formula IX, where $R_3$ is a substituted 1H-indol-7-yl group, preferably: 2-ethoxycarbonyl-1H-indol-7-yl this compound is commercially available.

If it is desired to produce the compound of formula IX, where $R_3$ is a substituted 6,7,8,9-tetrahydro-5H-carbazol-1-yl group, preferably: 8-oxo-6,7,8,9-tetrahydro-5H-carbazol-1-yl these compounds can be prepared as described in PCT Int. Appl. WO 2006112549.

If it is desired to produce the compound of formula IX, where $R_3$ is a substituted 2,3-dihydro-1H-indol-7-yl group, preferably: 2-oxo-2,3-dihydro-1H-indol-7-yl these compounds can be prepared as described in PCT Int. Appl. WO 2006112549.

If it is desired to produce the compound of formula IX, where $R_3$ is a substituted 1H-pyrrolo[2,3-c]pyridin-7-yl group, preferably: 2-methoxycarbonyl-1H-pyrrolo[2,3-c]pyridin-7-yl this compound can be prepared as described in PCT Int. Appl WO 2006112549.

If it is desired to produce the compound of formula IX, where $R_3$ is a substituted 4,5,6,6a-tetrahydro-3αH-cyclopenta[b]thiophen-2-yl group, preferably: 4-hydroxy-4-methyl-4,5,6,6a-tetrahydro-3αH-cyclopenta[b]thiophen-2-yl this compound can be prepared as described in PCT Int. Appl. WO 2004076420.

If it is desired to produce the compound of formula IX, where $R_3$ is a substituted 2H-[1,2,4]triazol-3-yl group, preferably: 2-fluoro-phenyl-2H-[1,2,4]triazol-3-yl, 3,5-dimethoxy-phenyl-2H-[1,2,4]triazol-3-yl, 2,4-dinitro-phenyl-2H-[1,2,4]triazol-3-yl, 2-methoxy-phenyl-2H-[1,2,4]triazol-3-yl, 4-chloro-phenyl-2H-[1,2,4]triazol-3-yl, 3,4,5-trimethoxy-phenyl-2H-[1,2,4]triazol-3-yl, 5-isopropyl-2H-[1,2,4]triazol-3-yl, or 2H-[1,2,4]triazol-3-yl these compounds are commercially available.

If it is desired to produce the compound of formula IX, where $R_3$ is a substituted or unsubstituted pyrimidin-4-yl group, preferably: 5-pyrimidin-4-yl, 2-methyl-pyrimidin-4-yl or 2-oxo-2,3-dihydro-pyrimidin-4-yl these compounds are commercially available.

If it is desired to produce the compound of formula IX, where $R_3$ is a substituted furazan-3-yl group, preferably: 4-carboxy-furazan-3-yl this compound is commercially available.

If it is desired to produce the compound of formula IX, where $R_3$ is a substituted pyridazin-3-yl group, preferably: 6-methyl-pyridazin-3-yl, pyridazin-3-yl or 6-chloro-pyridazin-3-yl these compounds are commercially available.

If it is desired to produce the compound of formula IX, where $R_3$ is a substituted or unsubstituted (Z)-4,6,8,10-tetrathia-5,7,9,11-tetraaza-cyclopentacyclodecen-5-yl group, preferably: (Z)-4,6,8,10-tetrathia-5,7,9,11-tetraaza-cyclopentacyclodecen-5-yl this compound is commercially available.

If it is desired to produce the compound of formula IX, where $R_3$ is a substituted or unsubstituted thiazol-4-yl group, preferably: thiazol-4-yl this compound can be prepared as described in PCT Int. Appl. WO 2004081001.

If it is desired to produce the compound of formula IX, where $R_3$ is a substituted dihydro-1H-[1,2,4]triazol-3-yl group, preferably: 5-thioxo-2,5-dihydro-1H-[1,2,4]triazol-3-yl this compound is commercially available.

If it is desired to produce the compound of formula IX, where $R_3$ is a substituted isoxazol-5-yl group, preferably: 3-methyl-isoxazol-5-yl this compound is commercially available.

If it is desired to produce the compound of formula IX, where $R_3$ is a substituted or unsubstituted 1H-imidazol-2-yl group, preferably: 1H-imidazol-2-yl this compound is commercially available.

If it is desired to produce the compound of formula IX, where $R_3$ is a substituted or unsubstituted 1H-benzoimidazol-2-yl group, preferably: 1H-benzoimidazol-2-yl this compound is commercially available.

If it is desired to produce the compound of formula IX, where $R_3$ is a substituted or unsubstituted [1,2,5]thiadiazol-3-yl group, preferably: [1,2,5]thiadiazol-3-yl this compound is commercially available.

If it is desired to produce the compound of formula IX, where $R_3$ is a substituted or unsubstituted oxazol-2-yl group, preferably: 5-oxazol-2-yl this compound is commercially available.

If it is desired to produce the compound of formula IX, where $R_3$ is a substituted or unsubstituted benzooxazol-2-yl group, preferably: 5-benzooxazol-2-yl this compound is commercially available.

If it is desired to produce the compound of formula IX, where $R_3$ is a substituted 4,5-dihydro-oxazol-2-yl group, preferably: 4-trifluoromethyl-phenyl-4,5-dihydro-oxazol-2-yl this compound is commercially available.

If it is desired to produce the compound of formula IX, where $R_3$ is a substituted or unsubstituted pyrimidin-2-yl group, preferably: 5-pyrimidin-2-yl or 4-methyl-pyrimidin-2-yl these compounds are commercially available.

If it is desired to produce the compound of formula IX, where $R_3$ is a substituted [1,2,4]oxadiazol-5-yl group, preferably: 3-methyl-[1,2,4]oxadiazol-5-yl this compound is commercially available.

If it is desired to produce the compound of formula IX, where $R_3$ is a substituted or unsubstituted isoxazol-3-yl group, preferably: 5-isoxazol-3-yl or 5-methyl-isoxazol-3-yl these compounds are commercially available.

If it is desired to produce the compound of formula IX, where $R_3$ is a substituted or unsubstituted [1,2,4]triazin-3-yl group, preferably: [1,2,4]triazin-3-yl this compound is commercially available.

If it is desired to produce the compound of formula IX, where $R_3$ is a substituted or unsubstituted [1,2,4]triazolo[1,5-a]pyridin-2-yl group, preferably: [1,2,4]triazolo[1,5-a]pyridin-2-yl this compound can be prepared as described in PCT Int. Appl. WO 2004081001.

The carboxylic acid of the compounds of formula VIII and the amines of formula IX may be converted to the compounds of formula I-x where Q is hydrogen through any conventional means to form an amide bond between a carboxylic acid and an amine (see for example, Montalbetti, C. A. G. N., Falque, V., *Tetrahedron*, 2005, 61, 10827-10852).

The carboxylic acid of the compounds of formula XII and the amines of formula IX may be converted to the compounds of formula XIII through any conventional means to form an amide bond between a carboxylic acid and an amine (see for example, Montalbetti, C. A. G. N., Falque, V., *Tetrahedron*, 2005, 61, 10827-10852).

The compounds of formula XIII may be produced from the compounds of formula II where Y is hydrogen and Y' is a halogen, preferably iodo, and VI. For the compounds of formula VI, $R_2$ may be aryl, substituted aryl, heteroaryl, substituted heteroaryl, alkyl, cycloalkyl, substituted cycloalkyl, heteroalkyl, substituted heteroalkyl, heterocycloalkyl, or substituted heterocycloalkyl, E may be a nitrogen linked substitutent and Z may be halogen, preferably bromide, or any functional group that may be displaced or coupled through a nitrogen. For example, the appropriate compound of formula II and the appropriate compound of formula VI may be treated under conditions that will provide for the displacement of Z or the coupling through Z to form the compound of formula XIII (see for example, New, J. S., Christopher, W. L., Jass, P. A., *J. Org. Chem.*, 1989, 54, 990-992)

The compounds of formula XIII may be produced from the compounds of formula II where Y is halogen, preferably chloro, and Y' is a halogen, preferably chloro, and VI. For the compounds of formula VI, $R_2$ may be aryl, substituted aryl, heteroaryl, substituted heteroaryl, alkyl, cycloalkyl, substituted cycloalkyl, heteroalkyl, substituted heteroalkyl, heterocycloalkyl, or substituted heterocycloalkyl, E may be a nitrogen linked substitutent and Z may be halogen, preferably bromide, or any functional group that may be displaced or coupled through a nitrogen. For example, the appropriate compound of formula II and the appropriate compound of formula VI may be treated under conditions that will provide for the displacement of Z or the coupling through Z to form the compound of formula I or I-x (see for example, New, J. S., Christopher, W. L., Jass, P. A., *J. Org. Chem.*, 1989, 54, 990-992)

The compounds of formula XIII where Y is halogen, preferably chloro, and Y' is a halogen, preferably chloro, can be converted to compounds of formula I or I-x where Q is hydrogen, Y is halogen, preferably chloro, X is oxygen and $R_1$ is aryl, substituted aryl, heteroaryl or substituted heteroaryl by treatment with the appropriate phenol. The appropriate phenol can be obtained through commercial sources or through chemical synthesis. Any conventional method of producing a phenol can also be utilized (see for example, Gonzalez, Concepcion; Castedo, Luis. Departamento de Quimica Organica, Facultad de Ciencias, Universidad de Santiago, Lugo, Spain. Editor(s): Rappoport, Zvi. Chemistry of Phenols (2003), 1 395-489. Publisher: John Wiley & Sons Ltd., Chichester, UK and references cited therein; George, T.; Mabon, R.; Sweeney, G.; Sweeney, J. B.; Tavassoli, A. J. Chem. Soc. Perkin 1 2000, 16, 2529-2574 and references cited therein). Any conventional method used to convert Y' of formula XIII to the appropriate aryl, substituted aryl, heteroaryl or substituted heteroaryl compound of formula I or I-x where Q is hydrogen and where X is oxygen can be utilized to effect this conversion (see for example, *J. Heterocyclic Chem.* 1995, 32, 1473). Compounds of formula I or I-x where Y is halogen, preferably chloro, may then treated under any conventional method to convert Y from a halogen to a hydrogen (see for example, Tavares, F. X., Boucheron, J. A., Dickerson, S. H., Griffin, R. J., Preugschat, F., Thomson, S. A., Wang, T. Y., Zhou, H.-Q. *J. Med. Chem.*, 2004, 47, 4716-4730). Compounds of formula I-x can be converted to compounds of formula I as previously described.

The compounds of XIII where Y is halogen, preferably chloro, and Y' is a halogen, preferably chloro, can be converted to compounds of formula I or I-x where Q is hydrogen, X is oxygen, Y is halogen, preferably chloro, and $R_1$ is aryl, substituted aryl, heteroaryl or substituted heteroaryl and by treatment with the appropriate reagent (see for example, Kweon, D.-H., Kang, Y.-J., Chung, H.-A., Yoo, Y.-J., *J. Heterocyclic Chem.* 1998, 35, 819-826). Compounds of formula I or I-x where Y is halogen, preferably chloro, may then treated under any conventional method to convert Y from a halogen to a hydrogen (see for example, Tavares, F. X., Boucheron, J. A., Dickerson, S. H., Griffin, R. J., Preugschat, F., Thomson, S. A., Wang, T. Y., Zhou, H.-Q. *J. Med. Chem.,* 2004, 47, 4716-4730). More preferably the following reagents, which are all commercially available, can be used: phenol, 2-methoxy-phenol, 3-methoxy-phenol, 4-methoxy-phenol, 2-trifluoromethyl-phenol, 3-trifluoromethyl-phenol, 4-trifluoromethyl-phenol, (2-hydroxy-phenyl)-pyrrolidin-1-yl-methanone, 2-cyclohexylphenol, 2-cyclopentylphenol, 2-phenylphenol, 1-naphthol, 5,6,7,8-tetrahydro-1-naphthol, 2'-hydroxyacetophenone, 2-hydroxybenzonitrile, o-cresol, 3-fluorophenol, 2-fluorophenol, 2,3-difluorophenol, 2,4-difluorophenol, 2,5-difluorophenol, 2,6-difluorophenol, 2-(methylsulfonyl)-phenol, 3-phenoxyphenol, 3-hydroxy-2-methylpyridine, 2-(1-pyrrolidino)-phenol, 2-(1-piperidino)-phenol, 2-(4-morpholino)-phenol, 3-hydroxypyridine, 8-hydroxyquinoline, 5-hydroxyisoquinoline, 5-hydroxyquinoline, 2,3,6-trimethyl-phenol, 2,2-dimethyl-2,3-dihydro-benzofuran-7-ol, 2-tert-butyl-phenol, 2,3-dichloro-phenol, 7-methyl-indan-4-ol, 3-fluoro-pyridin-2-ol, 1H-indol-4-ol, 3-hydroxy-2-methyl-pyran-4-one, 2-trifluoromethoxy-phenol, 6-methyl-pyridin-2-ol, 2-fluoro-5-methyl-phenol, 2-(2-hydroxy-ethyl)-phenol, 4,6-dimethyl-pyrimidin-2-ol, 2-methyl-5-trifluoromethyl-2,4-dihydro-pyrazol-3-one, 3-chloro-2-fluoro-phenol, 2,6-difluoro-3-methyl-phenol, 2-fluoro-4-methoxy-phenol, 2,4-dimethyl-phenol, 2-chloro-4-methoxy-phenol, 2-chloro-4-trifluoromethoxy-phenol, 3-ethoxy-2,6-difluoro-phenol, 2-chloro-3-methoxy-phenol, 2-chloro-phenol, 2,3-dihydro-benzo[1,4]dioxin-5-ol, 2-(2-chloro-phenyl)-ethanol and 2-chloro-3-trifluoromethyl-phenol.

The compounds of formula XIII where Y is halogen, preferably chloro, and Y' is a halogen, preferably chloro, can be converted to compounds of formula I or I-x where Q is hydrogen, X is oxygen, Y is halogen, preferably chloro and $R_1$ is alkyl, cycloalkyl, substituted cycloalkyl, heteroalkyl, substituted heteroalkyl, heterocycloalkyl or substituted heterocycloalkyl by treatment with the appropriate hydroxyl derivative. More preferably the sodium salt of the appropriate hydroxyl derivative (see for example, Tavares, F. X., Boucheron, J. A., Dickerson, S. H., Griffin, R. J., Preugschat, F., Thomson, S. A., Wang, T. Y., Zhou, H.-Q. *J. Med. Chem.,* 2004, 47, 4716-4730). More preferably the following alcohols, which are all commercially available, cyclopentanol, cyclopentyl-methanol, cyclobutanol and 2,6-dimethyl-cyclohexanol. Compounds of formula I or I-x where Y is halogen, preferably chloro, may then treated under any conventional method to convert Y from a halogen to a hydrogen (see for example, Tavares, F. X., Boucheron, J. A., Dickerson, S. H., Griffin, R. J., Preugschat, F., Thomson, S. A., Wang, T. Y., Zhou, H.-Q. *J. Med. Chem.,* 2004, 47, 4716-4730). Compounds of formula I-x can be converted to compounds of formula I as previously described.

The compounds of formula XIII where Y is halogen, preferably chloro, and Y' is a halogen, preferably chloro, can be converted to the compounds of formula I or I-x where Q is hydrogen, X is carbon, Y is halogen, Y is halogen, preferably chloro and $R_1$' is hydrogen, $R_1$ is aryl, substituted aryl, heteroaryl or substituted heteroaryl by treatment with an appropriate reagent such as a nitrile. This reagent can be obtained through commercial sources or through chemical synthesis. Any conventional method of producing an appropriate nitrile compound can also be utilized (see for example, Salturo, F., Bemis, G., Gao, H., In PCT Inter. Appl., Vertex Pharmaceutical Inc., WO 2000/17204). Any conventional method used to convert Y' of formula XIII, where Y' is a halogen preferably chloro, to the appropriate aryl, substituted aryl, heteroaryl or substituted heteroaryl compound of formula I or I-x where Q is hydrogen and where X is carbon can be utilized to effect this conversion (see for example, Salturo, F., et. al., PCT WO 2000/17204; Carroll, R. D., et. al., *J. Med. Chem.,* 1983, 26, 96-100; Haynes, N.-E., Kertesz, D. J., Pietranico-Cole, S. L., Qian, Y., Scott, N. R., Thakkar, K. C., Tilley, J. W., In PCT Inter. Appl., F. Hoffmann-La Roche AG; WO 2007/009913 A1). If an appropriate nitrile reagent is utilized, the nitrile can be removed using appropriate conditions (see for example, Haynes, N.-E., Kertesz, D. J., Pietranico-Cole, S. L., Qian, Y., Scott, N. R., Thakkar, K. C., Tilley, J. W., In PCT Inter. Appl., F. Hoffmann-La Roche AG; WO 2007/009913 A1). Compounds of formula I or I-x where Y is halogen, preferably chloro, may then treated under any conventional method to convert Y from a halogen to a hydrogen (see for example, Tavares, F. X., Boucheron, J. A., Dickerson, S. H., Griffin, R. J., Preugschat, F., Thomson, S. A., Wang, T. Y., Zhou, H.-Q. *J. Med. Chem.,* 2004, 47, 4716-4730). Compounds of formula I-x can be converted to compounds of formula I as previously described.

The compounds of formula XIII where Y is halogen, preferably chloro, and Y' is a halogen, preferably chloro, can be converted to the compounds of formula I or I-x where Q is hydrogen, X is carbon, Y is halogen, preferably chloro and $R_1$' is hydrogen or lower alkyl, $R_1$ is aryl, substituted aryl, heteroaryl or substituted heteroaryl by treatment with an appropriate bromide reagent as well (see for example, Menta, E., Oliva, A. *J. Heterocyclic Chem.,* 1997, 34, 27-32-; Krapcho, A. P., Ellis, M. *J. Fluorine Chem.,* 1998, 90, 139-147). Compounds of formula I or I-x where Y is halogen, preferably chloro, may then treated under any conventional method to convert Y from a halogen to a hydrogen (see for example, Tavares, F. X., Boucheron, J. A., Dickerson, S. H., Griffin, R. J., Preugschat, F., Thomson, S. A., Wang, T. Y., Zhou, H.-Q. *J. Med. Chem.,* 2004, 47, 4716-4730). Compounds of formula I-x can be converted to compounds of formula I as previously described.

The compounds of formula XIII where Y is halogen, preferably chloro, and Y' is a halogen, preferably chloro, can be converted to compounds of formula I or I-x where Q is hydrogen, X is nitrogen, Y is halogen, preferably chloro and $R_1$' is hydrogen or lower alkyl, $R_1$ is aryl, substituted aryl, heteroaryl or substituted heteroaryl by treatment with the appropriate reagent which will ultimately afford a compound of formula I or I-x where Q is hydrogen and where X is nitrogen. The appropriate reagent may be an aromatic amine which can be obtained through commercial sources or through chemical synthesis. Any conventional method of producing an appropriate aromatic amine can be utilized. Any conventional method used to convert Y' of formula XIII, where Y' is a halogen, preferably chloro, to the appropriate aryl, substituted aryl, heteroaryl or substituted heteroaryl compound of formula I or I-x where Q is hydrogen and where X is nitrogen can be utilized to effect this conversion (see for example, Halasz, B. D.-H., Monsieurs, K., Elias, O., Karolyhazy, L., Tapolcsanyi, P., Maes, B. U. W., Riedl, Z., Hajos, G., Dommisse, R. A., Lemiere, G. L. F., Kosmrlj, J., Matyus, P., *Tetrahedron,* 2004, 60, 2283-2291). Compounds of formula I or I-x where Y is halogen, preferably chloro, may then treated under any conventional method to convert Y from a halogen to a hydrogen (see for example, Tavares, F. X., Boucheron, J. A., Dickerson, S. H., Griffin, R. J., Preugschat, F., Thomson, S. A., Wang, T. Y., Zhou, H.-Q. *J. Med. Chem.,* 2004, 47, 4716-4730). Compounds of formula I-x can be converted to compounds of formula I as previously described.

The compounds of formula XIII where Y is halogen, preferably chloro, and Y' is a halogen, preferably chloro, can be converted to compounds of formula I or I-x where Q is hydrogen, X is sulfur, Y is halogen, preferably chloro, and $R_1$ is aryl, substituted aryl, heteroaryl, substituted heteroaryl, alkyl, cycloalkyl, substituted cycloalkyl, heteroalkyl, substituted heteroalkyl, heterocycloalkyl, or substituted heterocycloalkyl by treatment with the appropriate thiol (see for example, Chung, H.-A., Kang, Y.-J., Kweon, D.-H., Yoon, Y.-J., *J. Heterocyclic Chem.*, 1999, 36, 413-421). Compounds of formula I-x can be converted to compounds of formula I as previously described.

The compounds of formula I or I-x where Q is hydrogen and where Y is halogen, preferably chloro, X is sulfur, $R_1$ is aryl, substituted aryl, heteroaryl, substituted heteroaryl, alkyl, cycloalkyl, substituted cycloalkyl, heteroalkyl, substituted heteroalkyl, heterocycloalkyl, or substituted heterocycloalkyl and can be converted to the compounds of formula I or I-x where Q is hydrogen and where $R_1'$ is one connected oxygen (i.e. sulfoxide) or two connected oxygens (i.e. sulfone) through any conventional method of selectively oxidizing sulfur (see for example, Sotelo, E., Fraiz, N., Yanez, M., Terrades, V., Laguna, R., Cano, E., Ravina, E. *Bioorg. Med. Chem.*, 2002, 10, 2873-2882). Compounds of formula I-x can be converted to compounds of formula I as previously described.

The compounds of formula I where Q is hydrogen may be produced from the compounds of formula I-x. If the compounds of formula I-x, where Q is hydrogen contain an intermediate functional group, it may be transformed, converted or deprotected to the desired functionality using conventional methods (see for example, Greene, T. W. *Protective Groups in Organic Synthesis*; John Wiley & Sons, Inc.: New York, 1991). Also, if the compounds of formula I-x are a mixture of enantiomers or diastereomers, the appropriate chromatographic techniques, such as supercritical fluid chromatography, may be utilized to produce chirally pure or chirally enriched compounds of formula I where Q is hydrogen.

The compounds of formula I, where Q is hydrogen may be produced from compounds of formula VIII and the compounds of formula IX. For the compounds of formula VIII, X may be oxygen, carbon, nitrogen or sulfur. For the compounds of formula VIII, when X is carbon or nitrogen, $R_1'$ may be H or lower alkyl. For the compounds of formula VIII, when X is sulfur, $R_1'$ may have one connected oxygen (i.e. sulfoxide) or two connected oxygens (i.e. sulfone). For the compounds of formula VIII, when X is oxygen, carbon, nitrogen or sulfur, Y may be hydrogen, halogen or lower alkyl, and $R_1$ may be aryl, substituted aryl, heteroaryl, substituted heteroaryl, heteroalkyl, substituted heteroalkyl, lower alkyl, cycloalkyl, $(CH_2)_n$cycloalkyl, $(CH_2)_n$aryl, substituted $(CH_2)_n$aryl, substituted cycloalkyl, or substituted $(CH_2)_n$cycloalkyl. Additionally, the compounds of formula I may be produced from the compounds of formula VIII where the variables Y, X, $R_1$, $R_1'$ represent a substituted or unsubstituted fused aryl, heteroaryl, cycloalkyl or heterocycloalkyl system. For the compounds of formula VIII, $R_2$ may be aryl, substituted aryl, heteroaryl, substituted heteroaryl, alkyl, cycloalkyl, substituted cycloalkyl, heteroalkyl, substituted heteroalkyl, heterocycloalkyl, or substituted heterocycloalkyl. The carboxylic acid of the compounds of formula VIII and the amines of formula IX may be converted to the compounds of formula I, where Q is hydrogen through any conventional means to form an amide bond between a carboxylic acid and an amine that does not racemize the molecules chiral center (see for example, Montalbetti, C. A. G. N., Falque, V., *Tetrahedron*, 2005, 61, 10827-10852). If the compounds of formula I, where Q is hydrogen are a mixture of enantiomers or diastereomers, the appropriate chromatographic techniques, such as supercritical fluid chromatography, may be utilized to produce chirally pure or chirally enriched compounds of formula I, where Q is hydrogen.

The compounds of formula XIII where Y is hydrogen and Y' is a halogen, preferably iodo, can be converted to compounds of formula I or I-x where Q is hydrogen and where X is oxygen, $R_1$ is aryl, substituted aryl, heteroaryl or substituted heteroaryl by treatment with the appropriate phenol. The appropriate phenol can be obtained through commercial sources or through chemical synthesis. Any conventional method of producing a phenol can also be utilized (see for example, Gonzalez, Concepcion; Castedo, Luis. Departamento de Quimica Organica, Facultad de Ciencias, Universidad de Santiago, Lugo, Spain. Editor(s): Rappoport, Zvi. Chemistry of Phenols (2003), 1 395-489. Publisher: John Wiley & Sons Ltd., Chichester, UK and references cited therein; George, T.; Mabon, R.; Sweeney, G.; Sweeney, J. B.; Tavassoli, A. *J. Chem. Soc. Perkin* 1 2000, 16, 2529-2574 and references cited therein). Any conventional method used to convert Y' of formula XIII to the appropriate aryl, substituted aryl, heteroaryl or substituted heteroaryl compound of formula I or I-x where Q is hydrogen and where X is oxygen can be utilized to effect this conversion (see for example, *J. Heterocyclic Chem.* 1995, 32, 1473). Compounds of formula I-x can be converted to compounds of formula I as previously described.

The compounds of XIII where Y is hydrogen and Y' is a halogen, preferably iodo, can be converted to compounds of formula I or I-x where Q is hydrogen and where X is oxygen and $R_1$ is aryl, substituted aryl, heteroaryl or substituted heteroaryl and by treatment with the appropriate reagent (see for example, Kweon, D.-H., Kang, Y.-J., Chung, H.-A., Yoo, Y.-J., *J Heterocyclic Chem.* 1998, 35, 819-826). More preferably the following reagents, which are all commercially available, can be used: phenol, 2-methoxy-phenol, 3-methoxy-phenol, 4-methoxy-phenol, 2-trifluoromethyl-phenol, 3-trifluoromethyl-phenol, 4-trifluoromethyl-phenol, (2-hydroxy-phenyl)-pyrrolidin-1-yl-methanone, 2-cyclohexylphenol, 2-cyclopentylphenol, 2-phenylphenol, 1-naphthol, 5,6,7,8-tetrahydro-1-naphthol, 2'-hydroxyacetophenone, 2-hydroxybenzonitrile, o-cresol, 3-fluorophenol, 2-fluorophenol, 2,3-difluorophenol, 2,4-difluorophenol, 2,5-difluorophenol, 2,6-difluorophenol, 2-(methylsulfonyl)-phenol, 3-phenoxyphenol, 3-hydroxy-2-methylpyridine, 2-(1-pyrrolidino)-phenol, 2-(1-piperidino)-phenol, 2-(4-morpholino)-phenol, 3-hydroxypyridine, 8-hydroxyquinoline, 5-hydroxyisoquinoline, 5-hydroxyquinoline, 2,3,6-trimethyl-phenol, 2,2-dimethyl-2,3-dihydro-benzofuran-7-ol, 2-tert-butyl-phenol, 2,3-dichloro-phenol, 7-methyl-indan-4-ol, 3-fluoro-pyridin-2-ol, 1H-indol-4-ol, 3-hydroxy-2-methyl-pyran-4-one, 2-trifluoromethoxy-phenol, 6-methyl-pyridin-2-ol, 2-fluoro-5-methyl-phenol, 2-(2-hydroxy-ethyl)-phenol, 4,6-dimethyl-pyrimidin-2-ol, 2-methyl-5-trifluoromethyl-2,4-dihydro-pyrazol-3-one, 3-chloro-2-fluoro-phenol, 2,6-difluoro-3-methyl-phenol, 2-fluoro-4-methoxy-phenol, 2,4-dimethyl-phenol, 2-chloro-4-methoxy-phenol, 2-chloro-4-trifluoromethoxy-phenol, 3-ethoxy-2,6-difluoro-phenol, 2-chloro-3-methoxy-phenol, 2-chloro-phenol, 2,3-dihydro-benzo[1,4]dioxin-5-ol, 2-(2-chloro-phenyl)-ethanol and 2-chloro-3-trifluoromethyl-phenol.

The compounds of formula XIII where Y is hydrogen and Y' is a halogen, preferably iodo, can be converted to compounds of formula I or I-x where Q is hydrogen and where X is oxygen, $R_1$ is alkyl, cycloalkyl, substituted cycloalkyl, heteroalkyl, substituted heteroalkyl, heterocycloalkyl or substituted heterocycloalkyl by treatment with the appropriate hydroxyl derivative. More preferably the sodium salt of the appropriate hydroxyl derivative (see for example, Tavares, F.

X., Boucheron, J. A., Dickerson, S. H., Griffin, R. J., Preugschat, F., Thomson, S. A., Wang, T. Y., Zhou, H.-Q. *J. Med. Chem.,* 2004, 47, 4716-4730). More preferably the following alcohols, which are all commercially available, cyclopentanol, cyclopentyl-methanol, cyclobutanol and 2,6-dimethylcyclohexanol. Compounds of formula I-x can be converted to compounds of formula I as previously described.

The compounds of formula XIII where Y is hydrogen and Y' is a halogen, preferably iodo, can be converted to the compounds of formula I or I-x where Q is hydrogen and where X is carbon, $R_1'$ is hydrogen, $R_1$ is aryl, substituted aryl, heteroaryl or substituted heteroaryl by treatment with an appropriate reagent such as a nitrile. This reagent can be obtained through commercial sources or through chemical synthesis. Any conventional method of producing an appropriate nitrile compound can also be utilized (see for example, PCT Inter. Appl., WO 200017204). Any conventional method used to convert Y' of formula XIII, where Y' is a halogen preferably iodo, to the appropriate aryl, substituted aryl, heteroaryl or substituted heteroaryl compound of formula I or I-x where Q is hydrogen and where X is carbon can be utilized to effect this conversion (see for example, PCT Inter. Appl. WO 200017204; Carroll, R. D., et. al., *J. Med. Chem.,* 1983, 26, 96-100; PCT Inter. Appl. WO 2007009913). If an appropriate nitrile reagent is utilized, the nitrile can be removed using appropriate conditions (see for example PCT Inter. Appl. WO 2007009913). Compounds of formula I-x can be converted to compounds of formula I as previously described.

The compounds of formula XIII where Y is hydrogen and Y' is a halogen, preferably iodo, can be converted to the compounds of formula I or I-x where Q is hydrogen and where X is carbon, $R_1'$ is hydrogen or lower alkyl, $R_1$ is aryl, substituted aryl, heteroaryl or substituted heteroaryl by treatment with an appropriate bromide reagent as well (see for example, Menta, E., Oliva, A. *J. Heterocyclic Chem.,* 1997, 34, 27-32-; Krapcho, A. P., Ellis, M. *J. Fluorine Chem.,* 1998, 90, 139-147). Compounds of formula I-x can be converted to compounds of formula I as previously described.

The compounds of formula XIII where Y is hydrogen and Y' is a halogen, preferably iodo, can be converted to compounds of formula I or I-x where Q is hydrogen and where X is nitrogen, $R_1'$ is hydrogen or lower alkyl, $R_1$ is aryl, substituted aryl, heteroaryl or substituted heteroaryl by treatment with the appropriate reagent which will ultimately afford a compound of formula I or I-x where Q is hydrogen and where X is nitrogen. The appropriate reagent may be an aromatic amine which can be obtained through commercial sources or through chemical synthesis. Any conventional method of producing an appropriate aromatic amine can be utilized. Any conventional method used to convert Y' of formula XIII, where Y' is a halogen, preferably iodo, to the appropriate aryl, substituted aryl, heteroaryl or substituted heteroaryl compound of formula I or I-x where Q is hydrogen and where X is nitrogen can be utilized to effect this conversion (see for example, Halasz, B. D.-H., Monsieurs, K., Elias, O., Karolyhazy, L., Tapolcsanyi, P., Maes, B. U. W., Riedl, Z., Hajos, G., Dommisse, R. A., Lemiere, G. L. F., Kosmrlj, J., Matyus, P., *Tetrahedron,* 2004, 60, 2283-2291). Compounds of formula I-x can be converted to compounds of formula I as previously described.

The compounds of formula XIII where Y is hydrogen and Y' is a halogen, preferably iodo, can be converted to compounds of formula I or I-x where Q is hydrogen and where X is sulfur, Y is hydrogen, and $R_1$ is aryl, substituted aryl, heteroaryl, substituted heteroaryl, alkyl, cycloalkyl, substituted cycloalkyl, heteroalkyl, substituted heteroalkyl, heterocycloalkyl, or substituted heterocycloalkyl by treatment with the appropriate thiol (see for example, Chung, H.-A., Kang, Y.-J., Kweon, D.-H., Yoon, Y.-J., *J. Heterocyclic Chem.,* 1999, 36, 413-421). Compounds of formula I-x can be converted to compounds of formula I as previously described.

The compounds of formula I or I-x where Q is hydrogen and where Y is hydrogen, X is sulfur, $R_1$ is aryl, substituted aryl, heteroaryl, substituted heteroaryl, alkyl, cycloalkyl, substituted cycloalkyl, heteroalkyl, substituted heteroalkyl, heterocycloalkyl, or substituted heterocycloalkyl and can be converted to the compounds of formula I or I-x where Q is hydrogen and where $R_1'$ is one connected oxygen (i.e. sulfoxide) or two connected oxygens (i.e. sulfone) through any conventional method of selectively oxidizing sulfur (see for example, Sotelo, E., Fraiz, N., Yanez, M., Terrades, V., Laguna, R., Cano, E., Ravina, E. *Bioorg. Med. Chem.,* 2002, 10, 2873-2882). Compounds of formula I-x can be converted to compounds of formula I as previously described.

The compounds of formula XIV, where Q is a halogen, preferably chloro, are commercially available or synthetically accessible. The compounds of formula XIV, where Q is a halogen, preferably chloro, can be converted to the compounds of formula XIV where Q may be aryl, substituted aryl, heteroaryl or substituted heteroaryl linked through an oxygen by treatment with the appropriate phenol (see for example, PCT Inter. Appl. WO 2007/009913). The appropriate phenol can be obtained through commercial sources or through chemical synthesis. Any conventional method of producing a phenol can also be utilized (see for example, Gonzalez, Concepcion; Castedo, Luis. Departamento de Quimica Organica, Facultad de Ciencias, Universidad de Santiago, Lugo, Spain. Editor(s): Rappoport, Zvi. Chemistry of Phenols (2003), 1 395-489. Publisher: John Wiley & Sons Ltd., Chichester, UK and references cited therein; George, T.; Mabon, R.; Sweeney, G.; Sweeney, J. B.; Tavassoli, A. J. Chem. Soc. Perkin 1 2000, 16, 2529-2574 and references cited therein).

The compounds of formula XIV can be converted to the compounds of formula XV through any conditions that will transform an appropriate halopyridazine, preferably an appropriate chloropyridazine, to a pyridazinone (see for example, Salturo, F., et. al., PCT WO 00/17204; Carroll, R. D., et. al., *J. Med. Chem.,* 1983, 26, 96-100; PCT Inter. Appl. WO 2007009913).

The compounds of formula XVI may be produced from the compounds of formula XV and VI. For the compounds of formula XV, Q may be aryl, substituted aryl, heteroaryl or substituted heteroaryl linked through an oxygen. For the compounds of formula VI, $R_2$ may be aryl, substituted aryl, heteroaryl, substituted heteroaryl, alkyl, cycloalkyl, substituted cycloalkyl, heteroalkyl, substituted heteroalkyl, heterocycloalkyl, or substituted heterocycloalkyl, E may be an oxygen linked substitutent and Z may be halogen, preferably bromide, or any functional group that may be displaced or coupled through a nitrogen. For example, the appropriate compound of formula XV and the appropriate compound of formula VI may be treated under conditions that will provide for the displacement of Z or the coupling through Z to form the compound of formula XVI (see for example, New, J. S., Christopher, W. L., Jass, P. A., *J. Org. Chem.,* 1989, 54, 990-992).

The compounds of formula I(c) or I(c)-x may be produced from the compounds of formula XV and VI. For compounds of formula I(c) or I(c)-x, X and Y are hydrogen. For the compounds of formula XV, Q may be aryl, substituted aryl, heteroaryl or substituted heteroaryl linked through an oxygen. For the compounds of formula VI, $R_2$ may be aryl, substituted aryl, heteroaryl, substituted heteroaryl, alkyl, cycloalkyl, substituted cycloalkyl, heteroalkyl, substituted heteroalkyl, heterocycloalkyl, or substituted heterocycloalkyl, E may be a nitrogen linked substitutent and Z may be halogen, preferably bromide, or any functional group that may be displaced or coupled through a nitrogen. For example, the appropriate compound of formula XV and the appropriate compound of formula VI may be treated under conditions that will provide for the displacement of Z or the coupling through Z to form the compound of formula I(c) or I(c)-x (see for example, New, J. S., Christopher, W. L., Jass, P. A., *J. Org. Chem.*, 1989, 54, 990-992)

The compounds of formula XVII may be produced from compounds of formula XVI. For the compounds of formula XVI, Q may be aryl, substituted aryl, heteroaryl or substituted heteroaryl linked through an oxygen. For the compounds of formula XVI, $R_2$ may be aryl, substituted aryl, heteroaryl, substituted heteroaryl, alkyl, cycloalkyl, substituted cycloalkyl, heteroalkyl, substituted heteroalkyl, heterocycloalkyl, or substituted heterocycloalkyl. For the compounds of formula XVI, $R_4$ may be an alkyl or any substituent that may be removed through conventional methods to convert an ester to a carboxylic acid, preferably via hydrolysis (see for example, New, J. S., Christopher, W. L., Jass, P. A., *J. Org. Chem.*, 1989, 54, 990-992).

The compounds of formula I(c)-x may be produced from compounds of formula XVII and the compounds of formula IX. For compounds of formula I(c) or 1(c)-x, X and Y are hydrogen. For the compounds of formula XVII, Q may be aryl, substituted aryl, heteroaryl or substituted heteroaryl linked through an oxygen. For the compounds of formula XVII, $R_2$ may be aryl, substituted aryl, heteroaryl, substituted heteroaryl, alkyl, cycloalkyl, substituted cycloalkyl, heteroalkyl, substituted heteroalkyl, heterocycloalkyl, or substituted heterocycloalkyl. The carboxylic acid of the compounds of formula XVII and the amines of formula IX may be converted to the compounds of formula I(c)-x, where Q is aryl, substituted aryl, heteroaryl or substituted heteroaryl linked through an oxygen and the variables Y, X, $R_1$ and $R_1'$ are hydrogen, through any conventional means to form an amide bond between a carboxylic acid and an amine (see for example, Montalbetti, C. A. G. N., Falque, V., *Tetrahedron*, 2005, 61, 10827-10852).

The compounds of formula I(c), where Q is aryl, substituted aryl, heteroaryl or substituted heteroaryl linked through an oxygen, may be produced from the compounds of formula I(c)-x where Q is aryl, substituted aryl, heteroaryl or substituted heteroaryl linked through an oxygen. For compounds of formula I(c) or 1(c)-x, X and Y are hydrogen. If the compounds of formula I(c)-x, where Q is aryl, substituted aryl, heteroaryl or substituted heteroaryl linked through an oxygen, contain an intermediate functional group, it may be transformed, converted or deprotected to the desired functionality using conventional methods (see for example, Greene, T. W. *Protective Groups in Organic Synthesis*; John Wiley & Sons, Inc.: New York, 1991). Also, if the compounds of formula I(c)-x are a mixture of enantiomers or diastereomers, the appropriate chromatographic techniques, such as supercritical fluid chromatography, may be utilized to produce chirally pure or chirally enriched compounds of formula I(c), where Q may be aryl, substituted aryl, heteroaryl or substituted heteroaryl linked through an oxygen.

The compounds of formula I(c), where Q is aryl, substituted aryl, heteroaryl or substituted heteroaryl linked through an oxygen, may be produced from compounds of formula XVII and the compounds of formula IX. For compounds of formula I(c) or 1(c)-x, X and Y are hydrogen. For the compounds of formula XVII, $R_2$ may be aryl, substituted aryl, heteroaryl, substituted heteroaryl, alkyl, cycloalkyl, substituted cycloalkyl, heteroalkyl, substituted heteroalkyl, heterocycloalkyl, or substituted heterocycloalkyl. The carboxylic acid of the compounds of formula XVII and the amines of formula IX may be converted to the compounds of formula I(c), where Q is aryl, substituted aryl, heteroaryl or substituted heteroaryl linked through an oxygen, through any conventional means to form an amide bond between a carboxylic acid and an amine that does not racemize the molecules chiral center (see for example, Montalbetti, C. A. G. N., Falque, V., *Tetrahedron*, 2005, 61, 10827-10852). If the compounds of formula I(c), where Q is aryl, substituted aryl, heteroaryl or substituted heteroaryl linked through an oxygen, are a mixture of enantiomers or diastereomers, the appropriate chromatographic techniques, such as supercritical fluid chromatography, may be utilized to produce chirally pure or chirally enriched compounds of formula I(c), where Q is aryl, substituted aryl, heteroaryl or substituted heteroaryl linked through an oxygen.

Scheme 1

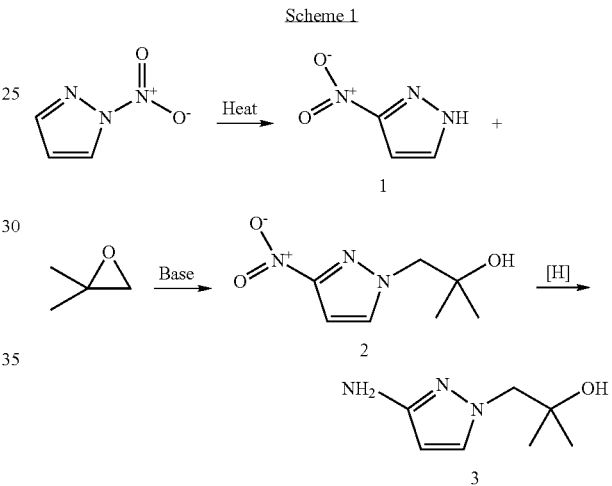

Compound 3 may be synthesized following the reactions outlined in Scheme 1. The nitropyrazole of compound 1 can be prepared by methods described in the literature (see for example, *J. Org. Chem.*, 1971, 36, 3081-4; *J. Org. Chem.*, 1973, 38, 1777-82; and *Org. Mass Spec.*, 1982, 17, 299). Compound 1 may then be treated with an epoxide, such as 2,2-dimethyl-oxirane, under basic conditions to produce compound 2 (see for example, Kotsuki, H., Hayakawa, H., Wakao, M., Shimanouchi, T., Ochi, M., *Tet. Asymm.*, 1995, 6(11), 2665-2668). The nitro group of compound 2 may then be converted to an amino group under standard reduction conditions to produce compound 3 as shown in Scheme 1 (see for example, Ferguson, I. J., Schofield, K., Barnett, J. W., Grimmett, M. R., *J. Chem. Soc., Perkin Trans. I*, 1977, 672-675; U.S. Pat. Appl. US 2008021032).

Scheme 2

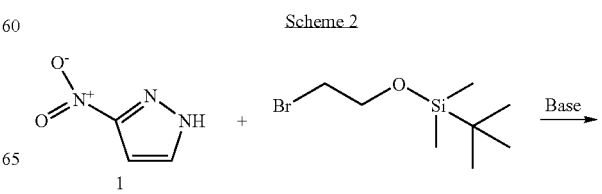

-continued

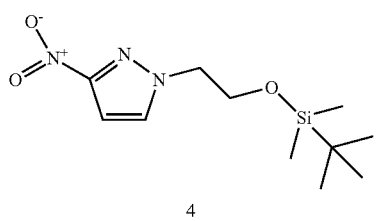
4

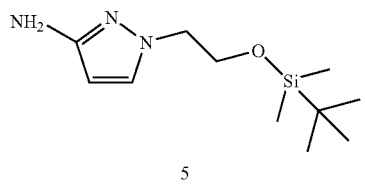
5

Compound 5 may be synthesized following the reactions outlined in Scheme 2. The nitropyrazole of compound 1 can be prepared by methods described in the literature (see for example, *J. Org. Chem.,* 1971, 36, 3081-4; *J. Org. Chem.,* 1973, 38, 1777-82; and *Org. Mass Spec.,* 1982, 17, 299). Compound 1 may then be treated with a commercially available or synthetically accessible reagent, for example, (2-bromo-ethoxy)-tert-butyl-dimethyl-silane, under basic conditions to produce compound 4 (see for example, Settimo, F. D., Primifiore, G., La Motta, C., Taliani, S., Simorini, F., Marini, A. M., Mugnaini, L., Lavecchia, A., Novellino, E., Tuscano, D., Martini, C., *J. Med. Chem.,* 2005, 48, 5162-5174). A commercially available alkyl halide containing an unprotected hydroxyl group may also be converted to an appropriate reagent for this alkylation (see for example, Greene, T. W. *Protective Groups in Organic Synthesis*; John Wiley & Sons, Inc.: New York, 1991, p. 77-81). The nitro group of compound 4 may then be converted to an amino group under standard reduction conditions to produce compound 5 as shown in Scheme 2 (see for example, Ferguson, I. J., Schofield, K., Barnett, J. W., Grimmett, M. R., *J. Chem. Soc., Perkin Trans. I,* 1977, 672-675; U.S. Pat. Appl. US 2008021032).

Scheme 3

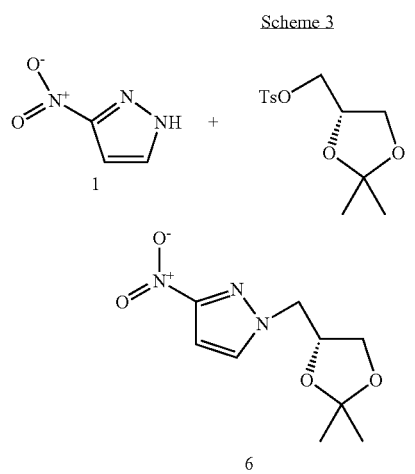

-continued

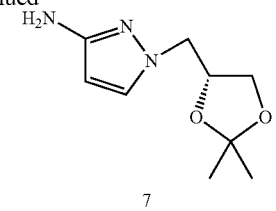
7

Compound 7 may be synthesized following the reactions outlined in Scheme 3. The nitropyrazole of compound 1 can be prepared by methods described in the literature (see for example, *J. Org. Chem.,* 1971, 36, 3081-4; *J. Org. Chem.,* 1973, 38, 1777-82; and *Org. Mass Spec.,* 1982, 17, 299). Compound 1 may then be treated with a commercially available or synthetically accessible reagent, for example, toluene-4-sulfonic acid (S)-2,2-dimethyl-[1,3]dioxolan-4-ylmethyl ester, under basic conditions to produce compound 6 (see for example, Koyama, M., Ohtani, N., Kai, F., Moriguchi, I., Inouye, S., *J. Med. Chem.,* 1987, 30, 552-562). The nitro group of compound 6 may then be converted to an amino group under standard reduction conditions to produce compound 7 as shown in Scheme 3 (see for example, Ferguson, I. J., Schofield, K., Barnett, J. W., Grimmett, M. R., *J. Chem. Soc., Perkin Trans.* 1, 1977, 672-675).

Scheme 4

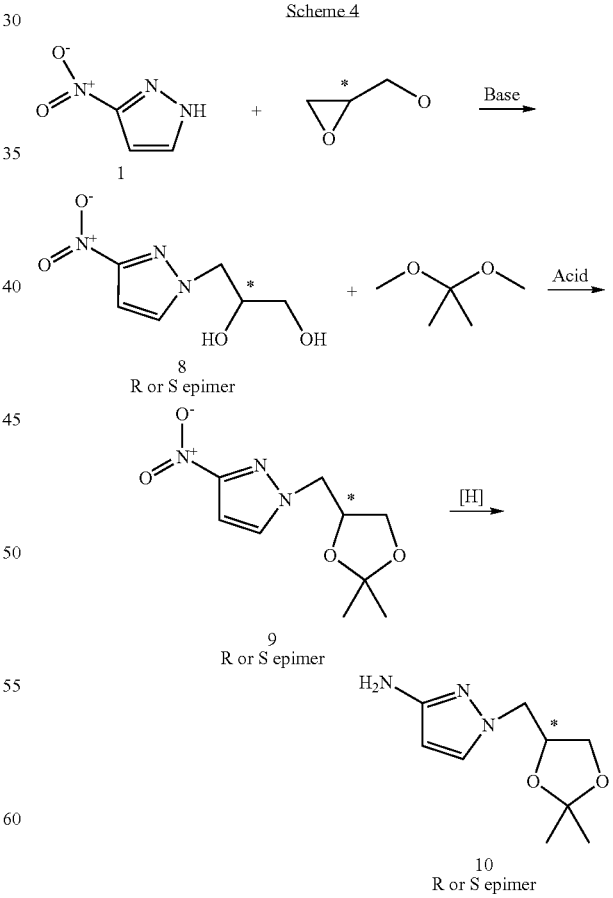

Compound 10 may be synthesized following the reactions outlined in Scheme 4. The nitropyrazole of compound 1 can be prepared by methods described in the literature (see for example, *J. Org. Chem.*, 1971, 36, 3081-4; *J. Org. Chem.*, 1973, 38, 1777-82; and *Org. Mass Spec.*, 1982, 17, 299). Compound 1 may then be treated with a commercially available or synthetically accessible reagent, for example, 1-oxiranyl-methanol, under basic conditions to produce compound 8 (see for example, Kotsuki, H., Hayakawa, H., Wakao, M., Shimanouchi, T., Ochi, M., *Tet. Asymm.*, 1995, 6(11), 2665-2668). Compound 8 may then be treated with 2,2-dimethoxypropane under acidic conditions to produce compound 9 (see for example, Greene, T. W. *Protective Groups in Organic Synthesis*; John Wiley & Sons, Inc.: New York, 1991, p. 123-127). The nitro group of compound 9 may then be converted to an amino group under standard reduction conditions to produce compound 10 as shown in Scheme 4 (see for example, Ferguson, I. J., Schofield, K., Barnett, J. W., Grimmett, M. R., *J. Chem. Soc., Perkin Trans. I*, 1977, 672-675).

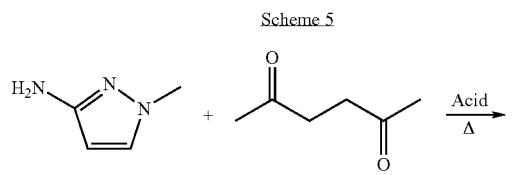

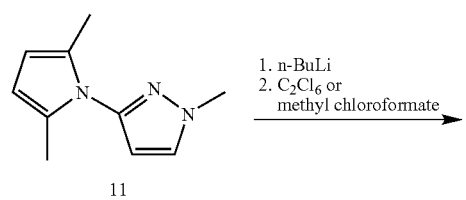

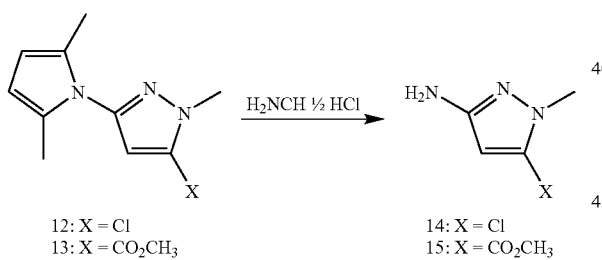

Compounds 14 and 15 may be synthesized following the reactions outlined in Scheme 5. Commercially available 1-methyl-1H-pyrazole-3-amine may be treated with acetonylacetone to afford compound 11 (see for example, Ragan, J. A., Makowski, T. W.; Castaldi, M. J.; Hill, P. D., *Synthesis*, 1998, 1599-1603; PCT Int. Appl. WO 2005044264). Compound 11 can then be converted to either compound 12 or compound 13 by methods described in the literature (see for example, Brooks, G., Davies, D. T., Jones, G. E., Markwell, R. E., Pearson, N. D. In PCT Int. Appl. WO 2003087098; European Pat. Appl. EP 0138622 A2) The dimethylpyrrole protecting group then can be removed to unmask the corresponding free amine to produce compound 14 and 15 as shown in Scheme 5 (see for example, Ragan, J. A., Makowski, T. W.; Castaldi, M. J.; Hill, P. D., *Synthesis*, 1998, 1599-1603; Jensen, M., Larsen, R., Sidler, D. R. In PCT Int Appl. WO 2005044264; European Pat. Appl. EP 0138622 A2).

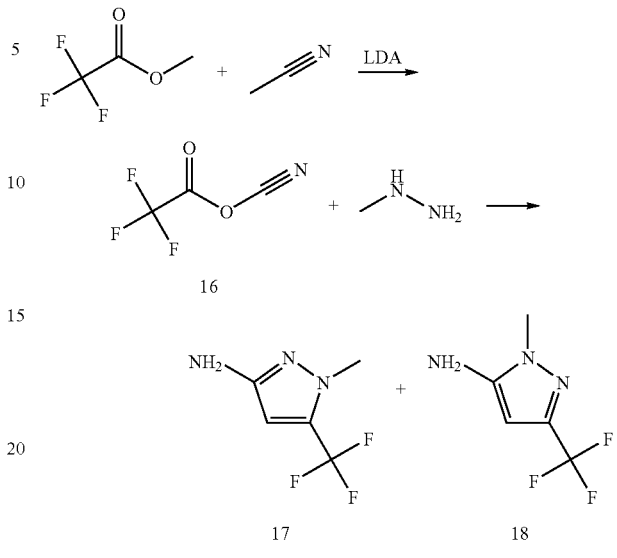

Compounds 17 and 18 may be synthesized following the reactions outlined in Scheme 6. Commercially available methyl trifluoracetate may be treated with acetonitrile in the presence of base to afford compound 16 (see for example European Pat. Appl. EP 0220025 A1). Compound 16 can then be treated with methylhydrazine at elevated temperatures to afford a mixture of compounds 17 and 18 as shown in Scheme 6 (see for example European Pat. Appl. EP 0542388).

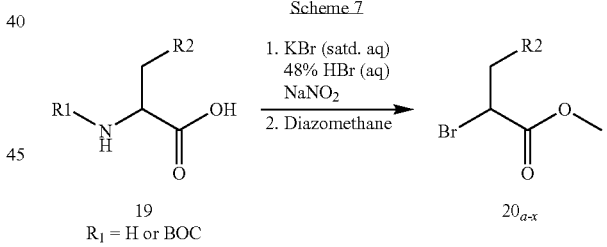

Compounds 20(a-x) can be synthesized following the reactions outlined in Scheme 7. The amino acid or protected amino acid, compound 19, can be converted to a diazonium species and then converted in situ to the bromide under standard conditions (see for example, Archer, C. H., Thomas, N. R., Gani, D. *Tet. Asymm.*, 1993, 4(6), 1141-1152; Dener, J. M., Zhang, L.-H., Rapoport, H. *J. Org. Chem.*, 1993, 58, 1159-1166; Souers, A. J., Schurer, S., Kwack, H., Virgilio, A. A., Ellman, J. A, *Synthesis*, 1999, 4, 583-585). The resulting halo-acid can either be maintained as the acid or can then be converted to an appropriately functionalized ester by any conventional method of converting an acid to an ester as described in reaction Scheme 7 (see for example, Archer, C. H., Thomas, N. R., Gani, D. *Tet. Asymm.*, 1993, 4(6), 1141-1152).

Scheme 8

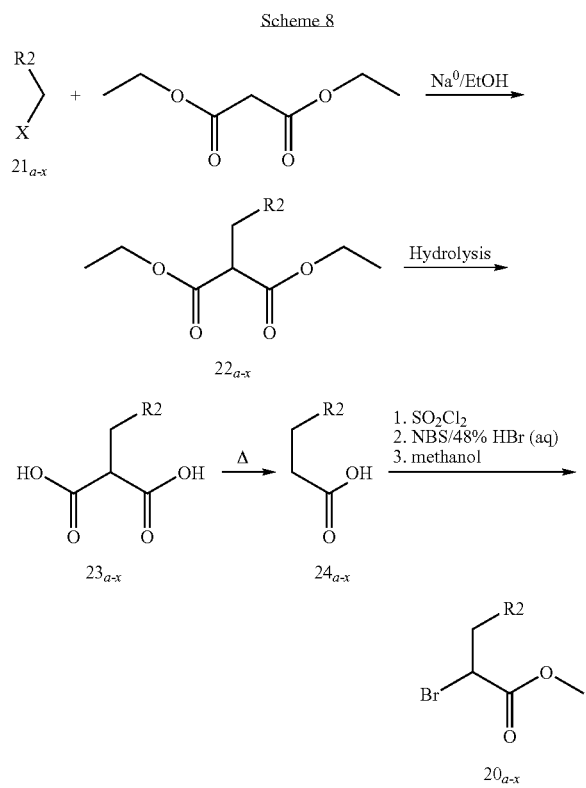

Scheme 9

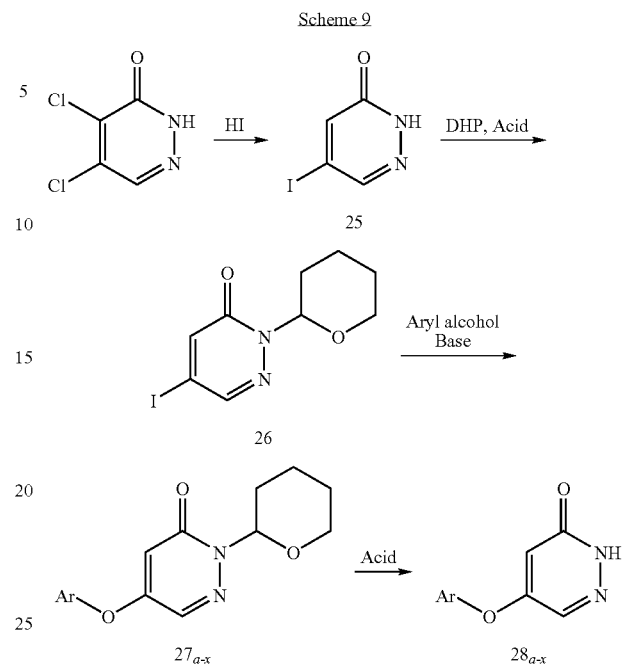

Compounds 20(a-x) can be synthesized following the reactions outlined in Scheme 8. The compounds of formula 21 (a-x), where X is halogen or any functional group that may be displaced or coupled through a carbon, may be purchased or produced from commercially available material under standard conditions (see for example, Fujimoto, R. A., Francis, J. E., Hutchison, A. J. in U.S. Pat. No. 4,977,144; Kortylewicz, Z. P., Galardy, R. E., *J. Med. Chem.*, 1990, 33, 263-273). Compound 21(a-x) may then be reacted with a malonate derivative under standard conditions to produce a substituted malonate (see for example, Kortylewicz, Z. P., Galardy, R. E., *J. Med. Chem.*, 1990, 33, 263-273). The resulting substituted malonate, compounds 22(a-x), can then be treated under hydrolysis conditions to form the resulting diacids (see for example, Kortylewicz, Z. P., Galardy, R. E., *J. Med. Chem.*, 1990, 33, 263-273). The diacids of compounds 23(a-x) can then be heated under such conditions that will promote a decarboxylation to form the appropriately substituted acids. (see for example, Kortylewicz, Z. P., Galardy, R. E., *J. Med. Chem.*, 1990, 33, 263-273). In some instances, the substituted acids of compounds 24(a-x) may be available from commercial sources. The resulting substituted acids, compounds 24(a-x), may then be treated under standard conditions to produce acid chlorides followed by in situ generation of the adjacent bromides (see for example, Epstein, J. W., Brabander, H. J., Fanshawe, W. J., Hofmann, C. M., McKenzie, T. C., Safir, S. R., Osterberg, A. C., Cosulich, D. B., Lovell, F. M., *J. Med. Chem.*, 1981, 24, 481-490). The acid chlorides can then be treated with an appropriate alcohol, to form compounds 20(a-x) as described in reaction Scheme 8.

Compounds 28(a-x) can be synthesized following the reactions outlined in Scheme 9. 4,5-Dichloro-2H-pyridazin-3-one is commercially available or can be prepared from commercially available 3,4-dichloro-5-hydroxy-5H-furan-2-one (see for example, Yanagita, M. *J. Pharm. Soc. of Japan*, 1952, 72, 1383-1384). 4,5-Dichloro-2H-pyridazin-3-one can be converted to compound 25 using conventional methods (see for example, Krajsovszky, G.; et al, *J. Molecular Structure*, 2005, 713, 235-243). The amino group of compound 25 can be protected under standard conditions to install a protecting group, for example tetrahydropyran (see for example, Greene, T. W. *Protective Groups in Organic Synthesis*; John Wiley & Sons, Inc.: New York, 1991, p. 394; Bryant, R. D., Kunng, F.-A., South, M. S. *J Heterocyclic Chem.*, 1995, 32, 1473-1476). Compound 26 may then be treated with a phenol-like reagent under standard conditions to form the oxygen linked aryl or heteroaryl derivative, compounds 27(a-x) (see for example, *J. Heterocyclic Chem.* 1995, 32, 1473). The amino protecting group can then be removed using conventional methods to produce the free amine of compounds 28(a-x) as described in reaction Scheme 9 (see for example, Greene, T. W. *Protective Groups in Organic Synthesis*; John Wiley & Sons, Inc.: New York, 1991; Bryant, R. D., Kunng, F.-A., South, M. S. *J. Heterocyclic Chem.*, 1995, 32, 1473-1476).

Scheme 10

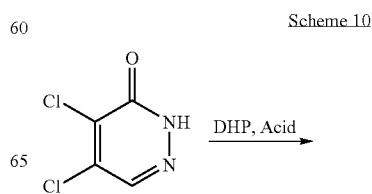

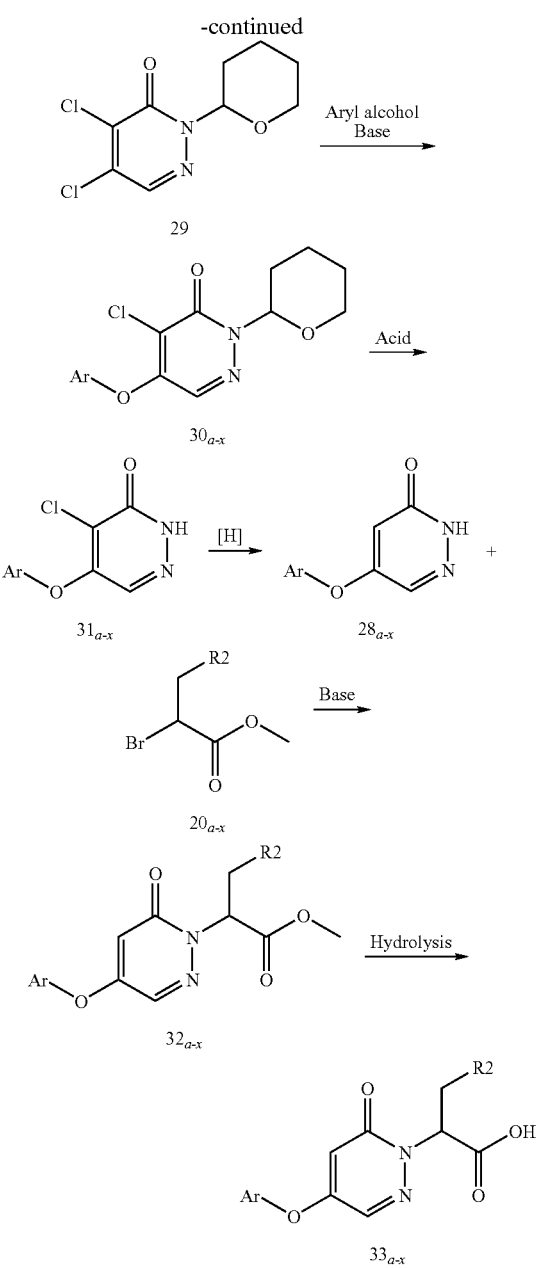

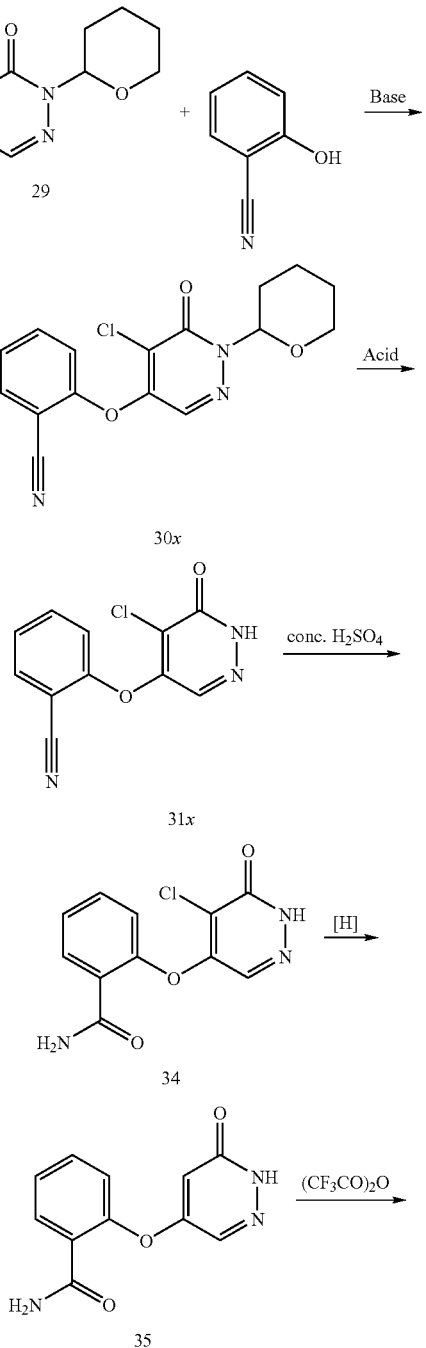

can be prepared as previously described in Scheme 7 and Scheme 8. Compounds 28(a-x) can be treated under standard deprotonation conditions, preferably sodium hydride, and then further reacted with the compounds 20(a-x) to afford compounds 32(a-x) (see for example, New, J. S., Christopher, W. L., Jass, P. A., *J. Org. Chem.*, 1989, 54, 990-992). The ester of compounds 32(a-x) can be hydrolyzed under standard hydrolysis condition to produce the acid, compounds 33(a-x), as described in reaction Scheme 10 (see for example, New, J. S., Christopher, W. L., Jass, P. A., *J. Org. Chem.*, 1989, 54, 990-992).

Compounds 33(a-x) can be synthesized following the reactions outlined in Scheme 10. The synthesis for compound 29 can be prepared as described in the literature (see for example, Bryant, R. D., et. al., *J. Heterocyclic Chem.*, 1995, 32, 1473-1476). Compound 29 can then be treated with a phenol-like reagent under standard conditions to form the oxygen linked aryl or heteroaryl derivative, compound 30(a-x), under basic conditions at elevated temperatures (see for example, Chung, H.-A., et. al., *J. Heterocyclic Chem.*, 1999, 36, 413-421). Compound 30(a-x) may then be treated with aqueous acid in the appropriate solvent at elevated temperatures or any conditions appropriate to remove a nitrogen linked protecting group, such as tetrahydropyran, to afford compounds 31 (a-x) (see for example, Bryant, R. D., et. al., *J. Heterocyclic Chem.*, 1995, 32, 1473-1476). The chloro of compounds 31(a-x) can be removed under standard hydrogenation conditions (see for example, Tavares, F. X., et. al., *J. Med. Chem.*, 2004, 47, 4716-4730). The alkylating reagents, compounds 20(a-x),

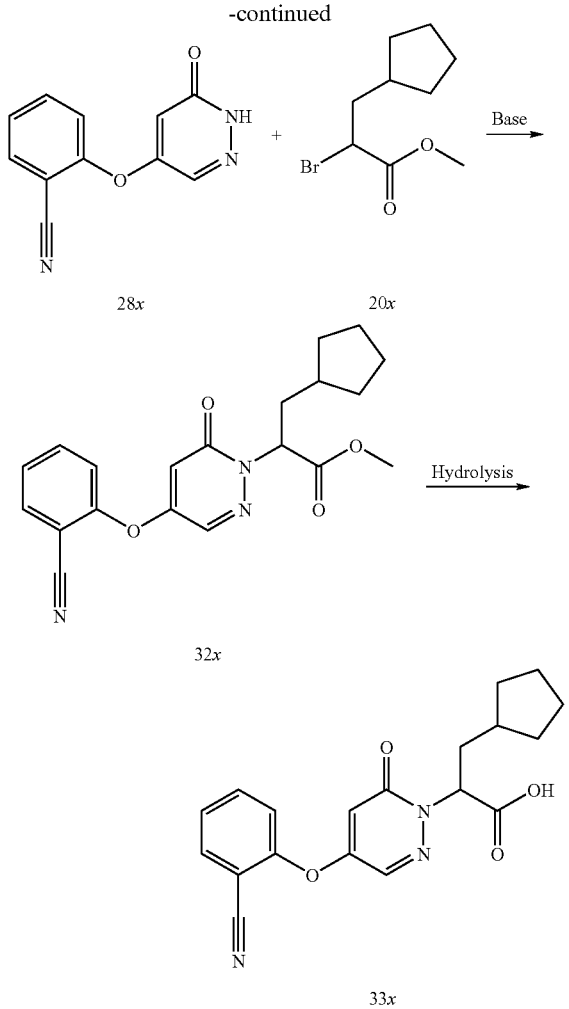

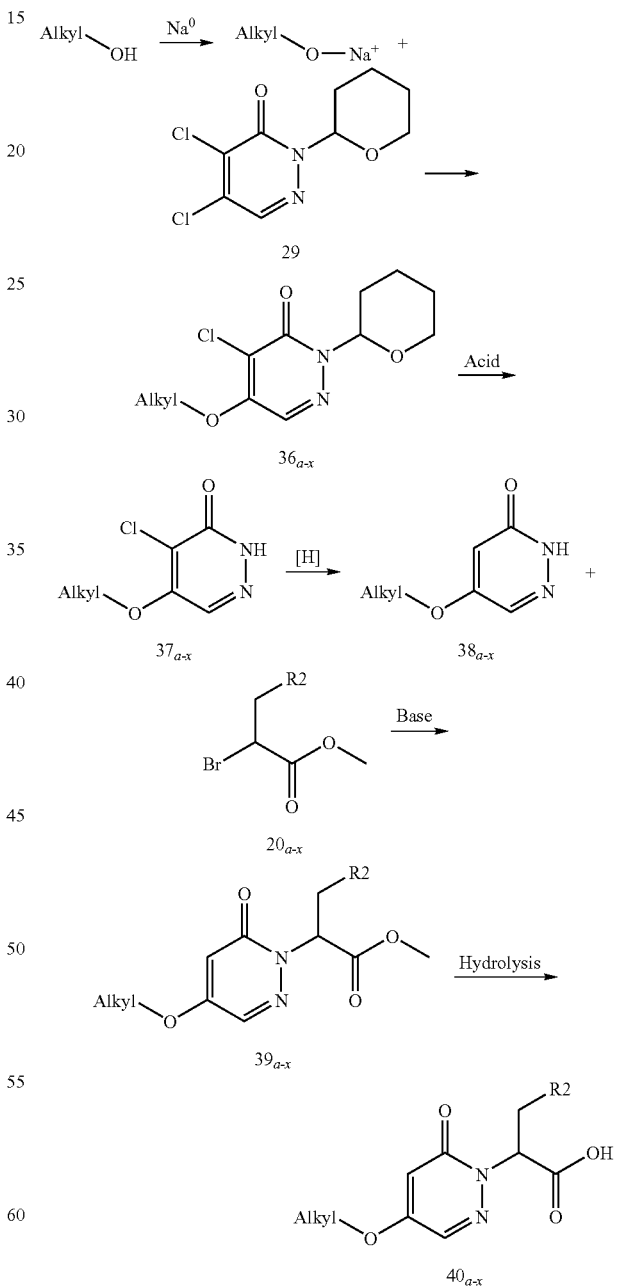

lating reagent, compound 20x, can be prepared as previously described in Scheme 7 and Scheme 8. Compound 28x can be treated under standard deprotonation conditions, preferably sodium hydride, then further reacted with the compound 20x to afford compound 32x (see for example, New, J. S., Christopher, W. L., Jass, P. A., *J. Org. Chem.*, 1989, 54, 990-992). The ester of compound 32x can be hydrolyzed under standard hydrolysis condition to produce the acid, compound 33x, as described in reaction Scheme 11 (see for example, New, J. S., Christopher, W. L., Jass, P. A., *J. Org. Chem.*, 1989, 54, 990-992).

Compound 33x can be synthesized following the reactions outlined in Scheme 11. The synthesis for compound 29 can be prepared as described in the literature (see for example, Bryant, R. D., et. al., *J. Heterocyclic Chem.*, 1995, 32, 1473-1476). Compound 29 can then be treated with a 2-hydroxy-benzonitrile under basic conditions at elevated temperatures to form 30x (see for example, Chung, H.-A., et. al., *J Heterocyclic Chem.*, 1999, 36, 413-421). Compound 30x may then be treated with aqueous acid in the appropriate solvent at elevated temperatures or any conditions appropriate to remove a nitrogen linked THP group to afford compound 31x as described in the following reference (see for example, Bryant, R. D., et. al., *J Heterocyclic Chem.*, 1995, 32, 1473-1476). Compound 31x can then be treated under the appropriate conditions to convert an aromatic nitrile to an aromatic amide to produce compound 34 (see for example, Clark, R. L., Pessolano, A. A., Shen, T.-Y., Jacobus, D. P., Jones, H., *J. Med. Chem.*, 1978, 21(9), 965-978). The chloro of compound 34 can be removed under standard hydrogenation conditions to produce compound 35 (see for example, Tavares, F. X., et. al., *J. Med. Chem.*, 2004, 47, 4716-4730). Compound 35 may then be treated under conditions to convert an aromatic amide to an aromatic nitrile to produce compound 28x (see for example, Fray, M. J., Allen, P., Bradley, P. R., Challenger, C. E., Closier, M., Evans, T. J., Lewis, M. L., Mathias, J. P., Nichols, C. L., Po-Ba, Y. M., Snow, H., Stefaniak, M. H., Vuong, H. V., *Heterocycles*, 2006, 67(2), 489-494). The alky- Compounds 40(a-x) can be synthesized following the reactions outlined in Scheme 12. The synthesis for compound 29 can be prepared as described in the literature (see for example, Bryant, R. D., et. al., *J. Heterocyclic Chem.*, 1995, 32, 1473-1476). Compound 29 can then be treated with the sodium salt of the desired alcohols which can be prepared under standard dissolving metal conditions (see for example, Alhaique, F., Riccieri, F. M., Santucci, E., *Tet. Lett.*, 1975, 3, 174-174). Compound 29 can then be treated with the appropriate salt of the required alcohols and heated to elevated temperatures to afford compounds 36(a-x) (see for example, Alhaique, F., Riccieri, F. M., Santucci, E., *Tet. Lett.*, 1975, 3, 174-174; Tavares, F. X., Boucheron, J. A., Dickerson, S. H., Griffin, R. J., Preugschat, F., Thomson, S. A., Wang, T. Y., Zhou, H.-Q. *J. Med. Chem.*, 2004, 47, 4716-4730). Compounds 36(a-x) may then be treated with aqueous acid in the appropriate solvent at elevated temperatures or any conditions appropriate to remove a nitrogen linked protecting group, such as tetrahydropyran, to afford compounds 37(a-x) (see for example, Bryant, R. D., et. al., *J. Heterocyclic Chem.*, 1995, 32, 1473-1476). The chloro of compounds 37(a-x) may be removed under standard hydrogenation conditions to produce compounds 38(a-x) (see for example, Tavares, F. X., et. al., *J. Med. Chem.*, 2004, 47, 4716-4730). The alkylating reagents, compounds 20(a-x), can be prepared as previously described in Scheme 7 and Scheme 8. Compounds 38(a-x) can be treated under standard deprotonation conditions, preferably sodium hydride, then further reacted with compounds 20(a-x) to afford compounds 39(a-x) (see for example, New, J. S., Christopher, W. L., Jass, P. A., *J. Org. Chem.*, 1989, 54, 990-992). The ester of compounds 39(a-x) can be hydrolyzed under standard hydrolysis condition to produce the acids, compounds 40(a-x), as described in reaction Scheme 12 (see for example, New, J. S., Christopher, W. L., Jass, P. A., *J. Org. Chem.*, 1989, 54, 990-992).

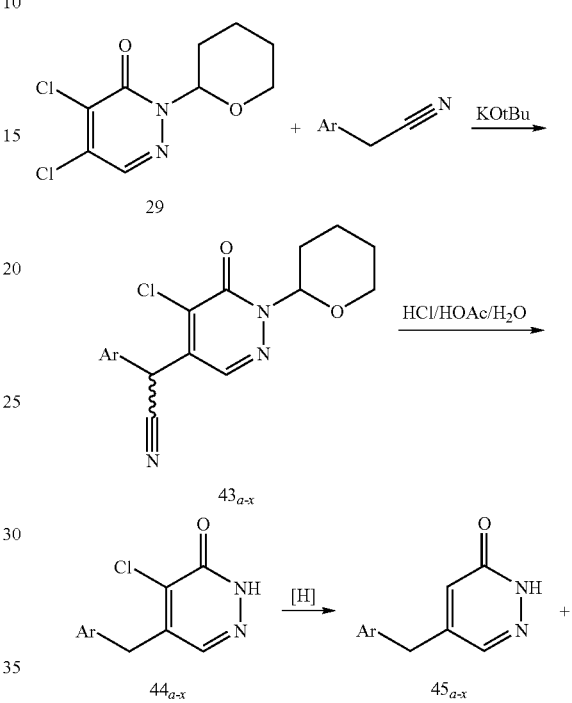

990-992). The alkylating reagents, compounds 20(a-x), can be prepared as previously described in Scheme 7 and Scheme 8. The ester of compounds 41 (a-x) can be hydrolyzed under standard hydrolysis condition to produce the acids, compounds 42(a-x), as described in reaction Scheme 13 (see for example, New, J. S., Christopher, W. L., Jass, P. A., *J. Org. Chem.*, 1989, 54, 990-992).

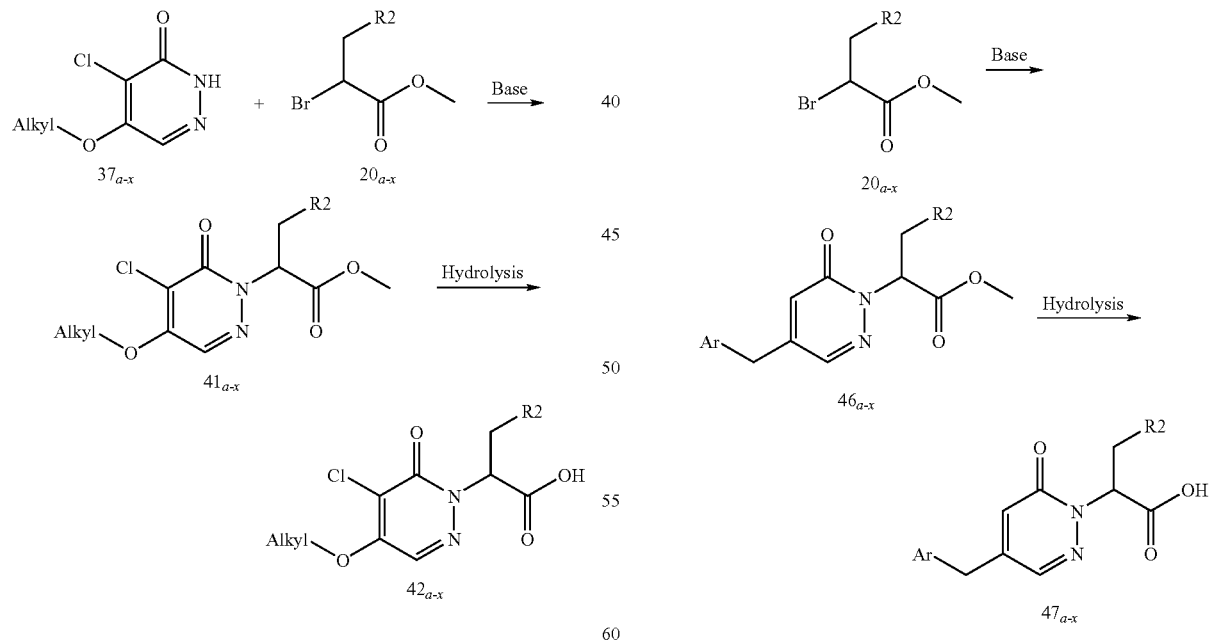

Compounds 42(a-x) can be synthesized following the reactions outlined in Scheme 13. Compounds 37(a-x), prepared as previously described in Scheme 12, can be treated under standard deprotonation conditions, preferably sodium hydride, then further reacted with compounds 20(a-x) to afford compounds 41 (a-x) (see for example, New, J. S., Christopher, W. L., Jass, P. A., *J. Org. Chem.*, 1989, 54, Compounds 47(a-x) can be synthesized following the reactions outlined in Scheme 14. The synthesis for compound 29 can be prepared as described in the literature (see for example, Bryant, R. D., et. al., *J. Heterocyclic Chem.*, 1995, 32, 1473-1476). Compound 29 can then be treated with an appropriate nitrile containing reagent under standard conditions to form the carbon linked aryl or heteroaryl derivative, compounds 43(a-x), under basic conditions at elevated temperatures (see for example, Salturo, F., et. al., PCT WO 2000/17204; Carroll, R. D., et. al., *J. Med. Chem.*, 1983, 26, 96-100; PCT Inter. Appl., WO 2007009913). The resulting nitrile containing compounds, compounds 43(a-x), can be treated with aqueous acid and heated at elevated temperatures to afford compounds 44(a-x) (see for example, Salturo, F., et. al., PCT WO 2000/17204; Carroll, R. D., et. al., J. Med. Chem., 1983, 26, 96-100; PCT Inter. Appl. WO 2007009913). The chloro of compounds 44(a-x) can be removed under standard hydrogenation conditions to produce compounds 45(a-x) (see for example, Tavares, F. X., et. al., *J. Med. Chem.*, 2004, 47, 4716-4730). The alkylating reagents, compounds 20(a-x), can be prepared as previously described in Scheme 7 and Scheme 8. Compounds 45(a-x) can be treated under standard deprotonation conditions, preferably sodium hydride, then further reacted with compounds 20(a-x) to afford compounds 46(a-x) (see for example, New, J. S., Christopher, W. L., Jass, P. A., *J. Org. Chem.*, 1989, 54, 990-992). The ester of compounds 46(a-x) can be hydrolyzed under standard hydrolysis condition to produce the acids, compounds 47(a-x), as described in reaction Scheme 14 (see for example, New, J. S., Christopher, W. L., Jass, P. A., *J. Org. Chem.*, 1989, 54, 990-992).

Scheme 15

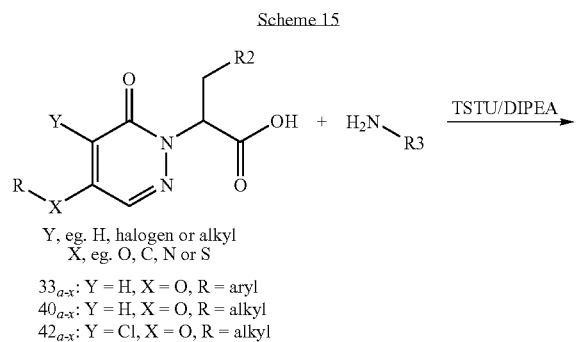

Y, eg. H, halogen or alkyl
X, eg. O, C, N or S $33_{a-x}$: Y = H, X = O, R = aryl
$40_{a-x}$: Y = H, X = O, R = alkyl
$42_{a-x}$: Y = Cl, X = O, R = alkyl

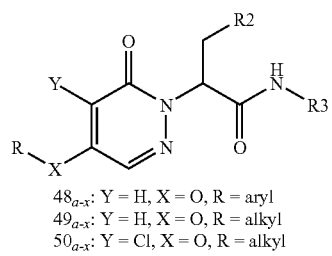

$48_{a-x}$: Y = H, X = O, R = aryl
$49_{a-x}$: Y = H, X = O, R = alkyl
$50_{a-x}$: Y = Cl, X = O, R = alkyl Compounds 48(a-x), 49(a-x) and 50(a-x) may be synthesized following the reactions outlined in Scheme 15. The carboxylic acids, compounds 33(a-x), or 40(a-x) or 42(a-x), and the appropriate commercially available or synthetically accessible amines such as the amino compounds described in reaction Schemes 1-6 may be treated under standard amide bond formation conditions to afford compounds 48(a-x), 49(a-x) and 50(a-x) (see for example, Montalbetti, C. A. G. N., Falque, V., *Tetrahedron*, 2005, 61, 10827-10852). Final deprotection or chemical conversion of 48(a-x), 49(a-x) and 50(a-x) may be required to produce the desired final compound.

Scheme 16

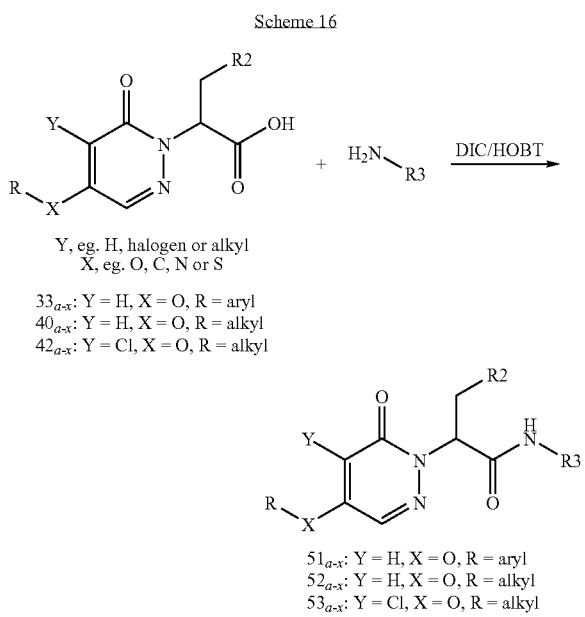

Y, eg. H, halogen or alkyl
X, eg. O, C, N or S $33_{a-x}$: Y = H, X = O, R = aryl
$40_{a-x}$: Y = H, X = O, R = alkyl
$42_{a-x}$: Y = Cl, X = O, R = alkyl $51_{a-x}$: Y = H, X = O, R = aryl
$52_{a-x}$: Y = H, X = O, R = alkyl
$53_{a-x}$: Y = Cl, X = O, R = alkyl Compounds 51(a-x), 52(a-x) and 53(a-x) may be synthesized following the reactions outlined in Scheme 16. The carboxylic acids, compounds 33(a-x), or 40(a-x) or 42(a-x), and the appropriate commercially available or synthetically accessible amines such as the amino compounds described in reaction Schemes 1-6 may be treated under standard amide bond formation conditions to afford compounds 51 (a-x), 52(a-x) and 53(a-x) (see for example, Montalbetti, C. A. G. N., Falque, V., *Tetrahedron*, 2005, 61, 10827-10852). Final deprotection or chemical conversion of 51 (a-x), 52(a-x) and 53(a-x) may be required to produce the desired final compound.

Scheme 17

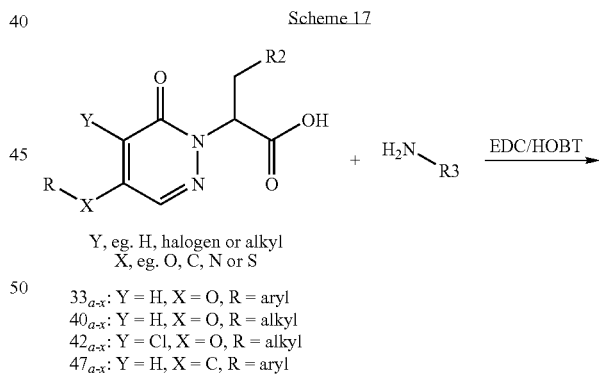

Y, eg. H, halogen or alkyl
X, eg. O, C, N or S $33_{a-x}$: Y = H, X = O, R = aryl
$40_{a-x}$: Y = H, X = O, R = alkyl
$42_{a-x}$: Y = Cl, X = O, R = alkyl
$47_{a-x}$: Y = H, X = C, R = aryl

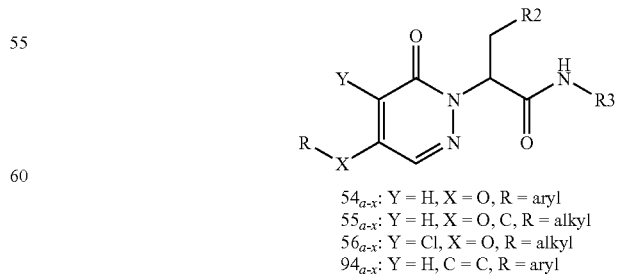

$54_{a-x}$: Y = H, X = O, R = aryl
$55_{a-x}$: Y = H, X = O, C, R = alkyl
$56_{a-x}$: Y = Cl, X = O, R = alkyl
$94_{a-x}$: Y = H, C = C, R = aryl Compounds 54(a-x), 55(a-x), 56(a-x), and 94(a-x) may be synthesized following the reactions outlined in Scheme 17.

The carboxylic acids, compounds 33(a-x), or 40(a-x) or 42(a-x), or 47(a-x) and the appropriate commercially available amine or synthetically accessible amines such as the amino compounds described in reaction Schemes 1-6 may be treated under standard amide bond formation conditions to afford compounds 54(a-x), 55(a-x), 56(a-x) and 94(a-x) (see for example, Montalbetti, C. A. G. N., Falque, V., *Tetrahedron*, 2005, 61, 10827-10852). Final deprotection or chemical conversion of 54(a-x), 55(a-x), 56(a-x) and 94(a-x) may be required to produce the desired final compound.

Scheme 18

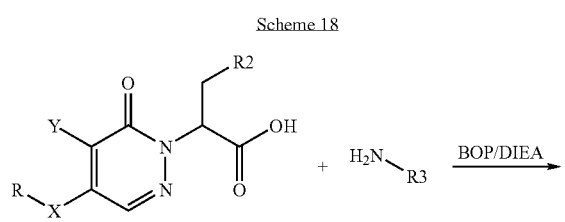

Y, eg. H, halogen or alkyl
X, eg. O, C, N or S

33$_{a-x}$: Y = H, X = O, R = aryl
40$_{a-x}$: Y = H, X = O, R = alkyl
42$_{a-x}$: Y = Cl, X = O, R = alkyl

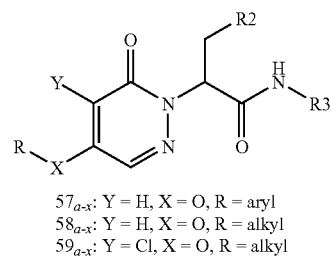

57$_{a-x}$: Y = H, X = O, R = aryl
58$_{a-x}$: Y = H, X = O, R = alkyl
59$_{a-x}$: Y = Cl, X = O, R = alkyl Compounds 57(a-x), 58(a-x) and 59(a-x) may be synthesized following the reactions outlined in Scheme 18. The carboxylic acids, compounds 33(a-x), or 40(a-x) or 42(a-x), and the appropriate commercially available or synthetically accessible amines such as the amino compounds described in reaction Schemes 1-6 may be treated under standard amide bond formation conditions to afford compounds 57(a-x), 58(a-x) and 59(a-x) (see for example, Montalbetti, C. A. G. N., Falque, V., *Tetrahedron*, 2005, 61, 10827-10852). Final deprotection or chemical conversion of 57(a-x), 58(a-x) and 59(a-x) may be required to produce the desired final compound.

Scheme 19

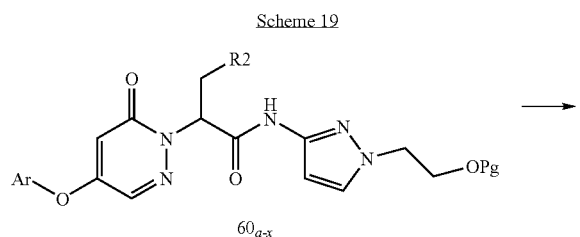

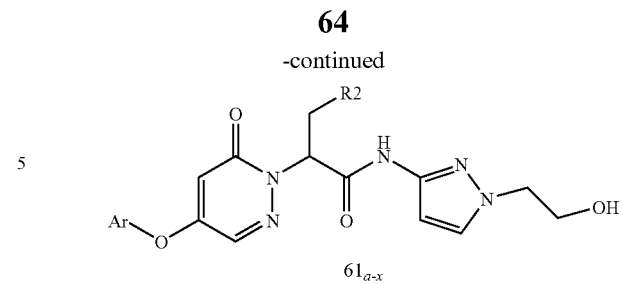

Compounds 61(a-x) may be synthesized following the reactions outlined in Scheme 19. The protecting groups, preferably silyl protecting groups, of compounds 60(a-x), may be removed to reveal the corresponding hydroxyl compounds, compounds 61(a-x). The protecting groups may be removed through conventional procedures known in the literature (see for example, Greene, T. W. *Protective Groups in Organic Synthesis*; John Wiley & Sons, Inc.: New York, 1991, p. 77-81).

Scheme 20

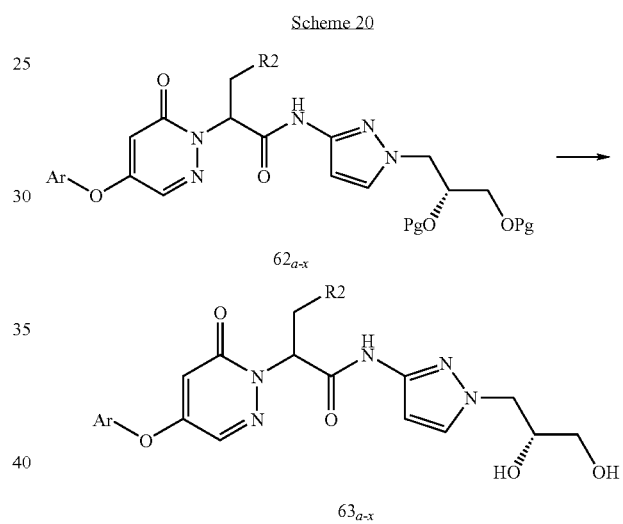

Compounds 63(a-x) may be synthesized following the reactions outlined in Scheme 20. The protected di-hydroxy compounds, compounds 62(a-x), may be converted to the corresponding di-hydroxyl compounds, compounds 63(a-x) through conventional procedures known in the literature (see for example, Greene, T. W. *Protective Groups in Organic Synthesis*; John Wiley & Sons, Inc.: New York, 1991, p. 123-127).

Scheme 21

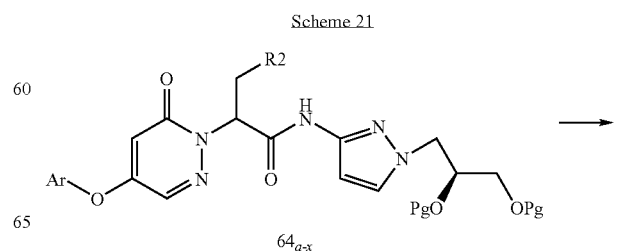

-continued

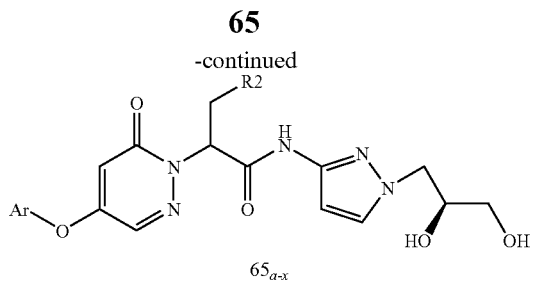

65ₐ₋ₓ

Compounds 65(a-x) may be synthesized following the reactions outlined in Scheme 21. The protected di-hydroxy compounds, compounds 64(a-x), may be converted to the corresponding di-hydroxyl compounds, compounds 65(a-x) through conventional procedures known in the literature (see for example, Greene, T. W. *Protective Groups in Organic Synthesis*; John Wiley & Sons, Inc.: New York, 1991, p. 123-127).

Scheme 22

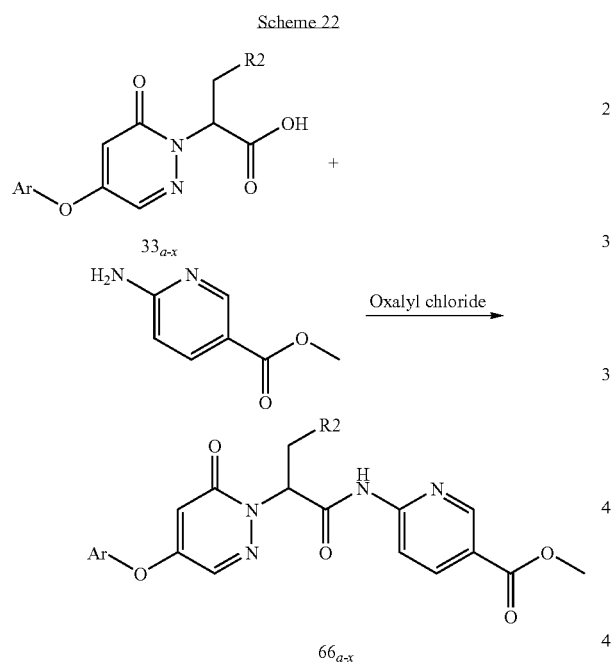

Compounds 66(a-x) may be synthesized following the reactions outlined in Scheme 22. The carboxylic acids, compounds 33(a-x) and the appropriate commercially available amine or synthetically accessible amines may be treated under standard amide bond formation conditions to afford compounds 66(a-x) (see for example, Montalbetti, C. A. G. N., Falque, V., *Tetrahedron*, 2005, 61, 10827-10852).

Scheme 23

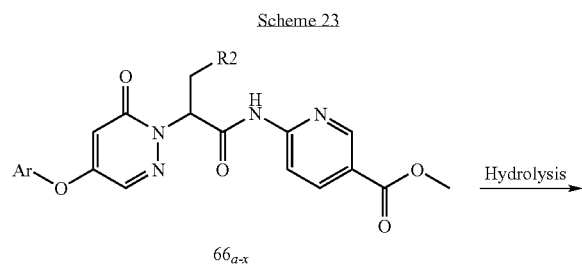

-continued

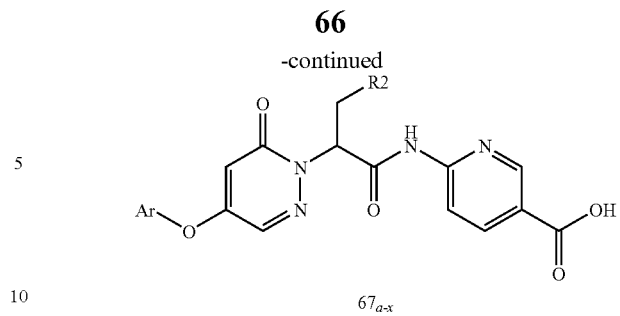

67ₐ₋ₓ

Compounds 67(a-x) may be synthesized following the reactions outlined in Scheme 23. The carboxylic acid ester, compounds 66(a-x) may be treated under standard basic hydrolysis conditions to produce compounds 67(a-x) (see for example PCT Inter. Appl. WO2005054200).

Scheme 24

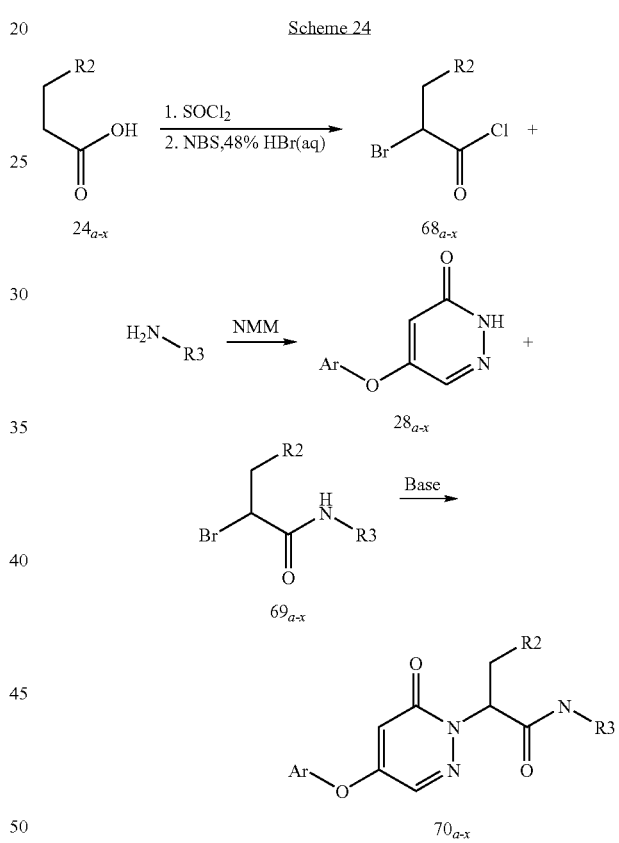

Compounds 70(a-x) may be synthesized following the reactions outlined in Scheme 24. The substituted acids of compounds 24(a-x) may be obtained through commercial sources or can be produced through reactions as described previously (Scheme 8). The resulting substituted acids, compounds 24(a-x), can then be treated under standard conditions to produce acid chlorides followed by in situ generation of the alpha bromides, compounds 68(a-x) (see for example PCT Int. Appl. WO 2003/055482). The acid chlorides may then be treated with an appropriately substituted amine (see for example PCT Int. Appl. WO 2007/104034 A2). Compounds 28(a-x) can be treated under standard deprotonation conditions, preferably sodium hydride, then further reacted with the compounds 69(a-x) to afford compounds 70(a-x) (see for example, New, J. S., Christopher, W. L., Jass, P. A., *J. Org.*

Chem., 1989, 54, 990-992). Final deprotection or chemical conversion of 70(a-x) may be required to produce the desired final compound.

Scheme 25

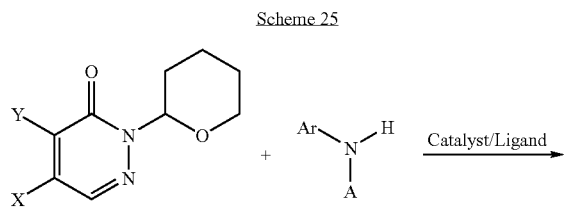

29: Y = Cl, X = Cl
or
26: Y = H, X = I

A = H or alkyl

Catalyst/Ligand

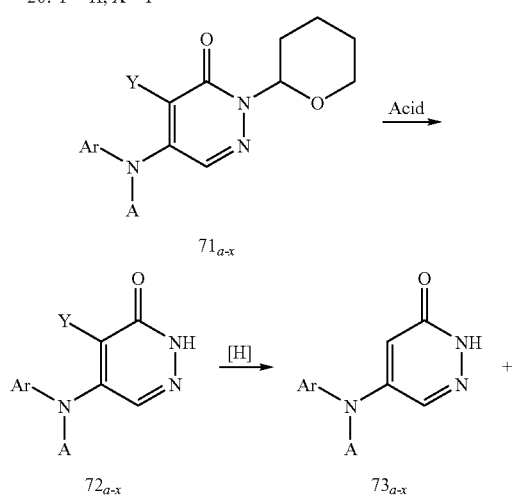

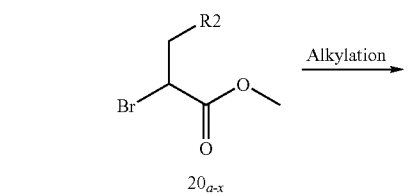

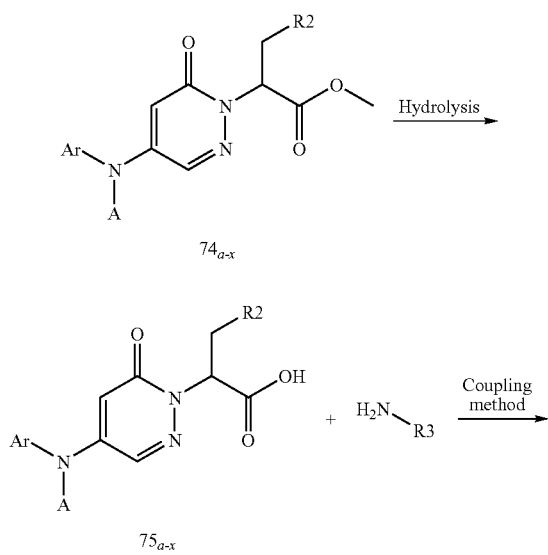

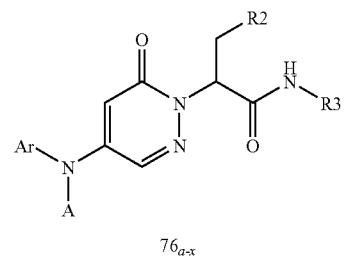

76$_{a\text{-}x}$

Compounds 76(a-x) can be synthesized following the reactions outlined in Scheme 25. The synthesis for compound 29 can be prepared as described in the literature (see for example, Bryant, R. D., et. al., J. Heterocyclic Chem., 1995, 32, 1473-1476). The synthesis for compound 26 can be prepared as described in Scheme 9 from 3,4-dichloro-5-hydroxy-5H-furan-2-one using conventional methods (see for example, Krajsovszky, G.; et al, J. Molecular Structure, 2005, 713, 235-243). Compound 29 or 26 may then be treated with a aryl or heteroaryl amine reagent under standard conditions to form the nitrogen linked aryl or heteroaryl derivatives, compounds 71 (a-x), (see for example, Halasz, B. D.-H., Monsieurs, K., Elias, O., Karolyhazy, L., Tapolcsanyi, P., Maes, B. U. W., Riedl, Z., Hajos, G., Dommisse, R. A., Lemiere, G. L. F., Kosmrlj, J., Matyus, P., Tetrahedron, 2004, 60, 2283-2291). Compound 71 (a-x) where Y is chloro can then be treated with aqueous acid in the appropriate solvent at elevated temperatures or any conditions appropriate to remove a nitrogen linked THP group to afford compounds 72(a-x) where Y is chloro as described in the following reference (see for example, Bryant, R. D., et. al., J. Heterocyclic Chem., 1995, 32, 1473-1476). In the compounds 72(a-x) where Y is chloro, the chloro functionality may be removed under standard hydrogenation conditions to produce compounds 73(a-x) (see for example, Tavares, F. X., et. al., J. Med. Chem., 2004, 47, 4716-4730). Compound 71 (a-x) where Y is hydrogen can then be treated with aqueous acid in the appropriate solvent at elevated temperatures or any conditions appropriate to remove a nitrogen linked THP group to afford compounds 73(a-x) where Y is hydrogen as described in the following reference (see for example, Bryant, R. D., et. al., J Heterocyclic Chem., 1995, 32, 1473-1476). The alkylating reagents, compounds 20(a-x), can be prepared as previously described in Scheme 7 and Scheme 8. Compounds 73(a-x) can be treated under standard deprotonation conditions, preferably sodium hydride, then further reacted with the compounds 20(a-x) to afford compounds 74(a-x) (see for example, New, J. S., Christopher, W. L., Jass, P. A., J. Org. Chem., 1989, 54, 990-992). The ester of compounds 74(a-x) can then be hydrolyzed under standard hydrolysis condition to produce the acids, compounds 75(a-x) (see for example, New, J. S., Christopher, W. L., Jass, P. A., J. Org. Chem., 1989, 54, 990-992). The carboxylic acids, compounds 75(a-x) and the appropriate commercially available amine or synthetically accessible amines such as the amino compounds described in reaction Schemes 1-6 may be treated under standard amide bond formation conditions to afford compounds 76(a-x), as described in reaction Scheme 25 (see for example, Montalbetti, C. A. G. N., Falque, V., Tetrahedron, 2005, 61, 10827-10852). Final deprotection or chemical conversion of 76(a-x) may be required to produce the desired final compound.

Scheme 26

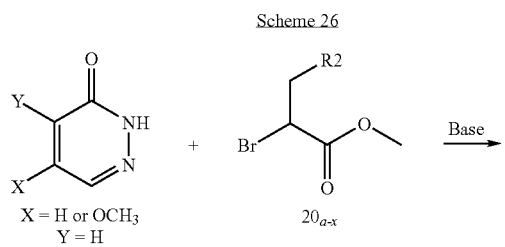

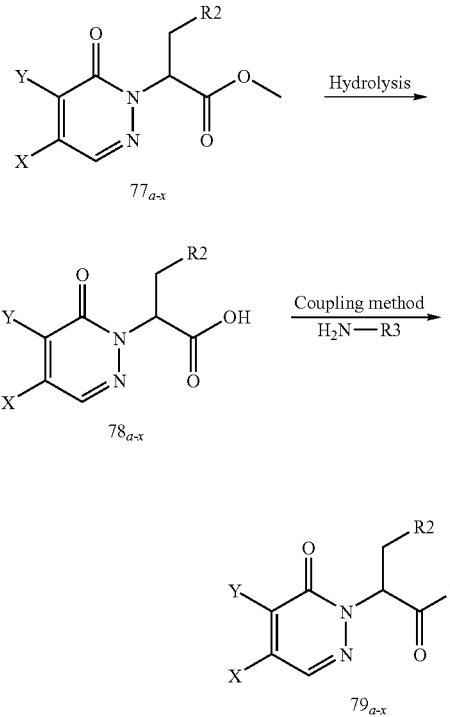

Scheme 27

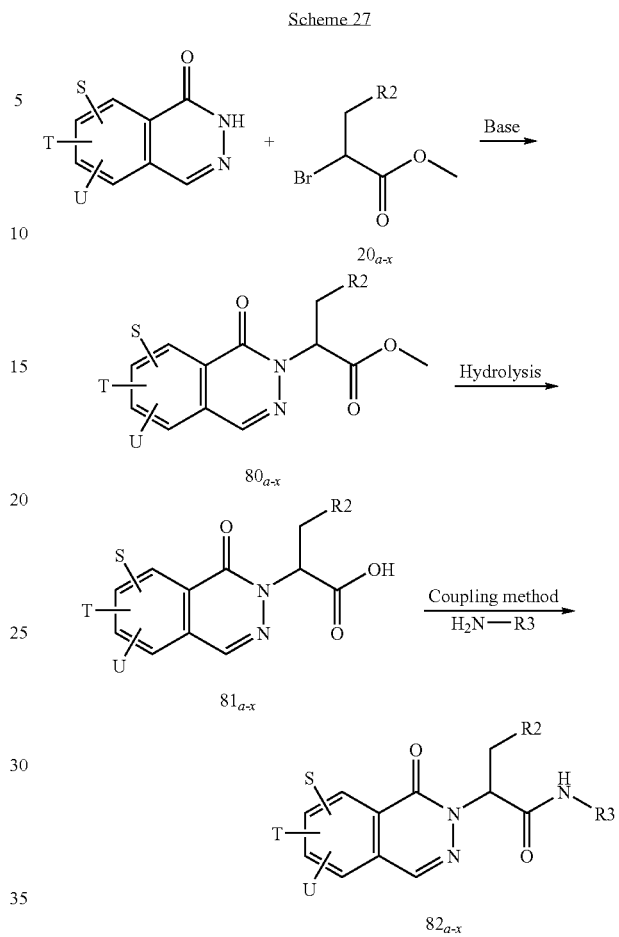

Compounds 79(a-x) may be synthesized following the reactions outlined in Scheme 26. The alkylating reagents, compounds 20(a-x), can be prepared as previously described in Scheme 7 and Scheme 8. Compounds 77(a-x) can be treated under standard deprotonation conditions, preferably sodium hydride, then further reacted with compounds 20(a-x) and the appropriately substituted pyridazinone compounds to afford compounds 77(a-x) (see for example, New, J. S., Christopher, W. L., Jass, P. A., *J. Org. Chem.,* 1989, 54, 990-992). The ester of compounds 77(a-x) can then be hydrolyzed under standard hydrolysis condition to produce the acids, compounds 78(a-x) (see for example, New, J. S., Christopher, W. L., Jass, P. A., *J. Org. Chem.,* 1989, 54, 990-992). The carboxylic acids, compounds 78(a-x) and the appropriate commercially available amine or synthetically accessible amines such as the amino compounds described in reaction Schemes 1-6 may be treated under standard amide bond formation conditions to afford compounds 79(a-x), as described in reaction Scheme 26 (see for example, Montalbetti, C. A. G. N., Falque, V., *Tetrahedron,* 2005, 61, 10827-10852). Final deprotection or chemical conversion of 79(a-x) may be required to produce the desired final compound.

Compounds 82(a-x) may be synthesized following the reactions outlined in Scheme 27. The alkylating reagents, compounds 20(a-x), can be prepared as previously described in Scheme 7 and Scheme 8. Compounds 80(a-x) can be prepared from the appropriately substituted commercially available or synthetically accessible 2H-phthalazin-1-one compounds, such as 6-methyl-1-(2H)-phthalazinone, 5-methyl-1-(2H)-phthalazinone, 6-methoxy-1-(2H)-phthalazinone, 8-methyl-1-(2H)-phthalazinone, or 5-fluoro-1-(2H)-phthalazinone (Napoletano, M.; Norcini, G.; Pellacini, F.; Marchini, F.; Morazzoni, G.; Fattori, R.; Ferlenga, P.; Pradella, L. *Bioorganic & Med. Chem. Lett.* 2001, 12, 5-8.; Francis, J. E.; Doebel, K. J.; Schutte, P. M.; Savarese, E. C.; Hopkins, S. E.; Bachmann, E. F. Canadian J. Chem. 1979, 57, 3320-31) under standard deprotonation conditions, preferably sodium hydride, and the compounds of formula 20(a-x) (see for example, New, J. S., Christopher, W. L., Jass, P. A., *J. Org. Chem.,* 1989, 54, 990-992). The ester of compounds 80(a-x) can then be hydrolyzed under standard hydrolysis conditions to produce the acids, compounds 81 (a-x) (see for example, New, J. S., Christopher, W. L., Jass, P. A., *J. Org. Chem.,* 1989, 54, 990-992). The carboxylic acids, compounds 81(a-x) and the appropriate commercially available amine or synthetically accessible amines such as the amino compounds described in reaction Schemes 1-6 may be treated under standard amide bond formation conditions to afford compounds 82(a-x), as described in reaction Scheme 27 (see for example, Montalbetti, C. A. G. N., Falque, V., *Tetrahedron,* 2005, 61, 10827-10852). Final deprotection or chemical conversion of 82(a-x) may be required to produce the desired final compound.

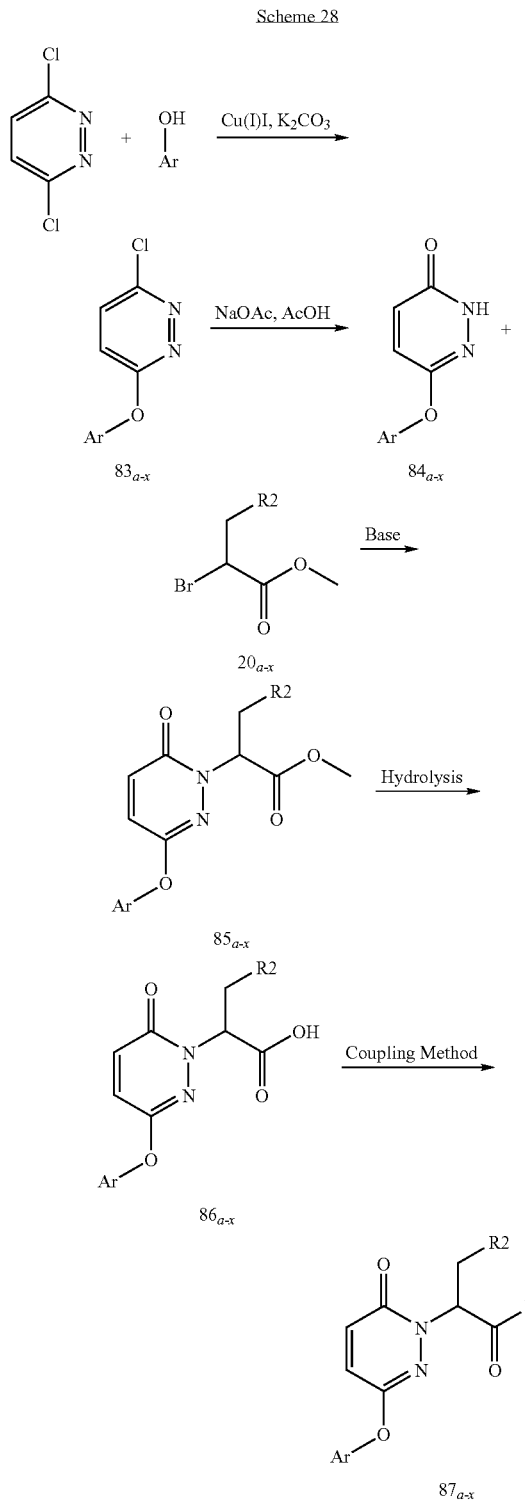

Scheme 28

Compounds 87(a-x) can be synthesized following the reactions outlined in Scheme 28. 3,6-Dichloro-pyridazine may be treated with a phenol-like reagent under standard conditions to form the oxygen linked aryl or heteroaryl derivatives, compounds 83(a-x) (see for example PCT Inter. Appl. WO 2007009913). Compound 83(a-x) can then be treated with sodium acetate in acetic acid at elevated temperatures to afford compounds 84(a-x) (see for example, see for example, PCT Inter. Appl. WO 00/17204; Carroll, R. D., et. al., *J. Med. Chem.*, 1983, 26, 96-100; PCT Inter. Appl., WO 2007/009913). The alkylating reagents, compounds 20(a-x), can be prepared as previously described in Scheme 7 and Scheme 8. Compounds 84(a-x) can be treated under standard deprotonation conditions, preferably sodium hydride, then further reacted with the compounds 20(a-x) to afford compounds 85(a-x) (see for example, New, J. S., Christopher, W. L., Jass, P. A., *J. Org. Chem.*, 1989, 54, 990-992). The ester of compounds 85(a-x) can be hydrolyzed under standard hydrolysis condition to produce the acid, compounds 86(a-x), as described in reaction Scheme 10 (see for example, New, J. S., Christopher, W. L., Jass, P. A., *J. Org. Chem.*, 1989, 54, 990-992). The carboxylic acids, compounds 86(a-x), and the appropriate commercially available amine or synthetically accessible amines such as the amino compounds described in reaction Schemes 1-6 may be treated under standard amide bond formation conditions to afford compounds 87(a-x), as described in reaction Scheme 28 (see for example, Montalbetti, C. A. G. N., Falque, V., *Tetrahedron*, 2005, 61, 10827-10852). Final deprotection or chemical conversion of 87(a-x) may be required to produce the desired final compound.

Scheme 29

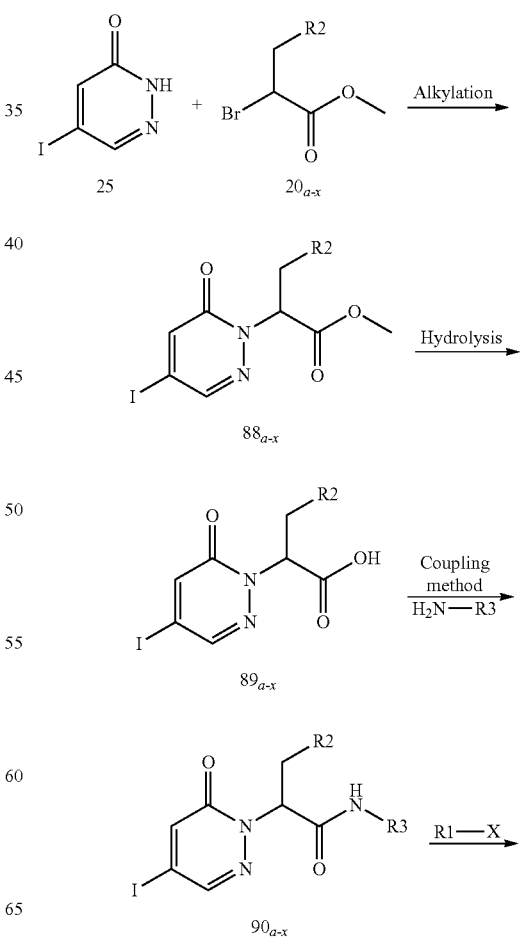

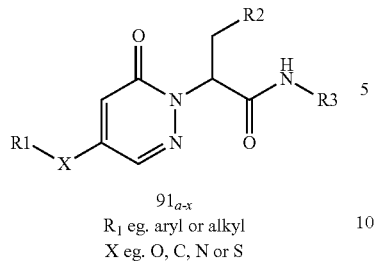

91<sub>a-x</sub>
R₁ eg. aryl or alkyl
X eg. O, C, N or S

Compounds 91 (a-x) can be synthesized following the reactions outlined in Scheme 29. The alkylating reagents, compounds 20(a-x), can be prepared as previously described in Scheme 7 and Scheme 8. Compound 25 can be prepared as previously described in Scheme 9. Compound 25 can be treated under standard deprotonation conditions, preferably sodium hydride, then further reacted with the compounds 20(a-x) to afford compounds 88(a-x) (see for example, New, J. S., Christopher, W. L., Jass, P. A., *J. Org. Chem.*, 1989, 54, 990-992). The ester of compounds 88(a-x) can be hydrolyzed under standard hydrolysis condition to produce the acid, compounds 89(a-x) (see for example, New, J. S., Christopher, W. L., Jass, P. A., *J. Org. Chem.*, 1989, 54, 990-992). The carboxylic acids, compounds 89(a-x), and the appropriate commercially available amine or synthetically accessible amine such as the amino compounds described in reaction Schemes 1-6 may be treated under standard amide bond formation conditions to afford compounds 90(a-x) (see for example, Montalbetti, C. A. G. N., Falque, V., *Tetrahedron*, 2005, 61, 10827-10852). Compound 90(a-x) may then be treated with an appropriate reagent under appropriate conditions to form the desired derivative, compounds 91 (a-x), as described in reaction Scheme 29 (see for example, Ma, D., Cai, Q. *Org. Lett.*, 2003, 5(21), 3799-3802; Chen, G., Chan, A. S. C., Kwong, *Tet. Lett.*, 2007, 48, 473-476). Final deprotection or chemical conversion of 91(a-x) may be required to produce the desired final compound.

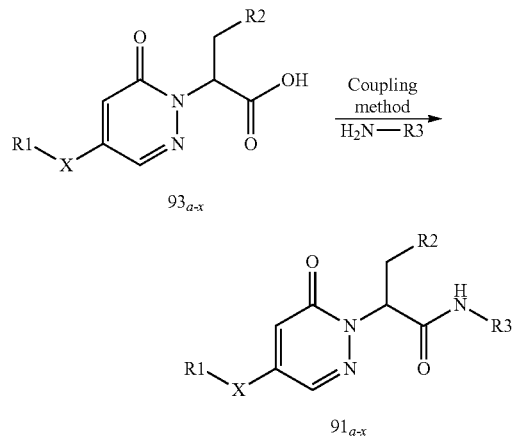

Compounds 91(a-x) can be synthesized following the reactions outlined in Scheme 30. Compounds 88(a-x) may be treated with an appropriate reagent under appropriate conditions to form the desired derivative, compounds 92(a-x) (see for example, Ma, D., Cai, Q. *Org. Lett.*, 2003, 5(21), 3799-3802; Chen, G., Chan, A. S. C., Kwong, *Tet. Lett.*, 2007, 48, 473-476). The ester of compounds 92(a-x) can be hydrolyzed under standard hydrolysis condition to produce the acid, compounds 93(a-x) (see for example, New, J. S., Christopher, W. L., Jass, P. A., *J. Org. Chem.*, 1989, 54, 990-992). The carboxylic acids, compounds 93(a-x), and the appropriate commercially available amine or synthetically accessible amine such as the amino compounds described in reaction Schemes 1-6 may be treated under standard amide bond formation conditions to afford compounds 91 (a-x), as described in reaction Scheme 30 (see for example, Montalbetti, C. A. G. N., Falque, V., *Tetrahedron*, 2005, 61, 10827-10852). Final deprotection or chemical conversion of 91 (a-x) may be required to produce the desired final compound.

Scheme 30

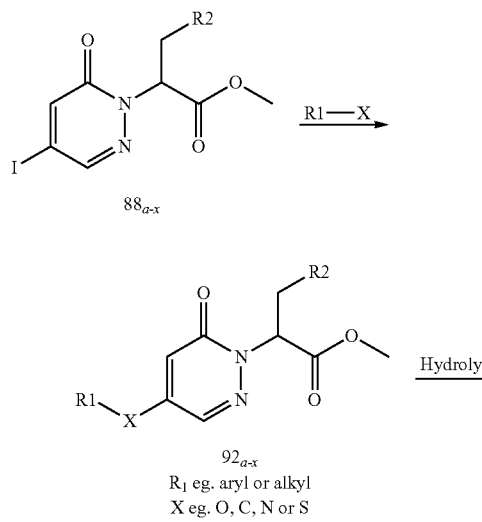

Scheme 31

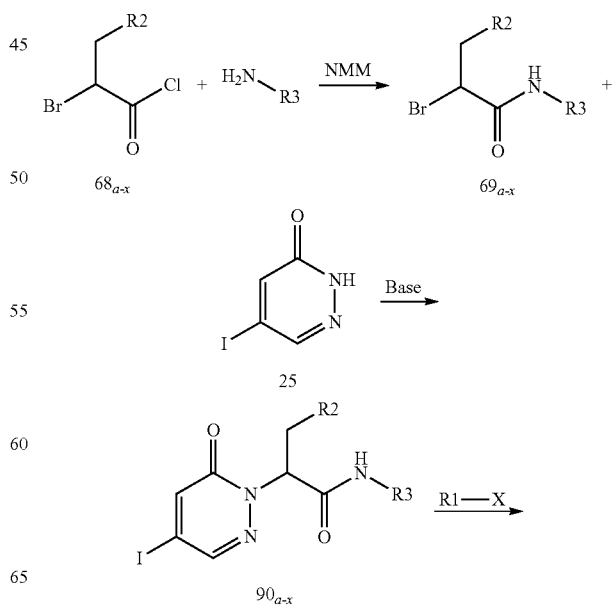

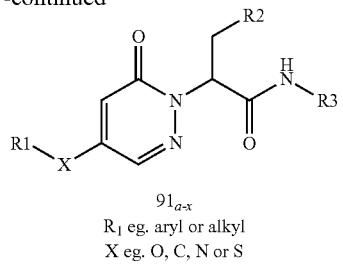

91$_{a-x}$

R$_1$ eg. aryl or alkyl
X eg. O, C, N or S

Compounds 91 (a-x) can be synthesized following the reactions outlined in Scheme 31. Compounds 68(a-x) can be prepared as previously described in Scheme 24 (see for example PCT Int. Appl. WO 2003055482). The acid chlorides 68(a-x) may then be treated with the appropriate commercially available amine or synthetically accessible amine such as the amino compounds described in reaction Schemes 1-6 to produce compounds 69(a-x) (see for example PCT Int. Appl. WO 2007104034). Compound 25 can be treated under standard deprotonation conditions, preferably sodium hydride, then further reacted with the compounds 69(a-x) to afford compounds 90(a-x) (see for example, New, J. S., Christopher, W. L., Jass, P. A., *J. Org. Chem.*, 1989, 54, 990-992). Compounds 90(a-x) may then be treated with an appropriate reagent under appropriate conditions to form the desired derivative, compounds 91 (a-x), as described in reaction Scheme 31 (see for example, Ma, D., Cai, Q. *Org. Lett.*, 2003, 5(21), 3799-3802; Chen, G., Chan, A. S. C., Kwong, *Tet. Lett.*, 2007, 48, 473-476). Final deprotection or chemical conversion of 91 (a-x) may be required to produce the desired final compound.

Compounds 99R and 99S may be synthesized following the reactions outlined in Scheme 32. Compound 104 can be prepared as described in PCT Int. Appl. 2006094770 and oxidized under Swern conditions to give the corresponding aldehyde 105 as described in *Org. Lett.*, 2005, 7, 1423. Aldehyde 105 can be treated with allyl magnesium bromide to afford a mixture of diasteromeric alcohols (1:1 ratio) 95R and 95S which can be chromatographically separated. Either diastereomer 95R or 95S can be treated with base, such as sodium hydride, and then allylated with allyl bromide to afford the corresponding ethers 96R or 96S. Either ether can undergo ring closure matathesis by treating with Grubbs second generation catalyst as described in *Org. Lett.*, 1999, 1, 953, to give dihydropyrans 97R or 97S. These compounds can be treated with catalytic amount of p-toluene sulfonic acid in methanol and tetrahydrofuran to deprotect the acetonide with a similar procedure described in *Tet. Lett.*, 1991, 32, 54, and the olefin can be hydrogenated to give the corresponding protected amino alcohols 98R or 98S. Oxidation of the amino alcohol to a corresponding amino acid can be carried out according to *J. Org. Chem.*, 1999, 64, 2564. The deprotection of the N-butoxycarbonyl group with acid may afford the corresponding amino acids 99R or 99S.

Scheme 33

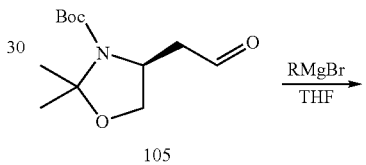

105

Scheme 32

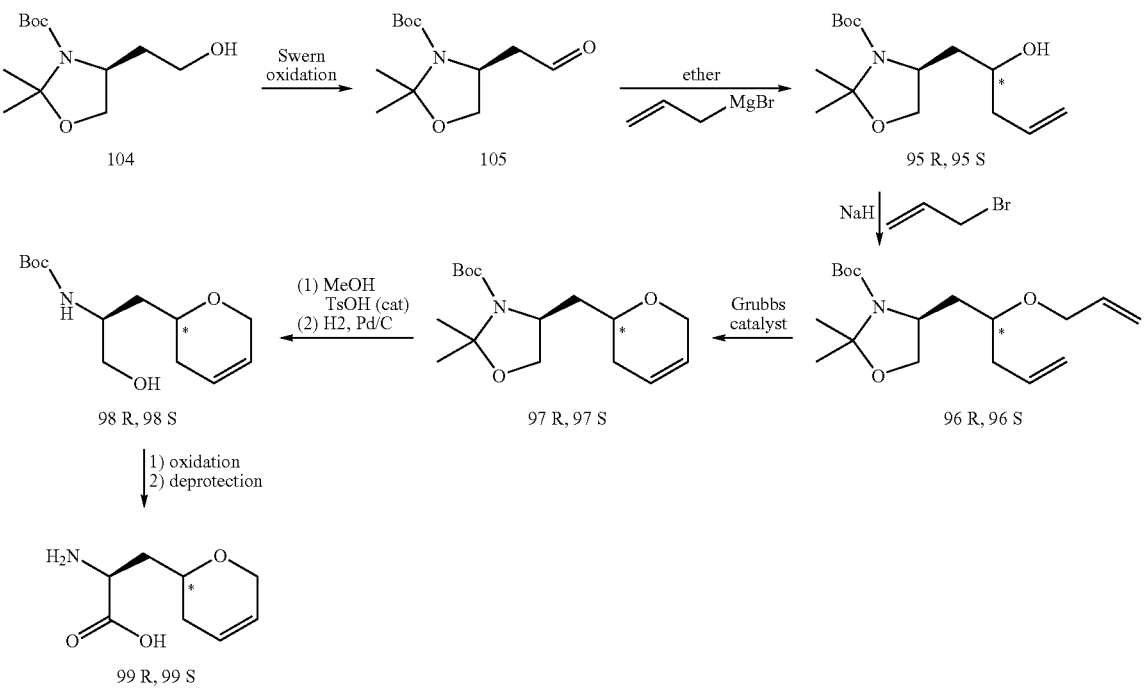

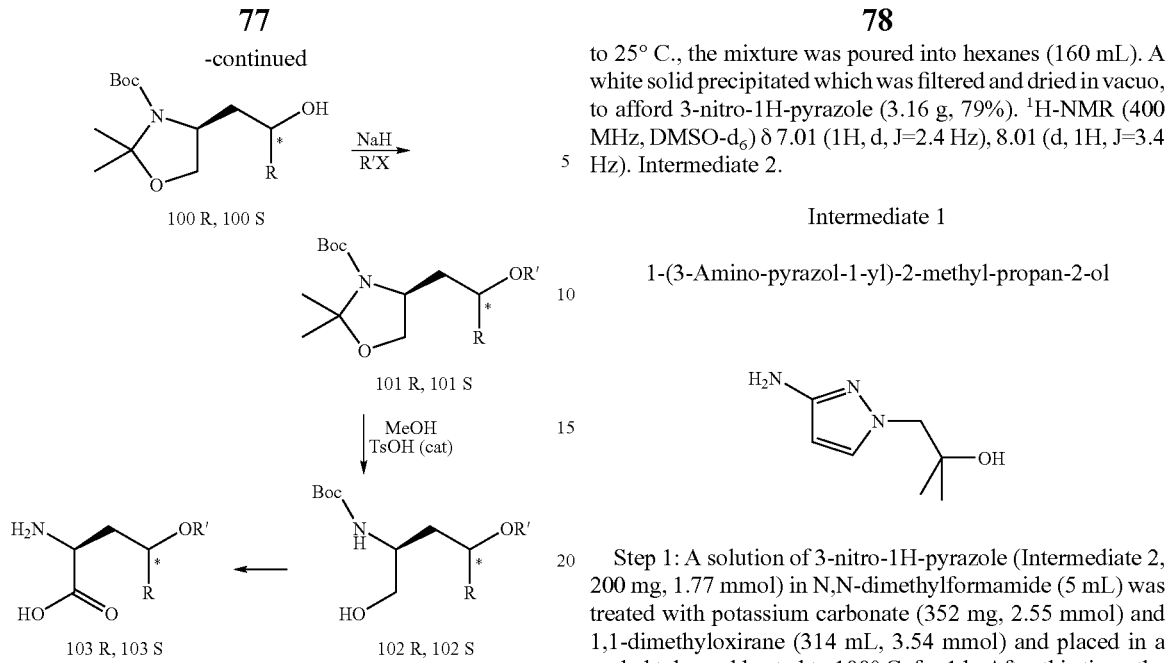

Compounds 103R and 103S may be synthesized following the reactions outlined in Scheme 33. Aldehyde 105 can be treated with alkyl magnesium bromides to afford a mixture of diasteromeric alcohols 100R and 100S (1:1 ratio) which can be chromatographically separated, where R can be alkyl group such as methyl. The Grignard addition reaction can be carried out with a similar method as described in Synlett, 2005, 13, 2083. Either diastereomer 100R or 100S can be treated with base, such as sodium hydride, and then alkylated with alkyl halides to afford the corresponding ethers 101R or 101S, where R' can be alkyl group such as ethyl. In the case where R' is ethyl group, ethyl iodide can be used as alkyl halide. These compounds can be treated with catalytic amount of p-toluene sulfonic acid in methanol and tetrahydrofuran to deprotect the acetonide with a similar procedure described in Tet. Lett., 1991, 32, 54, to give the corresponding protected amino alcohols 102R or 102S. Oxidation of the amino alcohol to a corresponding amino acid can be carried out according to J. Org. Chem., 1999, 64, 2564. The deprotection of the N-butoxycarbonyl group with acid may afford the corresponding amino acids 103R or 103S.

The invention will now be further described in the Examples below, which are intended as an illustration only and do not limit the scope of the invention.

EXAMPLES

Part I

Preparation of Preferred Intermediates

Intermediate 2

3-Nitro-1H-pyrazole

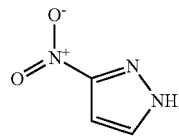

A solution of 1-nitro-1H-pyrazole (4.00 g, 35.4 mmol) in benzonitrile (40 mL) was refluxed for 2 h. After being cooled to 25° C., the mixture was poured into hexanes (160 mL). A white solid precipitated which was filtered and dried in vacuo, to afford 3-nitro-1H-pyrazole (3.16 g, 79%). $^1$H-NMR (400 MHz, DMSO-$d_6$) δ 7.01 (1H, d, J=2.4 Hz), 8.01 (d, 1H, J=3.4 Hz). Intermediate 2.

Intermediate 1

1-(3-Amino-pyrazol-1-yl)-2-methyl-propan-2-ol

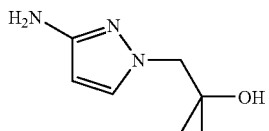

Step 1: A solution of 3-nitro-1H-pyrazole (Intermediate 2, 200 mg, 1.77 mmol) in N,N-dimethylformamide (5 mL) was treated with potassium carbonate (352 mg, 2.55 mmol) and 1,1-dimethyloxirane (314 mL, 3.54 mmol) and placed in a sealed tube and heated to 100° C. for 1 h. After this time, the reaction was cooled to 25° C., diluted with water (10 mL) and extracted with ethyl acetate (3×10 mL). The organic layers were then combined and dried over sodium sulfate, filtered and concentrated in vacuo. Silica gel column chromatography (AnaLogix, 12 g column, 50-60% ethyl acetate/hexanes) afforded 2-methyl-1-(3-nitro-pyrazol-1-yl)-propan-2-ol (175 mg, 54%) as a clear colorless oil; ES-HRMS m/e calcd for $C_7H_{11}N_3O_3$ (M+H)$^+$ 186.0873, observed 186.0873. $^1$H-NMR (300 MHz, CDCl$_3$) δ ppm 1.25 (s, 6H), 2.11 (br s, 1H), 4.18 (s, 2H), 6.92 (d, J=2.4 Hz, 1H), 7.60 (d, J=2.4 Hz, 1H).

Step 2: In a Parr shaker bottle was placed 2-methyl-1-(3-nitro-pyrazol-1-yl)-propan-2-ol (100 mg, 0.54 mmol), 10% palladium on activated carbon (10 mg) and ethanol (5 mL). The bottle was then placed on the Parr shaker under hydrogen (50 psi) for 1 h. The reaction was then filtered through a pad of diatomaceous earth, washed with ethanol, and concentrated in vacuo to afford 1-(3-amino-pyrazol-1-yl)-2-methyl-propan-2-ol (78 mg, 94%), which was taken on to the next step without characterization.

Intermediate 3

1-[2-(tert-Butyl-dimethyl-silanyloxy)-ethyl]-1H-pyrazol-3-ylamine

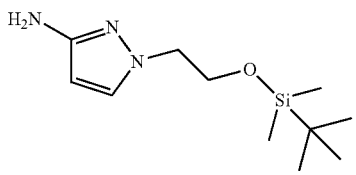

Step 1: A solution of 3-nitro-1H-pyrazole (Intermediate 2, 250 mg, 2.21 mmol) was dissolved in anhydrous N,N-dimethylformamide (5 mL) was treated with a 60% dispersion of sodium hydride in mineral oil (93 mg, 2.32 mmol) was added while stirring under nitrogen. After the effervescence ceased, the reaction stirred for an additional 10 min. At this time, the reaction was treated with (2-bromo-ethoxy)-tert-butyl-dimethyl-silane (598 mg, 2.50 mmol). The reaction continued to stir under nitrogen for 2 h. At this time, the solution was diluted with ethyl acetate (200 mL), washed with water (2×75 mL), a saturated aqueous sodium chloride solution (75 mL), dried over magnesium sulfate, filtered and concentrated in vacuo. Silica gel column chromatography (Merck silica gel 60, 40-63 µm; 5-25% ethyl acetate/hexanes) afforded 1-[2-(tert-butyl-dimethyl-silanyloxy)-ethyl]-3-nitro-1H-pyrazole (508 mg, 84%) as a yellow oil. $^1$H-NMR (400 MHz, DMSO-d$_6$) δ 0.00 (6H, s), 0.86 (9H, s), 4.03 (2H, t, J=5.6 Hz), 4.40 (2H, t, J=5.2 Hz), 7.11 (1H, d, J=2.4 Hz), 8.06 (1H, d, J=2.4 Hz).

Step 2: A solution of 1-[2-(tert-butyl-dimethyl-silanyloxy)-ethyl]-3-nitro-1H-pyrazole (500 mg, 1.80 mmol) in ethyl acetate (15 mL) and methanol (15 mL) was treated with 10% palladium on activated carbon (wet, 50 mg) The flask was charged with hydrogen gas via balloon. The reaction stirred at 25° C. for 16 h. The reaction was then filtered through a plug of silica gel (Merck, 60, 40-63 µm) layered with diatomaceous earth and concentrated in vacuo to afford 1-[2-(tert-butyl-dimethyl-silanyloxy)-ethyl]-1H-pyrazol-3-ylamine (391 mg, 90%) as a yellow oil. $^1$H-NMR (400 MHz, DMSO-d$_6$) δ 0.00 (6H, s), 0.83 (9H, s), 3.78 (2H, t, J=4.8 Hz), 3.87 (2H, t, J=6.0 Hz), 4.48 (2H, s), 5.33 (1H, d, J=2.0 Hz), 7.22 (1H, d, J=2.0 Hz).

Intermediate 4

1-((R)-2,2-Dimethyl-[1,3]dioxolan-4-ylmethyl)-1H-pyrazol-3-ylamine

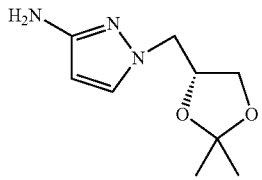

Step 1: A solution of 3-nitro-1H-pyrazole (Intermediate 2, 12.0 g, 106 mmol) in N,N-dimethylformamide (150 mL) was treated with para-toluenesulfonic acid (S)-2,2-dimethyl-[1,3]dioxolan-4-ylmethyl ester (25.5 g, 89.0 mmol), and potassium carbonate (24.5 g, 178 mmol). The reaction mixture was heated to 90° C. for 6 h under nitrogen. After this time, the reaction mixture was diluted with ethyl acetate, washed with water and a saturated aqueous sodium chloride solution, dried over sodium sulfate, filtered, rinsed and concentrated in vacuo. Silica gel column chromatography (ISCO 120 g, 5-30% ethyl acetate/hexanes) afforded 1-((R)-2,2-dimethyl-[1,3]dioxolan-4-ylmethyl)-3-nitro-1H-pyrazole (14.5 g, 73%) as a light yellow oil; ESI-LRMS m/e calcd for C$_9$H$_{13}$N$_3$O$_4$ [M+H$^+$] 228, found 228 [M+H$^+$].

Step 2: 1-((R)-2,2-Dimethyl-[1,3]dioxolan-4-ylmethyl)-3-nitro-1H-pyrazole (14.5 g) in ethanol (60 mL) was treated with 10% palladium on activated carbon (1.4 g). The mixture was placed on a Parr shaker and exposed to hydrogen (50 psi) for 16 h. After this time, the mixture was filtered through diatomaceous earth. The filtrate was concentrated in vacuo to afford 1-((R)-2,2-dimethyl-[1,3]dioxolan-4-ylmethyl)-1H-pyrazol-3-ylamine (12.4 g, 98%) as an amorphous yellow oil; ESI-LRMS m/e calcd for C$_9$H$_{15}$N$_3$O$_2$ [M+H$^+$] 198, found 198 [M+H$^+$]. $^1$H NMR (300 MHz, DMSO-d$_6$) δ ppm 1.24 (s, 3H), 1.30 (s, 3H), 3.70 (dd, J=8.5, 6.0 Hz, 1H), 3.85-4.02 (m, 3H), 4.28 (quin, J=6.0 Hz, 1H), 4.56 (s, 2H), 5.36 (d, J=2.1 Hz, 1H), 7.30 (d, J=2.1 Hz, 1H).

Intermediate 5

1-((S)-2,2-Dimethyl-[1,3]dioxolan-4-ylmethyl)-1H-pyrazol-3-ylamine

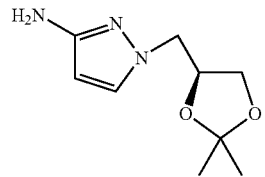

Step 1: A solution of 3-nitro-1H-pyrazole (Intermediate 2, 205 mg, 1.81 mmol) in anhydrous N,N-dimethylformamide (3.5 mL) was treated with (R)-glycidol (148 mg, 2.00 mmol) and potassium carbonate (770 mg, 5.58 mmol). The mixture was heated in a sealed vial at 120° C. for 1 h. After this time, the mixture was diluted with water (15 mL) and extracted with ethyl acetate (6×25 mL). The combined organic layers were washed with a saturated aqueous sodium chloride solution (15 mL), dried over magnesium sulfate, filtered and concentrated in vacuo. Silica gel column chromatography (Teledyne Isco RediSep Flash Column 40 g, 15-100% ethyl acetate/hexanes) afforded (S)-3-(3-nitro-pyrazol-1-yl)-propane-1,2-diol (118 mg, 34%) as a thick yellow oil. $^1$H-NMR (400 MHz, CD$_3$OD) δ 3.55 (2H, d, J=5.2 Hz), 4.02-4.05 (1H, m), 4.20 (1H, dd, J=13.6 Hz, 7.6 Hz), 4.39 (1H, dd, J=14.0 Hz, 3.6 Hz), 6.92 (1H, d, J=2.0 Hz), 7.79 (1H, d, J=2.0 Hz).

Step 2: A solution of (S)-3-(3-nitro-pyrazol-1-yl)-propane-1,2-diol (1 g, 5.34 mmol) in 2,2-dimethoxypropane (8.5 mL, 0.63M) and tetrahydrofuran (10 mL, 0.53 M) was treated with para-toluenesulfonic acid monohydrate (0.11 g, 0.57 mmol). The reaction was stirred under nitrogen at 25° C. overnight. After this time, the reaction was concentrated in vacuo. Silica gel column chromatography (Aspire 40 g, 20-45% ethyl acetate/hexanes) afforded 1-((S)-2,2-dimethyl-[1,3]dioxolan-4-ylmethyl)-3-nitro-1H-pyrazole (348.5 mg, 29%) as a viscous yellow/orange oil. The material was used without further purification.

Step 3: A solution of 1-((S)-2,2-dimethyl-[1,3]dioxolan-4-ylmethyl)-3-nitro-1H-pyrazole (348.4 mg, 1.53 mmol) in methanol (10 mL, 0.15M) in a high pressure reaction bottle was treated with 10% palladium on activated carbon (19.5 mg). The mixture was placed on a Parr shaker and exposed to hydrogen (40 psi) overnight. After this time, the reaction mixture was filtered through a pad of diatomaceous earth and rinsed with ethanol. The filtrate was concentrated in vacuo to afford 1-((S)-2,2-dimethyl-[1,3]dioxolan-4-ylmethyl)-1H- pyrazol-3-ylamine (237.4 mg, 1.20 mmol) as a viscous, yellow oil. The material was used without further purification.

Intermediate 7

3-(2,5-Dimethyl-pyrrol-1-yl)-1-methyl-1H-pyrazole

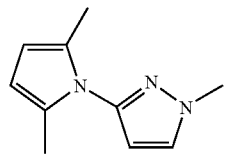

A solution of 1-methyl-1H-pyrazol-3-ylamine (0.92 g, 9.5 mmol) in benzene (4.8 mL) was treated with hexane-2,5-dione (1.34 mL, 11.4 mmol) and para-toluenesulfonic acid (182 mg, 0.95 mmol) and was heated to 115° C. under Dean-Stark conditions for 4 h. After this time, the reaction was cooled to 25° C., concentrated in vacuo and dried under high vacuum overnight. The resulting residue was dissolved in methylene chloride (100 mL) and was washed with water (1×150 mL), dried over sodium sulfate, filtered and concentrated in vacuo. Silica gel column chromatography (ISCO, 80 g, 1:4 ethyl acetate/hexanes) afforded 3-(2,5-dimethyl-pyrrol-1-yl)-1-methyl-1H-pyrazole (1.57 g, 94%) as a green oil; ES$^+$-HRMS m/e calcd for $C_{10}H_{13}N_3$ [M+H$^+$] 176.1182, found 176.1182.

Intermediate 6

5-Chloro-1-methyl-1H-pyrazol-3-ylamine

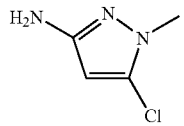

Step 1: A solution of 3-(2,5-dimethyl-pyrrol-1-yl)-1-methyl-1H-pyrazole (Intermediate 7, 0.51 g, 2.91 mmol) in tetrahydrofuran (25 mL) cooled to −70° C. was treated dropwise with a 2.5M solution of n-butyllithium in hexanes (1.3 mL, 3.25 mmol). The reaction was stirred at −70° C. for 2.6 h. After this time, the reaction was treated dropwise over 2-3 min with a solution of hexachloroethane (0.77 g, 3.2 mmol) in tetrahydrofuran (2.5 mL). The reaction was maintained at −70° C. for 20-25 min. After this time, the cooling bath was removed. The reaction continued to stir for 90 min, at which time the reaction was concentrated in vacuo. The residue was then partitioned between water (50 mL) and diethyl ether (1×50 mL). The organics were washed with a saturated aqueous sodium chloride solution (1×50 mL), dried over magnesium sulfate, filtered, rinsed with diethyl ether and concentrated in vacuo. Silica gel column chromatography (AnaLogix, 40 g, 5-10% ethyl acetate/hexanes) afforded 5-chloro-3-(2,5-dimethyl-pyrrol-1-yl)-1-methyl-1H-pyrazole (0.36 g, 60%) as a light brown solid; ES$^+$-HRMS m/e calcd for $C_{10}H_{12}N_3Cl$ [M+H$^+$] 210.0793, found 210.0792.

Step 2: A mixture of hydroxylamine hydrochloride (608.5 mg, 8.75 mmol) in ethanol (6.5 mL) was treated with a solution of potassium hydroxide (247.6 mg, 4.41 mmol) in water (3.6 mL) and ethanol (3.6 mL) followed by addition of 5-chloro-3-(2,5-dimethyl-pyrrol-1-yl)-1-methyl-1H-pyrazole (0.36 g, 1.75 mmol). The resulting reaction mixture was heated in a sealed tube at 105° C. for 2 d. After this time, the reaction was cooled to 25° C. The reaction was then diluted with water (50 mL) and extracted with diethyl ether (3×50 mL) and methylene chloride (1×50 mL). The combined organics were washed with a saturated aqueous sodium bicarbonate solution (4×50 mL), water (1×50 mL), a saturated aqueous sodium chloride solution (1×50 mL), dried over magnesium sulfate, filtered, rinsed with methylene chloride and concentrated in vacuo. Silica gel column chromatography (AnaLogix, 40 g, 10-100% ethyl acetate/hexanes) afforded 5-chloro-1-methyl-1H-pyrazol-3-ylamine (34.9 mg, 15%) as an orange solid; ES$^+$-HRMS m/e calcd for $C_4H_6N_4Cl$ [M+H$^+$] 132.0323, found 132.0323.

Intermediate 8

5-Amino-2-methyl-2H-pyrazole-3-carboxylic acid methyl ester

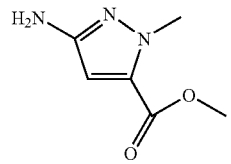

Step 1: A solution of 3-(2,5-dimethyl-pyrrol-1-yl)-1-methyl-1H-pyrazole (Intermediate 7, 0.56 g, 3.21 mmol) (Intermediate 7) in tetrahydrofuran (26.8 mL) cooled to −78° C. was treated dropwise with a 2.5M solution of n-butyllithium in hexanes (1.44 mL, 3.60 mmol). The reaction was stirred at −78° C. for 1.5 h. After this time, the reaction was treated dropwise with methyl chloroformate (0.28 mL, 3.63 mmol). After this time, the cooling bath was removed. The reaction continued to stir for 1 h, at which time the reaction was concentrated in vacuo. The residue was then partitioned between water (100 mL) and diethyl ether (3×75 mL). The organics were dried over sodium sulfate, filtered, and concentrated in vacuo. Silica gel column chromatography (ISCO, 40 g, 5-10% ethyl acetate/hexanes) afforded 5-(2,5-dimethyl-pyrrol-1-yl)-2-methyl-2H-pyrazole-3-carboxylic acid methyl ester (0.33 g, 44%) as an off-white solid; ES$^+$-HRMS m/e calcd for $C_{12}H_{15}N_3O_2$ [M+H$^+$] 234.1237, found 234.1237.

Step 2: A mixture of hydroxylamine hydrochloride (453 mg, 6.52 mmol) in ethanol (4.85 mL) was treated with a solution of potassium hydroxide (197.5 mg, 3.52 mmol) in water (2.93 mL) and ethanol (2.93 mL) followed by addition of 5-(2,5-dimethyl-pyrrol-1-yl)-2-methyl-2H-pyrazole-3-carboxylic acid methyl ester (0.32 g, 1.40 mmol). The resulting reaction mixture was heated in a sealed tube at 105° C. for 3 d. After this time, the reaction was cooled to 25° C. and then concentrated in vacuo. The residue was then partitioned between water (150 mL) and diethyl ether (3×75 mL). The combined organics were washed with a saturated aqueous sodium bicarbonate solution (2×150 mL), dried over sodium sulfate, filtered, and concentrated in vacuo. Silica gel column chromatography (AnaLogix, 40 g, 10-100% ethyl acetate/ hexanes) afforded 5-amino-2-methyl-2H-pyrazole-3-carboxylic acid methyl ester (34.9 mg, 16%) as an orange-brown solid; ES⁺-HRMS m/e calcd for $C_6H_9N_3O_2$ [M+H⁺] 156.0768, found 156.0767.

Intermediate 9

1-Methyl-5-trifluoromethyl-1H-pyrazol-3-ylamine

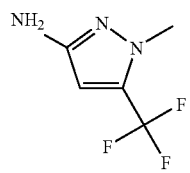

Step 1: A 1.8M solution of lithium diisopropylamide in tetrahydrofuran (49.9 mL, 89.8 mmol) cooled to −78° C. in a three-neck round-bottom flask was treated dropwise via an addition funnel with a solution of methyltrifluoroacetate (7.85 mL, 78.09 mmol) and acetonitrile (8.15 mL, 156.18 mmol) in tetrahydrofuran (100 mL). Upon complete addition, the reaction was maintained at −78° C. for 1 h. After this time, the reaction was warmed to 0° C. and maintained at 0° C. for 1 h. After this time, the reaction was further warmed to 25° C. and was then maintained at 25° C. for 1 h. After this time, the reaction was poured onto ice/water (~50 mL). The resulting bilayer was concentrated in vacuo to remove organics. The resulting liquid was extracted with diethyl ether (2×100 mL). The aqueous layer was acidified with a 2N aqueous hydrochloric acid solution and then further extracted with methylene chloride (2×75 mL) and diethyl ether (2×50 mL). All of the organic extracts were combined, dried over sodium sulfate, filtered and concentrated in vacuo to afford a crude mixture of 4,4,4-trifluoro-3-oxo-butyronitrile as an orange residue. The material was used without further purification.

Step 2: The crude 4,4,4-trifluoro-3-oxo-butyronitrile (assume 78.09 mmol) in ethanol (39 mL, 2M) at 25° C. was treated dropwise with methylhydrazine (4.11 mL, 78.09 mmol). The resulting solution was heated at reflux for 4 h. After this time, the reaction was cooled to 25° C., the reaction was stirred at 25° C. overnight. After this time, the reaction was concentrated in vacuo. Supercritical fluid chromatography (DAICEL OD, 10% methanol, 70 mL/min) afforded an inseparable mixture of 1-methyl-5-trifluoromethyl-1H-pyrazol-3-ylamine and 2-methyl-5-trifluoromethyl-2H-pyrazol-3-ylamine (500 mg, 4%) as a yellow oil. ¹H-NMR (300 MHz, DMSO-d₆) δ ppm 3.67 (s, 1.8H), 3.75 (s, 3H), 4.33 (s, 2H), 4.95 (s, 1.2H), 5.89 (s, 0.6H), 6.30 (s, 1H).

Intermediate 10

2-Bromo-3-cyclopentyl-propionic acid methyl ester

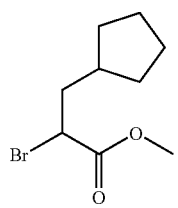

Step 1: A solution of 3-cyclopentyl-propionic acid (28.5 mL, 200 mmol) in carbon tetrachloride (20 mL) at 25° C. was treated with thionyl chloride (58.1 mL, 800 mmol). The reaction was then heated to 65° C. for 30 min. After this time, the reaction was removed from the heat and was then treated with N-bromosuccinimide (42.7 g, 240 mmol), carbon tetrachloride (100 mL) and a 48% aqueous hydrogen bromide solution (20 drops). The reaction was then heated to 85° C. overnight. After this time, the reaction was cooled to 25° C. and then further cooled to 0° C. The mixture was filtered through a pad of diatomaceous earth and washed with carbon tetrachloride (50 mL). The filtrate was cooled to 0° C. and then carefully treated with methanol until no further gas evolution was observed. After this time, the dark brown solution was concentrated in vacuo. The remaining liquid was then partitioned between water (150 mL) and pentane (3×100 mL). The combined organics were washed with a saturated aqueous sodium bicarbonate solution (2×150 mL), dried over sodium sulfate, filtered and concentrated in vacuo. Silica gel column chromatography (ISCO, 330 g, 99.5-98% hexanes/ethyl acetate) afforded 2-bromo-3-cyclopentyl-propionic acid methyl ester (32.3 g, 68%) as a yellow liquid; EI⁺-HRMS m/e calcd for $C_9H_{15}O_2Br$ [M+H⁺] 233.0177, found 233.0177.

In an analogous manner, there were obtained:

Intermediate 11

2-Bromo-4-methyl-pentanoic acid methyl ester

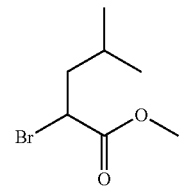

Using the method described in Intermediate 10, 4-methyl-pentanoic acid afforded 2-bromo-4-methyl-pentanoic acid methyl ester which was obtained as a colorless liquid (11.3 g, 68%); EI⁺-HRMS m/e calcd for $C_7H_{13}O_2Br$ [M+H⁺] 207.0021 found 207.0023.

Intermediate 12

2-Bromo-3-cyclohexyl-propionic acid methyl ester

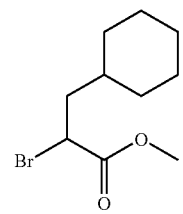

Using the method described in Intermediate 10, 3-cyclohexyl-propionic acid afforded 2-bromo-3-cyclohexyl-propionic acid methyl ester which was obtained as a light yellow liquid (8.82 g, 34%); EI+-HRMS m/e calcd for $C_{10}H_{17}O_2Br$ [M+] 248.0412 found 248.0408.

Intermediate 13

2-Bromo-3-phenyl-propionic acid methyl ester

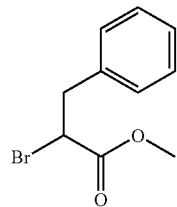

Using the method described in Intermediate 10, 3-phenyl-propionic acid afforded 2-bromo-3-phenyl-propionic acid methyl ester which was obtained as a clear liquid (9.49 g, 58%); EI+-HRMS m/e calcd for $C_{10}H_{11}O_2Br$ [M+H+] 240.9864 found 240.9863.

Intermediate 14

2-Bromo-3-(tetrahydro-pyran-4-yl)-propionic acid methyl ester

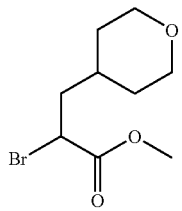

Step 1: 2-tert-Butoxycarbonylamino-3-(tetrahydro-pyran-4-yl)-propionic acid (500 mg, 1.82 mmol) at 25° C. was treated with a saturated aqueous potassium bromide solution (0.40 mL) and a 48% aqueous hydrogen bromide solution (1.22 mL). The reaction was stirred at 25° C. for 30 min. After this time, the resulting solution was cooled to 0° C. and was then treated portionwise with sodium nitrite (252 mg). Upon complete addition of the sodium nitrite, the reaction was stirred at 0° C. for 45 min and then at 25° C. for 30 min. The resulting brown solution was then extracted with diethyl ether (3×30 mL). The combined organics were dried over sodium sulfate, filtered, and concentrated in vacuo. The resulting residue was dissolved in diethyl ether, transferred to a flask with ground glass joints and was cooled to 0° C. Diazomethane was generated by treating a bilayer of 30% aqueous potassium hydroxide and diethyl ether with N-methyl-N'-nitro-N-nitrosoguanidine until a yellow color persisted. The upper ether layer was decanted off and then added to the cooled reaction until a yellow color persisted. The reaction was then allowed to warm to 25° C. and was stirred at 25° C. overnight. After this time, the reaction was concentrated in vacuo to afford 2-bromo-3-(tetrahydro-pyran-4-yl)-propionic acid methyl ester (301.3 mg, 65%) as a pale, green oil which was used without further purification; EI+-HRMS m/e calcd for $C_9H_{15}O_3Br$ [M+] 250.0205 found 250.0203.

In an analogous manner, there was obtained:

Intermediate 15

2-Bromo-3-(2,6-difluoro-phenyl)-propionic acid methyl ester

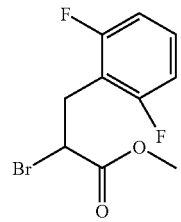

Using the method described in Intermediate 14, 2-amino-3-(2,6-difluoro-phenyl)-propionic acid afforded 2-bromo-3-(2,6-difluoro-phenyl)-propionic acid methyl ester which was obtained as a light yellow liquid (3.35 g, 48%); EI+-HRMS m/e calcd for $C_{10}H_9O_2BrF_2$ [M+H+] 276.9676 found 276.9676.

Intermediate 16

2-Bromo-3-cyclobutyl-propionic acid methyl ester

Step 1: A solution of cyclobutanemethanol (4.0 g, 46.4 mmol) in dichloromethane (28 mL) at 25° C. was treated with 4-dimethylaminopyridine (6.23 g, 50.9 mmol). The reaction was then cooled to 0° C. and was treated with para-toluenesulfonylchloride (8.95 g, 46.94 mmol). The reaction was allowed to slowly warm to 25° C. and was allowed to stir overnight. After this time, the reaction was partitioned between water (200 mL) and methylene chloride (2×200 mL). The combined organics were washed with a 1N aqueous hydrochloric acid solution and a saturated aqueous sodium chloride solution (1×200 mL), dried over magnesium sulfate, filtered and concentrated in vacuo to afford toluene-4-sulfonic acid cyclobutylmethyl ester (10.87 g, 97%) as colorless oil which was used without further purification.

Step 2: A solution of sodium ethoxide was prepared by treating ethanol (23 mL) at 25° C. portionwise with sodium metal (575 mg, 24.9 mmol). The reaction was stirred at 25° C. for 30 min at which time all of the sodium had dissolved. The reaction was then treated with diethylmalonate (4.83 mL, 31.8 mmol) and heated to 100° C. for 30 min. The reaction was then treated with toluene-4-sulfonic acid cyclobutylmethyl ester (5.46 g, 22.71 mmol) in ethanol (15 mL) over 10 min. The reaction then stirred at 100° C. overnight. After this time, the reaction was cooled to 25° C. and concentrated in vacuo. The residue was partitioned between water (100 mL) and diethyl ether (150 mL). The organics were washed with a 1N aqueous hydrochloric acid solution (100 mL), dried over sodium sulfate, filtered and was concentrated in vacuo. Silica gel column chromatography (ISCO, 80 g, 90-85% hexanes/ethyl acetate) afforded 2-cyclobutylmethyl-malonic acid diethyl ester (4.68 g, 90%) as a clear oil; EI+-HRMS m/e calcd for $C_{12}H_{20}O_4$ [M+] 228.1362, found 228.1362.

Step 3: A solution of 2-cyclobutylmethyl-malonic acid diethyl ester (4.68 g, 20.5 mmol) in ethanol (45.4 mL) was treated with a solution of potassium hydroxide (3.45 g, 61.5 mmol) in water (11.4 mL). The reaction was then heated to 110° C. overnight. After this time, the reaction was cooled to 25° C. and was concentrated in vacuo. The residue was diluted with water (50 mL) which was then acidified with a 2N aqueous hydrochloric acid solution and then extracted with a 90/10 methylene chloride/methanol solution (3×50 mL). The combined organics were dried over sodium sulfate, filtered and concentrated in vacuo to afford 2-cyclobutylmethyl-malonic acid (1.22 g, 34.7%) as a tan solid. This material was used without further purification.

Step 4: 2-Cyclobutylmethyl-malonic acid (1.20 g, 6.9 mmol) was heated at 195° C. for 2 h. After this time, the resulting brown solution was cooled to 25° C. and diluted with a 90/10 methylene chloride/methanol solution (50 mL). The organics were then washed with a saturated aqueous sodium chloride solution, concentrated in vacuo and azeotroped with acetonitrile (2×10 mL) to afford 3-cyclobutyl-propionic acid (770 mg, 85%) as brown oil. The material was used without further purification.

Step 5: A solution of 3-cyclobutyl-propionic acid (760 mg, 5.92 mmol) in carbon tetrachloride (0.59 mL) at 25° C. was treated with thionyl chloride (1.72 mL, 23.71 mmol). The reaction was then heated to 65° C. for 30 min. After this time, the reaction was removed from the heat and was then treated with N-bromosuccinimide (1.26 g, 7.11 mmol), carbon tetrachloride (3 mL) and a 48% aqueous hydrogen bromide solution (1 drop). The reaction was then heated to 85° C. for 3 h and was stirred at 25° C. overnight. After this time, the reaction was further cooled to 0° C. The mixture was filtered through a pad of diatomaceous earth and washed with carbon tetrachloride. The filtrate was cooled to 0° C. and then carefully treated with methanol until no further gas evolution was observed. After this time, the dark brown solution was concentrated in vacuo. The remaining liquid was then partitioned between water (100 mL) and pentane (3×75 mL). The combined organics were dried over sodium sulfate, filtered and concentrated in vacuo. Silica gel column chromatography (AnaLogix 12 g, 95/5 hexanes/ethyl acetate) afforded 2-bromo-3-cyclobutyl-propionic acid methyl ester (1.07 g, 81%) as a clear liquid; EI$^+$-HRMS m/e calcd for $C_8H_{13}O_2Br$ [M+H$^+$] 219.0021, found 219.0024.

Intermediate 17

2-Bromo-4-ethyl-hexanoic acid methyl ester

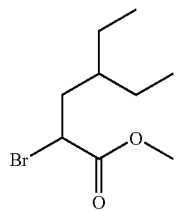

Step 1: A solution of sodium ethoxide was prepared by treating ethanol (24 mL) at 25° C. portionwise with sodium metal (595 mg, 25.9 mmol). The reaction was stirred at 25° C. until all of the sodium had dissolved. The reaction was then treated with diethylmalonate (5 mL, 32.9 mmol) and heated to 100° C. for 30 min. The reaction was then treated dropwise with a solution of 3-bromomethyl-pentane (4.58 g, 23.5 mmol) in ethanol (15.5 mL). The reaction then stirred at 100° C. overnight. After this time, the reaction was cooled to 25° C. and concentrated in vacuo. The residue was partitioned between water (100 mL) and diethyl ether (150 mL). The organics were washed with a 1N aqueous hydrochloric acid solution (150 mL), dried over sodium sulfate, filtered and concentrated in vacuo. Silica gel column chromatography (ISCO, 80 g, 90 hexanes/ethyl acetate) afforded 2-(2-ethyl-butyl)-malonic acid diethyl ester (4.8 g, 83%) as a clear liquid; EI$^+$-HRMS m/e calcd for $C_{13}H_{24}O_4$ [M+H] 245.1753, found 245.1757. $^1$H NMR (300 MHz, DMSO-d$_6$) δ ppm 0.80 (t, J=7.4 Hz, 6H) 1.17 (t, J=7.0 Hz, 6H) 1.20-1.36 (m, 5H) 1.71 (t, J=7.2 Hz, 2H) 3.45 (t, J=7.5 Hz, 1H) 4.11 (q, J=7.0 Hz, 4H).

Step 2: A solution of 2-(2-ethyl-butyl)-malonic acid diethyl ester (4.78 g, 19.5 mmol) in ethanol (43.5 mL) was treated with a solution of potassium hydroxide (3.3 g, 58.7 mmol) in water (10.9 mL). The reaction was then heated to 105° C. for 6 h. After this time, the reaction was concentrated in vacuo. The residue was diluted with water (50 mL) which was then acidified with a 2N aqueous hydrochloric acid solution and then extracted with a 90/10 methylene chloride/methanol solution (3×50 mL). The combined organics were dried over sodium sulfate, filtered and concentrated in vacuo to afford 2-(2-ethyl-butyl)-malonic acid (3.55 g, 96%) as an off-white solid, which was used without further purification; EI$^+$-HRMS m/e calcd for $C_9H_{16}O_4$ [M+Na]$^+$ 211.0941, found 211.0941. $^1$H NMR (300 MHz, DMSO-d$_6$) δ ppm 0.79 (t, J=7.4 Hz, 6H) 1.09-1.39 (m, 5H) 1.65 (t, J=7.1 Hz, 2H) 3.22 (t, J=7.5 Hz, 1H) 12.65 (br. s., 2H).

Step 3: 2-(2-Ethyl-butyl)-malonic acid (3.55 g, 18.8 mmol) was heated at 195° C. for 2 h. After this time, the solution was cooled to 25° C. and diluted with a 90/10 methylene chloride/methanol solution. The organics were then washed with a saturated aqueous sodium chloride solution, concentrated in vacuo and azeotroped with acetonitrile (2×50 mL) to afford 4-ethyl-hexanoic acid (1.24 mg, 45%) as yellow oil, which was used without further purification; EI$^+$-HRMS m/e calcd for $C_8H_{16}O_2$ [M–H]$^+$ 143.1072, found 143.1074. $^1$H NMR (300 MHz, DMSO-d$_6$) δ ppm 0.81 (t, J=7.2 Hz, 6H) 1.02-1.35 (m, 5H) 1.32-1.59 (m, 2H) 2.16 (t, J=7.8 Hz, 2H) 11.98 (br. s., 1H).

Step 4: A solution of 4-ethyl-hexanoic acid (1.24 mg, 8.5 mmol) in carbon tetrachloride (0.86 mL) at 25° C. was treated with thionyl chloride (2.5 mL, 34.3 mmol). The reaction was then heated to 65° C. for 30 min. After this time, the reaction was removed from the heat and was then treated with N-bromosuccinimide (1.84 g, 10.3 mmol), carbon tetrachloride (4.3 mL) and a 48% aqueous hydrogen bromide solution (2 drop). The reaction was then heated to 85° C. for 3 h and then cooled to 25° C. After this time, the reaction was further cooled to 0° C. The mixture was filtered through a pad of diatomaceous earth and washed with carbon tetrachloride (50 mL). The filtrate was then carefully treated with methanol (30 mL) and stirred at 25° C. for 15 min. After this time, the pale brown solution was concentrated in vacuo. The remaining liquid was then partitioned between water (50 mL) and pentane (3×50 mL). The combined organics were dried over sodium sulfate, filtered and concentrated in vacuo. Silica gel column chromatography (AnaLogix, 12 g, 95/5 hexanes/ethyl acetate) afforded 2-bromo-4-ethyl-hexanoic acid methyl ester (2.05 g, 100%) as a clear liquid; EI$^+$-HRMS m/e calcd for $C_9H_{17}O_2Br$ [M+] 236.0412, found 236.0412. $^1$H NMR (300 MHz, DMSO-d$_6$) δ ppm 0.81 (t, J=7.2 Hz, 6H), 1.10-1.39 (m, 4H), 1.40-1.56 (m, 1H), 2.21-2.33 (m, 2H), 3.71 (s, 3H), 4.53 (dd, J=8.3, 6.8 Hz, 1H).

4,5-Dichloropyridazin-3(2H)-one

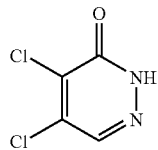

Step 1: Hydrazine sulfate (305.7 g, 2.35 mol) was added to a solution of 3,4-dichloro-5-hydroxy-5H-furan-2-one (419 g, 2.48 mol) and sodium acetate (212 g, 2.58 mol) in water (600 mL). The mixture was stirred at reflux for 4 h. After filtration and evaporation, the residual solid was recrystallized from ethanol to afford 4,5-dichloropyridazin-3(2H)-one (216 g, 67%) as an off-white solid. LC-MS 165 [M+H$^+$].

Intermediate 18

5-(2,6-Difluoro-phenoxy)-2H-pyridazin-3-one

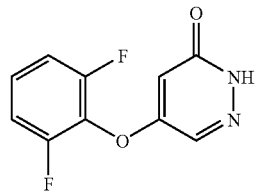

Step 1: 4,5-Dichloropyridazin-3(2H)-one (10 g, 60.61 mmol) was treated with 47% hydroiodic acid (75 mL) in a sealed tube, and the reaction was heated at 150° C. for 25 h. At this point, the reaction was filtered and washed with water (100 mL). The solids were treated with water (200 mL), heated to 50° C., and sodium thiosulfate was added with stirring until the solution turned a light brown color and a precipitate formed. The resulting mixture was filtered, and the filtrate was dried in vacuo. The resulting brown solid was washed with hot ethanol (roughly 78° C., 200 mL) and filtered. The red/brown filtrate was dried in vacuo. The resulting dark brown solid was triturated with methylene chloride (20 mL), triturated with hexanes (4×30 mL), and dried in vacuo to afford 5-iodo-2H-pyridazin-3-one (8.640 g, 64%) as a brown solid. The material was used without further purification.

Step 2: A mixture of 5-iodo-2H-pyridazin-3-one (8.640 g, 38.92 mmol) in tetrahydrofuran (150 mL) was treated with para-toluenesulfonic acid (1.49 g, 7.86 mmol) and 3,4-dihydro-2H-pyran (8.98 mL, 98.18 mmol). The reaction was stirred at 25° C. for 2 d. After this time, the reaction was filtered. The filtrate was treated with para-toluenesulfonic acid (6 g) and 3,4-dihydro-2H-pyran (9 mL), and the reaction stirred at 25° C. for 6 h. The reaction was concentrated in vacuo, taken up in ethyl acetate (400 mL), washed with a saturated aqueous sodium bicarbonate solution (400 mL), and a saturated aqueous sodium chloride solution. The aqueous layer was extracted with ethyl acetate (300 mL) and was washed with a saturated aqueous sodium chloride solution. The combined organics were dried over sodium sulfate, filtered, rinsed, and concentrated in vacuo. Silica gel column chromatography (AnaLogix, 400 g, 0% to 50% ethyl acetate/hexanes) afforded 5-iodo-2-(tetrahydro-pyran-2-yl)-2H-pyridazin-3-one (2.73 g, 23%) as a clear light brown, viscous oil. The material contained an impurity. However, it was used without further purification.

Step 3: A solution of 5-iodo-2-(tetrahydro-pyran-2-yl)-2H-pyridazin-3-one (204 mg, 0.67 mmol) in anhydrous N,N-dimethylformamide (8.5 mL, 0.08M) was treated with 2,6-difluorophenol (0.09 g, 0.69 mmol) and potassium carbonate (0.20 g, 1.45 mmol). The reaction was heated at 120° C. overnight. At this time, the reaction was diluted with water (25 mL) and extracted with methylene chloride (3×25 mL). The combined organics were washed with a saturated aqueous sodium chloride solution (25 mL), dried over magnesium sulfate, filtered, rinsed, and concentrated in vacuo. Silica gel column chromatography (AnaLogix, 24 g, 20% to 40% ethyl acetate/hexanes) afforded 5-(2,6-difluoro-phenoxy)-2-(tetrahydro-pyran-2-yl)-2H-pyridazin-3-one (99.7 mg, 49%) as an off-white solid. $^1$H-NMR (400 MHz, DMSO-d$_6$) δ ppm 1.43-1.56 (m, 2H), 1.57-1.76 (m, 2H), 1.88-2.01 (m, 1H), 2.01-2.16 (m, 1H), 3.53-3.63 (m, 1H), 3.90-3.98 (m, 1H), 5.82 (dd, J=10.5, 1.6 Hz, 1H), 6.04 (d, J=2.7 Hz, 1H), 7.34-7.43 (m, 2H), 7.43-7.55 (m, 1H), 8.23 (d, J=2.7 Hz, 1H).

Step 4: A solution of 5-(2,6-difluoro-phenoxy)-2-(tetrahydro-pyran-2-yl)-2H-pyridazin-3-one (92.3 mg, 0.30 mmol) in methanol (0.6 mL, 0.5M) was treated with a 6N aqueous hydrochloric acid solution (0.25 L, 1.2M). The reaction was heated at 110° C. for 1 h and then stood at 25° C. overnight. At this point, the reaction was charged with water (10 mL). The solids were crushed, filtered, rinsed, and dried in vacuo to afford 5-(2,6-difluoro-phenoxy)-2H-pyridazin-3-one (45.7 mg, 68%) as an off-white solid; $^1$H-NMR (400 MHz, DMSO-d$_6$) δ ppm 5.91 (s, 1H), 7.25-7.43 (m, 2H), 7.43-7.57 (m, 1H), 8.11 (d, J=2.6 Hz, 1H), 13.10 (brs, 1H).

Intermediate 20

4,5-Dichloro-2-(tetrahydropyran-2-yl)-2H-pyridazin-3-one

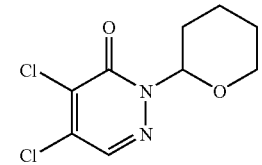

Step 1: A solution of 4,5-dichloropyridazin-3(2H)-one (10 g, 60.6 mmol) in tetrahydrofuran (60 mL, 1.0M) was treated with pyridinium para-toluene sulfonate (3.03 g, 12.1 mmol) and 3,4-dihydro-2H-pyran (8.5 mL, 93.2 mmol). The reaction was heated at reflux for 5 h and was then treated with a second aliquot of 3,4-dihydro-2H-pyran (5.5 mL, 60.3 mmol). The reaction was stirred at reflux overnight. After this time, the reaction was concentrated in vacuo, taken up in ethyl acetate (250 mL), and washed with a 2N aqueous sodium hydroxide solution (2×250 mL). The organics were then washed with a saturated aqueous sodium chloride solution (250 mL), dried over magnesium sulfate, filtered, rinsed, and concentrated in vacuo. Silica gel column chromatography (Biotage, 330 g, 10% ethyl acetate/hexanes) afforded 4,5-dichloro-2-(tetrahydropyran-2-yl)-2H-pyridazin-3-one (13.01 g, 86%) as an off-white solid; ES+-HRMS m/e calcd for $C_9H_{10}N_2O_2Cl_2$ [M+Na+] 271.0011, found 271.0012.

Intermediate 19

3-Cyclopentyl-2-(6-oxo-4-phenoxy-6H-pyridazin-1-yl)-propionic acid

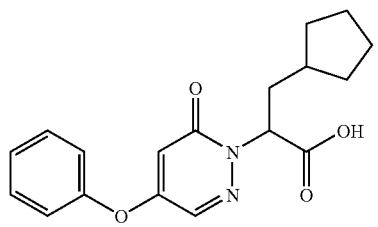

Step 1: A solution of 4,5-dichloro-2-(tetrahydropyran-2-yl)-2H-pyridazin-3-one (Intermediate 20, 2.50 g, 10.03 mmol) in acetonitrile (111 mL, 0.09M) was treated with potassium carbonate (1.38 g, 10.03 mmol) and phenol (944 mg, 10.03 mmol). The resulting reaction mixture was heated at reflux for 3 h and then was allowed to cool to 25° C. The reaction mixture was then partitioned between water (150 mL) and methylene chloride (3×100 mL). The combined organics were dried over sodium sulfate, filtered, rinsed, and concentrated in vacuo. Silica gel column chromatography (ISCO 80 g, 30% ethyl acetate/hexanes) afforded 4-chloro-5-phenoxy-2-(tetrahydro-pyran-2-yl)-2H-pyridazin-3-one (2.84 g, 92%) as a clear oil; ES+-HRMS m/e calcd for $C_{15}H_{15}N_2O_3Cl$ [M+H+] 307.0844, found 307.0843.

Step 2: A solution of 4-chloro-5-phenoxy-2-(tetrahydro-pyran-2-yl)-2H-pyridazin-3-one (2.84 g, 9.25 mmol) in methanol (6.17 mL, 1.5M) was treated with a 6N aqueous hydrochloric acid solution (7.71 mL, 1.2M). The reaction solution was heated to 110° C., where it stirred for 4 h and was then allowed to completely cool down to 25° C. The reaction was then diluted with water (200 mL). The resulting white precipitate was collected by filtration, washed with water (2×50 mL), and dried in vacuo to afford 4-chloro-5-phenoxy-2H-pyridazin-3-one (1.78 g, 86%) as a white solid; ES+-HRMS m/e calcd for $C_{10}H_7N_2O_2Cl$ [M+H+] 223.0269, found 223.0269.

Step 3: A pressure vial containing a mixture of 4-chloro-5-phenoxy-2H-pyridazin-3-one (1.76 g, 7.90 mmol), water (29.6 mL), and a 2N aqueous sodium hydroxide solution (4.26 mL) was treated with 10% palladium on carbon (174 mg, 10% weight of 4-chloro-5-phenoxy-2H-pyridazin-3-one). The reaction was then pressurized with hydrogen (50 psi), where it shook for 24 h. The resulting reaction mixture was diluted with methylene chloride (100 mL) and water (100 mL), filtered through a pad of diatomaceous earth, and rinsed. The layers were separated, and the organics were concentrated in vacuo. The aqueous layer was then acidified to pH 1-2 with a 2N aqueous hydrochloric acid solution. The resulting mixture was extracted with 90/10 methylene chloride/methanol (3×100 mL). These organics were combined, dried over sodium sulfate, filtered, rinsed, and concentrated in vacuo to afford 5-phenoxy-2H-pyridazin-3-one (1.44 g, 96%) as a white solid; ES+-HRMS m/e calcd for $C_{10}H_8N_2O_2$ [M+H+] 189.0659, found 189.0658.

Step 4: A solution of 5-phenoxy-2H-pyridazin-3-one (1.42 g, 7.54 mmol) in tetrahydrofuran (37.7 mL, 0.2M) cooled to 0° C. was treated with a 60% suspension of sodium hydride in mineral oil (362 mg, 9.05 mmol). The reaction stirred at 0° C. for 5 min and then at 25° C. for an additional 30 min. After this time, the reaction was treated with 2-bromo-3-cyclopentyl-propionic acid methyl ester (Intermediate 10, 1.95 g, 8.30 mmol). The reaction was then warmed to 50° C., where it stirred for 18 h. After this time, the reaction was partitioned between water (300 mL) and methylene chloride (3×100 mL). The combined organic layers were dried over sodium sulfate, filtered and concentrated in vacuo. Silica gel column chromatography (Isco 40 g, 20% ethyl acetate/hexanes) afforded 3-cyclopentyl-2-(6-oxo-4-phenoxy-6H-pyridazin-1-yl)-propionic acid methyl ester (1.72 g, 66%) as a clear oil; ES+-HRMS m/e calcd for $C_{19}H_{22}N_2O_4$ [M+H+] 343.1653, found 343.1652.

Step 5: A solution of 3-cyclopentyl-2-(6-oxo-4-phenoxy-6H-pyridazin-1-yl)-propionic acid methyl ester (1.70 g, 4.96 mmol) in methanol (8.3 mL, 0.6M) was treated with a 4N aqueous sodium hydroxide solution (1.37 mL, 5.46 mmol) and was stirred at 25° C. for 4 h. After this time, the reaction was poured into water (150 mL) which was acidified with a 3N aqueous hydrochloric acid solution and then was extracted into 90/10 methylene chloride/methanol (3×100 mL). The combined organics were dried over sodium sulfate, filtered and concentrated in vacuo to afford 3-cyclopentyl-2-(6-oxo-4-phenoxy-6H-pyridazin-1-yl)-propionic acid (1.60 g, 98%) as a white solid; ES+-HRMS m/e calcd for $C_{18}H_{20}N_2O_4$ [M+H+] 329.1496, found 329.2496. $^1$H NMR (300 MHz, DMSO-d$_6$) δ ppm 1.11 (br s, 2H), 1.35-1.78 (m, 7H), 1.86-2.05 (m, 1H), 2.10-2.25 (m, 1H), 5.31 (dd, J=10.9, 4.2 Hz, 1H), 5.73 (d, J=2.7 Hz, 1H), 7.30 (d, J=7.5 Hz, 2H), 7.37 (t, J=7.5 Hz, 1H), 7.53 (t, J=7.5 Hz, 2H), 8.10 (d, J=2.7 Hz, 1H), 13.02 (br s, 1H).

Intermediate 21

3-Cyclopentyl-2-[6-oxo-4-(2-trifluoromethyl-phenoxy)-6H-pyridazin-1-yl]-propionic acid

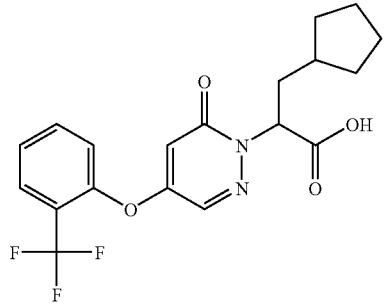

In an analogous manner to the stepwise sequence outlined in intermediate 19, starting from 4,5-dichloro-2-(tetrahydro-pyran-2-yl)-2H-pyridazin-3-one (Intermediate 20) and 2-trifluoromethyl-phenol and alkylating with 2-bromo-3-cyclopentyl-propionic acid methyl ester (Intermediate 10) afforded 3-cyclopentyl-2-[6-oxo-4-(2-trifluoromethyl-phenoxy)-6H-pyridazin-1-yl]-propionic acid as a white solid (2.74 g, 95% for the final step); ES+-HRMS m/e calcd for $C_{19}H_{19}N_2O_4F_3$ [M+H+] 397.1370, found 397.1367. $^1$H NMR (300 MHz, DMSO-d$_6$) δ ppm 1.03 (br s, 2H), 1.25-1.77 (m, 7H), 1.88-2.05 (m, 1H), 2.09-2.23 (m, 1H), 5.32 (dd, J=10.6, 3.9 Hz, 1H), 5.92 (d, J=2.4 Hz, 1H), 7.52-7.66 (m, 2H), 7.78-7.94 (m, 2H), 8.17 (d, J=2.4 Hz, 1H), 13.06 (br s, 1H).

Intermediate 22

3-Cyclopentyl-2-[6-oxo-4-(3-trifluoromethyl-phenoxy)-6H-pyridazin-1-yl]-propionic acid

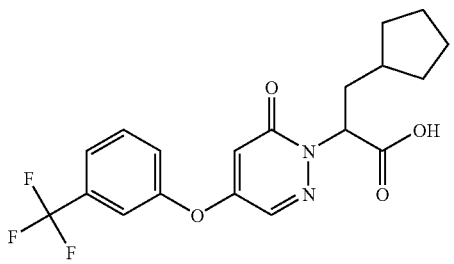

In an analogous manner to the stepwise sequence outlined in intermediate 19, starting from 4,5-dichloro-2-(tetrahydropyran-2-yl)-2H-pyridazin-3-one (Intermediate 20) and 3-trifluoromethyl-phenol and alkylating with 2-bromo-3-cyclopentyl-propionic acid methyl ester (Intermediate 10) afforded 3-cyclopentyl-2-[6-oxo-4-(3-trifluoromethyl-phenoxy)-6H-pyridazin-1-yl]-propionic acid as a white solid (774.7 mg, 93% for the final step); ES$^+$-HRMS m/e calcd for $C_{19}H_{19}N_2O_4F_3$ [M+H$^+$] 397.1370, found 397.1368. $^1$H NMR (400 MHz, DMSO-d$_6$) δ ppm 0.99-1.21 (m, 2H), 1.35-1.77 (m, 7H), 1.97 (ddd, J=13.7, 9.1, 4.3 Hz, 1H), 2.15-2.26 (m, 1H), 5.33 (dd, J=10.9, 4.3 Hz, 1H), 5.87 (d, J=2.8 Hz, 1H), 7.66 (d, J=7.0 Hz, 1H), 7.71-7.81 (m, 3H), 8.14 (d, J=2.8 Hz, 1H), 13.03 (br s, 1H).

Intermediate 23

3-Cyclopentyl-2-[6-oxo-4-(4-trifluoromethyl-phenoxy)-6H-pyridazin-1-yl]-propionic acid

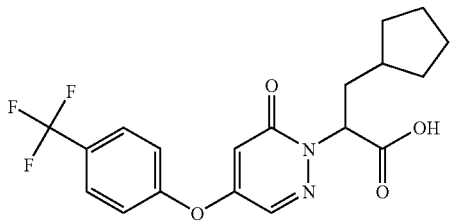

In an analogous manner to the stepwise sequence outlined in intermediate 19, starting from 4,5-dichloro-2-(tetrahydropyran-2-yl)-2H-pyridazin-3-one (Intermediate 20) and 4-trifluoromethyl-phenol and alkylating with 2-bromo-3-cyclopentyl-propionic acid methyl ester (Intermediate 10) afforded 3-cyclopentyl-2-[6-oxo-4-(4-trifluoromethyl-phenoxy)-6H-pyridazin-1-yl]-propionic acid as a white solid (715.2 mg, 88% for the final step); ES$^+$-HRMS m/e calcd for $C_{19}H_{19}N_2O_4F_3$ [M+H$^+$] 397.1370, found 397.1371. $^1$H NMR (400 MHz, DMSO-d$_6$) δ ppm 0.99-1.20 (m, 2H), 1.34-1.79 (m, 7H), 1.91-2.05 (m, 1H), 2.12-2.26 (m, 1H), 5.33 (dd, J=10.8, 4.2 Hz, 1H), 6.01 (d, J=2.9 Hz, 1H), 7.54 (d, J=8.5 Hz, 2H), 7.90 (d, J=8.5 Hz, 2H), 8.14 (d, J=2.9 Hz, 1H), 13.03 (br s, 1H).

Intermediate 24

3-Cyclopentyl-2-[4-(2-methoxy-phenoxy)-6-oxo-6H-pyridazin-1-yl]-propionic acid

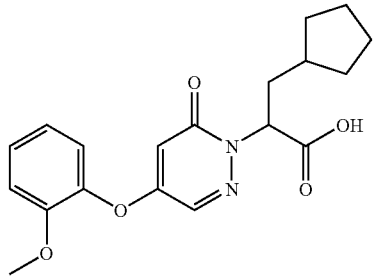

In an analogous manner to the stepwise sequence outlined in intermediate 19, starting from 4,5-dichloro-2-(tetrahydropyran-2-yl)-2H-pyridazin-3-one (Intermediate 20) and 2-methoxy-phenol and alkylating with 2-bromo-3-cyclopentyl-propionic acid methyl ester (Intermediate 10) afforded 3-cyclopentyl-2-[4-(2-methoxy-phenoxy)-6-oxo-6H-pyridazin-1-yl]-propionic acid as a white solid (614.1 mg, 95% for the final step); ES$^+$-HRMS m/e calcd for $C_{19}H_{22}N_2O_5$ [M+H$^+$] 359.1602, found 359.1601. $^1$H NMR (300 MHz, DMSO-d$_6$) δ ppm 1.11 (s, 2H), 1.31-1.78 (m, 7H), 1.86-2.06 (m, 1H), 2.09-2.24 (m, 1H), 3.79 (s, 3H), 5.30 (dd, J=10.7, 4.1 Hz, 1H), 5.59 (d, J=2.7 Hz, 1H), 7.05 (td, J=7.5, 1.5 Hz, 1H), 7.23-7.40 (m, 3H), 8.10 (d, J=2.7 Hz, 1H), 13.02 (br s, 1H).

Intermediate 25

3-Cyclopentyl-2-[4-(3-methoxy-phenoxy)-6-oxo-6H-pyridazin-1-yl]-propionic acid

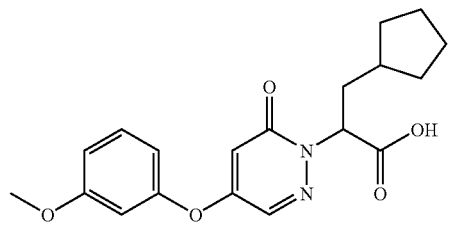

In an analogous manner to the stepwise sequence outlined in intermediate 19, starting from 4,5-dichloro-2-(tetrahydropyran-2-yl)-2H-pyridazin-3-one (Intermediate 20) and 3-methoxy-phenol and alkylating with 2-bromo-3-cyclopentyl-propionic acid methyl ester (Intermediate 10) afforded 3-cyclopentyl-2-[4-(3-methoxy-phenoxy)-6-oxo-6H-pyridazin-1-yl]-propionic acid as a white solid (159.4 mg, 42% for the final step); ES$^+$-HRMS m/e calcd for $C_{19}H_{22}N_2O_5$ [M+H$^+$] 359.1602, found 359.1600. $^1$H NMR (300 MHz, DMSO-d$_6$) δ ppm 1.04 (br s, 2H), 1.31-1.80 (m, 7H), 1.87-2.09 (m, 1H), 2.09-2.25 (m, 1H), 3.78 (s, 3H), 5.31 (dd, J=11.0, 4.1 Hz, 1H), 5.79 (d, J=2.7 Hz, 1H), 6.85 (dd, J=7.8, 1.8 Hz, 1H), 6.89-6.96 (m, 2H), 7.42 (t, J=8.2 Hz, 1H), 8.08 (d, J=2.7 Hz, 1H), 13.03 (br s, 1H).

Intermediate 26

3-Cyclopentyl-2-[4-(4-methoxy-phenoxy)-6-oxo-6H-pyridazin-1-yl]-propionic acid

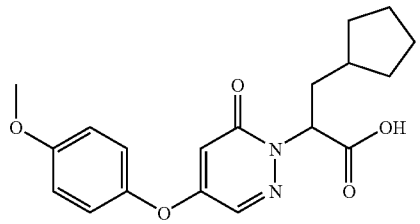

In an analogous manner to the stepwise sequence outlined in intermediate 19, starting from 4,5-dichloro-2-(tetrahydro-pyran-2-yl)-2H-pyridazin-3-one (Intermediate 20) and 4-methoxy-phenol and alkylating with 2-bromo-3-cyclopentyl-propionic acid methyl ester (Intermediate 10) afforded 3-cyclopentyl-2-[4-(4-methoxy-phenoxy)-6-oxo-6H-pyridazin-1-yl]-propionic acid as a light yellow solid (110.8 mg, 87% for the final step). $^1$H NMR (300 MHz, DMSO-$d_6$) δ ppm 1.06 (br s, 2H), 1.34-1.80 (m, 7H), 1.82-2.08 (m, 1H), 2.10-2.24 (m, 1H), 3.79 (s, 3H), 5.30 (dd, J=10.9, 4.2 Hz, 1H), 5.69 (d, J=2.4 Hz, 1H), 7.05 (d, J=9.1 Hz, 2H), 7.23 (d, J=9.1 Hz, 2H), 8.07 (d, J=2.4 Hz, 1H), 12.98 (br s, 1H).

Intermediate 27

3-Cyclopentyl-2-{6-oxo-4-[2-(pyrrolidine-1-carbonyl)-phenoxy]-6H-pyridazin-1-yl}-propionic acid

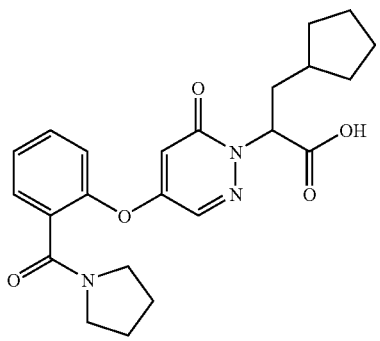

In an analogous manner to the stepwise sequence outlined in intermediate 19, starting from 4,5-dichloro-2-(tetrahydro-pyran-2-yl)-2H-pyridazin-3-one (Intermediate 20) and 2-(pyrrolidine-1-carbonyl)-phenol and alkylating with 2-bromo-3-cyclopentyl-propionic acid methyl ester (Intermediate 10) afforded 3-cyclopentyl-2-{6-oxo-4-[2-(pyrrolidine-1-carbonyl)-phenoxy]-6H-pyridazin-1-yl}-propionic acid as a white solid (100 mg, 32% for the final step). $^1$H NMR (300 MHz, DMSO-$d_6$) δ ppm 0.91-1.18 (m, 2H), 1.31-1.86 (m, 11H), 1.86-2.05 (m, 1H), 2.06-2.21 (m, 1H), 3.10-3.48 (m, 4H), 5.26 (dd, J=10.7, 4.1 Hz, 1H), 5.77 (d, J=2.4 Hz, 1H), 7.36 (d, J=7.8 Hz, 1H), 7.41 (d, J=7.2 Hz, 1H), 7.47-7.60 (m, 2H), 8.00 (d, J=2.4 Hz, 1H), 13.06 (br s, 1H).

Intermediate 28

2-[4-(2,6-Difluoro-phenoxy)-6-oxo-6H-pyridazin-1-yl]-4-methyl-pentanoic acid

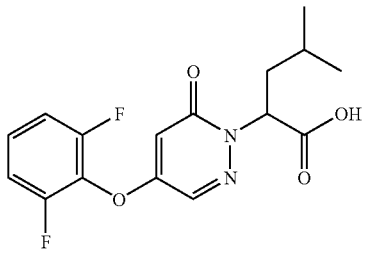

In an analogous manner to the stepwise sequence outlined in intermediate 19, starting from 4,5-dichloro-2-(tetrahydro-pyran-2-yl)-2H-pyridazin-3-one (Intermediate 20) and 2,6-difluoro-phenol and alkylating with 2-bromo-4-methyl-pentanoic acid methyl ester (Intermediate 11) afforded 2-[4-(2,6-difluoro-phenoxy)-6-oxo-6H-pyridazin-1-yl]-4-methyl-pentanoic acid as a white solid (1.48 g, 89% for the final step); ES$^+$-HRMS m/e calcd for $C_{16}H_{16}N_2O_4F_2$ [M+H$^+$] 361.0970, found 361.0969. $^1$H NMR (400 MHz, DMSO-$d_6$) δ ppm 0.86 (d, J=6.0 Hz, 6H), 1.24-1.45 (m, 1H), 1.84 (ddd, J=14.0, 9.5, 4.3 Hz, 1H), 2.04-2.18 (m, 1H), 5.39 (dd, J=11.1, 4.3 Hz, 1H), 6.08 (d, J=2.7 Hz, 1H), 7.30-7.44 (m, 2H), 7.44-7.57 (m, 1H), 8.28 (d, J=2.7 Hz, 1H), 13.09 (br s, 1H).

Intermediate 29

3-Cyclobutyl-2-[4-(2,6-difluoro-phenoxy)-6-oxo-6H-pyridazin-1-yl]-propionic acid

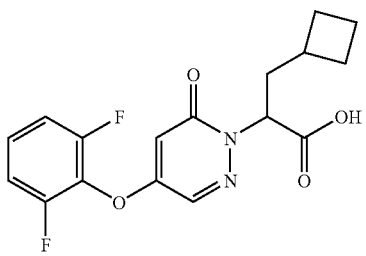

In an analogous manner to the stepwise sequence outlined in intermediate 19, starting from 4,5-dichloro-2-(tetrahydro-pyran-2-yl)-2H-pyridazin-3-one (Intermediate 20) and 2,6-difluoro-phenol and alkylating with 2-bromo-3-cyclobutyl-propionic acid methyl ester (Intermediate 16) afforded 3-cyclobutyl-2-[4-(2,6-difluoro-phenoxy)-6-oxo-6H-pyridazin-1-yl]-propionic acid as a white solid (520.5 mg, 82% for the final step); ES$^+$-HRMS m/e calcd for $C_{17}H_{16}N_2O_4F_2$ [M+H$^+$] 351.1151, found 351.1152. $^1$H NMR (400 MHz, DMSO-$d_6$) δ ppm 1.44-1.56 (m, 1H), 1.57-1.87 (m, 4H), 1.87-2.01 (m, 1H), 2.03-2.27 (m, 3H), 5.17-5.28 (m, 1H), 6.07 (d, J=2.7 Hz, 1H), 7.32-7.43 (m, 2H), 7.43-7.58 (m, 1H), 8.26 (d, J=2.7 Hz, 1H), 13.05 (br s, 1H).

Intermediate 30

2-[4-(2,6-Difluoro-phenoxy)-6-oxo-6H-pyridazin-1-yl]-3-phenyl-propionic acid

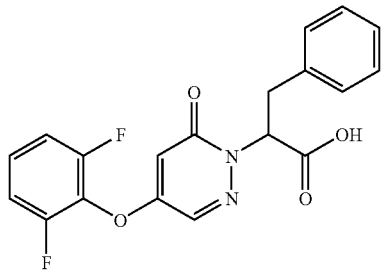

In an analogous manner to the stepwise sequence outlined in intermediate 19, starting from 4,5-dichloro-2-(tetrahydropyran-2-yl)-2H-pyridazin-3-one (Intermediate 20) and 2,6-difluoro-phenol and alkylating with 2-bromo-3-phenyl-propionic acid methyl ester (Intermediate 13) afforded 2-[4-(2,6-difluoro-phenoxy)-6-oxo-6H-pyridazin-1-yl]-3-phenyl-propionic acid as a white solid (555.8 mg, 96% for the final step); ES$^+$-HRMS m/e calcd for $C_{19}H_{14}N_2O_4F_2$ [M+H$^+$] 373.0995, found 373.0994. $^1$H NMR (400 MHz, DMSO-d$_6$) δ ppm 3.28-3.37 (m, 1H), 3.44 (dd, J=14.3, 4.7 Hz, 1H), 5.64 (dd, J=11.1, 4.7 Hz, 1H), 5.96 (d, J=2.7 Hz, 1H), 7.09-7.25 (m, 5H), 7.30-7.41 (m, 2H), 7.41-7.52 (m, 1H), 8.19 (d, J=2.7 Hz, 1H), 13.24 (br s, 1H).

Intermediate 31

2-[4-(2,6-Difluoro-phenoxy)-6-oxo-6H-pyridazin-1-yl]-4-ethyl-hexanoic acid

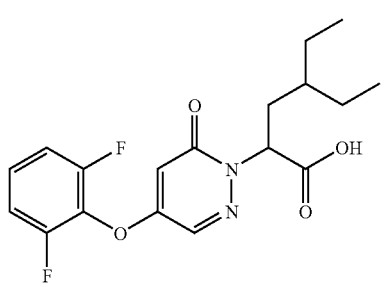

In an analogous manner to the stepwise sequence outlined in intermediate 19, starting from 4,5-dichloro-2-(tetrahydropyran-2-yl)-2H-pyridazin-3-one (Intermediate 20) and 2,6-difluoro-phenol and alkylating with 2-bromo-4-ethyl-hexanoic acid methyl ester (Intermediate 17) afforded 2-[4-(2,6-difluoro-phenoxy)-6-oxo-6H-pyridazin-1-yl]-4-ethyl-hexanoic acid as a white solid (599.8 mg, 88% for the final step); ES$^+$-HRMS m/e calcd for $C_{18}H_{20}N_2O_4F_2$ [M+H$^+$] 367.1464, found 367.1462. $^1$H NMR (400 MHz, DMSO-d$_6$) δ ppm 0.77 (m, 6H), 1.00 (br s, 1H), 1.09-1.44 (m, 4H), 1.93 (ddd, J=14.2, 9.4, 4.3 Hz, 1H), 2.11 (ddd, J=14.2, 10.8, 4.0 Hz, 1H), 5.38 (dd, J=10.8, 4.0 Hz, 1H), 6.09 (d, J=2.7 Hz, 1H), 7.32-7.43 (m, 2H), 7.43-7.57 (m, 1H), 8.28 (d, J=2.7 Hz, 1H), 13.11 (br s, 1H).

Intermediate 32

2-[4-(2,6-Difluoro-phenoxy)-6-oxo-6H-pyridazin-1-yl]-3-(tetrahydro-pyran-4-yl)-propionic acid

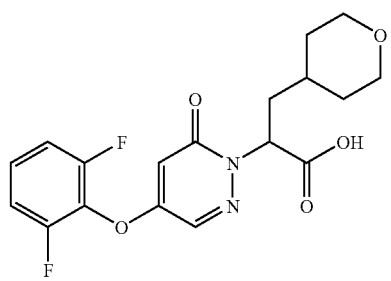

In an analogous manner to the stepwise sequence outlined in intermediate 19, starting from 4,5-dichloro-2-(tetrahydropyran-2-yl)-2H-pyridazin-3-one (Intermediate 20) and 2,6-difluoro-phenol and alkylating with 2-bromo-3-(tetrahydropyran-4-yl)-propionic acid methyl ester (Intermediate 14) afforded 2-[4-(2,6-difluoro-phenoxy)-6-oxo-6H-pyridazin-1-yl]-3-(tetrahydro-pyran-4-yl)-propionic acid as a white solid (223 mg, 88% for the final step); ES$^+$-HRMS m/e calcd for $C_{18}H_{18}N_2O_5F_2$ [M+H$^+$] 381.1257, found 381.1257. $^1$H NMR (400 MHz, DMSO-d$_6$) δ ppm 1.06-1.37 (m, 3H), 1.38-1.49 (m, 1H), 1.53-1.68 (m, 1H), 1.86-2.03 (m, 1H), 2.04-2.17 (m, 1H), 3.04-3.29 (m, 2H), 3.70-3.88 (m, 2H), 5.42 (dd, J=10.7, 4.3 Hz, 1H), 6.09 (d, J=2.8 Hz, 1H), 7.33-7.43 (m, 2H), 7.43-7.56 (m, 1H), 8.28 (d, J=2.8 Hz, 1H), 13.13 (br s, 1H).

Intermediate 33

3-Cyclohexyl-2-[4-(2,6-difluoro-phenoxy)-6-oxo-6H-pyridazin-1-yl]-propionic acid

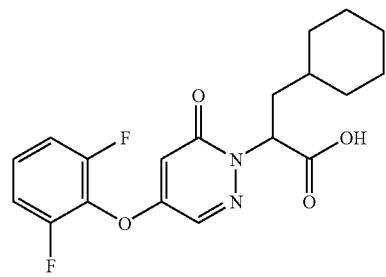

In an analogous manner to the stepwise sequence outlined in intermediate 19, starting from 4,5-dichloro-2-(tetrahydropyran-2-yl)-2H-pyridazin-3-one (Intermediate 20) and 2,6-difluoro-phenol and alkylating with 2-bromo-3-cyclohexyl-propionic acid methyl ester (Intermediate 12) afforded 3-cyclohexyl-2-[4-(2,6-difluoro-phenoxy)-6-oxo-6H-pyridazin-1-yl]-propionic acid as a white solid (1.3 g, 99% for the final step); ES$^+$-HRMS m/e calcd for $C_{19}H_{20}N_2O_4F_2$ [M+H$^+$] 379.1464, found 379.1463. $^1$H NMR (300 MHz, DMSO-d$_6$) δ ppm 0.63-1.31 (m, 6H) 1.33-2.19 (m, 7H) 5.38

(dd, J=10.9, 3.9 Hz, 1H) 6.08 (br s, 1H) 7.24-7.56 (m, 3H) 8.26 (d, J=2.7 Hz, 1H) 13.11 (br s, 1H).

Intermediate 34

2-[4-(2,6-Difluoro-phenoxy)-6-oxo-6H-pyridazin-1-yl]-3-(2,6-difluoro-phenyl)-propionic acid

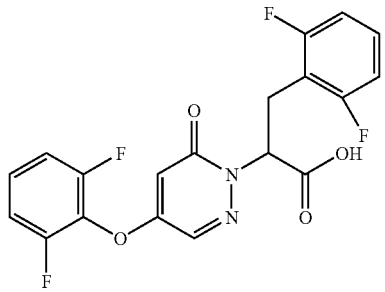

In an analogous manner to the stepwise sequence outlined in intermediate 19, starting from 4,5-dichloro-2-(tetrahydropyran-2-yl)-2H-pyridazin-3-one (Intermediate 20) and 2,6-difluoro-phenol and alkylating with 2-bromo-3-(2,6-difluoro-phenyl)-propionic acid methyl ester (Intermediate 15) afforded 2-[4-(2,6-difluoro-phenoxy)-6-oxo-6H-pyridazin-1-yl]-3-(2,6-difluoro-phenyl)-propionic acid as a light yellow solid (1.35 g, 98% for the final step). $^1$H NMR (300 MHz, DMSO-$d_6$) δ ppm 3.42 (d, J=7.6 Hz, 2H), 5.47 (t, J=7.6 Hz, 1H), 6.00 (d, J=2.7 Hz, 1H), 6.93-7.09 (m, 2H), 7.22-7.55 (m, 4H), 8.20 (d, J=2.7 Hz, 1H), 13.38 (br s, 1H).

Intermediate 35

2-[4-(2-Cyclohexyl-phenoxy)-6-oxo-6H-pyridazin-1-yl]-3-cyclopentyl-propionic acid

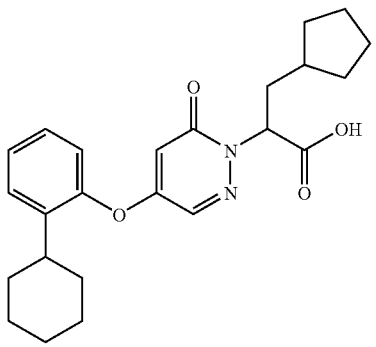

In an analogous manner to the stepwise sequence outlined in intermediate 19, starting from 4,5-dichloro-2-(tetrahydropyran-2-yl)-2H-pyridazin-3-one (Intermediate 20) and 2-cyclohexylphenol and alkylating with 2-bromo-3-cyclopentyl-propionic acid methyl ester (Intermediate 10) afforded 2-[4-(2-cyclohexylphenoxy)-6-oxo-6H-pyridazin-1-yl]-3-cyclopentylpropionic acid (17.1 g, 72%) as a white solid; LC-MS [M+H$^+$]=411.2; HPLC (0.17% trifluoroacetic acid in acetonitrile/water, 50%-100% acetonitrile, gradient, 1 mL/min, Venusil MP-C18, C18-15 cm×4.6 mm-5 µm), 254 nm, 95.8%, 214 nm, 97.2%. $^1$H-NMR (CDCl$_3$, 300 MHz) δ 1.04-1.77 (m, 19H), 2.05-2.11 (m, 1H), 2.22-2.31 (m, 1H), 2.59-2.66 (t, 1H), 5.27-5.32 (dd, J=10.2 Hz, 4.8 Hz, 1H), 5.88-5.89 (d, J=2.4 Hz, 1H), 6.98-7.00 (m, 1H), 7.19-7.26 (m, 2H), 7.34-7.37 (m, 1H), 7.84-7.85 (d, J=2.7 Hz, 1H).

Intermediate 36

3-Cyclopentyl-2-[4-(2-cyclopentyl-phenoxy)-6-oxo-6H-pyridazin-1-yl]-propionic acid

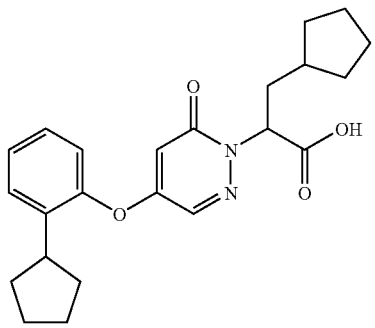

In an analogous manner to the stepwise sequence outlined in intermediate 19, starting from 4,5-dichloro-2-(tetrahydropyran-2-yl)-2H-pyridazin-3-one (Intermediate 20) and 2-cyclopentyl-phenol and alkylating with 2-bromo-3-cyclopentyl-propionic acid methyl ester (Intermediate 10) afforded 3-cyclopentyl-2-[4-(2-cyclopentyl-phenoxy)-6-oxo-6H-pyridazin-1-yl]-propionic acid (12.89 g, 88%) as a white solid; LC-MS [M+H$^+$]=397; HPLC (0.1% trifluoroacetic acid in acetonitrile/water, 50%-100% acetonitrile, gradient, 1 mL/min, Venusil MP-C18, C18-150 cm×4.6 mm-5 µm), 214 nm, 97.39%, 254 nm, 96.72%. $^1$H-NMR (300 MHz, CDCl$_3$) δ 7.88 (s, 1H), 7.29-7.41 (m, 1H), 7.22-7.26 (m, 2H), 6.98-7.01 (m, 1H), 5.91-5.92 (d, J=3, 1H), 5.49-5.54 (m, 1H), 3.03-3.12 (m, 1H), 2.28-2.38 (m, 1H), 2.09-2.18 (m, 1H), 1.95-1.98 (d, J=9 Hz, 2H), 1.50-1.79 (m, 13H), 1.09-1.26 (m, 2H).

Intermediate 37

2-[4-(Biphenyl-2-yloxy)-6-oxo-6H-pyridazin-1-yl]-3-cyclopentyl-propionic acid

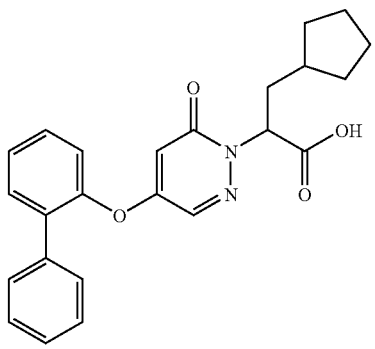

In an analogous manner to the stepwise sequence outlined in intermediate 19, starting from 4,5-dichloro-2-(tetrahydropyran-2-yl)-2H-pyridazin-3-one (Intermediate 20) and biphenyl-2-ol and alkylating with 2-bromo-3-cyclopentyl-propionic acid methyl ester (Intermediate 10) afforded 2-[4-(biphenyl-2-yloxy)-6-oxo-6H-pyridazin-1-yl]-3-cyclopentylpropionic acid (15.4 g, 75%) as a solid; HPLC (0.17% trifluoroacetic acid in acetonitrile/water, 50%-100% acetonitrile, gradient, 1 mL/min, Venusil MP-C18, C18-15 cm×4.6 mm-5 μm), purity>96% (214 nm). $^1$H-NMR (CDCl$_3$, 300 MHz) δ0.97-1.10 (m, 2H), 1.45-1.69 (m, 7H), 2.00-2.07 (m, 1H), 2.17-2.22 (m, 1H), 5.39 (dd, J=10.5, 1H), 5.83 (s, 1H), 7.17 (d, J=7.5, 1H), 7.24-7.48 (m, 8H), 7.65 (s, 1H).

Intermediate 38

3-Cyclopentyl-2-[4-(naphthalen-1-yloxy)-6-oxo-6H-pyridazin-1-yl]-propionic acid

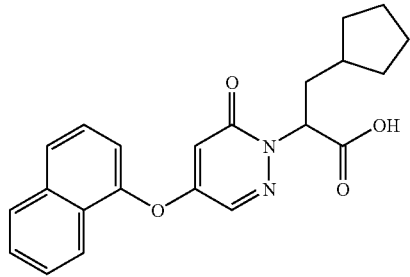

In an analogous manner to the stepwise sequence outlined in intermediate 19, starting from 4,5-dichloro-2-(tetrahydro-pyran-2-yl)-2H-pyridazin-3-one (Intermediate 20) and naphthalen-1-ol and alkylating with 2-bromo-3-cyclopentyl-propionic acid methyl ester (Intermediate 10) afforded 3-cyclopentyl-2-[4-(naphthalen-1-yloxy)-6-oxo-6H-pyridazin-1-yl]-propionic acid (9.1 g, 80%) as a solid; ESI-MS 379 [M+H$^+$]; HPLC (0.17% trifluoroacetic acid in acetonitrile/water, 50%-100% acetonitrile, gradient, 1 mL/min, Venusil MP-C18, C18-15 cm×4.6 mm-5 μm), >96% (purity). $^1$H-NMR (300 MHz, CDCl$_3$) δ 8.22-8.21 (d, 1H), 8.05-7.91 (m, 3H), 7.65-7.58 (m, 3H), 7.42-7.39 (d, 1H), 5.78-5.77 (t, 1H), 5.53-5.48 (m, 1H), 2.45-2.35 (m, 1H), 2.17-2.04 (m, 1H), 1.85-1.14 (m, 9H).

Intermediate 39

3-Cyclopentyl-2-[6-oxo-4-(5,6,7,8-tetrahydro-naphthalen-1-yloxy)-6H-pyridazin-1-yl]-propionic acid

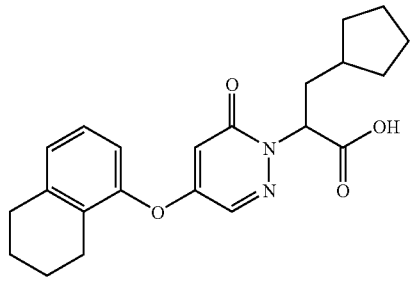

In an analogous manner to the stepwise sequence outlined in intermediate 19, starting from 4,5-dichloro-2-(tetrahydro-pyran-2-yl)-2H-pyridazin-3-one (Intermediate 20) and 5,6,7, 8-tetrahydro-naphthalen-1-ol and alkylating with 2-bromo-3-cyclopentyl-propionic acid methyl ester (Intermediate 10) afforded 3-cyclopentyl-2-[6-oxo-4-(5,6,7,8-tetrahydro-naphthalen-1-yloxy)-6H-pyridazin-1-yl]-propionic acid (13.02 g, 90%) as a white solid; LC-MS 383 [M+H$^+$]; HPLC [acetonitrile (0.1% trifluoroacetic acid) in water (0.1% trifluoroacetic acid)=50%~100%, gradient, 1 mL/min, Venusil MP-C18, C18-15 cm×4.6 mm-5 μm), 254 nm, 95%, 214 nm, 95%. $^1$H-NMR (300 MHz, CDCl$_3$): δ 7.88 (s, 1H), 7.15 (t, J=7.8 Hz, 1H), 7.03 (d, J=7.8 Hz, 1H), 6.83 (d, J=7.8 Hz, 1H), 5.88 (s, 1H), 5.50 (q, J=4.8 Hz, 1H), 2.81 (s, 2H), 2.55 (s, 2H), 2.17-2.40 (m, 1H), 2.09-2.16 (m, 1H), 1.50-1.90 (m, 11H), 1.14-1.21 (m, 2H).

Intermediate 40

2-[4-(2-Acetyl-phenoxy)-6-oxo-6H-pyridazin-1-yl]-3-cyclopentyl-propionic acid

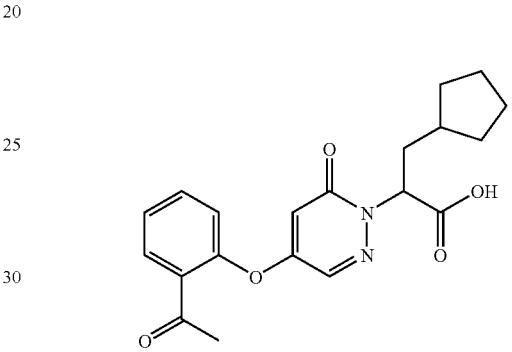

Step 1: A solution of 4,5-dichloro-2-(tetrahydro-pyran-2-yl)-2H-pyridazin-3-one (Intermediate 20, 60.0 g, 0.24 mol) in acetone (600 mL) was treated with potassium carbonate (28.4 g, 0.21 mol), tetrabutylammonium bromide (1.2 g), potassium iodide (38.4 g, 0.23 mol) and 1-(2-hydroxy-phenyl)-ethanone (38.4 g, 0.28 mol). The resulting reaction mixture was stirred at 25° C. for 120 h. After this time, the reaction was filtered. The filtrate was concentrated in vacuo. Silica gel column chromatography (1:10 ethyl acetate/petroleum ether) afforded 5-(2-acetyl-phenoxy)-4-chloro-2-(tetrahydro-pyran-2-yl)-2H-pyridazin-3-one (15 g, 18%).

Step 2: A solution of 5-(2-acetyl-phenoxy)-4-chloro-2-(tetrahydro-pyran-2-yl)-2H-pyridazin-3-one (15.0 g, 0.043 mol), concentrated hydrochloric acid (30 mL), water (45 mL) and methanol (130 mL) was heated at reflux for 2 h. At this time, the reaction was concentrated in vacuo. The residue was charged with water (200 mL) and then basified with a saturated aqueous sodium bicarbonate solution. The resulting material was collected by filtration, rinsed with water and petroleum ether, and dried to afford 5-(2-acetyl-phenoxy)-4-chloro-2H-pyridazin-3-one (9.0 g, 79%); ESI-MS 265 [M+H$^+$].

Step 3: A suspension of 5-(2-acetyl-phenoxy)-4-chloro-2H-pyridazin-3-one (6 g, 0.0227 mol) and palladium on carbon (2.5 g) in ethanol (180 mL) was heated to reflux and then treated with formic acid (1.2 g, 0.023 mol). The reaction stirred for 10 min at reflux and then ammonium formate (1.43 g, 0.023 mol) was added. The reaction stirred at reflux for another 10 min. At this time, a second portion of ammonium formate (0.3 g, 0.0048 mol) was added. After 5 min, the reaction was cooled to 25° C. and filtered. The filtrate was concentrated in vacuo to afford 5-(2-acetyl-phenoxy)-2H-pyridazin-3-one (4.7 g, 90%); ESI-MS 231 [M+H$^+$].

Step 4: Sodium hydride in mineral oil (3.65 g) was added to a solution of 5-(2-acetyl-phenoxy)-2H-pyridazin-3-one (16.3 g, 0.07 mol) in tetrahydrofuran (340 mL) at 0° C. The resulting mixture was stirred at 0° C. for 10 min and then was warmed to 20° C., where it stirred for 50 min. After this time, N,N-dimethylformamide (45 mL) and 2-bromo-3-cyclopentyl-propionic acid methyl ester (Intermediate 10, 25 g, 0.11 mol) were added to the reaction. The reaction was then warmed to 50° C. overnight. After this time, the reaction was concentrated in vacuo. Silica gel column chromatography afforded 2-[4-(2-acetyl-phenoxy)-6-oxo-6H-pyridazin-1-yl]-3-cyclopentyl-propionic acid methyl ester (23.4 g, 86%); ESI-MS 385 [M+H$^+$].

Step 5: A solution of 2-[4-(2-acetyl-phenoxy)-6-oxo-6H-pyridazin-1-yl]-3-cyclopentyl-propionic acid methyl ester (23.4 g, 0.061 mol) in 1,4-dioxane (230 mL) and hydrochloric acid (230 mL) was stirred at reflux overnight. After this time, the reaction was cooled to 25° C., concentrated in vacuo, and was treated with acetone (200 mL) and stirred at 25° C. for 1 h. The resulting precipitate was collected by filtration, washed with petroleum ether, acetone, ethyl acetate, and then dried to afford 2-[4-(2-acetyl-phenoxy)-6-oxo-6H-pyridazin-1-yl]-3-cyclopentyl-propionic acid (12 g, 53%); ESI-MS 371 [M+H$^+$]; HPLC: >98% (purity). $^1$H-NMR (300 MHz, DMSO-d$_6$) δ 1.14 (m, 2H), 1.45 (m, 7H), 1.98 (m, 1H), 2.02 (m, 1H); 5.34 (m, 1H); 5.77 (s, 1H); 7.43 (m, 1H); 7.54 (m, 1H); 7.76 (m, 1H); 7.95 (m, 1H); 8.13 (m, 1H) 13.01 (s, 1H).

Intermediate 41

3-Cyclopentyl-2-(6-oxo-4-o-tolyloxy-6H-pyridazin-1-yl)-propionic acid

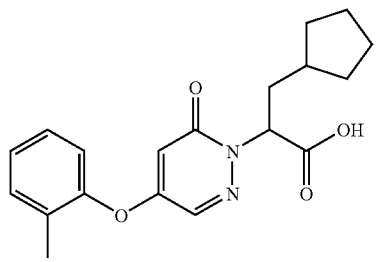

In an analogous manner to the stepwise sequence outlined in intermediate 19, starting from 4,5-dichloro-2-(tetrahydro-pyran-2-yl)-2H-pyridazin-3-one (Intermediate 20) and 2-methyl-phenol and alkylating with 2-bromo-3-cyclopentyl-propionic acid methyl ester (Intermediate 10) afforded 3-cyclopentyl-2-(6-oxo-4-o-tolyloxy-6H-pyridazin-1-yl)-propionic acid (12.2 g, 71%) as a white solid; LC-MS [M+H$^+$]=343.2; HPLC (0.17% trifluoroacetic acid in acetonitrile/water, 50%-100% acetonitrile, gradient, 1 mL/min, Venusil MP-C18, C18-15 cm×4.6 mm-5 μm), 254 nm, 98.5%, 214 nm, 99.6%. $^1$H-NMR (300 MHz, CDCl$_3$) δ 1.12-1.22 (m, 2H), 1.50-1.80 (m, 7H), 2.08-2.16 (m, 1H), 2.20 (s, 3H), 2.30-2.38 (m, 1H), 5.49-5.54 (dd, J=10.2, 4.8 Hz, 1H), 5.85-5.86 (d, J=2.7 Hz, 1H), 7.02-7.04 (d, J=7.2 Hz, 1H), 7.20-7.32 (m, 3H), 7.89-7.90 (d, J=2.7 Hz, 1H).

Intermediate 42

3-Cyclopentyl-2-[4-(3-fluoro-phenoxy)-6-oxo-6H-pyridazin-1-yl]-propionic acid

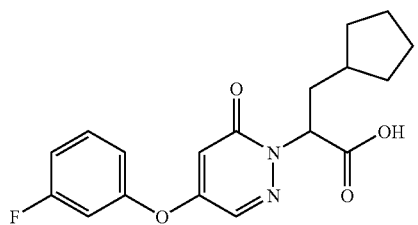

In an analogous manner to the stepwise sequence outlined in intermediate 19, starting from 4,5-dichloro-2-(tetrahydro-pyran-2-yl)-2H-pyridazin-3-one (Intermediate 20) and 3-fluoro-phenol and alkylating with 2-bromo-3-cyclopentyl-propionic acid methyl ester (Intermediate 10) afforded 3-cyclopentyl-2-[4-(3-fluoro-phenoxy)-6-oxo-6H-pyridazin-1-yl]-propionic acid (10.5 g, 71%); ESI-MS 347 [M+H$^+$] HPLC: >96% (purity). $^1$H-NMR (300 MHz, CDCl$_3$) δ 7.86 (s, 1H), 7.40-7.48 (m, 1H), 7.02-7.07 (t, 1H), 6.87-6.96 (m, 2H), 6.05 (s, 1H), 5.51-5.56 (m, 1H), 2.32-2.41 (m, 1H), 2.12-2.14 (m, 1H), 1.50-1.80 (m, 7H), 1.15-1.17 (m, 2H).

Intermediate 43

3-Cyclopentyl-2-[4-(2-fluoro-phenoxy)-6-oxo-6H-pyridazin-1-yl]-propionic acid

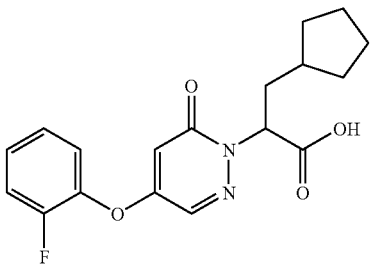

In an analogous manner to the stepwise sequence outlined in intermediate 19, starting from 4,5-dichloro-2-(tetrahydro-pyran-2-yl)-2H-pyridazin-3-one (Intermediate 20) and 2-fluoro-phenol and alkylating with 2-bromo-3-cyclopentyl-propionic acid methyl ester (Intermediate 10) afforded 3-cyclopentyl-2-[4-(2-fluoro-phenoxy)-6-oxo-6H-pyridazin-1-yl]-propionic acid (10.2 g, 70%); ESI-MS 347 [M+H$^+$]; HPLC: >98% (purity). $^1$H-NMR (300 MHz, CDCl$_3$) δ 7.91

(s, 1H), 7.18-7.33 (m, 4H), 5.98 (s, 1H), 5.51-5.56 (m, 1H), 2.30-2.40 (m, 1H), 2.07-2.16 (m, 1H), 1.50-1.80 (m, 7H), 1.11-1.21 (m, 2H).

Intermediate 44

3-Cyclopentyl-2-[4-(2,3-difluoro-phenoxy)-6-oxo-6H-pyridazin-1-yl]-propionic acid

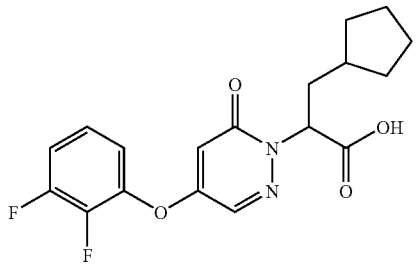

In an analogous manner to the stepwise sequence outlined in intermediate 19, starting from 4,5-dichloro-2-(tetrahydro-pyran-2-yl)-2H-pyridazin-3-one (Intermediate 20) and 2,3-difluoro-phenol and alkylating with 2-bromo-3-cyclopentyl-propionic acid methyl ester (Intermediate 10) afforded 3-cyclopentyl-2-[4-(2,3-difluoro-phenoxy)-6-oxo-6H-pyridazin-1-yl]-propionic acid (14.91 g, 63%) as a white solid; ESI-MS 364 [M+H$^+$]; HPLC: >95% (purity). $^1$H-NMR (300 MHz, CDCl$_3$) δ 7.89-7.90 (d, 1H), 7.12-7.19 (m, 2H), 6.99-7.03 (m, 1H), 6.01 (s, 1H), 5.51-5.56 (m, 1H), 2.29-2.39 (m, 1H), 2.07-2.16 (m, 1H), 1.50-1.81 (m, 7H), 1.10-1.25 (m, 2H).

Intermediate 45

3-Cyclopentyl-2-[4-(2,4-difluoro-phenoxy)-6-oxo-6H-pyridazin-1-yl]-propionic acid

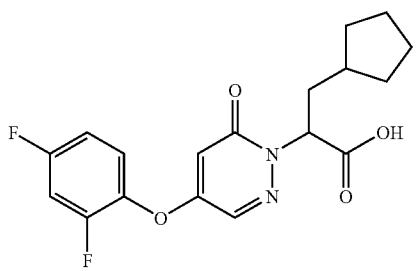

In an analogous manner to the stepwise sequence outlined in intermediate 19, starting from 4,5-dichloro-2-(tetrahydro-pyran-2-yl)-2H-pyridazin-3-one (Intermediate 20) and 2,4-difluoro-phenol and alkylating with 2-bromo-3-cyclopentyl-propionic acid methyl ester (Intermediate 10) afforded 3-cyclopentyl-2-[4-(2,4-difluoro-phenoxy)-6-oxo-6H-pyridazin-1-yl]-propionic acid (10 g, 53%) as a white solid; ESI-MS 364 [M+H$^+$]; HPLC: >98% (purity). $^1$H-NMR (300 MHz, CDCl$_3$) δ 7.89-7.90 (d, 1H), 7.15-7.21 (m, 1H), 6.94-7.05 (m, 2H), 5.94 (s, 1H), 5.50-5.55 (m, 1H), 2.30-2.40 (m, 1H), 2.09-2.16 (m, 1H), 1.50-1.79 (m, 7H), 1.14-1.21 (m, 2H).

Intermediate 46

3-Cyclopentyl-2-[4-(2,5-difluoro-phenoxy)-6-oxo-6H-pyridazin-1-yl]-propionic acid

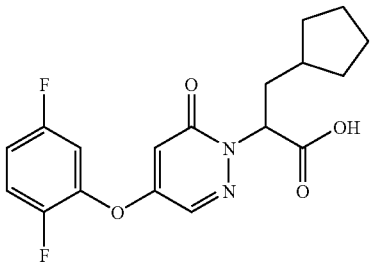

In an analogous manner to the stepwise sequence outlined in intermediate 19, starting from 4,5-dichloro-2-(tetrahydro-pyran-2-yl)-2H-pyridazin-3-one (Intermediate 20) and 2,5-difluoro-phenol and alkylating with 2-bromo-3-cyclopentyl-propionic acid methyl ester (Intermediate 10) afforded 3-cyclopentyl-2-[4-(2,5-difluoro-phenoxy)-6-oxo-6H-pyridazin-1-yl]-propionic acid (10.4 g, 59%) as a white solid; LC-MS 365 [M+H$^+$]; HPLC (0.17% trifluoroacetic acid in acetonitrile/water, 50%-100% acetonitrile, gradient, 1 mL/min, Venusil MP-C18, C18-15 cm×4.6 mm-5 μm), purity>95%. $^1$H-NMR (300 MHz, DMSO-d$_6$) δ 13.01 (bs, 1H), 8.16 (s, 1H), 7.53 (m, 1H), 7.26 (m, 1H), 6.00 (s, 1H), 5.30 (m, 1H), 1.01-2.19 (m, 11H).

Intermediate 47

3-Cyclopentyl-2-[4-(2,6-difluoro-phenoxy)-6-oxo-6H-pyridazin-1-yl]-propionic acid

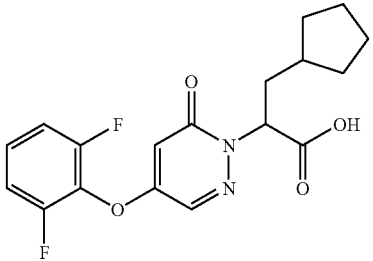

In an analogous manner to the stepwise sequence outlined in intermediate 19, starting from 4,5-dichloro-2-(tetrahydro-pyran-2-yl)-2H-pyridazin-3-one (Intermediate 20) and 2,6-difluoro-phenol and alkylating with 2-bromo-3-cyclopentyl-propionic acid methyl ester (Intermediate 10) afforded 3-cyclopentyl-2-[4-(2,6-difluoro-phenoxy)-6-oxo-6H-pyridazin-1-yl]-propionic acid (13.2 g, 58%) as a white solid; ESI-MS 364 [M+H$^+$]; HPLC: >98% (purity). $^1$H-NMR (300 MHz, CDCl$_3$) δ 7.93-7.94 (d, 1H), 7.22-7.39 (m, 1H), 7.03-

7.09 (m, 2H), 6.00 (s, 1H), 5.51-5.56 (m, 1H), 2.29-2.39 (m, 1H), 2.08-2.16 (m, 1H), 1.44-1.81 (m, 7H), 1.10-1.25 (m, 2H).

Intermediate 48

3-Cyclopentyl-2-[4-(2-methanesulfonyl-phenoxy)-6-oxo-6H-pyridazin-1-yl]-propionic acid

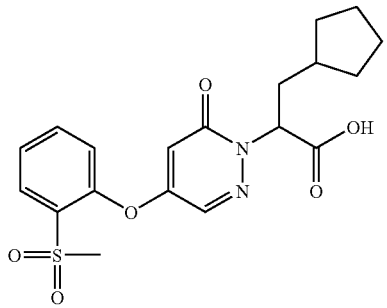

In an analogous manner to the stepwise sequence outlined in intermediate 19, starting from 4,5-dichloro-2-(tetrahydro-pyran-2-yl)-2H-pyridazin-3-one (Intermediate 20) and 2-methanesulfonyl-phenol and alkylating with 2-bromo-3-cyclopentyl-propionic acid methyl ester (Intermediate 10) afforded 3-cyclopentyl-2-[4-(2-methanesulfonyl-phenoxy)-6-oxo-6H-pyridazin-1-yl]-propionic acid (15 g, 68%) as a white solid; LC-MS: [M+H$^+$]=407; HPLC (0.17% trifluoroacetic acid in acetonitrile/water, 50%-100% acetonitrile, gradient, 1 mL/min, Venusil MP-C18, C18-15 cm×4.6 mm-5 μm), purity 98%. $^1$H-NMR (300 MHz, DMSO-d$_6$) δ 1.42 (m, 2H), 1.55 (m, 7H), 1.57 (s, 1H), 1.59 (s, 1H), 3.31 (s, 1H), 5.31 (m, 1H), 7.63 (m, 1H), 7.87 (s, 2H), 7.98 (m, 1H), 8.19 (s, 1H).

Intermediate 49

3-Cyclopentyl-2-[6-oxo-4-(3-phenoxy-phenoxy)-6H-pyridazin-1-yl]-propionic acid

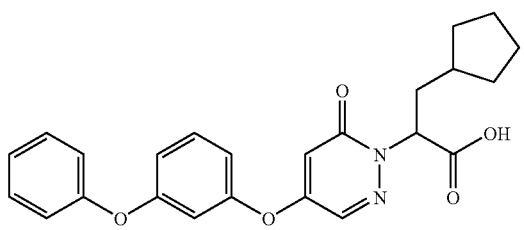

In an analogous manner to the stepwise sequence outlined in intermediate 19, starting from 4,5-dichloro-2-(tetrahydro-pyran-2-yl)-2H-pyridazin-3-one (Intermediate 20) and 3-phenoxy-phenol and alkylating with 2-bromo-3-cyclopentyl-propionic acid methyl ester (Intermediate 10) afforded 3-cyclopentyl-2-[6-oxo-4-(3-phenoxy-phenoxy)-6H-pyridazin-1-yl]-propionic acid (9.0 g, 66%); LC-MS [M+H$^+$]=421; purity>97%, HPLC conditions: C$_{18}$ column 4.6×112 mm, 5 μm, 1.0 mL/min, acetonitrile (0.1% trifluoroacetic acid) in water (0.1% trifluoroacetic acid)=100%~50%, detector 214 nm and 254 nm. $^1$H-NMR (300 MHz, CDCl$_3$): δ 1.09-1.25 (m, 2H), 1.49-1.80 (m, 7H), 2.05-2.17 (m, 1H), 2.29-2.39 (m, 1H), 5.52 (dd, J=4.5, 10.5 Hz, 1H), 6.05 (d, J=2.7 Hz, 1H), 6.73 (s, 1H), 6.82 (d, J=8.1 Hz, 1H), 6.94 (d, J=8.1 Hz, 1H), 7.05-7.20 (m, 3H), 7.27-7.42 (m, 3H), 7.81 (d, J=2.7 Hz, 1H).

Intermediate 50

3-Cyclopentyl-2-[4-(2-methyl-pyridin-3-yloxy)-6-oxo-6H-pyridazin-1-yl]-propionic acid

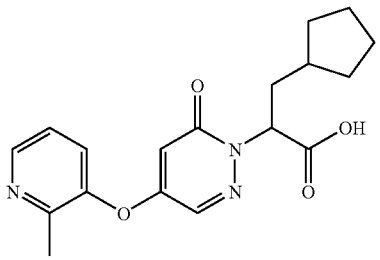

In an analogous manner to the stepwise sequence outlined in intermediate 19, starting from 4,5-dichloro-2-(tetrahydro-pyran-2-yl)-2H-pyridazin-3-one (Intermediate 20) and 2-methyl-pyridin-3-ol and alkylating with 2-bromo-3-cyclopentyl-propionic acid methyl ester (Intermediate 10) afforded 3-cyclopentyl-2-[4-(2-methyl-pyridin-3-yloxy)-6-oxo-6H-pyridazin-1-yl]-propionic acid (10.4 g, 67%) as a white solid; LC-MS 344 [M+H$^+$]; HPLC (0.17% trifluoroacetic acid in acetonitrile/water, 50%-100% acetonitrile, gradient, 1 mL/min, Venusil MP-C18, C$_{18}$-15 cm×4.6 mm-5 μm), purity>95% (214 nm). $^1$H-NMR (300 MHz, DMSO-d$_6$) δ 13.01 (bs, 1H), 8.21 (s, 1H), 8.14 (s, 1H), 7.73 (m, 1H), 7.36 (m, 1H), 5.79 (s, 1H), 5.30 (m, 1H), 1.01-2.19 (m, 11H).

Intermediate 51

3-Cyclopentyl-2-[6-oxo-4-(2-pyrrolidin-1-yl-phenoxy)-6H-pyridazin-1-yl]propionic acid

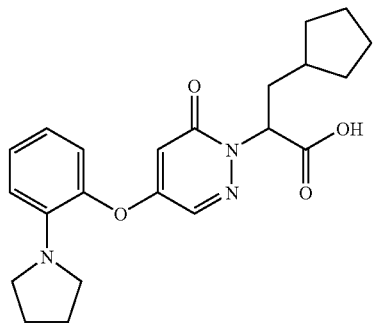

In an analogous manner to the stepwise sequence outlined in intermediate 19, starting from 4,5-dichloro-2-(tetrahydro-pyran-2-yl)-2H-pyridazin-3-one (Intermediate 20) and 2-pyrrolidin-1-yl-phenol and alkylating with 2-bromo-3-cyclopentyl-propionic acid methyl ester (Intermediate 10) afforded 3-cyclopentyl-2-[6-oxo-4-(2-pyrrolidin-1-yl-phenoxy)-6H-pyridazin-1-yl]propionic acid (9 g, 57%) as a yellow solid; LC-MS 398 [M+H$^+$]; HPLC [acetonitrile (0.1% trifluoroacetic acid) in water (0.1% trifluoroacetic acid)

=100%~50%, gradient, 1 mL/min, Venusil MP-C18, C18-15 cm×4.6 mm-5 μm], 254 nm, 97%, 214 nm, 96%. $^1$H-NMR (300 MHz, CDCl$_3$): δ 7.82 (s, 1H), 7.15 (t, J=7.2 Hz, 1H), 6.95 (d, J=7.5 Hz, 1H), 6.75-6.82 (m, 2H), 5.92 (s, 1H), 5.49 (s, 1H), 3.25 (s, 4H), 2.31 (s, 1H), 2.15 (s, 1H), 1.25-1.87 (m, 11H), 1.08-1.16 (m, 2H).

Intermediate 52

3-Cyclopentyl-2-[6-oxo-4-(2-piperidin-1-yl-phenoxy)-6H-pyridazin-1-yl]-propionic acid

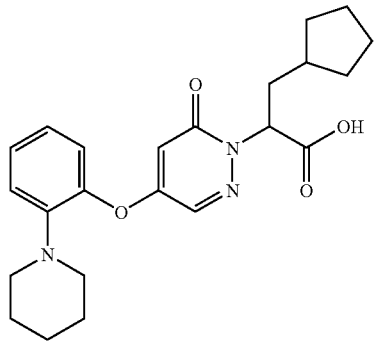

In an analogous manner to the stepwise sequence outlined in intermediate 19, starting from 4,5-dichloro-2-(tetrahydropyran-2-yl)-2H-pyridazin-3-one (Intermediate 20) and 2-(piperidin-1-yl)phenol and alkylating with 2-bromo-3-cyclopentyl-propionic acid methyl ester (Intermediate 10) afforded 3-cyclopentyl-2-[6-oxo-4-(2-piperidin-1-yl-phenoxy)-6H-pyridazin-1-yl]-propionic acid (3.3 g, 97%) as a white solid; ESI-MS 412 [M+H$^+$]; HPLC conditions (0.17% trifluoroacetic acid in acetonitrile/water, 50%-100% acetonitrile, gradient, 1 mL/min, Venusil MP-C18, C18-15 cm×4.6 mm-5 μm), purity>98%. $^1$H-NMR (300 MHz, CDCl$_3$) δ 7.78 (s, 1H), 7.08 (m, 4H), 5.99 (s, 1H), 5.52 (m, 1H), 2.93 (m, 4H), 2.35 (m, 1H), 2.12 (m, 1H), 1.60 (m, 13H), 1.16 (m, 2H).

Intermediate 53

3-Cyclopentyl-2-[4-(2-morpholin-4-yl-phenoxy)-6-oxo-6H-pyridazin-1-yl]-propionic acid

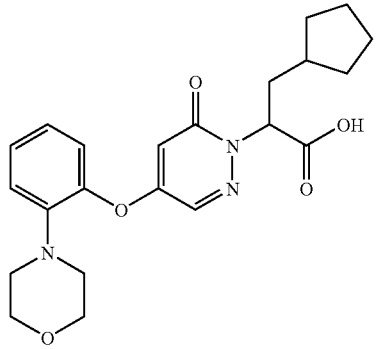

In an analogous manner to the stepwise sequence outlined in intermediate 19, starting from 4,5-dichloro-2-(tetrahydropyran-2-yl)-2H-pyridazin-3-one (Intermediate 20) and 2-morpholin-4-yl-phenol and alkylating with 2-bromo-3-cyclopentyl-propionic acid methyl ester (Intermediate 10) afforded 3-cyclopentyl-2-[4-(2-morpholin-4-yl-phenoxy)-6-oxo-6H-pyridazin-1-yl]-propionic acid (8.5 g, 64%) as a white solid; LC-MS: 414 [M+H$^+$]. HPLC: >99% (purity). $^1$H-NMR (300 MHz, DMSO-d$_6$): δ 12.9 (s, 1H), 8.00 (s, 1H), 7.1-7.3 (m, 4H), 5.76 (s, 1H), 5.3 (m, 1H); 3.3 (m, 4H), 2.9 (m, 4H), 1.0-2.2 (m, 11H).

Intermediate 54

3-Cyclopentyl-2-[6-oxo-4-(pyridin-3-yloxy)-6H-pyridazin-1-yl]-propionic acid

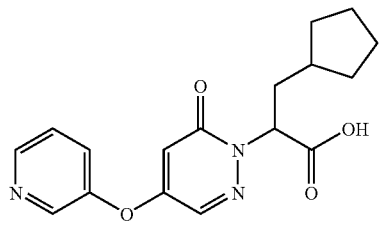

In an analogous manner to the stepwise sequence outlined in intermediate 19, starting from 4,5-dichloro-2-(tetrahydropyran-2-yl)-2H-pyridazin-3-one (Intermediate 20) and pyridin-3-ol and alkylating with 2-bromo-3-cyclopentyl-propionic acid methyl ester (Intermediate 10) afforded 3-cyclopentyl-2-[6-oxo-4-(pyridin-3-yloxy)-6H-pyridazin-1-yl]-propionic acid (10.5 g, 72%) as a solid; ESI-MS 330 [M+H$^+$]; HPLC: >96% (purity). $^1$H-NMR (300 MHz, DMSO-d$_6$): δ 1.11 (m, 2H), 1.52 (m, 7H), 2.01 (m, 1H), 2.22 (m, 1H), 5.32 (m, 1H), 5.89 (s, 1H), 7.56 (m, 1H), 7.84 (m, 1H), 8.15 (s, 1H), 8.59 (m, 2H), 13.00 (brs, 1H).

Intermediate 55

3-Cyclopentyl-2-[6-oxo-4-(quinolin-8-yloxy)-6H-pyridazin-1-yl]-propionic acid

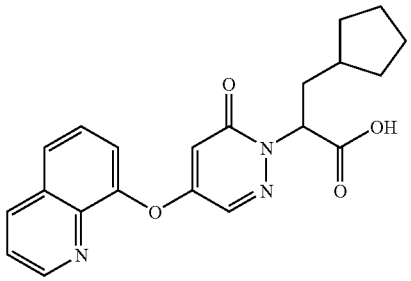

In an analogous manner to the stepwise sequence outlined in intermediate 19, starting from 4,5-dichloro-2-(tetrahydropyran-2-yl)-2H-pyridazin-3-one (Intermediate 20) and 8-hydroxyquinoline and alkylating with 2-bromo-3-cyclopentyl-propionic acid methyl ester (Intermediate 10) afforded 3-cyclopentyl-2-[6-oxo-4-(quinolin-8-yloxy)-6H-pyridazin-1-yl]-propionic acid (6.2 g, 64%) as a solid; LC-MS, [M+H$^+$]=380.2; HPLC (0.05% trifluoroacetic acid in acetonitrile/water, 30%-90% acetonitrile, gradient, 1 mL/min, Venusil MP-C18, C18-15 cm×4.6 mm-5 μm), 254 nm, 97.9%, 214 nm, 96.7%. $^1$H-NMR (DMSO-d$_6$, 300 MHz) δ 1.13-1.22 (m, 2H), 1.46-1.61 (m, 7H), 1.97-2.01 (m, 1H), 2.16-2.25 (m, 1H), 5.30-5.35 (dd, J=10.5, 3.9 Hz, 1H), 5.56-5.57 (d, J=2.4 Hz, 1H), 7.65-7.81 (m, 3H), 8.05-8.07 (d, J=7.8 Hz, 1H), 8.24-8.25 (d, J=2.7 Hz, 1H), 8.53-8.56 (d, J=8.1 Hz, 1H), 8.93-8.94 (d, J=3.0 Hz, 1H), 13.02 (s, br, 1H).

Intermediate 56

3-Cyclopentyl-2-[4-(isoquinolin-5-yloxy)-6-oxo-6H-pyridazin-1-yl]-propionic acid

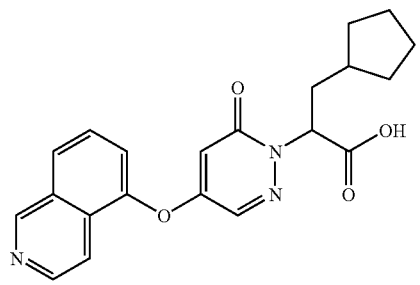

In an analogous manner to the stepwise sequence outlined in intermediate 19, starting from 4,5-dichloro-2-(tetrahydropyran-2-yl)-2H-pyridazin-3-one (Intermediate 20) and isoquinolin-5-ol and alkylating with 2-bromo-3-cyclopentyl-propionic acid methyl ester (Intermediate 10) afforded 3-cyclopentyl-2-[4-(isoquinolin-5-yloxy)-6-oxo-6H-pyridazin-1-yl]-propionic acid (10.1 g, 73%) as a brown solid; ESI-MS 380 [M+H$^+$]; HPLC: >96% (purity). $^1$H-NMR (300 MHz, DMSO-d$_6$): δ 1.11 (m, 2H), 1.52 (m, 7H), 2.01 (m, 1H), 2.22 (m, 1H), 5.32 (m, 1H), 5.89 (s, 1H), 7.77 (m, 3H), 8.14 (m, 1H), 8.27 (m, 1H), 8.59 (m, 1H), 9.46 (s, 1H), 13.00 (s, 1H).

Intermediate 57

3-Cyclopentyl-2-[6-oxo-4-(quinolin-5-yloxy)-6H-pyridazin-1-yl]-propionic acid

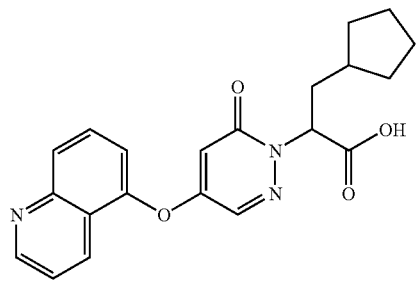

In an analogous manner to the stepwise sequence outlined in intermediate 19, starting from 4,5-dichloro-2-(tetrahydropyran-2-yl)-2H-pyridazin-3-one (Intermediate 20) and 5-hydroxy-quinoline and alkylating with 2-bromo-3-cyclopentyl-propionic acid methyl ester (Intermediate 10) afforded 3-cyclopentyl-2-[6-oxo-4-(quinolin-5-yloxy)-6H-pyridazin-1-yl]-propionic acid (20 g, 83%) as a solid; LC-MS, [M+H$^+$]=380.2; HPLC (0.17% trifluoroacetic acid in acetonitrile/water, 30%-90% acetonitrile, gradient, 1 mL/min, Venusil MP-C18, C18-15 cm×4.6 mm-5 µm) 254 nm, 95.8%; 214 nm, 99.8%. $^1$H-NMR (300 MHz, CDCl$_3$): δ 1.12-1.25 (m, 2H), 1.50-1.84 (m, 7H), 2.11-2.20 (m, 1H), 2.33-2.43 (m, 1H), 5.54-5.59 (dd, J=10.5, 4.5 Hz, 1H), 5.94-5.95 (d, J=2.7 Hz, 1H), 7.34-7.37 (d, J=7.8 Hz, 1H), 7.48-7.53 (dd, J=8.7, 4.5 Hz, 1H), 7.74-7.80 (t, 1H), 8.00-8.01 (d, J=3.0 Hz, 1H), 8.14-8.16 (d, J=8.4 Hz, 1H), 8.28-8.31 (d, J=8.4 Hz, 1H), 9.02-9.03 (d, J=3.0 Hz, 1H).

Intermediate 58

2-[4-(2-Cyano-phenoxy)-6-oxo-6H-pyridazin-1-yl]-3-cyclopentyl-propionic acid

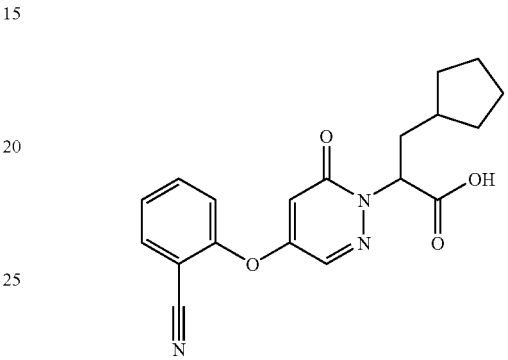

Step 1: A solution of 4,5-dichloro-2-(tetrahydropyran-2-yl)-2H-pyridazin-3-one (Intermediate 20, 60 g, 0.24 mol) in acetonitrile (500 mL) was treated with potassium carbonate (35.2 g, 0.26 mol) and 2-hydroxy-benzonitrile (29 g, 0.24 mol). The resulting reaction mixture was heated at reflux for 2 h and then allowed to cool to 25° C. The reaction mixture was then partitioned between water and methylene chloride. The organics were washed with a saturated aqueous sodium chloride solution, dried over sodium sulfate, filtered, rinsed, and concentrated in vacuo to afford 2-[5-chloro-6-oxo-1-(tetrahydro-pyran-2-yl)-1,6-dihydro-pyridazin-4-yloxy]-benzonitrile (79 g, 99%); ESI-MS 332 [M+H$^+$]; HPLC: >99% (purity). $^1$H-NMR (300 MHz, CDCl$_3$) δ 7.74-7.76 (m, 1H), 7.58-7.64 (m, 2H), 7.31-7.34 (m, 1H), 6.07-6.10 (d, 1H), 4.12-4.16 (d, 1H), 3.73-3.80 (t, 1H), 2.15-1.60 (m, 6H).

Step 2: A solution of 2-[5-chloro-6-oxo-1-(tetrahydro-pyran-2-yl)-1,6-dihydro-pyridazin-4-yloxy]-benzonitrile (61.8 g, 0.19 mol) in methanol (370 mL) was treated with a 6N aqueous hydrochloric acid solution (185 mL). The reaction was stirred at 90° C. for 4 h and then was allowed to cool to 25° C. The reaction was diluted with water. The resulting precipitate was collected by filtration, washed with water and dried in vacuo to afford 2-(5-chloro-6-oxo-1,6-dihydro-pyridazin-4-yloxy)-benzonitrile (43.1 g, 94%); ESI-MS 248 [M+H$^+$]; HPLC: >99% (purity). $^1$H-NMR (300 MHz, DMSO-d$_6$) δ 13.63 (s, 1H), 7.96-7.99 (m, 2H), 7.71-7.77 (m, 1H), 7.37-7.45 (m, 2H).

Step 3: A solution of 2-(5-chloro-6-oxo-1,6-dihydro-pyridazin-4-yloxy)-benzonitrile (43.1 g, 0.17 mol) in concentrated sulfuric acid (150 mL) was stirred at 110° C. for 1 h and was then allowed to cool to 25° C. The reaction was added dropwise to ice water. The resulting precipitate was collected by filtration, washed with cold water and dried in vacuo to afford 2-(5-chloro-6-oxo-1,6-dihydro-pyridazin-4-yloxy)-benzamide (44.5 g, 96%) as a white solid; ESI-MS 266 [M+H$^+$]; HPLC: >97% (purity). $^1$H-NMR (300 MHz, DMSO-d$_6$) δ 13.38 (s, 1H), 7.81 (s, 2H), 7.62-7.65 (m, 1H), 7.47-7.55 (m, 2H), 7.33-7.38 (m, 1H), 7.24-7.27 (m, 1H).

Step 4: A solution of 2-(5-chloro-6-oxo-1,6-dihydro-pyridazin-4-yloxy)-benzamide (44.5 g, 0.17 mol) in ethanol (100 mL) was treated with 10% palladium on carbon (4.5 g) and ammonium formate (21.1 g, 0.34 mol). The resulting mixture was heated to reflux for 5 min. The reaction was then cooled to 25° C. and filtered. The filtrate was concentrated in vacuo. Silica gel column chromatography afforded 2-(6-oxo-1,6-dihydro-pyridazin-4-yloxy)-benzamide (31.1 g, 80%) as a white solid; ESI-MS 232 [M+H$^+$]; HPLC: >95% (purity). $^1$H-NMR (300 MHz, CD$_3$OD) δ 7.95-7.96 (d, 1H), 7.78-7.81 (m, 1H), 7.63-7.68 (m, 1H), 7.45-7.50 (m, 1H), 7.29-7.31 (d, 1H), 5.83-5.84 (d, 1H).

Step 5: A solution of 2-(6-oxo-1,6-dihydro-pyridazin-4-yloxy)-benzamide (31.1 g, 0.14 mol) in methylene chloride and triethylamine (65.5 g, 0.65 mol) was treated dropwise with trifluoroacetic anhydride (62.2 g, 0.30 mol). The resulting solution was stirred at 25° C. for 5 min. After this time, the reaction was washed with a 2N aqueous hydrochloric acid solution and a saturated aqueous sodium bicarbonate solution, dried over sodium sulfate, filtered, rinsed and concentrated in vacuo to afford 2-(6-oxo-1,6-dihydro-pyridazin-4-yloxy)-benzonitrile (25.1 g, 87%) as a white solid; ESI-MS 214 [M+H$^+$]; HPLC: >95% (purity). $^1$H-NMR (300 MHz, CDCl$_3$) δ 11.75 (s, 1H), 7.91 (s, 1H), 7.71-7.81 (m, 2H), 7.44-7.49 (m, 1H), 7.28-7.30 (m, 1H), 5.98 (s, 1H).

Step 6: A solution of 2-(6-oxo-1,6-dihydro-pyridazin-4-yloxy)-benzonitrile (13.4 g, 62.9 mmol) in tetrahydrofuran (300 mL) cooled to −10° C. under nitrogen was treated with a 60% suspension of sodium hydride in mineral oil (3.5 g, 88.1 mmol). The reaction was stirred at −10° C. for 10 min and then warmed to 25° C. where it stirred for an additional 40 min. After this time, the reaction was treated with 2-bromo-3-cyclopentylpropionic acid methyl ester (Intermediate 10, 17.7 g, 75.5 mmol). The reaction was warmed to 50° C. for 18 h. After this time, the reaction was partitioned between water and methylene chloride. The aqueous layer was back extracted with methylene chloride. The combined organics were washed with a saturated aqueous sodium chloride solution, dried over sodium sulfate, filtered, rinsed and concentrated in vacuo. Silica gel column chromatography afforded 2-[4-(2-cyano-phenoxy)-6-oxo-6H-pyridazin-1-yl]-3-cyclopentyl-propionic acid methyl ester (14.7 g, 63%) as a pale yellow solid; ESI-MS 368 [M+H$^+$]; HPLC: >92% (purity). $^1$H-NMR (300 MHz, CDCl$_3$) δ 7.91 (s, 1H), 7.69-7.79 (m, 2H), 7.41-7.46 (m, 1H), 7.28-7.31 (m, 1H), 5.97 (s, 1H), 5.52-5.57 (m, 1H), 3.73 (s, 3H), 2.28-2.37 (m, 1H), 2.04-2.15 (m, 1H), 1.48-1.81 (m, 7H), 1.11-1.28 (m, 2H).

Step 7: A solution of 2-[4-(2-cyano-phenoxy)-6-oxo-6H-pyridazin-1-yl]-3-cyclopentyl-propionic acid methyl ester (30 g, 82 mmol) in methanol (30 mL) was treated with a 4N aqueous sodium hydroxide solution (26.5 mL, 106 mmol) and stirred at 25° C. for 18 h. At this point, the reaction was concentrated in vacuo and then diluted with water. The translucent aqueous solution was acidified to pH 4-5 with a 1N aqueous hydrochloric acid solution. The resulting precipitate was collected by filtration, rinsed and dried in vacuo to afford 2-[4-(2-cyano-phenoxy)-6-oxo-6H-pyridazin-1-yl]-3-cyclopentyl-propionic acid (12.0 g, 41%) as a white solid; ESI-MS 354 [M+H$^+$]; HPLC: >96% (purity). $^1$H-NMR (300 MHz, CDCl$_3$) δ 9.65 (s, 1H), 7.93 (s, 1H), 7.68-7.78 (m, 2H), 7.43-7.45 (m, 1H), 7.28-7.31 (m, 1H), 6.07 (s, 1H), 5.51-5.56 (m, 1H), 2.29-2.39 (m, 1H), 2.05-2.15 (m, 1H), 1.44-1.82 (m, 7H), 1.09-1.22 (m, 2H).

Intermediate 60

4-Chloro-5-cyclopentylmethoxy-2H-pyridazin-3-one

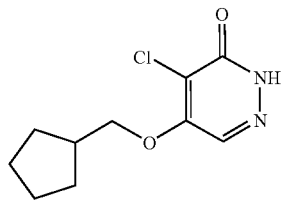

Step 1: The sodium salt of cyclopentyl-methanol was generated by treating cyclopentyl-methanol (32 mL) at 25° C. with solid sodium metal (0.41 g, 17.8 mmol). The reaction was stirred at 25° C. for 1.5 h and then was warmed to 50° C. for ~2 h. After this time, the reaction was treated with 4,5-dichloro-2-(tetrahydropyran-2-yl)-2H-pyridazin-3-one (Intermediate 20, 3.0 g, 12.04 mmol). The reaction was heated to 85° C. for 1 h. After this time, the reaction was cooled to 25° C. and was allowed to stir at 25° C. overnight. After this time, the reaction was concentrated in vacuo. The residue was then partitioned between water (250 mL) and ethyl acetate (1×250 mL). The organics were washed with a saturated aqueous sodium chloride solution (1×150 mL), dried over magnesium sulfate, filtered, rinsed with ethyl acetate, and concentrated in vacuo. Silica gel column chromatography (ISCO 120 g, 10-30% ethyl acetate/hexanes) afforded 4-chloro-5-cyclopentyl methoxy-2-(tetrahydro-pyran-2-yl)-2H-pyridazin-3-one (1.64 g, 44%) as an off-white solid; ES$^+$-HRMS m/e calcd for C$_{15}$H$_{21}$N$_2$O$_3$Cl [M+H$^+$] 335.1133, found 335.1132. $^1$H NMR (400 MHz, DMSO-d$_6$) δ ppm 1.26-1.39 (m, 2H), 1.45-1.82 (m, 10H), 1.90-2.00 (m, 1H), 1.99-2.14 (m, 1H), 2.23-2.38 (m, 1H), 3.52-3.73 (m, 1H), 3.95 (m, 1H), 4.26 (d, J=6.8 Hz, 2H), 5.87 (dd, J=10.6, 1.6 Hz, 1H), 8.29 (s, 1H).

Step 2: A solution of 4-chloro-5-cyclopentylmethoxy-2-(tetrahydro-pyran-2-yl)-2H-pyridazin-3-one (1.63 g, 5.21 mmol) in methanol (10 mL, 0.52M) was treated with a 6N aqueous hydrochloric acid solution (4.4 mL). The reaction solution was heated to 110° C., where it stirred for 2.5 h and was then allowed to cool to 25° C. The reaction was then diluted with water (100 mL) and brought to basic pH with a 4N aqueous sodium hydroxide solution. This solution was extracted with methylene chloride (1×100 mL). The aqueous layer was then acidified with a 3N aqueous hydrochloric acid solution. The resulting white precipitate was collected by filtration, washed with water, and dried in vacuo to afford 4-chloro-5-cyclopentylmethoxy-2H-pyridazin-3-one (1.06 mg, 89%) as a white solid; ES$^+$-HRMS m/e calcd for C$_{10}$H$_{13}$N$_2$O$_2$Cl [M+H$^+$] 229.0739, found 229.0738. $^1$H NMR (400 MHz, DMSO-d$_6$) δ ppm 1.26-1.40 (m, 2H), 1.47-1.68

(m, 4H), 1.70-1.82 (m, 2H), 2.22-2.38 (m, 1H), 4.22 (d, J=6.8 Hz, 2H), 8.19 (s, 1H), 13.28 (brs, 1H).

Intermediate 59

3-Cyclopentyl-2-(4-cyclopentylmethoxy-6-oxo-6H-pyridazin-1-yl)-propionic acid

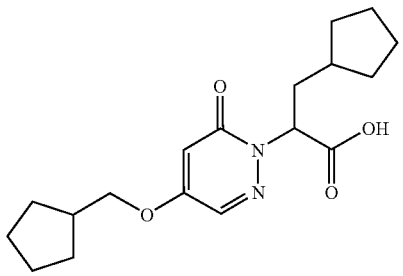

Step 1: A pressure vial containing a mixture of 4-chloro-5-cyclopentylmethoxy-2H-pyridazin-3-one (Intermediate 60, 0.75 g, 3.27 mmol), water (12 mL), and a 2N aqueous sodium hydroxide solution (2.1 mL) was treated with 10% palladium on carbon (75.1 mg, 10% weight of 4-chloro-5-cyclopentylmethoxy-2H-pyridazin-3-one). The reaction was then pressurized with hydrogen (40 psi), where it shook overnight. The resulting reaction mixture was removed from the hydrogenator and then warmed with a heat gun and quickly filtered through filter paper. The filter cake was rinsed with warm water and methylene chloride. The filtrate was filtered through filter paper to remove some residual catalyst and washed with methylene chloride. The filtrate was concentrated in vacuo to remove organics. Upon concentrating the aqueous layer was acidified with a 1N aqueous hydrochloric acid solution. The resulting precipitate was collected by filtration, rinsed with water and then dried in vacuo to afford 5-cyclopentylmethoxy-2H-pyridazin-3-one (499.6 mg, 78%) as an off-white solid; ES$^+$-HRMS m/e calcd for $C_{10}H_{14}N_2O_2$ [M+H$^+$] 195.1128, found 195.1128. $^1$H NMR (400 MHz, DMSO-d$_6$) δ ppm 1.23-1.38 (m, 2H), 1.46-1.67 (m, 4H), 1.68-1.82 (m, 2H), 2.23-2.34 (m, 1H), 3.87 (d, J=7.0 Hz, 2H), 6.17 (s, 1H), 7.65 (d, J=2.6 Hz, 1H), 12.61 (br s, 1H).

Step 2: A solution of 5-cyclopentylmethoxy-2H-pyridazin-3-one (494.8 mg, 2.54 mmol) in tetrahydrofuran (12 mL, 0.21 M) cooled to 0° C. was treated with a 60% suspension of sodium hydride in mineral oil (0.12 g, 3.0 mmol). The reaction stirred at 0° C. for 5 min and then at 25° C. for an additional 30 min. After this time, the reaction was treated with 2-bromo-3-cyclopentyl-propionic acid methyl ester (Intermediate 10, 0.67 g, 2.84 mmol). The reaction was then warmed to 50° C., where it stirred overnight. The reaction sat at 25° C. for 2 d. After this time, the reaction was partitioned between water (75 mL) and methylene chloride (3×75 mL). The combined organic layers were washed with a saturated aqueous sodium chloride solution (1×75 mL), dried over magnesium sulfate, filtered, rinsed and concentrated in vacuo. Silica gel column chromatography (AnaLogix 40 g, 10-30% ethyl acetate/hexanes) afforded 3-cyclopentyl-2-(4-cyclopentylmethoxy-6-oxo-6H-pyridazin-1-yl)-propionic acid methyl ester (713.9 mg, 80%) as a clear light yellow oil; ES$^+$-HRMS m/e calcd for $C_{19}H_{28}N_2O_4$ [M+H$^+$] 349.2122, found 349.2120. $^1$H NMR (400 MHz, DMSO-d$_6$) δ ppm 1.18 (m, 2H), 1.23-1.82 (m, 15H), 1.87-1.98 (m, 1H), 2.05-2.23 (m, 1H), 2.23-2.37 (m, 1H), 3.61 (s, 3H), 3.91 (d, J=7.0 Hz, 2H), 5.39 (dd, J=10.9, 4.3 Hz, 1H), 6.31 (d, J=2.8 Hz, 1H), 7.83 (d, J=2.8 Hz, 1H).

Step 3: A solution of 3-cyclopentyl-2-(4-cyclopentylmethoxy-6-oxo-6H-pyridazin-1-yl)-propionic acid methyl ester (702.6 g, 2.01 mmol) in methanol (1.3 mL, 1.55M) was treated with a 4N aqueous sodium hydroxide solution (0.55 mL, 2.22 mmol) and stirred at 25° C. overnight. After this time, the reaction was concentrated in vacuo. The resulting solids were then taken up in water (30 mL) and a 1N aqueous sodium hydroxide solution (20 mL) and extracted with methylene chloride (1×30 mL). The aqueous layer was then acidified with a 3N aqueous hydrochloric acid solution. The resulting precipitate was collected by filtration and dried in vacuo. The initial organics were treated with a 1N aqueous sodium hydroxide solution (50 mL), concentrated in vacuo, and then acidified with a 3N aqueous hydrochloric acid solution. The resulting precipitate was collected by filtration and dried in vacuo. The combined solids afforded 3-cyclopentyl-2-(4-cyclopentylmethoxy-6-oxo-6H-pyridazin-1-yl)-propionic acid (490.5 mg, 73%) as a white solid; ES$^+$-HRMS m/e calcd for $C_{18}H_{26}N_2O_4$ [M+H$^+$] 335.1966, found 335.1964. $^1$H NMR (400 MHz, DMSO-d$_6$) δ ppm 0.95-1.18 (m, 2H), 1.24-1.82 (m, 15H), 1.94 (ddd, J=13.6, 9.0, 4.0 Hz, 1H), 2.16 (ddd, J=13.8, 11.1, 5.1 Hz, 1H), 2.25-2.36 (m, 1H), 3.90 (d, J=7.0 Hz, 2H), 5.31 (dd, J=11.1, 4.0 Hz, 1H), 6.29 (d, J=2.8 Hz, 1H), 7.81 (d, J=2.8 Hz, 1H), 12.92 (br s, 1H).

Intermediate 61

3-Cyclopentyl-2-(4-cyclopentyloxy-6-oxo-6H-pyridazin-1-yl)-propionic acid

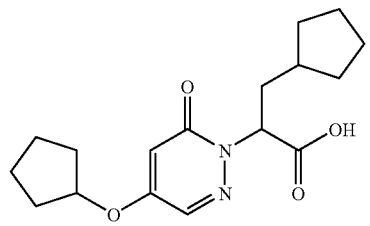

In an analogous manner to the stepwise sequence outlined in Intermediate 59, starting from cyclopentanol and 4,5-dichloro-2-(tetrahydro-pyran-2-yl)-2H-pyridazin-3-one (Intermediate 20) and 2-bromo-3-cyclopentyl-propionic acid methyl ester (Intermediate 10) afforded 3-cyclopentyl-2-(4-cyclopentyloxy-6-oxo-6H-pyridazin-1-yl)-propionic acid as a white solid (244.7 mg, 88%, total or for last step); ES$^+$-HRMS m/e calcd for $C_{17}H_{24}N_2O_4$ [M+H$^+$] 321.1809, found 321.1808. $^1$H NMR (400 MHz, DMSO-d$_6$) δ ppm 0.96-1.17 (m, 2H), 1.35-1.78 (m, 13H), 1.87-2.01 (m, 3H), 2.15 (ddd, J=13.8, 11.0, 5.0 Hz, 1H), 4.81-4.90 (m, 1H), 5.31 (dd, J=11.0, 4.2 Hz, 1H), 6.26 (d, J=2.8 Hz, 1H), 7.75 (d, J=2.8 Hz, 1H), 12.92 (br s, 1H).

Intermediate 62

2-(5-Chloro-4-cyclopentylmethoxy-6-oxo-6H-pyridazin-1-yl)-3-cyclopentyl-propionic acid

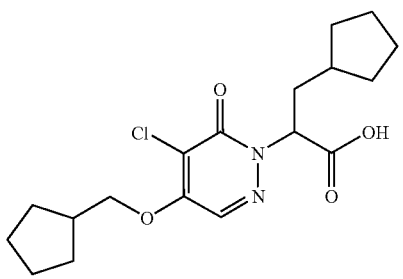

Step 1: A solution of 4-chloro-5-cyclopentylmethoxy-2H-pyridazin-3-one (Intermediate 60, 297.5 mg, 1.30 mmol) in tetrahydrofuran (6.5 mL, 0.2M) cooled to 0° C. was treated with a 60% suspension of sodium hydride in mineral oil (62.9 mg, 1.57 mmol). The reaction stirred at 0° C. for 15 min and then at 25° C. for an additional 30 min. After this time, the reaction was treated with 2-bromo-3-cyclopentyl-propionic acid methyl ester (Intermediate 10, 0.34 g, 1.44 mmol). The reaction was then warmed to 50° C., where it stirred overnight. After this time, the reaction was partitioned between water (75 mL) and methylene chloride (3×75 mL). The combined organic layers were washed with a saturated aqueous sodium chloride solution (1×75 mL), dried over magnesium sulfate, filtered and concentrated in vacuo. Silica gel column chromatography (AnaLogix 40 g, 10-30% ethyl acetate/hexanes) afforded 2-(5-chloro-4-cyclopentyl methoxy-6-oxo-6H-pyridazin-1-yl)-4-ethyl-heptanoic acid methyl ester (351 mg, 70%) as a clear oil; ES$^+$-HRMS m/e calcd for $C_{19}H_{27}N_2O_4Cl$ [M+H$^+$] 383.1732, found 383.1731. $^1$H NMR (400 MHz, DMSO-$d_6$) δ ppm 0.97-1.20 (m, 2H), 1.28-1.83 (m, 15H), 1.95-2.05 (m, 1H), 2.19 (ddd, J=14.0, 10.8, 5.1 Hz, 1H), 2.26-2.37 (m, 1H), 3.63 (s, 3H), 4.27 (d, J=6.8 Hz, 2H), 5.45 (dd, J=10.8, 4.4 Hz, 1H), 8.34 (s, 1H).

Step 2: A solution of 2-(5-chloro-4-cyclopentylmethoxy-6-oxo-6H-pyridazin-1-yl)-4-ethyl-heptanoic acid methyl ester (341.7 mg, 0.89 mmol) in methanol (0.6 mL, 1.49M) was treated with a 4N aqueous sodium hydroxide solution (0.24 mL, 0.98 mmol) and stirred at 25° C. for 3.5 h. After this time, the reaction was concentrated in vacuo. The residue was diluted with water (20 mL) and acidified with a 1N aqueous hydrochloric acid solution. The resulting gummy solids were collected by filtration, rinsed with water and dried in vacuo to afford 2-(5-chloro-4-cyclopentylmethoxy-6-oxo-6H-pyridazin-1-yl)-4-ethyl-heptanoic acid (296.1 mg, 90%) as a tacky, white solid; ES$^+$-HRMS m/e calcd for $C_{18}H_{25}N_2O_4Cl$ [M+H$^+$] 369.1576, found 369.1575. $^1$H NMR (400 MHz, DMSO-$d_6$) δ ppm 0.96-1.19 (m, 2H), 1.28-1.84 (m, 15H), 1.91-2.03 (m, 1H), 2.15-2.27 (m, 1H), 2.27-2.38 (m, 1H), 4.26 (d, J=6.8 Hz, 2H), 5.37 (dd, J=11.0, 4.2 Hz, 1H), 8.32 (s, 1H), 13.10 (br s, 1H).

Intermediate 63

3-Cyclopentyl-2-[6-oxo-4-(2-trifluoromethyl-benzyl)-6H-pyridazin-1-yl]-propionic acid

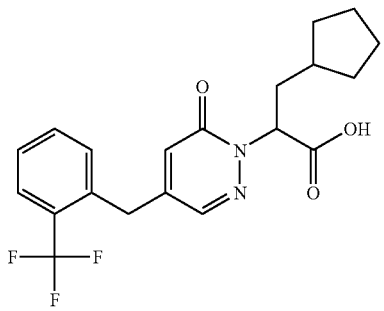

Step 1: A solution of 4,5-dichloro-2-(tetrahydropyran-2-yl)-2H-pyridazin-3-one (Intermediate 20, 1.0 g, 4.01 mmol) in tetrahydrofuran (16.7 mL, 0.24M) was treated with (2-trifluoromethyl-phenyl)-acetonitrile (743 mg, 4.01 mmol) followed by potassium tert-butoxide (676 mg, 6.02 mmol). The reaction was heated at 80° C. for 2 h. After this time, the reaction was cooled to 25° C. where it stirred overnight. The reaction mixture was then partitioned between water (100 mL) and methylene chloride (3×75 mL). The combined organics were dried over sodium sulfate, filtered, and concentrated in vacuo. Silica gel column chromatography (AnaLogix, 40 g, 20-40% ethyl acetate/hexanes) afforded [5-chloro-6-oxo-1-(tetrahydro-pyran-2-yl)-1,6-dihydro-pyridazin-4-yl]-(2-trifluoromethyl-phenyl)-acetonitrile (0.73 g, 45%) as a yellow solid; ES$^+$-HRMS m/e calcd for $C_{18}H_{15}N_3O_2F_3Cl$ [M+H$^+$] 398.0878, found 398.0878.

Step 2: A mixture of [5-chloro-6-oxo-1-(tetrahydro-pyran-2-yl)-1,6-dihydro-pyridazin-4-yl]-(2-trifluoromethyl-phenyl)-acetonitrile (550 mg, 1.38 mmol) in concentrated hydrochloric acid (8.4 mL), glacial acetic acid (2.1 mL) and water (2.1 mL) (4:1:1, 0.11 M) was heated to 120° C. overnight. After this time, the reaction was cooled to 25° C. and then poured onto ice, followed by rinsing with minimal water. The resulting aqueous mixture was brought to pH=4-5 by treatment with a 4N aqueous sodium hydroxide solution. The resulting tan solids were collected by filtration. The solids were subsequently washed with water (2×10 mL) and dried in vacuo to afford 4-chloro-5-(2-trifluoromethyl-benzyl)-2H-pyridazin-3-one (0.24 g, 62%) as a tan solid; ES$^+$-HRMS m/e calcd for $C_{12}H_8N_2OF_3Cl$ [M+H$^+$] 289.0350, found 289.0350.

Step 3: A pressure vial containing a mixture of 4-chloro-5-(2-trifluoromethyl-benzyl)-2H-pyridazin-3-one (328.1 mg, 1.1 mmol), ethanol (12.1 mL), and a 2N aqueous sodium hydroxide solution (0.61 mL) was treated with 10% palladium on carbon (121 mg). The reaction was then pressurized with hydrogen (50 psi), where it shook for 20 h. The resulting reaction mixture was removed from the hydrogenator and then filtered through a pad of diatomaceous earth, washing with ethanol. The filtrate was concentrated in vacuo to remove organics. The resulting residue was taken up in 90/10 methylene chloride/methanol (75 mL) and water (40 mL). The aqueous layer was acidified with a 2N aqueous hydrochloric acid solution to pH=1, and the layers were separated. The aqueous layer was then back extracted with a 90/10 methylene chloride/methanol solution (2×75 mL). The combined organic layers were dried over sodium sulfate, filtered, and concentrated in vacuo to afford 5-(2-trifluoromethyl-benzyl)-2H-pyridazin-3-one (223 mg, 77%) as a yellow solid; ES$^+$-HRMS m/e calcd for $C_{12}H_9N_2OF_3$ [M+H$^+$] 255.0740, found 255.0740. $^1$H NMR (300 MHz, DMSO-d$_6$) δ ppm 4.05 (s, 2H), 6.28 (s, 1H), 7.49 (d, J=7.8 Hz, 1H), 7.54 (d, J=7.8 Hz, 1H), 7.69 (t, J=7.8 Hz, 1H), 7.75 (d, J=2.1 Hz, 1H), 7.78 (d, J=7.8 Hz, 1H), 12.96 (br. s., 1H).

Step 4: A solution of 5-(2-trifluoromethyl-benzyl)-2H-pyridazin-3-one (219.6 mg, 0.86 mmol) in tetrahydrofuran (4.32 mL, 0.2M) cooled to 0° C. was treated with a 60% suspension of sodium hydride in mineral oil (41 mg, 1.03 mmol). The reaction stirred at 0° C. for 5 min and then at 25° C. for an additional 30 min. After this time, the reaction was treated with 2-bromo-3-cyclopentyl-propionic acid methyl ester (Intermediate 10, 223 mg, 0.95 mmol). The reaction was then warmed to 50° C., where it stirred overnight. After this time, the reaction was diluted with water (150 mL) and methylene chloride (30 mL) and the resulting bilayer was extracted with methylene chloride (3×75 mL). The combined organic layers were dried over sodium sulfate, filtered and concentrated in vacuo. Silica gel column chromatography (AnaLogix, 40 g, 25-40% ethyl acetate/hexanes) afforded 3-cyclopentyl-2-[6-oxo-4-(2-trifluoromethyl-benzyl)-6H-pyridazin-1-yl]-propionic acid methyl ester (155.9 mg, 44%) as a yellow oil; ES$^+$-HRMS m/e calcd for $C_{21}H_{23}N_2O_3F_3$ [M+H$^+$] 409.1734, found 409.1733.

Step 5: A solution of 3-cyclopentyl-2-[6-oxo-4-(2-trifluoromethyl-benzyl)-6H-pyridazin-1-yl]-propionic acid methyl ester (149.4 mg, 0.36 mmol) in methanol (0.61 mL, 0.6M) was treated with a 4N aqueous sodium hydroxide solution (0.1 mL, 0.40 mmol) and stirred at 25° C. for 3 h. After this time, the reaction was poured into water (50 mL) and 90/10 methylene chloride/methanol (30 mL) and was acidified with a 2N aqueous hydrochloric acid solution and then was extracted into a 90/10 methylene chloride/methanol (3×30 mL). The combined organics were dried over sodium sulfate, filtered and concentrated in vacuo to afford 3-cyclopentyl-2-[6-oxo-4-(2-trifluoromethyl-benzyl)-6H-pyridazin-1-yl]-propionic acid (130.6 mg, 90%) as a yellow solid. This material was used without further purification; ES$^+$-HRMS m/e calcd for $C_{20}H_{21}N_2O_3F_3$ [M+H$^+$] 395.1577, found 395.1574.

Intermediate 64

3-Cyclopentyl-2-[6-oxo-4-(3-trifluoromethyl-benzyl)-6H-pyridazin-1-yl]-propionic acid

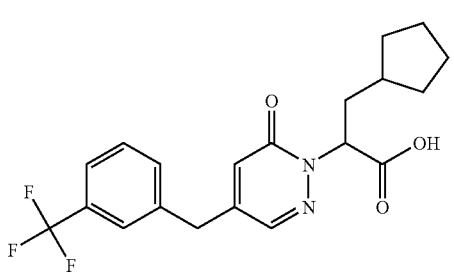

In an analogous manner to the stepwise sequence outlined in Intermediate 63, starting from 4,5-dichloro-2-(tetrahydro-pyran-2-yl)-2H-pyridazin-3-one (Intermediate 20) and (3-trifluoromethyl-phenyl)acetonitrile and alkylating with 2-bromo-3-cyclopentyl-propionic acid methyl ester (Intermediate 10) afforded 3-cyclopentyl-2-[6-oxo-4-(3-trifluoromethyl-benzyl)-6H-pyridazin-1-yl]-propionic acid (200.1 mg, 70% for Step 5) as a yellow solid; ES$^+$-HRMS m/e calcd for $C_{20}H_{21}N_2O_3F_3$ [M+H$^+$] 395.1577, found 395.1576. $^1$H NMR (300 MHz, DMSO-d$_6$) δ ppm 0.99 (br s, 2H), 1.30-1.78 (m, 7H), 1.83-2.05 (m, 1H), 2.07-2.24 (m, 1H), 3.99 (s, 2H), 5.31 (dd, J=10.6, 4.2 Hz, 1H), 6.73 (s, 1H), 7.50-7.69 (m, 3H), 7.73 (s, 1H), 7.95 (d, J=1.8 Hz, 1H), 12.97 (br s, 1H).

Intermediate 65

3-Cyclopentyl-2-[4-(2,6-difluoro-benzyl)-6-oxo-6H-pyridazin-1-yl]-propionic acid

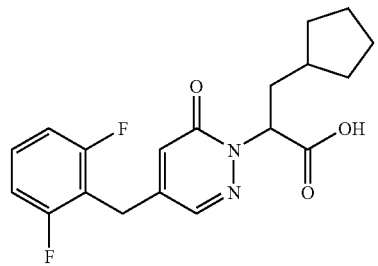

In an analogous manner to the stepwise sequence outlined in Intermediate 63, starting from 4,5-dichloro-2-(tetrahydro-pyran-2-yl)-2H-pyridazin-3-one (Intermediate 20) and (2,6-difluoro-phenyl)-acetonitrile and alkylating with 2-bromo-3-cyclopentyl-propionic acid methyl ester (Intermediate 10) afforded 3-cyclopentyl-2-[4-(2,6-difluoro-benzyl)-6-oxo-6H-pyridazin-1-yl]-propionic acid (175 mg, 88% for Step 5) as an off-white solid; ES$^+$-HRMS m/e calcd for $C_{20}H_{21}N_2O_3F_3$ [M+H$^+$] 395.1577, found 395.1576. $^1$H NMR (300 MHz, DMSO-d$_6$) δ ppm 0.91-1.21 (m, 2H), 1.33-1.75 (m, 7H), 1.82-2.04 (m, 1H), 2.07-2.24 (m, 1H), 3.96 (s, 2H), 5.31 (d, J=6.3 Hz, 1H), 6.48 (s, 1H), 7.09-7.25 (m, 2H), 7.37-7.53 (m, 1H), 7.90 (s, 1H), 12.97 (br s, 1H).

Intermediate 66

3-Cyclopentyl-2-[6-oxo-4-(2,3,6-trimethyl-phenoxy)-6H-pyridazin-1-yl]-propionic acid

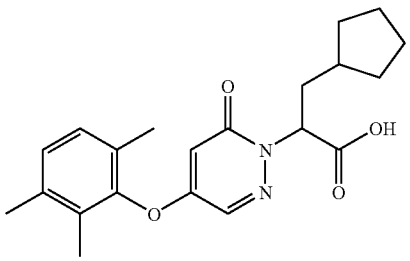

In an analogous manner to the stepwise sequence outlined in intermediate 19, starting from 4,5-dichloro-2-(tetrahydro-pyran-2-yl)-2H-pyridazin-3-one (Intermediate 20) and 2,3,6-trimethyl-phenol and alkylating with 2-bromo-3-cyclopentyl-propionic acid methyl ester (Intermediate 10) afforded 3-cyclopentyl-2-[6-oxo-4-(2,3,6-trimethyl-phenoxy)-6H-pyridazin-1-yl]-propionic acid as a white solid (11.5 g, 58% for the final step); LC-MS 371 [M+1]$^+$, $t_R$=3.92 min. Purity on HPLC: 98.5% (214 nm), 99.2% (254 nm), $t_R$=9.92 min. $^1$H NMR (300 MHz, CDCl$_3$): δ 7.94 (d, 1H, J=2.7 Hz), 7.02 (s, 2H), 5.74 (d, 1H, J=2.7 Hz), 5.52 (dd, 1H, J$_1$=10.2 Hz, J$_2$=5.4 Hz), 2.34~2.32 (m, 1H), 2.20~2.16 (m, 1H), 2.29 (s, 3H), 2.18 (s, 3H), 2.05 (s, 3H), 1.79~1.49 (m, 7H), 1.25~1.14 (m, 2H).

Intermediate 67

3-Cyclopentyl-2-[4-(2,2-dimethyl-2,3-dihydro-benzofuran-7-yloxy)-6-oxo-6H-pyridazin-1-yl]-propionic acid

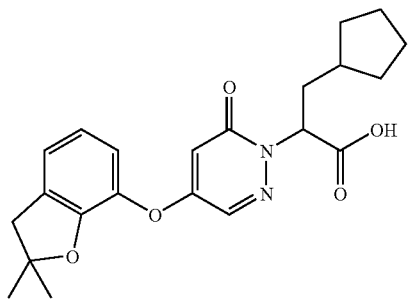

In an analogous manner to the stepwise sequence outlined in intermediate 19, starting from 4,5-dichloro-2-(tetrahydro-pyran-2-yl)-2H-pyridazin-3-one (Intermediate 20) and 2,2-dimethyl-2,3-dihydro-benzofuran-7-ol and alkylating with 2-bromo-3-cyclopentyl-propionic acid methyl ester (Intermediate 10) afforded 3-cyclopentyl-2-[4-(2,2-dimethyl-2,3-dihydro-benzofuran-7-yloxy)-6-oxo-6H-pyridazin-1-yl]-propionic acid as a white solid (14 g, 91% for the final step); LC-MS: $t_R$=3.73 min, 399 [M+H]$^+$. HPLC: $t_R$=6.52 min, 98.99% at 214 nm, 99.32% at 254 nm. $^1$H NMR (300 MHz, CD$_3$OD): δ 7.99 (s, 1H), 7.17-6.89 (m, 3H), 5.87 (s, 1H), 5.52-5.48 (m, 1H), 3.12 (s, 2H), 2.40-2.32 (m, 1H), 2.13-2.10 (m, 1H), 1.81-1.52 (m, 7H), 1.45 (s, 6H), 1.20-1.14 (m, 2H).

Intermediate 68

2-[4-(2-tert-Butyl-phenoxy)-6-oxo-6H-pyridazin-1-yl]-3-cyclopentyl-propionic acid

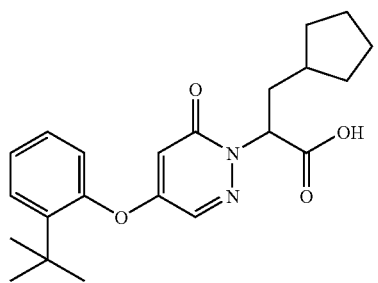

In an analogous manner to the stepwise sequence outlined in intermediate 19, starting from 4,5-dichloro-2-(tetrahydro-pyran-2-yl)-2H-pyridazin-3-one (Intermediate 20) and 2-tert-butyl-phenol and alkylating with 2-bromo-3-cyclopen-tyl-propionic acid methyl ester (Intermediate 10) afforded 2-[4-(2-tert-butyl-phenoxy)-6-oxo-6H-pyridazin-1-yl]-3-cyclopentyl-propionic acid as a white solid (13.2 g, 81% for the final step); LC-MS 385.2 [M+1]$^+$, $t_R$=5.86 min. Purity on HPLC: 95.7% (214 nm), 88.8% (254 nm), $t_R$=7.87. $^1$H NMR (300 MHz, CDCl$_3$): δ 10.85 (s, 1H), 7.83 (m, 1H, J=2.4 Hz), 7.44 (d, 1H, J=4.5 Hz), 7.20 (m, 2H), 6.97 (d, 1H, J=7.5 Hz), 6.06 (d, 1H, J=2.4 Hz), 5.36 (dd, 1H, J$_1$=9.6 Hz, J$_2$=4.2 Hz), 2.33~2.20 (m, 1H), 2.20~2.05 (m, 1H), 1.66~1.14 (m, 7H), 1.33 (s, 9H), 1.17~1.05 (m, 2H).

Intermediate 69

3-Cyclopentyl-2-[4-(2,6-dimethyl-cyclohexyloxy)-6-oxo-6H-pyridazin-1-yl]-propionic acid

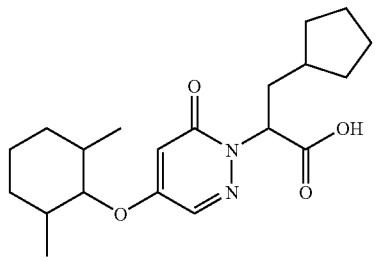

In an analogous manner to the stepwise sequence outlined in Intermediate 72, starting from 4,5-dichloro-2-(tetrahydro-pyran-2-yl)-2H-pyridazin-3-one (Intermediate 20) and 2,6-dimethyl-cyclohexanol and alkylating with 2-bromo-3-cyclopentyl-propionic acid methyl ester (Intermediate 10) afforded 3-cyclopentyl-2-[4-(2,6-dimethyl-cyclohexyloxy)-6-oxo-6H-pyridazin-1-yl]-propionic acid (10.5 g, 86% for the final step); LC-MS: 363 (M+1)$^+$, $t_R$=5.03 min. Purity on HPLC: $t_R$=10.3 min, 99.3% (214 nm), 99.0% (254 nm). $^1$H NMR (300 MHz, DMSO-d$_6$): δ 12.89 (s, 1H), 7.79-7.77 (m, 1H), 6.96-6.82 (m, 1H), 5.36 (dd, 1H, J=10.8 Hz, J=3.9 Hz), 4.58-4.15 (m, 1H), 2.20-0.76 (m, 25H).

Intermediate 70

3-Cyclopentyl-2-[4-(2,3-dichloro-phenoxy)-6-oxo-6H-pyridazin-1-yl]-propionic acid

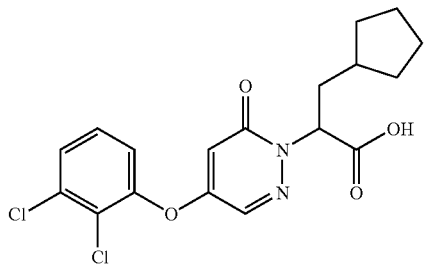

Step 1: A solution of 4,5-dichloropyridazin-3(2H)-one (5 g, 30.3 mmol) in a 57% aqueous hydroiodic acid solution (50 mL) was stirred at 150° C. for 24 h. The solution was cooled to 25° C. The resulting solid was collected by filtration, washed with a solution of sodium thiosulfate (2×16 mL) and water (2×10 mL) to afford 5-iodo-2H-pyridazin-3-one as a yellow solid (5 g, 60.0%).

Step 2: A solution of 5-iodo-2H-pyridazin-3-one (66 g, 0.30 mol) in tetrahydrofuran (500 mL) was treated with pyridinium para-toluene sulfonate (14.3 g, 0.057 mol) and 3,4-dihydro-2H-pyran (52 mL). The reaction mixture was stirred at reflux for 5 h. At this time, the reaction was treated with another aliquot of 3,4-dihydro-2H-pyran (32.5 mL). The solution was stirred at reflux overnight. At this time, the solution was concentrated in vacuo. Chromatography (ethyl acetate/petroleum ether=1/2) afforded 5-iodo-2-(tetrahydro-pyran-2-yl)-2H-pyridazin-3-one (89 g, 98%).

Step 3: A mixture of 5-iodo-2-(tetrahydro-pyran-2-yl)-2H-pyridazin-3-one (0.58 g, 1.90 mmol), 2,3-dichloro-phenol (0.31 g, 1.90 mmol), and potassium carbonate (0.28 g, 2.08 mmol) in acetonitrile (30 mL) was heated at reflux for 5 h. At this time, 5 mL of the reaction were transferred to a sealed tube reaction vessel and treated with another aliquot of potassium carbonate (0.1 g). The reaction mixture then stirred at 110° C. for 12 h. This afforded 5-(2,3-dichloro-phenoxy)-2-(tetrahydro-pyran-2-yl)-2H-pyridazin-3-one (48 mg). The remaining original reaction mixture was concentrated in vacuo and then charged with N,N-dimethylformamide (25 mL) and potassium carbonate (0.3 g). The mixture was stirred at 120° C. for 4 h. 5-(2,3-Dichloro-phenoxy)-2-(tetrahydro-pyran-2-yl)-2H-pyridazin-3-one was obtained as a white solid (0.38 g, 59%).

Step 4: In an analogous manner to the reaction outlined in Intermediate 18 step 4, starting from 5-(2,3-dichloro-phenoxy)-2-(tetrahydro-pyran-2-yl)-2H-pyridazin-3-one afforded 5-(2,3-dichloro-phenoxy)-2H-pyridazin-3-one as a white solid (189 mg, 66%)

In an analogous manner to the stepwise sequence outlined in Intermediate 19 steps 4-5, starting from 5-(2,3-dichloro-phenoxy)-2H-pyridazin-3-one alkylating with 2-bromo-3-cyclopentyl-propionic acid methyl ester (Intermediate 10) afforded 3-cyclopentyl-2-[4-(2,3-dichloro-phenoxy)-6-oxo-6H-pyridazin-1-yl]-propionic acid (12 g, 78% for the final step); LC-MS: 307 [M+1]$^+$, $t_R$=2.50 min. HPLC: 30.31% at 214 nm, 90.71% at 254 nm, $t_R$=3.81 min. $^1$H NMR (300 MHz, DMSO-d$_6$): δ 8.18 (s, 1H), 7.63 (d, 1H, J=2.1 Hz), 5.79 (d, 1H, J=10.2 Hz), 3.95 (d, 1H, J=12.3 Hz), 3.58 (d, 1H, J=3.3 Hz), 2.04~1.91 (m, 2H), 1.64~1.49 (m, 4H).

Intermediate 71

3-Cyclopentyl-2-[4-(7-methyl-indan-4-yloxy)-6-oxo-6H-pyridazin-1-yl]-propionic acid

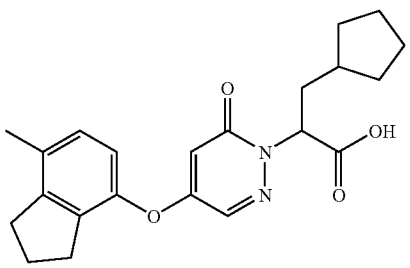

In an analogous manner to the stepwise sequence outlined in intermediate 19, starting from 4,5-dichloro-2-(tetrahydro-pyran-2-yl)-2H-pyridazin-3-one (Intermediate 20) and 7-methyl-indan-4-ol and alkylating with 2-bromo-3-cyclopentyl-propionic acid methyl ester (Intermediate 10) afforded 3-cyclopentyl-2-[4-(7-methyl-indan-4-yloxy)-6-oxo-6H-pyridazin-1-yl]-propionic acid (10 g, 86% for the final step); LC-MS: 383 [M+1]$^+$, $t_R$=3.77 min. HPLC: 97.75% at 214 nm, 98.81% at 254 nm, $t_R$=7.98 min. $^1$H NMR (300 MHz, CDCl$_3$): δ 7.85 (d, 1H, J=2.4 Hz), 7.01 (d, 1H, J=8.1 Hz), 6.77 (d, 1H, J=8.1 Hz), 5.88 (d, 1H, J=2.4 Hz), 5.49 (dd, 1H, J$_1$=10.2 Hz, J$_2$=4.8 Hz), 2.87 (t, 2H, J=7.5 Hz), 2.77 (t, 2H, J=7.5 Hz), 2.26 (s, 3H), 2.15~2.07 (m, 2H), 1.80~1.49 (m, 7H), 1.25~1.14 (m, 4H).

Intermediate 72

2-(4-Cyclobutoxy-6-oxo-6H-pyridazin-1-yl)-3-cyclopentyl-propionic acid

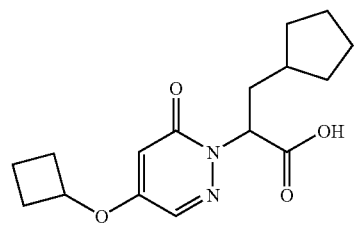

Step 1: A solution of cyclobutanol (7.2 g, 100 mmol) in tetrahydrofuran (200 mL) was treated with sodium hydride (3.6 g, 150 mmol) and stirred at 25° C. for 15 min. At this time, 4,5-dichloro-2-(tetrahydropyran-2-yl)-2H-pyridazin-3-one (Intermediate 20, 20.0 g, 80 mmol) in tetrahydrofuran was added dropwise. The resulting mixture was stirred at 25° C. for 2 h. At this time, the reaction was concentrated in vacuo. Chromatography (8/1 petroleum ether/ethyl acetate) afforded 4-chloro-5-cyclobutoxy-2-(tetrahydro-pyran-2-yl)-2H-pyridazin-3-one (16.3 g, 72%).

In an analogous manner to the stepwise sequence outlined in intermediate 19 (steps 2-5), starting from 4-chloro-5-cyclobutoxy-2-(tetrahydro-pyran-2-yl)-2H-pyridazin-3-one and alkylating with 2-bromo-3-cyclopentyl-propionic acid methyl ester (Intermediate 10) afforded 2-(4-cyclobutoxy-6-oxo-6H-pyridazin-1-yl)-3-cyclopentyl-propionic acid (9.0 g, 98% for the final step); LC-MS: 307 (M+1)$^+$, $t_R$=4.17 min. HPLC: $t_R$=12.71 min, (214 nm, 98.6%), (254 nm, 99.0%). $^1$H NMR (300 MHz, DMSO-d$_6$): δ 12.86 (s, 1H, broad), 7.80 (d, 1H J=4.8 Hz), 6.61 (d, 1H, J=5.1 Hz), 5.36 (dd, 1H, J=10.8 Hz, J=3.9 Hz), 4.58-4.14 (m, 1H), 2.20-0.76 (m, 17H).

Intermediate 73

3-Cyclopentyl-2-[4-(3-fluoro-pyridin-2-yloxy)-6-oxo-6H-pyridazin-1-yl]-propionic acid

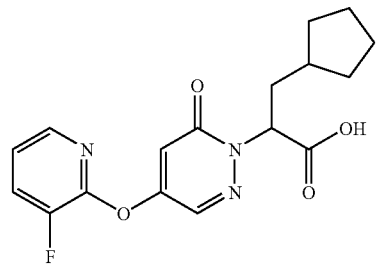

Step 1: A solution of 4,5-dichloropyridazin-3(2H)-one (5 g, 30.3 mmol) in 57% aqueous hydroiodic acid (50 mL) was stirred at 150° C. for 24 h. The solution was cooled to 25° C. and the resulting solid was filtered, washed with sodium thiosulfate (16 mL×2), then water (10 mL×2) to afford 5-iodopyridazin-3(2H)-one as a yellow solid (5 g, 60.0%).

Step 2: A solution of 5-iodopyridazin-3(2H)-one (52 g, 234 mmol) in tetrahydrofuran (1000 mL) was treated with sodium hydride (11.2 g, 280 mmol) at 0° C. The mixture was stirred at 0° C. for 5~10 min and then stirred at 25° C. for an additional 40~50 min. At this time, the reaction mixture was treated with 2-bromo-3-cyclopentyl-propionic acid methyl ester (Intermediate 10, 72.6 g, 281 mmol). The resulting reaction mixture was heated at 50° C. for 18 h and allowed to cool down to 25° C. The reaction mixture was then partitioned between water (500 mL) and methylene chloride (500 mL). The aqueous layer was back extracted with methylene chloride (1×300 mL). The combined organics were washed with a saturated aqueous sodium chloride solution (1×300 mL), dried over magnesium sulfate, filtered and concentrated in vacuo. Silica gel chromatography (8/1 ethyl acetate/petroleum ether) afforded 3-cyclopentyl-2-(4-iodo-6-oxo-6H-pyridazin-1-yl)-propionic acid methyl ester (60.1 g, 68.3%).

Step 3: A solution of 3-cyclopentyl-2-(4-iodo-6-oxo-6H-pyridazin-1-yl)-propionic acid methyl ester (0.38 g, 1 mmol) in N,N-dimethylformamide (10 mL) was treated with 3-fluoro-pyridin-2-ol (0.15 g, 1 mmol) and potassium carbonate (0.16 g, 1.2 mmol). The reaction was heated at 120° C. for 4 h and then concentrated in vacuo. The residue was partitioned between water and methylene chloride. The aqueous layer was back extracted with methylene chloride. The combined organics were washed with a saturated aqueous sodium chloride solution, and then concentrated in vacuo. Chromatography (1/1 ethyl acetate/petroleum ether) afforded 3-cyclopentyl-2-[4-(3-fluoro-pyridin-2-yloxy)-6-oxo-6H-pyridazin-1-yl]-propionic acid methyl ester (0.19 g, 53%).

Step 4: A mixture of 3-cyclopentyl-2-[4-(3-fluoro-pyridin-2-yloxy)-6-oxo-6H-pyridazin-1-yl]-propionic acid methyl ester (3 g, 8.3 mmol) in a 6N aqueous hydrochloric acid solution (40 mL) was heated at reflux for 36 h. At this time, the resulting precipitate was collected by filtration and washed with water to afford 3-cyclopentyl-2-[4-(3-fluoro-pyridin-2-yloxy)-6-oxo-6H-pyridazin-1-yl]-propionic acid (2.1 g, 73%); LC-MS: $t_R$=3.07 min, 348 [M+H]$^+$. HPLC: $t_R$=7.78 min, 97.01% at 214 nm, 97.79% at 254 nm. $^1$H NMR (300 MHz, DMSO-d$_6$): δ 13.11 (s, 1H), δ 8.25 (s, 1H), 7.69-7.67 (m, 1H), 7.57-7.51 (m, 1H), 7.24 (s, 1H), 6.40-6.34 (m, 1H), 5.39 (dd, 1H, J=10.5 Hz, J=3.9 Hz), 2.27-2.17 (m, 1H), 2.05-1.97 (m, 1H), 1.71-1.44 (m, 7H), 1.19-1.07 (m, 2H).

Intermediate 74

3-Cyclopentyl-2-[4-(1H-indol-4-yloxy)-6-oxo-6H-pyridazin-1-yl]-propionic acid

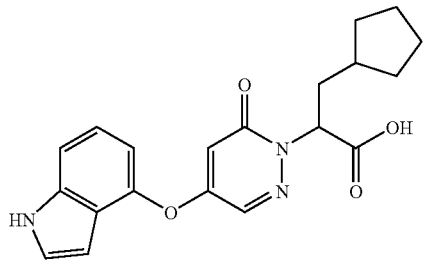

Step 1: A solution of 1H-indol-4-ol (3.5 g, 26.6 mmol) in N,N-dimethylformamide (40 mL) was treated with potassium carbonate (5.4 g, 39 mmol) and 3-cyclopentyl-2-(4-iodo-6-oxo-6H-pyridazin-1-yl)-propionic acid methyl ester (Intermediate 73 step 2.10 g, 26.6 mmol). The resulting reaction mixture was heated to 120° C. for 2 h. At this time, the reaction was cooled to 25° C. and then concentrated in vacuo. The residue was partitioned between water and methylene chloride. The aqueous phase was back extracted with methylene chloride. The combined organics was washed with a saturated aqueous sodium chloride solution, dried over anhydrous sodium sulfate, filtered and concentrated in vacuo. Chromatography afforded 3-cyclopentyl-2-[4-(1H-indol-4-yloxy)-6-oxo-6H-pyridazin-1-yl]-propionic acid methyl ester as a light oil (6.1 g, 60%).

Step 2: A solution of 3-cyclopentyl-2-[4-(1H-indol-4-yloxy)-6-oxo-6H-pyridazin-1-yl]-propionic acid methyl ester (500 mg, 1.3 mmol) in methanol (3 mL) was treated with a 4N aqueous sodium hydroxide solution (63 mg, 1.57 mmol). The reaction solution was stirred at 25° C. overnight. At this time, the reaction mixture was diluted with water (10 mL) and was acidified with a 1N aqueous hydrochloric acid solution until pH=2. The aqueous phase was extracted with ethyl acetate (3×20 mL). The combined organics were washed with a saturated aqueous sodium chloride solution, dried over anhydrous sodium sulfate, filtered and concentrated in vacuo. Chromatography afforded 3-cyclopentyl-2-[4-(1H-indol-4-yloxy)-6-oxo-6H-pyridazin-1-yl]-propionic acid as an off-white solid (0.2 g, 42%); LC-MS: 368 [M+1]$^+$, $t_R$=4.21 min. Purity on HPLC: 95.1% (254 nm), 96.6% (214 nm), $t_R$=7.26 min. $^1$H NMR (300 MHz, CDCl$_3$): δ 13.00 (s, 1H), 11.50 (s, 1H), 8.17 (d, 1H, J=2.4 Hz), 7.42 (d, 2H, J=7.8 Hz), 7.17 (t, 1H, J=7.8 Hz), 6.89 (d, 1H, J=7.8 Hz), 6.26 (s, 1H), 5.63 (d, 1H, J=2.4 Hz), 5.31 (dd, 1H, J$_1$=10.5 Hz, J$_2$=4.2 Hz), 2.23~2.13 (m, 1H), 2.02~1.94 (m, 1H), 1.59~1.44 (m, 7H), 1.18~1.04 (m, 2H).

Intermediate 75

3-Cyclopentyl-2-[4-(2-methyl-4-oxo-4H-pyran-3-yloxy)-6-oxo-6H-pyridazin-1-yl]-propionic acid

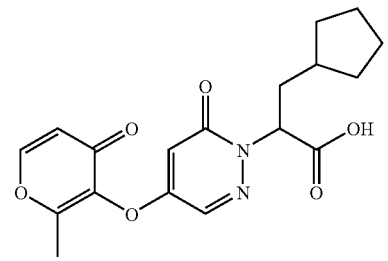

In an analogous manner to the stepwise sequence outlined in intermediate 19, starting from 4,5-dichloro-2-(tetrahydropyran-2-yl)-2H-pyridazin-3-one (Intermediate 20) and 3-hydroxy-2-methyl-pyran-4-one and alkylating with 2-bromo-3-cyclopentyl-propionic acid methyl ester (Intermediate 10) afforded 3-cyclopentyl-2-[4-(2-methyl-4-oxo-4H-pyran-3-yloxy)-6-oxo-6H-pyridazin-1-yl]-propionic acid as a white solid (3.4 g, 30% for the final step); LC-MS: 361.1 [M+1]$^+$ $t_R$=3.10 min. Purity on HPLC: 97.7% (214 nm), 99.0% (254 nm), $t_R$=5.79 min. $^1$H NMR (300 MHz, CDCl$_3$): δ 7.97 (s, 1H), 7.86 (d, 1H, J=5.4 Hz), 6.59 (d, 1H, J=5.4 Hz), 6.15 (s, 1H), 5.57 (dd, 1H, J$_1$=10.5 Hz, J$_2$=4.5 Hz), 2.42 (s, 3H), 2.36~2.23 (m, 1H), 2.23~2.16 (m, 1H), 1.81~1.57 (m, 7H), 1.32~1.20 (m, 2H).

Intermediate 76

3-Cyclopentyl-2-[6-oxo-4-(2-trifluoromethoxy-phenoxy)-6H-pyridazin-1-yl]-propionic acid

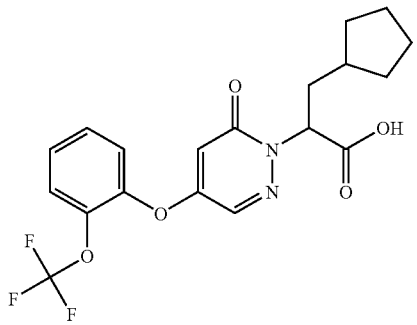

In an analogous manner to the stepwise sequence outlined in intermediate 19, starting from 4,5-dichloro-2-(tetrahydropyran-2-yl)-2H-pyridazin-3-one (Intermediate 20) and 2-trifluoromethoxy-phenol and alkylating with 2-bromo-3-cyclopentyl-propionic acid methyl ester (Intermediate 10) afforded 3-cyclopentyl-2-[6-oxo-4-(2-trifluoromethoxy-phenoxy)-6H-pyridazin-1-yl]-propionic acid as a white solid (14.11 g, 83% for the final step); LC-MS: 413.0 [M+1]$^+$, t$_R$=5.39 min. Purity on HPLC: 97.5% (214 nm), 97.9% (254 nm), t$_R$=8.94 min. $^1$H NMR (300 MHz, CDCl$_3$): δ 9.90 (s, 1H, broad), 7.89 (d, 1H, J=2.7 Hz), 7.40~7.33 (m, 3H), 7.24 (s, 1H), 5.96 (d, 1H, J=2.4 Hz), 5.53 (dd, 1H, J$_1$=10.2 Hz J$_2$=4.5 Hz), 2.86~2.38 (m, 1H), 2.29~2.07 (m, 1H), 1.79~1.49 (m, 7H), 1.20~1.08 (m, 2H).

Intermediate 77

3-Cyclopentyl-2-[4-(6-methyl-pyridin-2-yloxy)-6-oxo-6H-pyridazin-1-yl]-propionic acid

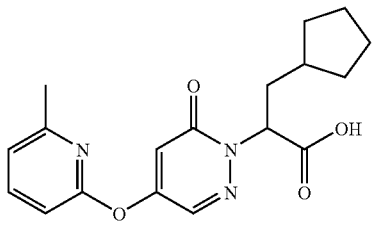

In an analogous manner to the stepwise sequence outlined in intermediate 19, starting from 4,5-dichloro-2-(tetrahydropyran-2-yl)-2H-pyridazin-3-one (Intermediate 20) and 6-methyl-pyridin-2-ol and alkylating with 2-bromo-3-cyclopentyl-propionic acid methyl ester (Intermediate 10) afforded 3-cyclopentyl-2-[4-(6-methyl-pyridin-2-yloxy)-6-oxo-6H-pyridazin-1-yl]-propionic acid (9.7 g, 66% for the final step); LC-MS: t$_R$=3.28 min, 344 [M+H]$^+$. HPLC: t$_R$=9.16 min, 95.62% at 214 nm, 96.87% at 254 nm. $^1$H NMR (300 MHz, DMSO-d$_6$): δ13.04 (broad, 1H), 8.07 (d, 1H, J=2.4 Hz), 7.89 (t, 1H, J=7.5 Hz), 7.21 (d, 1H, J=7.2 Hz), 7.06 (d, 1H, J=8.4 Hz), 6.52 (d, 1H, J=2.4 Hz), 5.36 (dd, 1H, J=10.5 Hz, J=4.2 Hz), 2.43 (s, 3H), 2.23-2.17 (m, 1H), 2.02-2.00 (m, 1H), 1.70-1.44 (m, 7H), 1.13-1.05 (m, 2H).

Intermediate 78

3-Cyclopentyl-2-[4-(2-fluoro-5-methyl-phenoxy)-6-oxo-6H-pyridazin-1-yl]-propionic acid

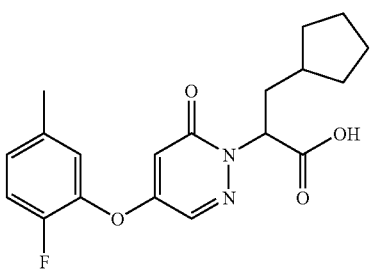

In an analogous manner to the stepwise sequence outlined in intermediate 19, starting from 4,5-dichloro-2-(tetrahydropyran-2-yl)-2H-pyridazin-3-one (Intermediate 20) and 2-fluoro-5-methyl-phenol and alkylating with 2-bromo-3-cyclopentyl-propionic acid methyl ester (Intermediate 10) afforded 3-cyclopentyl-2-[4-(2-fluoro-5-methyl-phenoxy)-6-oxo-6H-pyridazin-1-yl]-propionic acid as a white solid (14.5 g, 74% for the final step); LC-MS: 361 [M+1]$^+$, t$_R$=5.20 min. Purity on HPLC: 98.2% (214 nm), 98.9% (254 nm), t$_R$=8.93 min. $^1$H NMR (300 MHz, CDCl$_3$): δ9.54 (s, 1H broad), 7.89 (d, 1H, J=2.1), 7.14~7.08 (m, 2H), 6.99 (d, 1H, J=9.0), 5.98 (s, 1H), 5.53 (dd, 1H J$_1$=10.5 Hz, J$_2$=4.5 Hz), 2.35 (s, 3H), 2.39~2.20 (m, 1H), 2.15~2.06 (m, 1H), 1.79~1.49 (m, 7H), 1.20~1.11 (m, 3H).

Intermediate 79

3-Cyclopentyl-2-{4-[2-(2-hydroxy-ethyl)-phenoxy]-6-oxo-6H-pyridazin-1-yl}-propionic acid

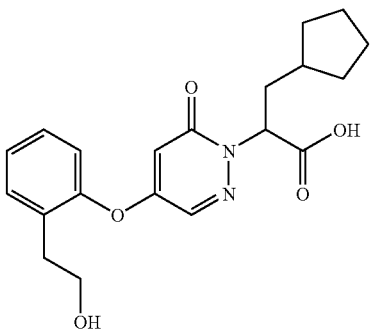

Step 1: A solution of 4,5-dichloropyridazin-3(2H)-one (25.5 g, 154 mmol) in tetrahydrofuran was treated with 60% sodium hydride (7.42 g, 185.5 mmol) at 0° C. The reaction was stirred at 0° C. for 10 min, and then stirred at 25° C. for 1 h. At this time, the reaction was treated with 2-bromo-3-cyclopentyl-propionic acid methyl ester (Intermediate 10, 54.5 g, 185.5 mmol), and was stirred for 2 d at 50° C. The reaction solution was partitioned between water and ethyl acetate. The aqueous phase was extracted with ethyl acetate.

The combined organic layers were washed with a saturated aqueous sodium chloride solution, dried over anhydrous sodium sulfate, filtered and concentrated in vacuo. Chromatography (1/15 ethyl acetate/petroleum ether) afforded 3-cyclopentyl-2-(4,5-dichloro-6-oxo-6H-pyridazin-1-yl)-propionic acid methyl ester (23 g, 46.8%).

Step 2: In an analogous manner to the reaction outlined in Intermediate 19 step 1, starting from 3-cyclopentyl-2-(4,5-dichloro-6-oxo-6H-pyridazin-1-yl)-propionic acid methyl ester and 2-(2-hydroxy-ethyl)-phenol afforded 2-{5-chloro-4-[2-(2-hydroxy-ethyl)-phenoxy]-6-oxo-6H-pyridazin-1-yl}-3-cyclopentyl-propionic acid methyl ester (10.1 g, 48%).

Step 3: In an analogous manner to the reaction outlined in Intermediate 58 step 4, starting from 2-{5-chloro-4-[2-(2-hydroxy-ethyl)-phenoxy]-6-oxo-6H-pyridazin-1-yl}-3-cyclopentyl-propionic acid methyl ester afforded 3-cyclopentyl-2-{4-[2-(2-hydroxy-ethyl)-phenoxy]-6-oxo-6H-pyridazin-1-yl}-propionic acid methyl ester (5.2 g, 90%).

Step 4: A solution of 3-cyclopentyl-2-{4-[2-(2-hydroxy-ethyl)-phenoxy]-6-oxo-6H-pyridazin-1-yl}-propionic acid methyl ester (386 mg, 1 mmol) in dioxane (5 mL) was treated with a 6N aqueous hydrochloric acid solution (5 mL). The reaction solution was stirred at 25° C. overnight and then concentrated in vacuo. Chromatography afforded 3-cyclopentyl-2-{4-[2-(2-hydroxy-ethyl)-phenoxy]-6-oxo-6H-pyridazin-1-yl}-propionic acid (156 mg, 42%); LC-MS: 373 $(M+1)^+$, $t_R$=3.28 min. Purity on HPLC: $t_R$=5.98 min, 97.9% (214 nm), 96.5% (254 nm). $^1$H NMR (300 MHz, DMSO-$d_6$): δ12.95 (s, 1H, broad), 8.14 (s, 1H), 7.46-7.20 (m, 4H), 6.37 (d, 1H, J=2.7 Hz), 5.31 (dd, 1H, J=10.5 Hz, J=4.5 Hz), 4.70 (t, 1H, J=5.4 Hz), 3.59-3.52 (m, 2H), 3.66 (t, J=6.6 Hz, 1H), 2.17-1.97 (m, 2H), 1.58-1.01 (m, 9H).

Intermediate 80

3-Cyclopentyl-2-[4-(4,6-dimethyl-pyrimidin-2-yloxy)-6-oxo-6H-pyridazin-1-yl]-propionic acid

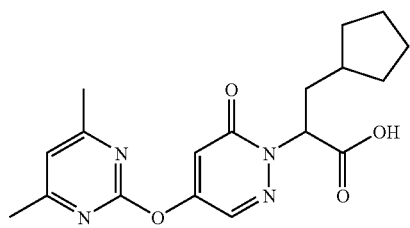

Step 1: A solution of 3-cyclopentyl-2-(4,5-dichloro-6-oxo-6H-pyridazin-1-yl)-propionic acid methyl ester (Intermediate 79 step 1, 15.4 g, 48 mmol) in N,N-dimethylformamide (150 mL) was treated with 4,6-dimethyl-pyrimidin-2-ol (5.98 g, 48 mmol) and potassium carbonate (8 g, 58 mmol). The reaction was heated at reflux for 12 h. At this time, the reaction was cooled to 25° C. and concentrated in vacuo. The residue was partitioned between water and methylene chloride. The aqueous layer was back extracted with methylene chloride. The combined organics were washed with a saturated aqueous sodium chloride solution, dried over magnesium sulfate, filtered, and concentrated in vacuo. Chromatography (5/1 petroleum ether/ethyl acetat) afforded 2-[5-chloro-4-(4,6-dimethyl-pyrimidin-2-yloxy)-6-oxo-6H-pyridazin-1-yl]-3-cyclopentyl-propionic acid methyl ester (7.47 g, 38%).

Step 2: A solution of 2-[5-chloro-4-(4,6-dimethyl-pyrimidin-2-yloxy)-6-oxo-6H-pyridazin-1-yl]-3-cyclopentyl-propionic acid methyl ester (0.37 g, 0.91 mmol) in ethanol (10 mL) was treated with palladium on carbon (0.037 g) and ammonium formate (0.14 g, 2.27 mmol). The resulting mixture was refluxed for 30 min. After cooling to 25° C., the reaction was filtered and the solid was rinsed with ethanol. The filtrate was concentrated in vacuo to afford crude 3-cyclopentyl-2-[4-(4,6-dimethyl-pyrimidin-2-yloxy)-6-oxo-6H-pyridazin-1-yl]-propionic acid methyl ester (0.45 g), which could be further purified by chromatography (5/1 petroleum ether/ethyl acetate).

Step 3: A solution of 3-cyclopentyl-2-[4-(4,6-dimethyl-pyrimidin-2-yloxy)-6-oxo-6H-pyridazin-1-yl]-propionic acid methyl ester (206 mg, 0.55 mmol) in tetrahydrofuran (4 mL) was treated with a 4N aqueous sodium hydroxide solution (0.17 mL) and was stirred at 25° C. for 4 h. The reaction was partitioned between water (3 mL) and ether. The aqueous layer was back extracted with ether. The aqueous layer was then acidified to pH 3-4 with a 1N aqueous hydrochloric acid solution. The resulting precipitate was filtered, rinsed with water (1 mL), and dried in vacuo to afford 3-cyclopentyl-2-[4-(4,6-dimethyl-pyrimidin-2-yloxy)-6-oxo-6H-pyridazin-1-yl]-propionic acid as a white solid (40 mg, 20%); LC-MS: $t_R$=3.71 min, 359 $[M+H]^+$. HPLC: $t_R$=7.02 min, 96.21% at 214 nm, 98.34% at 254 nm. $^1$H NMR (300 MHz, DMSO-$d_6$): δ13.03 (broad, 1H), 8.12 (d, 1H, J=2.7 Hz), 7.19 (s, 1H), 6.85 (d, 1H, J=2.4 Hz), 5.36 (dd, 1H, J=10.5 Hz, J=4.2 Hz), 2.41 (s, 6H), 2.24-2.14 (m, 1H), 2.05-1.97 (m, 1H), 1.71-1.44 (m, 7H), 1.17-1.04 (m, 2H).

Intermediate 81

3-Cyclopentyl-2-[4-(2-methyl-5-trifluoromethyl-2H-pyrazol-3-yloxy)-6-oxo-6H-pyridazin-1-yl]-propionic acid

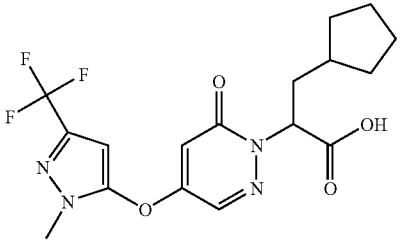

In an analogous manner to the stepwise sequence outlined in Intermediate 70, starting from 5-iodo-2-(tetrahydro-pyran-2-yl)-2H-pyridazin-3-one (Intermediate 70, step 2) and 2-methyl-5-trifluoromethyl-2,4-dihydro-pyrazol-3-one and alkylating with 2-bromo-3-cyclopentyl-propionic acid methyl ester (Intermediate 10) afforded 3-cyclopentyl-2-[4-(2-methyl-5-trifluoromethyl-2H-pyrazol-3-yloxy)-6-oxo-6H-pyridazin-1-yl]-propionic acid as a white solid (4.3 g, 64% for the final step); LC-MS: 401.1 $(M+1)^+$, $t_R$=4.39 min. Purity on HPLC: 97.0% (214 nm), 99.8% (254 nm), $t_R$=9.36 min. $^1$H NMR (300 MHz, CDCl$_3$): δ 9.00 (s, 1H), 7.91 (d, 1H), 6.46 (d, 1H, J=2.1 Hz), 6.27 (s, 1H), 5.55 (dd, 1H, $J_1$=7.8

Hz, J$_2$=4.2 Hz,), 3.81 (s, 3H), 2.36~2.20 (m, 1H), 2.20~2.05 (m, 1H), 1.78~1.47 (m, 7H), 1.28~1.10 (m, 2H).

Intermediate 82

2-[4-(3-Chloro-2-fluoro-phenoxy)-6-oxo-6H-pyridazin-1-yl]-3-cyclopentyl-propionic acid

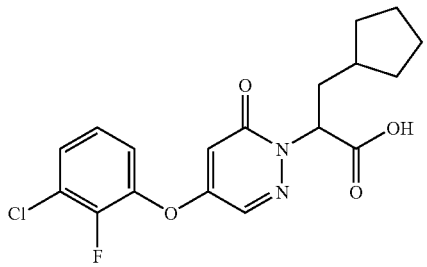

In an analogous manner to the stepwise sequence outlined in Intermediate 70, starting from 5-iodo-2-(tetrahydro-pyran-2-yl)-2H-pyridazin-3-one (Intermediate 70 step 2) and 3-chloro-2-fluoro-phenol and alkylating with 2-bromo-3-cyclopentyl-propionic acid methyl ester (Intermediate 10) afforded 2-[4-(3-chloro-2-fluoro-phenoxy)-6-oxo-6H-pyridazin-1-yl]-3-cyclopentyl-propionic acid as a white solid (4.4 g, 73% for the final step); LC-MS: t$_R$=4.80 min, 381 (M+H)$^+$. HPLC: t$_R$=8.83 min, 95.66% (214 nm), 95.56% (254 nm). $^1$H NMR (300 MHz, DMSO-d$_6$): δ 13.06 (broad, 1H), 8.21 (d, 1H, J=2.7 Hz), 7.63-7.58 (m, 1H), 7.54-7.49 (m, 1H), 7.38-7.33 (m, 1H), 6.07 (d, 1H, J=2.7 Hz), 5.33 (dd, 1H, J=11.0 Hz, J=4.2 Hz), 2.40-2.10 (m, 1H), 1.99-1.90 (m, 1H), 1.68-1.43 (m, 7H), 1.13-1.04 (m, 2H).

Intermediate 83

5-((S)-2,2-Dimethyl-[1,3]dioxolan-4-yl)-pyrazin-2-ylamine

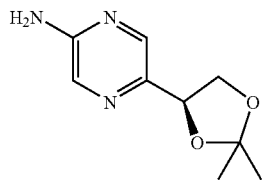

Prepared in U.S. Pat. No. 7,132,425

Intermediate 84

3-Cyclopentyl-2-[4-(2,6-difluoro-3-methyl-phenoxy)-6-oxo-6H-pyridazin-1-yl]-propionic acid

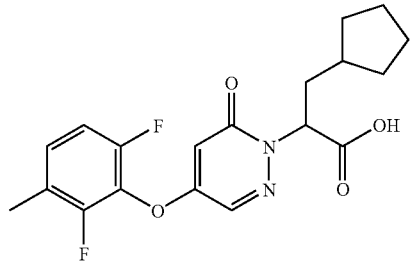

In an analogous manner to the stepwise sequence outlined in Intermediate 19, starting from 4,5-dichloro-2-(tetrahydro-pyran-2-yl)-2H-pyridazin-3-one (Intermediate 20) and 2,6-difluoro-3-methyl-phenol and alkylating with 2-bromo-3-cyclopentyl-propionic acid methyl ester (Intermediate 10) afforded impure 3-cyclopentyl-2-[4-(2,6-difluoro-3-methyl-phenoxy)-6-oxo-6H-pyridazin-1-yl]-propionic acid as an oily light brown semi-solid (716.0 mg, 87% for the final step) and was used in Example 107.

Intermediate 85

3-Cyclopentyl-2-(4-iodo-6-oxo-6H-pyridazin-1-yl)-propionic acid

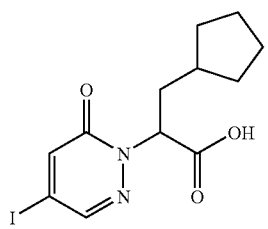

A solution of 3-cyclopentyl-2-(4-iodo-6-oxo-6H-pyridazin-1-yl)-propionic acid methyl ester (Intermediate 73, Step 2, 1.78 g, 4.73 mmol) in tetrahydrofuran (13 mL, 0.36M) was treated with a 4N aqueous sodium hydroxide solution (1.3 mL, 5.2 mmol) and stirred at 25° C. overnight. After this time, the reaction was concentrated in vacuo and the residue was diluted with water (50 mL) and was then acidified with a 1N aqueous hydrochloric acid solution. The precipitate was filtered and concentrated in vacuo to afford 3-cyclopentyl-2-(4-iodo-6-oxo-6H-pyridazin-1-yl)-propionic acid (1.45 g, 85%) as an off-white solid; ES$^+$-HRMS m/e calcd for C$_{12}$H$_{15}$N$_2$O$_3$I [M+H$^+$] 363.0200, found 363.0197. $^1$H NMR (400 MHz, DMSO-d$_6$) δ ppm 0.95-1.18 (m, 2H), 1.36-1.75 (m, 7H), 1.88-2.02 (m, 1H), 2.17 (ddd, J=13.9, 10.8, 5.1 Hz, 1H), 5.30 (dd, J=10.8, 4.3 Hz, 1H), 7.65 (d, J=1.9 Hz, 1H), 8.23 (d, J=1.9 Hz, 1H), 13.10 (s, 1H).

Intermediate 86

2-(4-Iodo-6-oxo-6H-pyridazin-1-yl)-4-methyl-pentanoic acid

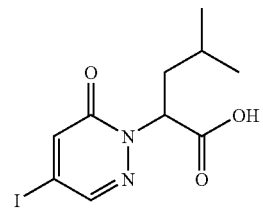

In an analogous manner to the stepwise sequence outlined in Intermediate 73, starting from 5-iodo-2H-pyridazin-3-one (Intermediate 18, Step 1) and 2-bromo-4-methyl-pentanoic acid methyl ester (Intermediate 11) afforded 2-(4-iodo-6-oxo-6H-pyridazin-1-yl)-4-methyl-pentanoic acid methyl ester which was reacted in an analogous manner to the reaction outlined in Intermediate 85 to afford 2-(4-iodo-6-oxo- 6H-pyridazin-1-yl)-4-methyl-pentanoic acid as a white solid (1.93 g, 91% for the final step); ES⁺-HRMS m/e calcd for $C_{10}H_{13}N_2O_3I$ [M+H⁺] 337.0044, found 337.0043. ¹H NMR (400 MHz, DMSO-$d_6$) δ ppm 0.85 (d, J=6.4 Hz, 6H), 1.24-1.42 (m, 1H), 1.82 (ddd, J=14.0, 9.6, 4.3 Hz, 1H), 1.97-2.16 (m, 1H), 5.35 (dd, J=10.9, 4.3 Hz, 1H), 7.65 (d, J=2.0 Hz, 1H), 8.24 (d, J=2.0 Hz, 1H), 13.12 (br. s., 1H).

Intermediate 87

3-Cyclopentyl-2-[6-oxo-4-(4-trifluoromethyl-pyrimidin-2-yloxy)-6H-pyridazin-1-yl]-propionic acid

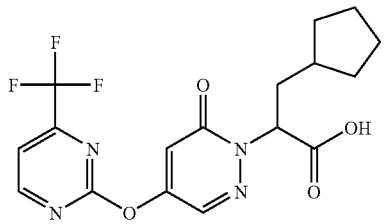

Step 1: A solution of 3-cyclopentyl-2-(4,5-dichloro-6-oxo-6H-pyridazin-1-yl)-propionic acid methyl ester (Intermediate 79 step 1, 18.0 g, 56.4 mmol) in a 4N aqueous sodium hydroxide solution (140 mL) was stirred at 60° C. overnight. The reaction solution was acidified with a 6N aqueous hydrochloric acid solution to pH=2~3. Ethyl acetate was added to the solution and was stirred for 10 min. The aqueous phase was extracted with ethyl acetate, the combined organics were washed with a saturated aqueous sodium chloride solution, dried over anhydrous sodium sulfate, filtered, and concentrated in vacuo. The residue was washed with diethyl ether (50 mL) to afford 2-(5-chloro-4-hydroxy-6-oxo-6H-pyridazin-1-yl)-3-cyclopentyl-propionic acid as a white solid (14.5 g, 90%).

Step 2: A solution of 2-(5-chloro-4-hydroxy-6-oxo-6H-pyridazin-1-yl)-3-cyclopentyl-propionic acid (14.5 g, 50.6 mmol) in ethanol (150 mL) was treated with 20% palladium on carbon (50% in water, 1.5 g) and ammonium formate (16 g, 75.9 mmol). The mixture was stirred at reflux for 2 h. At this time, the reaction was cooled to 25° C., filtered, and concentrated in vacuo. Water (50 mL) was added to the residue and the resulting solution was acidified with a 6N aqueous hydrochloric acid solution to pH=2~3. The solution was extracted with ethyl acetate (2×100 mL). The combined organics were dried over sodium sulfate and concentrated in vacuo to afford 3-cyclopentyl-2-(4-hydroxy-6-oxo-6H-pyridazin-1-yl)-propionic acid as a white solid (12.5 g, 98%).

Step 3: A solution of 3-cyclopentyl-2-(4-hydroxy-6-oxo-6H-pyridazin-1-yl)-propionic acid (12.5 g, 47.6 mmol) in methanol (150 mL) was treated dropwise with thionyl chloride (7.1 g, 59.5 mmol). The mixture was stirred at reflux for 1 h. At this time, the reaction was cooled to 25° C. and concentrated in vacuo. The resulting residue was partitioned between water and ethyl acetate. The combined organics were dried over sodium sulfate and concentrated in vacuo to afford 3-cyclopentyl-2-(4-hydroxy-6-oxo-6H-pyridazin-1-yl)-propionic acid methyl ester as a light yellow oil (10.5 g, 80%).

Step 4: A solution of 3-cyclopentyl-2-(4-hydroxy-6-oxo-6H-pyridazin-1-yl)-propionic acid methyl ester (3.0 g, 11.3 mmol) in N,N-dimethylformamide was treated with potassium carbonate (2.33 g, 16.9 mmol) and 2-chloro-4-trifluoromethyl-pyrimidine (3.1 g, 16.9 mmol). The reaction mixture was stirred at 110° C. for 1 h. At this time, the reaction was cooled to 25° C. and concentrated in vacuo. The residue was partitioned between water and ethyl acetate. The combined organics were washed with a saturated aqueous sodium chloride solution, dried over sodium sulfate, filtered, and concentrated in vacuo. Chromatography afforded 3-cyclopentyl-2-[6-oxo-4-(4-trifluoromethyl-pyrimidin-2-yloxy)-6H-pyridazin-1-yl]-propionic acid methyl ester as a light oil (4.0 g, 86%).

Step 5: A solution of 3-cyclopentyl-2-[6-oxo-4-(4-trifluoromethyl-pyrimidin-2-yloxy)-6H-pyridazin-1-yl]-propionic acid methyl ester (0.2 g, 0.48 mmol) in dioxane (2 mL) was treated with a 6N aqueous sodium hydroxide solution (2 mL). The reaction was stirred at 25° C. for 2 d. At this point, ethyl acetate (20 mL) was added and then the aqueous phase was back extracted with ethyl acetate. The combined organics were dried over sodium sulfate, filtered, and concentrated in vacuo. Preparative HPLC afforded 3-cyclopentyl-2-[6-oxo-4-(4-trifluoromethyl-pyrimidin-2-yloxy)-6H-pyridazin-1-yl]-propionic acid as a light oil (20 mg, 10%); ¹H NMR (300 MHz, DMSO-$d_6$): δ 9.13 (d, 1H, J=4.8 Hz), 8.24 (d, 1H, J=2.4 Hz), 7.96 (d, 1H, J=4.8 Hz), 7.04 (d, 1H, J=2.4 Hz), 5.38 (dd, 1H, $J_1$=4.5 Hz, $J_2$=10.5 Hz), 2.25~2.15 (m, 1H), 2.06~1.97 (m, 1H), 1.71~1.44 (m, 7H), 1.17~1.04 (m, 3H). LC-MS: 399.1 [M+1]⁺, $t_R$=3.04 min.

Intermediate 88

3-Cyclohexyl-2-[4-(2-fluoro-4-methoxy-phenoxy)-6-oxo-6H-pyridazin-1-yl]-propionic acid

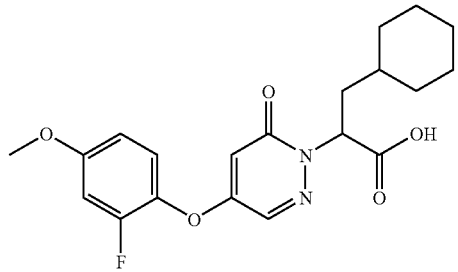

In an analogous manner to the stepwise sequence outlined in Intermediate 19, starting from 4,5-dichloro-2-(tetrahydro-pyran-2-yl)-2H-pyridazin-3-one (Intermediate 20) and 2-fluoro-4-methoxy-phenol and alkylating with 2-bromo-3-cyclohexyl-propionic acid methyl ester (Intermediate 12) afforded the lithium salt of 3-cyclohexyl-2-[4-(2-fluoro-4-methoxy-phenoxy)-6-oxo-6H-pyridazin-1-yl]-propionic acid as a white solid (0.32 g); ES⁺-HRMS m/e calcd for $C_{20}H_{23}N_2O_5F$ [M+H⁺] 391.1664, found 391.1664. ¹H NMR (300 MHz, DMSO-$d_6$) δ ppm 0.67-1.20 (m, 6H), 1.43-1.79 (m, 5H), 1.86-2.03 (m, 2H), 3.80 (s, 3H), 4.98-5.19 (m, 1H), 5.62 (d, J=2.6 Hz, 1H), 6.88 (ddd, J=9.1, 2.8, 0.9 Hz, 1H), 7.13 (dd, J=12.7, 2.8 Hz, 1H), 7.38 (t, J=9.1 Hz, 1H), 7.98 (d, J=2.6 Hz, 1H). (38738-117-2)

Intermediate 89

3-Cyclohexyl-2-[4-(2,4-dimethyl-phenoxy)-6-oxo-6H-pyridazin-1-yl]-propionic acid

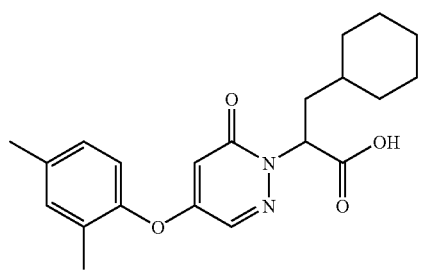

In an analogous manner to the stepwise sequence outlined in Intermediate 19, starting from 4,5-dichloro-2-(tetrahydro-pyran-2-yl)-2H-pyridazin-3-one (Intermediate 20) and 2,4-dimethyl-phenol and alkylating with 2-bromo-3-cyclohexyl-propionic acid methyl ester (Intermediate 12) afforded the lithium salt of 3-cyclohexyl-2-[4-(2,4-dimethyl-phenoxy)-6-oxo-6H-pyridazin-1-yl]-propionic acid as a light yellow solid (0.19 g); ES$^+$-HRMS m/e calcd for $C_{21}H_{26}N_2O_4$ [M+H$^+$] 371.1966, found 371.1966.
(38738-118-2)

Intermediate 90

2-[4-(2-Chloro-4-methoxy-phenoxy)-6-oxo-6H-pyridazin-1-yl]-3-cyclohexyl-propionic acid

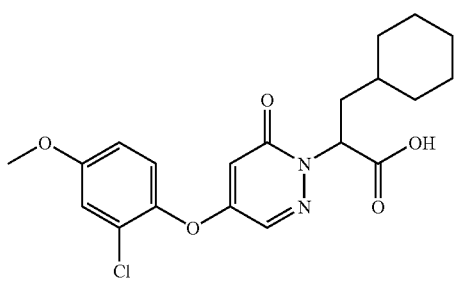

In an analogous manner to the stepwise sequence outlined in Intermediate 18, starting from 5-iodo-2-(tetrahydro-pyran-2-yl)-2H-pyridazin-3-one (Intermediate 18, step 2) and 2-chloro-4-methoxy-phenol afforded 5-(2-chloro-4-methoxy-phenoxy)-2H-pyridazin-3-one which was then reacted in an analogous manner to that outlined in the synthesis of Intermediate 19 (steps 4 and 5) alkylating with 2-bromo-3-cyclohexyl-propionic acid methyl ester (Intermediate 12) which afforded the lithium salt of 2-[4-(2-chloro-4-methoxy-phenoxy)-6-oxo-6H-pyridazin-1-yl]-3-cyclohexyl-propionic acid as a white solid (0.19 g); ES$^+$-HRMS m/e calcd for $C_{20}H_{23}N_2O_5Cl$ [M+H$^+$] 407.1368, found 407.1369. $^1$H NMR (300 MHz, DMSO-d$_6$) δ ppm 0.68-1.19 (m, 6H), 1.44-1.65 (m, 4H), 1.65-1.77 (m, 1H), 1.93 (t, J=6.9 Hz, 2H), 3.81 (s, 3H), 5.09 (t, J=7.7 Hz, 1H), 5.52 (d, J=3.0 Hz, 1H), 7.04 (dd, J=9.0, 3.0 Hz, 1H), 7.26 (d, J=3.0 Hz, 1H), 7.39 (d, J=9.0 Hz, 1H), 7.97 (d, J=3.0 Hz, 1H).
(38738-124-2)

Intermediate 91

2-[4-(2-Chloro-4-trifluoromethoxy-phenoxy)-6-oxo-6H-pyridazin-1-yl]-3-cyclohexyl-propionic acid

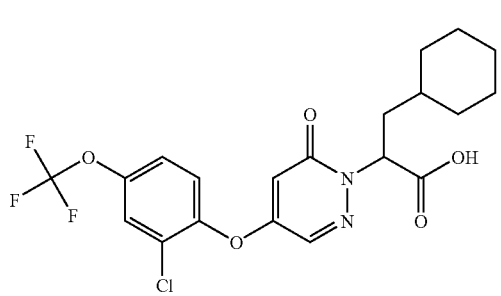

In an analogous manner to the stepwise sequence outlined in Intermediate 18, starting from 5-iodo-2-(tetrahydro-pyran-2-yl)-2H-pyridazin-3-one (Intermediate 18, step 2) and 2-chloro-4-trifluoromethoxy-phenol afforded 5-(2-chloro-4-trifluoromethoxy-phenoxy)-2H-pyridazin-3-one which was then reacted in an analogous manner to that outlined in the synthesis of Intermediate 19 (steps 4 and 5) alkylating with 2-bromo-3-cyclohexyl-propionic acid methyl ester (Intermediate 12) afforded 2-[4-(2-chloro-4-trifluoromethoxy-phenoxy)-6-oxo-6H-pyridazin-1-yl]-3-cyclohexyl-propionic acid as a white solid (190 mg, 72% for the final step); ES$^+$-HRMS m/e calcd for $C_{20}H_{20}N_2O_5F_3Cl$ [M+H$^+$] 461.1086, found 461.1085. $^1$H NMR (300 MHz, DMSO-d$_6$) δ ppm 0.74-1.28 (m, 5H), 1.35-1.80 (m, 6H), 1.80-1.96 (m, 1H), 1.98-2.11 (m, 1H), 5.40 (dd, J=10.9, 4.2 Hz, 1H), 5.95 (d, J=2.7 Hz, 1H), 7.54 (dd, J=9.0, 2.0 Hz, 1H), 7.68 (d, J=9.0 Hz, 1H), 7.87 (d, J=2.0 Hz, 1H), 8.21 (d, J=2.7 Hz, 1H), 13.03 (br. s., 1H).
(38738-125-2)

Intermediate 92

2-[4-(3-Ethoxy-2,6-difluoro-phenoxy)-6-oxo-6H-pyridazin-1-yl]-4-methyl-pentanoic acid

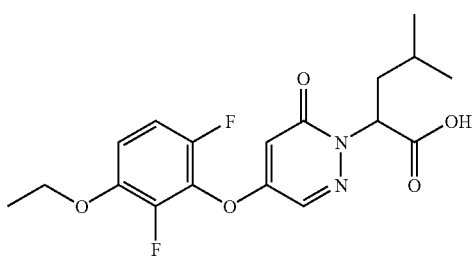

In an analogous manner to the stepwise sequence outlined in Intermediate 19, starting from 4,5-dichloro-2-(tetrahydro-pyran-2-yl)-2H-pyridazin-3-one (Intermediate 20) and 3-ethoxy-2,6-difluoro-phenol and alkylating with 2-bromo-4-methyl-pentanoic acid methyl ester (Intermediate 11) afforded the lithium salt of 2-[4-(3-ethoxy-2,6-difluoro-phenoxy)-6-oxo-6H-pyridazin-1-yl]-4-methyl-pentanoic acid as an off-white solid (0.15 g). $^1$H NMR (300 MHz, DMSO-$d_6$) δ ppm 0.83 (d, J=5.4 Hz, 6H), 1.19-1.34 (m, 1H), 1.34 (t, J=6.9 Hz, 3H), 1.73-1.92 (m, 1H), 1.95-2.16 (m, 1H), 4.13 (q, J=6.9 Hz, 2H), 5.32 (dd, J=11.2, 4.2 Hz, 1H), 6.06 (d, J=2.7 Hz, 1H), 7.20 (m, 1H), 7.29 (td, J=9.9, 2.1 Hz, 1H), 8.22 (d, J=2.7 Hz, 1H), 13.21 (br. s., 1H).
(38738-144-2)

Intermediate 93

2-[4-(3-Ethoxy-2,6-difluoro-phenoxy)-6-oxo-6H-pyridazin-1-yl]-3-(tetrahydro-pyran-4-yl)-propionic acid

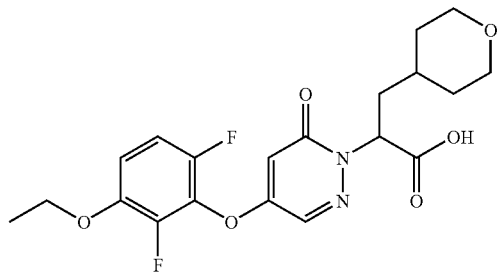

In an analogous manner to the stepwise sequence outlined in Intermediate 19, starting from 4,5-dichloro-2-(tetrahydro-pyran-2-yl)-2H-pyridazin-3-one (Intermediate 20) and 3-ethoxy-2,6-difluoro-phenol and alkylating with 2-bromo-3-(tetrahydro-pyran-4-yl)-propionic acid methyl ester (Intermediate 14) afforded the lithium salt of 2-[4-(3-ethoxy-2,6-difluoro-phenoxy)-6-oxo-6H-pyridazin-1-yl]-3-(tetrahydro-pyran-4-yl)-propionic acid as an off-white solid (175 mg, 94% for the final step). $^1$H NMR (300 MHz, DMSO-$d_6$) δ ppm 0.99-1.31 (m, 3H), 1.35 (t, J=6.9 Hz, 3H), 1.38-1.50 (m, 1H), 1.52-1.67 (m, 1H), 1.87-2.16 (m, 2H), 2.99-3.27 (m, 2H), 3.77 (br. s., 2H), 4.15 (q, J=6.9 Hz, 2H), 5.36 (d, J=6.6 Hz, 1H), 6.07 (br. s., 1H), 7.15-7.38 (m, 2H), 8.24 (d, J=2.7 Hz, 1H), 13.19 (br. s., 1H).
(38738-143-2)

Intermediate 94

2-(4-Iodo-6-oxo-6H-pyridazin-1-yl)-4-methyl-pentanoic acid [1-((R)-2,2-dimethyl-[1,3]dioxolan-4-ylmethyl)-1H-pyrazol-3-yl]-amide

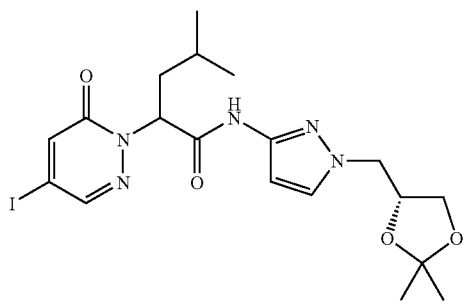

A solution of 1-((R)-2,2-dimethyl-[1,3]dioxolan-4-ylmethyl)-1H-pyrazol-3-ylamine (Intermediate 4, 708.7 mg, 3.59 mmol) in N,N-dimethylformamide was added to 2-(4-iodo-6-oxo-6H-pyridazin-1-yl)-4-methyl-pentanoic acid (Intermediate 86, 1.42 g, 4.23 mmol). At this point, the reaction was treated with 4-dimethylaminopyridine (21.9 mg, 0.18 mmol) followed by N-(3-dimethylaminopropyl)-N'-ethylcarbodiimide hydrochloride (823.7 mg, 4.31 mmol). The resulting reaction was stirred at 25° C. overnight. The reaction was then diluted with ethyl acetate (200 mL), was washed with water (200 mL) and a saturated aqueous sodium chloride solution (200 mL), filtered, and concentrated in vacuo onto silica gel. Chromatography (ISCO Combiflash, 10-60% ethyl acetate/hexanes) afforded 2-(4-iodo-6-oxo-6H-pyridazin-1-yl)-4-methyl-pentanoic acid [1-((R)-2,2-dimethyl-[1,3]dioxolan-4-ylmethyl)-1H-pyrazol-3-yl]-amide as a white/yellow solid (950 mg, 51%); ES$^+$-HRMS m/e calcd for $C_{19}H_{26}N_5O_4I$ [M+Na$^+$] 538.0921, found 538.0921. $^1$H NMR (300 MHz, DMSO-$d_6$) δ ppm 0.83 (d, J=5.7 Hz, 3H), 0.85 (d, J=5.7 Hz, 3H), 1.23 (s, 3H), 1.29 (s, 3H), 1.35 (br. s., 1H), 1.76 (ddd, J=13.3, 9.4, 4.2 Hz, 1H), 2.03-2.21 (m, 1H), 3.71 (dd, J=8.4, 6.0 Hz, 1H), 3.98 (dd, J=8.4, 6.5 Hz, 1H), 4.03-4.18 (m, 2H), 4.33 (quin, J=6.0 Hz, 1H), 5.47 (dd, J=11.0, 4.1 Hz, 1H), 6.36 (d, J=2.1 Hz, 1H), 7.58 (d, J=1.8 Hz, 1H), 7.59 (d, J=2.1 Hz, 1H), 8.23 (d, J=1.8 Hz, 1H), 10.82 (s, 1H).
(38738-140-3)

Intermediate 95

3-Cyclopentyl-2-(6-oxo-4-phenylsulfanyl-6H-pyridazin-1-yl)-propionic acid

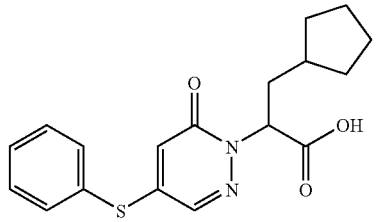

In an analogous manner to the stepwise sequence outlined in Intermediate 18, starting from 5-iodo-2-(tetrahydro-pyran-2-yl)-2H-pyridazin-3-one (Intermediate 18, step 2) and benzenethiol afforded 5-phenylsulfanyl-2H-pyridazin-3-one which was then reacted in an analogous manner to that outlined in the synthesis of intermediate 19 (steps 4 and 5) alkylating with 2-bromo-3-cyclopentyl-propionic acid methyl ester (Intermediate 10) afforded the lithium salt of 3-cyclopentyl-2-(6-oxo-4-phenylsulfanyl-6H-pyridazin-1-yl)-propionic acid as a white solid (98 mg, quantitative for the final step); ES$^+$-HRMS m/e calcd for $C_{18}H_{20}N_2O_3SI$ [M+H$^+$] 345.1268, found 345.1268. $^1$H NMR (300 MHz, DMSO-$d_6$) δ ppm 0.93-1.19 (m, 2H), 1.29-1.76 (m, 7H), 1.86-2.00 (m, 1H), 2.05-2.21 (m, 1H), 5.24 (dd, J=10.9, 3.9 Hz, 1H), 5.94

(d, J=2.1 Hz, 1H), 7.53-7.64 (m, 3H), 7.63-7.73 (m, 2H), 7.91 (d, J=2.1 Hz, 1H), 13.02 (br. s., 1H).

(38738-149-2)

Intermediate 96

2-[5-Chloro-4-(2-chloro-phenoxy)-6-oxo-6H-pyridazin-1-yl]-3-(tetrahydro-pyran-4-yl)-propionic acid

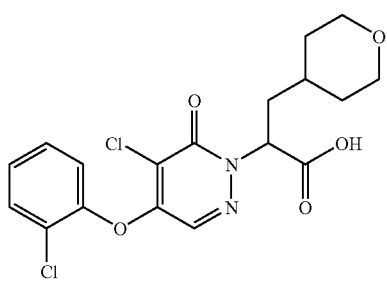

In an analogous manner to the stepwise sequence outlined in Intermediate 19 (steps 1-2), starting from 4,5-dichloro-2-(tetrahydropyran-2-yl)-2H-pyridazin-3-one (Intermediate 20) and 2-chloro-phenol followed by the stepwise sequence outlined in Intermediate 19 (steps 4 and 5) alkylating with 2-bromo-3-(tetrahydro-pyran-4-yl)-propionic acid methyl ester (Intermediate 14) afforded the lithium salt of 2-[5-chloro-4-(2-chloro-phenoxy)-6-oxo-6H-pyridazin-1-yl]-3-(tetrahydro-pyran-4-yl)-propionic acid. This material was used without further purification in Example 129. $^1$H NMR (300 MHz, CDCl$_3$) δ ppm 1.17 (s, 6H), 1.22-1.55 (m, 4H), 1.55-1.77 (m, 2H), 2.10-2.25 (m, 2H), 3.24-3.41 (m, 2H), 3.86-3.96 (m, 2H), 3.98 (s, 2H), 5.75 (t, J=7.5 Hz, 1H), 6.65 (d, J=1.8 Hz, 1H), 7.23-7.26 (m, 1H), 7.29-7.35 (m, 2H), 7.35-7.43 (m, 1H), 7.49 (s, 1H), 7.54 (d, J=7.8 Hz, 1H), 8.74 (br. s., 1H).

(ADS-39604-008)

Intermediate 97

2-[5-Chloro-4-(2-chloro-4-trifluoromethoxy-phenoxy)-6-oxo-6H-pyridazin-1-yl]-3-cyclohexyl-propionic acid

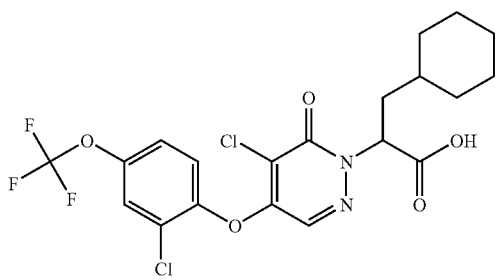

In an analogous manner to the stepwise sequence outlined in Intermediate 19 (steps 1-2), starting from 4,5-dichloro-2-(tetrahydropyran-2-yl)-2H-pyridazin-3-one (Intermediate 20) and 2-chloro-4-trifluoromethoxy-phenol followed by the stepwise sequence outlined in Intermediate 19 (steps 4 and 5) alkylating with 2-bromo-3-cyclohexyl-propionic acid methyl ester (Intermediate 12) afforded the lithium salt of 2-[5-chloro-4-(2-chloro-4-trifluoromethoxy-phenoxy)-6-oxo-6H-pyridazin-1-yl]-3-cyclohexyl-propionic acid This material was used without further purification in Example 130. $^1$H NMR (300 MHz, CDCl$_3$) δ ppm 0.76-1.40 (m, 6H), 1.15 (br. s., 6H), 1.56-1.83 (m, 6H), 1.97-2.22 (m, 2H), 3.94 (s, 2H), 5.67-5.78 (m, 1H), 6.68 (s, 1H), 7.17-7.33 (m, 3H), 7.43 (br. s., 1H), 7.49 (s, 1H), 8.55 (br. s., 1H).

(ADS-38578-295)

Intermediate 98

Acetic acid 2-(3-amino-5-methyl-pyrazol-1-yl)-1-methyl-ethyl ester

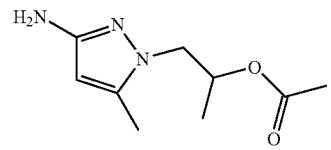

A solution of 1-(5-methyl-3-nitro-pyrazol-1-yl)-propan-2-one (500 mg, 2.9 mmol) in ethanol (15 ml) was treated with sodium borohydride (111 mg, 0.29 mmol). The reaction was stirred at 25° C. for 2.5 h. At this time, the reaction was poured onto water and was extracted into ethyl acetate. The organics were concentrated in vacuo to afford 1-(5-methyl-3-nitro-pyrazol-1-yl)-propan-2-ol (440 mg, 88%) which was used without further purification; ES$^+$-HRMS m/e calcd for C$_7$H$_{11}$N$_3$O$_3$ [M+H$^+$] 186.0873, found 186.0873.

(ADS-39604-010-I)

A solution of 1-(5-Methyl-3-Nitro-Pyrazol-1-Yl)-Propan-2-ol (440 Mg, 2.5 Mmol) in methylene chloride at 25° C. was treated with triethylamine (1.1 mL, 7.7 mmol), catalytic dimethylaminopyridine and acetic anhydride (0.29 mL, 3.0 mmol). The reaction was stirred at 25° C. for 1.5 h. At this time, the reaction was poured into water and was extracted into methylene chloride. The organics were concentrated in vacuo to afford acetic acid 1-methyl-2-(5-methyl-3-nitropyrazol-1-yl)-ethyl ester (440 mg, 75%) as a white solid which was used without further purification; ES$^+$-HRMS m/e calcd for C$_9$H$_{13}$N$_3$O$_4$ [M+Na$^+$] 250.0798, found 250.0798.

(ADS-39604-013-I)

A solution of acetic acid 1-methyl-2-(5-methyl-3-nitropyrazol-1-yl)-ethyl ester (440 mg, 1.93 mmol) in ethanol (20 mL) was treated with 10% palladium on carbon (270 mg).

The reaction was then stirred for 12 h under a balloon of hydrogen gas. At this time, the catalyst was removed by filtration through a pad of diatomaceous earth and was washed with ethanol. The filtrate was concentrated in vacuo

Intermediate 99

3-Cyclohexyl-2-[4-(2,3-dihydro-benzo[1,4]dioxin-5-yloxy)-6-oxo-6H-pyridazin-1-yl]-propionic acid

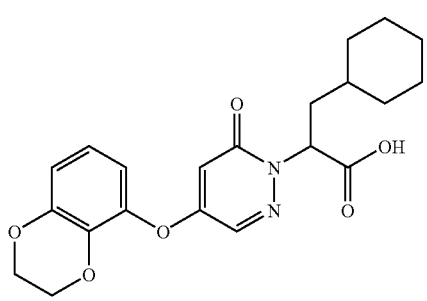

In an analogous manner to the stepwise sequence outlined in Intermediate 19, starting from 4,5-dichloro-2-(tetrahydropyran-2-yl)-2H-pyridazin-3-one (Intermediate 20) and 2,3-dihydro-benzo[1,4]dioxin-5-ol and alkylating with 2-bromo-3-cyclohexyl-propionic acid methyl ester (Intermediate 12) afforded 3-cyclohexyl-2-[4-(2,3-dihydro-benzo[1,4]dioxin-5-yloxy)-6-oxo-6H-pyridazin-1-yl]-propionic acid (30 mg, 89% for the final step) which was used in Example 133. (ADS-38578-289-A)

Intermediate 100

2-[4-(2-Chloro-phenoxy)-6-oxo-6H-pyridazin-1-yl]-4-methyl-pentanoic acid

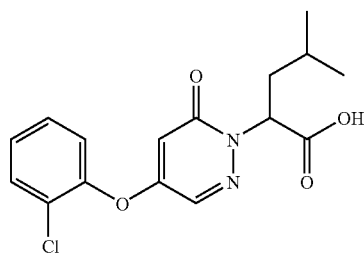

In an analogous manner to the stepwise sequence outlined in Intermediate 18, starting from 5-iodo-2-(tetrahydro-pyran-2-yl)-2H-pyridazin-3-one (Intermediate 18, step 2) and 2-chloro-phenol afforded 5-(2-chloro-4-trifluoromethoxy-phenoxy)-2H-pyridazin-3-one which was then reacted in an analogous manner to that outlined in the synthesis of Intermediate 19 (steps 4 and 5) alkylating with 2-bromo-4-methyl-pentanoic acid methyl ester (Intermediate 11) to afforded the lithium salt of 2-[4-(2-chloro-phenoxy)-6-oxo-6H-pyridazin-1-yl]-4-methyl-pentanoic acid as a white solid. This material was used crude without further purification in Example 134. (39604-7)

Intermediate 101

2-[4-(2-Chloro-phenoxy)-6-oxo-6H-pyridazin-1-yl]-3-(tetrahydro-pyran-4-yl)-propionic acid

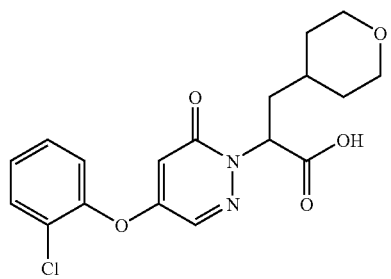

In an analogous manner to the stepwise sequence outlined in Intermediate 18, starting from 5-iodo-2-(tetrahydro-pyran-2-yl)-2H-pyridazin-3-one (Intermediate 18, step 2) and 2-chloro-phenol afforded 5-(2-chloro-phenoxy)-2H-pyridazin-3-one which was then reacted in an analogous manner to that outlined in the synthesis of Intermediate 19 (steps 4 and 5) alkylating with 2-bromo-3-(tetrahydro-pyran-4-yl)-propionic acid methyl ester (Intermediate 14) to afforded 2-[4-(2-chloro-phenoxy)-6-oxo-6H-pyridazin-1-yl]-3-(tetrahydro-pyran-4-yl)-propionic acid. This material was used crude without further purification in Example 135. $^1$H NMR (400 MHz, DMSO-$d_6$) δ ppm 1.08-1.38 (m, 3H), 1.45 (d, J=12.4 Hz, 1H), 1.60 (d, J=12.1 Hz, 1H), 1.88-2.00 (m, 1H), 2.04-2.17 (m, 1H), 3.09-3.25 (m, 2H), 3.74-3.85 (m, 2H), 5.42 (dd, J=10.8, 4.4 Hz, 1H), 5.73 (d, J=2.9 Hz, 1H), 7.36-7.47 (m, 1H), 7.47-7.55 (m, 2H), 7.71 (d, J=7.7 Hz, 1H), 8.21 (d, J=2.9 Hz, 1H), 13.10 (br. s., 1H).
(ADS-39604-003-I)

Intermediate 102

2-(5-Chloro-6-oxo-4-phenoxy-6H-pyridazin-1-yl)-3-cyclohexyl-propionic acid

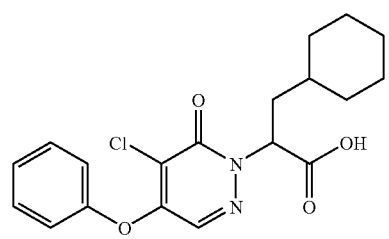

In an analogous manner to the stepwise sequence outlined in Intermediate 19 (steps 1-2), starting from 4,5-dichloro-2-(tetrahydropyran-2-yl)-2H-pyridazin-3-one (Intermediate 20) and phenol followed by the stepwise sequence outlined in Intermediate 19 (steps 4 and 5) alkylating with 2-bromo-3-cyclohexyl-propionic acid methyl ester (Intermediate 12)

afforded the lithium salt of 2-(5-chloro-6-oxo-4-phenoxy-6H-pyridazin-1-yl)-3-cyclohexyl-propionic acid. This material was used without further purification in Example 136.

(ADS-38578-297)

Part II

Preparation of Preferred Compounds

Example 1

3-Cyclopentyl-N-[1-(2-hydroxy-2-methyl-propyl)-1H-pyrazol-3-yl]-2-(6-oxo-4-phenoxy-6H-pyridazin-1-yl)-propionamide

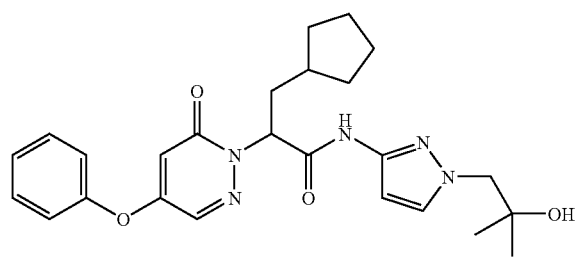

Step 1: A solution of 3-cyclopentyl-2-(6-oxo-4-phenoxy-6H-pyridazin-1-yl)-propionic acid (Intermediate 19, 100.6 mg, 0.30 mmol) in methylene chloride (1.70 mL, 0.18M) at 25° C. was treated with N,N-diisopropylethylamine (160 μL, 0.91 mmol) followed by N,N,N',N'-tetramethyl-O—(N-succinimidyl)uronium tetrafluoroborate (110.6 mg, 0.36 mmol). The resulting solution was stirred at 25° C. for 2.5 h. After this time, the reaction was treated with 1-(3-amino-pyrazol-1-yl)-2-methyl-propan-2-ol (Intermediate 1, 61.8 mg, 0.39 mmol). The resulting solution was stirred at 25° C. for 2 d. After this time, the reaction was partitioned between water (75 mL) and methylene chloride (3×75 mL). The combined organics were washed with water (3×100 mL), dried over sodium sulfate and concentrated in vacuo. Silica gel column chromatography (ISCO 40 g, 1/1-3/1 ethyl acetate/hexanes) afforded 3-cyclopentyl-N-[1-(2-hydroxy-2-methyl-propyl)-1H-pyrazol-3-yl]-2-(6-oxo-4-phenoxy-6H-pyridazin-1-yl)-propionamide (23.6 mg, 16.5%) as a white solid; ES$^+$-HRMS m/e calcd for $C_{25}H_{31}N_5O_4$ [M+H$^+$] 466.2449, found 466.2450. $^1$H-NMR (300 MHz, DMSO-d$_6$) δ ppm 1.05 (s, 3H), 1.06 (s, 3H), 1.00-1.76 (m, 9H), 1.91 (m, 1H), 2.28 (m, 1H), 3.89 (s, 2H), 4.67 (s, 1H), 5.46 (dd, J=3.9, J=11.2 Hz, 1H), 5.72 (d, J=2.7 Hz, 1H), 6.39 (d, J=2.1 Hz, 1H), 7.29 (d, J=7.5 Hz, 2H), 7.36 (t, J=7.5 Hz, 1H), 7.46-7.64 (m, 3H), 8.12 (d, J=2.7 Hz, 1H), 10.79 (s, 1H).

In an analogous manner, there were obtained:

Example 2

3-Cyclopentyl-2-(6-oxo-4-phenoxy-6H-pyridazin-1-yl)-N-thiazol-2-yl-propionamide

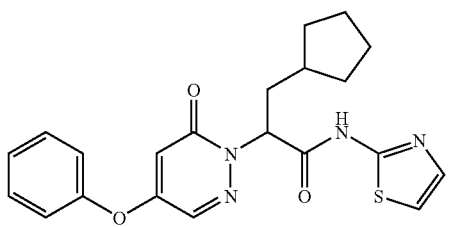

Using the method described in Example 1, 3-cyclopentyl-2-(6-oxo-4-phenoxy-6H-pyridazin-1-yl)-propionic acid (Intermediate 19) and thiazol-2-ylamine afforded 3-cyclopentyl-2-(6-oxo-4-phenoxy-6H-pyridazin-1-yl)-N-thiazol-2-yl-propionamide as a white solid (53.9 mg, 45.3%); ES$^+$-HRMS m/e calcd for $C_{21}H_{22}N_4O_3S$ [M+H$^+$] 411.1486, found 411.1485. $^1$H-NMR (300 MHz, DMSO-d$_6$) δ ppm 1.02-1.87 (m, 9H), 1.97 (m, 1H), 2.26 (m, 1H), 5.54 (dd, J=4.4, J=10.7 Hz, 1H), 5.57 (d, J=2.7 Hz, 1H), 7.23 (d, J=3.6 Hz, 1H), 7.30 (d, J=7.5 Hz, 2H), 7.37 (t, J=7.5 Hz, 1H), 7.49 (d, J=3.6 Hz, 1H), 7.53 (t, J=7.5 Hz, 2H), 8.16 (d, J=2.7 Hz, 1H), 12.55 (s, 1H).

Example 3

3-Cyclopentyl-N-(3-methyl-[1,2,4]thiadiazol-5-yl)-2-(6-oxo-4-phenoxy-6H-pyridazin-1-yl)-propionamide

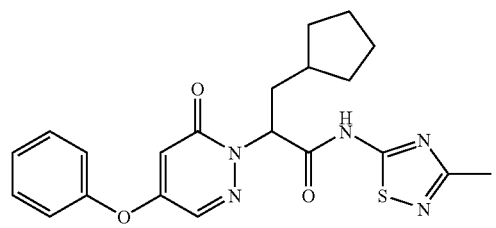

Using the method described in Example 1, 3-cyclopentyl-2-(6-oxo-4-phenoxy-6H-pyridazin-1-yl)-propionic acid (Intermediate 19) and 3-methyl-[1,2,4]thiadiazol-5-ylamine afforded 3-cyclopentyl-N-(3-methyl-[1,2,4]thiadiazol-5-yl)-2-(6-oxo-4-phenoxy-6H-pyridazin-1-yl)-propionamide as a white solid (23.8 mg, 12.1%); ES$^+$-HRMS m/e calcd for $C_{21}H_{23}N_5O_3S$ [M+H$^+$] 426.1595, found 426.1594. $^1$H-NMR (300 MHz, DMSO-d$_6$) δ ppm 1.01-1.77 (m, 9H), 2.03 (m, 1H), 2.27 (m, 1H), 2.44 (s, 3H), 5.57 (dd, J=4.5, J=10.6 Hz, 1H), 5.76 (d, J=2.8 Hz, 1H), 7.30 (d, J=7.5 Hz, 2H), 7.37 (t, J=7.5 Hz, 1H), 7.54 (t, J=7.5 Hz, 2H), 8.17 (d, J=2.8 Hz, 1H), 13.26 (s, 1H).

Example 4

3-Cyclopentyl-N-(5-methyl-[1,3,4]thiadiazol-2-yl)-2-(6-oxo-4-phenoxy-6H-pyridazin-1-yl)-propionamide

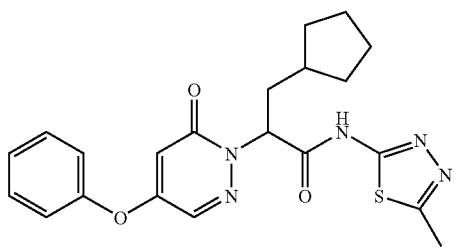

Using the method described in Example 1, 3-cyclopentyl-2-(6-oxo-4-phenoxy-6H-pyridazin-1-yl)-propionic acid (Intermediate 19) and 5-methyl-[1,3,4]thiadiazol-2-ylamine afforded 3-cyclopentyl-N-(5-methyl-[1,3,4]thiadiazol-2-yl)-2-(6-oxo-4-phenoxy-6H-pyridazin-1-yl)-propionamide as a white solid (60.1 mg, 31.4%); ES$^+$-HRMS m/e calcd for $C_{21}H_{23}N_5O_3S$ [M+Na$^+$] 448.1414, found 448.1413. $^1$H-NMR (300 MHz, DMSO-d$_6$) δ ppm 1.01-1.77 (m, 9H), 1.96 (m, 1H), 2.26 (m, 1H), 2.58 (s, 3H), 5.52 (dd, J=4.2, J=10.6 Hz, 1H), 5.73 (d, J=2.7 Hz, 1H), 7.28 (d, J=7.5 Hz, 2H), 7.35 (t, J=7.5 Hz, 1H), 7.52 (t, J=7.5 Hz, 2H), 8.14 (d, J=2.7 Hz, 1H), 12.82 (s, 1H).

Example 5

3-Cyclopentyl-N-[1-(2-hydroxy-2-methyl-propyl)-1H-pyrazol-3-yl]-2-[6-oxo-4-(4-trifluoromethyl-phenoxy)-6H-pyridazin-1-yl]-propionamide

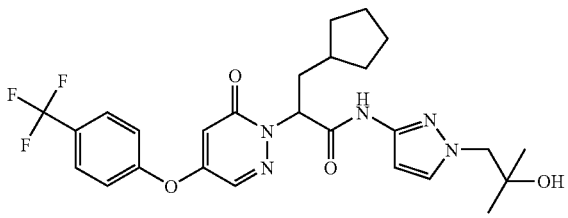

Using the method described in Example 1, 3-cyclopentyl-2-[6-oxo-4-(4-trifluoromethyl-phenoxy)-6H-pyridazin-1-yl]-propionic acid (Intermediate 23) and 1-(3-amino-pyrazol-1-yl)-2-methyl-propan-2-ol (Intermediate 1) afforded 3-cyclopentyl-N-[1-(2-hydroxy-2-methyl-propyl)-1H-pyrazol-3-yl]-2-[6-oxo-4-(4-trifluoromethyl-phenoxy)-6H-pyridazin-1-yl]-propionamide as a yellow solid (23.1 mg, 9%); ES$^+$-HRMS m/e calcd for $C_{26}H_{30}F_3N_5O_4$ [M+H$^+$] 534.2323 found 534.2324. $^1$H-NMR (400 MHz, DMSO-d$_6$) δ ppm 1.05 (s, 3H), 1.06 (s, 3H), 1.07 (m, 1H), 1.16-1.79 (m, 8H), 1.92 (m, 1H), 2.25 (m, 1H), 3.89 (s, 2H), 4.67 (s, 1H), 5.49 (dd, J=4.3, J=11.1 Hz, 1H), 6.01 (d, J=2.9 Hz, 1H), 6.40 (d, J=2.3 Hz, 1H), 7.53 (d, J=2.3 Hz, 1H), 7.53 (d, J=8.5 Hz, 2H), 7.90 (d, J=8.5 Hz, 2H), 8.16 (d, J=2.9 Hz, 1H), 10.80 (s, 1H).

Example 6

3-Cyclopentyl-N-[1-(2-hydroxy-2-methyl-propyl)-1H-pyrazol-3-yl]-2-[6-oxo-4-(3-trifluoromethyl-phenoxy)-6H-pyridazin-1-yl]-propionamide

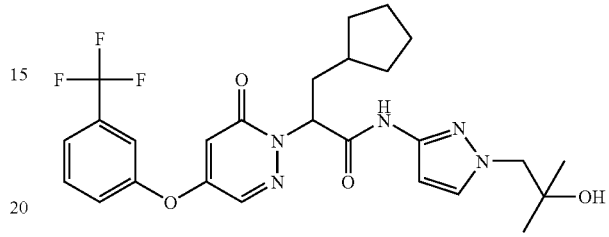

Using the method described in Example 1, 3-cyclopentyl-2-[6-oxo-4-(3-trifluoromethyl-phenoxy)-6H-pyridazin-1-yl]-propionic acid (Intermediate 22) and 1-(3-amino-pyrazol-1-yl)-2-methyl-propan-2-ol (Intermediate 1) afforded 3-cyclopentyl-N-[1-(2-hydroxy-2-methyl-propyl)-1H-pyrazol-3-yl]-2-[6-oxo-4-(3-trifluoromethyl-phenoxy)-6H-pyridazin-1-yl]-propionamide as a white solid (13.7 mg, 5%); ES$^+$-HRMS m/e calcd for $C_{26}H_{30}F_3N_5O_4$ [M+H$^+$] 534.2323 found 534.2323. $^1$H-NMR (400 MHz, DMSO-d$_6$) δ ppm 1.05 (s, 3H), 1.06 (s, 3H), 1.07 (m, 1H), 1.27-1.77 (m, 8H), 1.92 (m, 1H), 2.25 (m, 1H), 3.89 (s, 2H), 4.67 (s, 1H), 5.48 (dd, J=4.4, J=11.0 Hz, 1H), 5.86 (d, J=2.9 Hz, 1H), 6.40 (d, J=2.2 Hz, 1H), 7.53 (d, J=2.2 Hz, 1H), 7.65 (m, 1H), 7.70-7.83 (m, 3H), 8.16 (d, J=2.8 Hz, 1H), 10.80 (s, 1H).

Example 7

3-Cyclopentyl-N-[1-(2-hydroxy-2-methyl-propyl)-1H-pyrazol-3-yl]-2-[4-(3-methoxy-phenoxy)-6-oxo-6H-pyridazin-1-yl]-propionamide

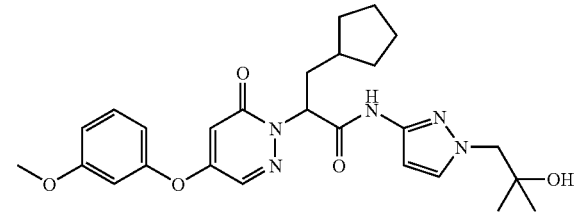

Using the method described in Example 1, 3-cyclopentyl-2-[4-(3-methoxy-phenoxy)-6-oxo-6H-pyridazin-1-yl]-propionic acid (Intermediate 25) and 1-(3-amino-pyrazol-1-yl)-2-methyl-propan-2-ol (Intermediate 1) afforded 3-cyclopentyl-N-[1-(2-hydroxy-2-methyl-propyl)-1H-pyrazol-3-yl]-2-[4-(3-methoxy-phenoxy)-6-oxo-6H-pyridazin-1-yl]-propionamide as an off-white solid (14.6 mg, 10.1%); ES$^+$-HRMS m/e calcd for $C_{26}H_{33}N_5O_5$ [M+Na$^+$] 518.2374 found 518.2378. $^1$H-NMR (300 MHz, DMSO-d$_6$) δ ppm 1.05 (s, 3H), 1.06 (s, 3H), 1.09 (m, 1H), 1.21-1.74 (m, 8H), 1.91 (m, 1H), 2.27 (m, 1H), 3.78 (s, 3H), 3.89 (s, 2H), 4.67 (s, 1H), 5.45 (m., 1H), 5.78 (br.s., 1H), 6.40 (s, 1H), 6.81-6.98 (m, 3H), 7.37-7.49 (m, 1H), 7.52 (d, J=2.1 Hz, 1H), 8.11 (d, J=2.4 Hz, 1H), 10.81 (s, 1H).

Example 8

3-Cyclopentyl-2-(4-cyclopentyloxy-6-oxo-6H-pyridazin-1-yl)-N-[1-(2-hydroxy-2-methyl-propyl)-1H-pyrazol-3-yl]-propionamide

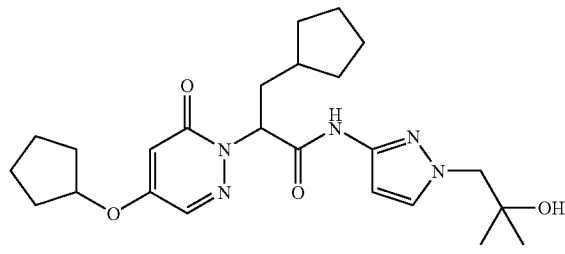

Using the method described in Example 1, 3-cyclopentyl-2-(4-cyclopentyloxy-6-oxo-6H-pyridazin-1-yl)-propionic acid (Intermediate 61) and 1-(3-amino-pyrazol-1-yl)-2-methyl-propan-2-ol (Intermediate 1) afforded 3-cyclopentyl-2-(4-cyclopentyloxy-6-oxo-6H-pyridazin-1-yl)-N-[1-(2-hydroxy-2-methyl-propyl)-1H-pyrazol-3-yl]-propionamide (49.8 mg, 23%) as a white solid; ES$^+$-HRMS m/e calcd for $C_{24}H_{35}N_5O_4$ [M+Na$^+$] 480.2581, found 480.2582. $^1$H-NMR (400 MHz, DMSO-d$_6$) δ ppm 1.05 (s, 3H), 1.06 (s, 3H), 1.05 (m, 1H), 1.25-1.80 (m, 14H), 1.83-2.00 (m, 3H), 2.28 (m, 1H), 3.89 (s, 2H), 4.67 (s, 1H), 4.86 (m, 1H), 5.45 (dd, J=4.3, J=11.1 Hz, 1H), 6.24 (d, J=2.8 Hz, 1H), 6.39 (d, J=2.3 Hz, 1H), 7.52 (d, J=2.3 Hz, 1H), 7.76 (d, J=2.8 Hz, 1H), 10.74 (s, 1H).

Example 9

3-Cyclopentyl-2-(4-cyclopentylmethoxy-6-oxo-6H-pyridazin-1-yl)-N-[1-(2-hydroxy-2-methyl-propyl)-1H-pyrazol-3-yl]-propionamide

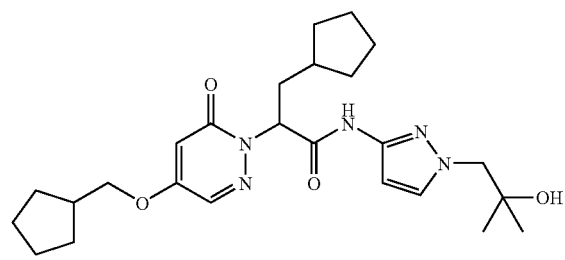

Using the method described in Example 1, 3-cyclopentyl-2-(4-cyclopentylmethoxy-6-oxo-6H-pyridazin-1-yl)-propionic acid (Intermediate 59) and 1-(3-amino-pyrazol-1-yl)-2-methyl-propan-2-ol (Intermediate 1) afforded 3-cyclopentyl-2-(4-cyclopentylmethoxy-6-oxo-6H-pyridazin-1-yl)-N-[1-(2-hydroxy-2-methyl-propyl)-1H-pyrazol-3-yl]-propionamide as a white solid (22.2 mg, 10%); ES$^+$-HRMS m/e calcd for $C_{25}H_{37}N_5O_4$ [M+H$^+$] 472.2919, found 472.2922. $^1$H-NMR (400 MHz, DMSO-d$_6$) δ ppm 1.05 (s, 3H), 1.06 (s, 3H), 1.05 (m, 1H), 1.25-1.97 (m, 18H), 2.26 (m, 1H), 3.89 (s, 2H), 3.90 (d, J=5.8 Hz, 2H), 4.67 (s, 1H), 5.46 (dd, J=4.2, J=11.2 Hz, 1H), 6.27 (d, J=2.8 Hz, 1H), 6.39 (d, J=2.2 Hz, 1H), 7.52 (d, J=2.2 Hz, 1H), 7.82 (d, J=2.8 Hz, 1H), 10.73 (s, 1H).

Example 10

2-(5-Chloro-4-cyclopentylmethoxy-6-oxo-6H-pyridazin-1-yl)-3-cyclopentyl-N-[1-(2-hydroxy-2-methyl-propyl)-1H-pyrazol-3-yl]-propionamide

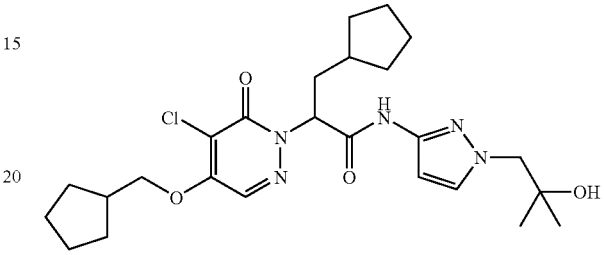

Using the method described in Example 1, 2-(5-chloro-4-cyclopentylmethoxy-6-oxo-6H-pyridazin-1-yl)-3-cyclopentyl-propionic acid (Intermediate 62) and 1-(3-amino-pyrazol-1-yl)-2-methyl-propan-2-ol (Intermediate 1) afforded 2-(5-chloro-4-cyclopentyl methoxy-6-oxo-6H-pyridazin-1-yl)-3-cyclopentyl-N-[1-(2-hydroxy-2-methyl-propyl)-1H-pyrazol-3-yl]-propionamide as a yellow solid (12.2 mg, 6%); ES$^+$-HRMS m/e calcd for $C_{25}H_{36}N_5O_4Cl$ [M+H$^+$] 506.2529, found 506.2532. $^1$H-NMR (400 MHz, DMSO-d$_6$) δ ppm 1.05 (s, 3H), 1.06 (s, 3H), 1.08 (m, 1H), 1.26-2.00 (m, 18H), 2.28 (m, 1H), 3.89 (s, 2H), 4.26 (d, J=6.8 Hz, 2H), 4.67 (s, 1H), 5.52 (dd, J=4.2, J=11.0 Hz, 1H), 6.39 (d, J=2.2 Hz, 1H), 7.53 (d, J=2.2 Hz, 1H), 8.35 (s, 1H), 10.83 (s, 1H).

Example 11

3-Cyclopentyl-N-[1-(2-hydroxy-2-methyl-propyl)-1H-pyrazol-3-yl]-2-[6-oxo-4-(2-trifluoromethyl-phenoxy)-6H-pyridazin-1-yl]-propionamide

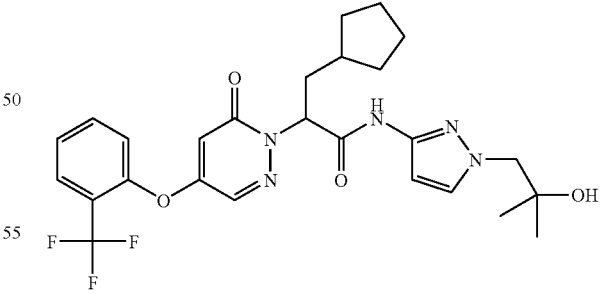

A solution of 3-cyclopentyl-2-[6-oxo-4-(2-trifluoromethyl-phenoxy)-6H-pyridazin-1-yl]-propionic acid (Intermediate 21, 200.4 mg, 0.50 mmol) in methylene chloride (5.0 mL, 0.10 M) at 25° C. was treated with N,N'-diisopropylcarbodiimide (80 μL, 0.51 mmol) and 1-hydroxybenzotriazole (70.3 mg, 0.52 mmol). The solution was stirred at 25° C. for 45 min. After this time, the reaction was added to a solution of 1-(3-amino-pyrazol-1-yl)-2-methyl-propan-2-ol (Intermediate 1, 95.3 mg, 0.61 mmol) in methylene chloride (2.0 mL) at 25° C. The reaction was stirred at 25° C. overnight. After this time, the reaction was diluted with methylene chloride (50 mL) and was washed with a 1N aqueous hydrochloric acid solution (2×50 mL), a saturated aqueous sodium bicarbonate solution (2×50 mL), water (1×50 mL) and a saturated aqueous sodium chloride solution (1×50 mL), dried over magnesium sulfate, filtered and concentrated in vacuo. Silica gel column chromatography (AnaLogix, 40 g, 1-4% methanol/methylene chloride) followed by silica gel column chromatography (AnaLogix 40 g, 1-3% methanol/methylene chloride) afforded 3-cyclopentyl-N-[1-(2-hydroxy-2-methyl-propyl)-1H-pyrazol-3-yl]-2-[6-oxo-4-(2-trifluoromethyl-phenoxy)-6H-pyridazin-1-yl]-propionamide (144.2 mg, 53%) as a white solid; ES$^+$-HRMS m/e calcd for $C_{26}H_{30}N_5O_4F_3$ [M+H$^+$] 534.2323, found 534.2321. $^1$H-NMR (400 MHz, DMSO-d$_6$) δ ppm 1.05 (s, 3H), 1.06 (s, 3H), 1.07 (m, 1H), 1.27-1.77 (m, 8H), 1.92 (m, 1H), 2.25 (m, 1H), 3.89 (s, 2H), 4.67 (s, 1H), 5.47 (dd, J=4.4, J=10.8 Hz, 1H), 5.91 (d, J=2.8 Hz, 1H), 6.40 (d, J=2.2 Hz, 1H), 7.52 (d, J=2.2 Hz, 1H), 7.53-7.63 (m, 2H), 7.83 (t, J=7.8 Hz, 1H), 7.90 (d, J=7.2 Hz, 1H), 8.18 (d, J=2.8 Hz, 1H), 10.84 (s, 1H).

Separation of enantiomers via supercritical fluid chromatography on a SFC DAICEL AD column, 35% methanol, 70 mL/min.

Example 11A (S)-3-Cyclopentyl-N-[1-(2-hydroxy-2-methyl-propyl)-1H-pyrazol-3-yl]-2-[6-oxo-4-(2-trifluoromethyl-phenoxy)-6H-pyridazin-1-yl]-propionamide

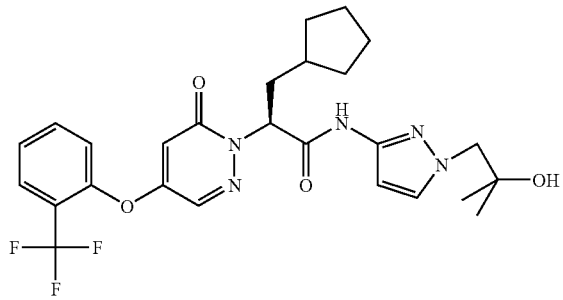

(S)-3-Cyclopentyl-N-[1-(2-hydroxy-2-methyl-propyl)-1H-pyrazol-3-yl]-2-[6-oxo-4-(2-trifluoromethyl-phenoxy)-6H-pyridazin-1-yl]-propionamide; ES$^+$-HRMS m/e calcd for $C_{26}H_{30}N_5O_4F_3$ [M+H$^+$] 534.2323, found 534.2323. $^1$H-NMR (400 MHz, DMSO-d$_6$) δ ppm 1.05 (s, 3H), 1.06 (s, 3H), 1.09 (m, 1H), 1.21-1.78 (m, 8H), 1.91 (m, 1H), 2.27 (m, 1H), 3.89 (s, 2H), 4.68 (s, 1H), 5.47 (dd, J=4.4, J=10.8 Hz, 1H), 5.91 (d, J=2.8 Hz, 1H), 6.40 (d, J=2.1 Hz, 1H), 7.53 (d, J=2.1 Hz, 1H), 7.54-7.63 (m, 2H), 7.83 (t, J=7.7 Hz, 1H), 7.90 (d, J=7.7 Hz, 1H), 8.18 (d, J=2.8 Hz, 1H), 10.84 (s, 1H).

Example 11B (R)-3-Cyclopentyl-N-[1-(2-hydroxy-2-methyl-propyl)-1H-pyrazol-3-yl]-2-[6-oxo-4-(2-trifluoromethyl-phenoxy)-6H-pyridazin-1-yl]-propionamide

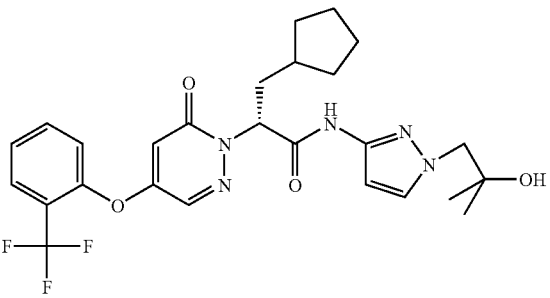

(R)-3-Cyclopentyl-N-[1-(2-hydroxy-2-methyl-propyl)-1H-pyrazol-3-yl]-2-[6-oxo-4-(2-trifluoromethyl-phenoxy)-6H-pyridazin-1-yl]-propionamide; ES$^+$-HRMS m/e calcd for $C_{26}H_{30}N_5O_4F_3$ [M+H$^+$] 534.2323, found 534.2324. $^1$H-NMR (400 MHz, DMSO-d$_6$) δ ppm 1.05 (s, 3H), 1.06 (s, 3H), 1.09 (m, 1H), 1.21-1.78 (m, 8H), 1.91 (m, 1H), 2.27 (m, 1H), 3.89 (s, 2H), 4.68 (s, 1H), 5.47 (dd, J=4.4, J=10.8 Hz, 1H), 5.91 (d, J=2.8 Hz, 1H), 6.40 (d, J=2.1 Hz, 1H), 7.53 (d, J=2.1 Hz, 1H), 7.54-7.63 (m, 2H), 7.83 (t, J=7.7 Hz, 1H), 7.90 (d, J=7.7 Hz, 1H), 8.18 (d, J=2.8 Hz, 1H), 10.84 (s, 1H).

In an analogous manner, there were obtained:

Example 12

3-Cyclopentyl-N-[1-(2-hydroxy-2-methyl-propyl)-1H-pyrazol-3-yl]-2-[4-(2-methoxy-phenoxy)-6-oxo-6H-pyridazin-1-yl]-propionamide

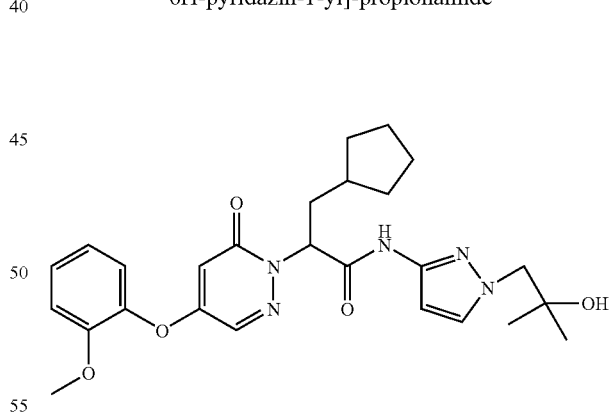

Using the method described in Example 11, 3-cyclopentyl-2-[4-(2-methoxy-phenoxy)-6-oxo-6H-pyridazin-1-yl]-propionic acid (Intermediate 24) and 1-(3-amino-pyrazol-1-yl)-2-methyl-propan-2-ol (Intermediate 1) afforded 3-cyclopentyl-N-[1-(2-hydroxy-2-methyl-propyl)-1H-pyrazol-3-yl]-2-[4-(2-methoxy-phenoxy)-6-oxo-6H-pyridazin-1-yl]-propionamide as a white solid (83.8 mg, 65%); ES$^+$-HRMS m/e calcd for $C_{26}H_{33}N_5O_5$ [M+H$^+$] 496.2555 found 496.2552. $^1$H-NMR (300 MHz, DMSO-d$_6$) δ ppm 1.04 (s, 3H), 1.06 (s, 3H), 1.09 (m, 1H), 1.21-1.74 (m, 8H), 1.91 (m, 1H), 2.27 (m, 1H), 3.80 (s, 3H), 3.89 (s, 2H), 4.68 (s, 1H), 5.45

(dd, J=4.2, J=11.2 Hz, 1H), 5.56 (d, J=2.7 Hz, 1H), 6.39 (d, J=2.1 Hz, 1H), 7.00-7.11 (m, 1H), 7.20-7.31 (m, 2H), 7.31-7.41 (m, 1H), 7.52 (d, J=2.1 Hz, 1H), 8.12 (d, J=2.7 Hz, 1H), 10.83 (s, 1H).

Example 13

N-(5-Chloro-1-methyl-1H-pyrazol-3-yl)-3-cyclopentyl-2-[6-oxo-4-(2-trifluoromethyl-phenoxy)-6H-pyridazin-1-yl]-propionamide

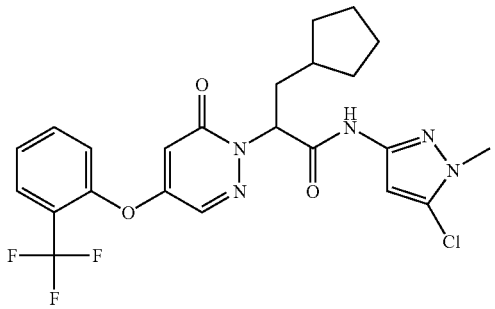

Using the method described in Example 11, 3-cyclopentyl-2-[6-oxo-4-(2-trifluoromethyl-phenoxy)-6H-pyridazin-1-yl]-propionic acid (Intermediate 21) and 5-chloro-1-methyl-1H-pyrazol-3-ylamine (Intermediate 6) afforded N-(5-chloro-1-methyl-1H-pyrazol-3-yl)-3-cyclopentyl-2-[6-oxo-4-(2-trifluoromethyl-phenoxy)-6H-pyridazin-1-yl]-propionamide as a white solid (51.7 mg, 30.6%); ES$^+$-HRMS m/e calcd for $C_{23}H_{23}N_5O_3F_3Cl$ [M+H$^+$] 510.1515 found 510.1514. $^1$H-NMR (300 MHz, DMSO-d$_6$) δ ppm 0.98-1.84 (m, 9H), 1.93 (m, 1H), 2.23 (m, 1H), 3.70 (s, 3H), 5.44 (dd, J=4.4, J=10.4 Hz, 1H), 5.92 (d, J=3.0 Hz, 1H), 6.48 (s, 1H), 7.49-7.64 (m, 2H), 7.83 (t, J=7.9 Hz, 1H), 7.90 (d, J=7.9 Hz, 1H), 8.18 (d, J=3.0 Hz, 1H), 10.95 (s, 1H).

Example 14

3-Cyclopentyl-N-(1-methyl-1H-pyrazol-3-yl)-2-[6-oxo-4-(2-trifluoromethyl-phenoxy)-6H-pyridazin-1-yl]-propionamide

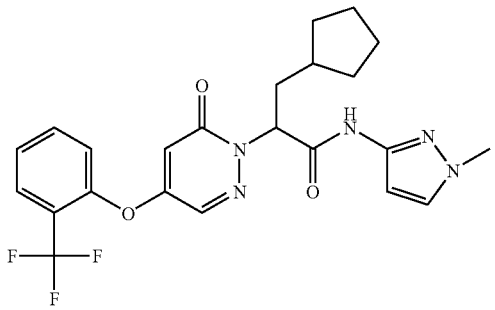

Using the method described in Example 11, 3-cyclopentyl-2-[6-oxo-4-(2-trifluoromethyl-phenoxy)-6H-pyridazin-1-yl]-propionic acid (Intermediate 21) and 1-methyl-1H-pyrazol-3-ylamine afforded 3-cyclopentyl-N-(1-methyl-1H-pyrazol-3-yl)-2-[6-oxo-4-(2-trifluoromethyl-phenoxy)-6H-pyridazin-1-yl]-propionamide as a white solid (78.7 mg, 65%); ES$^+$-HRMS m/e calcd for $C_{23}H_{24}N_5O_3F_3$ [M+H$^+$] 476.1904 found 476.1902. $^1$H-NMR (400 MHz, DMSO-d$_6$) δ ppm 1.06 (m, 1H), 1.26-1.77 (m, 8H), 1.91 (m, 1H), 2.25 (m, 1H), 3.73 (s, 3H), 5.46 (dd, J=4.6, J=10.5 Hz, 1H), 5.92 (d, J=3.0 Hz, 1H), 6.36 (d, J=2.1 Hz, 1H), 7.54 (d, J=2.1 Hz, 1H), 7.56-7.60 (m, 2H), 7.83 (t, J=7.8 Hz, 1H), 7.90 (d, J=7.8 Hz, 1H), 8.17 (d, J=3.0 Hz, 1H), 10.75 (s, 1H).

Example 15

3-Cyclopentyl-N-[1-(2-hydroxy-2-methyl-propyl)-1H-pyrazol-3-yl]-2-[4-(4-methoxy-phenoxy)-6-oxo-6H-pyridazin-1-yl]-propionamide

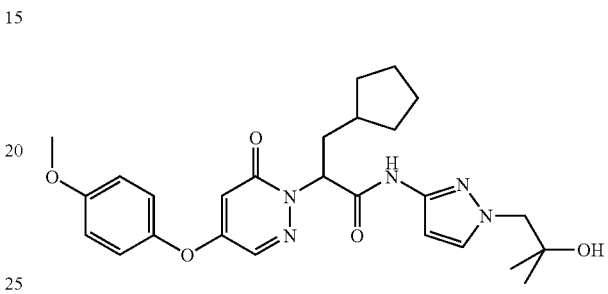

Using the method described in Example 11, 3-cyclopentyl-2-[4-(4-methoxy-phenoxy)-6-oxo-6H-pyridazin-1-yl]-propionic acid (Intermediate 26) and 1-(3-amino-pyrazol-1-yl)-2-methyl-propan-2-ol (Intermediate 1) afforded 3-cyclopentyl-N-[1-(2-hydroxy-2-methyl-propyl)-1H-pyrazol-3-yl]-2-[4-(4-methoxy-phenoxy)-6-oxo-6H-pyridazin-1-yl]-propionamide as a white solid (40.3 mg, 26%); ES$^+$-HRMS m/e calcd for $C_{26}H_{33}N_5O_5$ [M+H$^+$] 496.2555 found 496.2554. $^1$H-NMR (400 MHz, DMSO-d$_6$) δ ppm 1.05 (s, 3H), 1.06 (s, 3H), 1.09 (m, 1H), 1.19-1.78 (m, 8H), 1.91 (m, 1H), 2.28 (m, 1H), 3.79 (s, 3H), 3.89 (s, 2H), 4.67 (s, 1H), 5.46 (dd, J=4.0, J=11.1 Hz, 1H), 5.67 (d, J=2.8 Hz, 1H), 6.39 (d, J=2.3 Hz, 1H), 7.05 (d, J=9.1 Hz, 2H), 7.23 (d, J=9.1 Hz, 2H), 7.52 (d, J=2.3 Hz, 1H), 8.10 (d, J=2.8 Hz, 1H), 10.79 (s, 1H).

Example 16

5-{3-Cyclopentyl-2-[6-oxo-4-(2-trifluoromethyl-phenoxy)-6H-pyridazin-1-yl]-propionylamino}-2-methyl-2H-pyrazole-3-carboxylic acid methyl ester

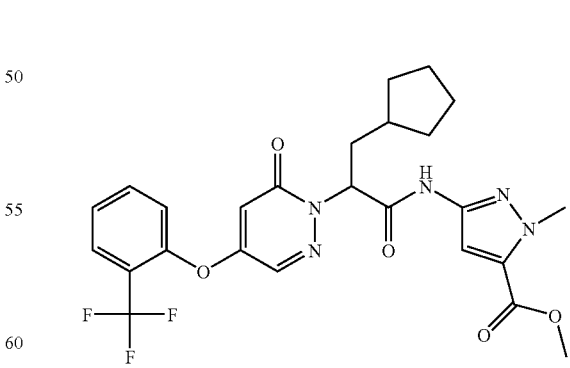

Using the method described in Example 11, 3-cyclopentyl-2-[6-oxo-4-(2-trifluoromethyl-phenoxy)-6H-pyridazin-1-yl]-propionic acid (Intermediate 21) and 5-amino-2-methyl-2H-pyrazole-3-carboxylic acid methyl ester (Intermediate 8) afforded 5-{3-cyclopentyl-2-[6-oxo-4-(2-trifluoromethylphenoxy)-6H-pyridazin-1-yl]-propionylamino}-2-methyl-2H-pyrazole-3-carboxylic acid methyl ester as a white solid (22.1 mg, 17%); ES+-HRMS m/e calcd for $C_{25}H_{26}N_5O_5F_3$ [M+H+] 534.1959 found 534.1959. $^1$H-NMR (400 MHz, DMSO-$d_6$) δ ppm 1.09 (m, 1H), 1.23-1.75 (m, 8H), 1.95 (m, 1H), 2.23 (m, 1H), 3.82 (s, 3H), 4.01 (s, 3H), 5.46 (dd, J=4.5, J=10.4 Hz, 1H), 5.93 (d, J=2.9 Hz, 1H), 6.95 (s, 1H), 7.53-7.60 (m, 2H), 7.83 (t, J=7.8 Hz, 1H), 7.90 (d, J=7.8 Hz, 1H), 8.19 (d, J=2.9 Hz, 1H), 11.06 (s, 1H).

Example 17

3-Cyclopentyl-N-[1-(2-hydroxy-2-methyl-propyl)-1H-pyrazol-3-yl]-2-[6-oxo-4-(5,6,7,8-tetrahydro-naphthalen-1-yloxy)-6H-pyridazin-1-yl]-propionamide

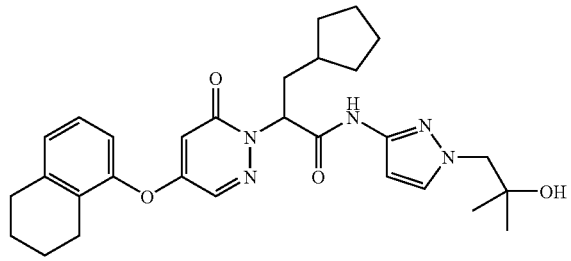

A solution of 3-cyclopentyl-2-[6-oxo-4-(5,6,7,8-tetrahydro-naphthalen-1-yloxy)-6H-pyridazin-1-yl]-propionic acid (Intermediate 39, 1.0 g, 2.61 mmol) in methylene chloride (26 mL, 0.10 M) at 25° C. was treated with 1-(3-dimethylaminopropyl)-3-ethylcarbodiimide (470 μL, 2.65 mmol) and 1-hydroxybenzotriazole (370 mg, 2.73 mmol). The solution was stirred at 25° C. for 2.5 h. After this time, the reaction was treated with a slurry of 1-(3-amino-pyrazol-1-yl)-2-methyl-propan-2-ol (Intermediate 1, 490 mg, 3.15 mmol) in methylene chloride at 25° C. The reaction was stirred at 25° C. overnight. After this time, the reaction was diluted with methylene chloride (250 mL) and was washed with a 1N aqueous hydrochloric acid solution (2×250 mL), a saturated aqueous sodium bicarbonate solution (1×250 mL), water (1×250 mL), and a saturated aqueous sodium chloride solution (1×250 mL), dried over magnesium sulfate, filtered and concentrated in vacuo. Silica gel column chromatography (AnaLogix, 115 g, 35-75% ethyl acetate/hexanes gradient) afforded 3-cyclopentyl-N-[1-(2-hydroxy-2-methyl-propyl)-1H-pyrazol-3-yl]-2-[6-oxo-4-(5,6,7,8-tetrahydro-naphthalen-1-yloxy)-6H-pyridazin-1-yl]-propionamide (730 mg, 54%) as a white solid; ES+-HRMS m/e calcd for $C_{29}H_{37}N_5O_4$ [M+H+] 520.2919, found 520.2920. $^1$H-NMR (400 MHz, DMSO-$d_6$) δ ppm 1.05 (s, 3H), 1.06 (s, 3H), 1.09 (m, 1H), 1.27-1.78 (m, 12H), 1.91 (m, 1H), 2.27 (m, 1H), 2.50 (m, 2H), 2.78 (m, 2H), 3.89 (s, 2H), 4.67 (s, 1H), 5.45 (dd, J=4.3, J=10.9 Hz, 1H), 5.57 (d, J=2.8 Hz, 1H), 6.40 (d, J=2.2 Hz, 1H), 7.01 (d, J=7.7 Hz, 1H), 7.09 (d, J=7.7 Hz, 1H), 7.23 (t, J=7.7 Hz, 1H), 7.53 (d, J=2.2 Hz, 1H), 8.13 (d, J=2.8 Hz, 1H), 10.80 (s, 1H).

Separation of enantiomers via supercritical fluid chromatography on a SFC DAICEL AD column, 55% methanol, 70 mL/min Example 17A (S)-3-Cyclopentyl-N-[1-(2-hydroxy-2-methyl-propyl)-1H-pyrazol-3-yl]-2-[6-oxo-4-(5,6,7,8-tetrahydro-naphthalen-1-yloxy)-6H-pyridazin-1-yl]-propionamide

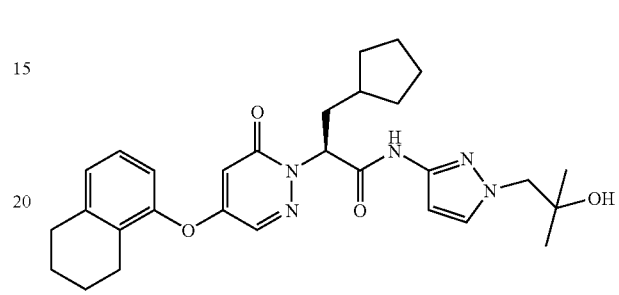

(S)-3-Cyclopentyl-N-[1-(2-hydroxy-2-methyl-propyl)-1H-pyrazol-3-yl]-2-[6-oxo-4-(5,6,7,8-tetrahydro-naphthalen-1-yloxy)-6H-pyridazin-1-yl]-propionamide; ES+-HRMS m/e calcd for $C_{29}H_{37}N_5O_4$ [M+H+] 520.2919, found 520.2915. $^1$H-NMR (400 MHz, DMSO-$d_6$) δ ppm 1.05 (s, 3H), 1.06 (s, 3H), 1.08 (m, 1H), 1.32 (m, 1H), 1.38-1.76 (m, 11H), 1.91 (m, 1H), 2.27 (m, 1H), 2.50 (br.s., 2H), 2.78 (br.s., 2H), 3.89 (s, 2H), 4.67 (s, 1H), 5.45 (dd, J=4.6, J=10.8 Hz, 1H), 5.57 (d, J=2.9 Hz, 1H), 6.40 (d, J=2.2 Hz, 1H), 7.01 (d, $J_o$=7.7 Hz, 1H), 7.09 (d, $J_o$=7.7 Hz, 1H), 7.23 (t, $J_o$=7.7 Hz, 1H), 7.52 (d, J=2.2 Hz, 1H), 8.13 (d, J=2.9 Hz, 1H), 10.80 (s, 1H).

Example 17B (R)-3-Cyclopentyl-N-[1-(2-hydroxy-2-methyl-propyl)-1H-pyrazol-3-yl]-2-[6-oxo-4-(5,6,7,8-tetrahydro-naphthalen-1-yloxy)-6H-pyridazin-1-yl]-propionamide

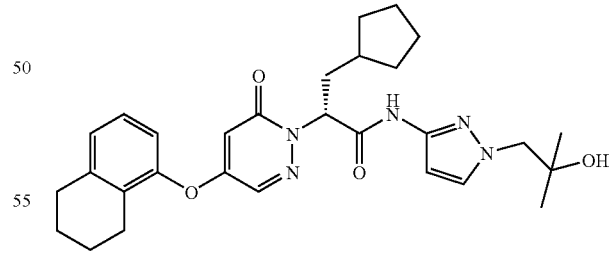

(R)-3-Cyclopentyl-N-[1-(2-hydroxy-2-methyl-propyl)-1H-pyrazol-3-yl]-2-[6-oxo-4-(5,6,7,8-tetrahydro-naphthalen-1-yloxy)-6H-pyridazin-1-yl]-propionamide; ES+-HRMS m/e calcd for $C_{29}H_{37}N_5O_4$ [M+H+] 520.2919, found 520.2916. $^1$H-NMR (400 MHz, DMSO-$d_6$) δ ppm 1.05 (s, 3H), 1.06 (s, 3H), 1.08 (m, 1H), 1.32 (m, 1H), 1.38-1.76 (m, 11H), 1.91 (m, 1H), 2.27 (m, 1H), 2.50 (br.s., 2H), 2.78 (br.s., 2H), 3.89 (s, 2H), 4.67 (s, 1H), 5.45 (dd, J=4.6, J=10.8 Hz, 1H), 5.57 (d, J=2.9 Hz, 1H), 6.40 (d, J=2.2 Hz, 1H), 7.01 (d, $J_o$=7.7 Hz, 1H), 7.09 (d, $J_o$=7.7 Hz, 1H), 7.23 (t, $J_o$=7.7 Hz, 1H), 7.52 (d, J=2.2 Hz, 1H), 8.13 (d, J=2.9 Hz, 1H), 10.80 (s, 1H).

In an analogous manner, there were obtained:

Example 18

3-Cyclopentyl-2-[4-(3-fluoro-phenoxy)-6-oxo-6H-pyridazin-1-yl]-N-[1-(2-hydroxy-2-methyl-propyl)-1H-pyrazol-3-yl]-propionamide

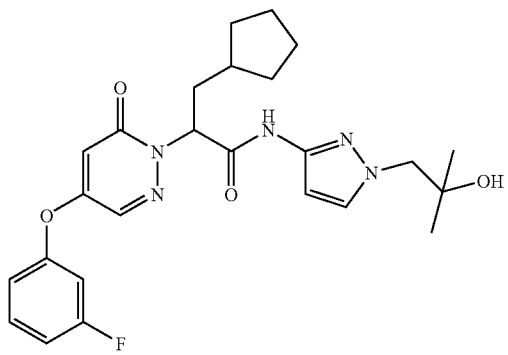

Using the method described in Example 17, 3-cyclopentyl-2-[4-(3-fluoro-phenoxy)-6-oxo-6H-pyridazin-1-yl]-propionic acid (Intermediate 42) and 1-(3-amino-pyrazol-1-yl)-2-methyl-propan-2-ol (Intermediate 1) afforded 3-cyclopentyl-2-[4-(3-fluoro-phenoxy)-6-oxo-6H-pyridazin-1-yl]-N-[1-(2-hydroxy-2-methyl-propyl)-1H-pyrazol-3-yl]-propionamide as a white solid (0.74 g, 53%); ES$^+$-HRMS m/e calcd for $C_{25}H_{30}N_5O_4F$ [M+H$^+$] 484.2355 found 484.2356. $^1$H-NMR (400 MHz, DMSO-d$_6$) δ ppm 1.05 (s, 3H), 1.06 (s, 3H), 1.10 (m, 1H), 1.27-1.75 (m, 8H), 1.92 (m, 1H), 2.28 (m, 1H), 3.89 (s, 2H), 4.67 (s, 1H), 5.48 (dd, J=4.3, J=10.9 Hz, 1H), 5.88 (d, J=2.9 Hz, 1H), 6.40 (d, J=2.3 Hz, 1H), 7.17 (dd, $J_m$=2.3 Hz, $J_o$=8.3 Hz, 1H), 7.22 (td, $J_m$=2.3 Hz, $J_o$=8.3 Hz, $^3J_F$=8.3 Hz, 1H), 7.31 (dt, $J_m$=2.3 Hz, $^3J_F$=9.9 Hz, 1H), 7.53 (d, J=2.3 Hz, 1H), 7.57 (dt, $J_o$=8.3 Hz, $^4J_F$=6.9 Hz, 1H), 8.13 (d, J=2.9 Hz, 1H), 10.80 (s, 1H).

Example 19

3-Cyclopentyl-2-[4-(2-fluoro-phenoxy)-6-oxo-6H-pyridazin-1-yl]-N-[1-(2-hydroxy-2-methyl-propyl)-1H-pyrazol-3-yl]-propionamide

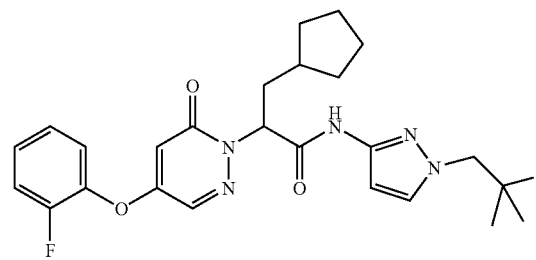

Using the method described in Example 17, 3-cyclopentyl-2-[4-(2-fluoro-phenoxy)-6-oxo-6H-pyridazin-1-yl]-propionic acid (Intermediate 43) and 1-(3-amino-pyrazol-1-yl)-2-methyl-propan-2-ol (Intermediate 1) afforded 3-cyclopentyl-2-[4-(2-fluoro-phenoxy)-6-oxo-6H-pyridazin-1-yl]-N-[1-(2-hydroxy-2-methyl-propyl)-1H-pyrazol-3-yl]-propionamide as a white solid (0.48 g, 69%); ES$^+$-HRMS m/e calcd for $C_{25}H_{30}N_5O_4F$ [M+H$^+$] 484.2355 found 484.2355. $^1$H-NMR (300 MHz, DMSO-d$_6$) δ ppm 1.05 (s, 3H), 1.06 (s, 3H), 1.10 (m, 1H), 1.25-1.75 (m, 8H), 1.92 (m, 1H), 2.28 (m, 1H), 3.89 (s, 2H), 4.67 (s, 1H), 5.47 (dd, J=4.1, J=10.7 Hz, 1H), 5.80 (d, J=2.7 Hz, 1H), 6.40 (d, J=2.1 Hz, 1H), 7.28-7.52 (m, 4H), 7.52 (d, J=2.1 Hz, 1H), 8.20 (d, J=2.7 Hz, 1H), 10.82 (s, 1H).

Separation of enantiomers via supercritical fluid chromatography on a SFC DAICEL AD column, 45% methanol, 70 mL/min.

Example 19A (S)-3-Cyclopentyl-2-[4-(2-fluoro-phenoxy)-6-oxo-6H-pyridazin-1-yl]-N-[1-(2-hydroxy-2-methyl-propyl)-1H-pyrazol-3-yl]-propionamide

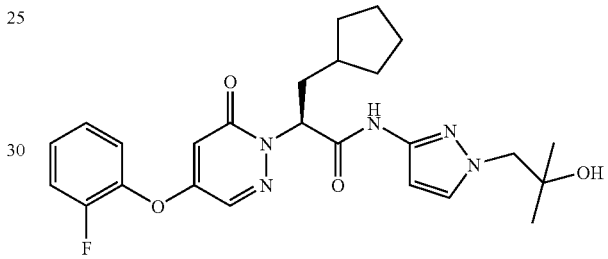

(S)-3-Cyclopentyl-2-[4-(2-fluoro-phenoxy)-6-oxo-6H-pyridazin-1-yl]-N-[1-(2-hydroxy-2-methyl-propyl)-1H-pyrazol-3-yl]-propionamide; ES$^+$-HRMS m/e calcd for $C_{25}H_{30}N_5O_4F$ [M+H$^+$] 484.2355 found 484.2353. $^1$H-NMR (400 MHz, DMSO-d$_6$) δ ppm 1.05 (s, 3H), 1.06 (s, 3H), 1.10 (m, 1H), 1.25-1.75 (m, 8H), 1.92 (m, 1H), 2.28 (m, 1H), 3.89 (s, 2H), 4.67 (s, 1H), 5.47 (dd, J=4.5, J=10.9 Hz, 1H), 5.80 (d, J=2.7 Hz, 1H), 6.40 (d, J=2.3 Hz, 1H), 7.34 (t, J=7.2 Hz, 1H) 7.38-7.46 (m, 1H), 7.46-7.52 (m, 2H), 7.53 (d, J=2.3 Hz, 1H), 8.20 (d, J=2.7 Hz, 1H), 10.83 (s, 1H).

Example 19B (R)-3-Cyclopentyl-2-[4-(2-fluoro-phenoxy)-6-oxo-6H-pyridazin-1-yl]-N-[1-(2-hydroxy-2-methyl-propyl)-1H-pyrazol-3-yl]-propionamide

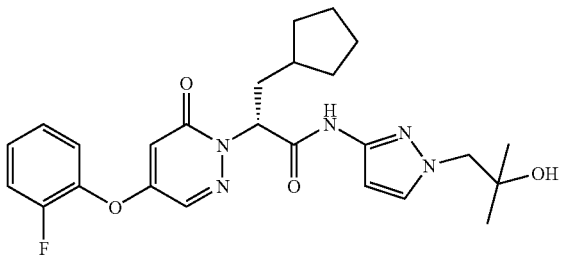

(R)-3-Cyclopentyl-2-[4-(2-fluoro-phenoxy)-6-oxo-6H-pyridazin-1-yl]-N-[1-(2-hydroxy-2-methyl-propyl)-1H-pyrazol-3-yl]-propionamide; ES$^+$-HRMS m/e calcd for $C_{25}H_{30}N_5O_4F$ [M+H$^+$] 484.2353 found 484.2355. $^1$H-NMR (400 MHz, DMSO-d$_6$) δ ppm 1.05 (s, 3H), 1.06 (s, 3H), 1.10 (m, 1H), 1.25-1.75 (m, 8H), 1.92 (m, 1H), 2.28 (m, 1H), 3.89 (s, 2H), 4.67 (s, 1H), 5.47 (dd, J=4.5, J=10.9 Hz, 1H), 5.80 (d, J=2.7 Hz, 1H), 6.40 (d, J=2.3 Hz, 1H), 7.34 (t, J=7.2 Hz, 1H) 7.38-7.46 (m, 1H), 7.46-7.52 (m, 2H), 7.53 (d, J=2.3 Hz, 1H), 8.20 (d, J=2.7 Hz, 1H), 10.83 (s, 1H).

Example 20

2-[4-(Naphthalen-1-yloxy)-6-oxo-6H-pyridazin-1-yl]-octanoic acid [1-(2-hydroxy-2-methyl-propyl)-1H-pyrazol-3-yl]-amide

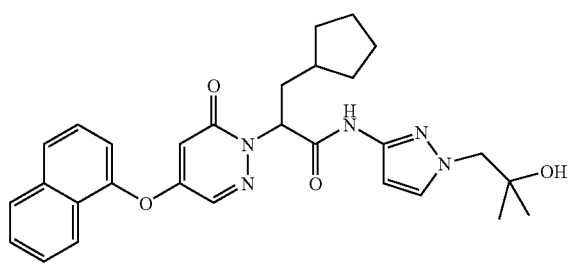

Using the method described in Example 17, 3-cyclopentyl-2-[4-(naphthalen-1-yloxy)-6-oxo-6H-pyridazin-1-yl]-propionic acid (Intermediate 38) and 1-(3-amino-pyrazol-1-yl)-2-methyl-propan-2-ol (Intermediate 1) afforded 2-[4-(naphthalen-1-yloxy)-6-oxo-6H-pyridazin-1-yl]-octanoic acid [1-(2-hydroxy-2-methyl-propyl)-1H-pyrazol-3-yl]-amide as a white solid (0.15 g, 11%); ES$^+$-HRMS m/e calcd for $C_{29}H_{33}N_5O_4$ [M+H$^+$] 516.2606 found 516.2604. $^1$H-NMR (300 MHz, DMSO-d$_6$) δ ppm 1.10-1.20 (br.s., 7H), 1.22-1.83 (m, 8H), 1.93 (m, 1H), 2.29 (m, 1H), 3.89 (s, 2H), 4.67 (s, 1H), 5.45 (m, 1H), 5.63 (s, 1H), 6.40 (s, 1H), 7.44-7.74 (m, 5H), 7.87-8.16 (m, 3H), 8.29 (s, 1H), 10.79 (s, 1H).

Example 21

2-[4-(2-Cyclohexyl-phenoxy)-6-oxo-6H-pyridazin-1-yl]-3-cyclopentyl-N-[1-(2-hydroxy-2-methyl-propyl)-1H-pyrazol-3-yl]-propionamide

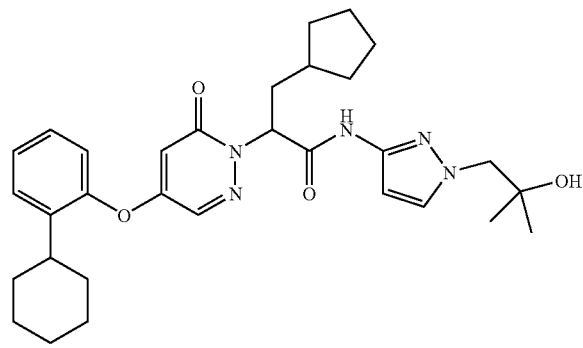

Using the method described in Example 17, 2-[4-(2-cyclohexyl-phenoxy)-6-oxo-6H-pyridazin-1-yl]-3-cyclopentyl-propionic acid (Intermediate 35) and 1-(3-amino-pyrazol-1-yl)-2-methyl-propan-2-ol (Intermediate 1) afforded 2-[4-(2-cyclohexyl-phenoxy)-6-oxo-6H-pyridazin-1-yl]-3-cyclopentyl-N-[1-(2-hydroxy-2-methyl-propyl)-1H-pyrazol-3-yl]-propionamide as a white solid (0.82 g, 62%); ES$^+$-HRMS m/e calcd for $C_{31}H_{41}N_5O_4$ [M+H$^+$] 548.3232 found 548.3233. $^1$H-NMR (300 MHz, DMSO-d$_6$) δ ppm 1.05 (s, 3H), 1.06 (s, 3H), 1.09 (m, 1H), 1.17-1.84 (m, 18H), 1.94 (m, 1H), 2.27 (m, 1H), 2.61 (m, 1H), 3.89 (s, 2H), 4.67 (s, 1H), 5.47 (dd, J=4.1, J=10.7 Hz, 1H), 5.61 (d, J=2.7 Hz, 1H), 6.40 (d, J=2.1 Hz, 1H), 7.15-7.24 (m, 1H), 7.27-7.38 (m, 2H), 7.47 (dd, J=3.6, J=5.7 Hz, 1H), 7.52 (d, J=2.1 Hz, 1H), 8.18 (d, J=2.7 Hz, 1H), 10.79 (s, 1H).

Example 22

3-Cyclopentyl-2-[4-(2-cyclopentyl-phenoxy)-6-oxo-6H-pyridazin-1-yl]-N-[1-(2-hydroxy-2-methyl-propyl)-1H-pyrazol-3-yl]-propionamide

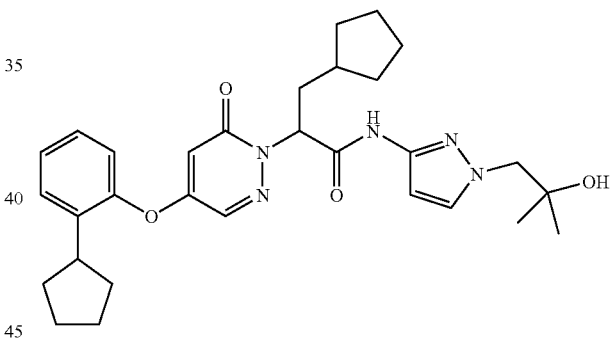

Using the method described in Example 17, 3-cyclopentyl-2-[4-(2-cyclopentyl-phenoxy)-6-oxo-6H-pyridazin-1-yl]-propionic acid (Intermediate 36) and 1-(3-amino-pyrazol-1-yl)-2-methyl-propan-2-ol (Intermediate 1) afforded 3-cyclopentyl-2-[4-(2-cyclopentyl-phenoxy)-6-oxo-6H-pyridazin-1-yl]-N-[1-(2-hydroxy-2-methyl-propyl)-1H-pyrazol-3-yl]-propionamide as a white solid (1.03 g, 75%); ES$^+$-HRMS m/e calcd for $C_{30}H_{39}N_5O_4$ [M+H$^+$] 534.3075 found 534.3076. $^1$H-NMR (300 MHz, DMSO-d$_6$) δ ppm 1.05 (s, 3H), 1.06 (s, 3H), 1.09 (m, 1H), 1.20-1.80 (m, 14H), 1.81-2.02 (m, 3H), 2.27 (m, 1H), 3.04 (m, 1H), 3.89 (s, 2H), 4.67 (s, 1H), 5.46 (dd, J=4.4, J=10.7 Hz, 1H), 5.59 (d, J=2.8 Hz, 1H), 6.40 (d, J=2.2 Hz, 1H), 7.19 (m, 1H), 7.27-7.37 (m, 2H), 7.49 (dd, J=3.6, J=5.7 Hz, 1H), 7.52 (d, J=2.2 Hz, 1H), 8.16 (d, J=2.8 Hz, 1H), 10.80 (s, 1H).

Separation of enantiomers via supercritical fluid chromatography on a SFC DAICEL AD column, 35% methanol, 70 mL/min.

Example 22A (S)-3-Cyclopentyl-2-[4-(2-cyclopentyl-phenoxy)-6-oxo-6H-pyridazin-1-yl]-N-[1-(2-hydroxy-2-methyl-propyl)-1H-pyrazol-3-yl]-propionamide

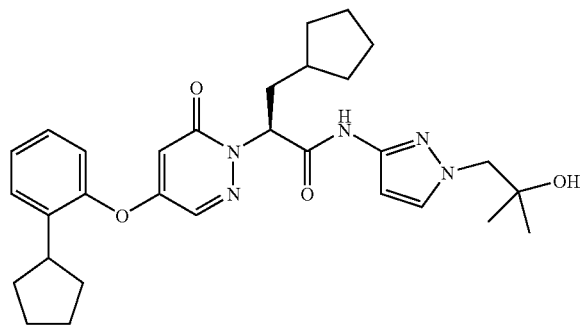

(S)-3-Cyclopentyl-2-[4-(2-cyclopentyl-phenoxy)-6-oxo-6H-pyridazin-1-yl]-N-[1-(2-hydroxy-2-methyl-propyl)-1H-pyrazol-3-yl]-propionamide; ES$^+$-HRMS m/e calcd for $C_{30}H_{39}N_5O_4$ [M+H$^+$] 534.3075 found 534.3075. $^1$H-NMR (300 MHz, DMSO-d$_6$) δ ppm 1.05 (s, 3H), 1.06 (s, 3H), 1.09 (m, 1H), 1.20-1.83 (m, 14H), 1.84-2.01 (m, 3H), 2.26 (m, 1H), 3.04 (m, 1H), 3.89 (s, 2H), 4.66 (s, 1H), 5.46 (dd, J=4.4, J=10.7 Hz, 1H), 5.59 (d, J=2.7 Hz, 1H), 6.40 (d, J=2.1 Hz, 1H), 7.19 (m, 1H), 7.27-7.37 (m, 2H), 7.49 (dd, J=3.6, J=5.7 Hz, 1H), 7.52 (d, J=2.1 Hz, 1H), 8.16 (d, J=2.7 Hz, 1H), 10.79 (s, 1H).

Example 22B (R)-3-Cyclopentyl-2-[4-(2-cyclopentyl-phenoxy)-6-oxo-6H-pyridazin-1-yl]-N-[1-(2-hydroxy-2-methyl-propyl)-1H-pyrazol-3-yl]-propionamide

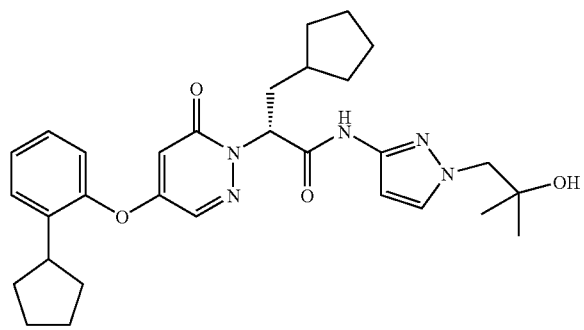

(R)-3-Cyclopentyl-2-[4-(2-cyclopentyl-phenoxy)-6-oxo-6H-pyridazin-1-yl]-N-[1-(2-hydroxy-2-methyl-propyl)-1H-pyrazol-3-yl]-propionamide; ES$^+$-HRMS m/e calcd for $C_{30}H_{39}N_5O_4$ [M+H$^+$] 534.3075 found 534.3073. $^1$H-NMR (300 MHz, DMSO-d$_6$) δ ppm 1.05 (s, 3H), 1.06 (s, 3H), 1.09 (m, 1H), 1.20-1.83 (m, 14H), 1.84-2.01 (m, 3H), 2.26 (m, 1H), 3.04 (m, 1H), 3.89 (s, 2H), 4.66 (s, 1H), 5.46 (dd, J=4.4, J=10.7 Hz, 1H), 5.59 (d, J=2.7 Hz, 1H), 6.40 (d, J=2.1 Hz, 1H), 7.19 (m, 1H), 7.27-7.37 (m, 2H), 7.49 (dd, J=3.6, J=5.7 Hz, 1H), 7.52 (d, J=2.1 Hz, 1H), 8.16 (d, J=2.7 Hz, 1H), 10.79 (s, 1H).

Example 23

2-[4-(Biphenyl-2-yloxy)-6-oxo-6H-pyridazin-1-yl]-3-cyclopentyl-N-[1-(2-hydroxy-2-methyl-propyl)-1H-pyrazol-3-yl]-propionamide

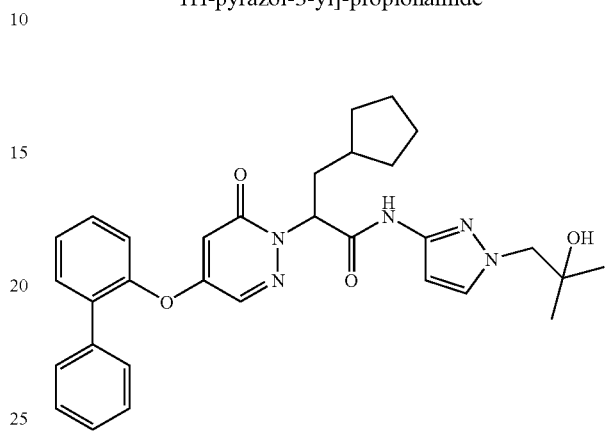

Using the method described in Example 17, 2-[4-(biphenyl-2-yloxy)-6-oxo-6H-pyridazin-1-yl]-3-cyclopentyl-propionic acid (Intermediate 37) and 1-(3-amino-pyrazol-1-yl)-2-methyl-propan-2-ol (Intermediate 1) afforded 2-[4-(biphenyl-2-yloxy)-6-oxo-6H-pyridazin-1-yl]-3-cyclopentyl-N-[1-(2-hydroxy-2-methyl-propyl)-1H-pyrazol-3-yl]-propionamide as a white solid (0.74 g, 50%); ES$^+$-HRMS m/e calcd for $C_{31}H_{35}N_5O_4$ [M+H$^+$] 542.2762 found 542.2759. $^1$H-NMR (400 MHz, DMSO-d$_6$) δ ppm 1.02 (m, 1H), 1.04 (s, 3H), 1.05 (s, 3H), 1.26 (m, 1H), 1.36-1.66 (m, 7H), 1.88 (m, 1H), 2.15 (m, 1H), 3.88 (s, 2H), 4.66 (s, 1H), 5.37 (dd, J=4.4, J=11.0 Hz, 1H), 5.62 (d, J=2.9 Hz, 1H), 6.37 (d, J=2.3 Hz, 1H), 7.29-7.36 (m, 1H), 7.37-7.43 (m, 3H), 7.44-7.60 (m, 6H), 7.97 (d, J=2.9 Hz, 1H), 10.73 (s, 1H).

Example 24

3-Cyclopentyl-N-[1-(2-hydroxy-2-methyl-propyl)-1H-pyrazol-3-yl]-2-(6-oxo-4-o-tolyloxy-6H-pyridazin-1-yl)-propionamide

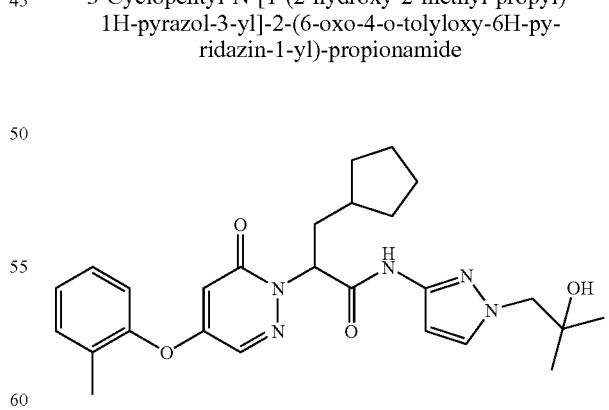

Using the method described in Example 17, 3-cyclopentyl-2-(6-oxo-4-o-tolyloxy-6H-pyridazin-1-yl)-propionic acid (Intermediate 41) and 1-(3-amino-pyrazol-1-yl)-2-methyl-propan-2-ol (Intermediate 1) afforded 3-cyclopentyl-N-[1-(2-hydroxy-2-methyl-propyl)-1H-pyrazol-3-yl]-2-(6-oxo-4-o-tolyloxy-6H-pyridazin-1-yl)-propionamide as a white solid (0.86 g, 58%); ES⁺-HRMS m/e calcd for C₂₆H₃₃N₅O₄ [M+H⁺] 480.2606 found 480.2605. ¹H-NMR (400 MHz, DMSO-d₆) δ ppm 1.05 (s, 3H), 1.06 (s, 3H), 1.09 (m, 1H), 1.27-1.75 (m, 8H), 1.92 (m, 1H), 2.16 (s, 3H), 2.27 (m, 1H), 3.89 (s, 2H), 4.67 (s, 1H), 5.45 (dd, J=4.3, J=10.9 Hz, 1H), 5.56 (d, J=2.8 Hz, 1H), 6.40 (d, J=2.3 Hz, 1H), 7.21 (dd, J$_o$=7.5 Hz, J$_m$=1.3 Hz, 1H), 7.28 (td, J$_o$=7.5 Hz, J$_m$=1.3 Hz, 1H), 7.34 (td, J$_o$=7.5 Hz, J$_m$=1.3 Hz, 1H), 7.41 (d, J$_o$=7.5 Hz, 1H), 7.53 (d, J=2.3 Hz, 1H), 8.15 (d, J=2.8 Hz, 1H), 10.80 (s, 1H).

Separation of enantiomers via supercritical fluid chromatography on a SFC DAICEL AD column, 40% methanol, 70 mL/min.

Example 24A (S)-3-Cyclopentyl-N-[1-(2-hydroxy-2-methyl-propyl)-1H-pyrazol-3-yl]-2-(6-oxo-4-o-tolyloxy-6H-pyridazin-1-yl)-propionamide

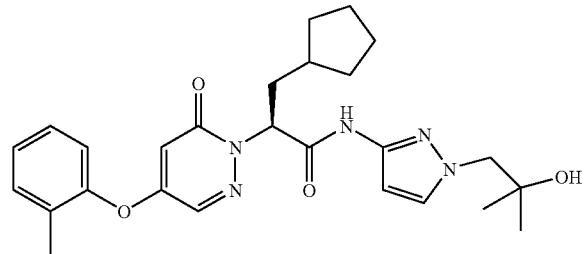

(S)-3-Cyclopentyl-N-[1-(2-hydroxy-2-methyl-propyl)-1H-pyrazol-3-yl]-2-(6-oxo-4-o-tolyloxy-6H-pyridazin-1-yl)-propionamide; ES⁺-HRMS m/e calcd for C₂₆H₃₃N₅O₄ [M+H⁺] 480.2606 found 480.2606. ¹H-NMR (300 MHz, DMSO-d₆) δ ppm 1.05 (s, 3H), 1.06 (s, 3H), 1.09 (m, 1H), 1.24-1.78 (m, 8H), 1.92 (m, 1H), 2.16 (s, 3H), 2.27 (m, 1H), 3.89 (s, 2H), 4.66 (s, 1H), 5.45 (dd, J=4.2, J=10.6 Hz, 1H), 5.56 (d, J=2.8 Hz, 1H), 6.41 (d, J=2.1 Hz, 1H), 7.21 (d, J$_o$=7.8 Hz, 1H), 7.24-7.38 (m, 2H), 7.41 (d, J$_o$=7.2 Hz, 1H), 7.52 (d, J=2.1 Hz, 1H), 8.14 (d, J=2.8 Hz, 1H), 10.79 (s, 1H).

Example 24B (R)-3-Cyclopentyl-N-[1-(2-hydroxy-2-methyl-propyl)-1H-pyrazol-3-yl]-2-(6-oxo-4-o-tolyloxy-6H-pyridazin-1-yl)-propionamide

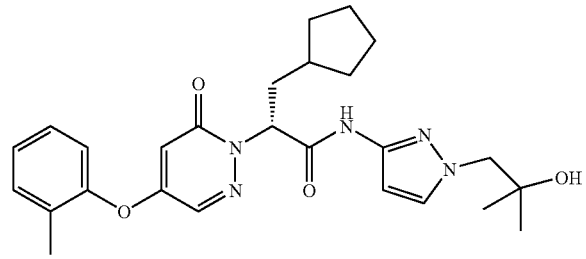

(R)-3-Cyclopentyl-N-[1-(2-hydroxy-2-methyl-propyl)-1H-pyrazol-3-yl]-2-(6-oxo-4-o-tolyloxy-6H-pyridazin-1-yl)-propionamide; ES⁺-HRMS m/e calcd for C₂₆H₃₃N₅O₄ [M+H⁺] 480.2606 found 480.2604. ¹H-NMR (300 MHz, DMSO-d₆) δ ppm 1.05 (s, 3H), 1.06 (s, 3H), 1.09 (m, 1H), 1.24-1.78 (m, 8H), 1.92 (m, 1H), 2.16 (s, 3H), 2.27 (m, 1H), 3.89 (s, 2H), 4.66 (s, 1H), 5.45 (dd, J=4.2, J=10.6 Hz, 1H), 5.56 (d, J=2.8 Hz, 1H), 6.41 (d, J=2.1 Hz, 1H), 7.21 (d, J$_o$=7.8 Hz, 1H), 7.24-7.38 (m, 2H), 7.41 (d, J$_o$=7.2 Hz, 1H), 7.52 (d, J=2.1 Hz, 1H), 8.14 (d, J=2.8 Hz, 1H), 10.79 (s, 1H).

Example 25

3-Cyclopentyl-N-[1-(2-hydroxy-2-methyl-propyl)-1H-pyrazol-3-yl]-2-[4-(2-methyl-pyridin-3-yloxy)-6-oxo-6H-pyridazin-1-yl]-propionamide

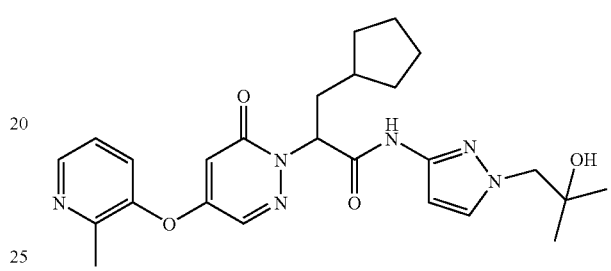

Using the method described in Example 17, 3-cyclopentyl-2-[4-(2-methyl-pyridin-3-yloxy)-6-oxo-6H-pyridazin-1-yl]-propionic acid (Intermediate 50) and 1-(3-amino-pyrazol-1-yl)-2-methyl-propan-2-ol (Intermediate 1) afforded 3-cyclopentyl-N-[1-(2-hydroxy-2-methyl-propyl)-1H-pyrazol-3-yl]-2-[4-(2-methyl-pyridin-3-yloxy)-6-oxo-6H-pyridazin-1-yl]-propionamide as an off-white solid (0.26 g, 18%); ES⁺-HRMS m/e calcd for C₂₅H₃₂N₆O₄ [M+H⁺] 481.2558 found 481.2556. ¹H-NMR (400 MHz, DMSO-d₆) δ ppm 1.05 (s, 3H), 1.06 (s, 3H), 1.09 (m, 1H), 1.27-1.74 (m, 8H), 1.92 (m, 1H), 2.28 (m, 1H), 2.38 (s, 3H), 3.89 (s, 2H), 4.67 (s, 1H), 5.47 (dd, J=4.4, J=10.8 Hz, 1H), 5.74 (d, J=2.9 Hz, 1H), 6.40 (d, J=2.1 Hz, 1H), 7.39 (dd, J$_o$=8.1 Hz, J$_o$=4.7 Hz, 1H), 7.53 (d, J=2.1 Hz, 1H), 7.73 (dd, J$_o$=8.1 Hz, J$_m$=1.3 Hz, 1H), 8.18 (d, J=2.9 Hz, 1H), 8.45 (dd, J$_o$=4.7 Hz, J$_m$=1.3 Hz, 1H), 10.81 (s, 1H).

Example 26

3-Cyclopentyl-N-[1-(2-hydroxy-2-methyl-propyl)-1H-pyrazol-3-yl]-2-[6-oxo-4-(2-pyrrolidin-1-yl-phenoxy)-6H-pyridazin-1-yl]-propionamide

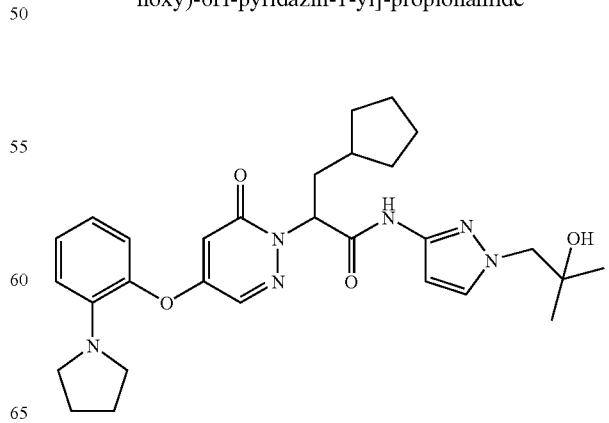

Using the method described in Example 17, 3-cyclopentyl-2-[6-oxo-4-(2-pyrrolidin-1-yl-phenoxy)-6H-pyridazin-1-yl]-propionic acid (Intermediate 51) and 1-(3-amino-pyrazol-1-yl)-2-methyl-propan-2-ol (Intermediate 1) afforded 3-cyclopentyl-N-[1-(2-hydroxy-2-methyl-propyl)-1H-pyrazol-3-yl]-2-[6-oxo-4-(2-pyrrolidin-1-yl-phenoxy)-6H-pyridazin-1-yl]-propionamide as a yellow solid (0.50 g, 34%); ES$^+$-HRMS m/e calcd for $C_{29}H_{38}N_6O_4$ [M+H$^+$] 535.3028 found 535.3027. $^1$H-NMR (400 MHz, DMSO-d$_6$) δ ppm 1.05 (s, 3H), 1.06 (s, 3H), 1.08 (m, 1H), 1.25-1.73 (m, 8H), 1.83 (m, 4H), 1.93 (m, 1H), 2.25 (m, 1H), 3.22 (m, 4H), 3.89 (s, 2H), 4.67 (s, 1H), 5.44 (dd, J=4.5, J=10.7 Hz, 1H), 5.54 (d, J=2.9 Hz, 1H), 6.39 (d, J=2.3 Hz, 1H), 6.79 (m, 1H), 6.89 (dd, $J_o$=8.3 Hz, $J_m$=1.1 Hz, 1H), 7.09 (dd, $J_o$=7.9 Hz, $J_m$=1.5 Hz, 1H), 7.19 (m, 1H), 7.52 (d, J=2.3 Hz, 1H), 8.12 (d, J=2.9 Hz, 1H), 10.80 (s, 1H).

Separation of enantiomers via supercritical fluid chromatography on a SFC DAICEL AD column, 40% methanol, 70 mL/min.

Example 26A (S)-3-Cyclopentyl-N-[1-(2-hydroxy-2-methyl-propyl)-1H-pyrazol-3-yl]-2-[6-oxo-4-(2-pyrrolidin-1-yl-phenoxy)-6H-pyridazin-1-yl]-propionamide

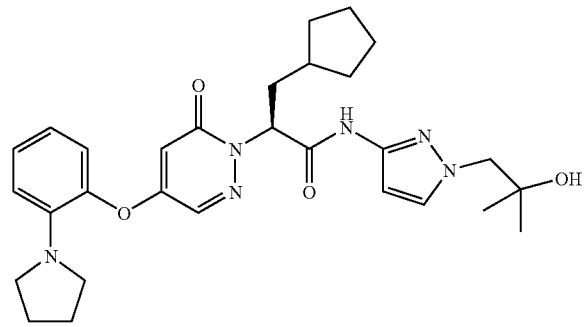

(S)-3-Cyclopentyl-N-[1-(2-hydroxy-2-methyl-propyl)-1H-pyrazol-3-yl]-2-[6-oxo-4-(2-pyrrolidin-1-yl-phenoxy)-6H-pyridazin-1-yl]-propionamide; ES$^+$-HRMS m/e calcd for $C_{29}H_{38}N_6O_4$ [M+H$^+$] 535.3028 found 535.3029. $^1$H-NMR (300 MHz, DMSO-d$_6$) δ ppm 1.04 (s, 3H), 1.06 (s, 3H), 1.07 (m, 1H), 1.20-1.74 (m, 8H), 1.82 (m, 4H), 1.92 (m, 1H), 2.25 (m, 1H), 3.22 (m, 4H), 3.89 (s, 2H), 4.66 (s, 1H), 5.44 (dd, J=4.2, J=10.6 Hz, 1H), 5.54 (d, J=2.7 Hz, 1H), 6.39 (d, J=2.1 Hz, 1H), 6.78 (t, $J_o$=7.7 Hz, 1H), 6.88 (d, $J_o$=7.7 Hz, 1H), 7.08 (dd, $J_o$=7.7 Hz, $J_m$=1.4 Hz, 1H), 7.18 (t, $J_o$=7.7 Hz, 1H), 7.52 (d, J=2.1 Hz, 1H), 8.11 (d, J=2.7 Hz, 1H), 10.78 (s, 1H).

Example 26B (R)-3-Cyclopentyl-N-[1-(2-hydroxy-2-methyl-propyl)-1H-pyrazol-3-yl]-2-[6-oxo-4-(2-pyrrolidin-1-yl-phenoxy)-6H-pyridazin-1-yl]-propionamide

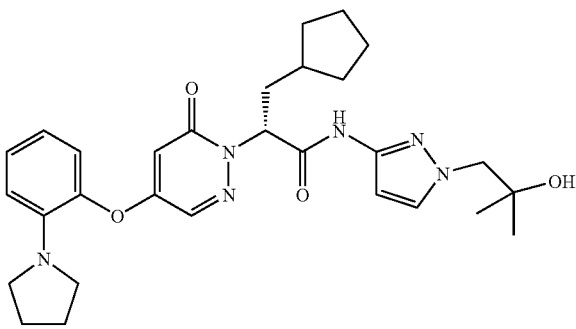

(R)-3-Cyclopentyl-N-[1-(2-hydroxy-2-methyl-propyl)-1H-pyrazol-3-yl]-2-[6-oxo-4-(2-pyrrolidin-1-yl-phenoxy)-6H-pyridazin-1-yl]-propionamide; ES$^+$-HRMS m/e calcd for $C_{29}H_{38}N_6O_4$ [M+H$^+$] 535.3028 found 535.3028. $^1$H-NMR (300 MHz, DMSO-d$_6$) δ ppm 1.04 (s, 3H), 1.06 (s, 3H), 1.07 (m, 1H), 1.20-1.74 (m, 8H), 1.82 (m, 4H), 1.92 (m, 1H), 2.25 (m, 1H), 3.22 (m, 4H), 3.89 (s, 2H), 4.66 (s, 1H), 5.44 (dd, J=4.2, J=10.6 Hz, 1H), 5.54 (d, J=2.7 Hz, 1H), 6.39 (d, J=2.1 Hz, 1H), 6.78 (t, $J_o$=7.7 Hz, 1H), 6.88 (d, $J_o$=7.7 Hz, 1H), 7.08 (dd, $J_o$=7.7 Hz, $J_m$=1.4 Hz, 1H), 7.18 (t, $J_o$=7.7 Hz, 1H), 7.52 (d, J=2.1 Hz, 1H), 8.11 (d, J=2.7 Hz, 1H), 10.78 (s, 1H).

Example 27

3-Cyclopentyl-N-[1-(2-hydroxy-2-methyl-propyl)-1H-pyrazol-3-yl]-2-[6-oxo-4-(2-piperidin-1-yl-phenoxy)-6H-pyridazin-1-yl]-propionamide

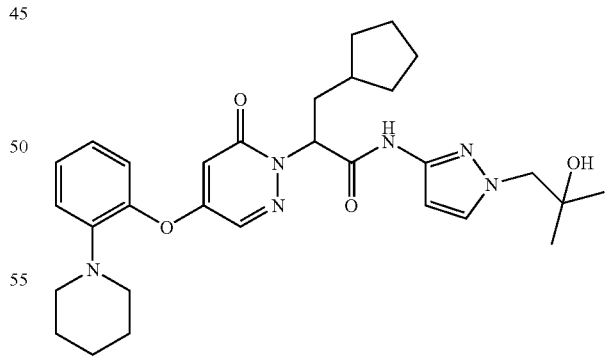

Using the method described in Example 17, 3-cyclopentyl-2-[6-oxo-4-(2-piperidin-1-yl-phenoxy)-6H-pyridazin-1-yl]-propionic acid (Intermediate 52) and 1-(3-amino-pyrazol-1-yl)-2-methyl-propan-2-ol (Intermediate 1) afforded 3-cyclopentyl-N-[1-(2-hydroxy-2-methyl-propyl)-1H-pyrazol-3-yl]-2-[6-oxo-4-(2-piperidin-1-yl-phenoxy)-6H-pyridazin-1-yl]-propionamide as a white solid (0.79 g, 55%); ES$^+$-HRMS m/e calcd for $C_{30}H_{40}N_6O_4$ [M+H$^+$] 549.3184 found 549.3186. $^1$H-NMR (400 MHz, DMSO-d$_6$) δ ppm 1.05 (s, 3H), 1.06 (s, 3H), 1.08 (m, 1H), 1.32 (m, 1H), 1.40 (br.s., 8H), 1.49-1.71 (m, 5H), 1.93 (m, 1H), 2.31 (m, 1H), 2.89 (m, 4H), 3.89 (s, 2H), 4.67 (s, 1H), 5.52 (dd, J=3.9, J=11.4 Hz, 1H), 5.71 (d, J=2.8 Hz, 1H), 6.39 (d, J=2.3 Hz, 1H), 7.09 (m, 1H), 7.13 (dd, J$_o$=8.1 Hz, J$_m$=1.3 Hz, 1H), 7.21 (dd, J$_o$=7.9 Hz, J$_m$=1.5 Hz, 1H), 7.28 (m, 1H), 7.52 (d, J=2.3 Hz, 1H), 8.01 (d, J=2.8 Hz, 1H), 10.73 (s, 1H).

Example 28

3-Cyclopentyl-N-[1-(2-hydroxy-2-methyl-propyl)-1H-pyrazol-3-yl]-2-[6-oxo-4-(pyridin-3-yloxy)-6H-pyridazin-1-yl]-propionamide

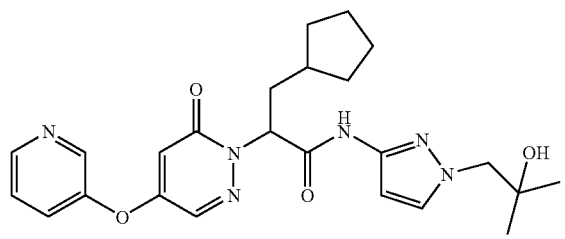

Using the method described in Example 17, 3-cyclopentyl-2-[6-oxo-4-(pyridin-3-yloxy)-6H-pyridazin-1-yl]-propionic acid (Intermediate 54) and 1-(3-amino-pyrazol-1-yl)-2-methyl-propan-2-ol (Intermediate 1) afforded 3-cyclopentyl-N-[1-(2-hydroxy-2-methyl-propyl)-1H-pyrazol-3-yl]-2-[6-oxo-4-(pyridin-3-yloxy)-6H-pyridazin-1-yl]-propionamide as an off-white solid (0.78 g, 53%); ES$^+$-HRMS m/e calcd for C$_{24}$H$_{30}$N$_6$O$_4$ [M+H$^+$] 467.2402 found 467.2399. $^1$H-NMR (400 MHz, DMSO-d$_6$) δ ppm 1.05 (s, 3H), 1.06 (s, 3H), 1.11 (m, 1H), 1.26-1.75 (m, 8H), 1.92 (m, 1H), 2.29 (m, 1H), 3.89 (s, 2H), 4.67 (s, 1H), 5.48 (dd, J=4.4, J=11.0 Hz, 1H), 5.88 (d, J=2.8 Hz, 1H), 6.40 (d, J=2.3 Hz, 1H), 7.53 (d, J=2.3 Hz, 1H), 7.57 (dd, J$_o$=8.4, 4.7 Hz, 1H), 7.83 (ddd, J$_o$=8.4 Hz, J$_m$=2.8, 1.2 Hz, H), 8.17 (d, J=2.8 Hz, 1H), 8.58 (dd, J$_o$=4.7 Hz, J$_m$=1.2 Hz, 1H), 8.61 (d, J$_m$=2.8 Hz, H), 10.80 (s, 1H).

Example 29

2-[4-(2-Cyano-phenoxy)-6-oxo-6H-pyridazin-1-yl]-3-cyclopentyl-N-[1-(2-hydroxy-2-methyl-propyl)-1H-pyrazol-3-yl]-propionamide

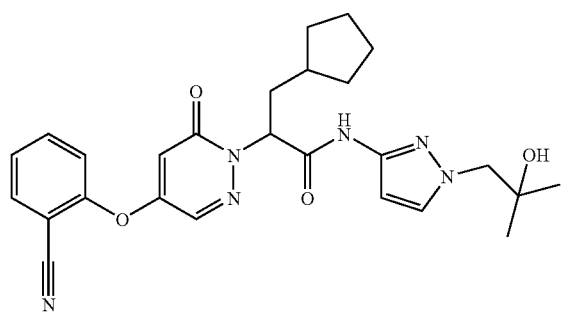

Using the method described in Example 17, 2-[4-(2-cyano-phenoxy)-6-oxo-6H-pyridazin-1-yl]-3-cyclopentyl-propionic acid (Intermediate 58) and 1-(3-amino-pyrazol-1-yl)-2-methyl-propan-2-ol (Intermediate 1) afforded 2-[4-(2-cyano-phenoxy)-6-oxo-6H-pyridazin-1-yl]-3-cyclopentyl-N-[1-(2-hydroxy-2-methyl-propyl)-1H-pyrazol-3-yl]-propionamide as a white solid (0.83 g, 58%); ES$^+$-HRMS m/e calcd for C$_{26}$H$_{30}$N$_6$O$_4$ [M+H$^+$] 491.2402 found 491.2402. $^1$H-NMR (400 MHz, DMSO-d$_6$) δ ppm 1.05 (s, 3H), 1.06 (s, 3H), 1.08 (m, 1H), 1.28-1.76 (m, 8H), 1.94 (m, 1H), 2.29 (m, 1H), 3.89 (s, 2H), 4.67 (s, 1H), 5.49 (dd, J=4.3, J=10.9 Hz, 1H), 6.08 (d, J=2.8 Hz, 1H), 6.41 (d, J=2.3 Hz, 1H), 7.53 (d, J=2.3 Hz, 1H), 7.54 (td, J$_o$=7.7 Hz, J$_m$=0.9 Hz, 1H), 7.58 (d, J$_o$=8.1 Hz, 1H), 7.81-7.91 (m, 1H), 8.03 (dd, J$_o$=7.7 Hz, J$_m$=1.6 Hz, 1H), 8.24 (d, J=2.8 Hz, 1H), 10.83 (s, 1H).

Separation of enantiomers via supercritical fluid chromatography on a SFC DAICEL AD column, 40% methanol, 70 mL/min.

Example 29A (S)-2-[4-(2-Cyano-phenoxy)-6-oxo-6H-pyridazin-1-yl]-3-cyclopentyl-N-[1-(2-hydroxy-2-methyl-propyl)-1H-pyrazol-3-yl]-propionamide

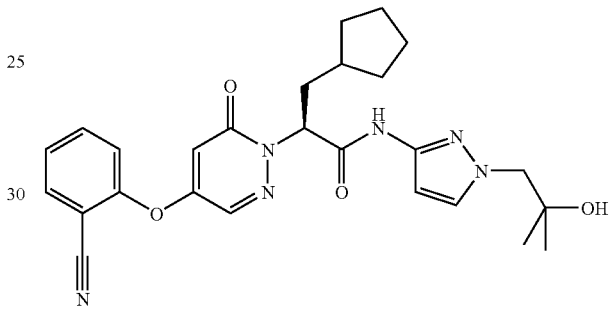

(S)-2-[4-(2-Cyano-phenoxy)-6-oxo-6H-pyridazin-1-yl]-3-cyclopentyl-N-[1-(2-hydroxy-2-methyl-propyl)-1H-pyrazol-3-yl]-propionamide; ES$^+$-HRMS m/e calcd for C$_{26}$H$_{30}$N$_6$O$_4$ [M+H$^+$] 491.2402 found 491.2399. $^1$H-NMR (300 MHz, DMSO-d$_6$) δ ppm 1.05 (s, 3H), 1.06 (s, 3H), 1.08 (m, 1H), 1.28-1.76 (m, 8H), 1.94 (m, 1H), 2.29 (m, 1H), 3.89 (s, 2H), 4.67 (s, 1H), 5.49 (dd, J=4.4, J=10.7 Hz, 1H), 6.08 (d, J=2.8 Hz, 1H), 6.41 (d, J=2.1 Hz, 1H), 7.49-7.63 (m, 3H), 7.81-7.91 (m, 1H), 8.02 (dd, J$_o$=7.7 Hz, J$_m$=1.4 Hz, 1H), 8.23 (d, J=2.8 Hz, 1H), 10.82 (s, 1H).

Example 29B (R)-2-[4-(2-Cyano-phenoxy)-6-oxo-6H-pyridazin-1-yl]-3-cyclopentyl-N-[1-(2-hydroxy-2-methyl-propyl)-1H-pyrazol-3-yl]-propionamide

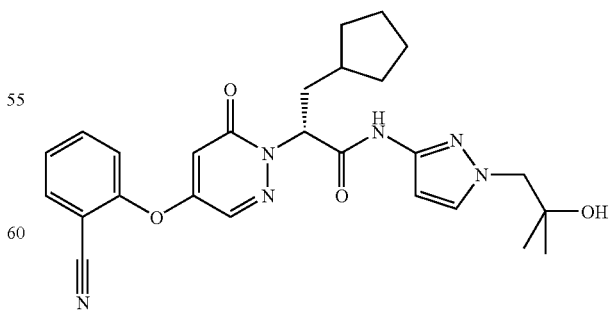

(R)-2-[4-(2-Cyano-phenoxy)-6-oxo-6H-pyridazin-1-yl]-3-cyclopentyl-N-[1-(2-hydroxy-2-methyl-propyl)-1H-pyrazol-3-yl]-propionamide; ES$^+$-HRMS m/e calcd for $C_{26}H_{30}N_6O_4$ [M+H$^+$] 491.2402 found 491.2399. $^1$H-NMR (300 MHz, DMSO-d$_6$) δ ppm 1.05 (s, 3H), 1.06 (s, 3H), 1.08 (m, 1H), 1.28-1.76 (m, 8H), 1.94 (m, 1H), 2.29 (m, 1H), 3.89 (s, 2H), 4.67 (s, 1H), 5.49 (dd, J=4.4, J=10.7 Hz, 1H), 6.08 (d, J=2.8 Hz, 1H), 6.41 (d, J=2.1 Hz, 1H), 7.49-7.63 (m, 3H), 7.81-7.91 (m, 1H), 8.02 (dd, J$_o$=7.7 Hz, J$_m$=1.4 Hz, 1H), 8.23 (d, J=2.8 Hz, 1H), 10.82 (s, 1H).

Example 30

3-Cyclopentyl-N-[1-(2-hydroxy-2-methyl-propyl)-1H-pyrazol-3-yl]-2-[4-(2-methanesulfonyl-phenoxy)-6-oxo-6H-pyridazin-1-yl]-propionamide

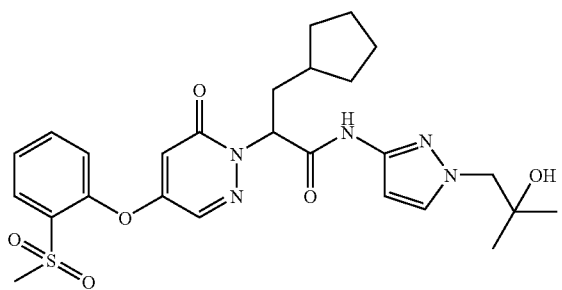

Using the method described in Example 17, 3-cyclopentyl-2-[4-(2-methanesulfonyl-phenoxy)-6-oxo-6H-pyridazin-1-yl]-propionic acid (Intermediate 48) and 1-(3-amino-pyrazol-1-yl)-2-methyl-propan-2-ol (Intermediate 1) afforded 3-cyclopentyl-N-[1-(2-hydroxy-2-methyl-propyl)-1H-pyrazol-3-yl]-2-[4-(2-methanesulfonyl-phenoxy)-6-oxo-6H-pyridazin-1-yl]-propionamide as a white solid (0.74 g, 54%); ES$^+$-HRMS m/e calcd for $C_{26}H_{33}N_5O_6S$ [M+Na$^+$] 566.2044 found 566.2045. $^1$H-NMR (400 MHz, DMSO-d$_6$) δ ppm 1.05 (s, 3H), 1.06 (s, 3H), 1.10 (m, 1H), 1.28-1.76 (m, 8H), 1.92 (m, 1H), 2.28 (m, 1H), 3.36 (s, 3H), 3.89 (s, 2H), 4.67 (s, 1H), 5.48 (dd, J=4.4, J=10.9 Hz, 1H), 5.96 (d, J=2.8 Hz, 1H), 6.41 (d, J=2.2 Hz, 1H), 7.53 (d, J=2.2 Hz, 1H), 7.56-7.66 (m, 2H), 7.87 (m, 1H), 8.00 (dd, J$_o$=8.0 Hz, J$_m$=1.6 Hz, 1H), 8.21 (d, J=2.8 Hz, 1H), 10.83 (s, 1H).

Separation of enantiomers via supercritical fluid chromatography on a SFC DAICEL AD column, 50% methanol, 70 mL/min.

Example 30A (S)-3-Cyclopentyl-N-[1-(2-hydroxy-2-methyl-propyl)-1H-pyrazol-3-yl]-2-[4-(2-methanesulfonyl-phenoxy)-6-oxo-6H-pyridazin-1-yl]-propionamide

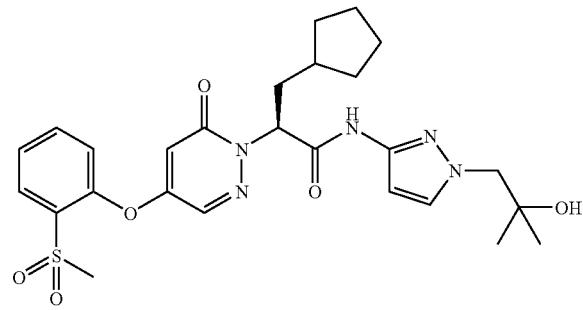

(S)-3-Cyclopentyl-N-[1-(2-hydroxy-2-methyl-propyl)-1H-pyrazol-3-yl]-2-[4-(2-methanesulfonyl-phenoxy)-6-oxo-6H-pyridazin-1-yl]-propionamide; ES$^+$-HRMS m/e calcd for $C_{26}H_{33}N_5O_6S$ [M+H$^+$] 544.2225 found 544.2226. $^1$H-NMR (300 MHz, DMSO-d$_6$) δ ppm 0.88-1.18 (m, 8H) 1.19-1.78 (m, 7H) 1.78-2.03 (m, 1H) 2.18-2.33 (m, 1H) 3.34 (s, 3H) 3.87 (s, 2H) 4.66 (s, 1H) 5.45 (dd, J=10.6, 4.2 Hz, 1H) 5.94 (d, J=2.7 Hz, 1H) 6.39 (d, J=2.1 Hz, 1H) 7.51 (d, J=2.1 Hz, 1H) 7.53-7.64 (m, 2H) 7.79-7.90 (m, 1H) 7.93-8.03 (m, 1H) 8.19 (d, J=2.7 Hz, 1H) 10.82 (s, 1H).

Example 30B (R)-3-Cyclopentyl-N-[1-(2-hydroxy-2-methyl-propyl)-1H-pyrazol-3-yl]-2-[4-(2-methanesulfonyl-phenoxy)-6-oxo-6H-pyridazin-1-yl]-propionamide

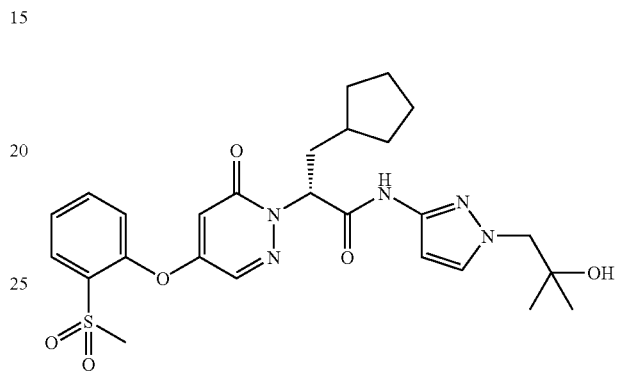

(R)-3-Cyclopentyl-N-[1-(2-hydroxy-2-methyl-propyl)-1H-pyrazol-3-yl]-2-[4-(2-methanesulfonyl-phenoxy)-6-oxo-6H-pyridazin-1-yl]-propionamide; ES$^+$-HRMS m/e calcd for $C_{26}H_{33}N_5O_6S$ [M+H$^+$] 544.2225 found 544.2226. $^1$H-NMR (300 MHz, DMSO-d$_6$) δ ppm 0.94-1.17 (m, 8H) 1.20-1.81 (m, 7H) 1.90 (m, 1H) 2.16-2.34 (m, 1H) 3.34 (s, 3H) 3.87 (s, 2H) 4.66 (s, 1H) 5.46 (dd, J=10.6, 4.2 Hz, 1H) 5.94 (d, J=2.8 Hz, 1H) 6.39 (d, J=2.1 Hz, 1H) 7.51 (d, J=2.1 Hz, 1H) 7.54-7.63 (m, 2H) 7.77-7.91 (m, 1H) 7.98 (dd, J=7.8, 1.5 Hz, 1H) 8.19 (d, J=2.8 Hz, 1H) 10.82 (s, 1H).

Example 31

3-Cyclopentyl-2-[4-(2,3-difluoro-phenoxy)-6-oxo-6H-pyridazin-1-yl]-N-[1-(2-hydroxy-2-methyl-propyl)-1H-pyrazol-3-yl]-propionamide

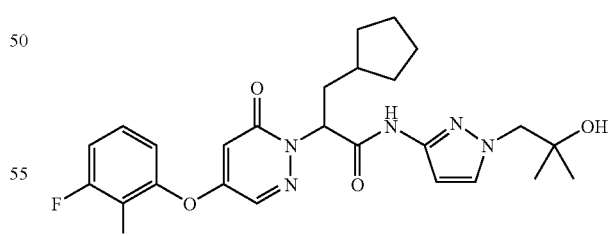

Using the method described in Example 17, 3-cyclopentyl-2-[4-(2,3-difluoro-phenoxy)-6-oxo-6H-pyridazin-1-yl]-propionic acid (Intermediate 44) and 1-(3-amino-pyrazol-1-yl)-2-methyl-propan-2-ol (Intermediate 1) afforded 3-cyclopentyl-2-[4-(2,3-difluoro-phenoxy)-6-oxo-6H-pyridazin-1-yl]-N-[1-(2-hydroxy-2-methyl-propyl)-1H-pyrazol-3-yl]-propionamide as a white solid (0.68 g, 53%); ES$^+$-HRMS m/e calcd for $C_{25}H_{29}N_5O_4F_2$ [M+H$^+$] 502.2261 found 502.2260. $^1$H-NMR (300 MHz, DMSO-d$_6$) δ ppm 1.05 (s, 3H), 1.06 (s, 3H), 1.08 (m, 1H), 1.24-1.77 (m, 8H), 1.92 (m, 1H), 2.28 (m, 1H), 3.89 (s, 2H), 4.68 (s, 1H), 5.47 (dd, J=4.1, J=10.7 Hz, 1H), 6.06 (d, J=2.6 Hz, 1H), 6.39 (d, J=2.2 Hz, 1H), 7.30-7.38 (m, 2H), 7.40-7.51 (m, 1H), 7.52 (d, J=2.2 Hz, 1H), 8.22 (d, J=2.6 Hz, 1H), 10.84 (s, 1H).

Separation of enantiomers via supercritical fluid chromatography on a SFC DAICEL AD column, 35% of a 1:1 solution of ethanol/acetonitrile, 70 mL/min.

Example 31A (S)-3-Cyclopentyl-2-[4-(2,3-difluoro-phenoxy)-6-oxo-6H-pyridazin-1-yl]-N-[1-(2-hydroxy-2-methyl-propyl)-1H-pyrazol-3-yl]-propionamide

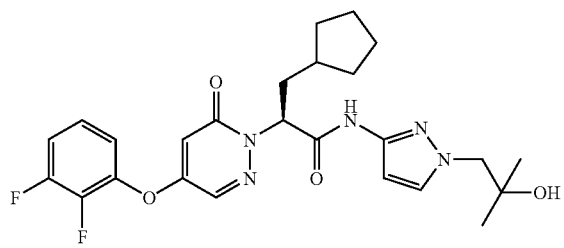

(S)-3-Cyclopentyl-2-[4-(2,3-difluoro-phenoxy)-6-oxo-6H-pyridazin-1-yl]-N-[1-(2-hydroxy-2-methyl-propyl)-1H-pyrazol-3-yl]-propionamide; ES$^+$-HRMS m/e calcd for C$_{25}$H$_{29}$N$_5$O$_4$F$_2$ [M+H$^+$] 502.2261 found 502.2257. $^1$H-NMR (400 MHz, DMSO-d$_6$) δ ppm 1.05 (s, 3H), 1.06 (s, 3H), 1.10 (m, 1H), 1.26-1.77 (m, 8H), 1.93 (m, 1H), 2.29 (m, 1H), 3.89 (s, 2H), 4.67 (s, 1H), 5.48 (dd, J=4.3, J=10.9 Hz, 1H), 6.07 (d, J=2.7 Hz, 1H), 6.40 (d, J=2.2 Hz, 1H), 7.30-7.38 (m, 2H), 7.42-7.51 (m, 1H), 7.53 (d, J=2.2 Hz, 1H), 8.22 (d, J=2.7 Hz, 1H), 10.82 (s, 1H).

Example 31B (R)-3-Cyclopentyl-2-[4-(2,3-difluoro-phenoxy)-6-oxo-6H-pyridazin-1-yl]-N-[1-(2-hydroxy-2-methyl-propyl)-1H-pyrazol-3-yl]-propionamide

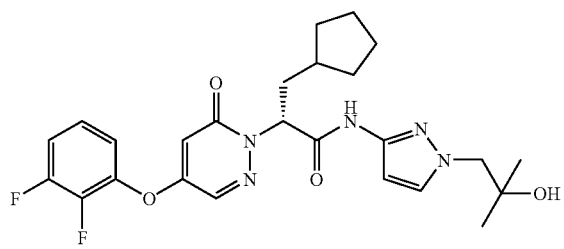

(R)-3-Cyclopentyl-2-[4-(2,3-difluoro-phenoxy)-6-oxo-6H-pyridazin-1-yl]-N-[1-(2-hydroxy-2-methyl-propyl)-1H-pyrazol-3-yl]-propionamide; ES$^+$-HRMS m/e calcd for C$_{25}$H$_{29}$N$_5$O$_4$F$_2$ [M+H$^+$] 502.2261 found 502.2259. $^1$H-NMR (400 MHz, DMSO-d$_6$) δ ppm 1.05 (s, 3H), 1.06 (s, 3H), 1.10 (m, 1H), 1.26-1.77 (m, 8H), 1.93 (m, 1H), 2.29 (m, 1H), 3.89 (s, 2H), 4.67 (s, 1H), 5.48 (dd, J=4.3, J=11.0 Hz, 1H), 6.07 (d, J=2.7 Hz, 1H), 6.40 (d, J=2.2 Hz, 1H), 7.30-7.38 (m, 2H), 7.42-7.51 (m, 1H), 7.53 (d, J=2.2 Hz, 1H), 8.22 (d, J=2.7 Hz, 1H), 10.82 (s, 1H).

Example 32

3-Cyclopentyl-2-[4-(2,4-difluoro-phenoxy)-6-oxo-6H-pyridazin-1-yl]-N-[1-(2-hydroxy-2-methyl-propyl)-1H-pyrazol-3-yl]-propionamide

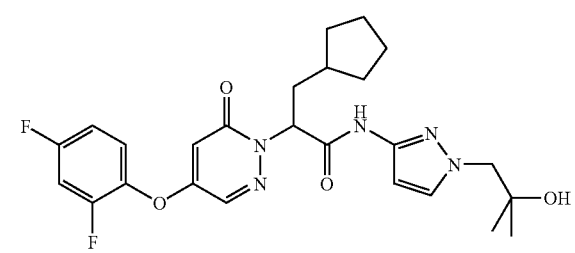

Using the method described in Example 17, 3-cyclopentyl-2-[4-(2,4-difluoro-phenoxy)-6-oxo-6H-pyridazin-1-yl]-propionic acid (Intermediate 45) and 1-(3-amino-pyrazol-1-yl)-2-methyl-propan-2-ol (Intermediate 1) afforded 3-cyclopentyl-2-[4-(2,4-difluoro-phenoxy)-6-oxo-6H-pyridazin-1-yl]-N-[1-(2-hydroxy-2-methyl-propyl)-1H-pyrazol-3-yl]-propionamide as a white solid (0.77 g, 64%); ES$^+$-HRMS m/e calcd for C$_{25}$H$_{29}$N$_5$O$_4$F$_2$ [M+H$^+$] 502.2261 found 502.2259. $^1$H-NMR (300 MHz, DMSO-d$_6$) δ ppm 1.05 (s, 3H), 1.06 (s, 3H), 1.08 (m, 1H), 1.24-1.77 (m, 8H), 1.92 (m, 1H), 2.28 (m, 1H), 3.89 (s, 2H), 4.68 (s, 1H), 5.47 (dd, J=4.1, J=10.9 Hz, 1H), 5.90 (d, J=2.6 Hz, 1H), 6.39 (d, J=2.2 Hz, 1H), 7.24 (m, 1H), 7.52 (d, J=2.2 Hz, 1H), 7.53-7.66 (m, 2H), 8.20 (d, J=2.6 Hz, 1H), 10.84 (s, 1H).

Separation of enantiomers via supercritical fluid chromatography on a SFC DAICEL AD column, 40% of 1:1 Ethanol/Acetonitrile solution, 70 mL/min.

Example 32A (S)-3-Cyclopentyl-2-[4-(2,4-difluoro-phenoxy)-6-oxo-6H-pyridazin-1-yl]-N-[1-(2-hydroxy-2-methyl-propyl)-1H-pyrazol-3-yl]-propionamide (S)-3-Cyclopentyl-2-[4-(2,4-difluoro-phenoxy)-6-oxo-6H-pyridazin-1-yl]-N-[1-(2-hydroxy-2-methyl-propyl)-1H-pyrazol-3-yl]-propionamide; ES$^+$-HRMS m/e calcd for C$_{25}$H$_{29}$N$_5$O$_4$F$_2$ [M+H$^+$] 502.2261 found 502.2258. $^1$H-NMR (300 MHz, DMSO-d$_6$) δ ppm 1.05 (s, 3H), 1.06 (s, 3H), 1.08 (m, 1H), 1.24-1.77 (m, 8H), 1.92 (m, 1H), 2.28 (m, 1H), 3.89 (s, 2H), 4.66 (s, 1H), 5.47 (dd, J=4.1, J=10.9 Hz, 1H), 5.90 (d, J=2.8 Hz, 1H), 6.39 (d, J=2.2 Hz, 1H), 7.24 (m, 1H), 7.52 (d, J=2.2 Hz, 1H), 7.53-7.66 (m, 2H), 8.19 (d, J=2.8 Hz, 1H), 10.81 (s, 1H).

Example 32B (R)-3-Cyclopentyl-2-[4-(2,4-difluoro-phenoxy)-6-oxo-6H-pyridazin-1-yl]-N-[1-(2-hydroxy-2-methyl-propyl)-1H-pyrazol-3-yl]-propionamide

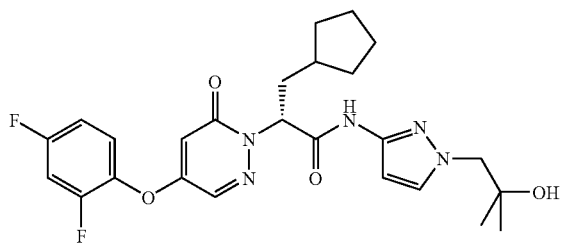

(R)-3-Cyclopentyl-2-[4-(2,4-difluoro-phenoxy)-6-oxo-6H-pyridazin-1-yl]-N-[1-(2-hydroxy-2-methyl-propyl)-1H-pyrazol-3-yl]-propionamide; ES$^+$-HRMS m/e calcd for $C_{25}H_{29}N_5O_4F_2$ [M+H$^+$] 502.2261 found 502.2259. $^1$H-NMR (300 MHz, DMSO-d$_6$) δ ppm 1.05 (s, 3H), 1.06 (s, 3H), 1.08 (m, 1H), 1.24-1.77 (m, 8H), 1.92 (m, 1H), 2.28 (m, 1H), 3.89 (s, 2H), 4.66 (s, 1H), 5.47 (dd, J=4.1, J=10.9 Hz, 1H), 5.90 (d, J=2.8 Hz, 1H), 6.39 (d, J=2.2 Hz, 1H), 7.24 (m, 1H), 7.52 (d, J=2.2 Hz, 1H), 7.53-7.66 (m, 2H), 8.19 (d, J=2.8 Hz, 1H), 10.81 (s, 1H).

Example 33

3-Cyclopentyl-2-[4-(2,5-difluoro-phenoxy)-6-oxo-6H-pyridazin-1-yl]-N-[1-(2-hydroxy-2-methyl-propyl)-1H-pyrazol-3-yl]-propionamide

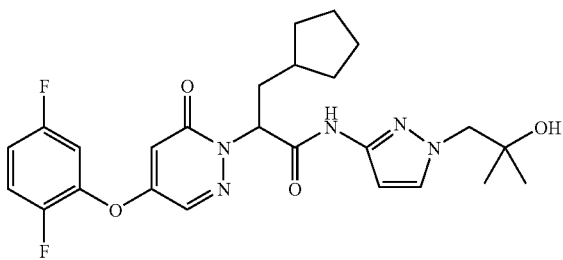

Using the method described in Example 17, 3-cyclopentyl-2-[4-(2,5-difluoro-phenoxy)-6-oxo-6H-pyridazin-1-yl]-propionic acid (Intermediate 46) and 1-(3-amino-pyrazol-1-yl)-2-methyl-propan-2-ol (Intermediate 1) afforded 3-cyclopentyl-2-[4-(2,5-difluoro-phenoxy)-6-oxo-6H-pyridazin-1-yl]-N-[1-(2-hydroxy-2-methyl-propyl)-1H-pyrazol-3-yl]-propionamide as a white solid (0.76 g, 63%); ES$^+$-HRMS m/e calcd for $C_{25}H_{29}N_5O_4F_2$ [M+H$^+$] 502.2261 found 502.2259. $^1$H-NMR (300 MHz, DMSO-d$_6$) δ ppm 1.05 (s, 3H), 1.06 (s, 3H), 1.08 (m, 1H), 1.24-1.77 (m, 8H), 1.92 (m, 1H), 2.28 (m, 1H), 3.89 (s, 2H), 4.68 (s, 1H), 5.47 (dd, J=4.1, J=11.0 Hz, 1H), 6.00 (d, J=2.7 Hz, 1H), 6.40 (d, J=2.1 Hz,1H), 7.24-7.35 (m, 1H), 7.53 (d, J=2.1 Hz, 1H), 7.53-7.62 (m, 2H), 8.21 (d, J=2.7 Hz, 1H), 10.84 (s, 1H).

Separation of enantiomers via supercritical fluid chromatography on a SFC DAICEL AD column, 35% of a 1:1 solution of methanol/acetonitrile, 70 mL/min.

Example 33A (S)-3-Cyclopentyl-2-[4-(2,5-difluoro-phenoxy)-6-oxo-6H-pyridazin-1-yl]-N-[1-(2-hydroxy-2-methyl-propyl)-1H-pyrazol-3-yl]-propionamide

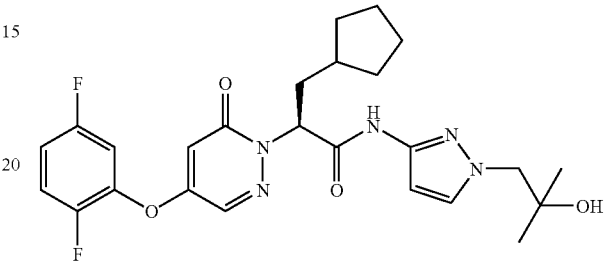

(S)-3-Cyclopentyl-2-[4-(2,5-difluoro-phenoxy)-6-oxo-6H-pyridazin-1-yl]-N-[1-(2-hydroxy-2-methyl-propyl)-1H-pyrazol-3-yl]-propionamide; ES$^+$-HRMS m/e calcd for $C_{25}H_{29}N_5O_4F_2$ [M+H$^+$] 502.2261 found 502.2260. $^1$H-NMR (400 MHz, DMSO-d$_6$) δ ppm 1.05 (s, 3H), 1.06 (s, 3H), 1.10 (m, 1H), 1.25-1.75 (m, 8H), 1.92 (m, 1H), 2.28 (m, 1H), 3.89 (s, 2H), 4.67 (s, 1H), 5.48 (dd, J=4.3, J=10.9 Hz, 1H), 6.01 (d, J=2.9 Hz, 1H), 6.40 (d, J=2.1 Hz, 1H), 7.24-7.36 (m, 1H), 7.53 (d, J=2.1 Hz, 1H), 7.54-7.63 (m, 2H), 8.21 (d, J=2.9 Hz, 1H), 10.82 (s, 1H).

Example 33B (R)-3-Cyclopentyl-2-[4-(2,5-difluoro-phenoxy)-6-oxo-6H-pyridazin-1-yl]-N-[1-(2-hydroxy-2-methyl-propyl)-1H-pyrazol-3-yl]-propionamide

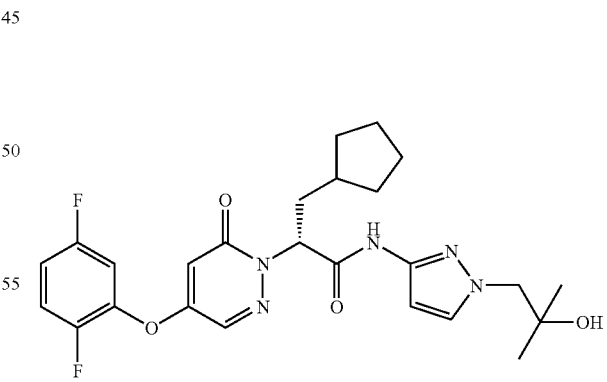

(R)-3-Cyclopentyl-2-[4-(2,5-difluoro-phenoxy)-6-oxo-6H-pyridazin-1-yl]-N-[1-(2-hydroxy-2-methyl-propyl)-1H-pyrazol-3-yl]-propionamide; ES$^+$-HRMS m/e calcd for $C_{25}H_{29}N_5O_4F_2$ [M+H$^+$] 502.2261 found 502.2259. $^1$H-NMR (400 MHz, DMSO-d$_6$) δ ppm 1.05 (s, 3H), 1.06 (s, 3H), 1.10 (m, 1H), 1.25-1.75 (m, 8H), 1.92 (m, 1H), 2.28 (m, 1H), 3.89 (s, 2H), 4.67 (s, 1H), 5.48 (dd, J=4.3, J=10.9 Hz, 1H), 6.01 (d, J=2.9 Hz, 1H), 6.40 (d, J=2.1 Hz, 1H), 7.24-7.36 (m, 1H), 7.53 (d, J=2.1 Hz, 1H), 7.54-7.63 (m, 2H), 8.21 (d, J=2.9 Hz, 1H), 10.82 (s, 1H).

Example 34

3-Cyclopentyl-N-[1-(2-hydroxy-2-methyl-propyl)-1H-pyrazol-3-yl]-2-[4-(2-morpholin-4-yl-phenoxy)-6-oxo-6H-pyridazin-1-yl]-propionamide

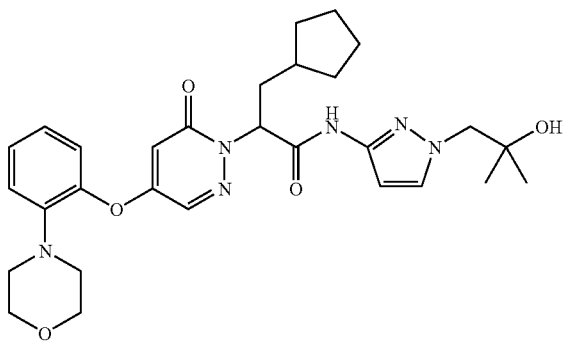

Using the method described in Example 17, 3-cyclopentyl-2-[4-(2-morpholin-4-yl-phenoxy)-6-oxo-6H-pyridazin-1-yl]-propionic acid (Intermediate 53) and 1-(3-amino-pyrazol-1-yl)-2-methyl-propan-2-ol (Intermediate 1) afforded 3-cyclopentyl-N-[1-(2-hydroxy-2-methyl-propyl)-1H-pyrazol-3-yl]-2-[4-(2-morpholin-4-yl-phenoxy)-6-oxo-6H-pyridazin-1-yl]-propionamide as a white solid (0.61 g, 51%); ES$^+$-HRMS m/e calcd for $C_{29}H_{38}N_6O_5$ [M+H$^+$] 551.2977 found 551.2976. $^1$H-NMR (300 MHz, DMSO-$d_6$) δ ppm 1.05 (s, 3H), 1.06 (s, 3H), 1.08 (m, 1H), 1.24-1.76 (m, 8H), 1.92 (m, 1H), 2.28 (m, 1H), 2.83-3.05 (m, 4H), 3.46-3.59 (m, 4H), 3.89 (s, 2H), 4.67 (s, 1H), 5.51 (dd, J=4.1, J=11.0 Hz, 1H), 5.74 (d, J=3.0 Hz, 1H), 6.39 (d, J=2.1 Hz, 1H), 7.09-7.18 (m, 2H), 7.25 (dd, J$_o$=7.8 Hz, J$_m$=1.5 Hz, 1H), 7.27-7.37 (m, 1H), 7.52 (d, J=2.1 Hz, 1H), 8.02 (d, J=3.0 Hz, 1H), 10.77 (s, 1H).

Example 35

3-Cyclopentyl-N-[1-(2-hydroxy-2-methyl-propyl)-1H-pyrazol-3-yl]-2-[6-oxo-4-(3-phenoxy-phenoxy)-6H-pyridazin-1-yl]-propionamide

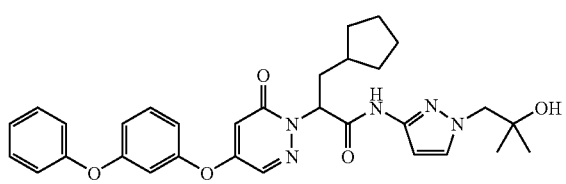

Using the method described in Example 17, 3-cyclopentyl-2-[6-oxo-4-(3-phenoxy-phenoxy)-6H-pyridazin-1-yl]-propionic acid (Intermediate 49) and 1-(3-amino-pyrazol-1-yl)-2-methyl-propan-2-ol (Intermediate 1) afforded 3-cyclopentyl-N-[1-(2-hydroxy-2-methyl-propyl)-1H-pyrazol-3-yl]-2-[6-oxo-4-(3-phenoxy-phenoxy)-6H-pyridazin-1-yl]-propionamide as a white solid (0.63 g, 48%); ES$^+$-HRMS m/e calcd for $C_{31}H_{35}N_5O_5$ [M+H$^+$] 558.2711 found 558.2706. $^1$H-NMR (300 MHz, DMSO-$d_6$) δ ppm 1.05 (s, 3H), 1.06 (s, 3H), 1.07 (m, 1H), 1.24-0-1.77 (m, 8H), 1.91 (m, 1H), 2.27 (m, 1H), 3.89 (s, 2H), 4.68 (s, 1H), 5.46 (dd, J=4.4, J=11.0 Hz, 1H), 5.89 (d, J=2.7 Hz, 1H), 6.39 (d, J=2.4 Hz, 1 Hr), 6.94 (m, 1H), 6.96 (d, J$_m$=1.5 Hz, 1H), 7.05 (m, 1H), 7.11 (dd, J$_o$=7.8 Hz, 2H), 7.19 (t, J$_o$=7.4 Hz, 1H), 7.38-7.55 (m, 4H), 8.10 (d, J=2.7 Hz, 1H), 10.79 (s, 1H).

Example 36

3-Cyclopentyl-2-[4-(2,6-difluoro-phenoxy)-6-oxo-6H-pyridazin-1-yl]-N-[1-(2-hydroxy-2-methyl-propyl)-1H-pyrazol-3-yl]-propionamide

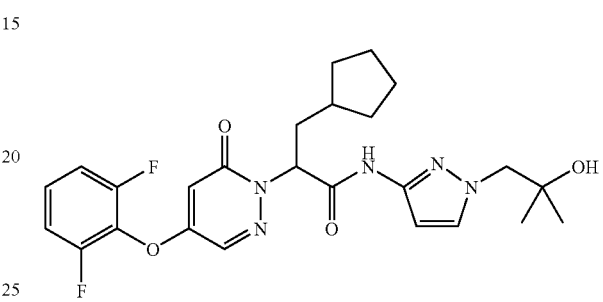

Using the method described in Example 17, 3-cyclopentyl-2-[4-(2,6-difluoro-phenoxy)-6-oxo-6H-pyridazin-1-yl]-propionic acid (Intermediate 47) and 1-(3-amino-pyrazol-1-yl)-2-methyl-propan-2-ol (Intermediate 1) afforded 3-cyclopentyl-2-[4-(2,6-difluoro-phenoxy)-6-oxo-6H-pyridazin-1-yl]-N-[1-(2-hydroxy-2-methyl-propyl)-1H-pyrazol-3-yl]-propionamide as a white solid (0.75 g, 62%); ES$^+$-HRMS m/e calcd for $C_{25}H_{29}N_5O_4F_2$ [M+H$^+$] 502.2261 found 502.2258. $^1$H-NMR (300 MHz, DMSO-$d_6$) δ ppm 1.05 (s, 3H), 1.06 (s, 3H), 1.09 (m, 1H), 1.24-1.75 (m, 8H), 1.93 (m, 1H), 2.28 (m, 1H), 3.89 (s, 2H), 4.68 (s, 1H), 5.47 (dd, J=4.2, J=10.9 Hz, 1H), 6.03 (d, J=3.0 Hz, 1H), 6.40 (d, J=2.1 Hz, 1H), 7.34-7.51 (m, 3H), 7.53 (d, J=2.1 Hz, 1H), 8.28 (d, J=3.0 Hz, 1H), 10.86 (s, 1H).

Separation of enantiomers via supercritical fluid chromatography on a SFC DAICEL AD column, 35% methanol, 70 mL/min.

Example 36A (S)-3-Cyclopentyl-2-[4-(2,6-difluoro-phenoxy)-6-oxo-6H-pyridazin-1-yl]-N-[1-(2-hydroxy-2-methyl-propyl)-1H-pyrazol-3-yl]-propionamide

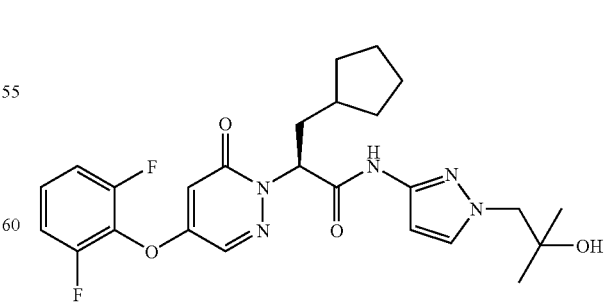

(S)-3-Cyclopentyl-2-[4-(2,6-difluoro-phenoxy)-6-oxo-6H-pyridazin-1-yl]-N-[1-(2-hydroxy-2-methyl-propyl)-1H-pyrazol-3-yl]-propionamide; ES$^+$-HRMS m/e calcd for $C_{25}H_{29}N_5O_4F_2$ [M+H$^+$] 502.2261 found 502.2258. $^1$H-NMR (400 MHz, DMSO-d$_6$) δ ppm 1.05 (s, 3H), 1.06 (s, 3H), 1.10 (m, 1H), 1.26-1.75 (m, 8H), 1.94 (m, 1H), 2.28 (m, 1H), 3.89 (s, 2H), 4.67 (s, 1H), 5.47 (dd, J=4.2, J=10.5 Hz, 1H), 6.03 (d, J=2.9 Hz, 1H), 6.40 (d, J=2.2 Hz, 1H), 7.36-7.43 (m, 2H), 7.43-7.51 (m, 1H), 7.53 (d, J=2.2 Hz, 1H), 8.28 (d, J=2.9 Hz, 1H), 10.85 (s, 1H).

Example 36B (R)-3-Cyclopentyl-2-[4-(2,6-difluoro-phenoxy)-6-oxo-6H-pyridazin-1-yl]-N-[1-(2-hydroxy-2-methyl-propyl)-1H-pyrazol-3-yl]-propionamide

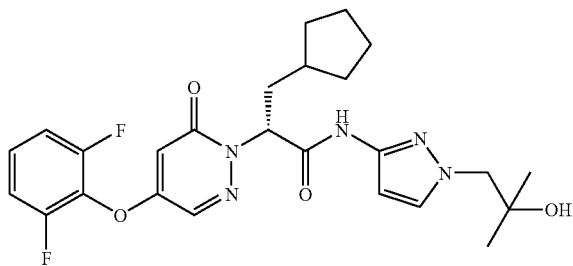

(R)-3-Cyclopentyl-2-[4-(2,6-difluoro-phenoxy)-6-oxo-6H-pyridazin-1-yl]-N-[1-(2-hydroxy-2-methyl-propyl)-1H-pyrazol-3-yl]-propionamide; ES$^+$-HRMS m/e calcd for $C_{25}H_{29}N_5O_4F_2$ [M+H$^+$] 502.2261 found 502.2258. $^1$H-NMR (400 MHz, DMSO-d$_6$) δ ppm 1.05 (s, 3H), 1.06 (s, 3H), 1.10 (m, 1H), 1.26-1.75 (m, 8H), 1.94 (m, 1H), 2.28 (m, 1H), 3.89 (s, 2H), 4.67 (s, 1H), 5.47 (dd, J=4.2, J=10.5 Hz, 1H), 6.03 (d, J=2.9 Hz, 1H), 6.40 (d, J=2.2 Hz, 1H), 7.36-7.43 (m, 2H), 7.43-7.51 (m, 1H), 7.53 (d, J=2.2 Hz, 1H), 8.28 (d, J=2.9 Hz, 1H), 10.85 (s, 1H).

Example 37

3-Cyclopentyl-N-[1-(2-hydroxy-2-methyl-propyl)-1H-pyrazol-3-yl]-2-[4-(isoquinolin-5-yloxy)-6-oxo-6H-pyridazin-1-yl]-propionamide

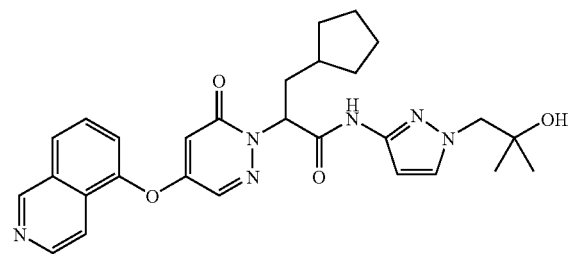

Using the method described in Example 17, 3-cyclopentyl-2-[4-(isoquinolin-5-yloxy)-6-oxo-6H-pyridazin-1-yl]-propionic acid (Intermediate 56) and 1-(3-amino-pyrazol-1-yl)-2-methyl-propan-2-ol (Intermediate 1) afforded 3-cyclopentyl-N-[1-(2-hydroxy-2-methyl-propyl)-1H-pyrazol-3-yl]-2-[4-(isoquinolin-5-yloxy)-6-oxo-6H-pyridazin-1-yl]-propionamide an off-white solid (0.56 g, 44%); ES$^+$-HRMS m/e calcd for $C_{28}H_{32}N_6O_4$ [M+H$^+$] 517.2558 found 517.2557. $^1$H-NMR (300 MHz, DMSO-d$_6$) δ ppm 1.04 (s, 3H), 1.06 (s, 3H), 1.10 (m, 1H), 1.22-1.80 (m, 8H), 1.92 (m, 1H), 2.29 (m, 1H), 3.89 (s, 2H), 4.68 (s, 1H), 5.46 (dd, J=4.2, J=10.6 Hz, 1H), 5.76 (d, J=2.8 Hz, 1H), 6.40 (d, J=2.2 Hz, 1H), 7.52 (d, J=2.2 Hz, 1H), 7.73-7.85 (m, 3H), 8.16 (m, 1H), 8.30 (d, J=2.8 Hz, 1H), 8.58 (d, J=5.7 Hz, 1H), 9.47 (s, 1H), 10.86 (s, 1H).

Separation of enantiomers via supercritical fluid chromatography on a SFC DAICEL AD column, 60% of a 1:1 solution of methanol/acetonitrile, 70 mL/min.

Example 37A (S)-3-Cyclopentyl-N-[1-(2-hydroxy-2-methyl-propyl)-1H-pyrazol-3-yl]-2-[4-(isoquinolin-5-yloxy)-6-oxo-6H-pyridazin-1-yl]-propionamide

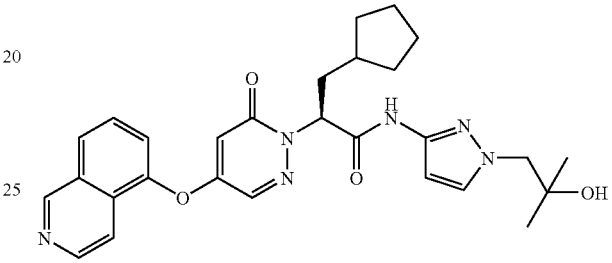

(S)-3-Cyclopentyl-N-[1-(2-hydroxy-2-methyl-propyl)-1H-pyrazol-3-yl]-2-[4-(isoquinolin-5-yloxy)-6-oxo-6H-pyridazin-1-yl]-propionamide; ES$^+$-HRMS m/e calcd for $C_{28}H_{32}N_6O_4$ [M+H$^+$] 517.2558 found 517.2555. $^1$H-NMR (400 MHz, DMSO-d$_6$) δ ppm 1.05 (s, 3H), 1.06 (s, 3H), 1.10 (m, 1H), 1.27-1.80 (m, 8H), 1.93 (m, 1H), 2.28 (m, 1H), 3.89 (s, 2H), 4.67 (s, 1H), 5.46 (dd, J=4.2, J=10.8 Hz, 1H), 5.76 (d, J=2.9 Hz, 1H), 6.40 (d, J=2.2 Hz, 1H), 7.53 (d, J=2.2 Hz, 1H), 7.76-7.83 (m, 3H), 8.16 (dd, J=6.1, 2.5 Hz, 1H), 8.30 (d, J=2.9 Hz, 1H), 8.59 (d, J=6.0 Hz, 1H), 9.47 (s, 1H), 10.80 (s, 1H).

Example 37B (R)-3-Cyclopentyl-N-[1-(2-hydroxy-2-methyl-propyl)-1H-pyrazol-3-yl]-2-[4-(isoquinolin-5-yloxy)-6-oxo-6H-pyridazin-1-yl]-propionamide

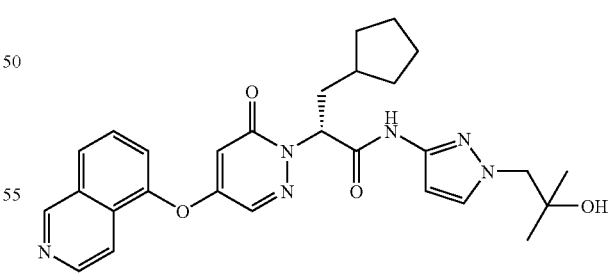

(R)-3-Cyclopentyl-N-[1-(2-hydroxy-2-methyl-propyl)-1H-pyrazol-3-yl]-2-[4-(isoquinolin-5-yloxy)-6-oxo-6H-pyridazin-1-yl]-propionamide; ES$^+$-HRMS m/e calcd for $C_{28}H_{32}N_6O_4$ [M+H$^+$] 517.2558 found 517.2554. $^1$H-NMR (400 MHz, DMSO-d$_6$) δ ppm 1.05 (s, 3H), 1.06 (s, 3H), 1.10 (m, 1H), 1.27-1.80 (m, 8H), 1.93 (m, 1H), 2.28 (m, 1H), 3.89 (s, 2H), 4.67 (s, 1H), 5.46 (dd, J=4.2, J=10.8 Hz, 1H), 5.76 (d, J=2.9 Hz, 1H), 6.40 (d, J=2.2 Hz, 1H), 7.53 (d, J=2.2 Hz, 1H), 7.76-7.83 (m, 3H), 8.16 (dd, J=6.1, 2.5 Hz, 1H), 8.30 (d, J=2.9 Hz, 1H), 8.59 (d, J=6.0 Hz, 1H), 9.47 (s, 1H), 10.80 (s, 1H).

Example 38

3-Cyclopentyl-N-[1-(2-hydroxy-2-methyl-propyl)-1H-pyrazol-3-yl]-2-[6-oxo-4-(quinolin-5-yloxy)-6H-pyridazin-1-yl]-propionamide

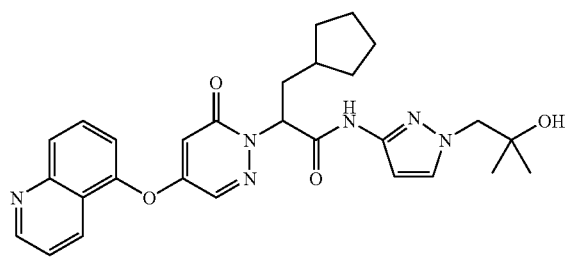

Using the method described in Example 17, 3-cyclopentyl-2-[6-oxo-4-(quinolin-5-yloxy)-6H-pyridazin-1-yl]-propionic acid (Intermediate 57) and 1-(3-amino-pyrazol-1-yl)-2-methyl-propan-2-ol (Intermediate 1) afforded 3-cyclopentyl-N-[1-(2-hydroxy-2-methyl-propyl)-1H-pyrazol-3-yl]-2-[6-oxo-4-(quinolin-5-yloxy)-6H-pyridazin-1-yl]-propionamide as a white solid (0.69 g, 59%); ES$^+$-HRMS m/e calcd for $C_{28}H_{32}N_6O_4$ [M+H$^+$] 517.2558 found 517.2557. $^1$H-NMR (300 MHz, DMSO-d$_6$) δ ppm 1.04 (s, 3H), 1.05 (s, 3H), 1.10 (m, 1H), 1.21-1.77 (m, 8H), 1.92 (m, 1H), 2.28 (m, 1H), 3.89 (s, 2H), 4.67 (s, 1H), 5.46 (dd, J=4.4, J=10.7 Hz, 1H), 5.78 (d, J=2.7 Hz, 1H), 6.40 (d, J=2.1 Hz, 1H), 7.52 (d, J=2.1 Hz, 1H), 7.57 (d, J$_o$=7.8 Hz, 1H), 7.62 (dd, J$_o$=8.5, 4.0 Hz, 1H), 7.86 (t, J$_o$=8.2 Hz, 1H), 8.04 (d, J$_o$=8.5 Hz, 1H), 8.29 (d, J=2.7 Hz, 1H), 8.39 (d, J$_o$=8.5 Hz, 1H), 9.01 (dd, J$_o$=4.0, J$_m$=1.5 Hz, 1H), 10.81 (s, 1H).

Example 39

3-Cyclopentyl-N-[1-(2-hydroxy-2-methyl-propyl)-1H-pyrazol-3-yl]-2-[6-oxo-4-(quinolin-8-yloxy)-6H-pyridazin-1-yl]-propionamide

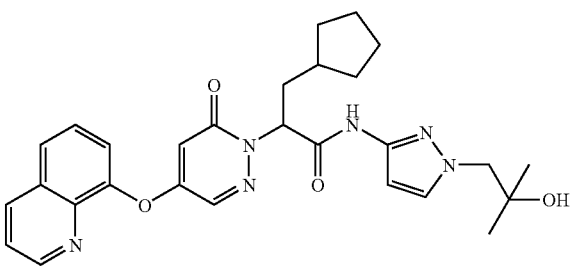

Using the method described in Example 17, 3-cyclopentyl-2-[6-oxo-4-(quinolin-8-yloxy)-6H-pyridazin-1-yl]-propionic acid (Intermediate 55) and 1-(3-amino-pyrazol-1-yl)-2-methyl-propan-2-ol (Intermediate 1) afforded 3-cyclopentyl-N-[1-(2-hydroxy-2-methyl-propyl)-1H-pyrazol-3-yl]-2-[6-oxo-4-(quinolin-8-yloxy)-6H-pyridazin-1-yl]-propionamide as an off-white solid (0.34 g, 25%); ES$^+$-HRMS m/e calcd for $C_{28}H_{32}N_6O_4$ [M+H$^+$] 517.2558 found 517.2558. $^1$H-NMR (400 MHz, DMSO-d$_6$) δ ppm 1.04 (s, 3H), 1.06 (s, 3H), 1.10 (m, 1H), 1.27-1.76 (m, 8H), 1.91 (m, 1H), 2.23 (m, 1H), 3.89 (s, 2H), 4.67 (s, 1H), 5.44 (dd, J=4.5, J=10.9 Hz, 1H), 5.50 (d, J=2.9 Hz, 1H), 6.40 (d, J=2.2 Hz, 1H), 7.52 (d, J=2.2 Hz, 1H), 7.65 (dd, J$_o$=8.3, 4.2 Hz, 1H), 7.72 (t, J$_o$=7.9 Hz, 1H), 7.76 (dd, J$_o$=7.5 Hz, J$_m$=1.5 Hz, 1H), 8.03 (dd, J$_o$=8.1 Hz, J$_m$=1.5 Hz, 1H), 8.24 (d, J=2.9 Hz, 1H), 8.52 (dd, J$_o$=8.3 Hz, J$_m$=1.7 Hz, 1H), 8.92 (dd, J$_o$=4.2 Hz, J$_m$=1.7 Hz, 1H), 10.81 (s, 1H).

Example 40

2-[4-(2-Acetyl-phenoxy)-6-oxo-6H-pyridazin-1-yl]-3-cyclopentyl-N-[1-(2-hydroxy-2-methyl-propyl)-1H-pyrazol-3-yl]-propionamide

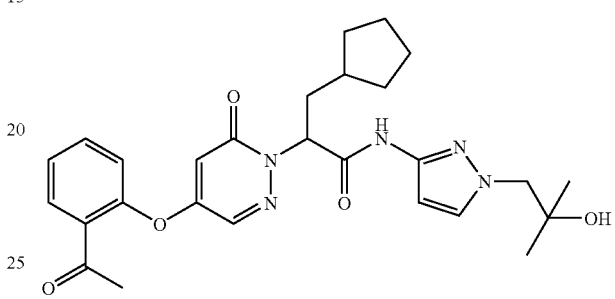

Using the method described in Example 17, 32-[4-(2-acetyl-phenoxy)-6-oxo-6H-pyridazin-1-yl]-3-cyclopentyl-propionic acid (Intermediate 40) and 1-(3-amino-pyrazol-1-yl)-2-methyl-propan-2-ol (Intermediate 1) afforded 2-[4-(2-acetyl-phenoxy)-6-oxo-6H-pyridazin-1-yl]-3-cyclopentyl-N-[1-(2-hydroxy-2-methyl-propyl)-1H-pyrazol-3-yl]-propionamide as a light yellow solid (0.68 g, 50%); ES$^+$-HRMS m/e calcd for $C_{27}H_{33}N_5O_5$ [M+H$^+$] 508.2555 found 508.2553. $^1$H-NMR (400 MHz, DMSO-d$_6$) δ ppm 1.05 (s, 3H), 1.06 (s, 3H), 1.10 (m, 1H), 1.28-1.76 (m, 8H), 1.92 (m, 1H), 2.28 (m, 1H), 2.53 (s, 3H), 3.89 (s, 2H), 4.67 (s, 1H), 5.46 (dd, J=4.5, J=10.7 Hz, 1H), 5.74 (d, J=2.8 Hz, 1H), 6.40 (d, J=2.2 Hz, 1H), 7.39 (d, J$_o$=7.7 Hz, 1H), 7.49 (td, J$_o$=7.7, J$_m$=1.0 Hz, 1H), 7.53 (d, J=2.2 Hz, 1H), 7.72 (td, J$_o$=7.7 Hz, J$_m$=1.7 Hz, 1H), 7.94 (dd, J$_o$=7.7 Hz, J$_m$=1.7 Hz, 1H), 8.14 (d, J=2.8 Hz, 1H), 10.81 (s, 1H).

Example 41

3-Cyclopentyl-N-[1-(2-hydroxy-2-methyl-propyl)-1H-pyrazol-3-yl]-2-{6-oxo-4-[2-(pyrrolidine-1-carbonyl)-phenoxy]-6H-pyridazin-1-yl}-propionamide

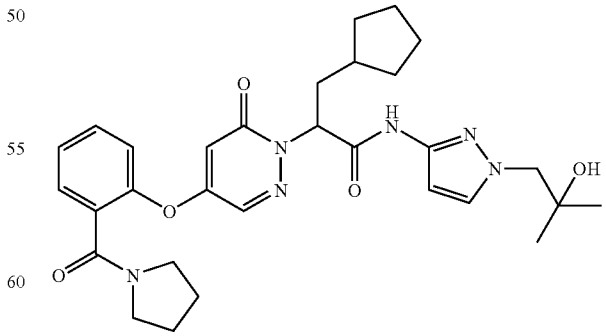

Using the method described in Example 17, 3-cyclopentyl-2-{6-oxo-4-[2-(pyrrolidine-1-carbonyl)-phenoxy]-6H-pyridazin-1-yl}-propionic acid (Intermediate 27) and 1-(3-amino-pyrazol-1-yl)-2-methyl-propan-2-ol (Intermediate 1)

afforded 3-cyclopentyl-N-[1-(2-hydroxy-2-methyl-propyl)-1H-pyrazol-3-yl]-2-{6-oxo-4-[2-(pyrrolidine-1-carbonyl)-phenoxy]-6H-pyridazin-1-yl}-propionamide as a light yellow solid (24.6 mg, 19%); ES$^+$-HRMS m/e calcd for $C_{30}H_{38}N_6O_5$ [M+H$^+$] 563.2977 found 563.2974. $^1$H-NMR (400 MHz, DMSO-d$_6$) δ ppm 1.03-1.08 (m, 7H) 1.25-2.03 (m, 13H) 2.19-2.40 (m, 1H) 3.21 (t, J=6.2 Hz, 2H) 3.28-3.36 (m, 2H) 3.89 (s, 2H) 4.67 (s, 1H) 5.47 (dd, J=11.1, 4.3 Hz, 1H) 5.79 (d, J=2.8 Hz, 1H) 6.40 (d, J=2.1 Hz, 1H) 7.38 (d, J=8.1 Hz, 1H) 7.41 (t, J=7.5 Hz, 1H) 7.49-7.54 (m, 2H) 7.54-7.61 (m, 1H) 8.07 (d, J=2.8 Hz, 1H) 10.80 (s, 1H).

Example 42

2-[4-(2,6-Difluoro-phenoxy)-6-oxo-6H-pyridazin-1-yl]-4-methyl-pentanoic acid [1-(2-hydroxy-2-methyl-propyl)-1H-pyrazol-3-yl]-amide

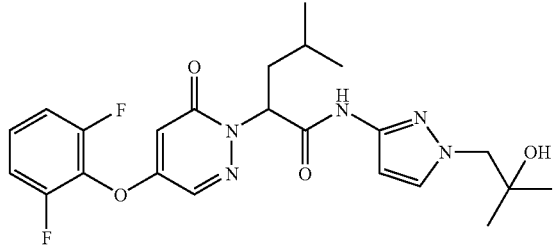

Using the method described in Example 17, 2-[4-(2,6-difluoro-phenoxy)-6-oxo-6H-pyridazin-1-yl]-4-methyl-pentanoic acid (Intermediate 28) and 1-(3-amino-pyrazol-1-yl)-2-methyl-propan-2-ol (Intermediate 1) afforded 2-[4-(2,6-difluoro-phenoxy)-6-oxo-6H-pyridazin-1-yl]-4-methyl-pentanoic acid [1-(2-hydroxy-2-methyl-propyl)-1H-pyrazol-3-yl]-amide as a white solid (0.63 g, 45%); ES$^+$-HRMS m/e calcd for $C_{23}H_{27}N_5O_4F_2$ [M+H$^+$] 476.2104 found 476.2104. $^1$H-NMR (400 MHz, DMSO-d$_6$) δ ppm 0.87 (d, J=6.6 Hz, 3H) 0.89 (d, J=6.6 Hz, 3H) 1.05 (s, 3H) 1.07 (s, 3H) 1.44 (br s, 1H) 1.73-1.86 (m, 1H) 2.11-2.27 (m, 1H) 3.89 (s, 2H) 4.67 (s, 1H) 5.53 (dd, J=11.2, 4.4 Hz, 1H) 6.04 (d, J=3.0 Hz, 1H) 6.40 (d, J=2.3 Hz, 1H) 7.34-7.44 (m, 2H) 7.44-7.52 (m, 1H) 7.53 (d, J=2.3 Hz, 1H) 8.28 (d, J=3.0 Hz, 1H) 10.85 (s, 1H).

Separation of enantiomers via supercritical fluid chromatography on a SFC DAICEL AD column, 25% methanol, 70 mL/min.

Example 42A (S)-2-[4-(2,6-Difluoro-phenoxy)-6-oxo-6H-pyridazin-1-yl]-4-methyl-pentanoic acid [1-(2-hydroxy-2-methyl-propyl)-1H-pyrazol-3-yl]-amide

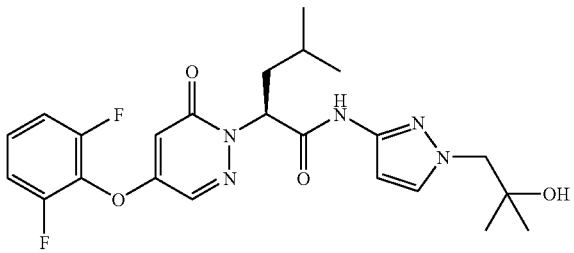

(S)-2-[4-(2,6-Difluoro-phenoxy)-6-oxo-6H-pyridazin-1-yl]-4-methyl-pentanoic acid [1-(2-hydroxy-2-methyl-propyl)-1H-pyrazol-3-yl]-amide; ES$^+$-HRMS m/e calcd for $C_{23}H_{27}N_5O_4F_2$ [M+H$^+$] 476.2104 found 476.2105. $^1$H-NMR (300 MHz, DMSO-d$_6$) δ ppm 0.86 (d, J=7.2 Hz, 3H) 0.88 (d, J=7.2 Hz, 3H) 1.05 (br s, 3H) 1.06 (br s, 3H) 1.43 (br s, 1H) 1.69-1.88 (m, 1H) 2.05-2.29 (m, 1H) 3.89 (s, 2H) 4.68 (s, 1H) 5.52 (dd, J=11.2, 4.2 Hz, 1H) 6.04 (d, J=2.7 Hz, 1H) 6.39 (d, J=2.1 Hz, 1H) 7.30-7.50 (m, 3H) 7.53 (d, J=2.1 Hz, 1H) 8.29 (d, J=2.7 Hz, 1H) 10.87 (s, 1H).

Example 42B (R)-2-[4-(2,6-Difluoro-phenoxy)-6-oxo-6H-pyridazin-1-yl]-4-methyl-pentanoic acid [1-(2-hydroxy-2-methyl-propyl)-1H-pyrazol-3-yl]-amide

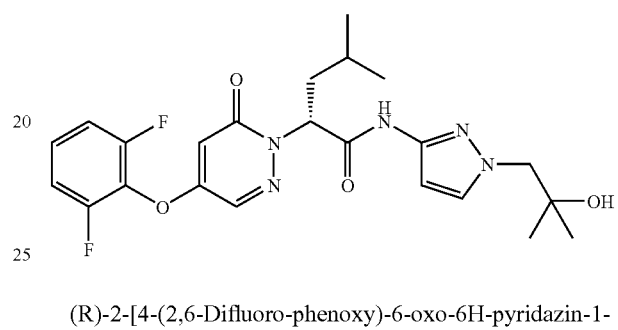

(R)-2-[4-(2,6-Difluoro-phenoxy)-6-oxo-6H-pyridazin-1-yl]-4-methyl-pentanoic acid [1-(2-hydroxy-2-methyl-propyl)-1H-pyrazol-3-yl]-amide; ES$^+$-HRMS m/e calcd for $C_{23}H_{27}N_5O_4F_2$ [M+H$^+$] 476.2104 found 476.2103. $^1$H-NMR (300 MHz, DMSO-d$_6$) δ ppm 0.82-0.92 (m, 6H) 1.05 (br s, 3H) 1.06 (br s, 3H) 1.44 (br s, 1H) 1.69-1.86 (m, 1H) 2.09-2.28 (m, 1H) 3.89 (s, 2H) 4.68 (s, 1H) 5.52 (dd, J=11.2, 4.2 Hz, 1H) 6.04 (d, J=2.7 Hz, 1H) 6.39 (d, J=2.1 Hz, 1H) 7.31-7.50 (m, 3H) 7.53 (d, J=2.1 Hz, 1H) 8.29 (d, J=2.7 Hz, 1H) 10.86 (s, 1H).

Example 43

2-[4-(2,6-Difluoro-phenoxy)-6-oxo-6H-pyridazin-1-yl]-N-[1-(2-hydroxy-2-methyl-propyl)-1H-pyrazol-3-yl]-3-(tetrahydro-pyran-4-yl)-propionamide

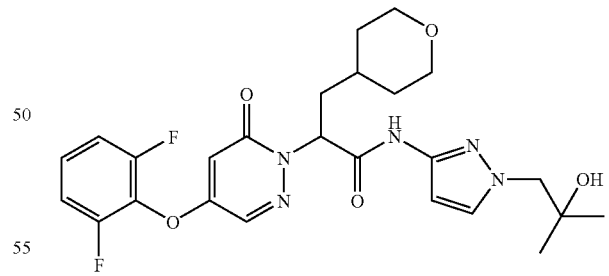

Using the method described in Example 17, 2-[4-(2,6-difluoro-phenoxy)-6-oxo-6H-pyridazin-1-yl]-3-(tetrahydro-pyran-4-yl)-propionic acid (Intermediate 32) and 1-(3-amino-pyrazol-1-yl)-2-methyl-propan-2-ol (Intermediate 1) afforded 2-[4-(2,6-difluoro-phenoxy)-6-oxo-6H-pyridazin-1-yl]-N-[1-(2-hydroxy-2-methyl-propyl)-1H-pyrazol-3-yl]-3-(tetrahydro-pyran-4-yl)-propionamide as a white solid (0.11 g, 37%); ES$^+$-HRMS m/e calcd for $C_{25}H_{29}N_5O_5F_2$ [M+H$^+$] 518.2210 found 518.2210. $^1$H-NMR (400 MHz, DMSO-d$_6$) δ ppm 1.05 (s, 3H) 1.07 (s, 3H) 1.12-1.62 (m, 5H)

1.81-1.96 (m, 1H) 2.13-2.28 (m, 1H) 3.08-3.28 (m, 2H) 3.70-3.86 (m, 2H) 3.90 (s, 2H) 4.67 (s, 1H) 5.55 (dd, J=11.1, 4.3 Hz, 1H) 6.04 (d, J=3.0 Hz, 1H) 6.40 (d, J=2.3 Hz, 1H) 7.34-7.43 (m, 2H) 7.43-7.52 (m, 1H) 7.53 (d, J=2.3 Hz, 1H) 8.30 (d, J=3.0 Hz, 1H) 10.86 (s, 1H).

Separation of enantiomers via supercritical fluid chromatography on a SFC DAICEL AD column, 25% methanol, 70 mL/min.

Example 43A (S)-2-[4-(2,6-Difluoro-phenoxy)-6-oxo-6H-pyridazin-1-yl]-N-[1-(2-hydroxy-2-methyl-propyl)-1H-pyrazol-3-yl]-3-(tetrahydro-pyran-4-yl)-propionamide

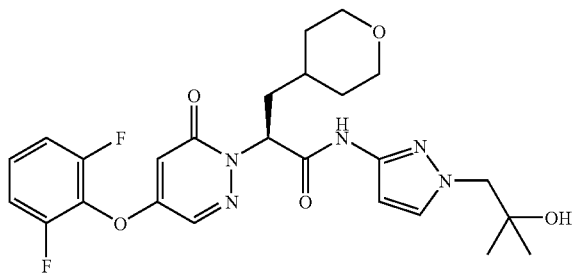

(S)-2-[4-(2,6-Difluoro-phenoxy)-6-oxo-6H-pyridazin-1-yl]-N-[1-(2-hydroxy-2-methyl-propyl)-1H-pyrazol-3-yl]-3-(tetrahydro-pyran-4-yl)-propionamide; ES$^+$-HRMS m/e calcd for $C_{25}H_{29}N_5O_5F_2$ [M+H$^+$] 518.2210 found 518.2209. $^1$H-NMR (300 MHz, DMSO-d$_6$) δ ppm 1.05 (br s, 3H) 1.06 (br s, 3H) 1.10-1.60 (m, 5H) 1.81-1.98 (m, 1H) 2.10-2.29 (m, 1H) 3.07-3.29 (m, 2H) 3.68-3.87 (m, 2H) 3.89 (s, 2H) 4.68 (s, 1H) 5.55 (dd, J=11.0, 3.8 Hz, 1H) 6.04 (d, J=2.7 Hz, 1H) 6.39 (d, J=2.1 Hz, 1H) 7.32-7.52 (m, 3H) 7.53 (d, J=2.1 Hz, 1H) 8.30 (d, J=2.7 Hz, 1H) 10.88 (s, 1H).

Example 43B (R)-2-[4-(2,6-Difluoro-phenoxy)-6-oxo-6H-pyridazin-1-yl]-N-[1-(2-hydroxy-2-methyl-propyl)-1H-pyrazol-3-yl]-3-(tetrahydro-pyran-4-yl)-propionamide

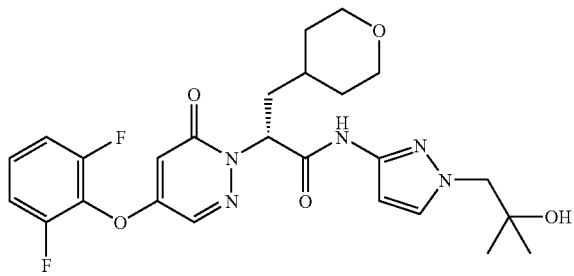

(R)-2-[4-(2,6-Difluoro-phenoxy)-6-oxo-6H-pyridazin-1-yl]-N-[1-(2-hydroxy-2-methyl-propyl)-1H-pyrazol-3-yl]-3-(tetrahydro-pyran-4-yl)-propionamide; ES$^+$-HRMS m/e calcd for $C_{25}H_{29}N_5O_5F_2$ [M+H$^+$] 518.2210 found 518.2208. $^1$H-NMR (300 MHz, DMSO-d$_6$) δ ppm 1.05 (br s, 3H) 1.06 (br s, 3H) 1.10-1.58 (m, 5H) 1.79-1.97 (m, 1H) 2.14-2.31 (m, 1H) 3.05-3.30 (m, 2H) 3.70-3.86 (m, 2H) 3.89 (s, 2H) 4.68 (s, 1H) 5.55 (dd, J=11.2, 3.9 Hz, 1H) 6.04 (d, J=2.7 Hz, 1H) 6.39 (d, J=2.1 Hz, 1H) 7.29-7.51 (m, 3H) 7.53 (d, J=2.1 Hz, 1H) 8.30 (d, J=2.7 Hz, 1H) 10.88 (s, 1H).

Example 44

2-[4-(2,6-Difluoro-phenoxy)-6-oxo-6H-pyridazin-1-yl]-N-[1-(2-hydroxy-2-methyl-propyl)-1H-pyrazol-3-yl]-3-phenyl-propionamide

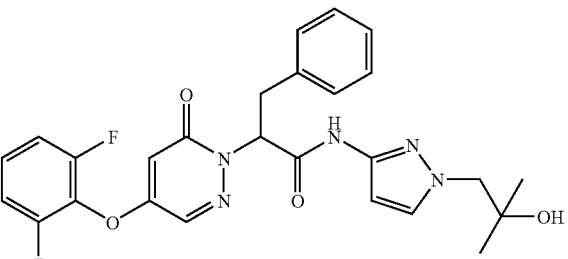

Using the method described in Example 17 from 2-[4-(2,6-difluoro-phenoxy)-6-oxo-6H-pyridazin-1-yl]-3-phenyl-propionic acid (Intermediate 30) and 1-(3-amino-pyrazol-1-yl)-2-methyl-propan-2-ol (Intermediate 1) afforded 2-[4-(2,6-difluoro-phenoxy)-6-oxo-6H-pyridazin-1-yl]-N-[1-(2-hydroxy-2-methyl-propyl)-1H-pyrazol-3-yl]-3-phenyl-propionamide was obtained as a white solid (0.26 g, 34%); ES$^+$-HRMS m/e calcd for $C_{26}H_{25}N_5O_4F_2$ [M+H$^+$] 510.1948 found 510.1949. $^1$H-NMR (400 MHz, DMSO-d$_6$) δ ppm 1.06 (s, 3H) 1.07 (s, 3H) 3.35-3.56 (m, 2H) 3.91 (s, 2H) 4.67 (s, 1H) 5.81 (dd, J=10.7, 4.9 Hz, 1H) 5.92 (d, J=3.0 Hz, 1H) 6.44 (d, J=2.3 Hz, 1H) 7.10-7.20 (m, 1H) 7.24 (t, J=7.1 Hz, 2H) 7.29 (d, J=7.1 Hz, 2H) 7.32-7.40 (m, 2H) 7.40-7.50 (m, 1H) 7.55 (d, J=2.3 Hz, 1H) 8.24 (d, J=3.0 Hz, 1H) 11.00 (s, 1H).

Example 45

3-Cyclopentyl-N-(1-methyl-5-trifluoromethyl-1H-pyrazol-3-yl)-2-[6-oxo-4-(2-trifluoromethyl-phenoxy)-6H-pyridazin-1-yl]-propionamide

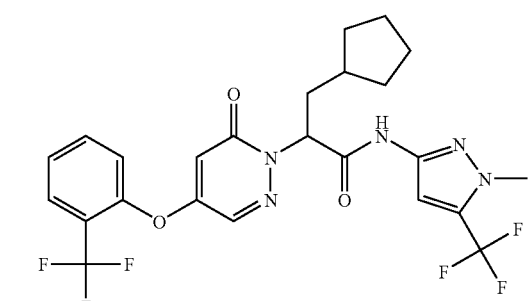

Using the method described in Example 17, 3-cyclopentyl-2-[6-oxo-4-(2-trifluoromethyl-phenoxy)-6H-pyridazin-1-yl]-propionic acid (Intermediate 21) and 1-methyl-5-trifluoromethyl-1H-pyrazol-3-ylamine (Intermediate 9) afforded 3-cyclopentyl-N-(1-methyl-5-trifluoromethyl-1H-pyrazol-3-yl)-2-[6-oxo-4-(2-trifluoromethyl-phenoxy)-6H-pyridazin-1-yl]-propionamide as a yellow solid (35.3 mg, 10%); ES⁺-HRMS m/e calcd for $C_{24}H_{23}N_5O_3F_6$ [M+Na⁺] 566.1597 found 566.1596. ¹H-NMR (400 MHz, CDCl₃) δ ppm 1.08-1.24 (m, 2H), 1.44-1.84 (m, 7H), 2.24 (t, J=7.5 Hz, 2H), 3.85 (s, 3H), 5.56 (t, J=7.5 Hz, 1H), 5.98 (d, J=3.0 Hz, 1H), 7.06 (s, 1H), 7.21 (d, J=7.9 Hz, 1H), 7.44 (t, J=7.9 Hz, 1H), 7.65 (t, J=7.9 Hz, 1H), 7.77 (d, J=7.9 Hz, 1H), 7.94 (d, J=3.0 Hz, 1H), 8.79 (s, 1H).

Example 46

3-Cyclopentyl-N-[1-(2-hydroxy-2-methyl-propyl)-1H-pyrazol-3-yl]-2-[6-oxo-4-(2-trifluoromethyl-benzyl)-6H-pyridazin-1-yl]-propionamide

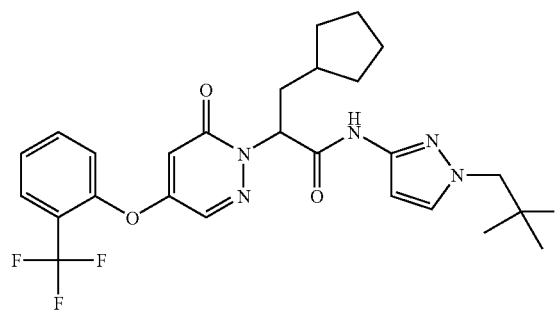

Using the method described in Example 17, 3-cyclopentyl-2-[6-oxo-4-(2-trifluoromethyl-benzyl)-6H-pyridazin-1-yl]-propionic acid (Intermediate 63) and 1-(3-amino-pyrazol-1-yl)-2-methyl-propan-2-ol (Intermediate 1) afforded 3-cyclopentyl-N-[1-(2-hydroxy-2-methyl-propyl)-1H-pyrazol-3-yl]-2-[6-oxo-4-(2-trifluoromethyl-benzyl)-6H-pyridazin-1-yl]-propionamide as an off-white solid (77 mg, 61%); ES⁺-HRMS m/e calcd for $C_{27}H_{32}N_5O_3F_3$ [M+H⁺] 532.2530, found 532.2530. ¹H-NMR (300 MHz, DMSO-d₆) δ ppm 1.04 (s, 3H), 1.06 (s, 3H), 1.08 (m, 1H), 1.21-1.74 (m, 8H), 1.90 (m, 1H), 2.26 (m, 1H), 3.88 (s, 2H), 4.09 (s, 2H), 4.66 (s, 1H), 5.46 (dd, J=3.9, J=10.6 Hz, 1H), 6.29-6.42 (m, 2H), 7.38-7.59 (m, 3H), 7.70 (t, J=7.4 Hz, 1H), 7.79 (d, J=7.4 Hz, 1H), 7.92 (d, J=2.1 Hz, 1H), 10.79 (s, 1H).

Example 47

3-Cyclopentyl-N-[1-(2-hydroxy-2-methyl-propyl)-1H-pyrazol-3-yl]-2-[6-oxo-4-(3-trifluoromethyl-benzyl)-6H-pyridazin-1-yl]-propionamide

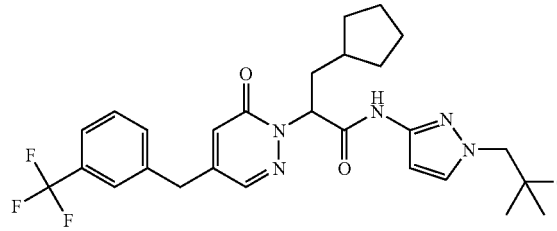

Using the method described in Example 17, 3-cyclopentyl-2-[6-oxo-4-(3-trifluoromethyl-benzyl)-6H-pyridazin-1-yl]-propionic acid (Intermediate 64) and 1-(3-amino-pyrazol-1-yl)-2-methyl-propan-2-ol (Intermediate 1) afforded 3-cyclopentyl-N-[1-(2-hydroxy-2-methyl-propyl)-1H-pyrazol-3-yl]-2-[6-oxo-4-(3-trifluoromethyl-benzyl)-6H-pyridazin-1-yl]-propionamide as a white solid (43.7 mg, 63%); ES⁺-HRMS m/e calcd for $C_{27}H_{32}N_5O_3F_3$ [M+H⁺] 532.2530, found 532.2526. ¹H-NMR (300 MHz, DMSO-d₆) δ ppm 1.03-1.08 (m, 1H) 1.04 (br s, 3H) 1.06 (br s, 3H) 1.17-1.73 (m, 8H) 1.90 (br s, 1H) 2.15-2.31 (m, 1H) 3.88 (s, 2H) 3.99 (s, 2H) 4.66 (s, 1H) 5.47 (dd, J=10.7, 4.4 Hz, 1H) 6.37 (d, J=2.1 Hz, 1H) 6.72 (s, 1H) 7.51 (d, J=2.1 Hz, 1H) 7.54-7.72 (m, 3H) 7.75 (s, 1H) 7.98 (d, J=2.1 Hz, 1H) 10.77 (s, 1H).

Example 48

3-Cyclopentyl-2-[4-(2,6-difluoro-benzyl)-6-oxo-6H-pyridazin-1-yl]-N-[1-(2-hydroxy-2-methyl-propyl)-1H-pyrazol-3-yl]-propionamide

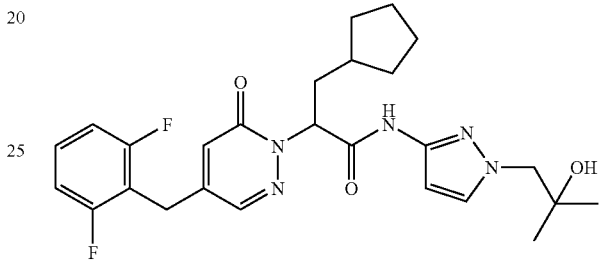

Using the method described in Example 17, 3-cyclopentyl-2-[4-(2,6-difluoro-benzyl)-6-oxo-6H-pyridazin-1-yl]-propionic acid (Intermediate 65) and 1-(3-amino-pyrazol-1-yl)-2-methyl-propan-2-ol (Intermediate 1) afforded 3-cyclopentyl-2-[4-(2,6-difluoro-benzyl)-6-oxo-6H-pyridazin-1-yl]-N-[1-(2-hydroxy-2-methyl-propyl)-1H-pyrazol-3-yl]-propionamide as a white solid (33.7 mg, 49%); ES⁺-HRMS m/e calcd for $C_{26}H_{31}N_5O_3F_2$ [M+H⁺] 500.2468, found 500.2465. ¹H-NMR (400 MHz, DMSO-d₆) δ ppm 1.03-1.08 (m, 1H) 1.04 (s, 3H) 1.06 (s, 3H) 1.20-1.74 (m, 8H) 1.84-1.98 (m, 1H) 2.19-2.30 (m, 1H) 3.88 (s, 2H) 3.97 (s, 2H) 4.66 (s, 1H) 5.46 (dd, J=11.1, 4.5 Hz, 1H) 6.37 (d, J=2.1 Hz, 1H) 6.45 (br s, 1H) 7.18 (t, J=8.0 Hz, 2H) 7.39-7.50 (m, 1H) 7.51 (d, J=2.1 Hz, 1H) 7.92 (d, J=2.1 Hz, 1H) 10.80 (s, 1H).

Example 49

3-Cyclobutyl-2-[4-(2,6-difluoro-phenoxy)-6-oxo-6H-pyridazin-1-yl]-N-[1-(2-hydroxy-2-methyl-propyl)-1H-pyrazol-3-yl]-propionamide

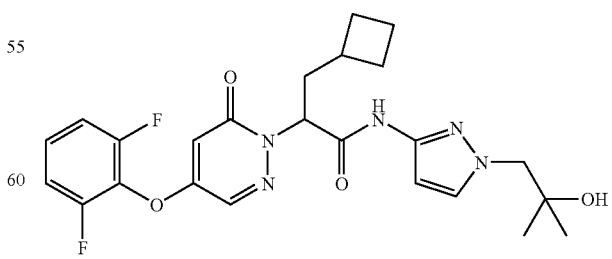

A solution of 3-cyclobutyl-2-[4-(2,6-difluoro-phenoxy)-6-oxo-6H-pyridazin-1-yl]-propionic acid (Intermediate 29, 151.8 mg, 0.43 mmol) in N,N-dimethylformamide (1.67 mL, 0.26M) at 25° C. was treated with N,N-diisopropylethylamine (0.21 mL, 1.29 mmol), (benzotriazol-1-yloxy)tris(dimethylamino)phosphonium hexafluorophosphate (0.28 g, 0.64 mmol) and 1-(3-amino-pyrazol-1-yl)-2-methyl-propan-2-ol (Intermediate 1, 0.08 g, 0.51 mmol). The reaction was stirred at 25° C. overnight. After this time, the reaction was diluted with ethyl acetate (100 mL) and was washed with a saturated aqueous ammonium chloride solution (1×150 mL), a saturated aqueous sodium bicarbonate solution (1×150 mL) and a saturated aqueous sodium chloride solution (1×150 mL), dried over sodium sulfate, filtered, rinsed and concentrated in vacuo. Silica gel column chromatography (AnaLogix 12 g, 75-100% gradient ethyl acetate/hexanes) afforded 3-cyclobutyl-2-[4-(2,6-difluoro-phenoxy)-6-oxo-6H-pyridazin-1-yl]-N-[1-(2-hydroxy-2-methyl-propyl)-1H-pyrazol-3-yl]-propionamide (107 mg, 51%) as an off-white solid; ES$^+$-HRMS m/e calcd for $C_{24}H_{27}N_5O_4F_2$ [M+H$^+$] 488.2104 found 488.2103. $^1$H-NMR (400 MHz, DMSO-d$_6$) δ ppm 1.06 (br s, 3H) 1.07 (br s, 3H) 1.45-1.66 (m, 1H) 1.69-1.89 (m, 4H) 1.88-2.03 (m, 1H) 2.02-2.41 (m, 3H) 3.90 (s, 2H) 4.67 (s, 1H) 5.35 (dd, J=10.1, 4.4 Hz, 1H) 6.02 (d, J=2.9 Hz, 1H) 6.40 (d, J=2.1 Hz, 1H) 7.34-7.44 (m, 2H) 7.44-7.51 (m, 1H) 7.53 (d, J=2.1 Hz, 1H) 8.27 (d, J=2.9 Hz, 1H) 10.83 (s, 1H).

Separation of enantiomers via supercritical fluid chromatography on a SFC DAICEL AD column, 35% methanol, 70 mL/min.

Example 49A (S)-3-Cyclobutyl-2-[4-(2,6-difluoro-phenoxy)-6-oxo-6H-pyridazin-1-yl]-N-[1-(2-hydroxy-2-methyl-propyl)-1H-pyrazol-3-yl]-propionamide

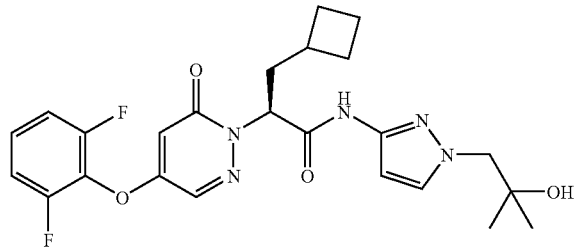

(S)-3-Cyclobutyl-2-[4-(2,6-difluoro-phenoxy)-6-oxo-6H-pyridazin-1-yl]-N-[1-(2-hydroxy-2-methyl-propyl)-1H-pyrazol-3-yl]-propionamide; ES$^+$-HRMS m/e calcd for $C_{24}H_{27}N_5O_4F_2$ [M+H$^+$] 488.2104 found 488.2103. $^1$H NMR (400 MHz, DMSO-d$_6$) δ ppm 1.06 (br. s., 3H), 1.07 (br. s., 3H), 1.50-1.66 (m, 1H), 1.69-2.01 (m, 5H), 2.04-2.37 (m, 3H), 3.90 (s, 2H), 4.67 (s, 1H), 5.35 (dd, J=10.1, 4.4 Hz, 1H), 6.02 (d, J=2.8 Hz, 1H), 6.40 (d, J=2.1 Hz, 1H), 7.34-7.43 (m, 2H), 7.43-7.51 (m, 1H), 7.53 (d, J=2.1 Hz, 1H), 8.27 (d, J=2.8 Hz, 1H), 10.83 (s, 1H).

Example 49B (R)-3-Cyclobutyl-2-[4-(2,6-difluoro-phenoxy)-6-oxo-6H-pyridazin-1-yl]-N-[1-(2-hydroxy-2-methyl-propyl)-1H-pyrazol-3-yl]-propionamide

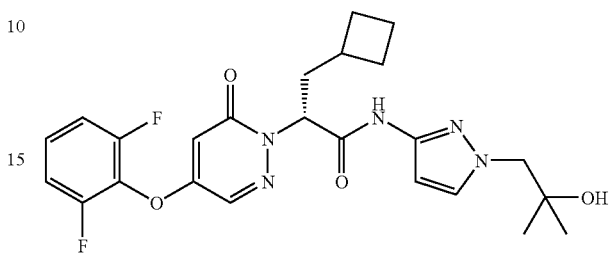

(R)-3-Cyclobutyl-2-[4-(2,6-difluoro-phenoxy)-6-oxo-6H-pyridazin-1-yl]-N-[1-(2-hydroxy-2-methyl-propyl)-1H-pyrazol-3-yl]-propionamide; ES$^+$-HRMS m/e calcd for $C_{24}H_{27}N_5O_4F_2$ [M+H$^+$] 488.2104 found 488.2104. $^1$H NMR (300 MHz, DMSO-d$_6$) δ ppm 1.05 (br. s., 3H), 1.06 (br. s., 3H), 1.59 (m, 1H), 1.66-2.01 (m, 5H), 2.00-2.40 (m, 3H), 3.89 (s, 2H), 4.68 (s, 1H), 5.34 (dd, J=9.8, 4.4 Hz, 1H), 6.01 (d, J=2.7 Hz, 1H), 6.39 (d, J=2.1 Hz, 1H), 7.31-7.51 (m, 3H), 7.53 (d, J=2.1 Hz, 1H), 8.27 (d, J=2.7 Hz, 1H), 10.84 (s, 1H).

In an analogous manner, there were obtained:

Example 50

2-[4-(2,6-Difluoro-phenoxy)-6-oxo-6H-pyridazin-1-yl]-3-(2,6-difluoro-phenyl)-N-[1-(2-hydroxy-2-methyl-propyl)-1H-pyrazol-3-yl]-propionamide

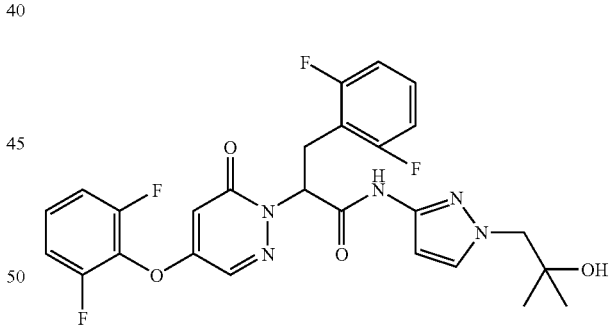

Using the method described in Example 49, 2-[4-(2,6-difluoro-phenoxy)-6-oxo-6H-pyridazin-1-yl]-3-(2,6-difluoro-phenyl)-propionic acid (Intermediate 34) and 1-(3-amino-pyrazol-1-yl)-2-methyl-propan-2-ol (Intermediate 1) afforded 2-[4-(2,6-difluoro-phenoxy)-6-oxo-6H-pyridazin-1-yl]-3-(2,6-difluoro-phenyl)-N-[1-(2-hydroxy-2-methyl-propyl)-1H-pyrazol-3-yl]-propionamide as a light yellow solid (571 mg, 65%); ES$^+$-HRMS m/e calcd for $C_{26}H_{23}N_5O_4F_4$ [M+H$^+$] 546.1759 found 546.1762. $^1$H-NMR (400 MHz, DMSO-d$_6$) δ ppm 1.04 (s, 6H) 3.39-3.58 (m, 2H) 3.88 (s, 2H) 4.66 (s, 1H) 5.70 (dd, J=9.7, 5.6 Hz, 1H) 5.90 (d, J=2.7 Hz, 1H) 6.47 (d, J=2.1 Hz, 1H) 6.96 (t, J=8.0 Hz, 2H)

7.19-7.34 (m, 1H) 7.34-7.41 (m, 2H) 7.42-7.51 (m, 1H) 7.54 (d, J=2.1 Hz, 1H) 8.20 (d, J=2.7 Hz, 1H) 10.67 (s, 1H).

Separation of enantiomers via supercritical fluid chromatography on a SFC DAICEL OJ column, 10% 1:1 ethanol/acetonitrile, 70 mL/min.

Example 50A (S)-2-[4-(2,6-Difluoro-phenoxy)-6-oxo-6H-pyridazin-1-yl]-3-(2,6-difluoro-phenyl)-N-[1-(2-hydroxy-2-methyl-propyl)-1H-pyrazol-3-yl]-propionamide

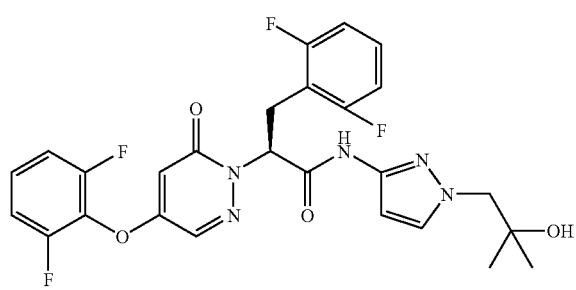

(S)-2-[4-(2,6-Difluoro-phenoxy)-6-oxo-6H-pyridazin-1-yl]-3-(2,6-difluoro-phenyl)-N-[1-(2-hydroxy-2-methyl-propyl)-1H-pyrazol-3-yl]-propionamide; ES$^+$-HRMS m/e calcd for $C_{26}H_{23}N_5O_4F_4$ [M+H$^+$] 546.1759 found 546.1762. $^1$H NMR (300 MHz, DMSO-d$_6$) δ ppm 1.04 (s, 6H), 3.38-3.57 (m, 2H), 3.87 (s, 2H), 4.67 (s, 1H), 5.70 (dd, J=9.7, 5.4 Hz, 1H), 5.90 (d, J=2.7 Hz, 1H), 6.47 (d, J=2.1 Hz, 1H), 6.96 (t, J=7.8 Hz, 2H), 7.21-7.51 (m, 4H), 7.54 (d, J=2.1 Hz, 1H), 8.20 (d, J=2.7 Hz, 1H), 10.68 (s, 1H).

Example 50B (R)-2-[4-(2,6-Difluoro-phenoxy)-6-oxo-6H-pyridazin-1-yl]-3-(2,6-difluoro-phenyl)-N-[1-(2-hydroxy-2-methyl-propyl)-1H-pyrazol-3-yl]-propionamide

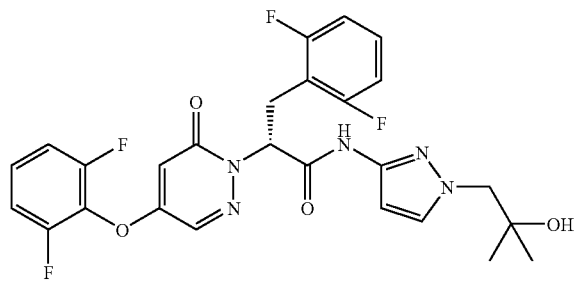

(R)-2-[4-(2,6-Difluoro-phenoxy)-6-oxo-6H-pyridazin-1-yl]-3-(2,6-difluoro-phenyl)-N-[1-(2-hydroxy-2-methyl-propyl)-1H-pyrazol-3-yl]-propionamide; ES$^+$-HRMS m/e calcd for $C_{26}H_{23}N_5O_4F_4$ [M+H$^+$] 546.1759 found 546.1761. $^1$H NMR (300 MHz, DMSO-d$_6$) δ ppm 1.02 (s, 6H), 3.37-3.56 (m, 2H), 3.86 (s, 2H), 4.65 (s, 1H), 5.68 (dd, J=9.7, 5.4 Hz, 1H), 5.88 (d, J=2.7 Hz, 1H), 6.45 (d, J=2.1 Hz, 1H), 6.94 (t, J=7.8 Hz, 2H), 7.19-7.50 (m, 4H), 7.52 (d, J=2.1 Hz, 1H), 8.19 (d, J=2.7 Hz, 1H), 10.66 (s, 1H).

Example 51

3-Cyclohexyl-2-[4-(2,6-difluoro-phenoxy)-6-oxo-6H-pyridazin-1-yl]-N-[1-(2-hydroxy-2-methyl-propyl)-1H-pyrazol-3-yl]-propionamide

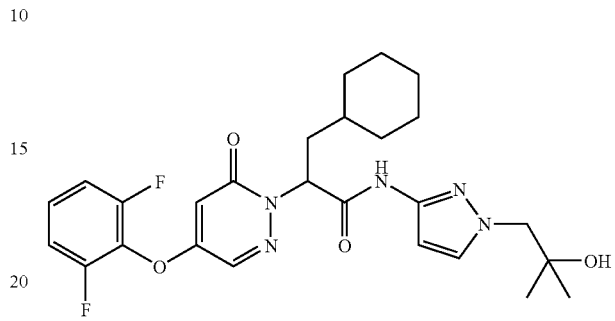

Using the method described in Example 49, 3-cyclohexyl-2-[4-(2,6-difluoro-phenoxy)-6-oxo-6H-pyridazin-1-yl]-propionic acid (Intermediate 33) and 1-(3-amino-pyrazol-1-yl)-2-methyl-propan-2-ol (Intermediate 1) afforded 3-cyclohexyl-2-[4-(2,6-difluoro-phenoxy)-6-oxo-6H-pyridazin-1-yl]-N-[1-(2-hydroxy-2-methyl-propyl)-1H-pyrazol-3-yl]-propionamide as a white solid (2.0 g, 98%); ES$^+$-HRMS m/e calcd for $C_{26}H_{31}N_5O_4F_2$ [M+H$^+$] 516.2417 found 516.2417. $^1$H-NMR (300 MHz, DMSO-d$_6$) δ ppm 0.78-1.26 (m, 6H) 1.03 (s, 3H) 1.04 (s, 3H) 1.45-1.70 (m, 5H) 1.73-1.91 (m, 1H) 2.01-2.24 (m, 1H) 3.87 (s, 2H) 4.66 (s, 1H) 5.52 (dd, J=11.0, 4.1 Hz, 1H) 6.02 (d, J=2.7 Hz, 1H) 6.37 (d, J=2.2 Hz, 1H) 7.24-7.49 (m, 3H) 7.51 (d, J=2.2 Hz, 1H) 8.27 (d, J=2.7 Hz, 1H) 10.83 (s, 1H).

Separation of enantiomers via supercritical fluid chromatography on a SFC DAICEL AD column, 25% methanol, 70 mL/min.

Example 51A (S)-3-Cyclohexyl-2-[4-(2,6-difluoro-phenoxy)-6-oxo-6H-pyridazin-1-yl]-N-[1-(2-hydroxy-2-methyl-propyl)-1H-pyrazol-3-yl]-propionamide

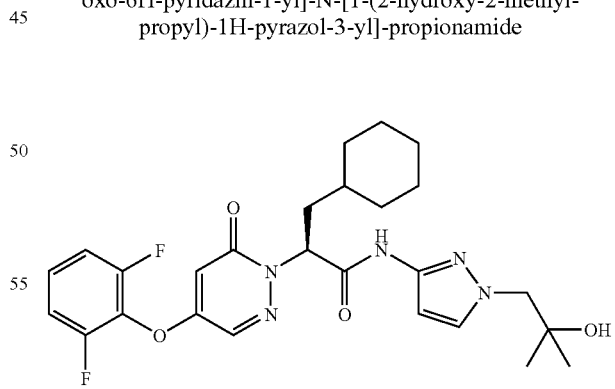

(S)-3-Cyclohexyl-2-[4-(2,6-difluoro-phenoxy)-6-oxo-6H-pyridazin-1-yl]-N-[1-(2-hydroxy-2-methyl-propyl)-1H-pyrazol-3-yl]-propionamide; ES$^+$-HRMS m/e calcd for $C_{26}H_{31}N_5O_4F_2$ [M+H$^+$] 516.2417 found 516.2417. $^1$H-NMR (300 MHz, DMSO-d$_6$) δ ppm 0.82-1.23 (m, 6H) 1.03 (br s, 3H) 1.04 (br s, 3H) 1.43-1.73 (m, 5H) 1.72-1.92 (m, 1H) 2.05-2.23 (m, 1H) 3.87 (s, 2H) 4.66 (s, 1H) 5.52 (dd, J=11.2, 3.9 Hz, 1H) 6.02 (d, J=2.7 Hz, 1H) 6.37 (d, J=2.1 Hz, 1H) 7.28-7.48 (m, 3H) 7.51 (d, J=2.1 Hz, 1H) 8.27 (d, J=2.7 Hz, 1H) 10.83 (s, 1H).

Example 51B (R)-3-Cyclohexyl-2-[4-(2,6-difluoro-phenoxy)-6-oxo-6H-pyridazin-1-yl]-N-[1-(2-hydroxy-2-methyl-propyl)-1H-pyrazol-3-yl]-propionamide

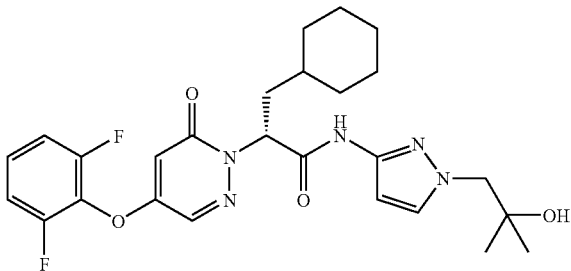

(R)-3-Cyclohexyl-2-[4-(2,6-difluoro-phenoxy)-6-oxo-6H-pyridazin-1-yl]-N-[1-(2-hydroxy-2-methyl-propyl)-1H-pyrazol-3-yl]-propionamide; ES$^+$-HRMS m/e calcd for $C_{26}H_{31}N_5O_4F_2$ [M+H$^+$] 516.2417 found 516.2417. $^1$H-NMR (300 MHz, DMSO-d$_6$) δ ppm 0.79-1.26 (m, 6H) 1.05 (br s, 3H) 1.06 (br s, 3H) 1.51-1.72 (m, 5H) 1.75-1.91 (m, 1H) 2.07-2.23 (m, 1H) 3.89 (s, 2H) 4.68 (s, 1H) 5.54 (dd, J=10.9, 3.9 Hz, 1H) 6.04 (d, J=2.7 Hz, 1H) 6.39 (d, J=2.1 Hz, 1H) 7.32-7.50 (m, 3H) 7.52 (d, J=2.1 Hz, 1H) 8.29 (d, J=2.7 Hz, 1H) 10.85 (s, 1H).

Example 52

2-[4-(2,6-Difluoro-phenoxy)-6-oxo-6H-pyridazin-1-yl]-4-ethyl-hexanoic acid [1-(2-hydroxy-2-methyl-propyl)-1H-pyrazol-3-yl]-amide

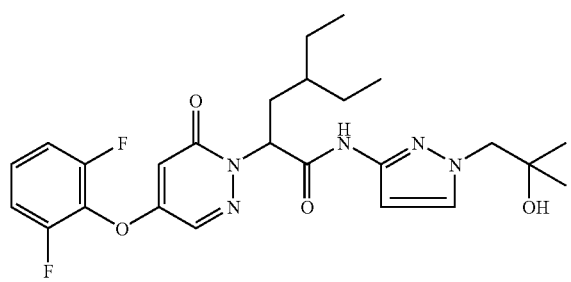

Using the method described in Example 49, 2-[4-(2,6-difluoro-phenoxy)-6-oxo-6H-pyridazin-1-yl]-4-ethyl-hexanoic acid (Intermediate 31) and 1-(3-amino-pyrazol-1-yl)-2-methyl-propan-2-ol (Intermediate 1) afforded 2-[4-(2,6-difluoro-phenoxy)-6-oxo-6H-pyridazin-1-yl]-4-ethyl-hexanoic acid [1-(2-hydroxy-2-methyl-propyl)-1H-pyrazol-3-yl]-amide as an off-white solid (50 mg, 31%); ES$^+$-HRMS m/e calcd for $C_{25}H_{31}N_5O_4F_2$ [M+H$^+$] 504.2417 found 504.2417. $^1$H-NMR (400 MHz, CDCl$_3$-d) δ ppm 0.86 (t, J=7.5 Hz, 3H) 0.87 (t, J=7.5 Hz, 3H) 1.08-1.14 (m, 1H) 1.15 (s, 3H) 1.16 (s, 3H) 1.21-1.50 (m, 4H) 2.01-2.19 (m, 1H) 2.19-2.37 (m, 1H) 3.93 (s, 2H) 5.67 (dd, J=9.6, 5.8 Hz, 1H) 6.01 (d, J=3.0 Hz, 1H) 6.72 (d, J=2.3 Hz, 1H) 7.08 (t, J=8.0 Hz, 2H) 7.27-7.33 (m, 2H) 8.01 (d, J=3.0 Hz, 1H) 8.59 (s, 1H).

Example 53

2-[4-(2,6-Difluoro-phenoxy)-6-oxo-6H-pyridazin-1-yl]-N-[1-(2-hydroxy-ethyl)-1H-pyrazol-3-yl]-3-(tetrahydro-pyran-4-yl)-propionamide Step 1: Using the method described in Example 49, 2-[4-(2,6-difluoro-phenoxy)-6-oxo-6H-pyridazin-1-yl]-3-(tetrahydro-pyran-4-yl)-propionic acid (Intermediate 32) and 1-[2-(tert-butyl-dimethyl-silanyloxy)-ethyl]-1H-pyrazol-3-ylamine (Intermediate 3) afforded N-{1-[2-(tert-butyl-dimethyl-silanyloxy)-ethyl]-1H-pyrazol-3-yl}-2-[4-(2,6-difluoro-phenoxy)-6-oxo-6H-pyridazin-1-yl]-3-(tetrahydro-pyran-4-yl)-propionamide as an orange oil (555.9 mg, 47%); ES$^+$-HRMS m/e calcd for $C_{29}H_{39}N_5O_5SiF_2$ [M+H$^+$] 488.2104 found 488.2103. $^1$H NMR (400 MHz, DMSO-d$_6$) δ ppm −0.07 (s, 6H) 0.80 (s, 9H) 1.12-1.33 (m, 2H) 1.33-1.45 (m, 1H) 1.46-1.58 (m, 2H) 1.84-1.90 (m, 1H) 1.90 (s, 6H) 2.13-2.25 (m, 1H) 3.10-3.28 (m, 2H) 3.73-3.83 (m, 2H) 3.86 (t, J=5.3 Hz, 2H) 4.06 (t, J=5.3 Hz, 2H) 5.54 (dd, J=10.9, 4.3 Hz, 1H) 6.04 (d, J=2.7 Hz, 1H) 6.36 (d, J=2.1 Hz, 1H) 7.29-7.43 (m, 2H) 7.43-7.52 (m, 1H) 7.53 (d, J=2.1 Hz, 1H) 8.28 (d, J=2.7 Hz, 1H) 10.82 (s, 1H).

Step 2: A solution of N-{1-[2-(tert-butyl-dimethyl-silanyloxy)-ethyl]-1H-pyrazol-3-yl}-2-[4-(2,6-difluoro-phenoxy)-6-oxo-6H-pyridazin-1-yl]-3-(tetrahydro-pyran-4-yl)-propionamide (540.6 mg, 0.89 mmol) in ethanol (4.5 mL) at 25° C. was treated with concentrated aqueous hydrochloric acid (9 drops). The reaction was stirred at 25° C. overnight. After this time, the reaction was diluted with ethyl acetate (150 mL) and was washed with a saturated aqueous sodium bicarbonate solution (2×100 mL), water (1×100 mL) and a saturated aqueous sodium chloride solution (1×100 mL). The organics were dried over magnesium sulfate, filtered, rinsed and then concentrated in vacuo. Silica gel column chromatography (AnaLogix 80 g, 1-10% methanol/methylene chloride) afforded 2-[4-(2,6-difluoro-phenoxy)-6-oxo-6H-pyridazin-1-yl]-N-[1-(2-hydroxy-ethyl)-1H-pyrazol-3-yl]-3-(tetrahydro-pyran-4-yl)-propionamide (298 mg, 68%) as a white solid; ES$^+$-HRMS m/e calcd for $C_{23}H_{25}N_5O_5F_2$ [M+H$^+$] 490.1897 found 490.1895. $^1$H-NMR (400 MHz, DMSO-d$_6$) δ ppm 1.12-1.34 (m, 2H) 1.34-1.46 (m, 1H) 1.46-1.59 (m, 2H) 1.90 (ddd, J=13.6, 9.0, 4.3 Hz, 1H) 2.12-2.28 (m, 1H) 3.08-3.29 (m, 2H) 3.69 (q, J=5.5 Hz, 2H) 3.74-3.89 (m, 2H) 4.02 (t, J=5.5 Hz, 2H) 4.86 (t, J=5.5 Hz, 1H) 5.54 (dd, J=11.0, 4.3 Hz, 1H) 6.04 (d, J=2.7 Hz, 1H) 6.36 (d, J=2.1 Hz, 1H) 7.32-7.43 (m, 2H) 7.43-7.53 (m, 1H) 7.56 (d, J=2.1 Hz, 1H) 8.29 (d, J=2.7 Hz, 1H) 10.84 (s, 1H).

Separation of enantiomers via supercritical fluid chromatography on a SFC DAICEL AD column, 30% methanol, 70 mL/min.

Example 53A (S)-2-[4-(2,6-Difluoro-phenoxy)-6-oxo-6H-pyridazin-1-yl]-N-[1-(2-hydroxy-ethyl)-1H-pyrazol-3-yl]-3-(tetrahydro-pyran-4-yl)-propionamide

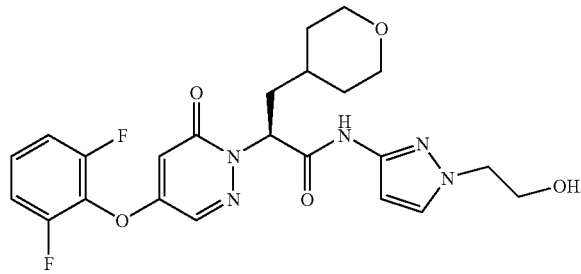

(S)-2-[4-(2,6-Difluoro-phenoxy)-6-oxo-6H-pyridazin-1-yl]-N-[1-(2-hydroxy-ethyl)-1H-pyrazol-3-yl]-3-(tetrahydro-pyran-4-yl)-propionamide; ES$^+$-HRMS m/e calcd for $C_{23}H_{25}N_5O_5F_2$ [M+H$^+$] 490.1897 found 490.1897. $^1$H NMR (300 MHz, DMSO-d$_6$) δ ppm 1.10-1.62 (m, 5H), 1.79-2.01 (m, 1H), 2.12-2.31 (m, 1H), 3.03-3.31 (m, 2H), 3.69 (q, J=5.4 Hz, 2H), 3.79 (br. s., 2H), 4.02 (t, J=5.4 Hz, 2H), 4.86 (t, J=5.4 Hz, 1H), 5.53 (dd, J=10.9, 4.2 Hz, 1H), 6.04 (d, J=2.7 Hz, 1H), 6.36 (d, J=2.1 Hz, 1H), 7.32-7.53 (m, 3H), 7.56 (d, J=2.1 Hz, 1H), 8.29 (d, J=2.7 Hz, 1H), 10.85 (s, 1H).

Example 53B (R)-2-[4-(2,6-Difluoro-phenoxy)-6-oxo-6H-pyridazin-1-yl]-N-[1-(2-hydroxy-ethyl)-1H-pyrazol-3-yl]-3-(tetrahydro-pyran-4-yl)-propionamide

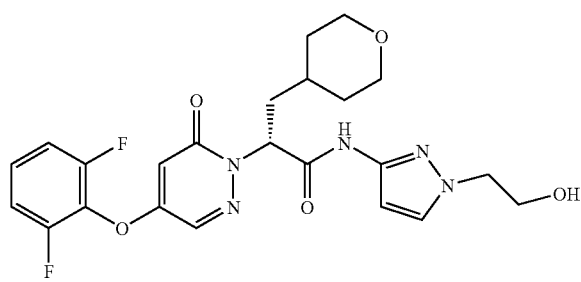

(R)-2-[4-(2,6-Difluoro-phenoxy)-6-oxo-6H-pyridazin-1-yl]-N-[1-(2-hydroxy-ethyl)-1H-pyrazol-3-yl]-3-(tetrahydro-pyran-4-yl)-propionamide; ES$^+$-HRMS m/e calcd for $C_{23}H_{25}N_5O_5F_2$ [M+H$^+$] 490.1897 found 490.1896. $^1$H NMR (300 MHz, DMSO-d$_6$) δ ppm 1.10-1.58 (m, 5H), 1.74-1.96 (m, 1H), 2.10-2.29 (m, 1H), 3.06-3.30 (m, 2H), 3.69 (q, J=5.4 Hz, 2H), 3.79 (br. s., 2H), 4.02 (t, J=5.4 Hz, 2H), 4.86 (t, J=5.4 Hz, 1H), 5.53 (dd, J=10.9, 4.2 Hz, 1H), 6.04 (d, J=2.7 Hz, 1H), 6.36 (d, J=2.1 Hz, 1H), 7.33-7.54 (m, 3H), 7.56 (d, J=2.1 Hz, 1H), 8.29 (d, J=2.7 Hz, 1H), 10.85 (s, 1H).

Example 54

2-[4-(2,6-Difluoro-phenoxy)-6-oxo-6H-pyridazin-1-yl]-4-ethyl-hexanoic acid [1-(2-hydroxy-ethyl)-1H-pyrazol-3-yl]-amide

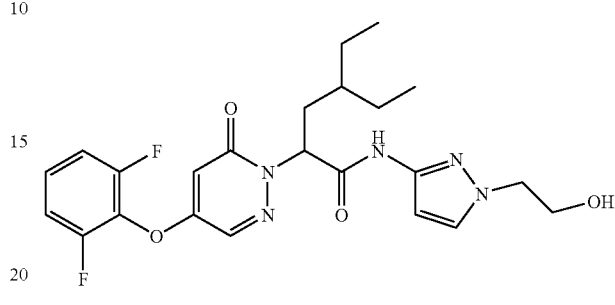

Using the method described in Example 49, 2-[4-(2,6-difluoro-phenoxy)-6-oxo-6H-pyridazin-1-yl]-4-ethyl-hexanoic acid (Intermediate 31) and 1-[2-(tert-butyl-dimethyl-silanyloxy)-ethyl]-1H-pyrazol-3-ylamine (Intermediate 3) afforded 2-[4-(2,6-difluoro-phenoxy)-6-oxo-6H-pyridazin-1-yl]-4-ethyl-hexanoic acid {1-[2-(tert-butyl-dimethyl-silanyloxy)-ethyl]-1H-pyrazol-3-yl}-amide as light yellow solid (472.6 mg, 49%). $^1$H NMR (300 MHz, DMSO-d$_6$) δ ppm −0.07 (s, 6H), 0.71-0.88 (m, 6H), 0.80 (s, 9H), 0.92-1.51 (m, 5H), 1.74-1.99 (m, 1H), 2.03-2.23 (m, 1H), 3.85 (t, J=5.1 Hz, 2H), 4.06 (t, J=5.1 Hz, 2H), 5.52 (dd, J=10.7, 4.4 Hz, 1H), 6.03 (d, J=2.7 Hz, 1H), 6.36 (d, J=2.1 Hz, 1H), 7.31-7.51 (m, 3H), 7.53 (d, J=2.1 Hz, 1H), 8.28 (d, J=2.7 Hz, 1H), 10.82 (s, 1H).

Using the method described in Example 53, Step 2, 2-[4-(2,6-difluoro-phenoxy)-6-oxo-6H-pyridazin-1-yl]-4-ethyl-hexanoic acid {1-[2-(tert-butyl-dimethyl-silanyloxy)-ethyl]-1H-pyrazol-3-yl}-amide afforded 2-[4-(2,6-difluoro-phenoxy)-6-oxo-6H-pyridazin-1-yl]-4-ethyl-hexanoic acid [1-(2-hydroxy-ethyl)-1H-pyrazol-3-yl]-amide as a light yellow solid (283.3 mg, 75%); ES$^+$-HRMS m/e calcd for $C_{23}H_{27}N_5O_4F_2$ [M+H$^+$] 476.2104 found 476.2103. $^1$H-NMR (400 MHz, DMSO-d$_6$) δ ppm 0.75-0.84 (m, 6H) 1.03-1.15 (m, 1H) 1.15-1.48 (m, 4H) 1.79-1.95 (m, 1H) 2.09-2.23 (m, 1H) 3.69 (t, J=5.7 Hz, 2H) 4.02 (t, J=5.7 Hz, 2H) 5.51 (dd, J=10.7, 4.3 Hz, 1H) 5.80 (br s, 1H) 6.03 (d, J=3.0 Hz, 1H) 6.37 (d, J=2.3 Hz, 1H) 7.34-7.42 (m, 2H) 7.42-7.53 (m, 1H) 7.55 (d, J=2.3 Hz, 1H) 8.27 (d, J=3.0 Hz, 1H) 10.80 (s, 1H).

Example 55

3-Cyclobutyl-2-[4-(2,6-difluoro-phenoxy)-6-oxo-6H-pyridazin-1-yl]-N-[1-(2-hydroxy-ethyl)-1H-pyrazol-3-yl]-propionamide

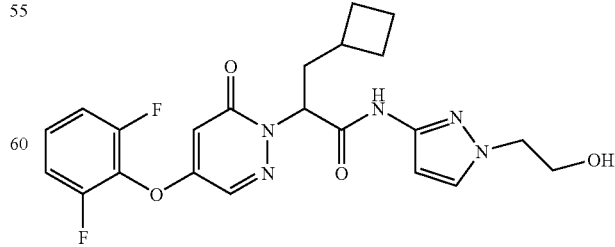

Using the method described in Example 49, 3-cyclobutyl-2-[4-(2,6-difluoro-phenoxy)-6-oxo-6H-pyridazin-1-yl]-propionic acid (Intermediate 29) and 1-[2-(tert-butyl-dimethyl-silanyloxy)-ethyl]-1H-pyrazol-3-ylamine (Intermediate 3) afforded N-{1-[2-(tert-butyl-dimethyl-silanyloxy)-ethyl]-1H-pyrazol-3-yl}-3-cyclobutyl-2-[4-(2,6-difluoro-phenoxy)-6-oxo-6H-pyridazin-1-yl]-propionamide as an off-white solid (342.2 mg, 40%); ES$^+$-HRMS m/e calcd for $C_{28}H_{37}N_5O_4SiF_2$ [M+H$^+$] 574.2656 found 574.2656. $^1$H NMR (400 MHz, DMSO-d$_6$) δ ppm −0.07 (s, 6H) 0.80 (s, 9H) 1.49-1.67 (m, 1H) 1.68-2.02 (m, 5H) 2.03-2.30 (m, 3H) 3.86 (t, J=5.2 Hz, 2H) 4.06 (t, J=5.2 Hz, 2H) 5.28-5.38 (m, 1H) 6.01 (d, J=2.7 Hz, 1H) 6.36 (d, J=2.1 Hz, 1H) 7.33-7.43 (m, 2H) 7.43-7.51 (m, 1H) 7.53 (d, J=2.1 Hz, 1H) 8.26 (d, J=2.7 Hz, 1H) 10.78 (s, 1H).

Using the method described in Example 53, Step 2, N-{1-[2-(tert-butyl-dimethyl-silanyloxy)-ethyl]-1H-pyrazol-3-yl}-3-cyclobutyl-2-[4-(2,6-difluoro-phenoxy)-6-oxo-6H-pyridazin-1-yl]-propionamide afforded 3-cyclobutyl-2-[4-(2,6-difluoro-phenoxy)-6-oxo-6H-pyridazin-1-yl]-N-[1-(2-hydroxy-ethyl)-1H-pyrazol-3-yl]-propionamide as a light yellow solid (253.6 mg, 94%); ES$^+$-HRMS m/e calcd for $C_{22}H_{23}N_5O_4F_2$ [M+H$^+$] 460.1791 found 460.1789. $^1$H-NMR (400 MHz, DMSO-d$_6$) δ ppm 1.53-1.66 (m, 1H) 1.66-2.04 (m, 5H) 2.05-2.37 (m, 3H) 3.70 (t, J=5.5 Hz, 2H) 4.03 (t, J=5.5 Hz, 2H) 5.48 (br s, 1H) 5.34 (dd, J=10.2, 4.5 Hz, 1H) 6.02 (d, J=3.0 Hz, 1H) 6.37 (d, J=2.3 Hz, 1H) 7.35-7.43 (m, 2H) 7.44-7.53 (m, 1H) 7.56 (d, J=2.3 Hz, 1H) 8.27 (d, J=3.0 Hz, 1H) 10.80 (s, 1H).

Example 56

3-Cyclohexyl-2-[4-(2,6-difluoro-phenoxy)-6-oxo-6H-pyridazin-1-yl]-N-[1-(2-hydroxy-ethyl)-1H-pyrazol-3-yl]-propionamide

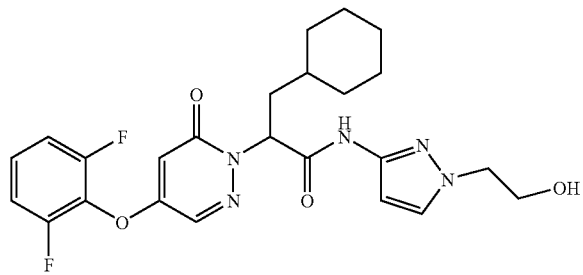

Using the method described in Example 49, 3-cyclohexyl-2-[4-(2,6-difluoro-phenoxy)-6-oxo-6H-pyridazin-1-yl]-propionic acid (Intermediate 33) and 1-[2-(tert-butyl-dimethyl-silanyloxy)-ethyl]-1H-pyrazol-3-ylamine (Intermediate 3) afforded N-{1-[2-(tert-butyl-dimethyl-silanyloxy)-ethyl]-1H-pyrazol-3-yl}-3-cyclohexyl-2-[4-(2,6-difluoro-phenoxy)-6-oxo-6H-pyridazin-1-yl]-propionamide as a white solid (1.42 g, 65%); ES$^+$-HRMS m/e calcd for $C_{30}H_{41}N_5O_4SiF_2$ [M+H$^+$] 602.2969 found 602.2971. $^1$H NMR (300 MHz, DMSO-d$_6$) δ ppm −0.07 (s, 6H) 0.80 (s, 9H) 0.84-1.30 (m, 6H) 1.63 (br s, 5H) 1.75-1.92 (m, 1H) 2.04-2.21 (m, 1H) 3.85 (t, J=5.1 Hz, 2H) 4.06 (t, J=5.1 Hz, 2H) 5.54 (dd, J=10.7, 4.1 Hz, 1H) 6.03 (d, J=2.7 Hz, 1H) 6.36 (d, J=2.1 Hz, 1H) 7.33-7.52 (m, 3H) 7.53 (d, J=2.1 Hz, 1H) 8.28 (d, J=2.7 Hz, 1H) 10.73-10.91 (m, 1H).

Using the method described in Example 53, Step 2, N-{1-[2-(tert-butyl-dimethyl-silanyloxy)-ethyl]-1H-pyrazol-3-yl}-3-cyclohexyl-2-[4-(2,6-difluoro-phenoxy)-6-oxo-6H-pyridazin-1-yl]-propionamide afforded 3-cyclohexyl-2-[4-(2,6-difluoro-phenoxy)-6-oxo-6H-pyridazin-1-yl]-N-[1-(2-hydroxy-ethyl)-1H-pyrazol-3-yl]-propionamide as a white solid (789 mg, 68%); ES$^+$-HRMS m/e calcd for $C_{24}H_{27}N_5O_4F_2$ [M+H$^+$] 488.2104 found 488.2105. $^1$H-NMR (300 MHz, DMSO-d$_6$) δ ppm 0.79-1.30 (m, 6H) 1.44-1.76 (m, 5H) 1.76-1.94 (m, 1H) 2.04-2.23 (m, 1H) 3.69 (q, J=5.3 Hz, 2H) 4.01 (t, J=5.3 Hz, 2H) 4.86 (t, J=5.3 Hz, 1H) 5.53 (dd, J=10.7, 3.8 Hz, 1H) 6.03 (d, J=1.8 Hz, 1H) 6.35 (s, 1H) 7.29-7.53 (m, 3H) 7.55 (s, 1H) 8.28 (d, J=2.7 Hz, 1H) 10.82 (s, 1H).

Separation of enantiomers via supercritical fluid chromatography on a SFC DAICEL AD column, 35% methanol, 70 mL/min.

Example 56A (S)-3-Cyclohexyl-2-[4-(2,6-difluoro-phenoxy)-6-oxo-6H-pyridazin-1-yl]-N-[1-(2-hydroxy-ethyl)-1H-pyrazol-3-yl]-propionamide

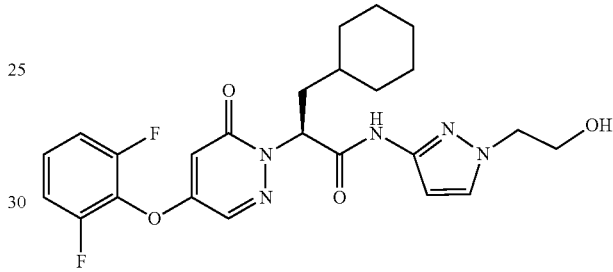

(S)-3-Cyclohexyl-2-[4-(2,6-difluoro-phenoxy)-6-oxo-6H-pyridazin-1-yl]-N-[1-(2-hydroxy-ethyl)-1H-pyrazol-3-yl]-propionamide; ES$^+$-HRMS m/e calcd for $C_{24}H_{27}N_5O_4F_2$ [M+H$^+$] 488.2104 found 488.2103. $^1$H NMR (300 MHz, DMSO-d$_6$) δ ppm 0.78-1.27 (m, 6H), 1.51-1.73 (m, 5H), 1.76-1.92 (m, 1H), 2.07-2.23 (m, 1H), 3.69 (q, J=5.4 Hz, 2H), 4.01 (t, J=5.4 Hz, 2H), 4.87 (t, J=5.4 Hz, 1H), 5.53 (dd, J=11.0, 4.1 Hz, 1H), 6.04 (d, J=2.6 Hz, 1H), 6.35 (d, J=2.1 Hz, 1H), 7.33-7.53 (m, 3H), 7.55 (d, J=2.1 Hz, 1H), 8.29 (d, J=2.6 Hz, 1H), 10.83 (s, 1H).

Example 56B (R)-3-Cyclohexyl-2-[4-(2,6-difluoro-phenoxy)-6-oxo-6H-pyridazin-1-yl]-N-[1-(2-hydroxy-ethyl)-1H-pyrazol-3-yl]-propionamide

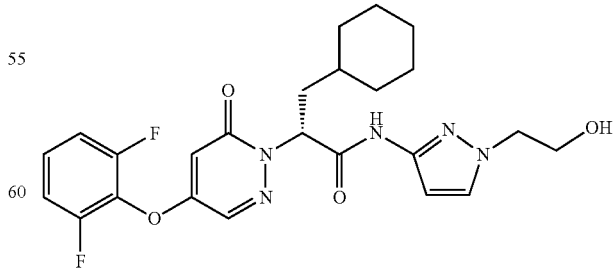

(R)-3-Cyclohexyl-2-[4-(2,6-difluoro-phenoxy)-6-oxo-6H-pyridazin-1-yl]-N-[1-(2-hydroxy-ethyl)-1H-pyrazol-3-yl]-propionamide; ES$^+$-HRMS m/e calcd for $C_{24}H_{27}N_5O_4F_2$

[M+Na⁺] 510.1923 found 510.1923. ¹H NMR (300 MHz, DMSO-d₆) δ ppm 0.78-1.29 (m, 6H), 1.63 (br. s., 5H), 1.75-1.92 (m, 1H), 2.07-2.22 (m, 1H), 3.69 (q, J=5.4 Hz, 2H), 4.01 (t, J=5.4 Hz, 2H), 4.87 (t, J=5.4 Hz, 1H), 5.53 (dd, J=10.9, 3.9 Hz, 1H), 6.04 (d, J=2.7 Hz, 1H), 6.35 (d, J=2.1 Hz, 1H), 7.31-7.53 (m, 3H), 7.55 (d, J=2.1 Hz, 1H), 8.29 (d, J=2.7 Hz, 1H), 10.83 (s, 1H).

Example 57

2-[4-(2,6-Difluoro-phenoxy)-6-oxo-6H-pyridazin-1-yl]-3-(2,6-difluoro-phenyl)-N-[1-(2-hydroxy-ethyl)-1H-pyrazol-3-yl]-propionamide

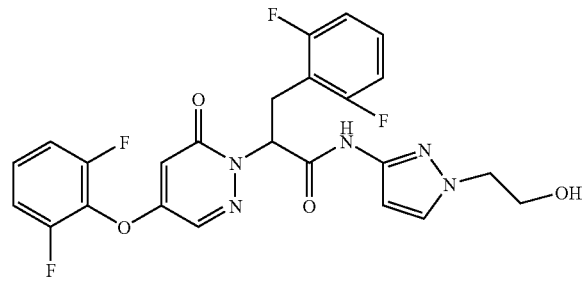

Using the method described in Example 49, 2-[4-(2,6-difluoro-phenoxy)-6-oxo-6H-pyridazin-1-yl]-3-(2,6-difluoro-phenyl)-propionic acid (Intermediate 34) and 1-[2-(tert-butyl-dimethyl-silanyloxy)-ethyl]-1H-pyrazol-3-ylamine (Intermediate 3) afforded N-{1-[2-(tert-butyl-dimethyl-silanyloxy)-ethyl]-1H-pyrazol-3-yl}-2-[4-(2,6-difluoro-phenoxy)-6-oxo-6H-pyridazin-1-yl]-3-(2,6-difluoro-phenyl)-propionamide as a light yellow solid (690 mg, 65%); ES⁺-HRMS m/e calcd for $C_{30}H_{33}N_5O_4SiF_4$ [M+H⁺] 632.2311 found 632.2311. ¹H NMR (300 MHz, DMSO-d₆) δ ppm −0.08 (s, 6H) 0.80 (s, 9H) 3.24-3.34 (m, 1H) 3.49 (dd, J=14.5, 5.7 Hz, 1H) 3.83 (t, J=5.1 Hz, 2H) 4.00-4.10 (m, 2H) 5.69 (dd, J=9.8, 5.6 Hz, 1H) 5.89 (d, J=2.7 Hz, 1H) 6.43 (d, J=2.1 Hz, 1H) 6.96 (t, J=8.0 Hz, 2H) 7.18-7.52 (m, 4H) 7.54 (d, J=2.1 Hz, 1H) 8.20 (d, J=2.7 Hz, 1H) 10.67 (s, 1H).

Using the method described in Example 53, Step 2, N-{1-[2-(tert-butyl-dimethyl-silanyloxy)-ethyl]-1H-pyrazol-3-yl}-2-[4-(2,6-difluoro-phenoxy)-6-oxo-6H-pyridazin-1-yl]-3-(2,6-difluoro-phenyl)-propionamide afforded 2-[4-(2,6-difluoro-phenoxy)-6-oxo-6H-pyridazin-1-yl]-3-(2,6-difluoro-phenyl)-N-[1-(2-hydroxy-ethyl)-1H-pyrazol-3-yl]-propionamide as an off-white solid (501.9 mg, 90%); ES⁺-HRMS m/e calcd for $C_{24}H_{19}N_5O_4F_4$ [M+H⁺] 518.1446 found 518.1446. ¹H-NMR (300 MHz, DMSO-d₆) δ ppm 3.38-3.58 (m, 2H) 3.67 (q, J=5.4 Hz, 2H) 4.00 (t, J=5.6 Hz, 2H) 4.86 (t, J=5.3 Hz, 1H) 5.68 (dd, J=9.7, 5.4 Hz, 1H) 5.89 (d, J=2.7 Hz, 1H) 6.43 (d, J=2.1 Hz, 1H) 6.96 (t, J=7.8 Hz, 2H) 7.16-7.53 (m, 4H) 7.56 (d, J=2.1 Hz, 1H) 8.19 (d, J=2.7 Hz, 1H), 10.66 (s, 1H).

Example 58

2-[4-(2,6-Difluoro-phenoxy)-6-oxo-6H-pyridazin-1-yl]-N-[1-(2-hydroxy-ethyl)-1H-pyrazol-3-yl]-3-phenyl-propionamide

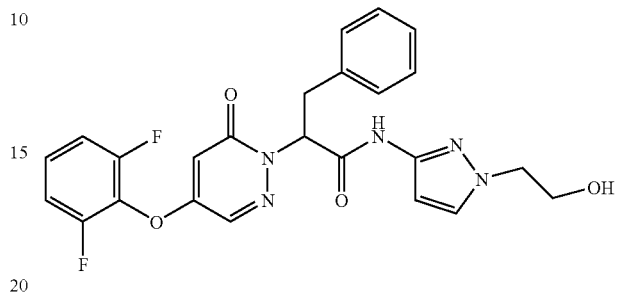

Using the method described in Example 49, 2-[4-(2,6-difluoro-phenoxy)-6-oxo-6H-pyridazin-1-yl]-3-phenyl-propionic acid (Intermediate 30) and 1-[2-(tert-butyl-dimethyl-silanyloxy)-ethyl]-1H-pyrazol-3-ylamine (Intermediate 3) afforded N-{1-[2-(tert-butyl-dimethyl-silanyloxy)-ethyl]-1H-pyrazol-3-yl}-2-[4-(2,6-difluoro-phenoxy)-6-oxo-6H-pyridazin-1-yl]-3-phenyl-propionamide as a light yellow solid (1.07 g, 57%); ES⁺-HRMS m/e calcd for $C_{30}H_{35}N_5O_4SiF_2$ [M+H⁺] 596.2499 found 596.2499. ¹H NMR (300 MHz, DMSO-d₆) δ ppm −0.06 (s, 6H) 0.80 (s, 9H) 3.36-3.50 (m, 2H) 3.86 (t, J=5.1 Hz, 2H) 4.08 (t, J=5.1 Hz, 2H) 5.75-5.88 (m, 1H) 5.93 (d, J=2.7 Hz, 1H) 6.40 (d, J=2.1 Hz, 1H) 7.06-7.53 (m, 8H) 7.56 (d, J=2.1 Hz, 1H) 8.25 (d, J=2.7 Hz, 1H) 10.99 (s, 1H).

Using the method described in Example 53, Step 2, N-{1-[2-(tert-butyl-dimethyl-silanyloxy)-ethyl]-1H-pyrazol-3-yl}-2-[4-(2,6-difluoro-phenoxy)-6-oxo-6H-pyridazin-1-yl]-3-phenyl-propionamide afforded 2-[4-(2,6-difluoro-phenoxy)-6-oxo-6H-pyridazin-1-yl]-N-[1-(2-hydroxy-ethyl)-1H-pyrazol-3-yl]-3-phenyl-propionamide (711 mg, 83%); ES⁺-HRMS m/e calcd for $C_{24}H_{21}N_5O_4F_2$ [M+H⁺] 482.1635 found 482.1634. ¹H-NMR (300 MHz, DMSO-d₆) δ ppm 3.38-3.58 (m, 2H) 3.70 (q, J=5.4 Hz, 2H) 4.03 (t, J=5.4 Hz, 2H) 4.87 (t, J=5.4 Hz, 1H) 5.80 (dd, J=9.8, 5.6 Hz, 1H) 5.93 (d, J=2.7 Hz, 1H) 6.40 (d, J=2.1 Hz, 1H) 7.08-7.53 (m, 8H) 7.58 (d, J=2.1 Hz, 1H) 8.24 (d, J=2.7 Hz, 1H) 10.99 (s, 1H).

Example 59

2-[4-(2,6-Difluoro-phenoxy)-6-oxo-6H-pyridazin-1-yl]-4-methyl-pentanoic acid [1-(2-hydroxy-ethyl)-1H-pyrazol-3-yl]-amide

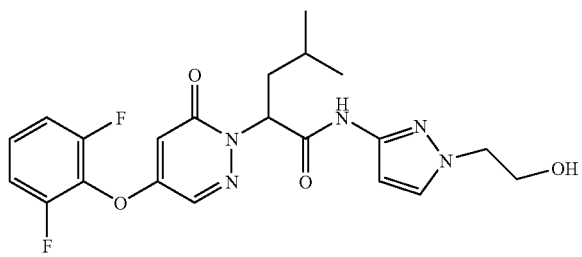

Using the method described in Example 49, 2-[4-(2,6-difluoro-phenoxy)-6-oxo-6H-pyridazin-1-yl]-4-methyl-pentanoic acid (Intermediate 28) and 1-[2-(tert-butyl-dimethyl-silanyloxy)-ethyl]-1H-pyrazol-3-ylamine (Intermediate 3) afforded 2-[4-(2,6-difluoro-phenoxy)-6-oxo-6H-pyridazin-1-yl]-4-methyl-pentanoic acid {1-[2-(tert-butyl-dimethyl-silanyloxy)-ethyl]-1H-pyrazol-3-yl}-amide as an off-white solid (1.15 g, 68%); ES+-HRMS m/e calcd for C₂₇H₃₇N₅O₄SiF₂ [M+H⁺] 562.2656 found 562.2658. ¹H NMR (300 MHz, DMSO-d₆) δ ppm −0.06 (s, 6H) 0.81 (s, 9H) 0.84-0.92 (m, 6H) 1.45 (m, 1H) 1.70-1.87 (m, 1H) 2.09-2.24 (m, 1H) 3.86 (t, J=5.1 Hz, 2H) 4.07 (t, J=5.1 Hz, 2H) 5.53 (dd, J=11.2, 4.2 Hz, 1H) 6.04 (d, J=2.7 Hz, 1H) 6.36 (d, J=2.0 Hz, 1H) 7.31-7.52 (m, 3H) 7.54 (d, J=2.0 Hz, 1H) 8.28 (d, J=2.7 Hz, 1H) 10.82 (s, 1H).

Using the method described in Example 53, Step 2, 2-[4-(2,6-difluoro-phenoxy)-6-oxo-6H-pyridazin-1-yl]-4-methyl-pentanoic acid {1-[2-(tert-butyl-dimethyl-silanyloxy)-ethyl]-1H-pyrazol-3-yl}-amide afforded 2-[4-(2,6-difluoro-phenoxy)-6-oxo-6H-pyridazin-1-yl]-4-methyl-pentanoic acid [1-(2-hydroxy-ethyl)-1H-pyrazol-3-yl]-amide as an off-white solid (763 mg, 84%); ES+-HRMS m/e calcd for C₂₁H₂₃N₅O₄F₂ [M+H⁺] 448.1791 found 448.1790. ¹H-NMR (300 MHz, DMSO-d₆) δ ppm 0.87 (t, J=6.8 Hz, 6H) 1.44 (br s, 1H) 1.72-1.90 (m, 1H) 2.09-2.25 (m, 1H) 3.69 (q, J=5.4 Hz, 2H) 4.02 (t, J=5.4 Hz, 1H) 4.86 (t, J=5.4 Hz, 1H) 5.51 (dd, J=11.0, 4.1 Hz, 1H) 6.04 (d, J=2.7 Hz, 1H) 6.36 (d, J=2.1 Hz, 1H) 7.30-7.53 (m, 3H) 7.55 (d, J=2.1 Hz, 1H) 8.28 (d, J=2.7 Hz, 1H) 10.83 (s, 1H).

Separation of enantiomers via supercritical fluid chromatography on a SFC PYRAMIDE column, 25% methanol, 70 mL/min.

Example 59A (S)-2-[4-(2,6-Difluoro-phenoxy)-6-oxo-6H-pyridazin-1-yl]-4-methyl-pentanoic acid [1-(2-hydroxy-ethyl)-1H-pyrazol-3-yl]-amide

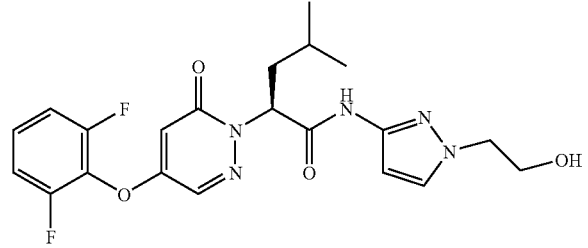

(S)-2-[4-(2,6-Difluoro-phenoxy)-6-oxo-6H-pyridazin-1-yl]-4-methyl-pentanoic acid [1-(2-hydroxy-ethyl)-1H-pyrazol-3-yl]-amide; ES+-HRMS m/e calcd for C₂₁H₂₃N₅O₄F₂ [M+H⁺] 448.1791 found 448.1792. ¹H NMR (300 MHz, DMSO-d₆) δ ppm 0.80-0.94 (m, 6H), 1.45 (br. s., 1H), 1.72-1.87 (m, 1H), 2.09-2.26 (m, 1H), 3.69 (br. s., 2H), 4.02 (t, J=5.6 Hz, 2H), 4.86 (br. s., 1H), 5.51 (dd, J=11.2, 4.2 Hz, 1H), 6.04 (d, J=2.7 Hz, 1H), 6.36 (d, J=2.1 Hz, 1H), 7.33-7.53 (m, 3H), 7.55 (d, J=2.1 Hz, 1H), 8.28 (d, J=2.7 Hz, 1H), 10.83 (s, 1H).

Example 59B (R)-2-[4-(2,6-Difluoro-phenoxy)-6-oxo-6H-pyridazin-1-yl]-4-methyl-pentanoic acid [1-(2-hydroxy-ethyl)-1H-pyrazol-3-yl]-amide

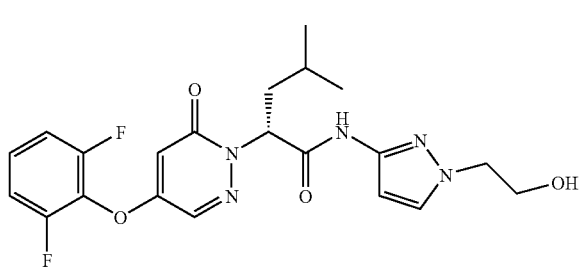

(R)-2-[4-(2,6-Difluoro-phenoxy)-6-oxo-6H-pyridazin-1-yl]-4-methyl-pentanoic acid [1-(2-hydroxy-ethyl)-1H-pyrazol-3-yl]-amide; ES+-HRMS m/e calcd for C₂₁H₂₃N₅O₄F₂ [M+Na⁺] 470.1610 found 470.1611. ¹H NMR (400 MHz, DMSO-d₆) δ ppm 0.87 (d, J=6.8 Hz, 3H), 0.89 (d, J=6.8 Hz, 3H), 1.45 (br. s., 1H), 1.72-1.87 (m, 1H), 2.10-2.25 (m, 1H), 3.69 (q, J=5.5 Hz, 2H), 4.02 (t, J=5.5 Hz, 2H), 4.86 (t, J=5.5 Hz, 1H), 5.51 (dd, J=11.2, 4.2 Hz, 1H), 6.04 (d, J=2.8 Hz, 1H), 6.36 (d, J=2.1 Hz, 1H), 7.34-7.43 (m, 2H), 7.43-7.53 (m, 1H), 7.56 (d, J=2.1 Hz, 1H), 8.28 (d, J=2.8 Hz, 1H), 10.82 (s, 1H).

Example 60

3-Cyclopentyl-2-[4-(2,6-difluoro-phenoxy)-6-oxo-6H-pyridazin-1-yl]-N-[1-(2-hydroxy-ethyl)-1H-pyrazol-3-yl]-propionamide

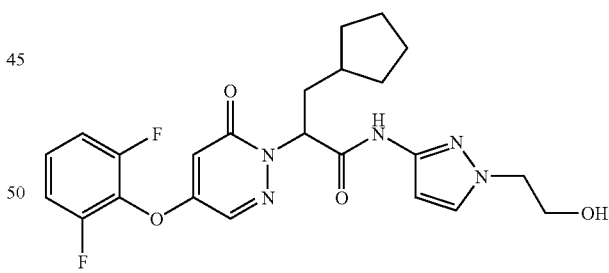

Using the method described in Example 17, 3-cyclopentyl-2-[4-(2,6-difluoro-phenoxy)-6-oxo-6H-pyridazin-1-yl]-propionic acid (Intermediate 47) and 1-[2-(tert-butyl-dimethyl-silanyloxy)-ethyl]-1H-pyrazol-3-ylamine (Intermediate 3) afforded N-{1-[2-(tert-butyl-dimethyl-silanyloxy)-ethyl]-1H-pyrazol-3-yl}-3-cyclopentyl-2-[4-(2,6-difluoro-phenoxy)-6-oxo-6H-pyridazin-1-yl]-propionamide as a white solid (840.3 mg, 52%); ES+-HRMS m/e calcd for C₂₉H₃₉N₅O₄SiF₂ [M+H⁺] 588.2812 found 588.2817. ¹H NMR (300 MHz, DMSO-d₆) δ ppm −0.07 (s, 6H), 0.80 (s, 9H), 1.08 (br s, 2H), 1.22-1.79 (m, 7H), 1.83-2.03 (m, 1H), 2.17-2.34 (m, 1H), 3.85 (t, J=5.1 Hz, 2H), 4.06 (t, J=5.1 Hz, 2H), 5.46 (dd, J=10.7, 4.4 Hz, 1H), 6.03 (d, J=2.7 Hz, 1H), 6.36 (d, J=2.1 Hz, 1H), 7.32-7.51 (m, 3H), 7.53 (d, J=2.1 Hz, 1H), 8.28 (d, J=2.7 Hz, 1H), 10.84 (s, 1H).

Using the method described in Example 53, Step 2, N-{1-[2-(tert-butyl-dimethyl-silanyloxy)-ethyl]-1H-pyrazol-3-yl}-3-cyclopentyl-2-[4-(2,6-difluoro-phenoxy)-6-oxo-6H-pyridazin-1-yl]-propionamide afforded 3-cyclopentyl-2-[4-(2,6-difluoro-phenoxy)-6-oxo-6H-pyridazin-1-yl]-N-[1-(2-hydroxy-ethyl)-1H-pyrazol-3-yl]-propionamide as a white solid (668 mg, 99%); ES⁺-HRMS m/e calcd for $C_{23}H_{25}N_5O_4F_2$ [M+H⁺] 474.1948 found 474.1949. ¹H-NMR (400 MHz, DMSO-$d_6$) δ ppm 1.09 (br s, 1H), 1.24-1.75 (m, 8H), 1.85-2.03 (m, 1H), 2.18-2.33 (m, 1H), 3.69 (d, J=5.5 Hz, 2H), 4.02 (t, J=5.5 Hz, 2H), 4.86 (t, J=5.5 Hz, 1H), 5.46 (dd, J=11.1, 4.3 Hz, 1H), 6.03 (d, J=3.0 Hz, 1H), 6.36 (d, J=2.3 Hz, 1H), 7.33-7.43 (m, 2H), 7.46 (s, 1H), 7.55 (d, J=2.3 Hz, 1H), 8.28 (d, J=3.0 Hz, 1H), 10.82 (s, 1H).

Separation of enantiomers via supercritical fluid chromatography on a SFC DAICEL AD column, 30% methanol, 70 mL/min.

Example 60A (S)-3-Cyclopentyl-2-[4-(2,6-difluoro-phenoxy)-6-oxo-6H-pyridazin-1-yl]-N-[1-(2-hydroxy-ethyl)-1H-pyrazol-3-yl]-propionamide

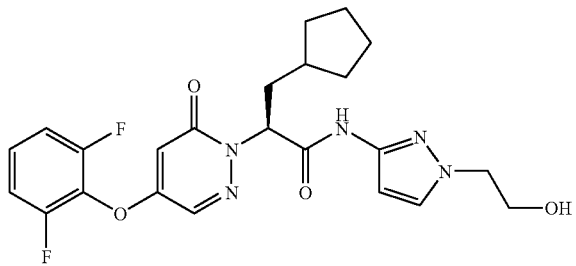

(S)-3-Cyclopentyl-2-[4-(2,6-difluoro-phenoxy)-6-oxo-6H-pyridazin-1-yl]-N-[1-(2-hydroxy-ethyl)-1H-pyrazol-3-yl]-propionamide; ES⁺-HRMS m/e calcd for $C_{23}H_{25}N_5O_4F_2$ [M+Na⁺] 496.1767 found 496.1768. ¹H-NMR (300 MHz, DMSO-$d_6$) δ ppm 0.99-1.20 (m, 1H) 1.24-1.80 (m, 8H) 1.79-2.04 (m, 1H) 2.17-2.34 (m, 1H) 3.69 (t, J=5.4 Hz, 2H) 4.01 (t, J=5.4 Hz, 2H) 4.78 (br s, 1H) 5.45 (dd, J=10.7, 4.1 Hz, 1H) 6.03 (d, J=2.7 Hz, 1H) 6.36 (d, J=1.8 Hz, 1H) 7.32-7.52 (m, 3H) 7.55 (d, J=1.8 Hz, 1H) 8.28 (d, J=2.7 Hz, 1H) 10.85 (s, 1H)

Example 60B (R)-3-Cyclopentyl-2-[4-(2,6-difluoro-phenoxy)-6-oxo-6H-pyridazin-1-yl]-N-[1-(2-hydroxy-ethyl)-1H-pyrazol-3-yl]-propionamide

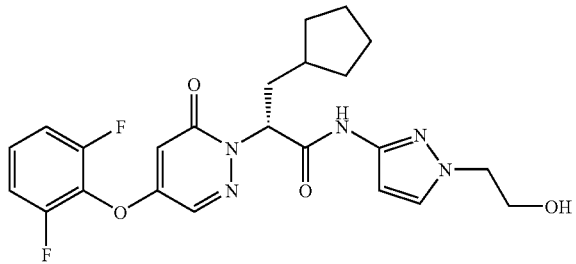

(R)-3-Cyclopentyl-2-[4-(2,6-difluoro-phenoxy)-6-oxo-6H-pyridazin-1-yl]-N-[1-(2-hydroxy-ethyl)-1H-pyrazol-3-yl]-propionamide; ES⁺-HRMS m/e calcd for $C_{23}H_{25}N_5O_4F_2$ [M+Na⁺] 496.1767 found 496.1765. ¹H-NMR (300 MHz, DMSO-$d_6$) δ ppm 0.96-1.20 (m, 1H) 1.20-1.78 (m, 8H) 1.85-2.04 (m, 1H) 2.18-2.35 (m, 1H) 3.69 (br s, 2H) 4.01 (t, J=5.4 Hz, 2H) 4.87 (br s, 1H) 5.45 (dd, J=10.7, 4.1 Hz, 1H) 6.04 (br s, 1H) 6.36 (d, J=2.1 Hz, 1H) 7.33-7.53 (m, 3H) 7.55 (d, J=2.1 Hz, 1H) 8.28 (d, J=2.7 Hz, 1H) 10.85 (s, 1H).

Example 61

2-[4-(2,6-Difluoro-phenoxy)-6-oxo-6H-pyridazin-1-yl]-4-methyl-pentanoic acid [1-((R)-2,3-dihydroxy-propyl)-1H-pyrazol-3-yl]-amide

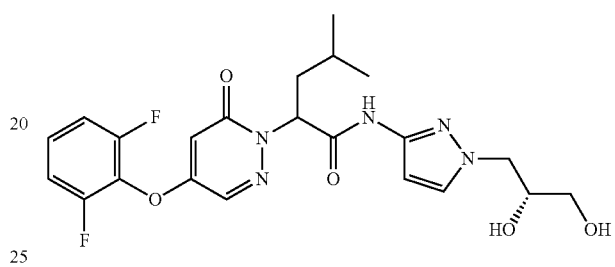

Step 1: Using the method described in Example 49, 2-[4-(2,6-difluoro-phenoxy)-6-oxo-6H-pyridazin-1-yl]-4-methyl-pentanoic acid (Intermediate 28) and 1-((R)-2,2-dimethyl-[1,3]dioxolan-4-ylmethyl)-1H-pyrazol-3-ylamine (Intermediate 4) afforded 2-[4-(2,6-difluoro-phenoxy)-6-oxo-6H-pyridazin-1-yl]-4-methyl-pentanoic acid [1-((R)-2,2-dimethyl-[1,3]dioxolan-4-ylmethyl)-1H-pyrazol-3-yl]-amide as an off-white solid as a mixture of diastereoisomers (1.21 g, 79%); ES⁺-HRMS m/e calcd for $C_{25}H_{29}N_5O_5F_2$ [M+H⁺] 518.2210 found 518.2214. ¹H NMR (400 MHz, DMSO-$d_6$) δ ppm 0.87 (d, J=6.6 Hz, 3H), 0.89 (d, J=6.6 Hz, 3H), 1.25 (s, 3H), 1.30, 1.31 (2×s, 3H), 1.38-1.51 (m, 1H), 1.74-1.85 (m, 1H), 2.12-2.24 (m, 1H), 3.74 (dd, J=8.4, 5.9 Hz, 1H), 3.97-4.17 (m, 3H), 4.35 (m, 1H), 5.52 (dd, J=11.2, 4.2 Hz, 1H), 6.04 (d, J=2.7 Hz, 1H), 6.39 (d, J=2.1 Hz, 1H), 7.35-7.43 (m, 2H), 7.43-7.55 (m, 1H), 7.60 (m, 1H), 8.28 (d, J=2.7 Hz, 1H), 10.85 (s, 1H).

Step 2: A solution of 2-[4-(2,6-difluoro-phenoxy)-6-oxo-6H-pyridazin-1-yl]-4-methyl-pentanoic acid [1-((R)-2,2-dimethyl-[1,3]dioxolan-4-ylmethyl)-1H-pyrazol-3-yl]-amide (1.21 g, 2.33 mmol) in methanol (23 mL, 0.1 M) at 25° C. was treated with para-toluenesulfonic acid monohydrate (66.3 mg, 0.34 mmol). The reaction was stirred at 25° C. overnight. After this time, the reaction was diluted with ethyl acetate (200 mL) and was washed with a saturated aqueous sodium bicarbonate solution (2×100 mL), water (1×100 mL) and a saturated aqueous sodium chloride solution (1×100 mL). The organics were dried over magnesium sulfate, filtered, rinsed and then concentrated in vacuo. Silica gel column chromatography (AnaLogix 80 g, 1-10% methanol/methylene chloride) afforded 2-[4-(2,6-difluoro-phenoxy)-6-oxo-6H-pyridazin-1-yl]-4-methyl-pentanoic acid [1-((R)-2,3-dihydroxy-propyl)-1H-pyrazol-3-yl]-amide (0.86 g, 77%) as a white solid as a mixture of diastereomers; ES⁺-HRMS m/e calcd for $C_{22}H_{25}N_5O_5F_2$ [M+H⁺] 478.1897 found 478.1896. ¹H-NMR (400 MHz, DMSO-$d_6$) δ ppm 0.87 (d, J=6.8 Hz, 3H) 0.89 (d, J=6.8 Hz, 3H) 1.38-1.51 (m, 1H) 1.80 (ddd, J=13.6, 9.4, 4.3 Hz, 1H) 2.10-2.26 (m, 1H) 3.21-3.51 (m, 2H) 3.71-3.81 (m, 1H) 3.82-3.92 (m, 1H) 4.09 (dd, J=13.6, 3.9 Hz, 1H) 4.70 (t, J=5.6 Hz, 1H) 4.91-4.96 (m, 1H) 5.52 (dd, J=11.0, 3.9 Hz, 1H) 6.04 (d, J=2.7 Hz, 1H) 6.36 (d, J=2.1 Hz, 1H) 7.35-7.43 (m, 2H) 7.43-7.52 (m, 1H) 7.53 (d, J=2.1 Hz, 1H) 8.28 (d, J=2.7 Hz, 1H) 10.82 (s, 1H).

Separation of enantiomers via supercritical fluid chromatography on a SFC DAICEL AD column, 30% methanol, 70 mL/min.

Example 61A (S)-2-[4-(2,6-Difluoro-phenoxy)-6-oxo-6H-pyridazin-1-yl]-4-methyl-pentanoic acid [1-((R)-2,3-dihydroxy-propyl)-1H-pyrazol-3-yl]-amide

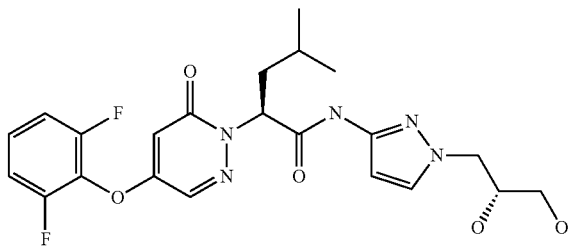

(S)-2-[4-(2,6-Difluoro-phenoxy)-6-oxo-6H-pyridazin-1-yl]-4-methyl-pentanoic acid [1-((R)-2,3-dihydroxy-propyl)-1H-pyrazol-3-yl]-amide; ES⁺-HRMS m/e calcd for $C_{22}H_{25}N_5O_5F_2$ [M+H⁺] 478.1897 found 478.1896. ¹H NMR (400 MHz, DMSO-$d_6$) δ ppm 0.87 (d, J=6.6 Hz, 3H) 0.89 (d, J=6.6 Hz, 3H) 1.45 (br. s., 1H) 1.73-1.87 (m, 1H) 2.11-2.24 (m, 1H) 3.20-3.38 (m, 2H) 3.68-3.82 (m, 1H) 3.81-3.94 (m, 1H) 4.09 (dd, J=13.5, 4.0 Hz, 1H) 4.70 (t, J=5.6 Hz, 1H) 4.93 (d, J=5.5 Hz, 1H) 5.52 (dd, J=11.1, 4.0 Hz, 1H) 6.04 (d, J=2.9 Hz, 1H) 6.36 (d, J=2.1 Hz, 1H) 7.31-7.44 (m, 2H) 7.44-7.51 (m, 1H) 7.53 (d, J=2.1 Hz, 1H) 8.28 (d, J=2.9 Hz, 1H) 10.82 (s, 1H).

Example 61B (R)-2-[4-(2,6-Difluoro-phenoxy)-6-oxo-6H-pyridazin-1-yl]-4-methyl-pentanoic acid [1-((R)-2,3-dihydroxy-propyl)-1H-pyrazol-3-yl]-amide

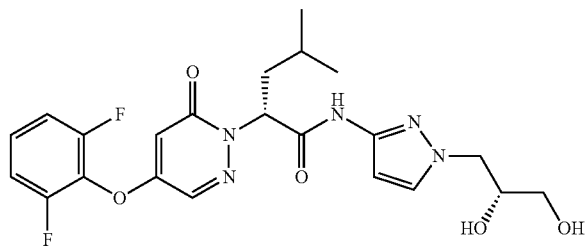

(R)-2-[4-(2,6-Difluoro-phenoxy)-6-oxo-6H-pyridazin-1-yl]-4-methyl-pentanoic acid [1-((R)-2,3-dihydroxy-propyl)-1H-pyrazol-3-yl]-amide; ES⁺-HRMS m/e calcd for $C_{22}H_{25}N_5O_5F_2$ [M+H⁺] 478.1897 found 478.1896. ¹H NMR (400 MHz, DMSO-$d_6$) δ ppm 0.87 (d, J=6.6 Hz, 3H), 0.89 (d, J=6.6 Hz, 3H), 1.45 (br. s., 1H), 1.73-1.86 (m, 1H), 2.07-2.25 (m, 1H), 3.21-3.32 (m, 2H), 3.72-3.82 (m, 1H), 3.86 (dd, J=13.6, 7.7 Hz, 1H), 4.09 (dd, J=13.6, 4.0 Hz, 1H), 4.71 (t, J=5.6 Hz, 1H), 4.94 (d, J=5.3 Hz, 1H), 5.51 (dd, J=11.0, 4.0 Hz, 1H), 6.04 (d, J=2.9 Hz, 1H), 6.36 (d, J=2.1 Hz, 1H), 7.34-7.44 (m, 2H), 7.44-7.51 (m, 1H), 7.53 (d, J=2.1 Hz, 1H), 8.28 (d, J=2.9 Hz, 1H), 10.82 (s, 1H).

Example 62

2-[4-(2,6-Difluoro-phenoxy)-6-oxo-6H-pyridazin-1-yl]-N-[1-((R)-2,3-dihydroxy-propyl)-1H-pyrazol-3-yl]-3-(tetrahydro-pyran-4-yl)-propionamide

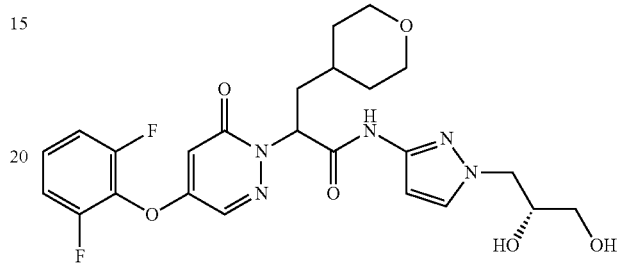

Using the method described in Example 49, 2-[4-(2,6-difluoro-phenoxy)-6-oxo-6H-pyridazin-1-yl]-3-(tetrahydro-pyran-4-yl)-propionic acid (Intermediate 32) and 1-((R)-2,2-dimethyl-[1,3]dioxolan-4-ylmethyl)-1H-pyrazol-3-ylamine (Intermediate 4) afforded 2-[4-(2,6-difluoro-phenoxy)-6-oxo-6H-pyridazin-1-yl]-N-[1-((R)-2,2-dimethyl-[1,3]dioxolan-4-ylmethyl)-1H-pyrazol-3-yl]-3-(tetrahydro-pyran-4-yl)-propionamide as an off-white solid as a mixture of diastereomers (0.60 g, 53%); ES⁺-HRMS m/e calcd for $C_{27}H_{31}N_5O_6F_2$ [M+H⁺] 560.2315 found 560.2319. ¹H NMR (400 MHz, DMSO-$d_6$) δ ppm 1.13-1.29 (m, 2H), 1.25 (s, 3H), 1.30, 1.31 (2×s, 3H), 1.35-1.59 (m, 3H), 1.84-1.94 (m, 1H), 2.15-2.26 (m, 1H), 3.09-3.27 (m, 2H), 3.70-3.85 (m, 3H), 3.97-4.18 (m, 3H), 4.31-4.40 (m, 1H), 5.54 (dd, J=11.1, 4.0 Hz, 1H), 6.04 (d, J=2.7 Hz, 1H), 6.39 (d, J=2.1 Hz, 1H), 7.34-7.43 (m, 2H), 7.43-7.53 (m, 1H), 7.60 (br s, 1H), 8.29 (d, J=2.7 Hz, 1H), 10.86, 10.87 (2×s, 1H).

Using the method described in Example 61, Step 2, 2-[4-(2,6-difluoro-phenoxy)-6-oxo-6H-pyridazin-1-yl]-N-[1-((R)-2,2-dimethyl-[1,3]dioxolan-4-ylmethyl)-1H-pyrazol-3-yl]-3-(tetrahydro-pyran-4-yl)-propionamide afforded 2-[4-(2,6-difluoro-phenoxy)-6-oxo-6H-pyridazin-1-yl]-N-[1-((R)-2,3-dihydroxy-propyl)-1H-pyrazol-3-yl]-3-(tetrahydro-pyran-4-yl)-propionamide as a white solid as a mixture of diastereomers (355.7 mg, 64%); ES⁺-HRMS m/e calcd for $C_{24}H_{27}N_5O_6F_2$ [M+H⁺] 520.2002 found 520.2002. ¹H-NMR (400 MHz, DMSO-$d_6$) δ ppm 1.12-1.35 (m, 2H) 1.35-1.46 (m, 1H) 1.47-1.58 (m, 2H) 1.81-1.97 (m, 1H) 2.14-2.29 (m, 1H) 3.07-3.31 (m, 3H) 3.39-3.50 (m, 1H) 3.69-3.94 (m, 4H) 4.09 (dd, J=13.6, 3.8 Hz, 1H) 4.70 (t, J=5.5 Hz, 1H) 4.94 (dd, J=5.3, 2.3 Hz, 1H) 5.54 (dd, J=10.9, 2.3 Hz, 1H) 6.04 (d, J=2.7 Hz, 1H) 6.36 (d, J=1.8 Hz, 1H) 7.33-7.43 (m, 2H) 7.44-7.51 (m, 1H) 7.53 (d, J=1.8 Hz, 1H) 8.29 (d, J=2.7 Hz, 1H) 10.84 (s, 1H).

Separation of enantiomers via supercritical fluid chromatography on a SFC DAICEL AD column, 30% methanol, 70 mL/min.

Example 62A (S)-2-[4-(2,6-Difluoro-phenoxy)-6-oxo-6H-pyridazin-1-yl]-N-[1-((R)-2,3-dihydroxy-propyl)-1H-pyrazol-3-yl]-3-(tetrahydro-pyran-4-yl)-propionamide

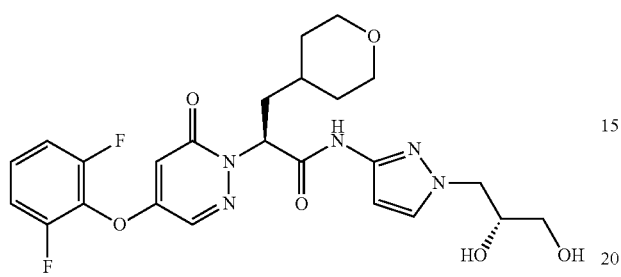

(S)-2-[4-(2,6-Difluoro-phenoxy)-6-oxo-6H-pyridazin-1-yl]-N-[1-((R)-2,3-dihydroxy-propyl)-1H-pyrazol-3-yl]-3-(tetrahydro-pyran-4-yl)-propionamide; ES$^+$-HRMS m/e calcd for $C_{24}H_{27}N_5O_6F_2$ [M+H$^+$] 520.2002 found 520.2002. $^1$H NMR (300 MHz, DMSO-d$_6$) δ ppm 1.11-1.66 (m, 5H), 1.75-1.98 (m, 1H), 2.10-2.33 (m, 1H), 3.09-3.32 (m, 4H), 3.69-3.94 (m, 4H), 4.09 (dd, J=13.4, 3.8 Hz, 1H), 4.71 (t, J=5.4 Hz, 1H), 4.94 (d, J=5.1 Hz, 1H), 5.54 (dd, J=10.9, 3.8 Hz, 1H), 6.04 (d, J=2.7 Hz, 1H), 6.36 (d, J=2.1 Hz, 1H), 7.28-7.50 (m, 3H), 7.53 (d, J=2.1 Hz, 1H), 8.29 (d, J=2.7 Hz, 1H), 10.85 (s, 1H).

Example 62B (R)-2-[4-(2,6-Difluoro-phenoxy)-6-oxo-6H-pyridazin-1-yl]-N-[1-((R)-2,3-dihydroxy-propyl)-1H-pyrazol-3-yl]-3-(tetrahydro-pyran-4-yl)-propionamide

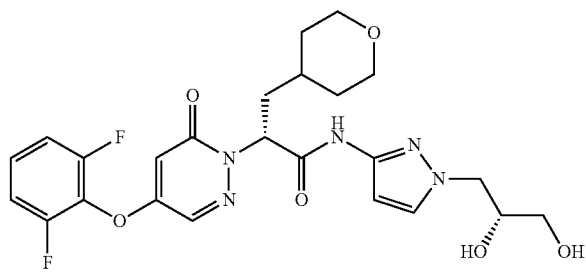

(R)-2-[4-(2,6-Difluoro-phenoxy)-6-oxo-6H-pyridazin-1-yl]-N-[1-((R)-2,3-dihydroxy-propyl)-1H-pyrazol-3-yl]-3-(tetrahydro-pyran-4-yl)-propionamide; ES$^+$-HRMS m/e calcd for $C_{24}H_{27}N_5O_6F_2$ [M+H$^+$] 520.2002 found 520.2003. $^1$H NMR (300 MHz, DMSO-d$_6$) δ ppm 1.09-1.62 (m, 5H), 1.78-1.98 (m, 1H), 2.09-2.30 (m, 1H), 3.08-3.32 (m, 4H), 3.69-3.94 (m, 4H), 4.09 (dd, J=13.4, 3.9 Hz, 1H), 4.71 (t, J=5.4 Hz, 1H), 4.95 (d, J=5.1 Hz, 1H), 5.53 (dd, J=10.7, 3.9 Hz, 1H), 6.04 (d, J=2.7 Hz, 1H), 6.36 (d, J=2.1 Hz, 1H), 7.31-7.49 (m, 3H), 7.53 (d, J=2.1 Hz, 1H), 8.29 (d, J=2.7 Hz, 1H), 10.85 (s, 1H).

Example 63

3-Cyclohexyl-2-[4-(2,6-difluoro-phenoxy)-6-oxo-6H-pyridazin-1-yl]-N-[1-((R)-2,3-dihydroxy-propyl)-1H-pyrazol-3-yl]-propionamide

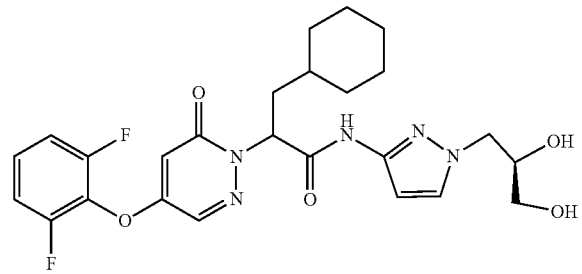

Using the method described in Example 49, 3-cyclohexyl-2-[4-(2,6-difluoro-phenoxy)-6-oxo-6H-pyridazin-1-yl]-propionic acid (Intermediate 33) and 1-((R)-2,2-dimethyl-[1,3]dioxolan-4-ylmethyl)-1H-pyrazol-3-ylamine (Intermediate 4) afforded 3-cyclohexyl-2-[4-(2,6-difluoro-phenoxy)-6-oxo-6H-pyridazin-1-yl]-N-[1-((R)-2,2-dimethyl-[1,3]dioxolan-4-ylmethyl)-1H-pyrazol-3-yl]-propionamide as a white solid as a mixture of diastereomers (2.01 g, 94%); ES$^+$-HRMS m/e calcd for $C_{28}H_{33}N_5O_5F_2$ [M+H$^+$] 558.2523 found 558.2521. $^1$H NMR (300 MHz, DMSO-d$_6$) δ ppm 0.80-1.19 (m, 6H) 1.23 (s, 3H) 1.29 (s, 3H) 1.61 (br s, 5H) 1.75-1.91 (m, 1H) 2.06-2.21 (m, 1H) 3.71 (dd, J=8.5, 5.8 Hz, 1H) 3.90-4.21 (m, 3H) 4.33 (quin, J=5.8 Hz, 1H) 5.52 (dd, J=10.9, 3.9 Hz, 1H) 6.02 (d, J=2.7 Hz, 1H) 6.36 (d, J=2.1 Hz, 1H) 7.28-7.54 (m, 3H) 7.57 (d, J=2.1 Hz, 1H) 8.27 (d, J=2.7 Hz, 1H) 10.83 (s, 1H).

Using the method described in Example 61, Step 2,3-cyclohexyl-2-[4-(2,6-difluoro-phenoxy)-6-oxo-6H-pyridazin-1-yl]-N-[1-((R)-2,2-dimethyl-[1,3]dioxolan-4-ylmethyl)-1H-pyrazol-3-yl]-propionamide afforded 3-cyclohexyl-2-[4-(2,6-difluoro-phenoxy)-6-oxo-6H-pyridazin-1-yl]-N-[1-((R)-2,3-dihydroxy-propyl)-1H-pyrazol-3-yl]-propionamide as a white solid as a mixture of diastereomers (1.49 g, 80%); ES$^+$-HRMS m/e calcd for $C_{25}H_{29}N_5O_5F_2$ [M+H$^+$] 518.2210 found 518.2211. $^1$H-NMR (300 MHz, DMSO-d$_6$) δ ppm 0.84-1.26 (m, 6H) 1.49-1.74 (m, 5H) 1.75-1.93 (m, 1H) 2.06-2.23 (m, 1H) 3.21-3.50 (m, 2H) 3.67-3.94 (m, 2H) 4.09 (dd, J=13.4, 3.8 Hz, 1H) 4.71 (t, J=5.4 Hz, 1H) 4.94 (d, J=4.5 Hz, 1H) 5.53 (dd, J=10.9, 3.3 Hz, 1H) 6.04 (d, J=2.7 Hz, 1H) 6.35 (d, J=2.1 Hz, 1H) 7.31-7.50 (m, 3H) 7.52 (d, J=2.1 Hz, 1H) 8.29 (d, J=2.7 Hz, 1H) 10.82 (s, 1H).

Separation of enantiomers via supercritical fluid chromatography on a SFC DAICEL AD column, 40% methanol, 70 mL/min.

Example 63A (S)-3-Cyclohexyl-2-[4-(2,6-difluoro-phenoxy)-6-oxo-6H-pyridazin-1-yl]-N-[1-((R)-2,3-dihydroxy-propyl)-1H-pyrazol-3-yl]-propionamide

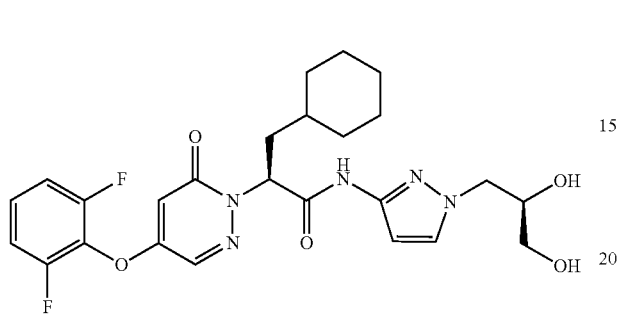

(S)-3-Cyclohexyl-2-[4-(2,6-difluoro-phenoxy)-6-oxo-6H-pyridazin-1-yl]-N-[1-((R)-2,3-dihydroxy-propyl)-1H-pyrazol-3-yl]-propionamide; ES+-HRMS m/e calcd for $C_{25}H_{29}N_5O_5F_2$ [M+H+] 518.2210 found 518.2210. $^1$H NMR (300 MHz, DMSO-$d_6$) δ ppm 0.83-1.26 (m, 6H), 1.50-1.73 (m, 5H), 1.76-1.92 (m, 1H), 2.07-2.24 (m, 1H), 3.19-3.32 (m, 2H), 3.69-3.93 (m, 2H), 4.08 (dd, J=13.6, 3.9 Hz, 1H), 4.71 (t, J=5.4 Hz, 1H), 4.94 (d, J=5.4 Hz, 1H), 5.53 (dd, J=11.2, 3.9 Hz, 1H), 6.04 (d, J=2.7 Hz, 1H), 6.35 (d, J=2.1 Hz, 1H), 7.31-7.50 (m, 3H), 7.52 (d, J=2.1 Hz, 1H), 8.29 (d, J=2.7 Hz, 1H), 10.83 (s, 1H).

Example 63B (R)-3-Cyclohexyl-2-[4-(2,6-difluoro-phenoxy)-6-oxo-6H-pyridazin-1-yl]-N-[1-((R)-2,3-dihydroxy-propyl)-1H-pyrazol-3-yl]-propionamide

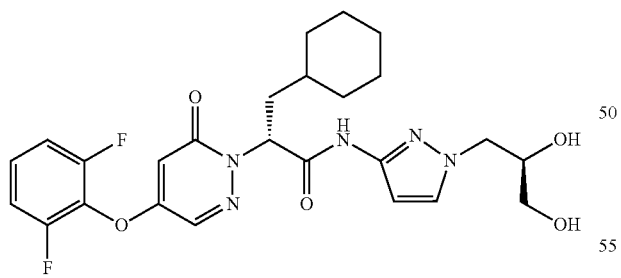

(R)-3-Cyclohexyl-2-[4-(2,6-difluoro-phenoxy)-6-oxo-6H-pyridazin-1-yl]-N-[1-((R)-2,3-dihydroxy-propyl)-1H-pyrazol-3-yl]-propionamide; ES+-HRMS m/e calcd for $C_{25}H_{29}N_5O_5F_2$ [M+H+] 518.2210 found 518.2213. $^1$H NMR (400 MHz, DMSO-$d_6$) δ ppm 0.85-1.24 (m, 6H), 1.49-1.73 (m, 5H), 1.75-1.91 (m, 1H), 2.06-2.23 (m, 1H), 3.20-3.37 (m, 2H), 3.70-3.82 (m, 1H), 3.82-3.92 (m, 1H), 4.09 (dd, J=13.5, 3.9 Hz, 1H), 4.70 (t, J=5.6 Hz, 1H), 4.94 (d, J=5.3 Hz, 1H), 5.53 (dd, J=11.0, 4.2 Hz, 1H), 6.04 (d, J=2.8 Hz, 1H), 6.36 (d, J=2.1 Hz, 1H), 7.34-7.43 (m, 2H), 7.43-7.51 (m, 1H), 7.53 (d, J=2.1 Hz, 1H), 8.29 (d, J=2.8 Hz, 1H), 10.81 (s, 1H).

Example 64

2-[4-(2,6-Difluoro-phenoxy)-6-oxo-6H-pyridazin-1-yl]-4-ethyl-hexanoic acid [1-((R)-2,3-dihydroxy-propyl)-1H-pyrazol-3-yl]-amide

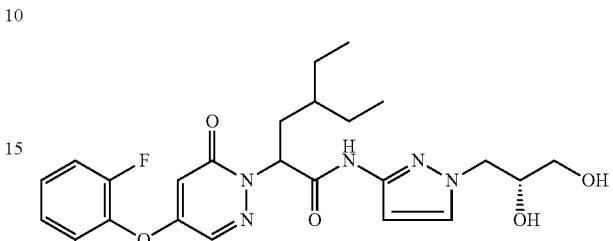

Using the method described in Example 49, 2-[4-(2,6-difluoro-phenoxy)-6-oxo-6H-pyridazin-1-yl]-4-ethyl-hexanoic acid (Intermediate 31) and 1-((R)-2,2-dimethyl-[1,3]dioxolan-4-ylmethyl)-1H-pyrazol-3-ylamine (Intermediate 4) afforded 2-[4-(2,6-difluoro-phenoxy)-6-oxo-6H-pyridazin-1-yl]-4-ethyl-hexanoic acid [1-((R)-2,2-dimethyl-[1,3]dioxolan-4-ylmethyl)-1H-pyrazol-3-yl]-amide as a viscous oil as a mixture of diastereomers. $^1$H NMR (300 MHz, CDCl$_3$) δ ppm 0.79-0.93 (m, 6H), 1.12 (br s, 1H), 1.20-1.54 (m, 4H), 1.34 (s, 3H), 1.38 (s, 3H), 2.02-2.19 (m, 1H), 2.19-2.34 (m, 1H), 3.68-3.77 (m, 1H), 4.04 (dd, J=8.6, 6.5 Hz, 1H), 4.10 (d, J=5.4 Hz, 2H), 4.32-4.47 (m, 1H), 5.66 (dd, J=9.1, 6.0 Hz, 1H), 6.00 (br s, 1H), 6.68 (s, 1H), 7.01-7.14 (m, 2H), 7.28-7.37 (m, 2H), 8.01 (d, J=2.7 Hz, 1H), 8.59 (br s, 1H).

Using the method described in Example 61, Step 2, 2-[4-(2,6-difluoro-phenoxy)-6-oxo-6H-pyridazin-1-yl]-4-ethyl-hexanoic acid [1-((R)-2,2-dimethyl-[1,3]dioxolan-4-ylmethyl)-1H-pyrazol-3-yl]-amide afforded 2-[4-(2,6-difluoro-phenoxy)-6-oxo-6H-pyridazin-1-yl]-4-ethyl-hexanoic acid [1-((R)-2,3-dihydroxy-propyl)-1H-pyrazol-3-yl]-amide as an off-white solid as a mixture of diastereomers (41 mg, 27%); ES+-HRMS m/e calcd for $C_{24}H_{29}N_5O_5F_2$ [M+H+] 506.2210 found 506.2212. $^1$H-NMR (400 MHz, CDCl$_3$) δ ppm 0.82-0.88 (m, 6H) 1.13 (m, 1H) 1.22-1.45 (m, 4H) 2.09 (m, 1H) 2.25 (m, 1H) 3.15 (br s, 2H) 3.52-3.67 (2×m, 2H) 4.03 (m, 1H) 4.13 (m, 2H) 5.65 (m, 1H) 6.01 (m, 1H) 6.64, 6.68 (2×d, J=2.4 Hz, 1H) 7.08 (m, 2H) 7.26-7.34 (m, 2H) 8.02 (2×d, J=2.9 Hz, 1H) 9.10, 9.15 (2×br s, 1H).

Example 65

3-Cyclopentyl-2-[4-(2,6-difluoro-phenoxy)-6-oxo-6H-pyridazin-1-yl]-N-[1-((S)-2,3-dihydroxy-propyl)-1H-pyrazol-3-yl]-propionamide

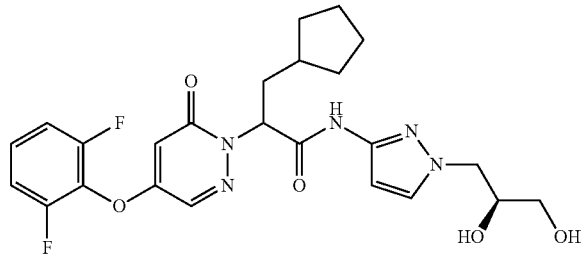

Using the method described in Example 17, 3-cyclopentyl-2-[4-(2,6-difluoro-phenoxy)-6-oxo-6H-pyridazin-1-yl]-propionic acid (Intermediate 47) and 1-((S)-2,2-dimethyl-[1,3]dioxolan-4-ylmethyl)-1H-pyrazol-3-ylamine (Intermediate 5) afforded 3-cyclopentyl-2-[4-(2,6-difluoro-phenoxy)-6-oxo-6H-pyridazin-1-yl]-N-[1-((S)-2,2-dimethyl-[1,3]dioxolan-4-ylmethyl)-1H-pyrazol-3-yl]-propionamide as a white solid as a mixture of diastereomers (142.6 mg, 38%). $^1$H NMR (300 MHz, DMSO-$d_6$) δ ppm 1.17 (m, 2H), 1.25 (s, 3H), 1.30 (s, 3H), 1.35-1.77 (m, 7H), 1.86-2.02 (m, 1H), 2.20-2.33 (m, 1H), 3.73 (dd, J=8.3, 5.9 Hz, 1H), 3.97-4.17 (m, 3H), 4.30-4.41 (m, 1H), 5.46 (dd, J=10.6, 4.2 Hz, 1H), 6.03 (d, J=2.6 Hz, 1H), 6.39 (d, J=2.1 Hz, 1H), 7.31-7.55 (m, 3H), 7.59 (br s, 1H), 8.22-8.33 (m, 1H), 10.73-10.94 (m, 1H).

A solution of 3-cyclopentyl-2-[4-(2,6-difluoro-phenoxy)-6-oxo-6H-pyridazin-1-yl]-N-[1-((S)-2,2-dimethyl-[1,3]dioxolan-4-ylmethyl)-1H-pyrazol-3-yl]-propionamide (142.4 mg, 0.26 mmol) in methanol (2.6 mL, 0.10M) at 25° C. was treated with para-toluenesulfonic acid monohydrate (7.7 mg, 0.04 mmol). The reaction was stirred at 25° C. overnight. After this time, the reaction was concentrated in vacuo. Silica gel column chromatography (AnaLogix 8 g, 1-10% methanol/methylene chloride) afforded 3-cyclopentyl-2-[4-(2,6-difluoro-phenoxy)-6-oxo-6H-pyridazin-1-yl]-N-[1-((S)-2,3-dihydroxy-propyl)-1H-pyrazol-3-yl]-propionamide (110.3 mg, 84%) as an off-white solid as a mixture of diastereomers; ES$^+$-HRMS m/e calcd for $C_{24}H_{27}N_5O_5F_2$ [M+H$^+$] 504.2053 found 504.2053. $^1$H-NMR (400 MHz, DMSO-$d_6$) δ ppm 1.03-1.18 (m, 1H) 1.22-1.76 (m, 8H) 1.88-2.01 (m, 1H) 2.17-2.35 (m, 1H) 3.19-3.32 (m, 2H) 3.70-3.80 (m, 1H) 3.82-3.93 (m, 1H) 4.09 (dd, J=13.3, 4.4 Hz, 1H) 4.70 (t, J=5.5 Hz, 1H) 4.94 (dd, J=5.5, 2.5 Hz, 1H) 5.40-5.51 (m, 1H) 6.03 (d, J=3.0 Hz, 1H) 6.36 (d, J=2.1 Hz, 1H) 7.35-7.43 (m, 2H) 7.44-7.51 (m, 1H) 7.53 (d, J=2.1 Hz, 1H) 8.28 (d, J=3.0 Hz, 1H) 10.83 (s, 1H).

Separation of diastereomers via supercritical fluid chromatography on a SFC DAICEL AD column, 30% methanol, 70 mL/min.

Example 65A (S)-3-Cyclopentyl-2-[4-(2,6-difluoro-phenoxy)-6-oxo-6H-pyridazin-1-yl]-N-[1-((S)-2,3-dihydroxy-propyl)-1H-pyrazol-3-yl]-propionamide

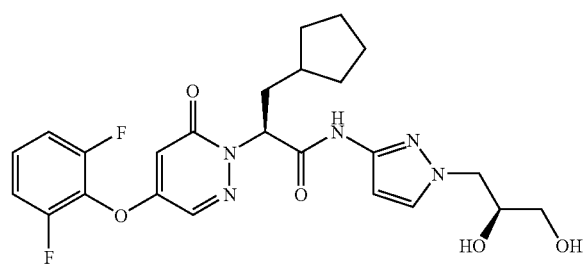

(S)-3-Cyclopentyl-2-[4-(2,6-difluoro-phenoxy)-6-oxo-6H-pyridazin-1-yl]-N-[1-((S)-2,3-dihydroxy-propyl)-1H-pyrazol-3-yl]-propionamide; ES$^+$-HRMS m/e calcd for $C_{24}H_{27}N_5O_5F_2$ [M+H$^+$] 504.2053 found 504.2053. $^1$H-NMR (300 MHz, DMSO-$d_6$) δ ppm 1.04-1.20 (m, 1H) 1.22-1.79 (m, 8H) 1.94 (br s, 1H) 2.17-2.34 (m, 1H) 3.21-3.32 (m, 2H) 3.72-3.91 (m, 2H) 4.09 (dd, J=13.3, 3.9 Hz, 1H) 4.72 (t, J=5.7 Hz, 1H) 4.96 (d, J=5.2 Hz, 1H) 5.45 (dd, J=10.9, 4.0 Hz, 1H) 6.04 (d, J=2.7 Hz, 1H) 6.36 (d, J=2.1 Hz, 1H) 7.30-7.51 (m, 3H) 7.53 (d, J=2.1 Hz, 1H) 8.29 (d, J=2.7 Hz, 1H) 10.85 (s, 1H).

Example 65B (R)-3-Cyclopentyl-2-[4-(2,6-difluoro-phenoxy)-6-oxo-6H-pyridazin-1-yl]-N-[1-((S)-2,3-dihydroxy-propyl)-1H-pyrazol-3-yl]-propionamide

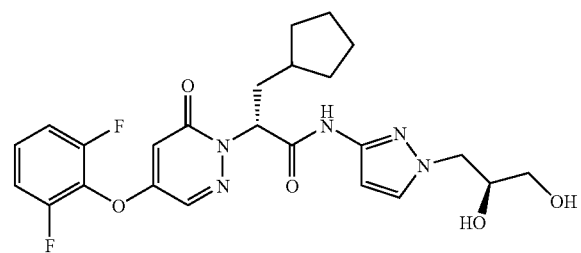

(R)-3-Cyclopentyl-2-[4-(2,6-difluoro-phenoxy)-6-oxo-6H-pyridazin-1-yl]-N-[1-((S)-2,3-dihydroxy-propyl)-1H-pyrazol-3-yl]-propionamide; ES$^+$-HRMS m/e calcd for $C_{24}H_{27}N_5O_5F_2$ [M+H$^+$] 504.2053 found 504.2055. $^1$H-NMR (300 MHz, DMSO-$d_6$) δ ppm 1.06-1.16 (m, 1H) 1.25-1.77 (m, 8H) 1.83-2.03 (m, 1H) 2.18-2.34 (m, 1H) 3.21-3.33 (m, 2H) 3.69-3.93 (m, 2H) 4.08 (dd, J=13.3, 3.9 Hz, 1H) 4.72 (t, J=5.7 Hz, 1H) 4.95 (d, J=5.2 Hz, 1H) 5.45 (dd, J=10.9, 4.0 Hz, 1H) 6.03 (d, J=2.7 Hz, 1H) 6.36 (d, J=2.1 Hz, 1H) 7.31-7.51 (m, 3H) 7.52 (d, J=2.1 Hz, 1H) 8.28 (d, J=2.7 Hz, 1H) 10.85 (s, 1H).

Example 66

6-{3-Cyclopentyl-2-[4-(2-cyclopentyl-phenoxy)-6-oxo-6H-pyridazin-1-yl]-propionylamino}-nicotinic acid methyl ester

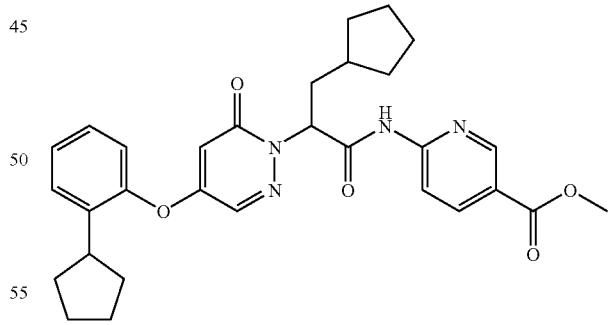

A solution of 3-cyclopentyl-2-[4-(2-cyclopentyl-phenoxy)-6-oxo-6H-pyridazin-1-yl]-propionic acid (Intermediate 36, 298 mg, 0.75 mmol) in methylene chloride (3.0 mL) at 25° C. was treated with a 2M solution of oxalyl chloride in methylene chloride (1.0 mL) followed by N,N-dimethylformamide (5 µL). The resulting solution was stirred at 25° C. for 25 min. After this time, the solution was concentrated in vacuo. The residue was resuspended in toluene (2.0 mL) and concentrated in vacuo. The residue was then treated with a solution of 6-amino-nicotinic acid methyl ester (114 mg, 0.75 mmol) and pyridine (120 μL, 1.5 mmol) in toluene. The reaction was stirred at 120° C. for 1.5 h in a sealed tube. After this time, the reaction mixture was concentrated in vacuo. The residue was partitioned between ethyl acetate and a citric acid solution. The organics were washed with water and then concentrated in vacuo. Silica gel column chromatography (20% ethyl acetate/hexanes) produced a solid which was triturated with hexanes/diethyl ether (20:1). Filtration and drying afforded 6-{3-cyclopentyl-2-[4-(2-cyclopentyl-phenoxy)-6-oxo-6H-pyridazin-1-yl]-propionylamino}-nicotinic acid methyl ester (186 mg, 46.7%) as a grey solid; ES+-HRMS m/e calcd for $C_{30}H_{34}N_4O_5$ [M+H+] 531.2602 found 531.2601. $^1$H-NMR (300 MHz, CDCl$_3$) δ ppm 1.05-2.37 (m, 19H), 3.04 (m, 1H), 3.92 (s, 3H), 5.64 (dd, J=6.9, J=8.2 Hz, 1H), 5.96 (d, J=2.8 Hz, 1H), 6.98 (m, 1H), 7.19-7.30 (m, 2H), 7.39 (m, 1H), 7.95 (d, J=2.8 Hz, 1H), 8.28 (s, 2H), 8.85 (s, 1H), 9.28 (br.s., 1H).

In an analogous manner, there were obtained:

Example 67

6-{3-Cyclopentyl-2-[6-oxo-4-(5,6,7,8-tetrahydro-naphthalen-1-yloxy)-6H-pyridazin-1-yl]-propionylamino}-nicotinic acid methyl ester

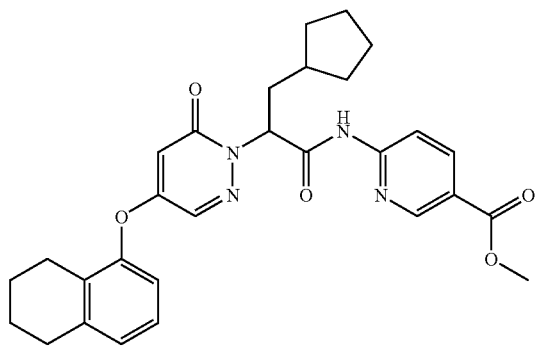

Using the method described in Example 66, 3-cyclopentyl-2-[6-oxo-4-(5,6,7,8-tetrahydro-naphthalen-1-yloxy)-6H-pyridazin-1-yl]-propionic acid (Intermediate 39) and 6-amino-nicotinic acid methyl ester afforded 6-{3-cyclopentyl-2-[6-oxo-4-(5,6,7,8-tetrahydro-naphthalen-1-yloxy)-6H-pyridazin-1-yl]-propionylamino}-nicotinic acid methyl ester as an off-white solid (153 mg, 38%); ES+-HRMS m/e calcd for $C_{29}H_{32}N_4O_5$ [M+H+] 517.2446 found 517.2442. $^1$H-NMR (300 MHz, CDCl$_3$) δ ppm 1.06-1.31 (m, 2H), 1.31-1.99 (m, 1H), 2.11-2.42 (m, 2H), 2.55 (br s, 2H), 2.81 (br s, 2H), 3.93 (s, 3H), 5.64 (t, J=7.4 Hz, 1H), 5.93 (s, 1H), 6.83 (d, J=7.7 Hz, 1H), 7.04 (d, J=7.7 Hz, 1H), 7.15 (t, J=7.7 Hz, 1H), 7.94 (s, 1H), 8.29 (s, 2H), 8.87 (s, 1H), 9.25 (br s, 1H).

Example 68

6-{3-Cyclopentyl-2-[4-(2,6-difluoro-phenoxy)-6-oxo-6H-pyridazin-1-yl]-propionylamino}-nicotinic acid methyl ester

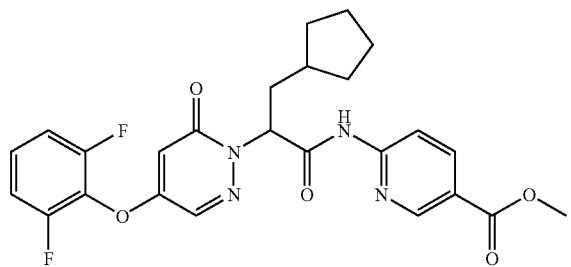

Using the method described in Example 66, 3-cyclopentyl-2-[4-(2,6-difluoro-phenoxy)-6-oxo-6H-pyridazin-1-yl]-propionic acid (Intermediate 47) and 6-amino-nicotinic acid methyl ester afforded 6-{3-cyclopentyl-2-[4-(2,6-difluoro-phenoxy)-6-oxo-6H-pyridazin-1-yl]-propionylamino}-nicotinic acid methyl ester as a pale, yellow solid (720 mg, 66%); ES+-HRMS m/e calcd for $C_{25}H_{24}N_4O_5F_2$ [M+H+] 499.1788 found 499.1784. $^1$H NMR (300 MHz, CDCl$_3$) δ ppm 1.19 (br s, 2H) 1.41-1.91 (m, 7H) 2.13-2.44 (m, 2H) 3.93 (s, 3H) 5.65 (dd, J=8.6, 6.5 Hz, 1H) 6.04 (br s, 1H) 7.00-7.16 (m, 2H) 7.28-7.34 (m, 1H) 8.03 (d, J=2.4 Hz, 1H) 8.14-8.44 (m, 2H) 8.88 (s, 1H) 9.11 (br s, 1H).

Separation of enantiomers via supercritical fluid chromatography on a SFC DAICEL AD column, 15% methanol, 70 mL/min.

Example 68A

6-{(S)-3-Cyclopentyl-2-[4-(2,6-difluoro-phenoxy)-6-oxo-6H-pyridazin-1-yl]-propionylamino}-nicotinic acid methyl ester

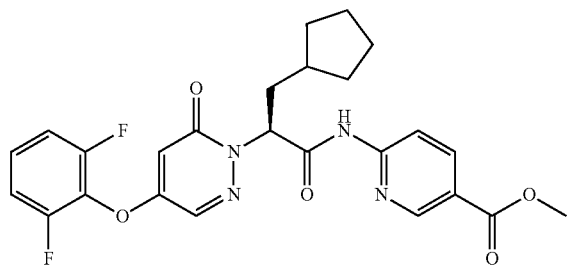

6-{(S)-3-Cyclopentyl-2-[4-(2,6-difluoro-phenoxy)-6-oxo-6H-pyridazin-1-yl]-propionylamino}-nicotinic acid methyl ester; ES+-HRMS m/e calcd for $C_{25}H_{24}N_4O_5F_2$ [M+H+] 499.1788 found 499.1787.

Example 68B

6-{(R)-3-Cyclopentyl-2-[4-(2,6-difluoro-phenoxy)-6-oxo-6H-pyridazin-1-yl]-propionylamino}-nicotinic acid methyl ester

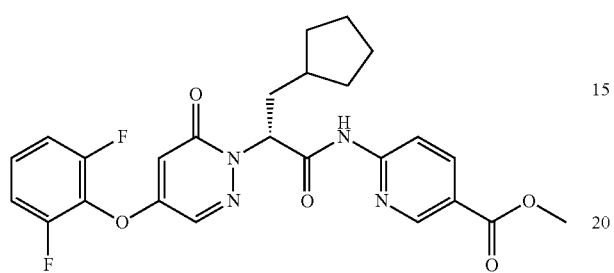

6-{(R)-3-Cyclopentyl-2-[4-(2,6-difluoro-phenoxy)-6-oxo-6H-pyridazin-1-yl]-propionylamino}-nicotinic acid methyl ester; ES$^+$-HRMS m/e calcd for $C_{25}H_{24}N_4O_5F_2$ [M+H$^+$] 499.1788 found 499.1788.

Example 69

6-[3-Cyclopentyl-2-(6-oxo-4-o-tolyloxy-6H-pyridazin-1-yl)-propionylamino]-nicotinic acid methyl ester

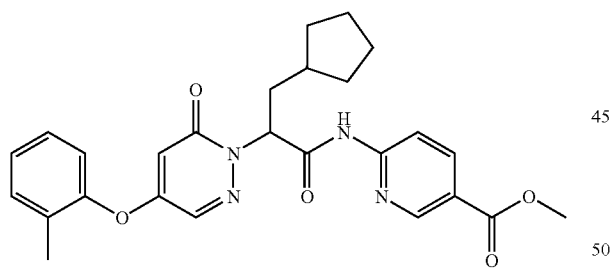

Using the method described in Example 66, 3-cyclopentyl-2-(6-oxo-4-o-tolyloxy-6H-pyridazin-1-yl)-propionic acid (Intermediate 41) and 6-amino-nicotinic acid methyl ester afforded 6-[3-cyclopentyl-2-(6-oxo-4-o-tolyloxy-6H-pyridazin-1-yl)-propionylamino]-nicotinic acid methyl ester as a yellow solid (230 mg, 32%); ESI-LRMS m/e calcd for $C_{26}H_{28}N_4O_5$ [M+] 477, found 477 [M+H$^+$]. $^1$H-NMR (300 MHz, DMSO-d$_6$) δ ppm 0.95-1.25 (m, 1H) 1.31-1.81 (m, 8H) 1.85-2.07 (m, 1H) 2.16 (s, 3H) 2.21-2.41 (m, 1H) 3.85 (s, 3H) 5.51-5.60 (m, 1H) 5.58 (d, J=2.8 Hz, 1H) 7.22 (dd, J=7.5, 1.5 Hz, 1H) 7.24-7.38 (m, 2H) 7.38-7.45 (m, 1H) 8.11 (d, J=8.8 Hz, 1H) 8.19 (d, J=2.8 Hz, 1H) 8.27 (dd, J=8.8, 2.4 Hz, 1H) 8.87 (d, J=2.4 Hz, 1H) 11.39 (s, 1H).

Example 70

6-{3-Cyclopentyl-2-[4-(2-fluoro-phenoxy)-6-oxo-6H-pyridazin-1-yl]-propionylamino}-nicotinic acid methyl ester

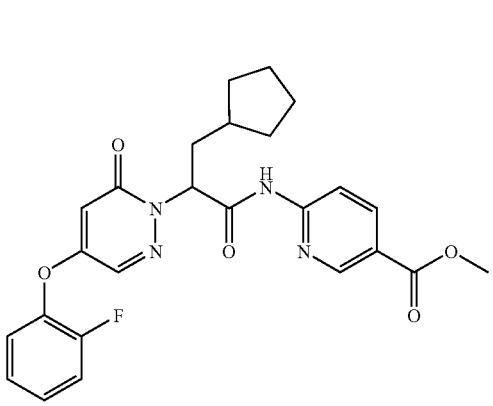

Using the method described in Example 66, 3-cyclopentyl-2-[4-(2-fluoro-phenoxy)-6-oxo-6H-pyridazin-1-yl]-propionic acid (Intermediate 43) and 6-amino-nicotinic acid methyl ester afforded 6-{3-cyclopentyl-2-[4-(2-fluoro-phenoxy)-6-oxo-6H-pyridazin-1-yl]-propionylamino}-nicotinic acid methyl ester as a yellow solid (200 mg, 30%); ESI-LRMS m/e calcd for $C_{25}H_{25}F\,N_4O_5$ [M+] 481, found 481 [M+H$^+$]. $^1$H-NMR (300 MHz, DMSO-d$_6$) δ ppm 1.00-1.21 (m, 1H) 1.26-1.84 (m, 8H) 1.87-2.05 (m, 1H) 2.22-2.40 (m, 1H) 3.86 (s, 3H) 5.58 (dd, J=10.9, 4.2 Hz, 1H) 5.82 (d, J=2.8 Hz, 1H) 7.29-7.56 (m, 4H) 8.10 (d, J=9.0 Hz, 1H) 8.24 (d, J=2.8 Hz, 1H) 8.28 (dd, J=9.0, 2.3 Hz, 1H) 8.87 (d, J=2.3 Hz, 1H) 11.42 (s, 1H).

Example 71

6-{3-Cyclopentyl-2-[4-(2-cyclopentyl-phenoxy)-6-oxo-6H-pyridazin-1-yl]-propionylamino}-nicotinic acid

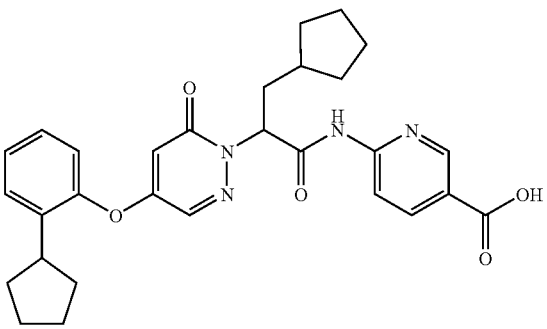

A solution of 6-{3-cyclopentyl-2-[4-(2-cyclopentyl-phenoxy)-6-oxo-6H-pyridazin-1-yl]-propionylamino}-nicotinic acid methyl ester (Example 66, 130 mg, 0.24 mmol) in tetrahydrofuran (5.0 mL) at 25° C. was treated with a 0.5N aqueous lithium hydroxide solution (1.0 mL) and methanol (1.0 mL). The resulting solution was stirred at 25° C. for 5 h. After this time, the solution was concentrated in vacuo. The residue was treated with a 1N aqueous hydrochloric acid solution (0.6 mL). The mixture was extracted with ethyl acetate. The organics were then washed with a saturated aqueous sodium chloride solution and then concentrated in vacuo. The resulting solids were triturated with hexanes and diethyl ether. The resulting solids were collected by filtration and dried in vacuo to afford 6-{3-cyclopentyl-2-[4-(2-cyclopentyl-phenoxy)-6-oxo-6H-pyridazin-1-yl]-propionylamino}-nicotinic acid (38 mg) as a solid; ES$^+$-HRMS m/e calcd for $C_{29}H_{32}N_4O_5$ [M+H$^+$] 517.2446 found 517.2443. $^1$H-NMR (300 MHz, DMSO-d$_6$) δ ppm 1.03-2.05 (m, 18H), 2.31 (m, 1H), 3.04 (m, 1H), 5.57 (dd, J=4.2, J=10.6 Hz, 1H), 5.61 (d, J=2.7 Hz, 1H), 7.20 (m, 1H), 7.27-7.38 (m, 2H), 7.49 (m, 1H), 8.08 (d, J$_o$=8.8 Hz, 1H), 8.20 (d, J=2.7 Hz, 1H), 8.24 (dd, J$_o$=8.8 Hz, J$_m$=2.2 Hz, 1H), 8.84 (d, J$_m$=2.2 Hz, 1H), 11.33 (s, 1H), 13.18 (br.s., 1H).

In an analogous manner, there were obtained:

Example 72

6-{3-Cyclopentyl-2-[6-oxo-4-(5,6,7,8-tetrahydro-naphthalen-1-yloxy)-6H-pyridazin-1-yl]-propionylamino}-nicotinic acid

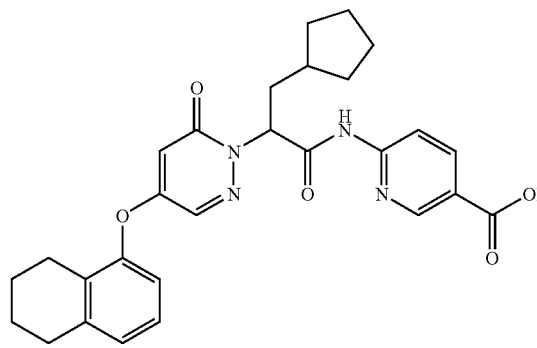

Using the method described in Example 71, 6-{3-cyclopentyl-2-[6-oxo-4-(5,6,7,8-tetrahydro-naphthalen-1-yloxy)-6H-pyridazin-1-yl]-propionylamino}-nicotinic acid methyl ester (Example 67) afforded 6-{3-cyclopentyl-2-[6-oxo-4-(5,6,7,8-tetrahydro-naphthalen-1-yloxy)-6H-pyridazin-1-yl]-propionylamino}-nicotinic acid as a white solid (60 mg, 12%); ES$^+$-HRMS m/e calcd for $C_{28}H_{30}N_4O_5$ [M+H$^+$] 503.2289 found 503.2287. $^1$H-NMR (300 MHz, DMSO-d$_6$) δ ppm 1.14 (m, 1H), 1.28-1.86 (m, 12H), 1.91 (m, 1H), 2.31 (m, 1H), 2.50 (br.s., 2H), 2.77 (br.s., 2H), 5.57 (m, 1H), 5.59 (d, J=2.1 Hz, 1H), 7.01 (d, J$_o$=7.8 Hz, 1H), 7.09 (d, J$_o$=7.5 Hz, 1H), 7.22 (t, J=7.7 Hz, 1H), 8.08 (d, J$_o$=8.7 Hz, 1H), 8.16 (d, J=2.1 Hz, 1H), 8.24 (d, J$_o$=8.7 Hz, 1H), 8.83 (br.s., 1H), 11.33 (s, 1H), 13.14 (br, 1H).

Separation of enantiomers via supercritical fluid chromatography on a SFC DAICEL AD column, 50% of a 1:1: ethanol/acetonitrile solution, 70 mL/min.

Example 72A

6-{(S)-3-Cyclopentyl-2-[6-oxo-4-(5,6,7,8-tetrahydro-naphthalen-1-yloxy)-6H-pyridazin-1-yl]-propionylamino}-nicotinic acid

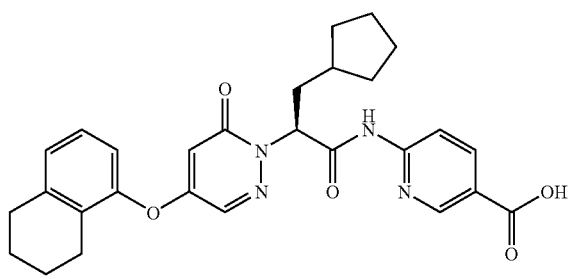

6-{(S)-3-Cyclopentyl-2-[6-oxo-4-(5,6,7,8-tetrahydro-naphthalen-1-yloxy)-6H-pyridazin-1-yl]-propionylamino}-nicotinic acid; ES$^+$-HRMS m/e calcd for $C_{28}H_{30}N_4O_5$ [M+H$^+$] 503.2289 found 503.2289.

Example 72B

6-{(R)-3-Cyclopentyl-2-[6-oxo-4-(5,6,7,8-tetrahydro-naphthalen-1-yloxy)-6H-pyridazin-1-yl]-propionylamino}-nicotinic acid

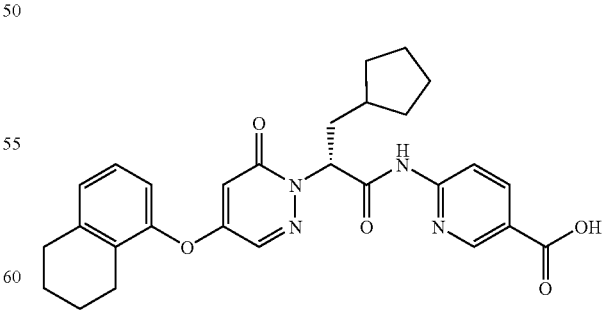

6-{(R)-3-Cyclopentyl-2-[6-oxo-4-(5,6,7,8-tetrahydro-naphthalen-1-yloxy)-6H-pyridazin-1-yl]-propionylamino}nicotinic acid; ES$^+$-HRMS m/e calcd for $C_{28}H_{30}N_4O_5$ [M+H$^+$] 503.2289 found 503.2288.

Example 73

6-{3-Cyclopentyl-2-[4-(2,6-difluoro-phenoxy)-6-oxo-6H-pyridazin-1-yl]-propionylamino}-nicotinic acid

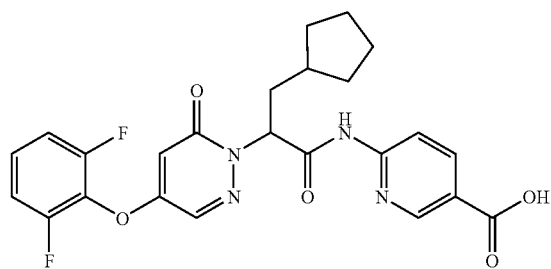

Using the method described in Example 71, 6-{3-cyclopentyl-2-[4-(2,6-difluoro-phenoxy)-6-oxo-6H-pyridazin-1-yl]-propionylamino}-nicotinic acid methyl ester (Example 68): 6-{3-cyclopentyl-2-[4-(2,6-difluoro-phenoxy)-6-oxo-6H-pyridazin-1-yl]-propionylamino}-nicotinic acid was obtained as a white solid (150 mg, 50%); ES⁺-HRMS m/e calcd for $C_{24}H_{22}N_4O_5F_2$ [M+H⁺] 485.1631 found 485.1630. ¹H NMR (300 MHz, DMSO-$d_6$) δ ppm 1.11 (br s, 1H) 1.26-1.85 (m, 8H) 1.85-2.08 (m, 1H) 2.21-2.41 (m, 1H) 5.58 (dd, J=10.7, 4.1 Hz, 1H) 6.07 (d, J=2.4 Hz, 1H) 7.23-7.62 (m, 3H) 8.08 (d, J=8.8 Hz, 1H) 8.24 (dd, J=8.8, 1.8 Hz, 1H) 8.32 (d, J=2.7 Hz, 1H) 8.84 (d, J=1.8 Hz, 1H) 11.38 (s, 1H) 13.20 (brs, 1H).

Separation of enantiomers via supercritical fluid chromatography on a SFC DAICEL AD column, 40% methanol, 70 mL/min.

Example 73A

6-{(S)-3-Cyclopentyl-2-[4-(2,6-difluoro-phenoxy)-6-oxo-6H-pyridazin-1-yl]-propionylamino}-nicotinic acid

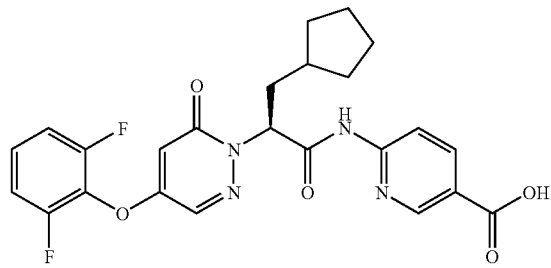

6-{(S)-3-Cyclopentyl-2-[4-(2,6-difluoro-phenoxy)-6-oxo-6H-pyridazin-1-yl]-propionylamino}-nicotinic acid; ES⁺-HRMS m/e calcd for $C_{24}H_{22}N_4O_5F_2$ [M+H⁺] 485.1631 found 485.1633.

Example 73B

6-{(R)-3-Cyclopentyl-2-[4-(2,6-difluoro-phenoxy)-6-oxo-6H-pyridazin-1-yl]-propionylamino}-nicotinic acid

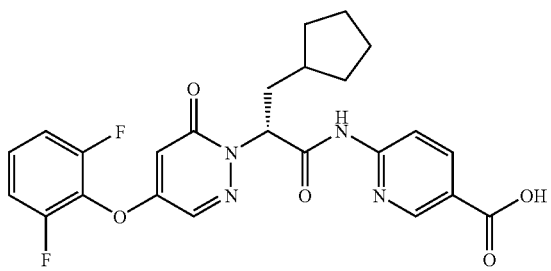

6-{(R)-3-Cyclopentyl-2-[4-(2,6-difluoro-phenoxy)-6-oxo-6H-pyridazin-1-yl]-propionylamino}-nicotinic acid; ES⁺-HRMS m/e calcd for $C_{24}H_{22}N_4O_5F_2$ [M+H⁺] 485.1631 found 485.1632.

Example 74

6-[3-Cyclopentyl-2-(6-oxo-4-o-tolyloxy-6H-pyridazin-1-yl)-propionylamino]-nicotinic acid

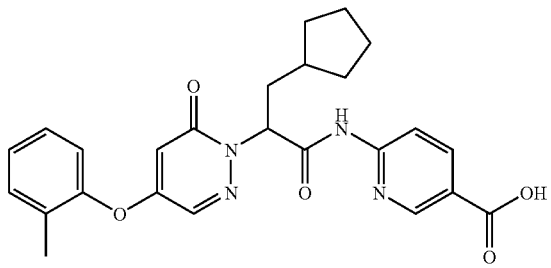

Using the method described in Example 71, 6-[3-cyclopentyl-2-(6-oxo-4-O-tolyloxy-6H-pyridazin-1-yl)-propionylamino]-nicotinic acid methyl ester (Example 69) afforded 6-[3-cyclopentyl-2-(6-oxo-4-o-tolyloxy-6H-pyridazin-1-yl)-propionylamino]-nicotinic acid as a white solid (70 mg, 35%); ESI-LRMS m/e calcd for $C_{26}H_{28}N_4O_5$ [M+] 463, found 463 [M+H⁺]. ¹H-NMR (300 MHz, DMSO-$d_6$) δ ppm 0.99-1.26 (m, 1H) 1.27-1.83 (m, 8H) 1.86-2.05 (m, 1H) 2.16 (s, 3H) 2.22-2.43 (m, 1H) 5.51-5.60 (m, 1H) 5.58 (d, J=2.8 Hz, 1H) 7.22 (dd, J=7.8, 1.5 Hz, 1H) 7.25-7.38 (m, 2H) 7.38-7.45 (m, 1H) 8.08 (d, J=8.8 Hz, 1H) 8.19 (d, J=2.8 Hz, 1H) 8.24 (dd, J=8.8, 2.1 Hz, 1H) 8.84 (d, J=2.1 Hz, 1H) 11.33 (s, 1H) 13.19 (brs, 1H).

Separation of enantiomers via supercritical fluid chromatography on a SFC DAICEL AD column, 40% of a 1:1 ethanol/acetonitrile solution, 70 mL/min.

Example 74A

6-[(S)-3-Cyclopentyl-2-(6-oxo-4-o-tolyloxy-6H-pyridazin-1-yl)-propionylamino]-nicotinic acid

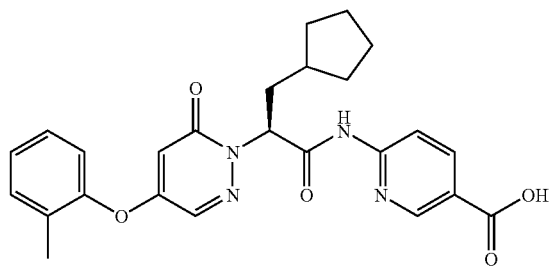

6-[(S)-3-Cyclopentyl-2-(6-oxo-4-o-tolyloxy-6H-pyridazin-1-yl)-propionylamino]-nicotinic acid. $^1$H-NMR (400 MHz, DMSO-d$_6$) δ ppm 1.12 (br s, 1H), 1.31-1.83 (m, 8H), 1.87-2.06 (m, 1H), 2.16 (s, 3H), 2.25-2.39 (m, 0H), 5.52-5.57 (m, 0H), 5.59 (d, J=2.3 Hz, 1H), 7.22 (d, J=7.7 Hz, 1H), 7.28 (t, J=7.2 Hz, 1H), 7.31-7.38 (m, 1H), 7.41 (d, J=7.2 Hz, 1H), 8.08 (d, J=8.5 Hz, 1H), 8.18 (d, J=2.3 Hz, 1H), 8.24 (d, J=8.5 Hz, 1H), 8.84 (s, 1H), 11.30 (s, 1H), 13.52 (br s, 1H).

Example 74B

6-[(R)-3-Cyclopentyl-2-(6-oxo-4-o-tolyloxy-6H-pyridazin-1-yl)-propionylamino]-nicotinic acid

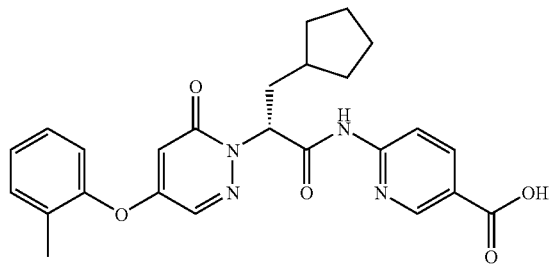

6-[(R)-3-Cyclopentyl-2-(6-oxo-4-o-tolyloxy-6H-pyridazin-1-yl)-propionylamino]-nicotinic acid. $^1$H-NMR (400 MHz, DMSO-d$_6$) δ ppm 1.12 (br s, 1H), 1.31-1.84 (m, 8H), 1.89-2.07 (m, 1H), 2.16 (s, 3H), 2.24-2.40 (m, 1H), 5.53-5.57 (m, 1H), 5.59 (d, J=2.1 Hz, 1H), 7.22 (d, J=7.7 Hz, 1H), 7.28 (t, J=7.1 Hz, 1H), 7.34 (m, 1H), 7.41 (d, J=7.1 Hz, 1H), 8.08 (d, J=8.6 Hz, 1H), 8.18 (d, J=2.1 Hz, 1H), 8.24 (d, J=8.6 Hz, 1H), 8.84 (s, 1H), 11.31 (s, 1H), 13.09 (br s, 1H).

Example 75

6-{3-Cyclopentyl-2-[4-(2-fluoro-phenoxy)-6-oxo-6H-pyridazin-1-yl]-propionylamino}-nicotinic acid

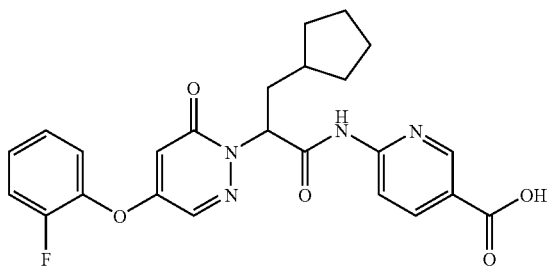

Using the method described in Example 71, 6-{3-cyclopentyl-2-[4-(2-fluoro-phenoxy)-6-oxo-6H-pyridazin-1-yl]-propionylamino}-nicotinic acid methyl ester (Example 70) afforded 6-{3-cyclopentyl-2-[4-(2-fluoro-phenoxy)-6-oxo-6H-pyridazin-1-yl]-propionylamino}-nicotinic acid as a white solid (100 mg, 51%); ESI-LRMS m/e calcd for C$_{24}$H$_{23}$FN$_4$O$_5$ [M+] 467, found 467 [M+H$^+$]. $^1$H-NMR (300 MHz, DMSO-d$_6$) δ ppm 1.12 (br s, 1H), 1.29-1.82 (m, 8H), 1.89-2.04 (m, 1H), 2.22-2.40 (m, 1H), 5.58 (dd, J=10.9, 4.5 Hz, 1H), 5.83 (d, J=2.7 Hz, 1H), 7.30-7.55 (m, 4H), 8.08 (d, J=8.8 Hz, 1H), 8.19-8.29 (m, 2H), 8.84 (d, J=2.7 Hz, 1H), 11.36 (s, 1H), 13.19 (br s, 1H).

Separation of enantiomers via supercritical fluid chromatography on a SFC DAICEL AD column, 40% of a 1:1 ethanol/acetonitrile solution, 70 mL/min.

Example 75A

6-{(S)-3-Cyclopentyl-2-[4-(2-fluoro-phenoxy)-6-oxo-6H-pyridazin-1-yl]-propionylamino}-nicotinic acid

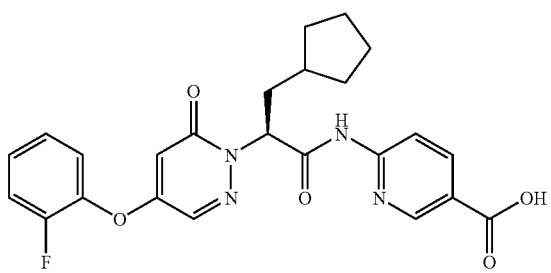

6-{(S)-3-Cyclopentyl-2-[4-(2-fluoro-phenoxy)-6-oxo-6H-pyridazin-1-yl]-propionylamino}-nicotinic acid. $^1$H-NMR (400 MHz, DMSO-d$_6$) δ ppm 1.12 (br s, 1H), 1.37-1.83 (m, 8H), 1.90-2.04 (m, 1H), 2.26-2.39 (m, 1H), 5.59 (dd, J=10.9, 3.8 Hz, 1H), 5.83 (d, J=2.3 Hz, 1H), 7.28-7.38 (m, 1H), 7.38-7.46 (m, 1H), 7.50 (t, J=8.7 Hz, 2H), 8.08 (d, J=8.7 Hz, 1H), 8.20-8.28 (m, 2H), 8.84 (s, 1H), 11.33 (s, 1H), 12.94 (br s, 1H).

Example 75B

6-{(R)-3-Cyclopentyl-2-[4-(2-fluoro-phenoxy)-6-oxo-6H-pyridazin-1-yl]-propionylamino}-nicotinic acid

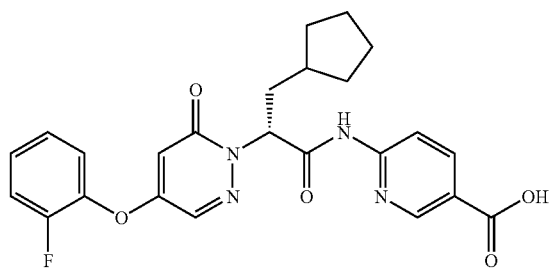

6-{(R)-3-Cyclopentyl-2-[4-(2-fluoro-phenoxy)-6-oxo-6H-pyridazin-1-yl]-propionylamino}-nicotinic acid. $^1$H-NMR (400 MHz, DMSO-$d_6$) δ ppm 1.12 (br s, 1H), 1.40-1.85 (m, 8H), 1.97 (br s, 1H), 2.27-2.40 (m, 1H), 5.59 (d, J=9.4 Hz, 1H), 5.83 (br s, 1H), 7.29-7.39 (m, 1H), 7.39-7.46 (m, 1H), 7.50 (t, J=8.5 Hz, 2H), 8.08 (d, J=8.5 Hz, 1H), 8.23 (br s, 2H), 8.84 (br s, 1H), 11.33 (br s, 1H).

Example 76

3-Cyclopentyl-2-[6-oxo-4-(2-trifluoromethyl-phenoxy)-6H-pyridazin-1-yl]-N-pyrazin-2-yl-propionamide

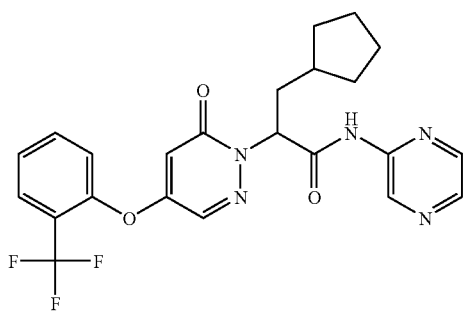

Step 1: A solution of 3-cyclopentyl-propionic acid (10 mL, 70.1 mmol) in carbon tetrachloride (7 mL, 10M) at 25° C. was treated with thionyl chloride (20.36 mL, 280.4 mmol) and then was heated to 65° C. for 30 min. After this time, the reaction was cooled to 25° C. and then was treated with N-bromosuccinimide (14.9 g, 84.1 mmol), carbon tetrachloride (35 mL) and a 48% aqueous hydrogen bromide solution (7 drops). The reaction mixture was heated to 85° C. overnight. After this time, the reaction was cooled to 25° C. The mixture was filtered through a pad of diatomaceous earth and was washed with carbon tetrachloride (2×40 mL). The filtrate was transferred to a 100 mL flask. Vacuum distillation afforded 2-bromo-3-cyclopentyl-propionyl chloride (11.6 g, 69%) as a yellow/orange liquid.

Step 2: A solution of 2-bromo-3-cyclopentyl-propionyl chloride (1.46 g, 6.09 mmol) in tetrahydrofuran (32.1 mL, 0.19M) cooled to 0° C. was treated with N-methylmorpholine (0.66 mL, 6.09 mmol). The reaction mixture was stirred at 0° C. for 5 min. After this time, the reaction was treated with pyrazin-2-ylamine (0.58 g, 6.09 mmol) and allowed to warm to 25° C. The reaction stirred at 25° C. for 2 d. After this time, the reaction mixture was partitioned between water (100 mL) and ethyl acetate (2×150 mL). The organics were dried over sodium sulfate, filtered and concentrated in vacuo. Silica gel column chromatography (AnaLogix, 115 g, 10-50% ethyl acetate/hexanes gradient) afforded 2-bromo-3-cyclopentyl-N-pyrazin-2-yl-propionamide (0.43 g, 24%) as a light brown solid; ES$^+$-HRMS m/e calcd for $C_{12}H_{16}N_3OBr$ [M+H$^+$] 298.0550, found 298.0550.

Step 3: A solution of 4,5-dichloro-2-(tetrahydropyran-2-yl)-2H-pyridazin-3-one (4.00 g, 16.05 mmol) (Intermediate 20) in acetonitrile (178 mL, 0.09M) was treated with potassium carbonate (2.21 g, 16.05 mmol) and 2-trifluoromethyl-phenol (2.60 g, 16.05 mmol). The resulting reaction mixture was heated to 105° C. for 18 h and then was allowed to cool to 25° C. The reaction mixture was partitioned between water (150 mL) and methylene chloride (3×100 mL). The combined organics were dried over sodium sulfate, filtered and concentrated in vacuo. Silica gel column chromatography (AnaLogix) afforded 4-chloro-2-(tetrahydro-pyran-2-yl)-5-(2-trifluoromethyl-phenoxy)-2H-pyridazin-3-one (4.79 g, 79%) as a white solid; ES$^+$-HRMS m/e calcd for $C_{16}H_{14}N_2O_3F_3Cl$ [M+H$^+$] 375.0718, found 375.0718. $^1$H NMR (300 MHz, DMSO-$d_6$) δ ppm 1.51 (d, 2H), 1.62-1.77 (m, 2H), 1.87-2.12 (m, 2H), 3.55-3.70 (m, 1H), 3.91-4.03 (m, 1H), 5.90 (dd, J=10.4, 2.0 Hz, 1H), 7.45-7.53 (m, 2H), 7.76 (t, J=7.8 Hz, 1H), 7.88 (d, J=7.5 Hz, 1H), 7.91 (s, 1H).

Step 4: A solution of 4-chloro-2-(tetrahydro-pyran-2-yl)-5-(2-trifluoromethyl-phenoxy)-2H-pyridazin-3-one (4.78 g, 12.78 mmol) in methanol (25.5 mL, 0.5M) was treated with a 6N aqueous hydrochloric acid solution (10.6 mL, 1.2M). The reaction solution was heated to 110° C., where it stirred for 4 h and was then allowed to cool down to 25° C. The reaction was diluted with water (250 mL) and extracted with a 90/10 methylene chloride/methanol solution (3×100 mL). The combined organic layers were dried over sodium sulfate, filtered, and dried in vacuo to afford 4-chloro-5-(2-trifluoromethyl-phenoxy)-2H-pyridazin-3-one (3.76 g, 100%) as a white solid; ES$^+$-HRMS m/e calcd for $C_{11}H_6N_2O_2F_3Cl$ [M+H$^+$] 291.0143, found 291.0142. $^1$H NMR (300 MHz, DMSO-$d_6$) δ ppm 7.41-7.51 (m, 2H), 7.74 (t, J=8.2 Hz, 1H), 7.79 (s, 1H), 7.86 (d, J=7.8 Hz, 1H), 13.59 (br. s., 1H).

Step 5: A pressure vial containing a mixture of 4-chloro-5-(2-trifluoromethyl-phenoxy)-2H-pyridazin-3-one (3.66 g, 12.59 mmol), water (70 mL), and a 2N aqueous sodium hydroxide solution (7 mL, 14 mmol) was treated with 10% palladium on carbon (0.37 mg, 10% weight of 4-chloro-5-(2-trifluoromethyl-phenoxy)-2H-pyridazin-3-one). The reaction was then pressurized with hydrogen (50 psi), where it shook for 4 d. The resulting reaction mixture was diluted with methylene chloride (100 mL) and water (100 mL) and filtered through a pad of diatomaceous earth. The filtrate was concentrated in vacuo. The aqueous residue was acidified with a 2N aqueous hydrochloric acid solution and was then extracted with a 90/10 methylene chloride/methanol solution. The combined organic layers were dried over sodium sulfate, filtered, and concentrated in vacuo. Silica gel column chromatography (ISCO, 120 g, 50%-70% ethyl acetate/hexanes) afforded 5-(2-trifluoromethyl-phenoxy)-2H-pyridazin-3-one (2.26 g, 70%) as a white solid. $^1$H NMR (300 MHz, DMSO-d$_6$) δ ppm 5.79 (d, J=2.7 Hz, 1H), 7.52-7.60 (m, 2H), 7.82 (t, J=8.5 Hz, 1H), 7.89 (d, J=8.2 Hz, 1H), 8.00 (d, J=2.7 Hz, 1H), 13.04 (br. s., 1H).

Step 6: A solution of 5-(2-trifluoromethyl-phenoxy)-2H-pyridazin-3-one (63.8 mg, 0.24 mmol) in tetrahydrofuran (1.24 mL) cooled to 0° C. was treated with a 60% suspension of sodium hydride in mineral oil (12 mg, 0.2 mmol). The reaction stirred at 0° C. for 5 min and then at 25° C. for an additional 30 min. After this time, the reaction was treated with 2-bromo-3-cyclopentyl-N-pyrazin-2-yl-propionamide (81.4 mg, 0.27 mmol) in a minimal amount of tetrahydrofuran. The reaction was then warmed to 50° C., where it stirred overnight. After this time, the reaction was partitioned between water (100 mL) and methylene chloride (2×100 mL). The combined organic layers were dried over sodium sulfate, filtered and concentrated in vacuo. Silica gel column chromatography (AnaLogix, 12 g, 50-75% ethyl acetate/hexanes) afforded 3-cyclopentyl-2-[6-oxo-4-(2-trifluoromethyl-phenoxy)-6H-pyridazin-1-yl]-N-pyrazin-2-yl-propionamide (31.8 mg, 27%) as a white solid; ES$^+$-HRMS m/e calcd for C$_{23}$H$_{22}$N$_5$O$_3$F$_3$ [M+H$^+$] 474.1748, found 474.1746. $^1$H-NMR (300 MHz, DMSO-d$_6$) δ ppm 1.10 (m, 1H), 1.23-1.75 (m, 8H), 1.98 (m, 1H), 2.30 (m, 1H), 5.58 (dd, J=4.4, J=11.0 Hz, 1H), 5.92 (d, J=2.7 Hz, 1H), 7.48-7.63 (m, 2H), 7.81 (t, J=7.1 Hz, 1H), 7.88 (d, J=7.8 Hz, 1H), 8.20 (d, J=2.7 Hz, 1H), 8.36 (d, J=2.7 Hz, 1H), 8.41 (br.s., 1H), 9.21 (s, 1H), 11.25 (s, 1H).

Example 77

3-Cyclopentyl-N-[1-(2-hydroxy-2-methyl-propyl)-1H-pyrazol-3-yl]-2-[4-(methyl-phenyl-amino)-6-oxo-6H-pyridazin-1-yl]-propionamide

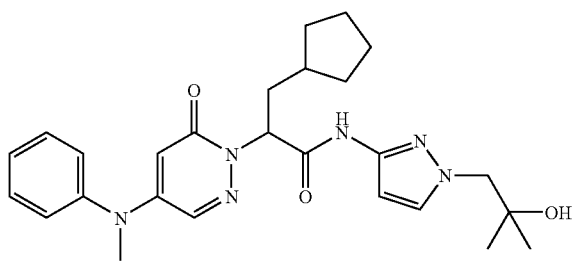

Step 1: A mixture of 4,5-dichloro-2-(tetrahydropyran-2-yl)-2H-pyridazin-3-one (2.0 g, 8.02 mmol) (Intermediate 20), sodium tert-butoxide (0.93 g, 9.67 mmol), tris(dibenzylideneacetone)dipalladium(0) (19 mg, 0.02 mmol) and N-phenyl-2-(di-tert-butylphosphino)indole (27.4 mg, 0.08 mmol) in a glass reaction tube was fitted with a septa and then evacuated via house vacuum followed by a nitrogen flush three times to remove air from the reaction system. The reaction was then treated with anhydrous toluene (8 mL, 1.0M) and N-methylaniline (1.05 mL, 9.69 mmol). The reaction was heated to 120° C. for 4 d. After this time, the reaction was cooled to 25° C. where it stirred for an additional 1 d. After this time, the reaction mixture was then partitioned between water (200 mL) and ethyl acetate (200 mL). The aqueous layer was back extracted with ethyl acetate (100 mL). The combined organics were dried over magnesium sulfate, filtered, and concentrated in vacuo. Silica gel column chromatography (AnaLogix, 115 g, 10-40% ethyl acetate/hexanes gradient) afforded 4-chloro-5-(methyl-phenyl-amino)-2-(tetrahydro-pyran-2-yl)-2H-pyridazin-3-one (277.2 mg, 11%) as an orange/red oil.

Step 2: A solution of 4-chloro-5-(methyl-phenyl-amino)-2-(tetrahydro-pyran-2-yl)-2H-pyridazin-3-one (272.5 mg, 0.85 mmol) in methanol (1.7 mL, 0.5M) was treated with a 6N aqueous hydrochloric acid solution (0.71 mL). The reaction solution was heated to 110° C., where it stirred for 4 h and was then allowed to completely cool down to 25° C. where it stirred overnight. After this time, the reaction was then diluted with water. The resulting solids were collected by filtration, washed with water, and dried in vacuo to afford 4-chloro-5-(methyl-phenyl-amino)-2H-pyridazin-3-one (159.2 mg, 79%) as a yellow solid that was used without further purification.

Step 3: A pressure vial containing a mixture of 4-chloro-5-(methyl-phenyl-amino)-2H-pyridazin-3-one (158.7 mg, 0.67 mmol), water (10 mL), and a 2N aqueous solution of sodium hydroxide (0.37 mL) was treated with 10% palladium on carbon (15.8 mg, 10% weight of 4-chloro-5-(methyl-phenyl-amino)-2H-pyridazin-3-one). The reaction was then pressurized with hydrogen (50 psi), where it shook overnight. The resulting reaction mixture was filtered through a pad of diatomaceous earth and rinsed with methanol. The filtrate was concentrated in vacuo. The resulting solution was acidified to pH 1-2 with a 1N aqueous hydrochloric acid solution and then extracted into methylene chloride (2×25 mL). Thin layer chromatography indicated the presence of starting material. The reaction was re-exposed to the same hydrogenation conditions. The reaction was hydrogenated (50 psi) for 2 d. After this time, the resulting reaction mixture was filtered through a pad of diatomaceous earth and rinsed with methanol. The filtrate was concentrated in vacuo. The resulting solution was acidified to pH 1-2 with a 1N aqueous hydrochloric acid solution and then extracted into methylene chloride (3×25 mL). The combined organics were dried over magnesium sulfate, filtered, rinsed, and concentrated in vacuo. Silica gel column chromatography (AnaLogix 24 g, 50-100% ethyl acetate/hexanes) afforded 5-(methyl-phenyl-amino)-2H-pyridazin-3-one (75.8 mg, 56%) as a yellow solid.

Step 4: A solution of 5-(methyl-phenyl-amino)-2H-pyridazin-3-one (74.3 mg, 0.36 mmol) in tetrahydrofuran (1.8 mL) cooled to 0° C. was treated with a 60% suspension of sodium hydride in mineral oil (19.7 mg, 0.49 mmol). Upon complete addition of the sodium hydride, the cooling bath was removed and additional tetrahydrofuran (1.8 mL) was added to facilitate stirring. The reaction was stirred at 25° C. for 2.25 h. After this time, the reaction was treated with 2-bromo-3-cyclopentyl-propionic acid methyl ester (Intermediate 10, 0.11 g, 0.46 mmol). The reaction was then warmed to 50° C., where it stirred overnight. After this time, the reaction was cooled to 25° C. and stirred overnight. At this point, the reaction was partitioned between water (25 mL) and methylene chloride (3×25 mL). The combined organic layers were washed with a saturated aqueous sodium chloride solution (1×25 mL), dried over magnesium sulfate, filtered and concentrated in vacuo. Silica gel column chromatography (AnaLogix 8 g, 15-35% ethyl acetate/hexanes) afforded 3-cyclopentyl-2-[4-(methyl-phenyl-amino)-6-oxo-6H-pyridazin-1-yl]-propionic acid methyl ester (67.4 mg, 51%) as a yellow oil.

Step 5: A solution of 3-cyclopentyl-2-[4-(methyl-phenyl-amino)-6-oxo-6H-pyridazin-1-yl]-propionic acid methyl ester (66.3 mg, 0.18 mmol) in methanol (0.5 mL, 0.37M) was treated with a 4N aqueous sodium hydroxide solution (0.05 mL, 0.2 mmol) and was stirred at 25° C. overnight. After this time, the reaction was diluted with water (10 mL), acidified with a 1N aqueous hydrochloric acid solution and then was extracted into methylene chloride (3×25 mL). The combined organics were washed with a saturated aqueous sodium chloride solution (1×25 mL), dried over magnesium sulfate, filtered and concentrated in vacuo to afford 3-cyclopentyl-2-[4-(methyl-phenyl-amino)-6-oxo-6H-pyridazin-1-yl]-propionic acid (67.3 mg) as a viscous, yellow oil. This material was used without further purification.

Step 6: A solution of 3-cyclopentyl-2-[4-(methyl-phenyl-amino)-6-oxo-6H-pyridazin-1-yl]-propionic acid (assume 0.18 mmol) in methylene chloride (1.8 mL, 0.1M) at 25° C. was treated with 1-(3-dimethylaminopropyl)-3-ethylcarbodiimide (34 µL, 0.19 mmol) followed by 1-hydroxybenzotriazole (26.3 mg, 0.19 mmol). The resulting solution was stirred at 25° C. for 3.5 h. After this time, the reaction was treated with 1-(3-amino-pyrazol-1-yl)-2-methyl-propan-2-ol (Intermediate 1, 36.8 mg, 0.23 mmol). The resulting solution was stirred at 25° C. for 2 d. After this time, the reaction was diluted with methylene chloride (25 mL) and was washed consecutively with a saturated ammonium chloride solution (1×25 mL), a saturated sodium bicarbonate solution (1×25 mL), water (1×25 mL) and a saturated aqueous sodium chloride solution (1×25 mL). The organics were then dried over magnesium sulfate, filtered, rinsed and concentrated in vacuo. Silica gel column chromatography (AnaLogix 8 g, 50-100% ethyl acetate/hexanes) afforded 3-cyclopentyl-N-[1-(2-hydroxy-2-methyl-propyl)-1H-pyrazol-3-yl]-2-[4-(methyl-phenyl-amino)-6-oxo-6H-pyridazin-1-yl]-propionamide (39.4 mg, 44% over two steps) as a yellow solid; ES$^+$-HRMS m/e calcd for $C_{26}H_{34}N_6O_3$ [M+H$^+$] 479.2765, found 479.2764. $^1$H-NMR (400 MHz, DMSO-d$_6$) δ ppm 1.04 (s, 3H) 1.05 (s, 3H) 1.06-1.11 (m, 1H) 1.16-1.33 (m, 1H) 1.37-1.74 (m, 7H) 1.84-1.99 (m, 1H) 2.17-2.30 (m, 1H) 3.33 (s, 3H) 3.88 (s, 2H) 4.66 (s, 1H) 5.39 (dd, J=10.5, 4.8 Hz, 1H) 6.40 (d, J=2.1 Hz, 1H) 6.71 (d, J=4.9 Hz, 1H) 6.96-7.03 (m, 2H) 7.03-7.11 (m, 1H) 7.22-7.31 (m, 2H) 7.51 (d, J=2.1 Hz, 1H) 7.82 (d, J=4.9 Hz, 1H) 10.55 (s, 1H).

Example 78

3-Cyclopentyl-N-[1-(2-hydroxy-2-methyl-propyl)-1H-pyrazol-3-yl]-2-(6-oxo-6H-pyridazin-1-yl)-propionamide

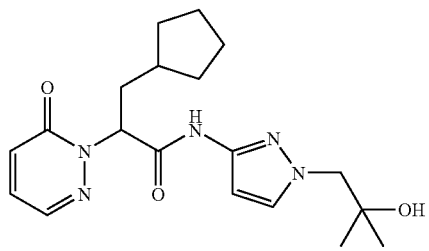

Step 1: A solution of 2H-pyridazin-3-one (2.0 g, 20.81 mmol) in tetrahydrofuran (104 mL, 0.2M) cooled to 0° C. was treated with a 60% dispersion of sodium hydride in mineral oil (839 mg, 24.97 mmol). The reaction was stirred at 25° C. for 30 min. After this time, the reaction was treated with 2-bromo-3-cyclopentyl-propionic acid methyl ester (Intermediate 10, 5.38 g, 22.89 mmol). The reaction was then warmed to 50° C. where it stirred overnight. After this time, the reaction was cooled to 25° C., was poured into water (150 mL) and was extracted into ethyl acetate (3×100 mL). The organics were dried over sodium sulfate, filtered and concentrated in vacuo. Silica gel column chromatography (ISCO 80 g, 30% ethyl acetate/hexanes) afforded 3-cyclopentyl-2-(6-oxo-6H-pyridazin-1-yl)-propionic acid methyl ester (3.0 g, 57%) as a tan oil; ES$^+$-HRMS m/e calcd for $C_{13}H_{18}N_2O_3$ [M+H$^+$] 251.1390 found 251.1389.
(38161-228)

Step 2: A solution of 3-cyclopentyl-2-(6-oxo-6H-pyridazin-1-yl)-propionic acid methyl ester (2.99 g, 11.97 mmol) in methanol (7.9 mL, 1.5M) was treated with a 4N aqueous sodium hydroxide solution (3.29 mL, 13.16 mmol) and stirred at 25° C. overnight. At this time, the reaction was concentrated in vacuo. The residue was partitioned between water (100 mL) which was acidified with a 2N aqueous hydrochloric acid solution and a solution of 90/10 methylene chloride/methanol (3×75 mL). The combined organics were dried over sodium sulfate, filtered and concentrated in vacuo to afford 3-cyclopentyl-2-(6-oxo-6H-pyridazin-1-yl)-propionic acid (2.45 g, 86%) as a light pink solid; ES$^+$-HRMS m/e calcd for $C_{12}H_{16}N_2O_3$ [M+H$^+$] 237.1234, found 237.1233.

Step 3: A solution of 3-cyclopentyl-2-(6-oxo-6H-pyridazin-1-yl)-propionic acid (183 mg, 0.77 mmol) in methylene chloride (4.30 mL, 0.18M) at 25° C. was treated with N,N,N',N'-tetramethyl-O—(N-succinimidyl)uronium tetrafluoroborate (0.28 g, 0.92 mmol) and N,N-diisopropylethylamine (0.40 mL, 2.32 mmol). The resulting solution was stirred at 25° C. for 2 h. After this time, the reaction was treated with 1-(3-amino-pyrazol-1-yl)-2-methyl-propan-2-ol (Intermediate 1, 156 mg, 1.0 mmol). The resulting solution was stirred at 25° C. for 2 d. After this time, the reaction was partitioned between water (75 mL) and methylene chloride (3×75 mL). The combined organics were dried over sodium sulfate, filtered and concentrated in vacuo. Silica gel column chromatography (ISCO, 40 g, 1-2% methanol/methylene chloride) afforded 3-cyclopentyl-N-[1-(2-hydroxy-2-methyl-propyl)-1H-pyrazol-3-yl]-2-(6-oxo-6H-pyridazin-1-yl)-propionamide as an off-white solid (21.9 mg, 7.6%); ES$^+$-HRMS m/e calcd for $C_{19}H_{27}N_5O_3$ [M+H$^+$] 374.2187 found 374.2187. $^1$H-NMR (300 MHz, DMSO-d$_6$) δ ppm 0.99-1.72 (m, 9H), 1.05 (s, 3H), 1.06 (s, 3H), 1.92 (m, 1H, CH), 2.28 (m, 1H), 3.89 (s, 2H), 4.67 (s, 1H), 5.52 (dd, J=4.2, J=10.6 Hz, 1H), 6.39 (d, J=2.3 Hz, 1H), 6.94 (dd, J$_o$=9.4 Hz, J$_m$=1.5 Hz, 1H), 7.42 (dd, J$_o$=9.4, J$_o$=3.8 Hz, 1H), 7.52 (d, J=2.3 Hz, 1H), 8.00 (dd, J$_o$=3.8 Hz, J$_m$=1.5 Hz, 1H), 10.79 (s, 1H).

In an analogous manner, there were obtained:

Example 79

3-Cyclopentyl-2-(6-oxo-6H-pyridazin-1-yl)-N-thiazol-2-yl-propionamide

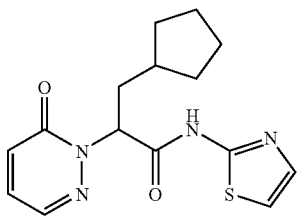

Using the method described in Example 78, Step 3,3-cyclopentyl-2-(6-oxo-6H-pyridazin-1-yl)-propionic acid (prepared as in Example 78, Step 2) and thiazol-2-ylamine afforded 3-cyclopentyl-2-(6-oxo-6H-pyridazin-1-yl)-N-thiazol-2-yl-propionamide as a white solid (39.9 mg, 29%); ES+-HRMS m/e calcd for $C_{15}H_{18}N_4O_2S$ [M+H+] 319.1223 found 319.1223. $^1$H-NMR (300 MHz, DMSO-$d_6$) δ ppm 1.00-1.75 (m, 9H), 1.99 (m, 1H, CH), 2.28 (m, 1H), 5.60 (dd, J=4.5, J=10.3 Hz, 1H), 6.98 (dd, $J_o$=9.4 Hz, $J_m$=1.5 Hz, 1H), 7.23 (d, J=3.6 Hz, 1H), 7.45 (dd, $J_o$=9.4, $J_o$=3.6 Hz, 1H), 7.49 (d, J=3.6 Hz, 1H), 8.02 (dd, $J_o$=3.6 Hz, $J_m$=1.5 Hz, 1H), 12.58 (s, 1H).

Example 80

3-Cyclopentyl-2-(4-methoxy-6-oxo-6H-pyridazin-1-yl)-N-thiazol-2-yl-propionamide

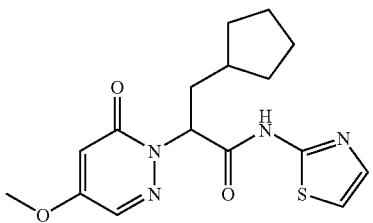

Step 1: A solution of 5-methoxy-2H-pyridazin-3-one (500 mg, 3.96 mmol) in tetrahydrofuran (19.8 mL, 0.2M) cooled to 0° C. was treated with a 60% dispersion of sodium hydride in mineral oil (190 mg, 4.75 mmol). The reaction was stirred at 25° C. for 30 min. After this time, the reaction was treated with 2-bromo-3-cyclopentyl-propionic acid methyl ester (Intermediate 10, 1.02 g, 4.36 mmol). The reaction was then warmed to 50° C. where it stirred overnight. After this time, the reaction was cooled to 25° C., was poured into water (100 mL) and was extracted into ethyl acetate (3×75 mL). The organics were dried over sodium sulfate, filtered and concentrated in vacuo. Silica gel column chromatography (ISCO 80 g, 40% ethyl acetate/hexanes) afforded 3-cyclopentyl-2-(4-methoxy-6-oxo-6H-pyridazin-1-yl)-propionic acid methyl ester (488 mg, 43%) as a clear oil; ES+-HRMS m/e calcd for $C_{14}H_{20}N_2O_4$ [M+H+] 281.1496 found 289.1495. $^1$H NMR (300 MHz, DMSO-$d_6$) δ ppm 0.92-1.16 (m, 2H), 1.33-1.64 (m, 6H), 1.63-1.78 (m, 1H), 1.89-2.03 (m, 1H), 2.16 (ddd, J=13.9, 10.9, 5.4 Hz, 1H), 3.61 (s, 3H), 3.82 (s, 3H), 5.39 (dd, J=10.7, 4.4 Hz, 1H), 6.32 (d, J=2.7 Hz, 1H), 7.84 (d, J=2.7 Hz, 1H).

Step 2: A solution of 3-cyclopentyl-2-(4-methoxy-6-oxo-6H-pyridazin-1-yl)-propionic acid methyl ester (458.8 mg, 1.63 mmol) in methanol (1.09 mL, 1.5M) was treated with a 4N aqueous sodium hydroxide solution (0.45 mL, 1.8 mmol) and was stirred at 25° C. overnight. At this time, the reaction was concentrated in vacuo. The residue was partitioned between water (100 mL), which was then acidified with a 2N aqueous hydrochloric acid solution to pH=2, and a 90/10 methylene chloride/methanol solution. The reaction was then extracted with a 90/10 methylene chloride/methanol solution (3×75 mL). The combined organics were dried over sodium sulfate, filtered and concentrated in vacuo to afford 3-cyclopentyl-2-(4-methoxy-6-oxo-6H-pyridazin-1-yl)-propionic acid (430 mg, 98%) as a white solid; ES+-HRMS m/e calcd for $C_{13}H_{18}N_2O_4$ [M+Na+] 289.1159, found 289.1159. $^1$H NMR (300 MHz, DMSO-$d_6$) δ ppm 0.93-1.22 (m, 2H), 1.33-1.78 (m, 7H), 1.84-2.03 (m, 1H), 2.06-2.21 (m, 1H), 3.82 (s, 3H), 5.32 (dd, J=10.9, 3.9 Hz, 1H), 6.30 (d, J=2.7 Hz, 1H), 7.82 (d, J=2.7 Hz, 1H), 12.96 (br. s., 1H).

Step 3: A solution of 3-cyclopentyl-2-(4-methoxy-6-oxo-6H-pyridazin-1-yl)-propionic acid (100 mg, 0.37 mmol) in methylene chloride (2.08 mL, 0.18M) at 25° C. was treated with N,N,N',N'-tetramethyl-O—(N-succinimidyl)uronium tetrafluoroborate (135.6 mg, 0.45 mmol) and N,N-diisopropylethylamine (0.196 mL, 1.12 mmol). The resulting solution was stirred at 25° C. for 2 h. After this time, the reaction was treated with thiazol-2-ylamine (49 mg, 0.48 mmol). The resulting solution was stirred at 25° C. for 1 d. After this time, the reaction was partitioned between water (75 mL) and methylene chloride (3×75 mL). The combined organics were dried over sodium sulfate, filtered and concentrated in vacuo. Silica gel column chromatography (ISCO, 40 g, 1% methanol/methylene chloride) afforded 3-cyclopentyl-2-(4-methoxy-6-oxo-6H-pyridazin-1-yl)-N-thiazol-2-yl-propionamide as a white solid (41.4 mg, 32%); ES+-HRMS m/e calcd for $C_{16}H_{20}N_4O_3S$ [M+H+] 349.1329, found 349.1328. $^1$H-NMR (300 MHz, DMSO-$d_6$) δ ppm 0.98-7.78 (m, 9H), 1.95 (m, 1H), 2.27 (m, 1H), 3.82 (s, 3H), 5.54 (dd, J=4.5, J=10.6 Hz, 1H), 6.32 (d, $J_m$=2.7 Hz, 1H), 7.23 (d, J=3.6 Hz, 1H), 7.48 (d, J=3.6 Hz, 1H), 7.88 (d, $J_m$=2.7 Hz, 1H), 12.53 (s, 1H).

Example 81

3-Cyclopentyl-N-[1-(2-hydroxy-2-methyl-propyl)-1H-pyrazol-3-yl]-2-(4-methoxy-6-oxo-6H-pyridazin-1-yl)-propionamide

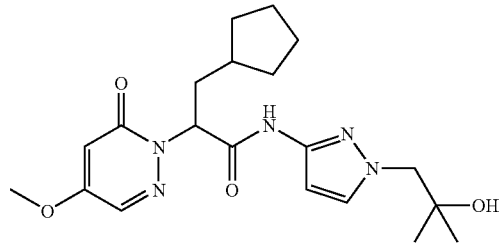

Using the method described in Example 80, Step 3,3-cyclopentyl-2-(4-methoxy-6-oxo-6H-pyridazin-1-yl)-propionic acid (as prepared in Example 80, Step 2) and 1-(3-amino-pyrazol-1-yl)-2-methyl-propan-2-ol (Intermediate 1) afforded 3-cyclopentyl-N-[1-(2-hydroxy-2-methyl-propyl)-1H-pyrazol-3-yl]-2-(4-methoxy-6-oxo-6H-pyridazin-1-yl)-propionamide as an off-white solid (45.1 mg, 29%); ES+-HRMS m/e calcd for $C_{20}H_{29}N_5O_4$ [M+H+] 404.2293 found 404.2292. $^1$H-NMR (300 MHz, DMSO-$d_6$) δ ppm 1.04 (m, 1H), 1.05 (s, 3H), 1.06 (s, 3H), 1.18-1.77 (m, 8H), 1.91 (m, 1H), 2.26 (m, 1H), 3.81 (s, 3H), 3.89 (s, 2H), 4.67 (s, 1H), 5.46

(dd, J=4.1, J=11.3 Hz, 1H), 6.29 (d, J=2.7 Hz, 1H), 6.39 (s, 1H), 7.52 (s, 1H), 7.84 (d, J=2.7 Hz, 1H), 10.73 (s, 1H).

Example 82

3-Cyclopentyl-N-(1-methyl-1H-pyrazol-3-yl)-2-(6-oxo-6H-pyridazin-1-yl)-propionamide

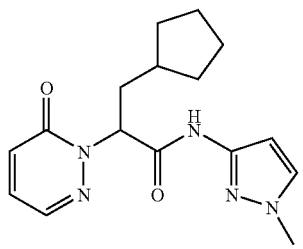

Using the method described in Example 78, Step 3, from 3-cyclopentyl-2-(6-oxo-6H-pyridazin-1-yl)-propionic acid (As prepared in Example 78, Step 2) and 1-methyl-1H-pyrazol-3-ylamine afforded 3-cyclopentyl-N-(1-methyl-1H-pyrazol-3-yl)-2-(6-oxo-6H-pyridazin-1-yl)-propionamide as a white solid (37.1 mg, 36%); ES+-HRMS m/e calcd for $C_{16}H_{21}N_5O_2$ [M+H+] 316.1768 found 316.1768. $^1$H-NMR (400 MHz, DMSO-$d_6$) δ ppm 1.07 (br s, 1H), 1.24-1.36 (m, 1H), 1.36-1.49 (m, 2H), 1.49-1.74 (m, 5H), 1.93 (ddd, J=13.4, 8.6, 4.5 Hz, 1H), 2.18-2.31 (m, 1H), 3.73 (s, 3H), 5.51 (dd, J=10.7, 4.7 Hz, 1H), 6.35 (d, J=2.0 Hz, 1H), 6.94 (dd, J=9.5, 1.5 Hz, 1H), 7.42 (dd, J=9.5, 3.7 Hz, 1H), 7.53 (d, J=2.0 Hz, 1H), 7.99 (dd, J=3.7, 1.5 Hz, 1H), 10.72 (s, 1H).

Example 83

3-Cyclopentyl-2-(1-oxo-1H-phthalazin-2-yl)-N-thiazol-2-yl-propionamide

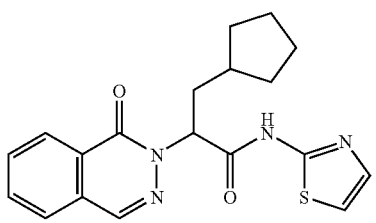

Step 1: A solution of 2H-phthalazin-1-one (1.33 g, 9.1 mmol) in tetrahydrofuran (45.5 mL, 0.2M) cooled to 0° C. was treated with a 60% dispersion of sodium hydride in mineral oil (437 mg, 10.9 mmol). The reaction was stirred at 0° C. for 5 min and then at 25° C. for 30 min. After this time, the reaction was treated with 2-bromo-3-cyclopentyl-propionic acid methyl ester (Intermediate 10, 2.35 g, 10 mmol). The reaction was then warmed to 50° C. where it stirred overnight. At this time, the reaction was cooled to 25° C., poured into water (100 mL), and extracted with methylene chloride (3×100 mL). The organics were dried over sodium sulfate, filtered and concentrated in vacuo. Silica gel column chromatography (ISCO, 80 g, 20-50% ethyl acetate/hexanes) afforded 3-cyclopentyl-2-(1-oxo-1H-phthalazin-2-yl)-propionic acid methyl ester (1.78 g, 61%) as a clear oil; ES+-HRMS m/e calcd for $C_{17}H_{20}N_2O_3$ [M+H+] 301.1547 found 301.1546.

Step 2: A solution of 3-cyclopentyl-2-(1-oxo-1H-phthalazin-2-yl)-propionic acid methyl ester (1.76 g, 5.85 mmol) in methanol (3.9 mL, 1.5M) was treated with a 4N aqueous sodium hydroxide solution (1.61 mL, 6.44 mmol) and stirred at 25° C. for 4 h. At this time, the reaction was concentrated in vacuo. The residue was diluted with water (100 mL) and was acidified with a 2N aqueous hydrochloric acid solution and then extracted with a solution of 90/10 methylene chloride/methanol (3×100 mL). The combined organics were dried over sodium sulfate, filtered and concentrated in vacuo to afford 3-cyclopentyl-2-(1-oxo-1H-phthalazin-2-yl)-propionic acid (1.58 g, 94%) as a white solid; ES+-HRMS m/e calcd for $C_{16}H_{18}N_2O_3$ [M+H+] 287.1390, found 287.1390.

Step 3: A solution of 3-cyclopentyl-2-(1-oxo-1H-phthalazin-2-yl)-propionic acid (0.31 g, 1.09 mmol) in methylene chloride (6.10 mL, 0.18M) at 25° C. was treated with N,N-diisopropylethylamine (0.57 mL, 3.29 mmol) and N,N,N',N'-tetramethyl-O—(N-succinimidyl)uronium tetrafluoroborate (0.39 g, 1.31 mmol). The resulting solution was stirred at 25° C. for 2 h. After this time, the reaction was treated with thiazol-2-ylamine (143 mg, 1.42 mmol). The resulting solution was stirred at 25° C. overnight. After this time, the reaction was partitioned between water (100 mL) and methylene chloride (3×75 mL). The combined organics were washed with water (1×100 mL), dried over sodium sulfate, filtered and concentrated in vacuo. Silica gel column chromatography (ISCO, 40 g, 50% ethyl acetate/hexanes) afforded 3-cyclopentyl-2-(1-oxo-1H-phthalazin-2-yl)-N-thiazol-2-yl-propionamide as a white solid (247.7 mg, 61%); ES+-HRMS m/e calcd for $C_{19}H_{20}N_4O_2S$ [M+H+] 369.1380 found 369.1378. $^1$H-NMR (300 MHz, DMSO-$d_6$) δ ppm 0.99-1.17 (m, 1H), 1.20-1.80 (m, 8H), 2.04-2.18 (m, 1H), 2.23-2.36 (m, 1H), 5.73 (dd, J=10.4, 4.4 Hz, 1H), 7.22 (d, J=3.4 Hz, 1H), 7.47 (d, J=3.4 Hz, 1H), 7.83-7.93 (m, 1H), 7.94-8.02 (m, 2H), 8.26 (d, J=7.8 Hz, 1H), 8.52 (s, 1H), 12.46 (s, 1H).

Example 84

3-Cyclopentyl-N-[1-(2-hydroxy-2-methyl-propyl)-1H-pyrazol-3-yl]-2-(1-oxo-1H-phthalazin-2-yl)-propionamide

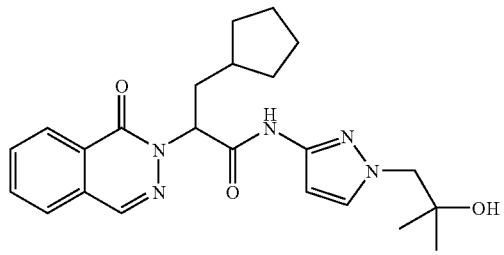

Using the method described in Example 83, Step 3,3-cyclopentyl-2-(1-oxo-1H-phthalazin-2-yl)-propionic acid (as prepared in Example 83, Step 2) and 1-(3-amino-pyrazol-1-yl)-2-methyl-propan-2-ol (Intermediate 1) afforded 3-cyclopentyl-N-[1-(2-hydroxy-2-methyl-propyl)-1H-pyrazol-3-yl]-2-(1-oxo-1H-phthalazin-2-yl)-propionamide as a white solid (48 mg, 11%); ES+-HRMS m/e calcd for $C_{23}H_{29}N_5O_3$ [M+H+] 319.1223 found 319.1223. $^1$H-NMR (300 MHz, DMSO-$d_6$) δ ppm 1.03 (s, 6H), 1.04-1.17 (m, 1H), 1.24-1.72 (m, 8H), 1.93-2.10 (m, 1H), 2.21-2.35 (m, 1H), 3.86 (s, 2H), 4.64 (s, 1H), 5.61 (dd, J=10.7, 4.1 Hz, 1H), 6.39 (d, J=2.1 Hz, 1H), 7.50 (d, J=2.1 Hz, 1H), 7.79-7.91 (m, 1H), 7.91-7.98 (m, 2H), 8.24 (d, J=7.5 Hz, 1H), 8.48 (s, 1H), 10.66 (s, 1H).

Example 85

3-Cyclopentyl-2-(1-oxo-1H-phthalazin-2-yl)-N-thiazol-2-yl-propionamide

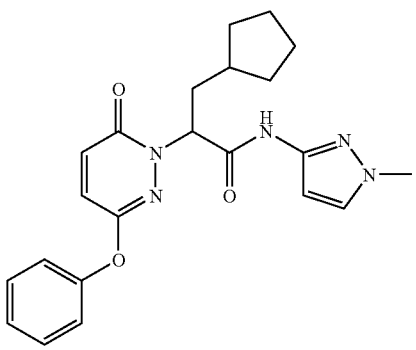

Step 1: A mixture of 3,6-dichloropyridazine (1.0 g, 5.23 mmol), phenol (0.50 g, 5.31 mmol), potassium carbonate (2.90 g, 20.98 mmol), and copper(I) iodide (0.59 g, 3.09 mmol) in dimethylsulfoxide (3.6 mL, 1.45 M) was heated to 90° C. overnight. After this time, the reaction was cooled to 25° C. and then poured into a 2N aqueous hydrochloric acid solution (75 mL) rinsing with water. The resulting mixture was filtered through filter paper and diluted with a saturated aqueous sodium chloride solution followed by extraction with ethyl acetate (150 mL). The organics were washed with a saturated aqueous sodium chloride solution (1×75 mL), dried over magnesium sulfate, filtered and concentrated in vacuo. Silica gel column chromatography (AnaLogix, 80 g, 5-24% ethyl acetate/hexanes) afforded 3-chloro-6-phenoxy-pyridazine (1.01 g, 93%) as a yellow solid. $^1$H-NMR (300 MHz, DMSO-d$_6$) δ ppm 7.14-7.35 (m, 3H), 7.47 (t, J=7.5 Hz, 2H), 7.59 (d, J=9.2 Hz, 1H), 7.96 (d, J=9.2 Hz, 1H).

Step 2: A mixture of 3-chloro-6-phenoxy-pyridazine (1.01 g, 4.89 mmol) and sodium acetate (1.40 g, 17.06 mmol) in glacial acetic acid (50 mL, 0.1M) was heated to 110° C. overnight. After this time the reaction was cooled to 25° C. and was diluted with water (450 mL). The reaction was brought to pH=5-6 by the addition of a 5N aqueous sodium hydroxide solution. The resulting solution was extracted with ethyl acetate (3×100 mL). The combined organics were washed with a saturated aqueous sodium chloride solution (1×100 mL), dried over magnesium sulfate, filtered, rinsed with ethyl acetate and concentrated in vacuo. The resulting oil was azeotroped with methanol four times and dried in vacuo to afford 6-phenoxy-2H-pyridazin-3-one (0.78 g, 86%) as a white solid. $^1$H-NMR (300 MHz, DMSO-d$_6$) δ ppm 7.00 (d, J=10.0 Hz, 1H), 7.13-7.27 (m, 3H), 7.34-7.46 (m, 3H), 12.29 (br s, 1H).

Step 3: A solution of 6-phenoxy-2H-pyridazin-3-one (0.78 g, 4.18 mmol) in tetrahydrofuran (21 mL, 0.2M) cooled to 0° C. was treated with a 60% dispersion of sodium hydride in mineral oil (0.2 g, 5.0 mmol). The reaction was stirred at 0° C. for 5 min and then at 25° C. for 35 min. After this time, the reaction was treated with 2-bromo-3-cyclopentyl-propionic acid methyl ester (Intermediate 10, 1.08 g, 4.59 mmol). The reaction was then warmed to 50° C. where it stirred overnight. After this time, the reaction was cooled to 25° C., poured into water (100 mL), and extracted into methylene chloride (3×100 mL). The combined organics were washed with a saturated aqueous sodium chloride solution (1×100 mL), dried over magnesium sulfate, filtered, rinsed with methylene chloride and concentrated in vacuo. Silica gel column chromatography (AnaLogix, 80 g, 20-40% ethyl acetate/hexanes) afforded 3-cyclopentyl-2-(6-oxo-3-phenoxy-6H-pyridazin-1-yl)-propionic acid methyl ester (1.03 g, 72%) as a light yellow oil. $^1$H-NMR (300 MHz, DMSO-d$_6$) δ ppm 0.98 (d, 2H), 1.32-1.71 (m, 7H), 1.71-1.84 (m, 1H), 1.84-2.05 (m, 1H), 3.59 (s, 3H), 5.19 (dd, J=10.9, 3.9 Hz, 1H), 7.10-7.18 (m, 3H), 7.22 (t, J=7.5 Hz, 1H), 7.42 (t, J=7.5 Hz, 2H), 7.48 (d, J=9.7 Hz, 1H).

Step 4: A solution of 3-cyclopentyl-2-(6-oxo-3-phenoxy-6H-pyridazin-1-yl)-propionic acid methyl ester (1.03 g, 3.03 mmol) in methanol (8.5 mL, 0.36M) was treated with a 4N aqueous sodium hydroxide solution (0.83 mL, 3.34 mmol) and stirred at 25° C. overnight. After this time, the reaction was concentrated in vacuo. The residue was diluted with water (100 mL) and acidified to pH=1 with a 3N aqueous hydrochloric acid solution. The resulting solids were collected by filtration, rinsed with water, air dried and then further dried in vacuo to afford 3-cyclopentyl-2-(6-oxo-3-phenoxy-6H-pyridazin-1-yl)-propionic acid (0.81 g, 81%) as a white solid. $^1$H-NMR (300 MHz, DMSO-d$_6$) δ ppm 0.94 (br s, 2H), 1.29-1.70 (m, 7H), 1.79 (br s, 1H), 1.85-2.05 (m, 1H), 5.08 (dd, J=10.6, 3.0 Hz, 1H), 7.06 (d, J=9.7 Hz, 1H), 7.10-7.25 (m, 3H), 7.34-7.45 (m, 3H).

Step 5: A solution of 3-cyclopentyl-2-(6-oxo-3-phenoxy-6H-pyridazin-1-yl)-propionic acid (0.30 g, 0.91 mmol) in methylene chloride (9.0 mL, 0.10M) at 25° C. was treated with 1-(3-dimethylaminopropyl)-3-ethylcarbodiimide (164 µL, 0.92 mmol) and 1-hydroxybenzotriazole (0.13 g, 0.96 mmol). The solution was stirred at 25° C. for 1.8 h. After this time, the reaction was treated with a solution of 1-methyl-1H-pyrazol-3-ylamine in methylene chloride at 25° C. The reaction was stirred at 25° C. for 5 d. After this time, the reaction was diluted with methylene chloride (100 mL) and was washed with a 1N aqueous hydrochloric acid solution (2×100 mL), a saturated aqueous sodium bicarbonate solution (2×100 mL), water (1×100 mL), and a saturated aqueous sodium chloride solution (1×100 mL), dried over magnesium sulfate, filtered, rinsed with methylene chloride and concentrated in vacuo. Silica gel column chromatography (AnaLogix, 40 g, 50-100% ethyl acetate/hexanes gradient) afforded 3-cyclopentyl-N-(1-methyl-1H-pyrazol-3-yl)-2-(6-oxo-3-phenoxy-6H-pyridazin-1-yl)-propionamide (76.7 mg, 21%) as a white solid; ES$^+$-HRMS m/e calcd for C$_{22}$H$_{25}$N$_5$O$_3$ [M+H$^+$] 408.2030 found 408.2030. $^1$H-NMR (400 MHz, DMSO-d$_6$) δ ppm 0.87-0.98 (m, 1H), 1.17-1.31 (m, 1H), 1.35-1.63 (m, 7H), 1.69 (ddd, J=13.1, 9.3, 3.6 Hz, 1H), 1.88-2.00 (m, 1H), 3.73 (s, 3H), 5.29 (dd, J=11.1, 3.6 Hz, 1H), 6.33

(d, J=2.0 Hz, 1H), 7.09 (d, J=9.8 Hz, 1H), 7.17-7.26 (m, 3H), 7.34-7.43 (m, 2H), 7.46 (d, J=9.8 Hz, 1H), 7.53 (d, J=2.0 Hz, 1H), 10.66 (s, 1H).

Example 88

3-Cyclopentyl-N-[1-(2-hydroxy-2-methyl-propyl)-1H-pyrazol-3-yl]-2-[6-oxo-4-(2,3,6-trimethyl-phenoxy)-6H-pyridazin-1-yl]-propionamide

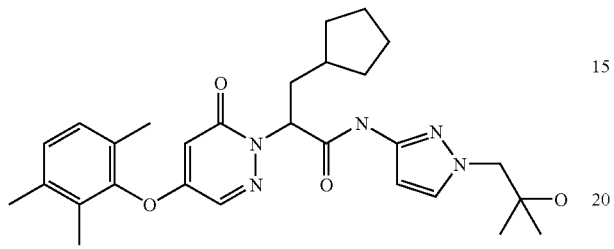

Using the method described in Example 49, 3-cyclopentyl-2-[6-oxo-4-(2,3,6-trimethyl-phenoxy)-6H-pyridazin-1-yl]-propionic acid (Intermediate 66) and 1-(3-amino-pyrazol-1-yl)-2-methyl-propan-2-ol (Intermediate 1) afforded 3-cyclopentyl-N-[1-(2-hydroxy-2-methyl-propyl)-1H-pyrazol-3-yl]-2-[6-oxo-4-(2,3,6-trimethyl-phenoxy)-6H-pyridazin-1-yl]-propionamide as a white solid (1.27 g, 93%); ES$^+$-HRMS m/e calcd for $C_{28}H_{37}N_5O_4$ [M+H$^+$] 508.2919 found 508.2921. $^1$H NMR (300 MHz, DMSO-d$_6$) δ ppm 0.98-1.18 (m, 1H), 1.04 (s, 3H), 1.05 (s, 3H), 1.23-1.79 (m, 8H), 1.83-1.98 (m, 1H), 2.01 (s, 3H), 2.06 (s, 3H), 2.17-2.32 (m, 1H), 2.25 (s, 3H), 3.89 (s, 2H), 4.68 (s, 1H), 5.37-5.50 (m, 2H), 6.39 (d, J=2.1 Hz, 1H), 7.01-7.19 (m, 2H), 7.52 (d, J=2.1 Hz, 1H), 8.19 (d, J=2.7 Hz, 1H), 10.83 (s, 1H).

Example 89

3-Cyclopentyl-2-[4-(2,2-dimethyl-2,3-dihydro-benzofuran-7-yloxy)-6-oxo-6H-pyridazin-1-yl]-N-[1-(2-hydroxy-2-methyl-propyl)-1H-pyrazol-3-yl]-propionamide

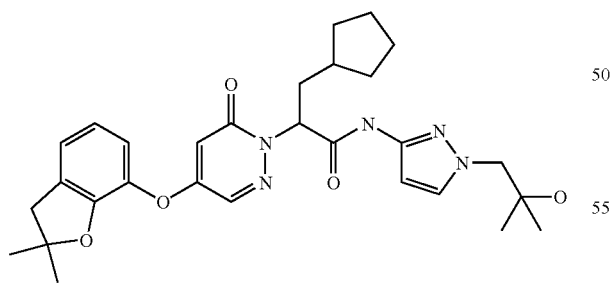

Using the method described in Example 49, 3-cyclopentyl-2-[4-(2,2-dimethyl-2,3-dihydro-benzofuran-7-yloxy)-6-oxo-6H-pyridazin-1-yl]-propionic acid (Intermediate 67) and 1-(3-amino-pyrazol-1-yl)-2-methyl-propan-2-ol (Intermediate 1) afforded 3-cyclopentyl-2-[4-(2,2-dimethyl-2,3-dihydro-benzofuran-7-yloxy)-6-oxo-6H-pyridazin-1-yl]-N-[1-(2-hydroxy-2-methyl-propyl)-1H-pyrazol-3-yl]-propionamide as a white solid (1.13 g, 84%); ES$^+$-HRMS m/e calcd for $C_{29}H_{37}N_5O_5$ [M+H$^+$] 536.2868 found 536.2866. $^1$H NMR (300 MHz, DMSO-d$_6$) δ ppm 1.04 (br. s., 3H), 1.06 (br. s., 3H), 1.06-1.16 (m, 1H), 1.24-1.74 (m, 8H), 1.40 (s, 6H), 1.91 (br. s., 1H), 2.20-2.35 (m, 1H), 3.09 (s, 2H), 3.89 (s, 2H), 4.68 (s, 1H), 5.46 (dd, J=11.0, 4.1 Hz, 1H), 5.69 (d, J=2.7 Hz, 1H), 6.39 (d, J=2.1 Hz, 1H), 6.90 t, 7.5 Hz, 1H), 7.06 (d, J=7.5 Hz, 1H), 7.19 (d, J=7.5 Hz, 1H), 7.52 (d, J=2.1 Hz, 1H), 8.11 (d, J=2.7 Hz, 1H), 10.84 (s, 1H).

Example 90

2-[4-(2-tert-Butyl-phenoxy)-6-oxo-6H-pyridazin-1-yl]-3-cyclopentyl-N-[1-(2-hydroxy-2-methyl-propyl)-1H-pyrazol-3-yl]-propionamide

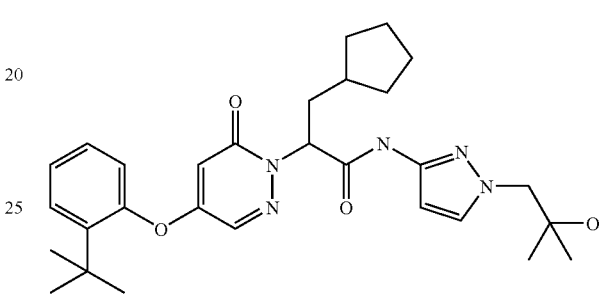

Using the method described in Example 49, 2-[4-(2-tert-butyl-phenoxy)-6-oxo-6H-pyridazin-1-yl]-3-cyclopentyl-propionic acid (Intermediate 68) and 1-(3-amino-pyrazol-1-yl)-2-methyl-propan-2-ol (Intermediate 1) afforded 2-[4-(2-tert-butyl-phenoxy)-6-oxo-6H-pyridazin-1-yl]-3-cyclopentyl-N-[1-(2-hydroxy-2-methyl-propyl)-1H-pyrazol-3-yl]-propionamide was obtained as an off-white solid (1.05 g, 77%); ES$^+$-HRMS m/e calcd for $C_{29}H_{39}N_5O_4$ [M+H$^+$] 522.3075 found 522.3077. $^1$H NMR (400 MHz, DMSO-d$_6$) δ ppm 1.03-1.08 (m, 8H), 1.32 (s, 9H), 1.37-1.78 (m, 7H), 1.81-2.02 (m, 1H), 2.17-2.36 (m, 1H), 3.89 (s, 2H), 4.67 (s, 1H), 5.47 (dd, J=10.7, 4.3 Hz, 1H), 5.79 (d, J=2.8 Hz, 1H), 6.40 (d, J=2.1 Hz, 1H), 7.16 (d, J=7.9 Hz, 1H), 7.23-7.30 (m, 1H), 7.31-7.38 (m, 1H), 7.50 (dd, J=7.8, 1.4 Hz, 1H), 7.53 (d, J=2.1 Hz, 1H), 8.15 (d, J=2.8 Hz, 1H), 10.81 (s, 1H).

Example 91

3-Cyclopentyl-N-[1-((R)-2,3-dihydroxy-propyl)-1H-pyrazol-3-yl]-2-[4-(2,6-dimethyl-cyclohexyloxy)-6-oxo-6H-pyridazin-1-yl]-propionamide

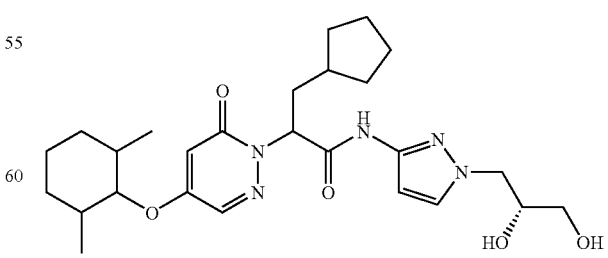

Step 1: Using the method described in Example 49, 3-cyclopentyl-2-[4-(2,6-dimethyl-cyclohexyloxy)-6-oxo-6H-pyridazin-1-yl]-propionic acid (Intermediate 69) and 1-((R)-2, 2-dimethyl-[1,3]dioxolan-4-ylmethyl)-1H-pyrazol-3-ylamine (Intermediate 4) afforded 3-cyclopentyl-2-[4-(2,6-dimethyl-cyclohexyloxy)-6-oxo-6H-pyridazin-1-yl]-N-[1-((R)-2,2-dimethyl-[1,3]dioxolan-4-ylmethyl)-1H-pyrazol-3-yl]-propionamide as an orange solid as a mixture of diastereomers (1.14 g, 76%).

Step 2: Using the method described in Example 61, Step 2,3-cyclopentyl-2-[4-(2,6-dimethyl-cyclohexyloxy)-6-oxo-6H-pyridazin-1-yl]-N-[1-((R)-2,2-dimethyl-[1,3]dioxolan-4-ylmethyl)-1H-pyrazol-3-yl]-propionamide afforded 3-cyclopentyl-N-[1-((R)-2,3-dihydroxy-propyl)-1H-pyrazol-3-yl]-2-[4-(2,6-dimethyl-cyclohexyloxy)-6-oxo-6H-pyridazin-1-yl]-propionamide as an off-white solid as a mixture of diastereomers and cis-trans isomers (870.8 mg, 82%); ES$^+$-HRMS m/e calcd for $C_{26}H_{39}N_5O_5$ [M+H$^+$] 502.3024 found 502.3023. $^1$H NMR (400 MHz, DMSO-d$_6$) δ ppm 0.75-0.89 (m, 5H), 0.93 (dd, J=6.6, 3.8 Hz, 1H), 1.08-1.78 (m, 16H), 1.96, 2.21 (2×m, 3H), 3.19-3.38 (m, 2H), 3.72-3.95 (m, 2H), 4.09 (dd, J=13.7, 4.2 Hz, 1H), 4.16, 4.58 (2×m, 1H), 4.70 (t, J=5.5 Hz, 1H), 4.91-4.97 (m, 1H), 5.49 (br. s., 1H), 6.34-6.39 (m, 1H), 6.73-7.01 (m, 1H), 7.52 (d, J=2.1 Hz, 1H), 7.72-7.85 (m, 1H), 10.45-10.92 (m, 1H).

Example 92

3-Cyclopentyl-2-[4-(2,3-dichloro-phenoxy)-6-oxo-6H-pyridazin-1-yl]-N-[1-((R)-2,3-dihydroxy-propyl)-1H-pyrazol-3-yl]-propionamide

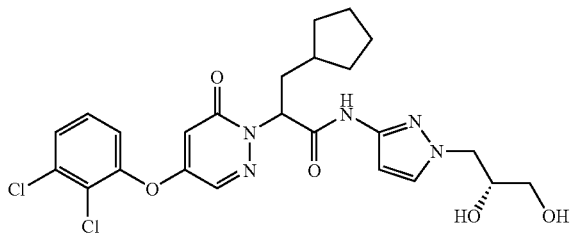

Step 1: Using the method described in Example 49, 3-cyclopentyl-2-[4-(2,3-dichloro-phenoxy)-6-oxo-6H-pyridazin-1-yl]-propionic acid (Intermediate 70) and 1-((R)-2,2-dimethyl-[1,3]dioxolan-4-ylmethyl)-1H-pyrazol-3-ylamine (Intermediate 4) afforded 3-cyclopentyl-2-[4-(2,3-dichloro-phenoxy)-6-oxo-6H-pyridazin-1-yl]-N-[1-((R)-2,2-dimethyl-[1,3]dioxolan-4-ylmethyl)-1H-pyrazol-3-yl]-propionamide as a light brown solid as a mixture of diastereomers (1.28 g, 88%).

Step 2: Using the method described in Example 61, Step 2,3-cyclopentyl-2-[4-(2,3-dichloro-phenoxy)-6-oxo-6H-pyridazin-1-yl]-N-[1-((R)-2,2-dimethyl-[1,3]dioxolan-4-ylmethyl)-1H-pyrazol-3-yl]-propionamide afforded 3-cyclopentyl-2-[4-(2,3-dichloro-phenoxy)-6-oxo-6H-pyridazin-1-yl]-N-[1-((R)-2,3-dihydroxy-propyl)-1H-pyrazol-3-yl]-propionamide as an off-white solid as a mixture of diastereomers (985.7 mg, 83%); ES$^+$-HRMS m/e calcd for $C_{24}H_{27}N_5O_5Cl_2$ [M+H$^+$] 536.1462 found 536.1463. $^1$H NMR (400 MHz, DMSO-d$_6$) δ ppm 1.03-1.16 (m, 1H), 1.27-1.77 (m, 8H), 1.85-2.00 (m, 1H), 2.21-2.32 (m, 1H), 3.21-3.32 (m, 1H), 3.39-3.51 (m, 1H), 3.72-3.81 (m, 1H), 3.81-3.94 (m, 1H), 4.09 (dd, J=13.6, 4.0 Hz, 1H), 4.71 (t, J=5.5 Hz, 1H), 4.94 (dd, J=5.3, 2.1 Hz, 1H), 5.43-5.50 (m, 1H), 5.90 (d, J=2.8 Hz, 1H), 6.36 (d, J=2.1 Hz, 1H), 7.48-7.55 (m, 3H), 7.63-7.71 (m, 1H), 8.21 (d, J=2.8 Hz, 1H), 10.81 (s, 1H).

Example 93

3-Cyclopentyl-N-[1-((R)-2,3-dihydroxy-propyl)-1H-pyrazol-3-yl]-2-[4-(7-methyl-indan-4-yloxy)-6-oxo-6H-pyridazin-1-yl]-propionamide

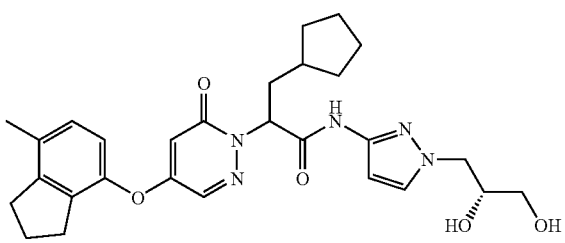

Step 1: Using the method described in Example 49, 3-cyclopentyl-2-[4-(7-methyl-indan-4-yloxy)-6-oxo-6H-pyridazin-1-yl]-propionic acid (Intermediate 71) and 1-((R)-2,2-dimethyl-[1,3]dioxolan-4-ylmethyl)-1H-pyrazol-3-ylamine (Intermediate 4) afforded 3-cyclopentyl-N-[1-((R)-2,2-dimethyl-[1,3]dioxolan-4-ylmethyl)-1H-pyrazol-3-yl]-2-[4-(7-methyl-indan-4-yloxy)-6-oxo-6H-pyridazin-1-yl]-propionamide as an off-white solid as a mixture of diastereomers (1.09 g, 74%).

Step 2: Using the method described in Example 61, Step 2,3-cyclopentyl-N-[1-((R)-2,2-dimethyl-[1,3]dioxolan-4-ylmethyl)-1H-pyrazol-3-yl]-2-[4-(7-methyl-indan-4-yloxy)-6-oxo-6H-pyridazin-1-yl]-propionamide afforded 3-cyclopentyl-N-[1-((R)-2,3-dihydroxy-propyl)-1H-pyrazol-3-yl]-2-[4-(7-methyl-indan-4-yloxy)-6-oxo-6H-pyridazin-1-yl]-propionamide as a white solid as a mixture of diastereomers (783.7 mg, 77%); ES$^+$-HRMS m/e calcd for $C_{28}H_{35}N_5O_5$ [M+H$^+$] 522.2711 found 522.2712. $^1$H NMR (400 MHz, DMSO-d$_6$) δ ppm 1.02-1.17 (m, 1H), 1.25-1.38 (m, 1H), 1.38-1.76 (m, 7H), 1.86-1.98 (m, 1H), 1.99-2.11 (m, 2H), 2.20-2.31 (m, 1H), 2.24 (s, 3H), 2.74 (t, J=7.4 Hz, 2H), 2.86 (t, J=7.4 Hz, 2H), 3.22-3.32 (m, 2H), 3.77 (br. s., 1H), 3.81-3.91 (m, 1H), 4.09 (dd, J=13.6, 4.0 Hz, 1H), 4.70 (t, J=5.4 Hz, 1H), 4.93 (dd, J=5.4, 1.5 Hz, 1H), 5.37-5.49 (m, 1H), 5.60 (d, J=2.8 Hz, 1H), 6.36 (d, J=2.0 Hz, 1H), 6.92 (d, J=8.1 Hz, 1H), 7.09 (d, J=8.1 Hz, 1H), 7.52 (d, J=2.0 Hz, 1H), 8.11 (d, J=2.8 Hz, 1H), 10.77 (s, 1H).

Example 94

2-(4-Cyclobutoxy-6-oxo-6H-pyridazin-1-yl)-3-cyclopentyl-N-[1-((R)-2,3-dihydroxy-propyl)-1H-pyrazol-3-yl]-propionamide

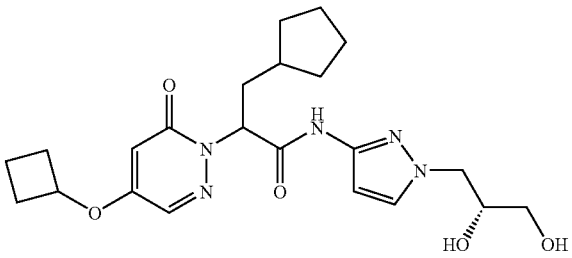

Step 1: Using the method described in Example 49, 2-(4-cyclobutoxy-6-oxo-6H-pyridazin-1-yl)-3-cyclopentyl-propionic acid (Intermediate 72) and 1-((R)-2,2-dimethyl-[1,3]

dioxolan-4-ylmethyl)-1H-pyrazol-3-ylamine (Intermediate 4) afforded 2-(4-cyclobutoxy-6-oxo-6H-pyridazin-1-yl)-3-cyclopentyl-N-[1-((R)-2,2-dimethyl-[1,3]dioxolan-4-ylmethyl)-1H-pyrazol-3-yl]-propionamide as an off-white solid as a mixture of diastereomers (0.38 g, 24%).

Step 2: Using the method described in Example 61, Step 2,2-(4-cyclobutoxy-6-oxo-6H-pyridazin-1-yl)-3-cyclopentyl-N-[1-((R)-2,2-dimethyl-[1,3]dioxolan-4-ylmethyl)-1H-pyrazol-3-yl]-propionamide afforded 2-(4-cyclobutoxy-6-oxo-6H-pyridazin-1-yl)-3-cyclopentyl-N-[1-((R)-2,3-dihydroxy-propyl)-1H-pyrazol-3-yl]-propionamide as a white solid as a mixture of diastereomers (148.7 mg, 43%); ES+-HRMS m/e calcd for $C_{22}H_{31}N_5O_5$ [M+H+] 446.2398 found 446.2399. $^1$H NMR (400 MHz, DMSO-$d_6$) δ ppm 1.01-1.14 (m, 1H), 1.29 (br. s., 1H), 1.42 (br. s., 2H), 1.47-1.74 (m, 6H), 1.74-2.01 (m, 2H), 2.01-2.15 (m, 2H), 2.17-2.30 (m, 1H), 2.37-2.47 (m, 2H), 3.22-3.31 (m, 2H), 3.68-3.81 (m, 1H), 3.81-3.92 (m, 1H), 4.08 (d, J=13.6 Hz, 1H), 4.66-4.75 (m, 2H), 4.93 (dd, J=5.3, 2.6 Hz, 1H), 5.49 (dd, J=10.8, 4.2 Hz, 1H), 6.36 (d, J=2.0 Hz, 1H), 6.60 (d, J=4.8 Hz, 1H), 7.52 (d, J=2.0 Hz, 1H), 7.81 (d, J=4.8 Hz, 1H), 10.65 (s, 1H).

Example 95

3-Cyclopentyl-N-[1-((R)-2,3-dihydroxy-propyl)-1H-pyrazol-3-yl]-2-[4-(3-fluoro-pyridin-2-yloxy)-6-oxo-6H-pyridazin-1-yl]-propionamide

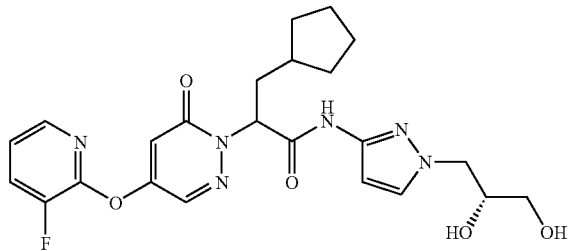

Step 1: Using the method described in Example 49, 3-cyclopentyl-2-[4-(3-fluoro-pyridin-2-yloxy)-6-oxo-6H-pyridazin-1-yl]-propionic acid (Intermediate 73) and 1-((R)-2,2-dimethyl-[1,3]dioxolan-4-ylmethyl)-1H-pyrazol-3-ylamine (Intermediate 4) afforded 3-cyclopentyl-N-[1-((R)-2,2-dimethyl-[1,3]dioxolan-4-ylmethyl)-1H-pyrazol-3-yl]-2-[4-(3-fluoro-pyridin-2-yloxy)-6-oxo-6H-pyridazin-1-yl]-propionamide as a yellow solid as a mixture of diastereomers (1.29 g, 85%).

Step 2: Using the method described in Example 61, Step 2,3-cyclopentyl-N-[1-((R)-2,2-dimethyl-[1,3]dioxolan-4-ylmethyl)-1H-pyrazol-3-yl]-2-[4-(3-fluoro-pyridin-2-yloxy)-6-oxo-6H-pyridazin-1-yl]-propionamide afforded 3-cyclopentyl-N-[1-((R)-2,3-dihydroxy-propyl)-1H-pyrazol-3-yl]-2-[4-(3-fluoro-pyridin-2-yloxy)-6-oxo-6H-pyridazin-1-yl]-propionamide as an off-white solid as a mixture of diastereomers (722.4 mg, 60%); ES+-HRMS m/e calcd for $C_{23}H_{27}N_6O_5F$ [M+H+] 487.2100 found 487.2099. $^1$H NMR (400 MHz, DMSO-$d_6$) δ ppm 1.08-1.17 (m, 1H), 1.28-1.80 (m, 8H), 1.91-2.03 (m, 1H), 2.23-2.38 (m, 1H), 3.21-3.33 (m, 2H), 3.72-3.83 (m, 1H), 3.82-3.95 (m, 1H), 4.10 (dd, J=13.6, 4.0 Hz, 1H), 4.71 (t, J=5.5 Hz, 1H), 4.95 (dd, J=5.3, 2.6 Hz, 1H), 5.53 (dd, J=10.4, 3.4 Hz, 1H), 6.35-6.42 (m, 2H), 7.23 (d, J=2.3 Hz, 1H), 7.51-7.60 (m, 2H), 7.65 (d, J=7.0 Hz, 1H), 8.27 (d, J=2.3 Hz, 1H), 10.87 (s, 1H).

Example 96

3-Cyclopentyl-N-[1-((R)-2,3-dihydroxy-propyl)-1H-pyrazol-3-yl]-2-[4-(1H-indol-4-yloxy)-6-oxo-6H-pyridazin-1-yl]-propionamide

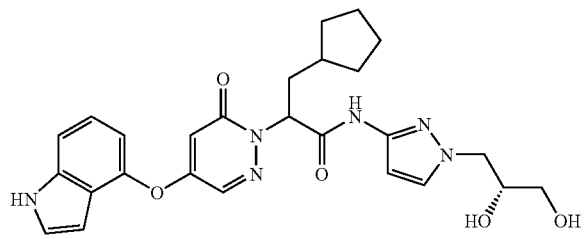

Step 1: Using the method described in Example 49, 3-cyclopentyl-2-[4-(1H-indol-4-yloxy)-6-oxo-6H-pyridazin-1-yl]-propionic acid (Intermediate 74) and 1-((R)-2,2-dimethyl-[1,3]dioxolan-4-ylmethyl)-1H-pyrazol-3-ylamine (Intermediate 4) afforded 3-cyclopentyl-N-[1-((R)-2,2-dimethyl-[1,3]dioxolan-4-ylmethyl)-1H-pyrazol-3-yl]-2-[4-(1H-indol-4-yloxy)-6-oxo-6H-pyridazin-1-yl]-propionamide as a light tan solid as a mixture of diastereomers (0.95 g, 64%).

Step 2: Using the method described in Example 61, Step 2,3-cyclopentyl-N-[1-((R)-2,2-dimethyl-[1,3]dioxolan-4-ylmethyl)-1H-pyrazol-3-yl]-2-[4-(1H-indol-4-yloxy)-6-oxo-6H-pyridazin-1-yl]-propionamide afforded 3-cyclopentyl-N-[1-((R)-2,3-dihydroxy-propyl)-1H-pyrazol-3-yl]-2-[4-(1H-indol-4-yloxy)-6-oxo-6H-pyridazin-1-yl]-propionamide as an off-white solid as a mixture of diastereomers (0.49 g, 56%); ES+-HRMS m/e calcd for $C_{26}H_{30}N_6O_5$ [M+H+] 507.2351 found 507.2351. $^1$H NMR (300 MHz, DMSO-$d_6$) δ ppm 1.00-1.15 (m, 1H), 1.22-1.75 (m, 8H), 1.81-2.00 (m, 1H), 2.16-2.31 (m, 1H), 3.16-3.30 (m, 2H), 3.68-3.91 (m, 2H), 4.06 (dd, J=13.4, 3.8 Hz, 1H), 4.69 (t, J=5.4 Hz, 1H), 4.92 (d, J=5.1 Hz, 1H), 5.41 (dd, J=10.6, 3.8 Hz, 1H), 5.58 (d, J=2.7 Hz, 1H), 6.27 (br. s., 1H), 6.35 (d, J=2.1 Hz, 1H), 6.88 (d, J=7.8 Hz, 1H), 7.15 (t, J=7.8 Hz, 1H), 7.35-7.43 (m, 2H), 7.50 (d, J=2.1 Hz, 1H), 8.17 (d, J=2.7 Hz, 1H), 10.76 (s, 1H), 11.48 (br. s., 1H).

Example 97

3-Cyclopentyl-N-[1-((R)-2,3-dihydroxy-propyl)-1H-pyrazol-3-yl]-2-[4-(2-methyl-4-oxo-4H-pyran-3-yloxy)-6-oxo-6H-pyridazin-1-yl]-propionamide

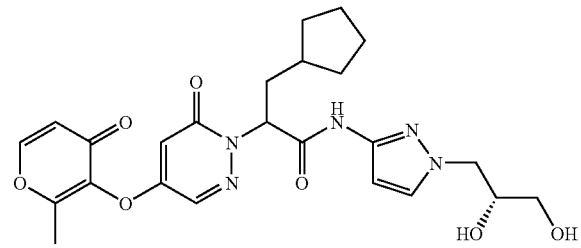

Step 1: Using the method described in Example 49, 3-cyclopentyl-2-[4-(2-methyl-4-oxo-4H-pyran-3-yloxy)-6-oxo-6H-pyridazin-1-yl]-propionic acid (Intermediate 75) and 1-((R)-2,2-dimethyl-[1,3]dioxolan-4-ylmethyl)-1H-pyrazol-3-ylamine (Intermediate 4) afforded 3-cyclopentyl-N-[1-((R)-2,2-dimethyl-[1,3]dioxolan-4-ylmethyl)-1H-pyrazol-3-yl]-2-[4-(2-methyl-4-oxo-4H-pyran-3-yloxy)-6-oxo-6H-pyridazin-1-yl]-propionamide as a white solid as a mixture of diastereomers (1.37 g, 92%).

Step 2: Using the method described in Example 61, Step 2,3-cyclopentyl-N-[1-((R)-2,2-dimethyl-[1,3]dioxolan-4-ylmethyl)-1H-pyrazol-3-yl]-2-[4-(2-methyl-4-oxo-4H-pyran-3-yloxy)-6-oxo-6H-pyridazin-1-yl]-propionamide afforded 3-cyclopentyl-N-[1-((R)-2,3-dihydroxy-propyl)-1H-pyrazol-3-yl]-2-[4-(2-methyl-4-oxo-4H-pyran-3-yloxy)-6-oxo-6H-pyridazin-1-yl]-propionamide as a light orange solid as a mixture of diastereomers (0.40 g, 33%); ES$^+$-HRMS m/e calcd for $C_{24}H_{29}N_5O_7$ [M+H$^+$] 500.2140 found 500.2141. $^1$H NMR (300 MHz, DMSO-d$_6$) δ ppm 1.10 (br. s., 1H), 1.26-1.79 (m, 8H), 1.90 (br. s., 1H), 2.15-2.28 (m, 1H), 2.30 (br. s., 3H), 3.30 (br. s., 2H), 3.70-3.92 (m, 2H), 4.08 (d, J=13.6 Hz, 1H), 4.64-4.77 (m, 1H), 4.96 (br. s., 1H), 5.43 (d, J=10.0 Hz, 1H), 6.17 (br. s., 1H), 6.36 (s, 1H), 6.49 (dd, J=5.7, 2.1 Hz, 1H), 7.52 (br. s., 1H), 8.12 (br. s., 1H), 8.22 (dd, J=5.6, 2.0 Hz, 1H), 10.83 (br. s., 1H).

Example 98

3-Cyclopentyl-N-[1-((R)-2,3-dihydroxy-propyl)-1H-pyrazol-3-yl]-2-[6-oxo-4-(2-trifluoromethoxy-phenoxy)-6H-pyridazin-1-yl]-propionamide

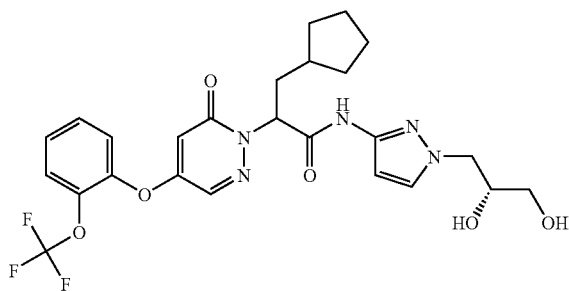

Step 1: Using the method described in Example 49, 3-cyclopentyl-2-[6-oxo-4-(2-trifluoromethoxy-phenoxy)-6H-pyridazin-1-yl]-propionic acid (Intermediate 76) and 1-((R)-2,2-dimethyl-[1,3]dioxolan-4-ylmethyl)-1H-pyrazol-3-ylamine (Intermediate 4) afforded 3-cyclopentyl-N-[1-((R)-2,2-dimethyl-[1,3]dioxolan-4-ylmethyl)-1H-pyrazol-3-yl]-2-[6-oxo-4-(2-trifluoromethoxy-phenoxy)-6H-pyridazin-1-yl]-propionamide as an off-white foam as a mixture of diastereomers (1.37 g, 96%).

Step 2: Using the method described in Example 61, Step 2,3-cyclopentyl-N-[1-((R)-2,2-dimethyl-[1,3]dioxolan-4-ylmethyl)-1H-pyrazol-3-yl]-2-[6-oxo-4-(2-trifluoromethoxy-phenoxy)-6H-pyridazin-1-yl]-propionamide afforded 3-cyclopentyl-N-[1-((R)-2,3-dihydroxy-propyl)-1H-pyrazol-3-yl]-2-[6-oxo-4-(2-trifluoromethoxy-phenoxy)-6H-pyridazin-1-yl]-propionamide as an off-white solid as a mixture of diastereomers (0.99 g, 82%); ES$^+$-HRMS m/e calcd for $C_{25}H_{28}N_5O_6F_3$ [M+H$^+$] 552.2065 found 552.2065. $^1$H NMR (300 MHz, DMSO-d$_6$) δ ppm 1.00-1.18 (m, 1H), 1.23-1.77 (m, 8H), 1.85-2.00 (m, 1H), 2.19-2.34 (m, 1H), 3.21-3.33 (m, 2H), 3.69-3.94 (m, 2H), 4.08 (dd, J=13.6, 3.6 Hz, 1H), 4.72 (t, J=5.4 Hz, 1H), 4.95 (d, J=4.8 Hz, 1H), 5.46 (dd, J=10.6, 3.6 Hz, 1H), 5.84 (d, J=2.7 Hz, 1H), 6.36 (d, J=2.1 Hz, 1H), 7.42-7.61 (m, 4H), 7.64 (d, J=7.5 Hz, 1H), 8.19 (d, J=2.1 Hz, 1H), 10.82 (s, 1H).

Example 99

3-Cyclopentyl-N-[1-((R)-2,3-dihydroxy-propyl)-1H-pyrazol-3-yl]-2-[4-(6-methyl-pyridin-2-yloxy)-6-oxo-6H-pyridazin-1-yl]-propionamide

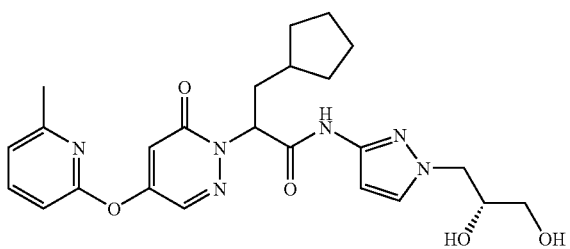

Step 1: Using the method described in Example 49, 3-cyclopentyl-2-[4-(6-methyl-pyridin-2-yloxy)-6-oxo-6H-pyridazin-1-yl]-propionic acid (Intermediate 77) and 1-((R)-2,2-dimethyl-[1,3]dioxolan-4-ylmethyl)-1H-pyrazol-3-ylamine (Intermediate 4) afforded 3-cyclopentyl-N-[1-((R)-2,2-dimethyl-[1,3]dioxolan-4-ylmethyl)-1H-pyrazol-3-yl]-2-[4-(6-methyl-pyridin-2-yloxy)-6-oxo-6H-pyridazin-1-yl]-propionamide as a light tan foam as a mixture of diastereomers (0.95 g, 62%).

Step 2: Using the method described in Example 61, Step 2,3-cyclopentyl-N-[1-((R)-2,2-dimethyl-[1,3]dioxolan-4-ylmethyl)-1H-pyrazol-3-yl]-2-[4-(6-methyl-pyridin-2-yloxy)-6-oxo-6H-pyridazin-1-yl]-propionamide afforded 3-cyclopentyl-N-[1-((R)-2,3-dihydroxy-propyl)-1H-pyrazol-3-yl]-2-[4-(6-methyl-pyridin-2-yloxy)-6-oxo-6H-pyridazin-1-yl]-propionamide as an off-white solid as a mixture of diastereomers (0.65 g, 75%); ES$^+$-HRMS m/e calcd for $C_{24}H_{30}N_6O_5$ [M+H$^+$] 483.2351 found 483.2351. $^1$H NMR (300 MHz, DMSO-d$_6$) δ ppm 1.02-1.19 (m, 1H), 1.22-1.77 (m, 8H), 1.94 (br. s., 1H), 2.18-2.34 (m, 1H), 2.42 (s, 3H), 3.21-3.32 (m, 2H), 3.72-3.92 (m, 2H), 4.09 (dd, J=13.6, 3.9 Hz, 1H), 4.71 (t, J=5.5 Hz, 1H), 4.94 (d, J=5.5 Hz, 1H), 5.49 (dd, J=10.6, 3.9 Hz, 1H), 6.37 (d, J=2.1 Hz, 1H), 6.48 (d, J=2.7 Hz, 1H), 7.05 (d, J=7.7 Hz, 1H), 7.20 (d, J=7.7 Hz, 1H), 7.53 (d, J=2.1 Hz, 1H), 7.88 (t, J=7.7 Hz, 1H), 8.08 (d, J=2.7 Hz, 1H), 10.82 (s, 1H).

Example 100

3-Cyclopentyl-N-[1-((R)-2,3-dihydroxy-propyl)-1H-pyrazol-3-yl]-2-[4-(2-fluoro-5-methyl-phenoxy)-6-oxo-6H-pyridazin-1-yl]-propionamide

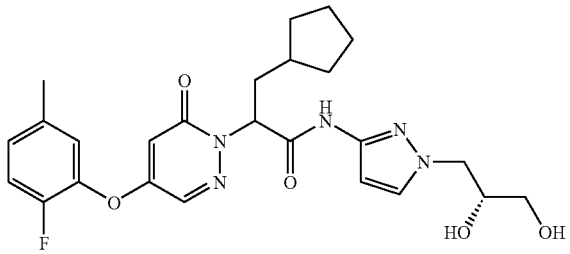

Step 1: Using the method described in Example 49, 3-cyclopentyl-2-[4-(2-fluoro-5-methyl-phenoxy)-6-oxo-6H-pyridazin-1-yl]-propionic acid (Intermediate 78) and 1-((R)-2,2-dimethyl-[1,3]dioxolan-4-ylmethyl)-1H-pyrazol-3- ylamine (Intermediate 4) afforded 3-cyclopentyl-N-[1-((R)-2,2-dimethyl-[1,3]dioxolan-4-ylmethyl)-1H-pyrazol-3-yl]-2-[4-(2-fluoro-5-methyl-phenoxy)-6-oxo-6H-pyridazin-1-yl]-propionamide as a light tan foam as a mixture of diastereomers (1.45 g, 97%).

Step 2: Using the method described in Example 61, Step 2,3-cyclopentyl-N-[1-((R)-2,2-dimethyl-[1,3]dioxolan-4-ylmethyl)-1H-pyrazol-3-yl]-2-[4-(2-fluoro-5-methyl-phenoxy)-6-oxo-6H-pyridazin-1-yl]-propionamide afforded 3-cyclopentyl-N-[1-((R)-2,3-dihydroxy-propyl)-1H-pyrazol-3-yl]-2-[4-(2-fluoro-5-methyl-phenoxy)-6-oxo-6H-pyridazin-1-yl]-propionamide as an off-white solid as a mixture of diastereomers (1.07 g, 80%); ES+-HRMS m/e calcd for $C_{25}H_{30}N_5O_5F$ [M+H+] 500.2304 found 500.2301. $^1$H NMR (300 MHz, DMSO-$d_6$) δ ppm 1.03-1.18 (m, 1H), 1.25-1.76 (m, 8H), 1.86-1.99 (m, 1H), 2.20-2.31 (m, 1H), 2.32 (s, 3H), 3.20-3.32 (m, 2H), 3.72-3.92 (m, 2H), 4.09 (dd, J=13.4, 3.8 Hz, 1H), 4.71 (t, J=5.4 Hz, 1H), 4.94 (d, J=5.4 Hz, 1H), 5.45 (dd, J=10.7, 3.5 Hz, 1H), 5.80 (d, J=2.7 Hz, 1H), 6.36 (d, J=2.1 Hz, 1H), 7.16-7.26 (m, 1H), 7.25-7.41 (m, 2H), 7.52 (d, J=2.1 Hz, 1H), 8.19 (d, J=2.7 Hz, 1H), 10.81 (s, 1H).

Example 101

3-Cyclopentyl-N-[1-((R)-2,3-dihydroxy-propyl)-1H-pyrazol-3-yl]-2-{4-[2-(2-hydroxy-ethyl)-phenoxy]-6-oxo-6H-pyridazin-1-yl}-propionamide

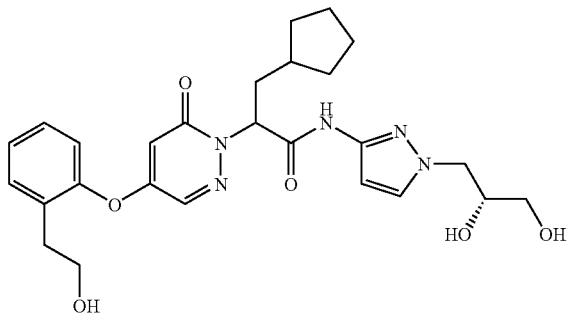

Step 1: Using the method described in Example 49, 3-cyclopentyl-2-{4-[2-(2-hydroxy-ethyl)-phenoxy]-6-oxo-6H-pyridazin-1-yl}-propionic acid (Intermediate 79) and 1-((R)-2,2-dimethyl-[1,3]dioxolan-4-ylmethyl)-1H-pyrazol-3-ylamine (Intermediate 4) afforded impure 3-cyclopentyl-N-[1-((R)-2,2-dimethyl-[1,3]dioxolan-4-ylmethyl)-1H-pyrazol-3-yl]-2-{4-[2-(2-hydroxy-ethyl)-phenoxy]-6-oxo-6H-pyridazin-1-yl}-propionamide as a white foam as a mixture of diastereomers (0.70 g, 95%).

Step 2: Using the method described in Example 61, Step 2,3-cyclopentyl-N-[1-((R)-2,2-dimethyl-[1,3]dioxolan-4-ylmethyl)-1H-pyrazol-3-yl]-2-{4-[2-(2-hydroxy-ethyl)-phenoxy]-6-oxo-6H-pyridazin-1-yl}-propionamide afforded 3-cyclopentyl-N-[1-((R)-2,3-dihydroxy-propyl)-1H-pyrazol-3-yl]-2-{4-[2-(2-hydroxy-ethyl)-phenoxy]-6-oxo-6H-pyridazin-1-yl}-propionamide as a white solid as a mixture of diastereomers (0.04 g, 7%); ES+-HRMS m/e calcd for $C_{26}H_{33}N_5O_6$ [M+H+] 512.2504 found 512.2503. $^1$H NMR (300 MHz, DMSO-$d_6$) δ ppm 0.98-1.18 (m, 1H), 1.18-1.79 (m, 8H), 1.91 (br. s., 1H), 2.14-2.30 (m, 1H), 2.65 (t, J=6.8 Hz, 2H), 3.20-3.29 (m, 2H), 3.48-3.58 (m, 2H), 3.82 (br. s., 2H), 4.07 (dd, J=13.6, 3.9 Hz, 1H), 4.69 (t, J=5.0 Hz, 2H), 4.92 (d, J=5.0 Hz, 1H), 5.42 (dd, J=10.6, 3.9 Hz, 1H), 5.61 (d, J=2.7 Hz, 1H), 6.34 (d, J=1.8 Hz, 1H), 7.18 (d, J=7.5 Hz, 1H), 7.24-7.38 (m, 2H), 7.42 (d, J=7.2 Hz, 1H), 7.50 (s, 1H), 8.12 (d, J=2.7 Hz, 1H), 10.77 (s, 1H).

Example 102

3-Cyclopentyl-N-[1-((R)-2,3-dihydroxy-propyl)-1H-pyrazol-3-yl]-2-[4-(4,6-dimethyl-pyrimidin-2-yloxy)-6-oxo-6H-pyridazin-1-yl]-propionamide

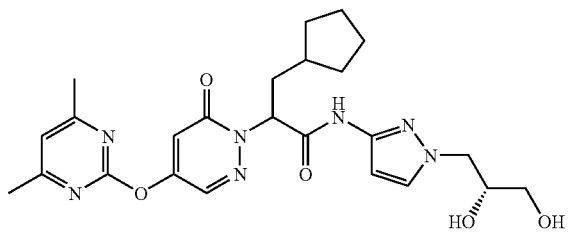

Step 1: Using the method described in Example 49, 3-cyclopentyl-2-[4-(4,6-dimethyl-pyrimidin-2-yloxy)-6-oxo-6H-pyridazin-1-yl]-propionic acid (Intermediate 80) and 1-((R)-2,2-dimethyl-[1,3]dioxolan-4-ylmethyl)-1H-pyrazol-3-ylamine (Intermediate 4) afforded 3-cyclopentyl-N-[1-((R)-2,2-dimethyl-[1,3]dioxolan-4-ylmethyl)-1H-pyrazol-3-yl]-2-[4-(4,6-dimethyl-pyrimidin-2-yloxy)-6-oxo-6H-pyridazin-1-yl]-propionamide as a light yellow solid as a mixture of diastereomers (0.68 g, 92%).

Step 2: Using the method described in Example 61, Step 2,3-cyclopentyl-N-[1-((R)-2,2-dimethyl-[1,3]dioxolan-4-ylmethyl)-1H-pyrazol-3-yl]-2-[4-(4,6-dimethyl-pyrimidin-2-yloxy)-6-oxo-6H-pyridazin-1-yl]-propionamide afforded 3-cyclopentyl-N-[1-((R)-2,3-dihydroxy-propyl)-1H-pyrazol-3-yl]-2-[4-(4,6-dimethyl-pyrimidin-2-yloxy)-6-oxo-6H-pyridazin-1-yl]-propionamide as an off-white solid as a mixture of diastereomers (0.43 g, 69%); ES+-HRMS m/e calcd for $C_{24}H_{31}N_7O_5$ [M+H+] 498.2460 found 498.2460. $^1$H NMR (300 MHz, DMSO-$d_6$) δ ppm 0.98-1.17 (m, 1H), 1.23-1.79 (m, 8H), 1.86-2.05 (m, 1H), 2.17-2.35 (m, 1H), 2.40 (s, 6H), 3.20-3.32 (m, 2H), 3.69-3.95 (m, 2H), 4.09 (dd, J=13.3, 3.7 Hz, 1H), 4.71 (t, J=5.4 Hz, 1H), 4.95 (d, J=4.5 Hz, 1H), 5.50 (dd, J=10.3, 3.7 Hz, 1H), 6.38 (d, J=1.5 Hz, 1H), 6.82 (d, J=2.4 Hz, 1H), 7.19 (s, 1H), 7.53 (s, 1H), 8.13 (d, J=2.4 Hz, 1H), 10.84 (s, 1H).

Example 103

3-Cyclopentyl-N-[1-((R)-2,3-dihydroxy-propyl)-1H-pyrazol-3-yl]-2-[4-(2-methyl-5-trifluoromethyl-2H-pyrazol-3-yloxy)-6-oxo-6H-pyridazin-1-yl]-propionamide

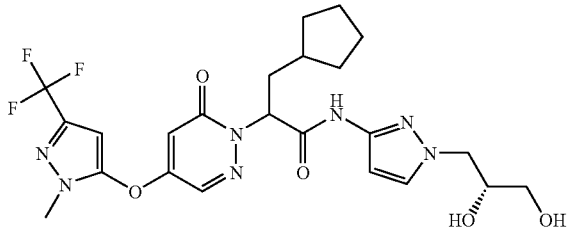

Step 1: Using the method described in Example 49, 3-cyclopentyl-2-[4-(2-methyl-5-trifluoromethyl-2H-pyrazol-3-yloxy)-6-oxo-6H-pyridazin-1-yl]-propionic acid (Intermediate 81) and 1-((R)-2,2-dimethyl-[1,3]dioxolan-4-ylmethyl)-1H-pyrazol-3-ylamine (Intermediate 4) afforded 3-cyclopentyl-N-[1-((R)-2,2-dimethyl-[1,3]dioxolan-4-ylmethyl)-1H-pyrazol-3-yl]-2-[4-(2-methyl-5-trifluoromethyl-2H-pyrazol-3-yloxy)-6-oxo-6H-pyridazin-1-yl]-propionamide as an off-white solid as a mixture of diastereomers (1.27 g, 88%).

Step 2: Using the method described in Example 61, Step 2,3-cyclopentyl-N-[1-((R)-2,2-dimethyl-[1,3]dioxolan-4-ylmethyl)-1H-pyrazol-3-yl]-2-[4-(2-methyl-5-trifluoromethyl-2H-pyrazol-3-yloxy)-6-oxo-6H-pyridazin-1-yl]-propionamide afforded 3-cyclopentyl-N-[1-((R)-2,3-dihydroxy-propyl)-1H-pyrazol-3-yl]-2-[4-(2-methyl-5-trifluoromethyl-2H-pyrazol-3-yloxy)-6-oxo-6H-pyridazin-1-yl]-propionamide as a white solid as a mixture of diastereomers (0.90 g, 78%); ES$^+$-HRMS m/e calcd for $C_{23}H_{28}N_7O_5F_3$ [M+H$^+$] 540.2177 found 540.2175. $^1$H NMR (300 MHz, DMSO-d$_6$) δ ppm 1.01-1.19 (m, 1H), 1.26-1.81 (m, 8H), 1.84-2.02 (m, 1H), 2.17-2.38 (m, 1H), 3.20-3.33 (m, 2H), 3.67-3.94 (m, 2H), 3.81 (s, 3H), 4.09 (dd, J=13.6, 3.6 Hz, 1H), 4.72 (t, J=5.3 Hz, 1H), 4.95 (d, J=4.2 Hz, 1H), 5.49 (dd, J=10.1, 3.5 Hz, 1H), 6.36 (d, J=1.8 Hz, 1H), 6.43 (d, J=2.7 Hz, 1H), 6.82 (s, 1H), 7.53 (s, 1H), 8.24 (d, J=2.7 Hz, 1H), 10.83 (br. s., 1H).

Example 104

2-[4-(3-Chloro-2-fluoro-phenoxy)-6-oxo-6H-pyridazin-1-yl]-3-cyclopentyl-N-[1-((R)-2,3-dihydroxy-propyl)-1H-pyrazol-3-yl]-propionamide

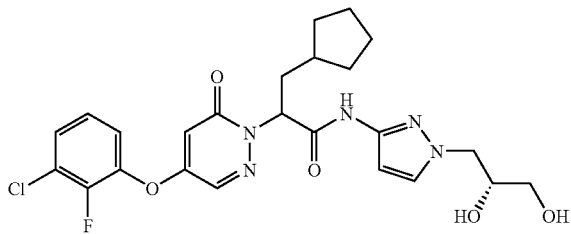

Step 1: Using the method described in Example 49, 2-[4-(3-chloro-2-fluoro-phenoxy)-6-oxo-6H-pyridazin-1-yl]-3-cyclopentyl-propionic acid (Intermediate 82) and 1-((R)-2,2-dimethyl-[1,3]dioxolan-4-ylmethyl)-1H-pyrazol-3-ylamine (Intermediate 4) afforded 2-[4-(3-chloro-2-fluoro-phenoxy)-6-oxo-6H-pyridazin-1-yl]-3-cyclopentyl-N-[1-((R)-2,2-dimethyl-[1,3]dioxolan-4-ylmethyl)-1H-pyrazol-3-yl]-propionamide as an off-white solid as a mixture of diastereomers (1.24 g, 84%).

Step 2: Using the method described in Example 61, Step 2, 2-[4-(3-chloro-2-fluoro-phenoxy)-6-oxo-6H-pyridazin-1-yl]-3-cyclopentyl-N-[1-((R)-2,2-dimethyl-[1,3]dioxolan-4-ylmethyl)-1H-pyrazol-3-yl]-propionamide afforded 2-[4-(3-chloro-2-fluoro-phenoxy)-6-oxo-6H-pyridazin-1-yl]-3-cyclopentyl-N-[1-((R)-2,3-dihydroxy-propyl)-1H-pyrazol-3-yl]-propionamide as a white solid as a mixture of diastereomers (0.94 g, 83%); ES$^+$-HRMS m/e calcd for $C_{24}H_{27}N_5O_5FCl$ [M+H$^+$] 520.1758 found 520.1759. $^1$H NMR (300 MHz, DMSO-d$_6$) δ ppm 1.00-1.16 (m, 1H), 1.24-1.77 (m, 8H), 1.86-2.00 (m, 1H), 2.19-2.37 (m, 1H), 3.20-3.33 (m, 2H), 3.71-3.92 (m, 2H), 4.09 (dd, J=13.6, 3.6 Hz, 1H), 4.71 (t, J=5.4 Hz, 1H), 4.94 (d, J=4.8 Hz, 1H), 5.46 (dd, J=10.4, 3.5 Hz, 1H), 6.03 (d, J=2.7 Hz, 1H), 6.36 (d, J=1.5 Hz, 1H), 7.35 (t, J=8.2 Hz, 1H), 7.48 (m, J=7.2 Hz, 1H), 7.52 (s, 1H), 7.60 (t, J=7.2 Hz, 1H), 8.21 (d, J=2.7 Hz, 1H), 10.81 (s, 1H).

Example 105

3-Cyclopentyl-2-[4-(2,6-difluoro-phenoxy)-6-oxo-6H-pyridazin-1-yl]-N-[1-((R)-2,3-dihydroxy-propyl)-1H-pyrazol-3-yl]-propionamide

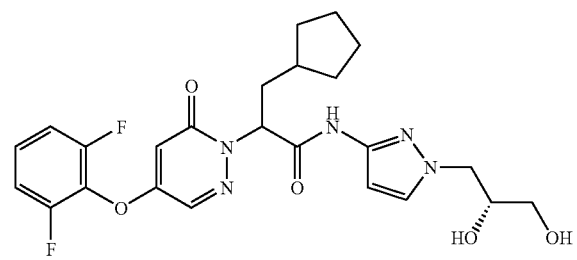

Step 1: Using the method described in Example 49, 3-cyclopentyl-2-[4-(2,6-difluoro-phenoxy)-6-oxo-6H-pyridazin-1-yl]-propionic acid (Intermediate 47) and 1-((R)-2,2-dimethyl-[1,3]dioxolan-4-ylmethyl)-1H-pyrazol-3-ylamine (Intermediate 4) afforded 3-cyclopentyl-2-[4-(2,6-difluoro-phenoxy)-6-oxo-6H-pyridazin-1-yl]-N-[1-((R)-2,2-dimethyl-[1,3]dioxolan-4-ylmethyl)-1H-pyrazol-3-yl]-propionamide as a white solid as a mixture of diastereoisomers (4.56 g, 90%).

Step 2: Using the method described in Example 61, Step 2,3-cyclopentyl-2-[4-(2,6-difluoro-phenoxy)-6-oxo-6H-pyridazin-1-yl]-N-[1-((R)-2,2-dimethyl-[1,3]dioxolan-4-ylmethyl)-1H-pyrazol-3-yl]-propionamide afforded 3-cyclopentyl-2-[4-(2,6-difluoro-phenoxy)-6-oxo-6H-pyridazin-1-yl]-N-[1-((R)-2,3-dihydroxy-propyl)-1H-pyrazol-3-yl]-propionamide as an off-white solid as a mixture of diastereomers (3.67 g, 87%); ES$^+$-HRMS m/e calcd for $C_{24}H_{27}N_5O_5F_2$ [M+H$^+$] 504.2053 found 504.2051. $^1$H NMR (300 MHz, DMSO-d$_6$) δ ppm 0.99-1.22 (m, 1H), 1.22-1.80 (m, 8H), 1.83-2.02 (m, 1H), 2.17-2.35 (m, 1H), 3.21-3.32 (m, 2H), 3.66-3.94 (m, 2H), 4.08 (dd, J=13.3, 3.9 Hz, 1H), 4.71 (t, J=5.6 Hz, 1H), 4.94 (d, J=4.2 Hz, 1H), 5.45 (dd, J=10.7, 3.9 Hz, 1H), 6.03 (d, J=2.8 Hz, 1H), 6.36 (d, J=2.1 Hz, 1H), 7.32-7.51 (m, 3H), 7.52 (d, J=2.1 Hz, 1H), 8.28 (d, J=2.8 Hz, 1H), 10.84 (s, 1H).

Separation of enantiomers via supercritical fluid chromatography on a SFC DAICEL AD column, 30% methanol, 70 mL/min Example 105A (S)-3-Cyclopentyl-2-[4-(2,6-difluoro-phenoxy)-6-oxo-6H-pyridazin-1-yl]-N-[1-((R)-2,3-dihydroxy-propyl)-1H-pyrazol-3-yl]-propionamide

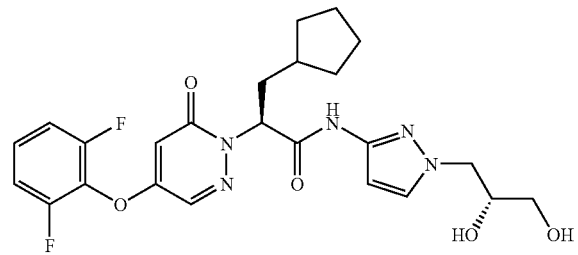

(S)-3-Cyclopentyl-2-[4-(2,6-difluoro-phenoxy)-6-oxo-6H-pyridazin-1-yl]-N-[1-((R)-2,3-dihydroxy-propyl)-1H-pyrazol-3-yl]-propionamide; ES+-HRMS m/e calcd for $C_{24}H_{27}N_5O_5F_2$ [M+H+] 504.2053 found 504.2056. $^1$H NMR (300 MHz, DMSO-$d_6$) δ ppm 1.01-1.17 (m, 1H), 1.26-1.76 (m, 8H), 1.87-2.01 (m, 1H), 2.19-2.35 (m, 1H), 3.21-3.32 (m, 2H), 3.71-3.92 (m, 2H), 4.09 (dd, J=13.6, 4.0 Hz, 1H), 4.70 (t, J=5.6 Hz, 1H), 4.94 (d, J=5.1 Hz, 1H), 5.46 (dd, J=10.9, 4.0 Hz, 1H), 6.03 (d, J=2.7 Hz, 1H), 6.36 (d, J=2.1 Hz, 1H), 7.34-7.50 (m, 3H), 7.52 (d, J=2.1 Hz, 1H), 8.28 (d, J=2.7 Hz, 1H), 10.83 (s, 1H).

Example 105B (R)-3-Cyclopentyl-2-[4-(2,6-difluoro-phenoxy)-6-oxo-6H-pyridazin-1-yl]-N-[1-((R)-2,3-dihydroxy-propyl)-1H-pyrazol-3-yl]-propionamide

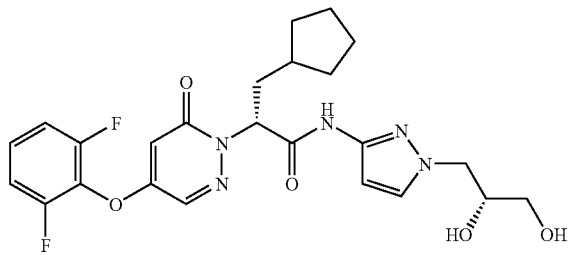

(R)-3-Cyclopentyl-2-[4-(2,6-difluoro-phenoxy)-6-oxo-6H-pyridazin-1-yl]-N-[1-((R)-2,3-dihydroxy-propyl)-1H-pyrazol-3-yl]-propionamide; ES+-HRMS m/e calcd for $C_{24}H_{27}N_5O_5F_2$ [M+H+] 504.2053 found 504.2052. $^1$H NMR (400 MHz, DMSO-$d_6$) δ ppm 1.07 (br. s., 1H), 1.25-1.77 (m, 8H), 1.89-2.03 (m, 1H), 2.20-2.34 (m, 1H), 3.20-3.32 (m, 2H), 3.72-3.82 (m, 1H), 3.86 (dd, J=13.5, 7.5 Hz, 1H), 4.09 (dd, J=13.5, 3.8 Hz, 1H), 4.70 (t, J=5.5 Hz, 1H), 4.94 (d, J=5.3 Hz, 1H), 5.45 (dd, J=10.7, 4.3 Hz, 1H), 6.03 (d, J=2.7 Hz, 1H), 6.36 (d, J=2.1 Hz, 1H), 7.34-7.43 (m, 2H), 7.43-7.51 (m, 1H), 7.52 (d, J=2.1 Hz, 1H), 8.28 (d, J=2.7 Hz, 1H), 10.82 (s, 1H).

Example 106

3-Cyclopentyl-2-[4-(2,6-difluoro-phenoxy)-6-oxo-6H-pyridazin-1-yl]-N-[5-((R)-1,2-dihydroxy-ethyl)-pyrazin-2-yl]-propionamide

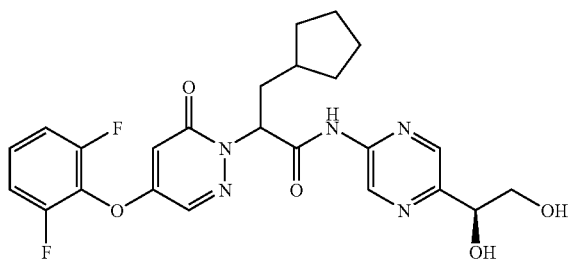

Step 1: Using the method described in Example 76, Step 2,5-((S)-2,2-dimethyl-[1,3]dioxolan-4-yl)-pyrazin-2-ylamine (Intermediate 83, WO2004052869) and 2-bromo-3-cyclopentyl-propionyl chloride (Example 76, Step 1) afforded 2-bromo-3-cyclopentyl-N-[5-((R)-2,2-dimethyl-[1,3]dioxolan-4-yl)-pyrazin-2-yl]-propionamide as an orange oil (1.74 g, 51%).

Step 2: Using the method described in Example 76, Step 6,5-(2,6-difluoro-phenoxy)-2H-pyridazin-3-one (Intermediate 18) and 2-bromo-3-cyclopentyl-N-[5-((R)-2,2-dimethyl-[1,3]dioxolan-4-yl)-pyrazin-2-yl]-propionamide afforded 3-cyclopentyl-2-[4-(2,6-difluoro-phenoxy)-6-oxo-6H-pyridazin-1-yl]-N-[5-((R)-2,2-dimethyl-[1,3]dioxolan-4-yl)-pyrazin-2-yl]-propionamide as a yellow solid (690 mg, 41%).

Step 3: A solution of 3-cyclopentyl-2-[4-(2,6-difluoro-phenoxy)-6-oxo-6H-pyridazin-1-yl]-N-[5-((R)-2,2-dimethyl-[1,3]dioxolan-4-yl)-pyrazin-2-yl]-propionamide (685 mg, 1.26 mmol) in methanol (12.6 mL, 0.1 M) and methylene chloride (5 mL) was treated with para-toluenesulfonic acid (36 mg, 0.18 mmol). The reaction stirred at 25° C. overnight. At this time, the reaction was diluted with ethyl acetate (100 mL) and washed with a saturated aqueous sodium bicarbonate solution (150 mL), water (150 mL), and a saturated aqueous sodium chloride solution (150 mL). The organics were dried over sodium sulfate, filtered, and concentrated in vacuo to afford 3-cyclopentyl-2-[4-(2,6-difluoro-phenoxy)-6-oxo-6H-pyridazin-1-yl]-N-[5-((R)-1,2-dihydroxy-ethyl)-pyrazin-2-yl]-propionamide as an off-white solid (0.50 g, 81%); ES+-HRMS m/e calcd for $C_{24}H_{25}N_5O_5F_2$ [M+H+] 502.1897 found 502.1894. $^1$H NMR (300 MHz, DMSO-$d_6$) δ ppm 1.04-1.21 (m, 1H), 1.27-1.85 (m, 8H), 1.91-2.08 (m, 1H), 2.22-2.41 (m, 1H), 3.50-3.62 (m, 1H), 3.62-3.73 (m, 1H), 4.62 (q, J=5.1 Hz, 1H), 4.72 (t, J=5.7 Hz, 1H), 5.52-5.64 (m, 2H), 6.07 (d, J=2.5 Hz, 1H), 7.33-7.56 (m, 3H), 8.31 (d, J=2.5 Hz, 1H), 8.45 (s, 1H), 9.13 (s, 1H), 11.25 (br. s., 1H).

Example 107

3-Cyclopentyl-2-[4-(2,6-difluoro-3-methyl-phenoxy)-6-oxo-6H-pyridazin-1-yl]-N-[1-((R)-2,3-dihydroxy-propyl)-1H-pyrazol-3-yl]-propionamide

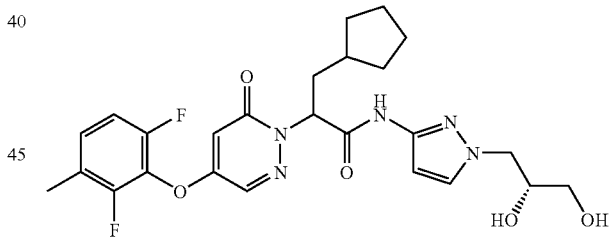

Step 1: Using the method described in Example 49, 3-cyclopentyl-2-[4-(2,6-difluoro-3-methyl-phenoxy)-6-oxo-6H-pyridazin-1-yl]-propionic acid (Intermediate 84) and 1-((R)-2,2-dimethyl-[1,3]dioxolan-4-ylmethyl)-1H-pyrazol-3-ylamine (Intermediate 4) afforded 3-cyclopentyl-2-[4-(2,6-difluoro-3-methyl-phenoxy)-6-oxo-6H-pyridazin-1-yl]-N-[1-((R)-2,2-dimethyl-[1,3]dioxolan-4-ylmethyl)-1H-pyrazol-3-yl]-propionamide as a light yellow solid as a mixture of diastereomers (503.6 mg, 48%).

Step 2: Using the method described in Example 61, Step 2,3-cyclopentyl-2-[4-(2,6-difluoro-3-methyl-phenoxy)-6-oxo-6H-pyridazin-1-yl]-N-[1-((R)-2,2-dimethyl-[1,3]dioxolan-4-ylmethyl)-1H-pyrazol-3-yl]-propionamide afforded 3-cyclopentyl-2-[4-(2,6-difluoro-3-methyl-phenoxy)-6-oxo-6H-pyridazin-1-yl]-N-[1-((R)-2,3-dihydroxy-propyl)-1H-pyrazol-3-yl]-propionamide as a white solid as a mixture of diastereomers (254 mg, 54%); ES+-HRMS m/e calcd for $C_{25}H_{29}N_5O_5F_2$ [M+H+] 518.2210 found 518.2208. $^1$H NMR (400 MHz, DMSO-$d_6$) δ ppm 1.05-1.16 (m, 1H), 1.24-1.75

(m, 8H), 1.88-2.01 (m, 1H), 2.21-2.31 (m, 1H), 2.28 (s, 3H), 3.21-3.32 (m, 2H), 3.69-3.83 (m, 1H), 3.86 (ddd, J=13.4, 7.7, 1.8 Hz, 1H), 4.09 (dd, J=13.4, 3.6 Hz, 1H), 4.70 (t, J=5.5 Hz, 1H), 4.94 (dd, J=5.2, 1.8 Hz, 1H), 5.46 (dd, J=10.2, 3.6 Hz, 1H), 6.01 (d, J=2.7 Hz, 1H), 6.36 (d, J=2.1 Hz, 1H), 7.28 (t, J=9.2 Hz, 1H), 7.31-7.41 (m, 1H), 7.53 (d, J=2.1 Hz, 1H), 8.27 (d, J=2.8 Hz, 1H), 10.82 (s, 1H).

Example 108

2-[4-(2,6-Difluoro-phenoxy)-6-oxo-6H-pyridazin-1-yl]-3-(2,6-difluoro-phenyl)-N-[1-((R)-2,3-dihydroxy-propyl)-1H-pyrazol-3-yl]-propionamide

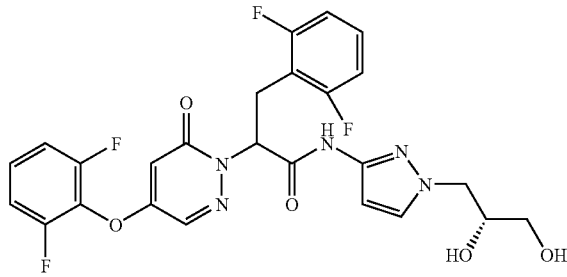

Step 1: Using the method described in Example 49, 2-[4-(2,6-difluoro-phenoxy)-6-oxo-6H-pyridazin-1-yl]-3-(2,6-difluoro-phenyl)-propionic acid (Intermediate 34) and 1-((R)-2,2-dimethyl-[1,3]dioxolan-4-ylmethyl)-1H-pyrazol-3-ylamine (Intermediate 4) afforded 2-[4-(2,6-difluoro-phenoxy)-6-oxo-6H-pyridazin-1-yl]-3-(2,6-difluoro-phenyl)-N-[1-((R)-2,2-dimethyl-[1,3]dioxolan-4-ylmethyl)-1H-pyrazol-3-yl]-propionamide as an off-white solid as a mixture of diastereomers (367.9 mg, 59%).

Step 2: Using the method described in Example 61, Step 2, 2-[4-(2,6-difluoro-phenoxy)-6-oxo-6H-pyridazin-1-yl]-3-(2,6-difluoro-phenyl)-N-[1-((R)-2,2-dimethyl-[1,3]dioxolan-4-ylmethyl)-1H-pyrazol-3-yl]-propionamide afforded 2-[4-(2,6-difluoro-phenoxy)-6-oxo-6H-pyridazin-1-yl]-3-(2,6-difluoro-phenyl)-N-[1-((R)-2,3-dihydroxy-propyl)-1H-pyrazol-3-yl]-propionamide as a white solid as a mixture of diastereomers (241.3 mg, 70%); ES$^+$-HRMS m/e calcd for $C_{25}H_{21}N_5O_5F_4$ [M+H$^+$] 548.1552 found 548.1553. $^1$H NMR (400 MHz, DMSO-$d_6$) δ ppm 3.20-3.32 (m, 2H), 3.40-3.56 (m, 2H), 3.69-3.80 (m, 1H), 3.80-3.91 (m, 1H), 4.08 (dd, J=13.6, 3.8 Hz, 1H), 4.69 (t, J=5.6 Hz, 1H), 4.94 (dd, J=5.2, 1.2 Hz, 1H), 5.63-5.76 (m, 1H), 5.90 (br. s., 1H), 6.44 (d, J=2.7 Hz, 1H), 6.97 (t, J=7.9 Hz, 2H), 7.23-7.33 (m, 1H), 7.37 (t, J=8.7 Hz, 2H), 7.41-7.51 (m, 1H), 7.54 (s, 1H), 8.20 (d, J=2.7 Hz, 1H), 10.66 (s, 1H).

Example 109

4-Methyl-2-[4-(naphthalen-1-yloxy)-6-oxo-6H-pyridazin-1-yl]-pentanoic acid [1-((R)-2,3-dihydroxy-propyl)-1H-pyrazol-3-yl]-amide

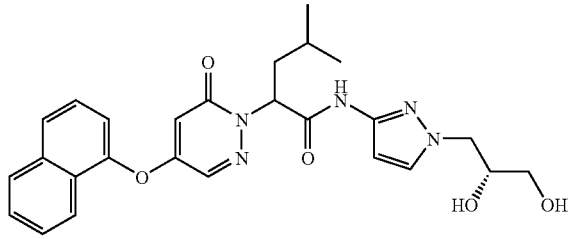

Step 1: A solution of 2-(4-iodo-6-oxo-6H-pyridazin-1-yl)-4-methyl-pentanoic acid (Intermediate 86, 1.93 g, 5.74 mmol) in N,N-dimethylformamide (26 mL, 0.22M) at 25° C. was treated with N,N-diisopropylethylamine (2.8 mL, 16.94 mmol), (benzotriazol-1-yloxy)tris(dimethylamino)phosphonium hexafluorophosphate (3.81 g, 8.61 mmol) and 1-((R)-2,2-dimethyl-[1,3]dioxolan-4-ylmethyl)-1H-pyrazol-3-ylamine (Intermediate 4, 1.31 g, 6.64 mmol). The reaction was stirred at 25° C. over 2 nights. After this time, the reaction was diluted with ethyl acetate (150 mL) and was washed with a saturated aqueous ammonium chloride solution (150 mL), a saturated aqueous sodium bicarbonate solution (150 mL) and a saturated aqueous sodium chloride solution (150 mL), dried over magnesium sulfate, filtered, rinsed and concentrated in vacuo. Silica gel column chromatography (AnaLogix 80 g, 25-75% gradient ethyl acetate/hexanes) afforded 2-[4-(benzotriazol-1-yloxy)-6-oxo-6H-pyridazin-1-yl]-4-methyl-pentanoic acid [1-((R)-2,2-dimethyl-[1,3]dioxolan-4-ylmethyl)-1H-pyrazol-3-yl]-amide (1.52 g, 51%) as a light yellow solid as a mixture of diastereomers.

Step 2: A solution of 2-[4-(benzotriazol-1-yloxy)-6-oxo-6H-pyridazin-1-yl]-4-methyl-pentanoic acid [1-((R)-2,2-dimethyl-[1,3]dioxolan-4-ylmethyl)-1H-pyrazol-3-yl]-amide (0.30 g, 0.57 mmol) in acetonitrile (12 mL, 0.048M) was treated with cesium carbonate (0.37 g, 1.14 mmol) and naphthalen-1-ol (0.10 g, 0.69 mmol). The resulting reaction mixture was stirred at 25° C. for 2 h. The reaction mixture was then concentrated in vacuo and partitioned between water (100 mL) and ethyl acetate (100 mL). The organics were washed with a saturated aqueous sodium chloride solution (50 mL), dried over magnesium sulfate, filtered, rinsed, and concentrated in vacuo. Silica gel column chromatography (AnaLogix 40 g, 25-75% ethyl acetate/hexanes) afforded 4-methyl-2-[4-(naphthalen-1-yloxy)-6-oxo-6H-pyridazin-1-yl]-pentanoic acid [1-((R)-2,2-dimethyl-[1,3]dioxolan-4-ylmethyl)-1H-pyrazol-3-yl]-amide (208.7 mg, 68%) as a light orange solid as a mixture of diastereomers.

Step 3: Using the method described in Example 61, Step 2,4-methyl-2-[4-(naphthalen-1-yloxy)-6-oxo-6H-pyridazin-1-yl]-pentanoic acid [1-((R)-2,2-dimethyl-[1,3]dioxolan-4-ylmethyl)-1H-pyrazol-3-yl]-amide afforded 4-methyl-2-[4-(naphthalen-1-yloxy)-6-oxo-6H-pyridazin-1-yl]-pentanoic acid [1-((R)-2,3-dihydroxy-propyl)-1H-pyrazol-3-yl]-amide as an off-white solid as a mixture of diastereomers (158.1 mg, 82%); ES$^+$-HRMS m/e calcd for $C_{26}H_{29}N_5O_5$ [M+H$^+$] 492.2242 found 492.2244. $^1$H NMR (400 MHz, DMSO-$d_6$) δ ppm 0.87 (d, J=6.6 Hz, 3H), 0.90 (d, J=6.6 Hz, 3H), 1.47 (br. s., 1H), 1.72-1.84 (m, 1H), 2.13-2.25 (m, 1H), 3.19-3.32 (m, 2H), 3.78 (d, J=4.9 Hz, 1H), 3.80-3.94 (m, 1H), 4.08 (dd, J=13.6, 4.0 Hz, 1H), 4.70 (t, J=5.4 Hz, 1H), 4.93 (dd, J=5.4, 1.5 Hz, 1H), 5.50 (dd, J=10.8, 2.9 Hz, 1H), 5.64 (d, J=2.8 Hz, 1H), 6.36 (d, J=2.1 Hz, 1H), 7.49 (d, J=7.5 Hz, 1H), 7.52 (d, J=2.1 Hz, 1H), 7.59-7.68 (m, 3H), 7.88-7.94 (m, 1H), 7.96 (d, J=8.3 Hz, 1H), 8.05-8.11 (m, 1H), 8.29 (d, J=2.8 Hz, 1H), 10.77 (s, 1H).

Separation of enantiomers via supercritical fluid chromatography on a SFC KROMASIL OD column, 25% methanol, 70 mL/min.

Example 109A (S)-4-Methyl-2-[4-(naphthalen-1-yloxy)-6-oxo-6H-pyridazin-1-yl]-pentanoic acid [1-((R)-2,3-dihydroxy-propyl)-1H-pyrazol-3-yl]-amide

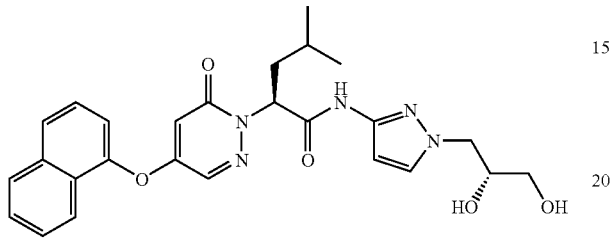

(S)-4-Methyl-2-[4-(naphthalen-1-yloxy)-6-oxo-6H-pyridazin-1-yl]-pentanoic acid [1-((R)-2,3-dihydroxy-propyl)-1H-pyrazol-3-yl]-amide; ES$^+$-HRMS m/e calcd for $C_{26}H_{29}N_5O_5$ [M+H$^+$] 492.2242 found 492.2238. $^1$H NMR (400 MHz, DMSO-d$_6$) δ ppm 0.87 (d, J=6.6 Hz, 3H), 0.91 (d, J=6.6 Hz, 3H), 1.40-1.55 (m, 1H), 1.79 (ddd, J=13.5, 9.4, 4.2 Hz, 1H), 2.10-2.27 (m, 1H), 3.19-3.32 (m, 2H), 3.72-3.81 (m, 1H), 3.86 (dd, J=13.6, 7.7 Hz, 1H), 4.08 (dd, J=13.6, 4.2 Hz, 1H), 4.70 (t, J=5.6 Hz, 1H), 4.94 (d, J=5.3 Hz, 1H), 5.50 (dd, J=11.1, 4.2 Hz, 1H), 5.64 (d, J=2.8 Hz, 1H), 6.36 (d, J=2.1 Hz, 1H), 7.49 (d, J=7.5 Hz, 1H), 7.53 (d, J=2.1 Hz, 1H), 7.59-7.67 (m, 3H), 7.89-7.94 (m, 1H), 7.96 (d, J=8.1 Hz, 1H), 8.03-8.12 (m, 1H), 8.30 (d, J=2.8 Hz, 1H), 10.77 (s, 1H).

Example 109B (R)-4-Methyl-2-[4-(naphthalen-1-yloxy)-6-oxo-6H-pyridazin-1-yl]-pentanoic acid [1-((R)-2,3-dihydroxy-propyl)-1H-pyrazol-3-yl]-amide

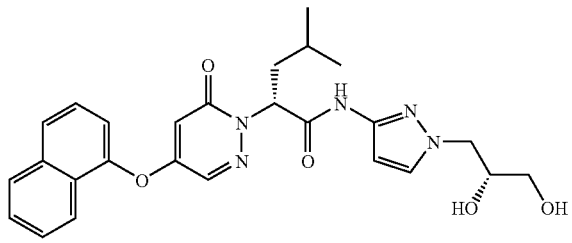

(R)-4-Methyl-2-[4-(naphthalen-1-yloxy)-6-oxo-6H-pyridazin-1-yl]-pentanoic acid [1-((R)-2,3-dihydroxy-propyl)-1H-pyrazol-3-yl]-amide; ES$^+$-HRMS m/e calcd for $C_{26}H_{29}N_5O_5$ [M+H$^+$] 492.2242 found 492.2239. $^1$H NMR (400 MHz, DMSO-d$_6$) δ ppm 0.87 (d, J=6.6 Hz, 3H), 0.90 (d, J=6.6 Hz, 3H), 1.40-1.53 (m, 1H), 1.79 (ddd, J=13.6, 9.4, 4.2 Hz, 1H), 2.13-2.24 (m, 1H), 3.20-3.32 (m, 2H), 3.71-3.81 (m, 1H), 3.86 (dd, J=13.6, 7.5 Hz, 1H), 4.08 (dd, J=13.6, 4.2 Hz, 1H), 4.70 (t, J=5.4 Hz, 1H), 4.93 (d, J=5.3 Hz, 1H), 5.50 (dd, J=11.0, 4.2 Hz, 1H), 5.64 (d, J=2.8 Hz, 1H), 6.36 (d, J=2.1 Hz, 1H), 7.49 (d, J=7.5 Hz, 1H), 7.52 (d, J=2.1 Hz, 1H), 7.58-7.68 (m, 3H), 7.88-7.94 (m, 1H), 7.96 (d, J=8.1 Hz, 1H), 8.05-8.11 (m, 1H), 8.30 (d, J=2.8 Hz, 1H), 10.77 (s, 1H).

Example 110

4-Methyl-2-[6-oxo-4-(5,6,7,8-tetrahydro-naphthalen-1-yloxy)-6H-pyridazin-1-yl]-pentanoic acid [1-((R)-2,3-dihydroxy-propyl)-1H-pyrazol-3-yl]-amide

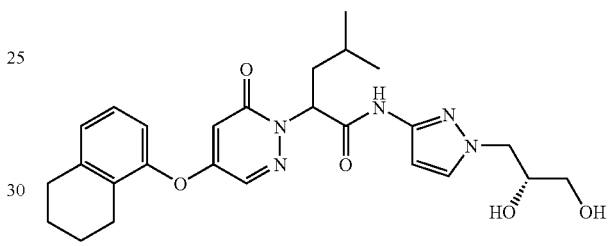

Step 1: Using the method described in Example 109, Step 2, 2-[4-(benzotriazol-1-yloxy)-6-oxo-6H-pyridazin-1-yl]-4-methyl-pentanoic acid [1-((R)-2,2-dimethyl-[1,3]dioxolan-4-ylmethyl)-1H-pyrazol-3-yl]-amide (Example 109, Step 1) and 5,6,7,8-tetrahydro-naphthalen-1-ol afforded 4-methyl-2-[6-oxo-4-(5,6,7,8-tetrahydro-naphthalen-1-yloxy)-6H-pyridazin-1-yl]-pentanoic acid [1-((R)-2,2-dimethyl-[1,3]dioxolan-4-ylmethyl)-1H-pyrazol-3-yl]-amide as a white solid as a mixture of diastereomers (197.3 mg, 77%).

Step 2: Using the method described in Example 61, Step 2,4-methyl-2-[6-oxo-4-(5,6,7,8-tetrahydro-naphthalen-1-yloxy)-6H-pyridazin-1-yl]-pentanoic acid [1-((R)-2,2-dimethyl-[1,3]dioxolan-4-ylmethyl)-1H-pyrazol-3-yl]-amide afforded 4-methyl-2-[6-oxo-4-(5,6,7,8-tetrahydro-naphthalen-1-yloxy)-6H-pyridazin-1-yl]-pentanoic acid [1-((R)-2,3-dihydroxy-propyl)-1H-pyrazol-3-yl]-amide as a white solid as a mixture of diastereomers (145.9 mg, 81%); ES$^+$-HRMS m/e calcd for $C_{26}H_{33}N_5O_5$ [M+H$^+$] 496.2555 found 496.2554. $^1$H NMR (400 MHz, DMSO-d$_6$) δ ppm 0.87 (d, J=6.6 Hz, 3H), 0.89 (d, J=6.6 Hz, 3H), 1.45 (br. s., 1H), 1.72 (br. s., 4H), 1.75-1.85 (m, 1H), 2.07-2.25 (m, 1H), 2.78 (br. s., 2H), 3.21-3.31 (m, 2H), 3.71-3.83 (m, 1H), 3.86 (dd, J=13.4, 8.1 Hz, 1H), 4.09 (dd, J=13.4, 4.0 Hz, 1H), 4.70 (t, J=5.1 Hz, 1H), 4.93 (d, J=4.7 Hz, 1H), 5.50 (dd, J=11.0, 3.5 Hz, 1H), 5.58 (d, J=2.8 Hz, 1H), 6.36 (d, J=2.0 Hz, 1H), 7.01 (d, J=7.9 Hz, 1H), 7.09 (d, J=7.7 Hz, 1H), 7.14-7.29 (m, 1H), 7.52 (d, J=2.0 Hz, 1H), 8.13 (d, J=2.8 Hz, 1H), 10.76 (s, 1H).

Separation of enantiomers via supercritical fluid chromatography on a SFC DAICEL OJ column, 10% methanol, 70 mL/min.

Example 110A (S)-4-Methyl-2-[6-oxo-4-(5,6,7,8-tetrahydro-naphthalen-1-yloxy)-6H-pyridazin-1-yl]-pentanoic acid [1-((R)-2,3-dihydroxy-propyl)-1H-pyrazol-3-yl]-amide

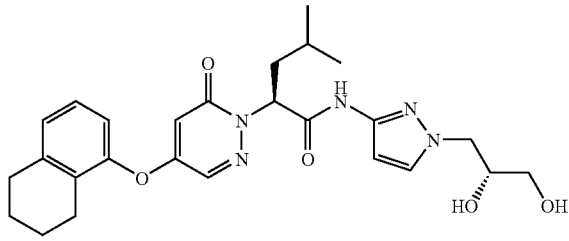

(S)-4-Methyl-2-[6-oxo-4-(5,6,7,8-tetrahydro-naphthalen-1-yloxy)-6H-pyridazin-1-yl]-pentanoic acid [1-((R)-2,3-dihydroxy-propyl)-1H-pyrazol-3-yl]-amide; ES$^+$-HRMS m/e calcd for $C_{26}H_{33}N_5O_5$ [M+H$^+$] 496.2555 found 496.2555. $^1$H NMR (400 MHz, DMSO-d$_6$) δ ppm 0.87 (d, J=6.6 Hz, 3H), 0.89 (d, J=6.6 Hz, 3H), 1.45 (br. s., 1H), 1.72 (br. s., 4H), 1.74-1.84 (m, 1H), 2.09-2.24 (m, 1H), 2.78 (br. s., 2H), 3.22-3.36 (m, 2H), 3.71-3.81 (m, 1H), 3.86 (dd, J=13.6, 7.7 Hz, 1H), 4.09 (dd, J=13.6, 4.0 Hz, 1H), 4.70 (t, J=5.5 Hz, 1H), 4.94 (d, J=5.3 Hz, 1H), 5.49 (dd, J=11.0, 4.2 Hz, 1H), 5.58 (d, J=2.8 Hz, 1H), 6.36 (d, J=2.1 Hz, 1H), 7.01 (d, J=7.9 Hz, 1H), 7.09 (d, J=7.9 Hz, 1H), 7.23 (t, J=7.9 Hz, 1H), 7.53 (d, J=2.1 Hz, 1H), 8.13 (d, J=2.8 Hz, 1H), 10.76 (s, 1H).

Example 110B (R)-4-Methyl-2-[6-oxo-4-(5,6,7,8-tetrahydro-naphthalen-1-yloxy)-6H-pyridazin-1-yl]-pentanoic acid [1-((R)-2,3-dihydroxy-propyl)-1H-pyrazol-3-yl]-amide

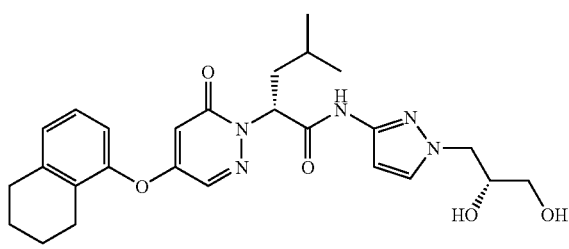

(R)-4-Methyl-2-[6-oxo-4-(5,6,7,8-tetrahydro-naphthalen-1-yloxy)-6H-pyridazin-1-yl]-pentanoic acid [1-((R)-2,3-dihydroxy-propyl)-1H-pyrazol-3-yl]-amide; ES$^+$-HRMS m/e calcd for $C_{26}H_{33}N_5O_5$ [M+H$^+$] 496.2555 found 496.2555. $^1$H NMR (400 MHz, DMSO-d$_6$) δ ppm 0.87 (d, J=6.6 Hz, 3H), 0.89 (d, J=6.6 Hz, 3H), 1.44 (br. s., 1H), 1.72 (br. s., 4H), 1.75-1.83 (m, 1H), 2.08-2.25 (m, 1H), 2.78 (br. s., 2H), 3.21-3.32 (m, 2H), 3.71-3.82 (m, 1H), 3.86 (dd, J=13.6, 7.5 Hz, 1H), 4.09 (dd, J=13.6, 4.0 Hz, 1H), 4.70 (t, J=5.5 Hz, 1H), 4.93 (d, J=5.5 Hz, 1H), 5.50 (dd, J=10.9, 4.3 Hz, 1H), 5.58 (d, J=2.8 Hz, 1H), 6.36 (d, J=2.1 Hz, 1H), 7.01 (d, J=7.9 Hz, 1H), 7.09 (d, J=7.9 Hz, 1H), 7.23 (t, J=7.9 Hz, 1H), 7.52 (d, J=2.1 Hz, 1H), 8.13 (d, J=2.8 Hz, 1H), 10.76 (s, 1H)

Example 111

2-[4-(1H-Indol-4-yloxy)-6-oxo-6H-pyridazin-1-yl]-4-methyl-pentanoic acid [1-((R)-2,3-dihydroxy-propyl)-1H-pyrazol-3-yl]-amide Step 1: A solution of 2-[4-(benzotriazol-1-yloxy)-6-oxo-6H-pyridazin-1-yl]-4-methyl-pentanoic acid [1-((R)-2,2-dimethyl-[1,3]dioxolan-4-ylmethyl)-1H-pyrazol-3-yl]-amide (Example 109, Step 1, 0.25 g, 0.47 mmol) in acetonitrile (10 mL, 0.048M) was treated with cesium carbonate (0.31 g, 0.95 mmol) and 1H-indol-4-ol (75.4 mg, 0.56 mmol). The resulting reaction mixture was stirred at 25° C. for 3.5 h. At this time, the reaction was treated with N,N-dimethylformamide (1.0 mL) and the reaction was heated at 80° C. overnight. The reaction mixture was then concentrated in vacuo and partitioned between water (75 mL) and ethyl acetate (75 mL). The emulsified bilayer was filtered through filter paper and rinsed with water and ethyl acetate. The layers were separated, and the organics were washed with a saturated aqueous sodium chloride solution (50 mL). The combined aqueous layers were acidified with a 1N aqueous hydrochloric acid solution and extracted with ethyl acetate (50 mL). The combined organic layers were dried over magnesium sulfate, filtered, rinsed, and concentrated in vacuo. Silica gel column chromatography (AnaLogix 24 g, 1-10% methanol/methylene chloride) afforded 2-[4-(1H-indol-4-yloxy)-6-oxo-6H-pyridazin-1-yl]-4-methyl-pentanoic acid [1-((R)-2,2-dimethyl-[1,3]dioxolan-4-ylmethyl)-1H-pyrazol-3-yl]-amide (207.1 mg, 81%) as a viscous brown/black oil as a mixture of diastereomers.

Step 2: Using the method described in Example 61, Step 2, 2-[4-(1H-indol-4-yloxy)-6-oxo-6H-pyridazin-1-yl]-4-methyl-pentanoic acid [1-((R)-2,2-dimethyl-[1,3]dioxolan-4-ylmethyl)-1H-pyrazol-3-yl]-amide [1-((R)-2,2-dimethyl-[1,3]dioxolan-4-ylmethyl)-1H-pyrazol-3-yl]-amide afforded 2-[4-(1H-indol-4-yloxy)-6-oxo-6H-pyridazin-1-yl]-4-methyl-pentanoic acid [1-((R)-2,3-dihydroxy-propyl)-1H-pyrazol-3-yl]-amide as a brown solid as a mixture of diastereomers (66.7 mg, 37%); ES$^+$-HRMS m/e calcd for $C_{24}H_{28}N_6O_5$ [M+H$^+$] 481.2194 found 481.2194. $^1$H NMR (400 MHz, DMSO-d$_6$) δ ppm 0.87 (d, J=6.6 Hz, 3H), 0.90 (d, J=6.6 Hz, 3H), 1.47 (br. s., 1H), 1.70-1.87 (m, 1H), 2.11-2.25 (m, 1H), 3.21-3.32 (m, 2H), 3.72-3.81 (m, 1H), 3.86 (ddd, J=13.6, 7.5, 1.7 Hz, 1H), 4.08 (dd, J=13.6, 3.9 Hz, 1H), 4.70 (t, J=5.2 Hz, 1H), 4.93 (dd, J=5.2, 1.7 Hz, 1H), 5.49 (dd, J=11.0, 3.3 Hz, 1H), 5.61 (d, J=2.8 Hz, 1H), 6.29 (br. s., 1H), 6.36 (d, J=2.1 Hz, 1H), 6.90 (d, J=7.5 Hz, 1H), 7.17 (t, J=7.9

Hz, 1H), 7.34-7.48 (m, 2H), 7.52 (d, J=2.1 Hz, 1H), 8.18 (d, J=2.8 Hz, 1H), 10.76 (s, 1H), 11.50 (br. s., 1H).

Example 112

2-[4-(4-Hydroxy-indol-1-yl)-6-oxo-6H-pyridazin-1-yl]-4-methyl-pentanoic acid [1-((R)-2,3-dihydroxy-propyl)-1H-pyrazol-3-yl]-amide

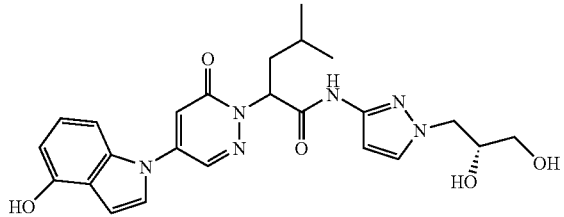

Step 1: A solution of 2-[4-(benzotriazol-1-yloxy)-6-oxo-6H-pyridazin-1-yl]-4-methyl-pentanoic acid [1-((R)-2,2-dimethyl-[1,3]dioxolan-4-ylmethyl)-1H-pyrazol-3-yl]-amide (Example 109, Step 1, 0.50 g, 0.95 mmol) in N,N-dimethylformamide (4 mL, 0.24M) was treated with cesium carbonate (0.62 g, 1.90 mmol) and 1H-indol-4-ol (0.15 g, 1.13 mmol). The resulting reaction mixture was stirred at 80° C. overnight. The reaction mixture was then concentrated in vacuo, diluted with water (100 mL), and acidified with a 1N aqueous hydrochloric acid solution. Ethyl acetate (75 mL) was added, and the mixture was filtered through filter paper, rinsing with water and ethyl acetate. The layers were separated, and the aqueous layer was back extracted with ethyl acetate (75 mL). The combined organics were washed with a saturated aqueous sodium chloride solution (100 mL), dried over magnesium sulfate, filtered, rinsed, and concentrated in vacuo. Silica gel column chromatography (AnaLogix 40 g, 1-10% methanol/methylene chloride) followed by chromatography (Pursuit C-18 column 5×25 cm, 0.05% trifluoroacetic acid/water/acetonitrile linear gradient, 50 ml/min, 45 min run) afforded impure 2-[4-(4-hydroxy-indol-1-yl)-6-oxo-6H-pyridazin-1-yl]-4-methyl-pentanoic acid [1-((R)-2,2-dimethyl-[1,3]dioxolan-4-ylmethyl)-1H-pyrazol-3-yl]-amide (66 mg).

Step 2: Using the method described in Example 61, Step 2, impure 2-[4-(4-hydroxy-indol-1-yl)-6-oxo-6H-pyridazin-1-yl]-4-methyl-pentanoic acid [1-((R)-2,2-dimethyl-[1,3]dioxolan-4-ylmethyl)-1H-pyrazol-3-yl]-amide afforded 2-[4-(4-hydroxy-indol-1-yl)-6-oxo-6H-pyridazin-1-yl]-4-methyl-pentanoic acid [1-((R)-2,3-dihydroxy-propyl)-1H-pyrazol-3-yl]-amide as a brown solid as a mixture of diastereomers (36.7 mg, 8% over two steps); ES$^+$-HRMS m/e calcd for $C_{24}H_{28}N_6O_5$ [M+H$^+$] 481.2194 found 481.2195. $^1$H NMR (400 MHz, DMSO-d$_6$) δ ppm 0.91 (d, J=6.6 Hz, 3H), 0.92 (d, J=6.6 Hz, 3H), 1.52 (br. s., 1H), 1.79-1.91 (m, 1H), 2.18-2.28 (m, 1H), 3.24-3.36 (m, 2H), 3.74-3.83 (m, 1H), 3.82-3.92 (m, 1H), 4.10 (dd, J=13.4, 4.0 Hz, 1H), 4.71 (t, J=5.6 Hz, 1H), 4.94, 4.95 (2×d, J=5.4 Hz, 1H), 5.54-5.68 (m, 1H), 6.39 (d, J=2.1 Hz, 1H), 6.61 (d, J=8.1 Hz, 1H), 6.86 (d, J=3.5 Hz, 1H), 7.07 (d, J=2.6 Hz, 1H), 7.10 (t, J=8.1 Hz, 1H), 7.25 (d, J=8.1 Hz, 1H), 7.54 (d, J=2.1 Hz, 1H), 7.74 (d, J=3.5 Hz, 1H), 8.55 (d, J=2.6 Hz, 1H), 9.84 (s, 1H), 10.83 (s, 1H).

Example 113

2-{4-[1-((R)-2,3-Dihydroxy-propyl)-1H-indol-4-yloxy]-6-oxo-6H-pyridazin-1-yl}-4-methyl-pentanoic acid (1-methyl-1H-pyrazol-3-yl)-amide Step 1: Using the method described in Example 109, Step 1,2-(4-iodo-6-oxo-6H-pyridazin-1-yl)-4-methyl-pentanoic acid (Intermediate 86) and 1-methyl-1H-pyrazol-3-ylamine afforded 2-[4-(benzotriazol-1-yloxy)-6-oxo-6H-pyridazin-1-yl]-4-methyl-pentanoic acid (1-methyl-1H-pyrazol-3-yl)-amide as a light yellow solid (366.5 mg, 58%).

Step 2: A solution of 2-[4-(benzotriazol-1-yloxy)-6-oxo-6H-pyridazin-1-yl]-4-methyl-pentanoic acid (1-methyl-1H-pyrazol-3-yl)-amide (170.3 mg, 0.403 mmol) in acetonitrile (8.4 mL, 0.048M) was treated with cesium carbonate (0.26 g, 0.798 mmol) and 1H-indol-4-ol (64.3 mg, 0.483 mmol). The resulting reaction mixture was heated at 80° C. overnight. At this time, the reaction mixture was allowed to cool to 25° C. and was treated with a saturated aqueous ammonium chloride solution (5 drops). The reaction was then concentrated in vacuo onto silica gel. Silica gel column chromatography (AnaLogix 24 g, 1-10% methanol/methylene chloride) afforded impure 2-[4-(1H-indol-4-yloxy)-6-oxo-6H-pyridazin-1-yl]-4-methyl-pentanoic acid (1-methyl-1H-pyrazol-3-yl)-amide (110.9 mg, 65%) as a brown solid.

Step 3: A solution of 2-[4-(1H-indol-4-yloxy)-6-oxo-6H-pyridazin-1-yl]-4-methyl-pentanoic acid (1-methyl-1H-pyrazol-3-yl)-amide (34.0 mg, 0.0809 mmol) in N,N-dimethylformamide (1.0 mL) was treated with potassium carbonate (23.1 mg, 0.16 mmol) and toluene-4-sulfonic acid (S)-2,2-dimethyl-[1,3]dioxolan-4-yl ester (25.5 mg, 0.08 mmol). The resulting reaction mixture was heated at 90° C. overnight. At this time, the reaction mixture was allowed to cool to 25° C., concentrated in vacuo and was treated with a saturated aqueous ammonium chloride solution (2 drops). The reaction was then concentrated in vacuo onto silica gel. Silica gel column chromatography (AnaLogix 12 g, 1-5% methanol/methylene chloride) afforded 2-{4-[1-((R)-2,2-dimethyl-[1,3]dioxolan-4-ylmethyl)-1H-indol-4-yloxy]-6-oxo-6H-pyridazin-1-yl}-4-methyl-pentanoic acid (1-methyl-1H-pyrazol-3-yl)-amide (9.0 mg, 21%) as a viscous brown oil.

Step 4: Using the method described in Example 61, Step 2, 2-{4-[1-((R)-2,2-dimethyl-[1,3]dioxolan-4-ylmethyl)-1H-indol-4-yloxy]-6-oxo-6H-pyridazin-1-yl}-4-methyl-pentanoic acid (1-methyl-1H-pyrazol-3-yl)-amide afforded 2-{4-[1-((R)-2,3-dihydroxy-propyl)-1H-indol-4-yloxy]-6-oxo-6H-pyridazin-1-yl}-4-methyl-pentanoic acid (1-methyl-1H-pyrazol-3-yl)-amide as a brown solid as a mixture of diastereomers (5.8 mg, 72%); ES$^+$-HRMS m/e calcd for $C_{25}H_{30}N_6O_5$ [M+H$^+$] 495.2351 found 495.2352. $^1$H NMR (400 MHz, DMSO-d$_6$) δ ppm 0.84-0.94 (m, 6H), 1.41-1.60

(m, 1H), 1.76-1.90 (m, 1H), 2.00-2.28 (m, 1H), 3.51 (m, 2H), 3.73, 3.74 (2×s, 3H), 3.77-3.92 (m, 1H), 3.98-4.25 (m, 2 H), 4.70, 4.81 (2×t, J=5.8 Hz, 1H), 5.00 (m, 1H), 5.50, 5.63 (2×m, 1H), 6.29, 6.85 (2×d, J=3.4 Hz, 1H), 6.36, 6.38 (2×d, J=2.1 Hz, 1H), 6.77, 6.92 (2×d, J=8.0 Hz, 1H), 7.10, 7.21 (2×d, J=2.7 Hz, 1H), 7.18-7.26 (m, 1H), 7.39, 7.50 (2×d, J=8.0 Hz, 1H), 7.39, 7.79 (2×d, J=3.4 Hz, 1H), 7.54, 7.55 (2×d, J=2.1 Hz, 1H), 8.19, 8.56 (2×d, J=2.7 Hz, 1H), 10.70, 10.78 (2×s, 1H).

Example 114

2-{4-[2-(2-Chloro-phenyl)-ethoxy]-6-oxo-6H-pyridazin-1-yl}-3-cyclopentyl-N-[1-((R)-2,3-dihydroxy-propyl)-1H-pyrazol-3-yl]-propionamide

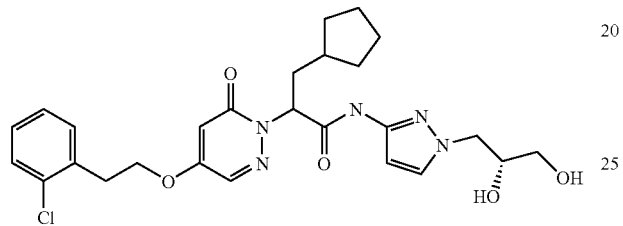

Step 1: A solution of 3-cyclopentyl-2-(4-iodo-6-oxo-6H-pyridazin-1-yl)-propionic acid (Intermediate 85, 1.44 g, 3.98 mmol) in N,N-dimethylformamide (18 mL, 0.22M) at 25° C. was treated with N,N-diisopropylethylamine (2.0 mL, 12.10 mmol), (benzotriazol-1-yloxy)tris(dimethylamino)phosphonium hexafluorophosphate (2.64 g, 5.97 mmol) and 1-((R)-2,2-dimethyl-[1,3]dioxolan-4-ylmethyl)-1H-pyrazol-3-ylamine (Intermediate 4, 0.88 g, 4.46 mmol). The reaction was stirred at 25° C. over 3 nights. After this time, the reaction was diluted with ethyl acetate (150 mL) and was washed with a saturated aqueous ammonium chloride solution (150 mL), a saturated aqueous sodium bicarbonate solution (150 mL) and a saturated aqueous sodium chloride solution (150 mL), dried over magnesium sulfate, filtered, rinsed and concentrated in vacuo. Silica gel column chromatography (AnaLogix 80 g, 25-75% gradient ethyl acetate/hexanes) afforded 2-[4-(benzotriazol-1-yloxy)-6-oxo-6H-pyridazin-1-yl]-3-cyclopentyl-N-[1-((R)-2,2-dimethyl-[1,3]dioxolan-4-ylmethyl)-1H-pyrazol-3-yl]-propionamide (1.11 g, 51%) as an off-white solid as a mixture of diastereomers.

Step 2: A solution of 2-[4-(benzotriazol-1-yloxy)-6-oxo-6H-pyridazin-1-yl]-3-cyclopentyl-N-[1-((R)-2,2-dimethyl-[1,3]dioxolan-4-ylmethyl)-1H-pyrazol-3-yl]-propionamide (0.30 g, 0.54 mmol) in acetonitrile (10 mL, 0.055M) was treated with cesium carbonate (0.36 g, 1.10 mmol) and 2-(2-chloro-phenyl)-ethanol (86 μL, 0.65 mmol). The resulting reaction mixture was stirred at 25° C. overnight. The reaction mixture was then heated at 75° C. for 5.5-6 h. At this time, the reaction was partitioned between water and methylene chloride. The organics were dried over sodium sulfate, filtered, rinsed, and concentrated in vacuo. Silica gel column chromatography (AnaLogix 12 g, 50-75% ethyl acetate/hexanes) afforded 2-{4-[2-(2-chloro-phenyl)-ethoxy]-6-oxo-6H-pyridazin-1-yl}-3-cyclopentyl-N-[1-((R)-2,2-dimethyl-[1,3]dioxolan-4-ylmethyl)-1H-pyrazol-3-yl]-propionamide (114.1 mg, 37%) as a light yellow solid as a mixture of diastereomers.

Step 3: Using the method described in Example 61, Step 2, 2-{4-[2-(2-chloro-phenyl)-ethoxy]-6-oxo-6H-pyridazin-1-yl}-3-cyclopentyl-N-[1-((R)-2,2-dimethyl-[1,3]dioxolan-4-ylmethyl)-1H-pyrazol-3-yl]-propionamide afforded 2-{4-[2-(2-chloro-phenyl)-ethoxy]-6-oxo-6H-pyridazin-1-yl}-3-cyclopentyl-N-[1-((R)-2,3-dihydroxy-propyl)-1H-pyrazol-3-yl]-propionamide as a light yellow solid as a mixture of diastereomers (82.9 mg, 82%); ES$^+$-HRMS m/e calcd for $C_{26}H_{32}N_5O_5Cl$ [M+H$^+$] 530.2165 found 530.2165. $^1$H NMR (300 MHz, DMSO-d$_6$) δ ppm 1.20-1.70 (m, 9H), 1.80-1.95 (m, 1H), 2.14-2.30 (m, 1H), 3.17 (t, J=6.6 Hz, 2H), 3.21-3.31 (m, 2H), 3.68-3.91 (m, 2H), 4.06 (dd, J=13.4, 3.8 Hz, 1H), 4.27 (t, J=6.6 Hz, 2H), 4.69 (t, J=5.6 Hz, 1H), 4.92 (d, J=5.1 Hz, 1H), 5.43 (dd, J=10.7, 3.5 Hz, 1H), 6.33 (d, J=2.4 Hz, 1H), 6.35 (d, J=2.7 Hz, 1H), 7.24-7.31 (m, 2H), 7.41-7.48 (m, 2H), 7.50 (d, J=2.4 Hz, 1H), 7.78 (d, J=2.7 Hz, 1H), 10.68 (s, 1H).

Example 115

3-Cyclopentyl-N-[1-((R)-2,3-dihydroxy-propyl)-1H-pyrazol-3-yl]-2-[6-oxo-4-(4-trifluoromethyl-pyrimidin-2-yloxy)-6H-pyridazin-1-yl]-propionamide

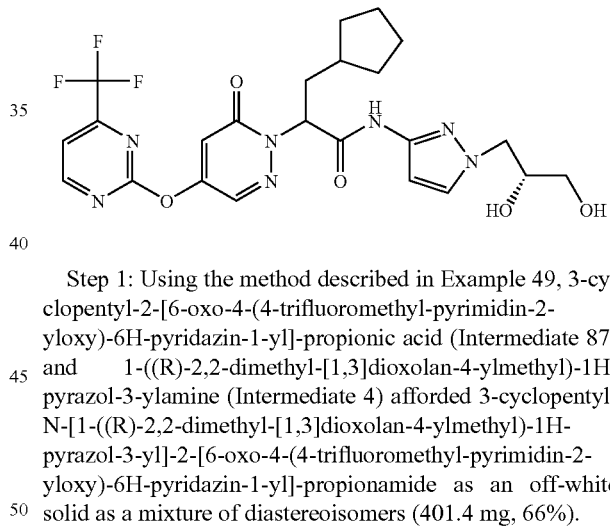

Step 1: Using the method described in Example 49, 3-cyclopentyl-2-[6-oxo-4-(4-trifluoromethyl-pyrimidin-2-yloxy)-6H-pyridazin-1-yl]-propionic acid (Intermediate 87) and 1-((R)-2,2-dimethyl-[1,3]dioxolan-4-ylmethyl)-1H-pyrazol-3-ylamine (Intermediate 4) afforded 3-cyclopentyl-N-[1-((R)-2,2-dimethyl-[1,3]dioxolan-4-ylmethyl)-1H-pyrazol-3-yl]-2-[6-oxo-4-(4-trifluoromethyl-pyrimidin-2-yloxy)-6H-pyridazin-1-yl]-propionamide as an off-white solid as a mixture of diastereoisomers (401.4 mg, 66%).

Step 2: Using the method described in Example 61, Step 2, 3-cyclopentyl-N-[1-((R)-2,2-dimethyl-[1,3]dioxolan-4-ylmethyl)-1H-pyrazol-3-yl]-2-[6-oxo-4-(4-trifluoromethyl-pyrimidin-2-yloxy)-6H-pyridazin-1-yl]-propionamide afforded 3-cyclopentyl-N-[1-((R)-2,3-dihydroxy-propyl)-1H-pyrazol-3-yl]-2-[6-oxo-4-(4-trifluoromethyl-pyrimidin-2-yloxy)-6H-pyridazin-1-yl]-propionamide as an off-white solid as a mixture of diastereomers (199.8 mg, 53%); ES$^+$-HRMS m/e calcd for $C_{23}H_{26}N_7O_5F_3$ [M+H$^+$] 538.2021 found 538.2021. $^1$H NMR (400 MHz, DMSO-d$_6$) δ ppm 1.10 (m, 1H), 1.27-1.77 (m, 8H), 1.97 (m, 1H), 2.28 (m, 1H), 3.23-3.32, 3.44 (2×m, 2H), 3.77 (m, 1H), 3.82-3.91 (m, 1H), 4.05-4.13 (m, 1H), 4.71 (br. s., 1H), 4.49 (br. s., 1H), 5.47, 5.52 (2×dd, J=4.1, 10.8 Hz, 1H), 6.08, 7.01 (2×d, J=2.7 Hz, 1H), 6.37, 6.38 (2×d, J=2.0 Hz, 1H), 7.54 (m, 1H), 7.97 (d, J=5.0 Hz, 1H), 8.25, 8.43 (2×d, J=2.7 Hz, 1H), 9.14 (d, J=5.0 Hz, 1H), 10.83, 10.86 (2×s, 1H).

Example 116

3-Cyclohexyl-2-[4-(2-fluoro-4-methoxy-phenoxy)-6-oxo-6H-pyridazin-1-yl]-N-[1-(2-hydroxy-2-methyl-propyl)-1H-pyrazol-3-yl]-propionamide

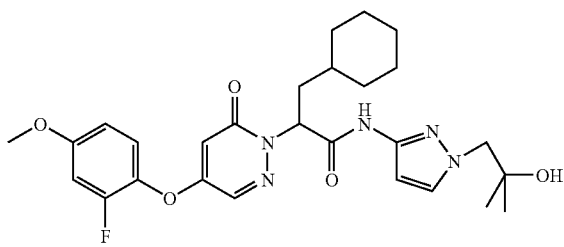

Using the method described in Example 49, 3-cyclohexyl-2-[4-(2-fluoro-4-methoxy-phenoxy)-6-oxo-6H-pyridazin-1-yl-propionic acid (Intermediate 88) and 1-(3-amino-pyrazol-1-yl)-2-methyl-propan-2-ol (Intermediate 1) afforded 3-cyclohexyl-2-[4-(2-fluoro-4-methoxy-phenoxy)-6-oxo-6H-pyridazin-1-yl]-N-[1-(2-hydroxy-2-methyl-propyl)-1H-pyrazol-3-yl]-propionamide as a light yellow solid (353 mg, 82%); ES$^+$-HRMS m/e calcd for $C_{27}H_{34}N_5O_5F$ [M+H$^+$] 528.2617 found 528.2617. $^1$H NMR (300 MHz, DMSO-d$_6$) δ ppm 0.76-1.32 (m, 6H), 1.05 (s, 3H), 1.06 (s, 3H), 1.48-1.73 (m, 5H), 1.73-1.90 (m, 1H), 2.08-2.24 (m, 1H), 3.80 (s, 3H), 3.89 (s, 2H), 4.67 (s, 1H), 5.53 (dd, J=11.2, 3.6 Hz, 1H), 5.76 (d, J=2.7 Hz, 1H), 6.39 (d, J=2.1 Hz, 1H), 6.89 (dd, J=9.1, 2.5 Hz, 1H), 7.13 (dd, J=12.7, 2.5 Hz, 1H), 7.41 (t, J=9.1 Hz, 1H), 7.52 (d, J=2.1 Hz, 1H), 8.18 (d, J=2.7 Hz, 1H), 10.82 (s, 1H).

Example 117

3-Cyclohexyl-2-[4-(2,4-dimethyl-phenoxy)-6-oxo-6H-pyridazin-1-yl]-N-[1-(2-hydroxy-2-methyl-propyl)-1H-pyrazol-3-yl]-propionamide

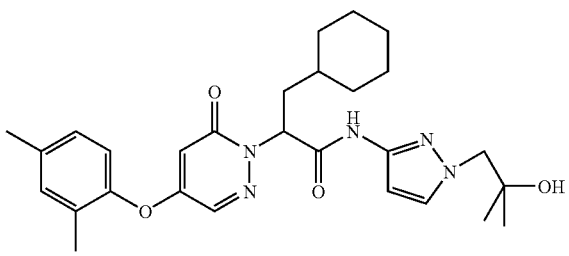

Using the method described in Example 49, 3-cyclohexyl-2-[4-(2,4-dimethyl-phenoxy)-6-oxo-6H-pyridazin-1-yl]-propionic acid (Intermediate 89) and 1-(3-amino-pyrazol-1-yl)-2-methyl-propan-2-ol (Intermediate 1) afforded 3-cyclohexyl-2-[4-(2,4-dimethyl-phenoxy)-6-oxo-6H-pyridazin-1-yl]-N-[1-(2-hydroxy-2-methyl-propyl)-1H-pyrazol-3-yl]-propionamide as a light yellow solid (202 mg, 75%); ES$^+$-HRMS m/e calcd for $C_{28}H_{37}N_5O_4$ [M+H$^+$] 508.2919 found 508.2920. $^1$H NMR (300 MHz, DMSO-d$_6$) δ ppm 0.85-1.29 (m, 6H), 1.04 (s, 3H), 1.06 (s, 3H), 1.52-1.73 (m, 5H), 1.73-1.90 (m, 1H), 2.11 (s, 3H), 2.11-2.22 (m, 1H), 2.31 (s, 3H), 3.89 (s, 2H), 4.67 (s, 1H), 5.47-5.58 (m, 2H), 6.39 (d, J=2.1 Hz, 1H), 7.08 (d, J=8.2 Hz, 1H), 7.10-7.15 (m, 1H), 7.21 (s, 1H), 7.52 (d, J=2.1 Hz, 1H), 8.14 (d, J=2.7 Hz, 1H), 10.79 (s, 1H).

Example 118

2-[4-(2-Chloro-4-methoxy-phenoxy)-6-oxo-6H-pyridazin-1-yl]-3-cyclohexyl-N-[1-(2-hydroxy-2-methyl-propyl)-1H-pyrazol-3-yl]-propionamide

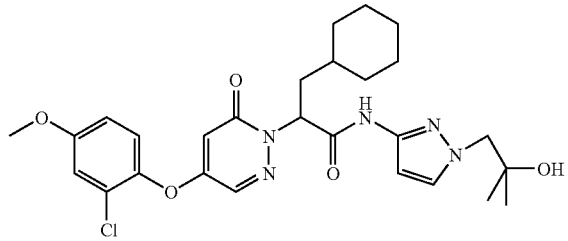

Using the method described in Example 49, 2-[4-(2-chloro-4-methoxy-phenoxy)-6-oxo-6H-pyridazin-1-yl]-3-cyclohexyl-propionic acid (Intermediate 90) and 1-(3-amino-pyrazol-1-yl)-2-methyl-propan-2-ol (Intermediate 1) afforded 2-[4-(2-chloro-4-methoxy-phenoxy)-6-oxo-6H-pyridazin-1-yl]-3-cyclohexyl-N-[1-(2-hydroxy-2-methyl-propyl)-1H-pyrazol-3-yl]-propionamide as an off-white solid (190 mg, 63%); ES$^+$-HRMS m/e calcd for $C_{27}H_{34}N_5O_5Cl$ [M+H$^+$] 544.2321 found 544.2324. $^1$H NMR (300 MHz, DMSO-d$_6$) δ ppm 0.88-1.22 (m, 6H), 1.05 (s, 3H), 1.06 (s, 3H), 1.62 (br. s., 5H), 1.74-1.88 (m, 1H), 2.06-2.24 (m, 1H), 3.81 (s, 3H), 3.89 (s, 2H), 4.67 (s, 1H), 5.53 (dd, J=11.2, 3.9 Hz, 1H), 5.65 (d, J=2.7 Hz, 1H), 6.39 (d, J=1.8 Hz, 1H), 7.04 (dd, J=9.0, 3.0 Hz, 1H), 7.27 (d, J=3.0 Hz, 1H), 7.43 (d, J=9.0 Hz, 1H), 7.52 (d, J=1.8 Hz, 1H), 8.18 (d, J=2.7 Hz, 1H), 10.83 (s, 1H).

Example 119

2-[4-(2-Chloro-4-trifluoromethoxy-phenoxy)-6-oxo-6H-pyridazin-1-yl]-3-cyclohexyl-N-[1-(2-hydroxy-2-methyl-propyl)-1H-pyrazol-3-yl]-propionamide

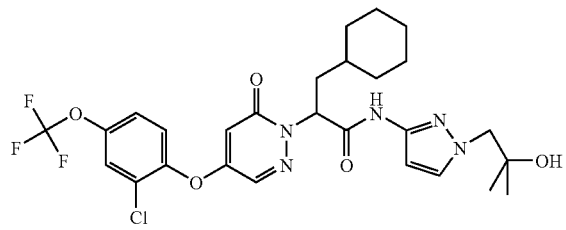

Using the method described in Example 49, 2-[4-(2-chloro-4-trifluoromethoxy-phenoxy)-6-oxo-6H-pyridazin-1-yl]-3-cyclohexyl-propionic acid (Intermediate 91) and 1-(3-amino-pyrazol-1-yl)-2-methyl-propan-2-ol (Intermediate 1) afforded 2-[4-(2-chloro-4-trifluoromethoxy-phenoxy)-6-oxo-6H-pyridazin-1-yl]-3-cyclohexyl-N-[1-(2-hydroxy-2-methyl-propyl)-1H-pyrazol-3-yl]-propionamide as a white solid (130 mg, 52%); ES$^+$-HRMS m/e calcd for $C_{27}H_{31}N_5O_5F_3Cl$ [M+H$^+$] 598.2039 found 598.2038. $^1$H NMR (300 MHz, DMSO-$d_6$) δ ppm 0.84-1.26 (m, 6H), 1.05 (br. s., 6H), 1.63 (br. s., 5H), 1.74-1.91 (m, 1H), 2.07-2.23 (m, 1H), 3.89 (s, 2H), 4.67 (s, 1H), 5.48-5.60 (m, 1H), 5.91 (d, J=2.7 Hz, 1H), 6.39 (s, 1H), 7.45-7.60 (m, 2H), 7.67 (dd, J=9.1, 2.1 Hz, 1H), 7.87 (br. s., 1H), 8.22 (d, J=2.7 Hz, 1H), 10.82 (s, 1H).

Example 120

2-[4-(3-Ethoxy-2,6-difluoro-phenoxy)-6-oxo-6H-pyridazin-1-yl]-4-methyl-pentanoic acid [1-((R)-2,2-dimethyl-[1,3]dioxolan-4-ylmethyl)-1H-pyrazol-3-yl]-amide

Step 1: Using the method described in Example 49, 2-[4-(3-ethoxy-2,6-difluoro-phenoxy)-6-oxo-6H-pyridazin-1-yl]-4-methyl-pentanoic acid (Intermediate 92) and 1-((R)-2,2-dimethyl-[1,3]dioxolan-4-ylmethyl)-1H-pyrazol-3-ylamine (Intermediate 4) afforded 2-[4-(3-ethoxy-2,6-difluoro-phenoxy)-6-oxo-6H-pyridazin-1-yl]-4-methyl-pentanoic acid [1-((R)-2,2-dimethyl-[1,3]dioxolan-4-ylmethyl)-1H-pyrazol-3-yl]-amide as an off-white solid as a mixture of diastereoisomers (164 mg, 78%).

Step 2: Using the method described in Example 61, Step 2, 2-[4-(3-ethoxy-2,6-difluoro-phenoxy)-6-oxo-6H-pyridazin-1-yl]-4-methyl-pentanoic acid [1-((R)-2,2-dimethyl-[1,3]dioxolan-4-ylmethyl)-1H-pyrazol-3-yl]-amide afforded 2-[4-(3-ethoxy-2,6-difluoro-phenoxy)-6-oxo-6H-pyridazin-1-yl]-4-methyl-pentanoic acid [1-((R)-2,3-dihydroxy-propyl)-1H-pyrazol-3-yl]-amide as a white solid as a mixture of diastereomers (143 mg, 73%); ES$^+$-HRMS m/e calcd for $C_{24}H_{29}N_5O_6F_2$ [M+Na$^+$] 544.1978 found 544.1975. $^1$H NMR (300 MHz, DMSO-$d_6$) δ ppm 0.86, 0.88 (2×d, J=6.8 Hz, 6H), 1.35 (t, J=6.9 Hz, 3H), 1.40-1.52 (m, 1H), 1.71-1.89 (m, 1H), 2.07-2.24 (m, 1H), 3.22-3.33 (m, 2H), 3.66-3.92 (m, 2H), 4.02-4.13 (m, 1H), 4.15 (q, J=6.9 Hz, 2H), 4.71 (t, J=5.6 Hz, 1H), 4.94 (dd, J=5.1, 1.5 Hz, 1H), 5.51 (dd, J=11.0, 3.8 Hz, 1H), 6.07 (d, J=2.7 Hz, 1H), 6.36 (d, J=2.1 Hz, 1H), 7.15-7.26 (m, 1H), 7.31 (td, J=10.0, 1.5 Hz, 1H), 7.53 (d, J=2.1 Hz, 1H), 8.28 (d, J=2.7 Hz, 1H), 10.83 (s, 1H).

Example 121

N-[1-((R)-2,3-Dihydroxy-propyl)-1H-pyrazol-3-yl]-2-[4-(3-ethoxy-2,6-difluoro-phenoxy)-6-oxo-6H-pyridazin-1-yl]-3-(tetrahydro-pyran-4-yl)-propionamide

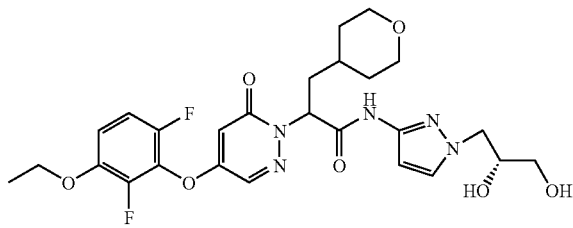

Step 1: Using the method described in Example 49, 2-[4-(3-ethoxy-2,6-difluoro-phenoxy)-6-oxo-6H-pyridazin-1-yl]-3-(tetrahydro-pyran-4-yl)-propionic acid (Intermediate 93) and 1-((R)-2,2-dimethyl-[1,3]dioxolan-4-ylmethyl)-1H-pyrazol-3-ylamine (Intermediate 4) afforded N-[1-((R)-2,2-dimethyl-[1,3]dioxolan-4-ylmethyl)-1H-pyrazol-3-yl]-2-[4-(3-ethoxy-2,6-difluoro-phenoxy)-6-oxo-6H-pyridazin-1-yl]-3-(tetrahydro-pyran-4-yl)-propionamide as an off-white solid as a mixture of diastereoisomers (138 mg, 55%).

Step 2: Using the method described in Example 61, Step 2, N-[1-((R)-2,2-dimethyl-[1,3]dioxolan-4-ylmethyl)-1H-pyrazol-3-yl]-2-[4-(3-ethoxy-2,6-difluoro-phenoxy)-6-oxo-6H-pyridazin-1-yl]-3-(tetrahydro-pyran-4-yl)-propionamide afforded N-[1-((R)-2,3-dihydroxy-propyl)-1H-pyrazol-3-yl]-2-[4-(3-ethoxy-2,6-difluoro-phenoxy)-6-oxo-6H-pyridazin-1-yl]-3-(tetrahydro-pyran-4-yl)-propionamide as a white solid as a mixture of diastereomers (110 mg, 85%); ES$^+$-HRMS m/e calcd for $C_{26}H_{31}N_5O_7F_2$ [M+H$^+$] 564.2265 found 564.2266. $^1$H NMR (300 MHz, DMSO-$d_6$) δ ppm 1.05-1.31 (m, 2H), 1.28-1.44 (m, 1H), 1.35 (t, J=6.9 Hz, 3H), 1.49 (br. s., 2H), 1.80-1.96 (m, 1H), 2.10-2.30 (m, 1H), 3.03-3.31 (m, 4H), 3.71-3.91 (m, 4H), 4.03-4.12 (m, 1H), 4.15 (q, J=6.9 Hz, 2H), 4.71 (t, J=5.4 Hz, 1H), 4.95 (dd, J=5.3, 1.7 Hz, 1H), 5.53 (dd, J=10.7, 3.2 Hz, 1H), 6.07 (d, J=2.7 Hz, 1H), 6.36 (d, J=2.1 Hz, 1H), 7.14-7.26 (m, 1H), 7.31 (td, J=10.0, 1.8 Hz, 1H), 7.53 (d, J=2.1 Hz, 1H), 8.29 (d, J=2.7 Hz, 1H), 10.85 (s, 1H).

Example 122

2-[4-(2-Chloro-phenylamino)-6-oxo-6H-pyridazin-1-yl]-4-methyl-pentanoic acid [1-((R)-2,3-dihydroxy-propyl)-1H-pyrazol-3-yl]-amide

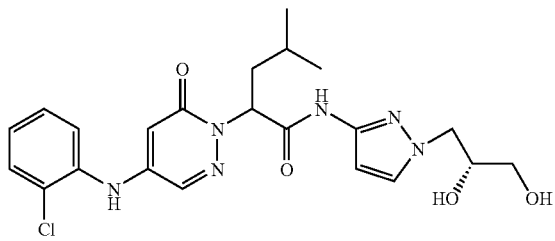

Step 1: A vial containing 2-(4-iodo-6-oxo-6H-pyridazin-1-yl)-4-methyl-pentanoic acid [1-((R)-2,2-dimethyl-[1,3]dioxolan-4-ylmethyl)-1H-pyrazol-3-yl]-amide (Intermediate 94, 51.5 mg, 0.10 mmol), potassium carbonate (23.5 mg, 0.170 mmol), 2,2'-bis(diphenylphosphino)-1,1'-binaphthalene (6.9 mg, 0.01 mmol), and palladium (II) acetate (2.7 mg, 0.0120 mmol) was evacuated, charged with a nitrogen atmosphere, and treated with toluene (1 mL) and 2-chloroaniline (12.6 μL, 0.12 mmol). The vial was sealed, and the reaction was warmed to 120° C., where it stirred for 3.5 h, followed by stirring at 25° C. overnight. At this point, the reaction was partitioned between ethyl acetate (5 mL) and water (5 mL). The organic layer was washed with a 10% aqueous ammonium chloride solution (5 mL) and a saturated aqueous sodium chloride solution (5 mL). The organics were dried over sodium sulfate, filtered, and concentrated in vacuo onto silica gel. Chromatography (20-90% ethyl acetate/hexanes) afforded 2-[4-(2-chloro-phenylamino)-6-oxo-6H-pyridazin-1-yl]-4-methyl-pentanoic acid [1-((R)-2,2-dimethyl-[1,3]dioxolan-4-ylmethyl)-1H-pyrazol-3-yl]-amide as a white/yellow solid (41.2 mg, 80%).

Step 2: A solution of 2-[4-(2-chloro-phenylamino)-6-oxo-6H-pyridazin-1-yl]-4-methyl-pentanoic acid [1-((R)-2,2-dimethyl-[1,3]dioxolan-4-ylmethyl)-1H-pyrazol-3-yl]-amide (41.2 mg, 0.08 mmol) in tetrahydrofuran (2 mL) was treated with a 1 M aqueous hydrochloric acid solution (2 mL), and the reaction stirred at 25° C. overnight. At this point, the reaction was dried under nitrogen and suspended in ethyl acetate (20 mL), then washed with a 1:1 aqueous sodium bicarbonate/water solution (20 mL total) and a saturated aqueous sodium chloride solution (10 mL). The organics were dried over sodium sulfate, concentrated in vacuo, and dried from methylene chloride, ethanol, and diethyl ether, and in a vacuum oven at 50° C. for 3 h to afford 2-[4-(2-chloro-phenylamino)-6-oxo-6H-pyridazin-1-yl]-4-methyl-pentanoic acid [1-((R)-2,3-dihydroxy-propyl)-1H-pyrazol-3-yl]-amide as a light yellow solid (29.6 mg, 78%); ES$^+$-HRMS m/e calcd for $C_{22}H_{27}N_6O_4Cl$ [M+H$^+$] 475.1855 found 475.1855. $^1$H NMR (300 MHz, DMSO-d$_6$) δ ppm 0.86 (d, J=6.6 Hz, 3H), 0.88 (d, J=6.6 Hz, 3H), 1.44 (br. s., 1H), 1.62-1.81 (m, 1H), 2.00-2.22 (m, 1H), 3.20-3.32 (m, 2H), 3.70-3.92 (m, 2H), 4.08 (dd, J=13.4, 3.8 Hz, 1H), 4.71 (t, J=5.6 Hz, 1H), 4.94 (dd, J=5.1, 1.8 Hz, 1H), 5.49 (dd, J=11.0, 4.1 Hz, 1H), 5.54 (d, J=2.7 Hz, 1H), 6.35 (d, J=2.1 Hz, 1H), 7.28 (td, J=7.8, 1.2 Hz, 1H), 7.40 (td, J=7.8, 1.2 Hz, 1H), 7.47 (dd, J=7.8, 1.2 Hz, 1H), 7.52 (d, J=2.1 Hz, 1H), 7.60 (dd, J=7.8, 1.2 Hz, 1H), 7.86 (d, J=2.7 Hz, 1H), 8.94 (s, 1H), 10.65 (s, 1H).

Example 123

3-Cyclopentyl-N-[1-(2-hydroxy-2-methyl-propyl)-1H-pyrazol-3-yl]-2-(6-oxo-4-phenylsulfanyl-6H-pyridazin-1-yl)-propionamide

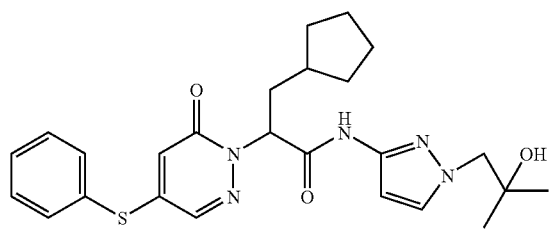

Using the method described in Example 49, 3-cyclopentyl-2-(6-oxo-4-phenylsulfanyl-6H-pyridazin-1-yl)-propionic acid (Intermediate 95) and 1-(3-amino-pyrazol-1-yl)-2-methyl-propan-2-ol (Intermediate 1) afforded 3-cyclopentyl-N-[1-(2-hydroxy-2-methyl-propyl)-1H-pyrazol-3-yl]-2-(6-oxo-4-phenylsulfanyl-6H-pyridazin-1-yl)-propionamide was obtained as an off-white solid (83.5 mg, 61%); ES$^+$-HRMS m/e calcd for $C_{25}H_{31}N_5O_3S$ [M+H$^+$] 482.2221 found 482.2221. $^1$H NMR (300 MHz, DMSO-d$_6$) δ ppm 1.04 (br. s., 3H), 1.05 (br. s., 3H), 1.19-1.78 (m, 9H), 1.78-2.00 (m, 1H), 2.10-2.32 (m, 1H), 3.88 (s, 2H), 4.67 (s, 1H), 5.42 (dd, J=10.9, 4.2 Hz, 1H), 5.95 (d, J=2.4 Hz, 1H), 6.38 (d, J=2.4 Hz, 1H), 7.52 (d, J=2.4 Hz, 1H), 7.56-7.70 (m, 5H), 7.94 (d, J=2.4 Hz, 1H), 10.79 (s, 1H).

Example 124

2-(4-Benzenesulfinyl-6-oxo-6H-pyridazin-1-yl)-3-cyclopentyl-N-[1-(2-hydroxy-2-methyl-propyl)-1H-pyrazol-3-yl]-propionamide

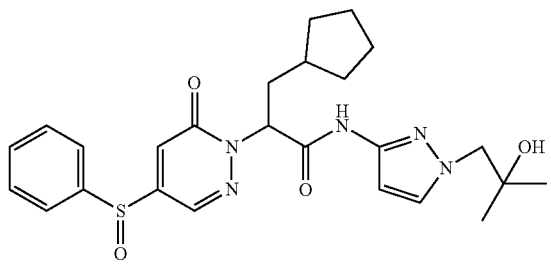

(See Example 125)

Example 125

2-(4-Benzenesulfonyl-6-oxo-6H-pyridazin-1-yl)-3-cyclopentyl-N-[1-(2-hydroxy-2-methyl-propyl)-1H-pyrazol-3-yl]-propionamide

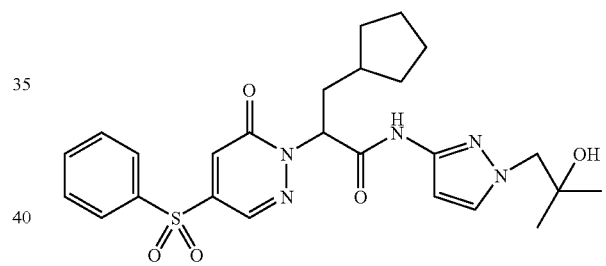

A solution of 3-cyclopentyl-N-[1-(2-hydroxy-2-methyl-propyl)-1H-pyrazol-3-yl]-2-(6-oxo-4-phenylsulfanyl-6H-pyridazin-1-yl)-propionamide (30 mg, 0.06 mmol) in tetrahydrofuran (1 mL) was treated with m-chloroperbenzoic acid (10.8 mg, 0.06 mmol). In a separate flask, a solution of 3-cyclopentyl-N-[1-(2-hydroxy-2-methyl-propyl)-1H-pyrazol-3-yl]-2-(6-oxo-4-phenylsulfanyl-6H-pyridazin-1-yl)-propionamide (30 mg, 0.06 mmol) in tetrahydrofuran (1 mL) was treated with m-chloroperbenzoic acid (21.5 mg, 0.12 mmol). Both reactions were stirred at 25° C. for 3 nights. At this time, each reaction was individually concentrated in vacuo. Two separate HPLC purifications (30-100% acetonitrile/water, C18 Pursuit Agilient, 20×150mm, 30 ml/min) were combined to afford 2-(4-benzenesulfinyl-6-oxo-6H-pyridazin-1-yl)-3-cyclopentyl-N-[1-(2-hydroxy-2-methyl-propyl)-1H-pyrazol-3-yl]-propionamide (6.9 mg, 11%) as a white solid; ES$^+$-HRMS m/e calcd for $C_{25}H_{31}N_5O_4S$ [M+H$^+$] 498.2170 found 498.2171. $^1$H NMR (300 MHz, DMSO-d$_6$) δ ppm 1.04 (2×s, 6H), 1.19-1.70 (m, 9H), 1.88-2.01 (m, 1H), 2.10-2.26 (m, 1H), 3.87 (s, 2H), 4.66 (s, 1H), 5.47 (dd, J=10.6, 4.2 Hz, 1H), 6.35 (d, J=2.4 Hz, 1H), 7.51 (dd, J=2.4 Hz, 1H), 7.54 (dd, J=2.4 Hz, 1H), 7.73 (t, J=7.5 Hz, 2H), 7.85 (t, J=7.5 Hz, 1H), 8.14 (d, J=7.5 Hz, 2H), 8.47 (d, J=2.4 Hz, 1H), 10.87 (s, 1H);

and 2-(4-benzenesulfonyl-6-oxo-6H-pyridazin-1-yl)-3-cyclopentyl-N-[1-(2-hydroxy-2-methyl-propyl)-1H-pyrazol-3-yl]-propionamide (14.9 mg, 23%) as a white solid; ES$^+$-HRMS m/e calcd for $C_{25}H_{31}N_5O_5S$ [M+H$^+$] 514.2119 found 514.2121. $^1$H NMR (300 MHz, DMSO-d$_6$) δ ppm 1.04 (s, 3H), 1.04 (s, 3H), 1.20-1.70 (m, 9H), 1.86-2.02 (m, 1H), 2.07-2.31 (m, 1H), 3.87 (s, 2H), 4.66 (s, 1H), 5.47 (dd, J=10.4, 4.4 Hz, 1H), 6.35 (d, J=2.4 Hz, 1H), 7.51 (d, J=2.4 Hz, 1H), 7.52 (d, J=2.4 Hz, 1H), 7.73 (t, J=7.5 Hz, 2H), 7.85 (t, J=7.5 Hz, 1H), 8.14 (d, J=7.5 Hz, 2H), 8.47 (d, J=2.4 Hz, 1H), 10.87 (s, 1H).

Example 126

2-[4-(2-Chloro-3-trifluoromethyl-phenoxy)-6-oxo-6H-pyridazin-1-yl]-4-methyl-pentanoic acid [1-((R)-2,3-dihydroxy-propyl)-1H-pyrazol-3-yl]-amide

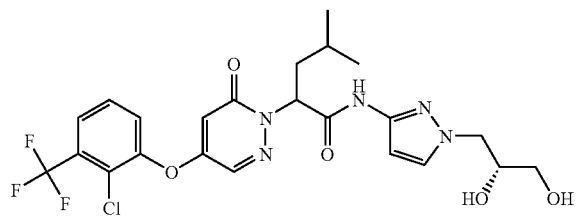

Step 1: A solution of 2-(4-iodo-6-oxo-6H-pyridazin-1-yl)-4-methyl-pentanoic acid [1-((R)-2,2-dimethyl-[1,3]dioxolan-4-ylmethyl)-1H-pyrazol-3-yl]-amide (Intermediate 94, 51.5 mg, 0.10 mmol) in N,N-dimethylformamide (2 mL) at 25° C. was treated with 2-chloro-3-trifluoromethyl-phenol (23.6 mg, 0.12 mmol) and cesium carbonate (65.2 mg, 0.20 mmol). The reaction was stirred at 25° C. over 3 nights. At this time, the reaction was warmed to 80° C. overnight. At this time, the reaction was filtered, rinsed with dimethylsulfoxide (1 mL) and then purified by HPLC chromatography (50-100% acetonitrile/water, C18 Pursuit Agilient, 20×150 mm, 30 ml/min) to afford 2-[4-(2-chloro-3-trifluoromethyl-phenoxy)-6-oxo-6H-pyridazin-1-yl]-4-methyl-pentanoic acid [1-((R)-2,2-dimethyl-[1,3]dioxolan-4-ylmethyl)-1H-pyrazol-3-yl]-amide as a white solid as a mixture of diastereomers (39 mg, 67%); ES$^+$-HRMS m/e calcd for $C_{26}H_{29}N_5O_5F_3Cl$ [M+H$^+$] 584.1882 found 584.1885. $^1$H NMR (300 MHz, DMSO-d$_6$) δ ppm 0.79-0.95 (m, 6H), 1.24 (s, 3H), 1.29, 1.30 (2×s, 3H), 1.45 (br. s., 1H), 1.69-1.87 (m, 1H), 1.99-2.32 (m, 1H), 3.73 (dd, J=8.4, 5.7 Hz, 1H), 4.00 (dd, J=8.4, 6.2 Hz, 1H), 4.04-4.22 (m, 2H), 4.27-4.43 (m, 1H), 5.53 (dd, J=11.2, 4.2 Hz, 1H), 5.95 (d, J=2.7 Hz, 1H), 6.38 (d, J=2.4 Hz, 1H), 7.59 (s, 1H), 7.70 (t, J=8.2 Hz, 1H), 7.87 (t, J=7.5 Hz, 2H), 8.25 (d, J=2.7 Hz, 1H), 10.85 (s, 1H)

Step 2: Using the method described in Example 61, Step 2, 2-[4-(2-chloro-3-trifluoromethyl-phenoxy)-6-oxo-6H-pyridazin-1-yl]-4-methyl-pentanoic acid [1-((R)-2,2-dimethyl-[1,3]dioxolan-4-ylmethyl)-1H-pyrazol-3-yl]-amide afforded 2-[4-(2-chloro-3-trifluoromethyl-phenoxy)-6-oxo-6H-pyridazin-1-yl]-4-methyl-pentanoic acid [1-((R)-2,3-dihydroxy-propyl)-1H-pyrazol-3-yl]-amide as a white solid as a mixture of diastereomers (56.4 mg, 89%); ES$^+$-HRMS m/e calcd for $C_{23}H_{25}N_5O_5F_3Cl$ [M+H$^+$] 544.1569 found 544.1569. $^1$H NMR (300 MHz, DMSO-d$_6$) δ ppm 0.87, 0.89 (2×d, J=7.1 Hz, 6H), 1.45 (br. s., 1H), 1.68-1.85 (m, 1H), 2.08-2.25 (m, 1H), 3.22-3.32 (m, 2H), 3.71-3.92 (m, 2H), 4.08 (dd, J=13.4, 3.0 Hz, 1H), 4.71 (t, J=5.3 Hz, 1H), 4.94 (d, J=5.1 Hz, 1H), 5.51 (dd, J=10.4, 3.0 Hz, 1H), 5.94 (d, J=2.7 Hz, 1H), 6.36 (s, 1H), 7.52 (s, 1H), 7.69 (t, J=7.2 Hz, 1H), 7.85, 7.88 (2×d, J=7.6 Hz, 2H), 8.24 (d, J=2.7 Hz, 1H), 10.81 (s, 1H).

Example 127

2-[4-(2-Chloro-3-methoxy-phenoxy)-6-oxo-6H-pyridazin-1-yl]-4-methyl-pentanoic acid [1-((R)-2,3-dihydroxy-propyl)-1H-pyrazol-3-yl]-amide

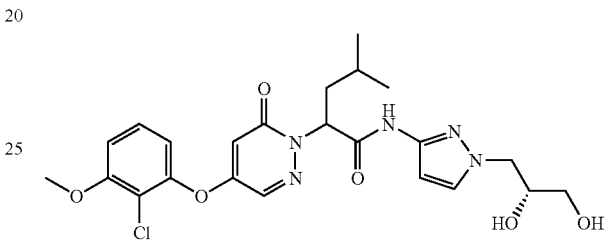

Step 1: Using the method described in Example 126, Step 1,2-(4-iodo-6-oxo-6H-pyridazin-1-yl)-4-methyl-pentanoic acid [1-((R)-2,2-dimethyl-[1,3]dioxolan-4-ylmethyl)-1H-pyrazol-3-yl]-amide (Intermediate 94) and 2-chloro-3-methoxy-phenol afforded 2-[4-(2-chloro-3-methoxy-phenoxy)-6-oxo-6H-pyridazin-1-yl]-4-methyl-pentanoic acid [1-((R)-2,2-dimethyl-[1,3]dioxolan-4-ylmethyl)-1H-pyrazol-3-yl]-amide as a white solid as a mixture of diastereomers (42 mg, 77%); ES$^+$-HRMS m/e calcd for $C_{26}H_{32}N_5O_6Cl$ [M+H$^+$] 546.2114 found 546.2114. $^1$H NMR (300 MHz, DMSO-d$_6$) δ ppm 0.78-0.97 (m, 6H), 1.24 (s, 3H), 1.30 (2×s, 3H), 1.45 (br. s., 1H), 1.69-1.87 (m, 1H), 2.05-2.25 (m, 1H), 3.73 (dd, J=8.5, 5.7 Hz, 1H), 3.92 (s, 3H), 4.00 (dd, J=8.5, 6.3 Hz, 1H), 4.04-4.19 (m, 2H), 4.35 (quin, J=5.8 Hz, 1H), 5.51 (dd, J=11.0, 4.1 Hz, 1H), 5.71 (d, J=2.7 Hz, 1H), 6.38 (d, J=2.4 Hz, 1H), 7.06 (d, J=8.2 Hz, 1H), 7.18 (d, J=8.2 Hz, 1H), 7.45 (t, J=8.2 Hz, 1H), 7.59 (s, 1H), 8.19 (d, J=2.7 Hz, 1H), 10.84 (s, 1H).

Step 2: Using the method described in Example 61, Step 2, 2-[4-(2-chloro-3-methoxy-phenoxy)-6-oxo-6H-pyridazin-1-yl]-4-methyl-pentanoic acid [1-((R)-2,2-dimethyl-[1,3]dioxolan-4-ylmethyl)-1H-pyrazol-3-yl]-amide afforded 2-[4-(2-chloro-3-methoxy-phenoxy)-6-oxo-6H-pyridazin-1-yl]-4-methyl-pentanoic acid [1-((R)-2,3-dihydroxy-propyl)-1H-pyrazol-3-yl]-amide as a white solid as a mixture of diastereomers (34.5 mg, 89%); ES$^+$-HRMS m/e calcd for $C_{23}H_{28}N_5O_6Cl$ [M+H$^+$] 506.1801 found 506.1803. $^1$H NMR (300 MHz, DMSO-d$_6$) δ ppm 0.83-0.91 (m, 6H), 1.44 (br. s., 1H), 1.69-1.85 (m, 1H), 2.10-2.24 (m, 1H), 3.19-3.31 (m, 2H), 3.70-3.90 (m, 2H), 3.92 (s, 3H), 4.08 (dd, J=13.4, 3.6 Hz, 1H), 4.71 (t, J=5.6 Hz, 1H), 4.94 (d, J=4.2 Hz, 1H), 5.50 (dd, J=11.0, 3.3 Hz, 1H), 5.71 (d, J=2.7 Hz, 1H), 6.35 (d, J=2.1 Hz, 1H), 7.06 (d, J=8.2 Hz, 1H), 7.18 (d, J=8.2 Hz, 1H), 7.45 (t, J=8.2 Hz, 1H), 7.52 (d, J=2.1 Hz, 1H), 8.19 (d, J=2.7 Hz, 1H), 10.81 (s, 1H).

Example 128

2-[4-(2-Chloro-phenoxy)-6-oxo-6H-pyridazin-1-yl]-3-cyclopentyl-N-[1-((R)-2,3-dihydroxy-propyl)-1H-pyrazol-3-yl]-propionamide

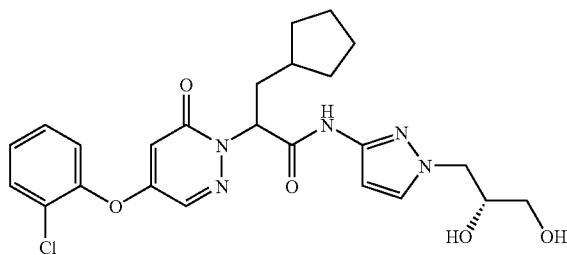

Step 1: Using the method described in Example 126, Step 1, 2-[4-(benzotriazol-1-yloxy)-6-oxo-6H-pyridazin-1-yl]-3-cyclopentyl-N-[1-((R)-2,2-dimethyl-[1,3]dioxolan-4-ylmethyl)-1H-pyrazol-3-yl]-propionamide (Example 114, Step 1) and 2-chloro-phenol afforded 2-[4-(2-chloro-phenoxy)-6-oxo-6H-pyridazin-1-yl]-3-cyclopentyl-N-[1-((R)-2,2-dimethyl-[1,3]dioxolan-4-ylmethyl)-1H-pyrazol-3-yl]-propionamide as a white solid as a mixture of diastereomers (99.4 mg, 80%); ES$^+$-HRMS m/e calcd for $C_{27}H_{32}N_5O_5Cl$ [M+H$^+$] 542.2165 found 542.2167. $^1$H NMR (300 MHz, DMSO-d$_6$) δ ppm 1.09 (br. s., 1H), 1.28 (br. s., 1H), 1.24 (s, 3H), 1.30 (d, J=1.8 Hz, 3H), 1.37-1.76 (m, 7H), 1.85-2.00 (m, 1H), 2.18-2.33 (m, 1H), 3.73 (dd, J=8.5, 5.7 Hz, 1H), 4.00 (dd, J=8.3, 6.5 Hz, 1H), 4.04-4.19 (m, 2H), 4.27-4.41 (m, 1H), 5.45 (dd, J=10.6, 4.2 Hz, 1H), 5.69 (d, J=3.0 Hz, 1H), 6.39 (d, J=2.1 Hz, 1H), 7.35-7.47 (m, 1H), 7.51 (m, 2H), 7.59 (s, 1H), 7.70 (d, J=7.8 Hz, 1H), 8.20 (d, J=3.0 Hz, 1H), 10.85 (br. s., 1H).

Step 2: Using the method described in Example 61, Step 2, 2-[4-(2-chloro-phenoxy)-6-oxo-6H-pyridazin-1-yl]-3-cyclopentyl-N-[1-((R)-2,2-dimethyl-[1,3]dioxolan-4-ylmethyl)-1H-pyrazol-3-yl]-propionamide afforded 2-[4-(2-chloro-phenoxy)-6-oxo-6H-pyridazin-1-yl]-3-cyclopentyl-N-[1-((R)-2,3-dihydroxy-propyl)-1H-pyrazol-3-yl]-propionamide as a white solid as a mixture of diastereomers (86.6 mg, 94%); ES$^+$-HRMS m/e calcd for $C_{24}H_{28}N_5O_5Cl$ [M+H$^+$] 502.1852 found 502.1851. $^1$H NMR (300 MHz, DMSO-d$_6$) δ ppm 1.02-1.19 (m, 1H), 1.22-1.76 (m, 8H), 1.84-2.00 (m, 1H), 2.18-2.35 (m, 1H), 3.21-3.32 (m, 2H), 5.69 (d, J=2.7 Hz, 1H), 6.36 (d, J=2.1 Hz, 1H), 7.36-7.47 (m, 1H), 7.47-7.57 (m, 3H), 7.70 (d, J=7.8 Hz, 1H), 8.20 (d, J=2.7 Hz, 1H), 10.82 (s, 1H).

3.66-3.92 (m, 2H), 4.08 (dd, J=13.4, 3.8 Hz, 1H), 4.71 (t, J=5.6 Hz, 1H), 4.94 (d, J=4.8 Hz, 1H), 5.43 (d, J=3.6 Hz, 1H),

Example 129

2-[5-Chloro-4-(2-chloro-phenoxy)-6-oxo-6H-pyridazin-1-yl]-N-[1-(2-hydroxy-2-methyl-propyl)-1H-pyrazol-3-yl]-3-(tetrahydro-pyran-4-yl)-propionamide

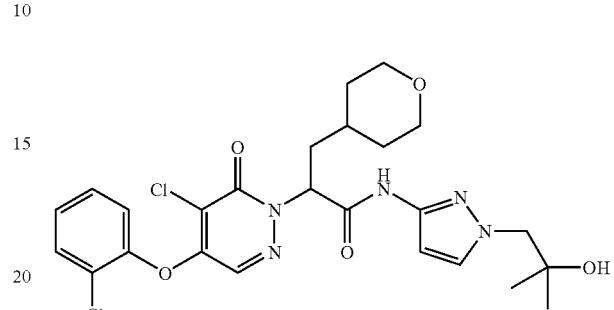

Using the method described in Example 49 from 2-[5-chloro-4-(2-chloro-phenoxy)-6-oxo-6H-pyridazin-1-yl]-3-(tetrahydro-pyran-4-yl)-propionic acid (Intermediate 96) and 1-(3-amino-pyrazol-1-yl)-2-methyl-propan-2-ol (Intermediate 1) afforded 2-[5-chloro-4-(2-chloro-phenoxy)-6-oxo-6H-pyridazin-1-yl]-N-[1-(2-hydroxy-2-methyl-propyl)-1H-pyrazol-3-yl]-3-(tetrahydro-pyran-4-yl)-propionamide (354 mg); ES$^+$-HRMS m/e calcd for $C_{25}H_{29}N_5O_5Cl_2$ [M+H$^+$] 550.1619 found 550.1622. $^1$H NMR (300 MHz, CDCl$_3$) δ ppm 1.17 (s, 6H), 1.22-1.55 (m, 4H), 1.55-1.77 (m, 2H), 2.10-2.25 (m, 2H), 3.24-3.41 (m, 2H), 3.86-3.96 (m, 2H), 3.98 (s, 2H), 5.75 (t, J=7.5 Hz, 1H), 6.65 (d, J=1.8 Hz, 1H), 7.23-7.26 (m, 1H), 7.29-7.35 (m, 2H), 7.35-7.43 (m, 1H), 7.49 (s, 1H), 7.54 (d, J=7.8 Hz, 1H), 8.74 (br. s., 1H).

Example 130

2-[5-Chloro-4-(2-chloro-4-trifluoromethoxy-phenoxy)-6-oxo-6H-pyridazin-1-yl]-3-cyclohexyl-N-[1-(2-hydroxy-2-methyl-propyl)-1H-pyrazol-3-yl]-propionamide

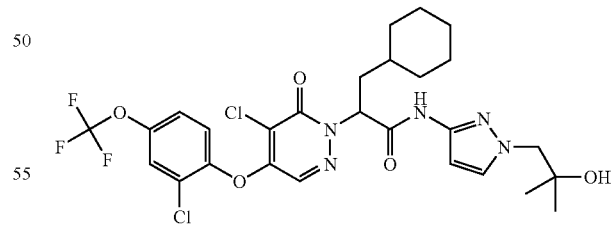

Using the method described in Example 49, 2-[5-chloro-4-(2-chloro-4-trifluoromethoxy-phenoxy)-6-oxo-6H-pyridazin-1-yl]-3-cyclohexyl-propionic acid (Intermediate 97) and 1-(3-amino-pyrazol-1-yl)-2-methyl-propan-2-ol (Intermediate 1) afforded 2-[5-chloro-4-(2-chloro-4-trifluoromethoxy-phenoxy)-6-oxo-6H-pyridazin-1-yl]-3-cyclohexyl-propionic acid (180 mg); ES$^+$-HRMS m/e calcd for $C_{27}H_{30}N_5O_5F_3Cl_2$ [M+H$^+$] 632.1649 found 632.1646. $^1$H NMR (300 MHz, CDCl$_3$) δ ppm 0.76-1.40 (m, 6H), 1.15 (br.

s., 6H), 1.56-1.83 (m, 6H), 1.97-2.22 (m, 2H), 3.94 (s, 2H), 5.67-5.78 (m, 1H), 6.68 (s, 1H), 7.17-7.33 (m, 3H), 7.43 (br. s., 1H), 7.49 (s, 1H), 8.55 (br. s., 1H).

Example 131

Acetic acid 2-{3-[2-[4-(2,6-difluoro-phenoxy)-6-oxo-6H-pyridazin-1-yl]-3-(tetrahydro-pyran-4-yl)-propionylamino]-5-methyl-pyrazol-1-yl}-1-methyl-ethyl ester

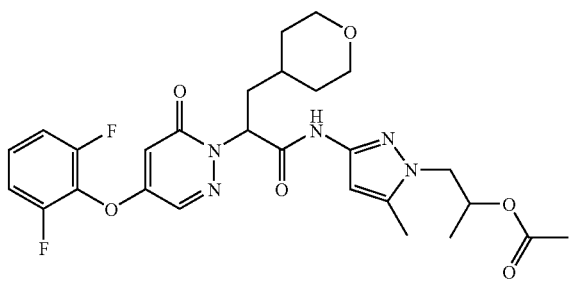

Using the method described in Example 49, 2-[4-(2,6-difluoro-phenoxy)-6-oxo-6H-pyridazin-1-yl]-3-(tetrahydro-pyran-4-yl)-propionic acid (Intermediate 32) and acetic acid 2-(3-amino-5-methyl-pyrazol-1-yl)-1-methyl-ethyl ester (Intermediate 98) afforded acetic acid 2-{3-[2-[4-(2,6-difluoro-phenoxy)-6-oxo-6H-pyridazin-1-yl]-3-(tetrahydro-pyran-4-yl)-propionylamino]-5-methyl-pyrazol-1-yl}-1-methyl-ethyl ester as a mixture of diastereomers (180 mg, 39%); ES$^+$-HRMS m/e calcd for $C_{27}H_{31}N_5O_6F_2$ [M+H$^+$] 560.2315 found 560.2313. $^1$H NMR (400 MHz, DMSO-d$_6$) δ ppm 1.09-1.45 (m, 4H), 1.17, 1.18 (2×d, J=6.4 Hz, 3H), 1.45-1.58 (m, 2H), 1.77-1.92 (m, 1H), 1.94, 1.95 (2×s, 3H), 2.22 (s, 3H), 3.09-3.28 (m, 2H), 3.73-3.86 (m, 2H), 3.97-4.14 (m, 2H), 5.01-5.18 (m, 1H), 5.53 (dd, J=10.7, 3.2 Hz, 1H), 6.04 (d, J=2.3 Hz, 1H), 6.21 (s, 1H), 7.33-7.43 (m, 2H), 7.44-7.54 (m, 1H), 8.29 (d, J=2.3 Hz, 1H), 10.75, 10.77 (2×s, 1H).

Example 132

2-[4-(2,6-Difluoro-phenoxy)-6-oxo-6H-pyridazin-1-yl]-N-[1-(2-hydroxy-propyl)-5-methyl-1H-pyrazol-3-yl]-3-(tetrahydro-pyran-4-yl)-propionamide

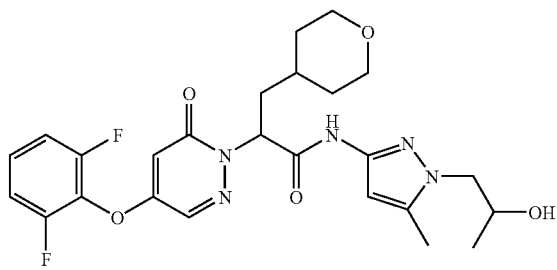

A solution of acetic acid 2-{3-[2-[4-(2,6-difluoro-phenoxy)-6-oxo-6H-pyridazin-1-yl]-3-(tetrahydro-pyran-4-yl)-propionylamino]-5-methyl-pyrazol-1-yl}-1-methyl-ethyl ester (Example 131, 170 mg, 0.31 mmol) in tetrahydrofuran (10 mL) and water (2 mL) at 25° C. was treated with lithium hydroxide monohydrate (40 mg, 0.93 mmol). The reaction was stirred at 25° C. for 4.5 h. At this time, the reaction was concentrated in vacuo. Silica gel column chromatography (0 to 60% tetrahydrofuran/hexanes) afforded 2-[4-(2,6-difluoro-phenoxy)-6-oxo-6H-pyridazin-1-yl]-N-[1-(2-hydroxy-propyl)-5-methyl-1H-pyrazol-3-yl]-3-(tetrahydro-pyran-4-yl)-propionamide as a white solid (113 mg, 70%); ES$^+$-HRMS m/e calcd for $C_{25}H_{29}N_5O_5F_2$ [M+H$^+$] 518.2210 found 518.2207. $^1$H NMR (300 MHz, CDCl$_3$) δ ppm 1.21 (d, J=6.0 Hz, 3H), 1.28-1.51 (m, 3H), 1.54-1.74 (m, 2H), 1.86 (br. s., 1H), 2.14-2.22 (m, 2H), 2.25 (s, 3H), 3.34 (q, J=10.8 Hz, 2H), 3.72-3.84 (m, 1H), 3.88-4.01 (m, 3H), 4.14 (br. s., 1H), 5.64-5.75 (m, 1H), 6.01 (br. s., 1H), 6.49 (s, 1H), 7.09 (t, J=8.5 Hz, 2H), 7.29-7.36 (m, 1H), 8.02 (br. s., 1H), 8.67 (br. s., 1H).

Example 133

3-Cyclohexyl-2-[4-(2,3-dihydro-benzo[1,4]dioxin-5-yloxy)-6-oxo-6H-pyridazin-1-yl]-N-[1-(2-hydroxy-2-methyl-propyl)-1H-pyrazol-3-yl]-propionamide

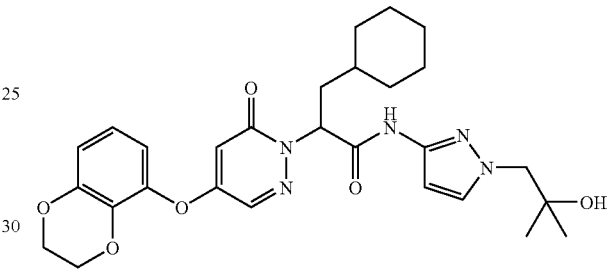

Using the method described in Example 49, 3-cyclohexyl-2-[4-(2,3-dihydro-benzo[1,4]dioxin-5-yloxy)-6-oxo-6H-pyridazin-1-yl]-propionic acid (Intermediate 99) and 1-(3-amino-pyrazol-1-yl)-2-methyl-propan-2-ol (Intermediate 1) afforded 3-cyclohexyl-2-[4-(2,3-dihydro-benzo[1,4]dioxin-5-yloxy)-6-oxo-6H-pyridazin-1-yl]-N-[1-(2-hydroxy-2-methyl-propyl)-1H-pyrazol-3-yl]-propionamide as an off-white solid (40 mg, 22%); ES$^+$-HRMS m/e calcd for $C_{28}H_{35}N_5O_6$ [M+H$^+$] 538.2660 found 538.2660. $^1$H NMR (300 MHz, CDCl$_3$) δ ppm 0.73-1.34 (m, 6H), 1.16 (br. s., 3H), 1.16 (br. s., 3H), 1.54-1.85 (m, 5H), 1.96-2.29 (m, 2H), 3.99 (s, 2H), 4.20-4.37 (m, 4H), 5.59-5.79 (m, 1H), 6.00 (d, J=2.7 Hz, 1H), 6.64-6.77 (m, 2H), 6.78-6.95 (m, 2H), 7.32 (s, 1H), 7.96 (d, J=2.7 Hz, 1H), 8.77 (br. s., 1H).

Example 134

2-[4-(2-Chloro-phenoxy)-6-oxo-6H-pyridazin-1-yl]-4-methyl-pentanoic acid [1-(2-hydroxy-2-methyl-propyl)-1H-pyrazol-3-yl]-amide

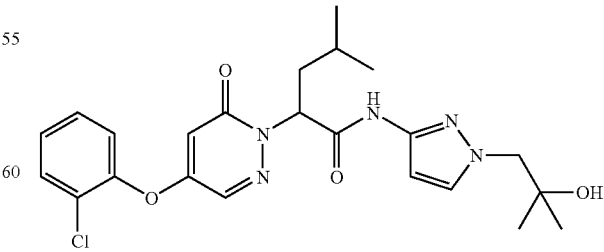

Using the method described in Example 49, the lithium salt of 2-[4-(2-chloro-phenoxy)-6-oxo-6H-pyridazin-1-yl]-4-methyl-pentanoic acid (Intermediate 100) and 1-(3-aminopyrazol-1-yl)-2-methyl-propan-2-ol (Intermediate 1) afforded 2-[4-(2-chloro-phenoxy)-6-oxo-6H-pyridazin-1-yl]-4-methyl-pentanoic acid [1-(2-hydroxy-2-methyl-propyl)-1H-pyrazol-3-yl]-amide (230 mg); ES⁺-HRMS m/e calcd for $C_{23}H_{28}N_5O_4Cl$ [M+H⁺] 474.1903 found 474.1903. ¹H NMR (400 MHz, CDCl₃) δ ppm 0.95 (d, J=6.5 Hz, 3H), 0.96 (d, J=6.5 Hz, 3H), 1.14 (s, 3H), 1.15 (s, 3H), 1.44-1.59 (m, 1H), 2.04 (ddd, J=14.1, 8.3, 6.0 Hz, 1H), 2.16-2.29 (m, 1H), 2.94 (br. s., 1H), 3.94 (s, 2H), 5.66 (dd, J=9.4, 5.8 Hz, 1H), 5.88 (d, J=2.8 Hz, 1H), 6.72 (d, J=2.1 Hz, 1H), 7.20 (dd, J=7.9, 1.5 Hz, 1H), 7.27-7.32 (m, 2H), 7.36 (td, J=7.9, 1.5 Hz, 1H), 7.52 (dd, J=7.9, 1.5 Hz, 1H), 7.96 (d, J=2.8 Hz, 1H), 8.69 (br. s., 1H).

Example 135

2-[4-(2-Chloro-phenoxy)-6-oxo-6H-pyridazin-1-yl]-N-[1-(2-hydroxy-2-methyl-propyl)-1H-pyrazol-3-yl]-3-(tetrahydro-pyran-4-yl)-propionamide

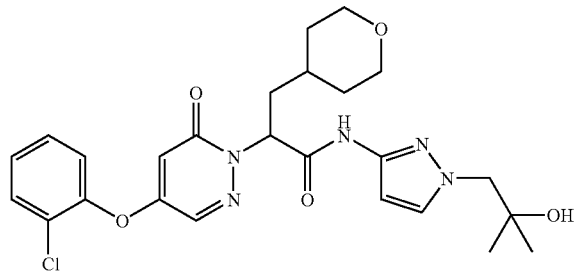

Using the method described in Example 49, 2-[4-(2-chloro-phenoxy)-6-oxo-6H-pyridazin-1-yl]-3-(tetrahydro-pyran-4-yl)-propionic acid (Intermediate 101) and 1-(3-amino-pyrazol-1-yl)-2-methyl-propan-2-ol (Intermediate 1) afforded 2-[4-(2-chloro-phenoxy)-6-oxo-6H-pyridazin-1-yl]-N-[1-(2-hydroxy-2-methyl-propyl)-1H-pyrazol-3-yl]-3-(tetrahydro-pyran-4-yl)-propionamide as a white solid (560 mg); ES⁺-HRMS m/e calcd for $C_{25}H_{30}N_5O_5Cl$ [M+H⁺] 516.2008 found 516.2008. ¹H NMR (400 MHz, DMSO-d₆) δ ppm 1.05 (s, 3H), 1.06 (s, 3H), 1.14-1.34 (m, 2H), 1.35-1.45 (m, 1H), 1.46-1.57 (m, 2H), 1.84-1.93 (m, 1H), 2.17-2.27 (m, 1H), 3.09-3.27 (m, 2H), 3.74-3.86 (m, 2H), 3.89 (s, 2H), 4.67 (s, 1H), 5.55 (dd, J=11.1, 4.0 Hz, 1H), 5.70 (d, J=2.8 Hz, 1H), 6.40 (d, J=2.1 Hz, 1H), 7.38-7.47 (m, 1H), 7.49-7.56 (m, 3H), 7.71 (d, J=7.9 Hz, 1H), 8.22 (d, J=2.8 Hz, 1H), 10.85 (s, 1H). Separation of enantiomers via supercritical fluid chromatography on a SFC DAICEL AD column, 45% methanol, 70 mL/min.

Example 135A (S)-2-[4-(2-Chloro-phenoxy)-6-oxo-6H-pyridazin-1-yl]-N-[1-(2-hydroxy-2-methyl-propyl)-1H-pyrazol-3-yl]-3-(tetrahydro-pyran-4-yl)-propionamide

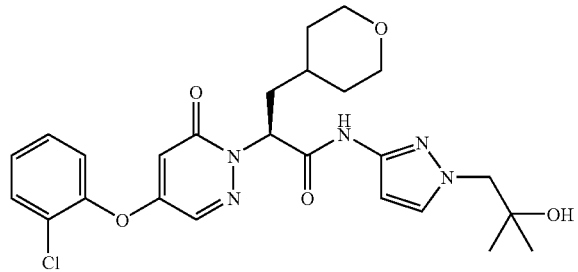

(S)-2-[4-(2-Chloro-phenoxy)-6-oxo-6H-pyridazin-1-yl]-N-[1-(2-hydroxy-2-methyl-propyl)-1H-pyrazol-3-yl]-3-(tetrahydro-pyran-4-yl)-propionamide; ¹H NMR (400 MHz, DMSO-d₆) δ ppm 1.05 (s, 3H), 1.07 (s, 3H), 1.12-1.35 (m, 2H), 1.35-1.45 (m, 1H), 1.46-1.59 (m, 2H), 1.82-1.98 (m, 1H), 2.15-2.28 (m, 1H), 3.07-3.29 (m, 2H), 3.74-3.87 (m, 2H), 3.90 (s, 2H), 4.67 (s, 1H), 5.55 (dd, J=11.0, 4.2 Hz, 1H), 5.70 (d, J=2.8 Hz, 1H), 6.40 (d, J=2.1 Hz, 1H), 7.39-7.46 (m, 1H), 7.48-7.52 (m, 2H), 7.53 (d, J=2.1 Hz, 1H), 7.71 (d, J=7.9 Hz, 1H), 8.22 (d, J=2.8 Hz, 1H), 10.85 (s, 1H)

Example 135B (R)-2-[4-(2-Chloro-phenoxy)-6-oxo-6H-pyridazin-1-yl]-N-[1-(2-hydroxy-2-methyl-propyl)-1H-pyrazol-3-yl]-3-(tetrahydro-pyran-4-yl)-propionamide

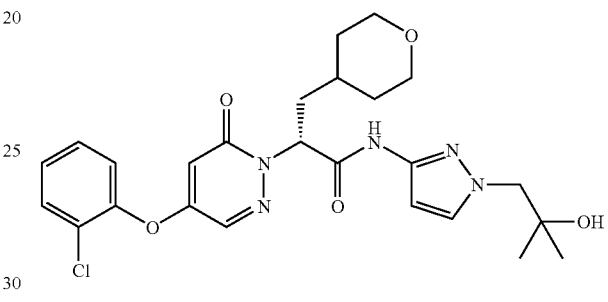

(R)-2-[4-(2-Chloro-phenoxy)-6-oxo-6H-pyridazin-1-yl]-N-[1-(2-hydroxy-2-methyl-propyl)-1H-pyrazol-3-yl]-3-(tetrahydro-pyran-4-yl)-propionamide; ¹H NMR (400 MHz, DMSO-d₆) δ ppm 1.05 (s, 3H), 1.07 (s, 3H), 1.14-1.35 (m, 3H), 1.35-1.45 (m, 1H), 1.46-1.57 (m, 2H), 1.84-1.95 (m, 1H), 2.15-2.28 (m, 1H), 3.09-3.30 (m, 2H), 3.75-3.86 (m, 2H), 3.90 (s, 2H), 4.67 (s, 1H), 5.55 (dd, J=11.0, 4.2 Hz, 1H), 5.70 (d, J=2.8 Hz, 1H), 6.40 (d, J=2.1 Hz, 1H), 7.38-7.46 (m, 1H), 7.49-7.52 (m, 2H), 7.53 (d, J=2.1 Hz, 1H), 7.71 (d, J=7.9 Hz, 1H), 8.22 (d, J=2.8 Hz, 1H), 10.85 (s, 1H)

Example 136

2-(5-Chloro-6-oxo-4-phenoxy-6H-pyridazin-1-yl)-3-cyclohexyl-N-[1-(2-hydroxy-2-methyl-propyl)-1H-pyrazol-3-yl]-propionamide

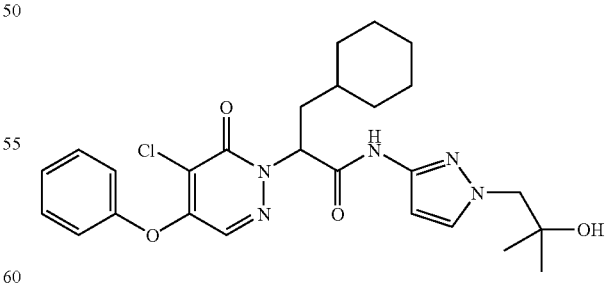

Using the method described in Example 49, 2-(5-chloro-6-oxo-4-phenoxy-6H-pyridazin-1-yl)-3-cyclohexyl-propionic acid (Intermediate 102) and 1-(3-amino-pyrazol-1-yl)-2-methyl-propan-2-ol (Intermediate 1) afforded 2-(5-chloro-6-oxo-4-phenoxy-6H-pyridazin-1-yl)-3-cyclohexyl-N-[1-(2-hydroxy-2-methyl-propyl)-1H-pyrazol-3-yl]- propionamide (136 mg); ES+-HRMS m/e calcd for C$_{26}$H$_{32}$N$_5$O$_5$Cl [M+H+] 514.2216 found 514.2214. $^1$H NMR (300 MHz, CDCl$_3$) δ ppm 0.72-0.98 (m, 2H), 1.09 (br. s., 10H), 1.47-1.80 (m, 5H), 1.88-2.16 (m, 2H), 3.87 (s, 2H), 5.68 (dd, J=8.6, 6.2 Hz, 1H), 6.62 (s, 1H), 7.08 (d, J=7.8 Hz, 2H), 7.20-7.29 (m, 2H), 7.30-7.47 (m, 2H), 7.52 (s, 1H), 8.51 (s, 1H).

Example 137

2-[4-(2-Chloro-phenoxy)-6-oxo-6H-pyridazin-1-yl]-4-methyl-pentanoic acid [1-((R)-2,3-dihydroxy-propyl)-1H-pyrazol-3-yl]-amide

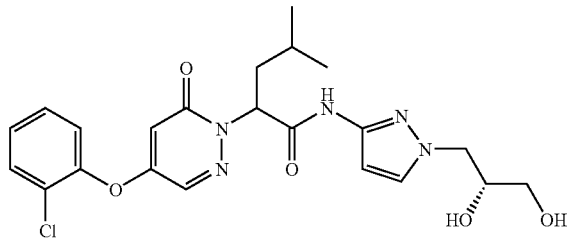

Step 1: A solution 2-(4-iodo-6-oxo-6H-pyridazin-1-yl)-4-methyl-pentanoic acid [1-((R)-2,2-dimethyl-[1,3]dioxolan-4-ylmethyl)-1H-pyrazol-3-yl]-amide (Intermediate 94, 257.5 mg, 0.50 mmol) in N,N-dimethylformamide (5 mL) was prepared, and an aliquot of this solution (1 mL, assume 0.10 mmol) was taken and treated with 2-chlorophenol (14.2 mg, 0.11 mmol) and triethylamine. The reaction vial was sealed and heated at 80° C. overnight. The reaction was then treated with (benzotriazol-1-yloxy)tris(dimethylamino)phosphonium hexafluorophosphate (48.6 mg, 0.11 mmol) and the reaction stirred at 25° C. overnight. At this point, the reaction was treated with cesium carbonate (2 eq.) and the reaction stirred at 80° C. overnight, at which time the reaction was filtered. Purification by HPLC (c18, 50-100% acetonitrile/water) afforded 2-[4-(2-chloro-phenoxy)-6-oxo-6H-pyridazin-1-yl]-4-methyl-pentanoic acid [1-((R)-2,2-dimethyl-[1,3]dioxolan-4-ylmethyl)-1H-pyrazol-3-yl]-amide as a white solid (30.1 mg, 58%).

Step 2: Using the method described in Example 61, Step 2, 2-[4-(2-chloro-phenoxy)-6-oxo-6H-pyridazin-1-yl]-4-methyl-pentanoic acid [1-((R)-2,2-dimethyl-[1,3]dioxolan-4-ylmethyl)-1H-pyrazol-3-yl]-amide afforded 2-[4-(2-chloro-phenoxy)-6-oxo-6H-pyridazin-1-yl]-4-methyl-pentanoic acid [1-((R)-2,3-dihydroxy-propyl)-1H-pyrazol-3-yl]-amide as a white solid as a mixture of diastereomers (22.3 mg, 80%); ES+-HRMS m/e calcd for C$_{22}$H$_{26}$N$_5$O$_5$Cl [M+Na+] 498.1514 found 498.1516. $^1$H NMR (300 MHz, DMSO-d$_6$) δ ppm 0.86 (d, J=7.0 Hz, 3H), 0.89 (d, J=7.0 Hz, 3H), 1.43 (br. s., 1H), 1.68-1.87 (m, 1H), 2.11-2.24 (m, 1H), 3.20-3.33 (m, 2H), 3.71-3.91 (m, 2H), 4.08 (dd, J=13.4, 3.8 Hz, 1H), 4.71 (t, J=5.6 Hz, 1H), 4.94 (d, J=5.4 Hz, 1H), 5.51 (dd, J=10.4, 3.8 Hz, 1H), 5.69 (d, J=2.7 Hz, 1H), 6.36 (d, J=2.1 Hz, 1H), 7.37-7.46 (m, 1H), 7.48-7.53 (m, 3H), 7.70 (d, J=7.8 Hz, 1H), 8.20 (d, J=2.7 Hz, 1H), 10.81 (s, 1H).

Example 138

In Vitro Glucokinase Activity

The compounds of formula I which include the compounds set forth in the Examples activated glucokinase in vitro by the procedure of this Example. In this manner, they increase the flux of glucose metabolism which causes increased insulin secretion. Therefore, the compounds of formula I are glucokinase activators useful for increasing insulin secretion.

Glucokinase In Vitro Assay Protocol: Glucokinase (GK) was assayed by coupling the production of glucose-6-phosphate to the generation of NADH with glucose-6-phosphate dehydrogenase (G6PDH, 0.75-1 k units/mg; Boehringer Mannheim, Indianapolis, Ind.) from *Leuconostoc mesenteroides* as the coupling enzyme (Scheme 2):

Scheme 2

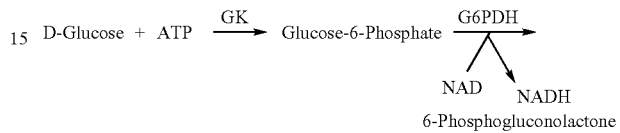

Recombinant human liver GK1 was expressed in *E. coli* as a glutathione S-transferase fusion protein (GST-GK) [Liang et al, 1995] and was purified by chromatography over a glutathione-Sepharose 4B affinity column using the procedure provided by the manufacturer (Amersham Pharmacia Biotech, Piscataway, N.J.). Previous studies have demonstrated that the enzymatic properties of native GK and GST-GK are essentially identical (Liang et al, 1995; Neet et al., 1990).

The assay was conducted at 30° C. in a flat bottom 96-well tissue culture plate from Costar (Cambridge, Mass.) with a final incubation volume of 120 μL. The incubation reaction contained the following: 25 mM Hepes buffer (pH 7.1), 25 mM KCl, 5 mM D-glucose, 1 mM ATP, 1.8 mM NAD, 2 mM MgCl$_2$, 1 μM sorbitol-6-phosphate, 1 mM dithiothreitol, test drug or 10% DMSO, ~7 units/ml G6PDH, and GK (see below). All organic reagents were >98% pure and were from Boehringer Mannheim with the exceptions of D-glucose and Hepes which were from Sigma Chemical Co, St Louis, Mo. Test compounds were dissolved in DMSO and were added to the incubation reaction minus GST-GK in a volume of 12 μL to yield a final DMSO concentration of 10%. This mix was pre-incubated in the temperature controlled chamber of a SPECTRAmax 250 microplate spectrophotometer (Molecular Devices Corporation, Sunnyvale, Calif.) for 10 minutes to allow temperature equilibrium and then the reaction was started by the addition of 20 μL GST-GK.

After addition of enzyme, the increase in optical density (OD) at 340 nm was monitored spectrophotometrically to determine the rate of change (OD$_{340}$ per min). The GK activity (OD$_{340}$/min) in control wells (10% DMSO minus GK activators) was compared with the activity in wells containing test GK activators, and the concentration of activator that produced a 50% increase in the activity of GK, i.e., the SC$_{1.5}$, was calculated. The table below provides the in vitro glucokinase activity for the compounds in the Examples:

| Example | SC1.5 average (uM) |
|---------|--------------------|
| 1 | 0.707 |
| 2 | 0.206 |
| 3 | 2.07 |
| 4 | 6.205 |
| 5 | 2.267 |
| 6 | 0.844 |
| 7 | 0.428 |
| 8 | 1.323 |

-continued

| Example | SC1.5 average (uM) |
|---|---|
| 9 | 1.548 |
| 10 | 11.438 |
| 11 | 0.206 |
| 11A | 0.099 |
| 11B | 6.893 |
| 12 | 0.117 |
| 13 | 0.179 |
| 14 | 0.256 |
| 15 | 1.025 |
| 16 | 4.548 |
| 17 | 0.113 |
| 17A | 0.051 |
| 17B | 9.14 |
| 18 | 0.634 |
| 19 | 0.14 |
| 19A | 0.104 |
| 19B | 3.411 |
| 20 | 0.058 |
| 21 | 0.873 |
| 22 | 0.347 |
| 22A | 0.263 |
| 22B | >30 (1.22 fold activation @ 30 uM) |
| 23 | 0.868 |
| 24 | 0.174 |
| 24A | 0.1 |
| 24B | 5.88 |
| 25 | 1.773 |
| 26 | 0.196 |
| 26A | 0.102 |
| 26B | 26.027 |
| 27 | 2.385 |
| 28 | 1.925 |
| 29 | 0.227 |
| 29A | 0.159 |
| 29B | 11.185 |
| 30 | 2.975 |
| 30A | 1.566 |
| 30B | >30 (1.16 fold activation @ 30 uM) |
| 31 | 0.209 |
| 31A | 0.18 |
| 31B | 15.901 |
| 32 | 0.745 |
| 32A | 0.502 |
| 32B | 26.185 |
| 33 | 0.356 |
| 33A | 0.265 |
| 33B | 8.849 |
| 34 | 1.72 |
| 35 | 2.173 |
| 36 | 0.063 |
| 36A | 0.034 |
| 36B | 1.596 |
| 37 | 0.566 |
| 37A | 0.238 |
| 37B | 18.488 |
| 38 | 0.776 |
| 39 | 0.499 |
| 40 | 0.228 |
| 41 | 8.414 |
| 42 | 0.349 |
| 42A | 0.17 |
| 42B | 5.981 |
| 43 | 0.232 |
| 43A | 0.148 |
| 43B | 7.536 |
| 44 | 1.032 |
| 45 | >30 (1.15 fold activation @ 30 uM) |
| 46 | 1.947 |
| 47 | 1.366 |
| 48 | 1.495 |
| 49 | 0.305 |
| 50 | 0.466 |
| 51 | 0.087 |
| 51A | 0.038 |
| 51B | 0.838 |
| 52 | 0.456 |
| 53 | 0.469 |
| 54 | 0.544 |
| 55 | 0.468 |
| 56 | 0.153 |
| 57 | 0.986 |
| 58 | 2.719 |
| 59 | 0.576 |
| 60 | 0.166 |
| 60A | 0.066 |
| 60B | 1.942 |
| 61 | 0.383 |
| 62 | 0.373 |
| 63 | 0.117 |
| 64 | 0.551 |
| 65 | 0.102 |
| 65A | 0.049 |
| 65B | 3.148 |
| 66 | 1.74 |
| 67 | 0.132 |
| 68 | 0.013 |
| 68A | 0.008 |
| 68B | 0.597 |
| 69 | 0.033 |
| 70 | 0.036 |
| 71 | 0.312 |
| 72 | 0.098 |
| 72A | 0.044 |
| 72B | 0.226 |
| 73 | 0.026 |
| 73A | 0.012 |
| 73B | 0.507 |
| 74 | 0.067 |
| 74A | 0.043 |
| 74B | 0.245 |
| 75 | 0.058 |
| 75A | 0.033 |
| 75B | 0.796 |
| 76 | 0.376 |
| 77 | 21.07 |
| 78 | 14.436 |
| 79 | 14.605 |
| 80 | 3.208 |
| 81 | 7.484 |
| 82 | >30 (1.3 fold activation @ 30 uM) |
| 83 | 8.783 |
| 84 | 15.983 |
| 85 | >30 (1.3 fold activation @ 30 uM) |
| 88 | 0.204 |
| 89 | 0.568 |
| 90 | 0.5 |
| 91 | >30 (1.28 fold activation @ 30 uM) |
| 92 | 0.135 |
| 93 | 0.114 |
| 94 | >30 (1.33 fold activation @ 30 uM) |
| 95 | 12.633 |
| 96 | 0.067 |
| 97 | 1.895 |
| 98 | 0.244 |
| 99 | 1.277 |
| 100 | 0.101 |
| 101 | 0.732 |
| 102 | 0.56 |
| 103 | 2.591 |
| 104 | 0.139 |
| 105 | 0.072 |
| 106 | 0.082 |
| 107 | 0.042 |
| 108 | 0.521 |
| 109 | 0.293 |
| 110 | 0.29 |
| 111 | 0.554 |
| 112 | 2.606 |
| 113 | 2.308 |
| 114 | 1.656 |
| 115 | 0.376 |
| 116 | 0.543 |
| 117 | 0.352 |
| 118 | 0.237 |
| 119 | 0.811 |
| 120 | 0.18 |

-continued

| Example | SC1.5 average (uM) |
|---|---|
| 121 | 0.088 |
| 122 | >30 (1.36 fold activation @ 30 uM) |
| 123 | 0.441 |
| 124 | 2.461 |
| 125 | 2.611 |
| 126 | 1.221 |
| 127 | 0.334 |
| 128 | 0.093 |
| 129 | 1.006 |
| 130 | 10.224 |
| 131 | >30 (1.18 fold activation @ 30 uM) |
| 132 | >30 (1.18 fold activation @ 30 uM) |
| 133 | 0.135 |
| 134 | 0.693 |
| 135 | 0.235 |
| 136 | 1.17 |
| 137 | 0.731 |

REFERENCES

Liang, Y., Kesavan, P., Wang, L., Niswender, K., Tanizawa, Y., Permut, M. A., Magnuson, M., and Matschinsky, F. M. Variable effects of maturity-onset-diabetes-of-youth (MODY)-associated glucokinase mutations on the substrate interactions and stability of the enzyme. *Biochem. J.* 309: 167-173, 1995.

Neet, K., Keenan, R. P., and Tippett, P. S. Observation of a kinetic slow transition in monomeric glucokinase. *Biochemistry* 29; 770-777, 1990.

Example 139

In Vivo Glucokinase Activity

Glucokinase Activator in vivo Screen Protocol in Lean and Diet Induced Obese Mice: Lean or Diet-induced Obese (DIO) C57BL/6J mice were orally dosed via gavage with Glucokinase (GK) activator following a two hour fasting period. Blood glucose determinations were made at various (e.g. 0, 1, 2, 4 and 8 hours post-oral gavage) times during the study.

C57Bl/6J mice were obtained from Jackson Laboratory (Bar Harbor, Me.) and were maintained in a light-dark cycle with lights on from 0600-1800 hr. For studies in lean mice, the mice were received at age ten weeks and given ad libitum access to control diet (LabDiet 5001 chow, PMI Nutrition, Brentwood, Mo.), and were at least age 11 weeks at the time of study. For studies in the DIO model, the mice were received at age five weeks and given ad libitum access to Bio-Serv F3282 High Fat Diet (Frenchtown, N.J.), and were at least age 16 weeks at the time of study. The experiments were conducted during the light phase of the light-dark cycle. Mice (n=6) are weighed and fasted for a two hour period prior to oral treatment. GK activators are formulated in Gelucire vehicle (Ethanol:Gelucire44/14:PEG400q.s. 4:66:30 v/w/v. For studies in lean mice, the mice were dosed orally with 5.0 μL per gram of body weight (i.e. 5 ml/kg×10.0 mg/ml formulation to equal a 50 mg/kg dose). For studies in DIO mice, the mice were dosed orally with 5.0 μL per gram of body weight (i.e. 5.0 ml/kg×5 mg/ml formulation to equal a 25 mg/kg dose). Immediately prior to dosing, a pre-dose (time zero) blood glucose reading was acquired by snipping off a small portion of the animal's tail and collecting 15 μL blood into a heparinized capillary tube for analysis. Following GK activator administration, additional blood glucose readings were taken at various time points post dose from the same tail wound. Results were interpreted by comparing the mean blood glucose values of vehicle treated mice with GK activator treated mice over the study period.

The Table below provides data for % glucose lowering of a representative number of compounds of the present invention vs control at 4 hours post 50 mg/kg dose in lean C57BL/6J mice:

| Example | % glucose lowering @ 4 H |
|---|---|
| 2 | −41.9 |
| 8 | −5.6 |
| 11 | −48.9 |
| 12 | −49.3 |
| 13 | −45.8 |
| 14 | −46.7 |
| 17 | −35.2 |
| 19 | −49.2 |
| 22 | −31.6 |
| 24 | −62.1 |
| 29 | −27.8 |
| 33 | −30.2 |
| 36 | −60.9 |
| 71 | −61.7 |

It is to be understood that the invention is not limited to the particular embodiments of the invention described above, as variations of the particular embodiments may be made and still fall within the scope of the appended claims.

What is claimed is:
1. A compound, wherein said compound is:
3-Cyclopentyl-N-[1-(2-hydroxy-2-methyl-propyl)-1H-pyrazol-3-yl]-2-(6-oxo-4-phenoxy-6H-pyridazin-1-yl)-propionamide;
3-Cyclopentyl-2-(6-oxo-4-phenoxy-6H-pyridazin-1-yl)-N-thiazol-2-yl-propionamide;
3-Cyclopentyl-N-(3-methyl-[1,2,4]thiadiazol-5-yl)-2-(6-oxo-4-phenoxy-6H-pyridazin-1-yl)-propionamide;
3-Cyclopentyl-N-(5-methyl-[1,3,4]thiadiazol-2-yl)-2-(6-oxo-4-phenoxy-6H-pyridazin-1-yl)-propionamide;
3-Cyclopentyl-N-[1-(2-hydroxy-2-methyl-propyl)-1H-pyrazol-3-yl]-2-[6-oxo-4-(4-trifluoromethyl-phenoxy)-6H-pyridazin-1-yl]-propionamide;
3-Cyclopentyl-N-[1-(2-hydroxy-2-methyl-propyl)-1H-pyrazol-3-yl]-2-[6-oxo-4-(3-trifluoromethyl-phenoxy)-6H-pyridazin-1-yl]propionamide;
3-Cyclopentyl-N-[1-(2-hydroxy-2-methyl-propyl)-1H-pyrazol-3-yl]-2-[4-(3-methoxy-phenoxy)-6-oxo-6H-pyridazin-1-yl]-propionamide;
3-Cyclopentyl-2-(4-cyclopentyloxy-6-oxo-6H-pyridazin-1-yl)-N-[1-(2-hydroxy-2-methyl-propyl)-1H-pyrazol-3-yl]-propionamide;
3-Cyclopentyl-2-(4-cyclopentylmethoxy-6-oxo-6H-pyridazin-1-yl)-N-[1-(2-hydroxy-2-methyl-propyl)-1H-pyrazol-3-yl]-propionamide;
2-(5-Chloro-4-cyclopentylmethoxy-6-oxo-6H-pyridazin-1-yl)-3-cyclopentyl-N-[1-(2-hydroxy-2-methyl-propyl)-1H-pyrazol-3-yl]-propionamide;
3-Cyclopentyl-N-[1-(2-hydroxy-2-methyl-propyl)-1H-pyrazol-3-yl]-2-[6-oxo-4-(2-trifluoromethyl-phenoxy)-6H-pyridazin-1-yl]-propionamide;
(S)-3-Cyclopentyl-N-[1-(2-hydroxy-2-methyl-propyl)-1H-pyrazol-3-yl]-2-[6-oxo-4-(2-trifluoromethyl-phenoxy)-6H-pyridazin-1-yl]propionamide;
(R)-3-Cyclopentyl-N-[1-(2-hydroxy-2-methyl-propyl)-1H-pyrazol-3-yl]-2-[6-oxo-4-(2-trifluoromethyl-phenoxy)-6H-pyridazin-1-yl]-propionamide;

3-Cyclopentyl-N-[1-(2-hydroxy-2-methyl-propyl)-1H-pyrazol-3-yl]-2-[4-(2-methoxy-phenoxy)-6-oxo-6H-pyridazin-1-yl]-propionamide;
N-(5-Chloro-1-methyl-1H-pyrazol-3-yl)-3-cyclopentyl-2-[6-oxo-4-(2-trifluoromethyl-phenoxy)-6H-pyridazin-1-yl]-propionamide;
3-Cyclopentyl-N-(1-methyl-1H-pyrazol-3-yl)-2-[6-oxo-4-(2-trifluoromethyl-phenoxy)-6H-pyridazin-1-yl]-propionamide;
3-Cyclopentyl-N-[1-(2-hydroxy-2-methyl-propyl)-1H-pyrazol-3-yl]-2-[4-(4-methoxy-phenoxy)-6-oxo-6H-pyridazin-1-yl]-propionamide;
5-{3-Cyclopentyl-2-[6-oxo-4-(2-trifluoromethyl-phenoxy)-6H-pyridazin-1-yl]-propionylamino}-2-methyl-2H-pyrazole-3-carboxylicacidmethylester;
3-Cyclopentyl-N-[1-(2-hydroxy-2-methyl-propyl)-1H-pyrazol-3-yl]-2-[6-oxo-4-(5,6,7,8-tetrahydro-naphthalen-1-yloxy)-6H-pyridazin-1-yl]-propionamide;
(S)-3-Cyclopentyl-N-[1-(2-hydroxy-2-methyl-propyl)-1H-pyrazol-3-yl]-2-[6-oxo-4-(5,6,7,8-tetrahydro-naphthalen-1-yloxy)-6H-pyridazin-1-yl]-propionamide;
(R)-3-Cyclopentyl-N-[1-(2-hydroxy-2-methyl-propyl)-1H-pyrazol-3-yl]-2-[6-oxo-4-(5,6,7,8-tetrahydro-naphthalen-1-yloxy)-6H-pyridazin-1-yl]-propionamide;
3-Cyclopentyl-2-[4-(3-fluoro-phenoxy)-6-oxo-6H-pyridazin-1H-(2-hydroxy-2-methyl-propyl)-1H-pyrazol-3-yl]-propionamide;
3-Cyclopentyl-2-[4-(2-fluoro-phenoxy)-6-oxo-6H-pyridazin-1-yl]-N-[1-(2-hydroxy-2-methyl-propyl)-1H-pyrazol-3-yl]-propionamide;
(S)-3-Cyclopentyl-2-[4-(2-fluoro-phenoxy)-6-oxo-6H-pyridazin-1-yl]-N-[1-(2-hydroxy-2-methyl-propyl)-1H-pyrazol-3-yl]-propionamide;
(R)-3-Cyclopentyl-2-[4-(2-fluoro-phenoxy)-6-oxo-6H-pyridazin-1-yl]-N-[1-(2-hydroxy-2-methyl-propyl)-1H-pyrazol-3-yl]-propionamide;
2-[4-(Naphthalen-1-yloxy)-6-oxo-6H-pyridazin-1-yl]-octanoicacid[1-(2-hydroxy-2-methyl-propyl)-1H-pyrazol-3-yl]-amide;
2-[4-(2-Cyclohexyl-phenoxy)-6-oxo-6H-pyridazin-1-yl]-3-cyclopentyl-N-[1-(2-hydroxy-2-methyl-propyl)-1H-pyrazol-3-yl]-propionamide;
3-Cyclopentyl-2-[4-(2-cyclopentyl-phenoxy)-6-oxo-6H-pyridazin-1-yl]-N-[1-(2-hydroxy-2-methyl-propyl)-1H-pyrazol-3-yl]-propionamide;
(S)-3-Cyclopentyl-2-[4-(2-cyclopentyl-phenoxy)-6-oxo-6H-pyridazin-1-yl]-N-[1-(2-hydroxy-2-methyl-propyl)-1H-pyrazol-3-yl]-propionamide;
(R)-3-Cyclopentyl-2-[4-(2-cyclopentyl-phenoxy)-6-oxo-6H-pyridazin-1-yl]-N-[1-(2-hydroxy-2-methyl-propyl)-1H-pyrazol-3-yl]-propionamide;
2-[4-(Biphenyl-2-yloxy)-6-oxo-6H-pyridazin-1-yl]-3-cyclopentyl-N-[1-(2-hydroxy-2-methyl-propyl)-1H-pyrazol-3-yl]-propionamide;
3-Cyclopentyl-N-[1-(2-hydroxy-2-methyl-propyl)-1H-pyrazol-3-yl]-2-(6-oxo-4-o-tolyloxy-6H-pyridazin-1-yl)-propionamide;
(S)-3-Cyclopentyl-N-[1-(2-hydroxy-2-methyl-propyl)-1H-pyrazol-3-yl]-2-(6-oxo-4-o-tolyloxy-6H-pyridazin-1-yl)-propionamide;
(R)-3-Cyclopentyl-N-[1-(2-hydroxy-2-methyl-propyl)-1H-pyrazol-3-yl]-2-(6-oxo-4-o-tolyloxy-6H-pyridazin-1-yl)-propionamide;
3-Cyclopentyl-N-[1-(2-hydroxy-2-methyl-propyl)-1H-pyrazol-3-yl]-2-[4-(2-methyl-pyridin-3-yloxy)-6-oxo-6H-pyridazin-1-yl]-propionamide;
3-Cyclopentyl-N-[1-(2-hydroxy-2-methyl-propyl)-1H-pyrazol-3-yl]-2-[6-oxo-4-(2-pyrrolidin-1-yl-phenoxy)-6H-pyridazin-1-yl]-propionamide;
(S)-3-Cyclopentyl-N-[1-(2-hydroxy-2-methyl-propyl)-1H-pyrazol-3-yl]-2-[6-oxo-4-(2-pyrrolidin-1-yl-phenoxy)-6H-pyridazin-1-yl]-propionamide;
(R)-3-Cyclopentyl-N-[1-(2-hydroxy-2-methyl-propyl)-1H-pyrazol-3-yl]-2-[6-oxo-4-(2-pyrrolidin-1-yl-phenoxy)-6H-pyridazin-1-yl]-propionamide;
3-Cyclopentyl-N-[1-(2-hydroxy-2-methyl-propyl)-1H-pyrazol-3-yl]-2-[6-oxo-4-(2-piperidin-1-yl-phenoxy)-6H-pyridazin-1-yl]-propionamide;
3-Cyclopentyl-N-[1-(2-hydroxy-2-methyl-propyl)-1H-pyrazol-3-yl]-2-[6-oxo-4-(pyridin-3-yloxy)-6H-pyridazin-1-yl]-propionamide;
2-[4-(2-Cyano-phenoxy)-6-oxo-6H-pyridazin-1-yl]-3-cyclopentyl-N-[1-(2-hydroxy-2-methyl-propyl)-1H-pyrazol-3-yl]-propionamide;
(S)-2-[4-(2-Cyano-phenoxy)-6-oxo-6H-pyridazin-1-yl]-3-cyclopentyl-N-[1-(2-hydroxy-2-methyl-propyl)-1H-pyrazol-3-yl]-propionamide;
(R)-2-[4-(2-Cyano-phenoxy)-6-oxo-6H-pyridazin-1-yl]-3-cyclopentyl-N-[1-(2-hydroxy-2-methyl-propyl)-1H-pyrazol-3-yl]-propionamide;
3-Cyclopentyl-N-[1-(2-hydroxy-2-methyl-propyl)-1H-pyrazol-3-yl]-2-[4-(2-methanesulfonyl-phenoxy)-6-oxo-6H-pyridazin-1-yl]-propionamide;
(S)-3-Cyclopentyl-N-[1-(2-hydroxy-2-methyl-propyl)-1H-pyrazol-3-yl]-2-[4-(2-methanesulfonyl-phenoxy)-6-oxo-6H-pyridazin-1-yl]-propionamide;
(R)-3-Cyclopentyl-N-[1-(2-hydroxy-2-methyl-propyl)-1H-pyrazol-3-yl]-2-[4-(2-methanesulfonyl-phenoxy)-6-oxo-6H-pyridazin-1-yl]-propionamide;
3-Cyclopentyl-2-[4-(2,3-difluoro-phenoxy)-6-oxo-6H-pyridazin-1-yl]-N-[1-(2-hydroxy-2-methyl-propyl)-1H-pyrazol-3-yl]-propionamide;
(S)-3-Cyclopentyl-2-[4-(2,3-difluoro-phenoxy)-6-oxo-6H-pyridazin-1-yl]-N-[1-(2-hydroxy-2-methyl-propyl)-1H-pyrazol-3-yl]-propionamide;
(R)-3-Cyclopentyl-2-[4-(2,3-difluoro-phenoxy)-6-oxo-6H-pyridazin-1-yl]-N-[1-(2-hydroxy-2-methyl-propyl)-1H-pyrazol-3-yl]-propionamide;
3-Cyclopentyl-2-[4-(2,4-difluoro-phenoxy)-6-oxo-6H-pyridazin-1-yl]-N-[1-(2-hydroxy-2-methyl-propyl)-1H-pyrazol-3-yl]-propionamide;
(S)-3-Cyclopentyl-2-[4-(2,4-difluoro-phenoxy)-6-oxo-6H-pyridazin-1-yl]-N-[1-(2-hydroxy-2-methyl-propyl)-1H-pyrazol-3-yl]-propionamide;
(R)-3-Cyclopentyl-2-[4-(2,4-difluoro-phenoxy)-6-oxo-6H-pyridazin-1-yl]-N-[1-(2-hydroxy-2-methyl-propyl)-1H-pyrazol-3-yl]propionamide;
3-Cyclopentyl-2-[4-(2,5-difluoro-phenoxy)-6-oxo-6H-pyridazin-1-yl]-N-[1-(2-hydroxy-2-methyl-propyl)-1H-pyrazol-3-yl]-propionamide;
(S)-3-Cyclopentyl-2-[4-(2,5-difluoro-phenoxy)-6-oxo-6H-pyridazin-1-yl]-N-[1-(2-hydroxy-2-methyl-propyl)-1H-pyrazol-3-yl]-propionamide;
(R)-3-Cyclopentyl-2-[4-(2,5-difluoro-phenoxy)-6-oxo-6H-pyridazin-1-yl]-N-[1-(2-hydroxy-2-methyl-propyl)-1H-pyrazol-3-yl]-propionamide;
3-Cyclopentyl-N-[1-(2-hydroxy-2-methyl-propyl)-1H-pyrazol-3-yl]-2-[4-(2-morpholin-4-yl-phenoxy)-6-oxo-6H-pyridazin-1-yl]-propionamide;
3-Cyclopentyl-N-[1-(2-hydroxy-2-methyl-propyl)-1H-pyrazol-3-yl]-2-[6-oxo-4-(3-phenoxy-phenoxy)-6H-pyridazin-1-yl]-propionamide;

3-Cyclopentyl-2-[4-(2,6-difluoro-phenoxy)-6-oxo-6H-pyridazin-1-yl]-N-[1-(2-hydroxy-2-methyl-propyl)-1H-pyrazol-3-yl]-propionamide;

(S)-3-Cyclopentyl-2-[4-(2,6-difluoro-phenoxy)-6-oxo-6H-pyridazin-1-yl]-N-[1-(2-hydroxy-2-methyl-propyl)-1H-pyrazol-3-yl]-propionamide;

(R)-3-Cyclopentyl-2-[4-(2,6-difluoro-phenoxy)-6-oxo-6H-pyridazin-1-yl]-N-[1-(2-hydroxy-2-methyl-propyl)-1H-pyrazol-3-yl]-propionamide;

3-Cyclopentyl-N-[1-(2-hydroxy-2-methyl-propyl)-1H-pyrazol-3-yl]-2-[4-(isoquinolin-5-yloxy)-6-oxo-6H-pyridazin-1-yl]-propionamide;

(S)-3-Cyclopentyl-N-[1-(2-hydroxy-2-methyl-propyl)-1H-pyrazol-3-yl]-2-[4-(isoquinolin-5-yloxy)-6-oxo-6H-pyridazin-1-yl]propionamide;

(R)-3-Cyclopentyl-N-[1-(2-hydroxy-2-methyl-propyl)-1H-pyrazol-3-yl]-2-[4-(isoquinolin-5-yloxy)-6-oxo-6H-pyridazin-1-yl]propionamide;

3-Cyclopentyl-N-[1-(2-hydroxy-2-methyl-propyl)-1H-pyrazol-3-yl]-2-[6-oxo-4-(quinolin-5-yloxy)-6H-pyridazin-1-yl]-propionamide;

3-Cyclopentyl-N-[1-(2-hydroxy-2-methyl-propyl)-1H-pyrazol-3-yl]-2-[6-oxo-4-(quinolin-8-yloxy)-6H-pyridazin-1-yl]-propionamide;

2-[4-(2-Acetyl-phenoxy)-6-oxo-6H-pyridazin-1-yl]-3-cyclopentyl-N-[1-(2-hydroxy-2-methyl-propyl)-1H-pyrazol-3-yl]-propionamide;

3-Cyclopentyl-N-[1-(2-hydroxy-2-methyl-propyl)-1H-pyrazol-3-yl]-2-{6-oxo-4-[2-(pyrrolidine-1-carbonyl)-phenoxy]-6H-pyridazin-1-yl}-propionamide;

2-[4-(2,6-Difluoro-phenoxy)-6-oxo-6H-pyridazin-1-yl]-4-methyl-pentanoicacid[1-(2-hydroxy-2-methyl-propyl)-1H-pyrazol-3-yl]-amide;

(S)-2-[4-(2,6-Difluoro-phenoxy)-6-oxo-6H-pyridazin-1-yl]-4-methyl-pentanoicacid[1-(2-hydroxy-2-methyl-propyl)-1H-pyrazol-3-yl]-amide;

(R)-2-[4-(2,6-Difluoro-phenoxy)-6-oxo-6H-pyridazin-1-yl]-4-methyl-pentanoicacid[1-(2-hydroxy-2-methyl-propyl)-1H-pyrazol-3-yl]-amide;

2-[4-(2,6-Difluoro-phenoxy)-6-oxo-6H-pyridazin-1-yl]-N-[1-(2-hydroxy-2-methyl-propyl)-1H-pyrazol-3-yl]-3-(tetrahydro-pyran-4-yl)-propionamide;

(S)-2-[4-(2,6-Difluoro-phenoxy)-6-oxo-6H-pyridazin-1-yl]-N-[1-(2-hydroxy-2-methyl-propyl)-1H-pyrazol-3-yl]-3-(tetrahydro-pyran-4-yl)-propionamide;

(R)-2-[4-(2,6-Difluoro-phenoxy)-6-oxo-6H-pyridazin-1-yl]-N-[1-(2-hydroxy-2-methyl-propyl)-1H-pyrazol-3-yl]-3-(tetrahydro-pyran-4-yl)-propionamide;

2-[4-(2,6-Difluoro-phenoxy)-6-oxo-6H-pyridazin-1-yl]-N-[1-(2-hydroxy-2-methyl-propyl)-1H-pyrazol-3-yl]-3-phenyl-propionamide;

3-Cyclopentyl-N-(1-methyl-5-trifluoromethyl-1H-pyrazol-3-yl)-2-[6-oxo-4-(2-trifluoromethyl-phenoxy)-6H-pyridazin-1-yl]-propionamide;

3-Cyclopentyl-N-[1-(2-hydroxy-2-methyl-propyl)-1H-pyrazol-3-yl]-2-[6-oxo-4-(2-trifluoromethyl-benzyl)-6H-pyridazin-1-yl]-propionamide;

3-Cyclopentyl-N-[1-(2-hydroxy-2-methyl-propyl)-1H-pyrazol-3-yl]-2-[6-oxo-4-(3-trifluoromethyl-benzyl)-6H-pyridazin-1-yl]-propionamide;

3-Cyclopentyl-2-[4-(2,6-difluoro-benzyl)-6-oxo-6H-pyridazin-1-yl]-N-[1-(2-hydroxy-2-methyl-propyl)-1H-pyrazol-3-yl]-propionamide;

3-Cyclobutyl-2-[4-(2,6-difluoro-phenoxy)-6-oxo-6H-pyridazin-1-yl]-N-[1-(2-hydroxy-2-methyl-propyl)-1H-pyrazol-3-yl]-propionamide;

2-[4-(2,6-Difluoro-phenoxy)-6-oxo-6H-pyridazin-1-yl]-3-(2,6-difluoro-phenyl)-N-[1-(2-hydroxy-2-methyl-propyl)-1H-pyrazol-3-yl]-propionamide;

3-Cyclohexyl-2-[4-(2,6-difluoro-phenoxy)-6-oxo-6H-pyridazin-1-yl]-N-[1-(2-hydroxy-2-methyl-propyl)-1H-pyrazol-3-yl]-propionamide;

(S)-3-Cyclohexyl-2-[4-(2,6-difluoro-phenoxy)-6-oxo-6H-pyridazin-1-yl]-N-[1-(2-hydroxy-2-methyl-propyl)-1H-pyrazol-3-yl]-propionamide;

(R)-3-Cyclohexyl-2-[4-(2,6-difluoro-phenoxy)-6-oxo-6H-pyridazin-1-yl]-N-[1-(2-hydroxy-2-methyl-propyl)-1H-pyrazol-3-yl]-propionamide;

2-[4-(2,6-Difluoro-phenoxy)-6-oxo-6H-pyridazin-1-yl]-4-ethyl-hexanoicacid[1-(2-hydroxy-2-methyl-propyl)-1H-pyrazol-3-yl]-amide;

2-[4-(2,6-Difluoro-phenoxy)-6-oxo-6H-pyridazin-1-yl]-N-[1-(2-hydroxy-ethyl)-1H-pyrazol-3-yl]-3-(tetrahydro-pyran-4-yl)-propionamide;

2-[4-(2,6-Difluoro-phenoxy)-6-oxo-6H-pyridazin-1-yl]-4-ethyl-hexanoicacid[1-(2-hydroxy-ethyl)-1H-pyrazol-3-yl]-amide;

3-Cyclobutyl-2-[4-(2,6-difluoro-phenoxy)-6-oxo-6H-pyridazin-1-yl]-N-[1-(2-hydroxy-ethyl)-1H-pyrazol-3-yl]-propionamide;

3-Cyclohexyl-2-[4-(2,6-difluoro-phenoxy)-6-oxo-6H-pyridazin-1-yl]-N-[1-(2-hydroxy-ethyl)-1H-pyrazol-3-yl]-propionamide;

2-[4-(2,6-Difluoro-phenoxy)-6-oxo-6H-pyridazin-1-yl]-3-(2,6-difluoro-phenyl)-N-[1-(2-hydroxy-ethyl)-1H-pyrazol-3-yl]propionamide;

2-[4-(2,6-Difluoro-phenoxy)-6-oxo-6H-pyridazin-1-yl]-N-[1-(2-hydroxy-ethyl)-1H-pyrazol-3-yl]-3-phenyl-propionamide;

2-[4-(2,6-Difluoro-phenoxy)-6-oxo-6H-pyridazin-1-yl]-4-methyl-pentanoicacid[1-(2-hydroxy-ethyl)-1H-pyrazol-3-yl]-amide;

3-Cyclopentyl-2-[4-(2,6-difluoro-phenoxy)-6-oxo-6H-pyridazin-1-yl]-N-[1-(2-hydroxy-ethyl)-1H-pyrazol-3-yl]-propionamide;

(S)-3-Cyclopentyl-2-[4-(2,6-difluoro-phenoxy)-6-oxo-6H-pyridazin-1-yl]-N-[1-(2-hydroxy-ethyl)-1H-pyrazol-3-yl]-propionamide;

(R)-3Cyclopentyl-2-[4-(2,6-difluoro-phenoxy)-6-oxo-6H-pyridazin-1-yl]-N-[1(2-hydroxy-ethyl)-1H-pyrazol-3-yl]-propionamide;

2-[4-(2,6-Difluoro-phenoxy)-6-oxo-6H-pyridazin-1-yl]-4-methyl-pentanoicacid[1((R)-2,3-dihydroxy-propyl)-1H-pyrazol-3-yl]-amide;

2-[4-(2,6-Difluoro-phenoxy)-6-oxo-6H-pyridazin-1-yl]-N-[1-((R)-2,3dihydroxy-propyl)-1H-pyrazol-3-yl]-3-(tetrahydro-pyran-4-yl)-propionamide;

3Cyclohexyl-2-[4-(2,6-difluoro-phenoxy)-6-oxo-6H-pyridazin-1-yl]-N-[1-((R)-2,3-dihydroxy-propyl)-1H-pyrazol-3-yl]-propionamide;

2-[4-(2,6-Difluoro-phenoxy)-6-oxo-6H-pyridazin-1-yl]-4-ethyl-hexanoicacid[1-((R)-2,3-dihydroxy-propyl)-1H-pyrazol-3-yl]-amide;

3-Cyclopentyl-2-[4-(2,6-difluoro-phenoxy)-6-oxo-6H-pyridazin-1-yl]-N-[1-((S)-2,3-dihydroxy-propyl)-1H-pyrazol-3-yl]-propionamide;

(S)-3-Cyclopentyl-2-[4-(2,6-difluoro-phenoxy)-6-oxo-6H-pyridazin-1-yl]-N-[1-((S)-2,3-dihydroxy-propyl)-1H-pyrazol-3-yl]-propionamide;

(R)-3-Cyclopentyl-2-[4-(2,6-difluoro-phenoxy)-6-oxo-6H-pyridazin-1-yl]-N-[1-((S)-2,3-dihydroxy-propyl)-1H-pyrazol-3-yl]-propionamide;

6-{3-Cyclopentyl-2-[4-(2-cyclopentyl-phenoxy)-6-oxo-6H-pyridazin-1-yl]-propionylamino}-nicotinic acid methyl ester;
6-{3-Cyclopentyl-2-[6-oxo-4-(5,6,7,8-tetrahydro-naphthalen-1-yloxy)-6H-pyridazin-1-yl]-propionylamino}-nicotinic acid methyl ester;
6-{3-Cyclopentyl-2-[4-(2,6-difluoro-phenoxy)-6-oxo-6H-pyridazin-1-yl]-propionylamino}-nicotinic acid methyl ester;
6-{(S)-3-Cyclopentyl-2-[4-(2,6-difluoro-phenoxy)-6-oxo-6H-pyridazin-1-yl]-propionylamino}nicotinic acid methyl ester;
6-{(R)-3-Cyclopentyl-2-[4-(2,6-difluoro-phenoxy)-6-oxo-6H-pyridazin-1-yl]-propionylamino}-nicotinic acid methyl ester;
6-[3-Cyclopentyl-2-(6-oxo-4-o-tolyloxy-6H-pyridazin-1-yl)-propionylamino]-nicotinic acid methyl ester;
6-{3-Cyclopentyl-2-[4-(2-fluoro-phenoxy)-6-oxo-6H-pyridazin-1-yl]-propionylamino}-nicotinic acid methyl ester;
6-{3-Cyclopentyl-2-[4-(2-cyclopentyl-phenoxy)-6-oxo-6H-pyridazin-1-yl]-propionylamino}-nicotinic acid;
6-{3-Cyclopentyl-2-[6-oxo-4-(5,6,7,8-tetrahydro-naphthalen-1-yloxy)-6H-pyridazin-1-yl]-propionylamino}-nicotinic acid;
6-{(S)-3-Cyclopentyl-2-[6-oxo-4-(5,6,7,8tetrahydro-naphthalen-1-yloxy)-6H-pyridazin-1-yl]-propionylamino}-nicotinic acid;
6-{(R)-3Cyclopentyl-2-[6-oxo-4-(5,6,7,8-tetrahydro-naphthalen-1-yloxy)-6H-pyridazin-1-yl]-propionylamino}-nicotinic acid;
6-{3-Cyclopentyl-2-[4-(2,6-difluoro-phenoxy)-6-oxo-6H-pyridazin-1-yl]-propionylamino}-nicotinic acid;
6-{(S)-3-Cyclopentyl-2-[4-(2,6-difluoro-phenoxy)-6-oxo-6H-pyridazin-1-yl]-propionylamino}-nicotinic acid;
6-{(R)-3-Cyclopentyl-2-[4-(2,6-difluoro-phenoxy)-6-oxo-6H-pyridazin-1-yl]-propionylamino}-nicotinic acid;
6-[3-Cyclopentyl-2-(6-oxo-4-o-tolyloxy-6H-pyridazin-1-yl)-propionylamino]-nicotinic acid;
6-[(S)-3-Cyclopentyl-2-(6-oxo-4-o-tolyloxy-6H-pyridazin-1-yl)-propionylamino]-nicotinic acid;
6-[(R)-3-Cyclopentyl-2-(6-oxo-4-o-tolyloxy-6H-pyridazin-1-yl)-propionylamino]nicotinic acid;
6-{3-Cyclopentyl-2-[4-(2-fluoro-phenoxy)-6-oxo-6H-pyridazin-1-yl]propionylamino}-nicotinic acid;
6-{(S)-3-Cyclopentyl-2-[4-(2-fluoro-phenoxy)-6-oxo-6H-pyridazin-1-yl]-propionylamino}-nicotinic acid;
6-{(R)-3-Cyclopentyl-2-[4-(2-fluoro-phenoxy)-6-oxo-6H-pyridazin-1-yl]-propionylamino}-nicotinic acid;
3-Cyclopentyl-2-[6-oxo-4-(2-trifluoromethyl-phenoxy)-6H-pyridazin-1-yl]-N-pyrazin-2-yl-propionamide;
3-Cyclopentyl-N-[1-(2-hydroxy-2-methyl-propyl)-1H-pyrazol-3-yl]-2-[4-(methyl-phenyl-amino)-6-oxo-6H-pyridazin-1-yl]-propionamide;
3-Cyclopentyl-N-[1-(2-hydroxy-2-methyl-propyl)-1H-pyrazol-3-yl]-2-(6-oxo-6H-pyridazin-1-yl)-propionamide;
3-Cyclopentyl-2-(6-oxo-6H-pyridazin-1-yl)-N-thiazol-2-yl-propionamide;
3-Cyclopentyl-2-(4-methoxy-6-oxo-6H-pyridazin-1-yl)-N-thiazol-2-yl-propionamide;
3-Cyclopentyl-N-[1-(2-hydroxy-2-methyl-propyl)-1H-pyrazol-3-yl]-2-(4-methoxy-6-oxo-6H-pyridazin-1-yl)-propionamide;
3-Cyclopentyl-N-(1-methyl-1H-pyrazol-3-yl)-2-(6-oxo-6H-pyridazin-1-yl)-propionamide;
3-Cyclopentyl-2-(1-oxo-1H-phthalazin-2-yl)-N-thiazol-2-yl-propionamide;
3-Cyclopentyl-N-[1-(2-hydroxy-2-methyl-propyl)-1H-pyrazol-3-yl]-2-(1-oxo-1H-phthalazin-2-yl)-propionamide;
3-Cyclopentyl-2-(1-oxo-1H-phthalazin-2-yl)-N-thiazol-2-yl-propionamide;
3-Cyclopentyl-N-[1-(2-hydroxy-2-methyl-propyl)-1H-pyrazol-3-yl]-2-[6-oxo-4-(2,3,6-trimethyl-phenoxy)-6H-pyridazin-1-yl]-propionamide;
3-Cyclopentyl-2-[4-(2,2-dimethyl-2,3-dihydro-benzofuran-7-yloxy)-6-oxo-6H-pyridazin-1-yl]-N-[1-(2-hydroxy-2-methyl-propyl)-1H-pyrazol-3-yl]-propionamide;
2-[4-(2-tert-Butyl-phenoxy)-6-oxo-6H-pyridazin-1-yl]-3-cyclopentyl-N-[1-(2-hydroxy-2-methyl-propyl)-1H-pyrazol-3-yl]-propionamide;
3-Cyclopentyl-N-[1-((R)-2,3-dihydroxy-propyl)-1H-pyrazol-3-yl]-2-[4-(2,6-dimethyl-cyclohexyloxy)-6-oxo-6H-pyridazin-1-yl]-propionamide;
3-Cyclopentyl-2-[4-(2,3-dichloro-phenoxy)-6-oxo-6H-pyridazin-1-yl]-N-[1-((R)-2,3-dihydroxy-propyl)-1H-pyrazol-3-yl]propionamide;
3-Cyclopentyl-N-[1-((R)-2,3-dihydroxy-propyl)-1H-pyrazol-3-yl]-2-[4-(7-methyl-indan-4-yloxy)-6-oxo-6H-pyridazin-1-yl]-propionamide;
2-(4-Cyclobutoxy-6-oxo-6H-pyridazin-1-yl)-3-cyclopentyl-N-[1-((R)-2,3-dihydroxy-propyl)-1H-pyrazol-3-yl]-propionamide;
3-Cyclopentyl-N-[1-((R)-2,3-dihydroxy-propyl)-1H-pyrazol-3-yl]-2-[4-(3-fluoro-pyridin-2-yloxy)-6-oxo-6H-pyridazin-1-yl]-propionamide;
3-Cyclopentyl-N-[1-((R)-2,3-dihydroxy-propyl)-1H-pyrazol-3-yl]-2-[4-(1H-indol-4-yloxy)-6-oxo-6H-pyridazin-1-yl]-propionamide;
3-Cyclopentyl-N-[1((R)-2,3-dihydroxy-propyl)-1H-pyrazol-3-yl]-2-[4-(2-methyl-4-oxo-4H-pyran-3-yloxy)-6-oxo-6H-pyridazin-1-yl]-propionamide;
3-Cyclopentyl-N-[1-((R)-2,3-dihydroxy-propyl)-1H-pyrazol-3-yl]-2-[6-oxo-4-(2-trifluoromethoxy-phenoxy)-6H-pyridazin-1-yl]-propionamide;
3-Cyclopentyl-N-[1-((R)-2,3-dihydroxy-propyl)-1H-pyrazol-3-yl]-2-[4-(6-methyl-pyridin-2-yloxy)-6-oxo-6H-pyridazin-1-yl]-propionamide;
3-Cyclopentyl-N-[1-(R)-2,3-dihydroxy-propyl)-1H-pyrazol-3-yl]-2-[4-(2-fluoro-5-methyl-phenoxy)-6-oxo-6H-pyridazin-1-yl]-propionamide;
3-Cyclopentyl-N-[1-((R)-2,3-dihydroxy-propyl)-1H-pyrazol-3-yl]-2-{4-[2-(2-hydroxy-ethyl)-phenoxy]-6-oxo-6H-pyridazin-1-yl}-propionamide;
3-Cyclopentyl-N-[1((R)-2,3-dihydroxy-propyl)-1H-pyrazol-3-yl]-2-[4-(4,6-dimethyl-pyrimidin-2-yloxy)-6-oxo-6H-pyridazin-1-yl]-propionamide;
3-Cyclopentyl-N-[1-((R)-2,3-dihydroxy-propyl)-1H-pyrazol-3-yl]-2-[4-(2-methyl-5-trifluoromethyl-2H-pyrazol-3-yloxy)-6-oxo-6H-pyridazin-1-yl]-propionamide;
2-[4-(3-Chloro-2-fluoro-phenoxy)-6-oxo-6H-pyridazin-1-yl]-3-cyclopentyl-N-[1-((R)-2,3-dihydroxy-propyl)-1H-pyrazol-3-yl]-propionamide;
3-Cyclopentyl-2-[4-(2,6-difluoro-phenoxy)-6-oxo-6H-pyridazin-1-yl]-N-[1-((R)-2,3-dihydroxy-propyl)-1H-pyrazol-3-yl]-propionamide;

(S)-3-Cyclopentyl-2-[4-(2,6-difluoro-phenoxy)-6-oxo-6H-pyridazin-1-yl]-N-[1-((R)-2,3-dihydroxy-propyl)-1H-pyrazol-3-yl]-propionamide;
(R)-3-Cyclopentyl-2-[4-(2,6-difluoro-phenoxy)-6-oxo-6H-pyridazin-1-yl]-N-[1-((R)-2,3-dihydroxy-propyl)-1H-pyrazol-3-yl]-propionamide;
3-Cyclopentyl-2-[4-(2,6-difluoro-phenoxy)-6-oxo-6H-pyridazin-1-yl]-N-[5-((R)-1,2-dihydroxy-ethyl)-pyrazin-2-yl]-propionamide;
3-Cyclopentyl-2-[4-(2,6-difluoro-3-methyl-phenoxy)-6-oxo-6H-pyridazin-1-yl]-N-[1-((R)-2,3-dihydroxy-propyl)-1H-pyrazol-3-yl]-propionamide;
2-[4-(2,6-Difluoro-phenoxy)-6-oxo-6H-pyridazin-1-yl]-3-(2,6-difluoro-phenyl)-N-[1-((R)-2,3-dihydroxy-propyl)-1H-pyrazol-3-yl]-propionamide;
4-Methyl-2-[4-(naphthalen-1-yloxy)-6-oxo-6H-pyridazin-1-yl]-pentanoic acid [1-((R)-2,3-dihydroxy-propyl)-1H-pyrazol-3-yl]-amide;
(S)-4-Methyl-2-[4-(naphthalen-1-yloxy)-6-oxo-6H-pyridazin-1-yl]-pentanoic acid [1-((R)-2,3-dihydroxy-propyl)-1H-pyrazol-3-yl]-amide;
(R)-4-Methyl-2-[4-(naphthalen-1-yloxy)-6-oxo-6H-pyridazin-1-yl]-pentanoic acid [1-((R)-2,3-dihydroxy-propyl)-1H-pyrazol-3-yl]-amide;
4-Methyl-2-[6-oxo-4-(5,6,7,8-tetrahydro-naphthalen-1-yloxy)-6H-pyridazin-1-yl]-pentanoic acid [1-((R)-2,3-dihydroxy-propyl)-1H-pyrazol-3-yl]-amide;
(S)-4-Methyl-2-[6-oxo-4-(5,6,7,8-tetrahydro-naphthalen-1-yloxy)-6H-pyridazin-1-yl]-pentanoic acid [1-((R)-2,3-dihydroxy-propyl)-1H-pyrazol-3-yl]-amide;
(R)-4-Methyl-2-[6-oxo-4-(5,6,7,8-tetrahydro-naphthalen-1-yloxy)-6H-pyridazin-1-yl]-pentanoic acid [1-((R)-2,3-dihydroxy-propyl)-1H-pyrazol-3-yl]-amide;
2-[4-(1H-Indol-4-yloxy)-6-oxo-6H-pyridazin-1-yl]-4-methyl-pentanoic acid [1-(R)-2,3-dihydroxy-propyl)-1H-pyrazol-3-yl]-amide;
2-[4-(4-Hydroxy-indol-1-yl)-6-oxo-6H-pyridazin-1-yl]-4-methyl-pentanoic acid [1-((R)-2,3-dihydroxy-propyl)-1H-pyrazol-3-yl]-amide;
2-{4-[1-((R)-2,3-Dihydroxy-propyl)-1H-indol-4-yloxy]-6-oxo-6H-pyridazin-1-yl}-4-methyl-pentanoic acid (1methyl-1H-pyrazol-3-yl)-amide;
2-{4-[2-(2-Chloro-phenyl)-ethoxy]-6-oxo-6H-pyridazin-1-yl}-3-cyclopentyl-N-[1-((R)-2,3-dihydroxy-propyl)-1H-pyrazol-3-yl]-propionamide;
3-Cyclopentyl-N-[1-((R)-2,3-dihydroxy-propyl)-1H-pyrazol-3-yl]-2-[6-oxo-4-(4-trifluoromethyl-pyrimidin-2-yloxy)-6H-pyridazin-1-yl]-propionamide;
3-Cyclohexyl-2-[4-(2-fluoro-4-methoxy-phenoxy)-6-oxo-6H-pyridazin-1-yl]-N-[1-(2-hydroxy-2-methyl-propyl)-1H-pyrazol-3-yl]-propionamide;
3-Cyclohexyl-2-[4-(2,4-dimethyl-phenoxy)-6-oxo-6H-pyridazin-1-yl]-N-[1-(2-hydroxy-2-methyl-propyl)-1H-pyrazol-3-yl]-propionamide;
2-[4-(2-Chloro-4-methoxy-phenoxy)-6-oxo-6H-pyridazin-1-yl]-3-cyclohexyl-N-[1-(2-hydroxy-2-methyl-propyl)-1H-pyrazol-3-yl]-propionamide;
2-[4-(2-Chloro-4-trifluoromethoxy-phenoxy)-6-oxo-6H-pyridazin-1-yl]-3-cyclohexyl-N-[1-(2-hydroxy-2-methyl-propyl)-1H-pyrazol-3-yl]-propionamide;
2-[4-(3-Ethoxy-2,6-difluoro-phenoxy)-6-oxo-6H-pyridazin-1-yl]-4-methyl-pentanoic acid [1-((R)-2,2-dimethyl-[1,3]dioxolan-4-ylmethyl)-1H-pyrazol-3-yl]-amide;
N-[1-((R)-2,3-Dihydroxy-propyl)-1H-pyrazol-3-yl]-2-[4-(3-ethoxy-2,6-difluoro-phenoxy)-6-oxo-6H-pyridazin-1-yl]-3-(tetrahydro-pyran-4-yl)-propionamide;
2-[4-(2-Chloro-phenylamino)-6-oxo-6H-pyridazin-1-yl]-4-methyl-pentanoic acid [1-((R)-2,3-dihydroxy-propyl)-1H-pyrazol-3-yl]-amide;
3-Cyclopentyl-N-[1-(2-hydroxy-2-methyl-propyl)-1H-pyrazol-3-yl]-2-(6-oxo-4-phenylsulfanyl-6H-pyridazin-1-yl)-propionamide;
2-(4-Benzenesulfinyl-6-oxo-6H-pyridazin-1-yl)-3-cyclopentyl-N-[1-(2-hydroxy-2-methyl-propyl)-1H-pyrazol-3-yl]-propionamide;
2-(4-Benzenesulfonyl-6-oxo-6H-pyridazin-1-yl)-3-cyclopentyl-N-[1-(2-hydroxy-2-methyl-propyl)-1H-pyrazol-3-yl]-propionamide;
2-[4-(2-Chloro-3-trifluoromethyl-phenoxy)-6-oxo-6H-pyridazin-1-yl]-4-methyl-pentanoic acid [1-((R)-2,3-dihydroxy-propyl)-1H-pyrazol-3-yl]-amide;
2-[4-(2-Chloro-3-methoxy-phenoxy)-6-oxo-6H-pyridazin-1-yl]-4-methyl-pentanoic acid [1-((R)-2,3-dihydroxy-propyl)-1H-pyrazol-3-yl]-amide;
2-[4-(2-Chloro-phenoxy)-6-oxo-6H-pyridazin-1-yl]-3-cyclopentyl-N-[1-((R)-2,3-dihydroxy-propyl)-1H-pyrazol-3-yl]-propionamide;
2-[5-Chloro-4-(2-chloro-phenoxy)-6-oxo-6H-pyridazin-1-yl]-N-[1-(2-hydroxy-2-methyl-propyl)-1H-pyrazol-3-yl]-3-(tetrahydro-pyran-4-yl)-propionamide;
2-[5-Chloro-4-(2-chloro-4-trifluoromethoxy-phenoxy)-6-oxo-6H-pyridazin-1-yl]-3-cyclohexyl-propionic acid;
Acetic acid 2-{3-[2-[4-(2,6-difluoro-phenoxy)-6-oxo-6H-pyridazin-1-yl]-3-(tetrahydro-pyran-4-yl)-propionylamino]-5-methyl-pyrazol-1-yl}-1-methyl-ethyl ester;
2-[4-(2,6-Difluoro-phenoxy)-6-oxo-6H-pyridazin-1-yl]-N-[1-(2-hydroxy-propyl)-5-methyl-1H-pyrazol-3-yl]-3-(tetrahydro-pyran-4-yl)-propionamide;
3-Cyclohexyl-2-[4-(2,3-dihydro-benzo[1,4]dioxin-5-yloxy)-6-oxo-6H-pyridazin-1-yl]N-[1-(2-hydroxy-2-methyl-propyl)-1H-pyrazol-3-yl]-propionamide;
2-[4-(2-Chloro-phenoxy)-6-oxo-61-1-pyridazin-1-yl]-4-methyl-pentanoic acid [1-(2-hydroxy-2-methyl-propyl)-1H-pyrazol-3-yl]-amide;
2-[4-(2-Chloro-phenoxy)-6-oxo-6H-pyridazin-1-yl]-N-[1-(2-hydroxy-2-methyl-propyl)-1H-pyrazol-3-yl]-3-(tetrahydro-pyran-4-yl)-propionamide;
(S)-2-[4-(2-Chloro-phenoxy)-6-oxo-6H-pyridazin-1-yl]-N-[1-(2-hydroxy-2-methyl-propyl)-1H-pyrazol-3-yl]-3-(tetrahydro-pyran-4-yl)-propionamide;
(R)-2-[4-(2-Chloro-phenoxy)-6-oxo-6H-pyridazin-1-yl]-N-[1-(2-hydroxy-2-methyl-propyl)-1H-pyrazol-3-yl]-3-(tetrahydro-pyran-4-yl)-propionamide;
2-(5-Chloro-6-oxo-4-phenoxy-6H-pyridazin-1-yl)-3-cyclohexyl-N-[1-(2-hydroxy-2-methyl-propyl)-1H-pyrazol-3-yl]-propionamide; or
2-[4-(2-Chloro-phenoxy)-6-oxo-6H-pyridazin-1-yl]-4-methyl-pentanoic acid [1-((R)-2,3-dihydroxy-propyl)-1H-pyrazol-3-yl]-amide.

2. A pharmaceutical composition, comprising a therapeutically effective amount of a compound according to claim 1 or a pharmaceutically acceptable salt thereof and a pharmaceutically acceptable carrier.

* * * * *